(12) United States Patent
Cigan et al.

(10) Patent No.: US 12,378,566 B2
(45) Date of Patent: *Aug. 5, 2025

(54) PLANT GENOME MODIFICATION USING GUIDE RNA/CAS ENDONUCLEASE SYSTEMS AND METHODS OF USE

(71) Applicants: E. I. DU PONT DE NEMOURS AND COMPANY, Wilmington, DE (US); PIONEER HI-BRED INTERNATIONAL, INC., Johnston, IA (US)

(72) Inventors: Andrew Mark Cigan, Madison, WI (US); Saverio Carl Falco, Wilmington, DE (US); Huirong Gao, Johnston, IA (US); Zhongsen Li, Hockessin, DE (US); Zhan-Bin Liu, Clive, IA (US); L. Aleksander Lyznik, Johnston, IA (US); Jinrui Shi, Johnston, IA (US); Sergei Svitashev, Johnston, IA (US); Joshua K. Young, Johnston, IA (US)

(73) Assignees: PIONEER HI-BRED INTERNATIONAL, INC., Johnston, IA (US); E.I. DU PONT DE NEMOURS AND COMPANY, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/055,614

(22) Filed: Nov. 15, 2022

(65) Prior Publication Data
US 2023/0323374 A1    Oct. 12, 2023

Related U.S. Application Data

(63) Continuation of application No. 14/913,614, filed as application No. PCT/US2014/051778 on Aug. 20, 2014, now abandoned.

(60) Provisional application No. 62/023,239, filed on Jul. 11, 2014, provisional application No. 61/953,090, filed on Mar. 14, 2014, provisional application No. 61/937,045, filed on Feb. 7, 2014, provisional application No. 61/882,532, filed on Sep. 25, 2013, provisional application No. 61/868,706, filed on Aug. 22, 2013.

(51) Int. Cl.
| | |
|---|---|
| *C12N 15/82* | (2006.01) |
| *C12N 15/00* | (2006.01) |
| *C12N 15/63* | (2006.01) |
| *A01H 1/00* | (2006.01) |

(52) U.S. Cl.
CPC ......... *C12N 15/8213* (2013.01); *C12N 15/00* (2013.01); *C12N 15/63* (2013.01); *C12N 15/8205* (2013.01); *C12N 15/8207* (2013.01); *C12N 15/8216* (2013.01); *C12N 15/8247* (2013.01); *C12N 15/8262* (2013.01); *A01H 1/00* (2013.01)

(58) Field of Classification Search
None
See application file for complete search history.

(56) References Cited

U.S. PATENT DOCUMENTS

| | | | |
|---|---|---|---|
| 5,036,006 | A | 7/1991 | Sanford et al. |
| 5,639,947 | A | 6/1997 | Hiatt |
| 5,959,177 | A | 9/1999 | Hein et al. |
| 6,410,329 | B1 | 6/2002 | Hansen et al. |
| 6,518,485 | B1 | 2/2003 | Connett-Porceddu et al. |
| 6,603,061 | B1 | 8/2003 | Armstrong et al. |
| 6,627,797 | B1 | 9/2003 | Duvick et al. |
| 7,292,055 | B2 | 11/2007 | Egitto et al. |
| 7,868,149 | B2 | 1/2011 | Boukharov et al. |
| 8,012,752 | B2 | 9/2011 | Jayakumar et al. |
| 8,124,860 | B2 | 2/2012 | Gallie et al. |

(Continued)

FOREIGN PATENT DOCUMENTS

| | | |
|---|---|---|
| CN | 103667338 A | 3/2014 |
| DE | 102015006335 A1 | 11/2016 |

(Continued)

OTHER PUBLICATIONS

Deng et al.. A novel method for induction of plant regeneration via somatic embryogenesis. Plant Science. vol. 177, Issue Jul. 1, 2009, pp. 43-48. (Year: 2009).*

(Continued)

*Primary Examiner* — Cynthia E Collins

(57) ABSTRACT

Compositions and methods are provided for genome modification of a target sequence in the genome of a plant or plant cell. The methods and compositions employ a guide RNA/Cas endonuclease system to provide an effective system for modifying or altering target sites within the genome of a plant, plant cell or seed. Also provided are compositions and methods employing a guide polynucleotide/Cas endonuclease system for genome modification of a nucleotide sequence in the genome of a cell or organism, for gene editing, and/or for inserting or deleting a polynucleotide of interest into or from the genome of a cell or organism. Once a genomic target site is identified, a variety of methods can be employed to further modify the target sites such that they contain a variety of polynucleotides of interest. Breeding methods and methods for selecting plants utilizing a two component RNA guide and Cas endonuclease system are also disclosed. Compositions and methods are also provided for editing a nucleotide sequence in the genome of a cell.

18 Claims, 45 Drawing Sheets

Figure 2A:
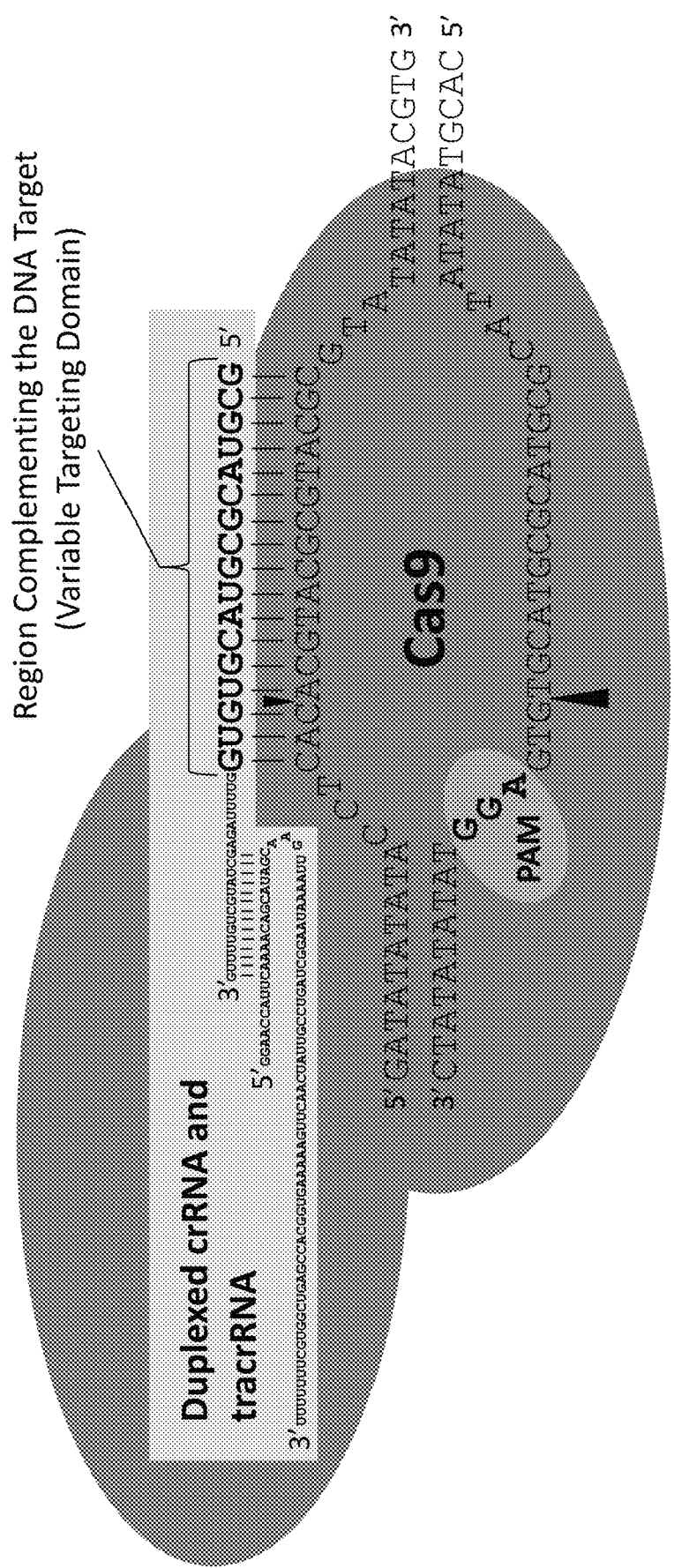

Specification includes a Sequence Listing.

(56) References Cited

U.S. PATENT DOCUMENTS

| | | |
|---|---|---|
| 8,575,424 B2 | 11/2013 | Yau et al. |
| 8,581,036 B2 | 11/2013 | Samboju et al. |
| 8,586,361 B2 | 11/2013 | Tao et al. |
| 8,609,420 B2 | 12/2013 | Samuel et al. |
| 8,653,327 B2 | 2/2014 | Samboju et al. |
| 8,680,366 B2 | 3/2014 | Eudes et al. |
| 8,697,359 B1 | 4/2014 | Zhang |
| 8,722,410 B2 | 5/2014 | Samuel et al. |
| 8,771,945 B1 | 7/2014 | Zhang |
| 8,795,965 B2 | 8/2014 | Zhang |
| 8,865,406 B2 | 10/2014 | Zhang |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,163,284 B2 | 10/2015 | Liu et al. |
| 9,187,755 B2 | 11/2015 | Samuel et al. |
| 9,382,548 B2 | 7/2016 | Eudes et al. |
| 9,476,057 B2 | 10/2016 | Samuel et al. |
| 9,493,782 B2 | 11/2016 | Cigan et al. |
| 9,518,266 B2 | 12/2016 | Bruce et al. |
| 9,719,108 B2 | 8/2017 | Samuel et al. |
| 9,840,713 B2 | 12/2017 | Zhang |
| 9,885,033 B2 | 2/2018 | Joung et al. |
| 10,113,162 B2 | 10/2018 | Mathis et al. |
| 10,227,576 B1 | 3/2019 | Cameron et al. |
| 10,287,594 B2 | 5/2019 | Beetham et al. |
| 10,329,547 B1 | 6/2019 | Cameron et al. |
| 10,519,457 B2 | 12/2019 | Li et al. |
| 10,557,146 B2 | 2/2020 | Gao et al. |
| 10,870,859 B2 | 12/2020 | Li et al. |
| 11,427,830 B2 | 8/2022 | Li et al. |
| 2004/0034888 A1 | 2/2004 | Liu et al. |
| 2004/0231016 A1 | 11/2004 | Wang et al. |
| 2004/0235099 A1 | 11/2004 | Payne et al. |
| 2007/0083945 A1 | 4/2007 | Byrum et al. |
| 2007/0178593 A1 | 8/2007 | Miller et al. |
| 2007/0199095 A1 | 8/2007 | Allen et al. |
| 2008/0047031 A1 | 2/2008 | Tao et al. |
| 2009/0070891 A1 | 3/2009 | Foley et al. |
| 2009/0100536 A1 | 4/2009 | Adams et al. |
| 2009/0104700 A1 | 4/2009 | Samuel et al. |
| 2009/0111186 A1 | 4/2009 | Held et al. |
| 2009/0133152 A1 | 5/2009 | Lyznik |
| 2010/0076057 A1 | 3/2010 | Sontheimer et al. |
| 2010/0159598 A1 | 6/2010 | Jayakumar et al. |
| 2010/0311168 A1 | 12/2010 | Samuel et al. |
| 2010/0313293 A1 | 12/2010 | Albertsen et al. |
| 2011/0035836 A1 | 2/2011 | Eudes et al. |
| 2011/0165679 A1 | 7/2011 | Gordon-Kamm et al. |
| 2011/0203012 A1 | 8/2011 | Dotson et al. |
| 2011/0247100 A1 | 10/2011 | Samboju et al. |
| 2012/0023619 A1 | 1/2012 | Samboju et al. |
| 2012/0023620 A1 | 1/2012 | Yau et al. |
| 2012/0244569 A1 | 9/2012 | Samuel et al. |
| 2013/0011828 A1 | 1/2013 | Barrangou et al. |
| 2013/0157369 A1 | 6/2013 | Miller |
| 2013/0198888 A1 | 8/2013 | Falco et al. |
| 2013/0263324 A1 | 10/2013 | Lassner et al. |
| 2013/0326725 A1 | 12/2013 | Shukla et al. |
| 2014/0020131 A1 | 1/2014 | Bidney et al. |
| 2014/0068797 A1 | 3/2014 | Doudna et al. |
| 2014/0090113 A1 | 3/2014 | Cogan et al. |
| 2014/0096284 A1 | 4/2014 | Martin-Ortigosa et al. |
| 2014/0179006 A1 | 6/2014 | Zhang |
| 2014/0179770 A1 | 6/2014 | Zhang et al. |
| 2014/0182012 A1 | 6/2014 | Eudes et al. |
| 2014/0186843 A1 | 7/2014 | Zhang et al. |
| 2014/0186919 A1 | 7/2014 | Zhang et al. |
| 2014/0186958 A1* | 7/2014 | Zhang .................. C12N 15/01 435/320.1 |
| 2014/0189896 A1 | 7/2014 | Zhang et al. |
| 2014/0196170 A1 | 7/2014 | Qiao et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0242702 A1 | 8/2014 | Chen et al. |
| 2014/0242703 A1 | 8/2014 | Samuel et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0273235 A1 | 9/2014 | Voytas |
| 2014/0310830 A1 | 10/2014 | Zhang et al. |
| 2014/0335620 A1 | 11/2014 | Zhang et al. |
| 2014/0342456 A1 | 11/2014 | Mali et al. |
| 2014/0357530 A1 | 12/2014 | Zhang et al. |
| 2014/0370558 A1 | 12/2014 | Mathis et al. |
| 2015/0020223 A1 | 1/2015 | Zhang et al. |
| 2015/0044191 A1 | 2/2015 | Liu et al. |
| 2015/0044772 A1 | 2/2015 | Zhao |
| 2015/0059010 A1 | 2/2015 | Cigan et al. |
| 2015/0067922 A1* | 3/2015 | Yang .................. C12N 15/8289 435/468 |
| 2015/0079681 A1 | 3/2015 | Zhang |
| 2015/0082478 A1 | 3/2015 | Cigan et al. |
| 2015/0167000 A1 | 6/2015 | Voytas et al. |
| 2015/0167001 A1 | 6/2015 | D'Halluin |
| 2015/0184171 A1 | 7/2015 | D'Halluin |
| 2015/0225734 A1* | 8/2015 | Voytas .................. C12N 9/22 435/468 |
| 2015/0284727 A1 | 10/2015 | Kim et al. |
| 2015/0291967 A1 | 10/2015 | Mathis et al. |
| 2016/0024524 A1 | 1/2016 | Joung et al. |
| 2016/0032297 A1 | 2/2016 | Deschamps et al. |
| 2016/0145631 A1 | 5/2016 | Voytas et al. |
| 2016/0168592 A1 | 6/2016 | Church et al. |
| 2016/0201072 A1 | 7/2016 | Cigan et al. |
| 2016/0208271 A1 | 7/2016 | Cigan et al. |
| 2016/0208272 A1 | 7/2016 | Cigan et al. |
| 2016/0251667 A1 | 9/2016 | Cigan et al. |
| 2016/0289691 A1 | 10/2016 | Beetham et al. |
| 2016/0304846 A1 | 10/2016 | Liu et al. |
| 2016/0340746 A1 | 11/2016 | Makarov et al. |
| 2017/0022521 A1 | 1/2017 | Samuel et al. |
| 2017/0029880 A1 | 2/2017 | Fang et al. |
| 2017/0166912 A1 | 6/2017 | Brower-Toland et al. |
| 2017/0183677 A1 | 6/2017 | Gao et al. |
| 2018/0002715 A1 | 1/2018 | Cigan et al. |
| 2018/0057832 A1 | 3/2018 | Li |
| 2018/0087104 A1 | 3/2018 | Joung et al. |
| 2018/0142263 A1 | 5/2018 | May et al. |
| 2018/0163203 A1 | 6/2018 | Bennett et al. |
| 2018/0230476 A1 | 8/2018 | Cigan et al. |
| 2018/0258417 A1 | 9/2018 | Cigan et al. |
| 2018/0258438 A1 | 9/2018 | Chaky et al. |
| 2018/0273960 A1 | 9/2018 | Cigan et al. |
| 2018/0282763 A1 | 10/2018 | Cigan et al. |
| 2018/0327785 A1 | 11/2018 | Cigan et al. |
| 2018/0346895 A1 | 12/2018 | Cigan et al. |
| 2018/0371479 A1 | 12/2018 | Cigan et al. |
| 2019/0040405 A1 | 2/2019 | Cigan et al. |
| 2019/0100745 A1 | 4/2019 | Cigan et al. |
| 2019/0100762 A1 | 4/2019 | Cigan et al. |
| 2019/0136248 A1 | 5/2019 | Cigan et al. |
| 2019/0161742 A1 | 5/2019 | Cigan et al. |
| 2019/0264232 A1 | 8/2019 | Hou et al. |
| 2020/0157554 A1 | 5/2020 | Cigan et al. |
| 2022/0177900 A1 | 6/2022 | Cigan et al. |
| 2022/0364107 A1 | 11/2022 | Gao et al. |

(56) References Cited

U.S. PATENT DOCUMENTS

| | | |
|---|---|---|
| 2023/0193304 A1 | 6/2023 | Li et al. |
| 2023/0235345 A1 | 7/2023 | Cigan et al. |

FOREIGN PATENT DOCUMENTS

| | | | |
|---|---|---|---|
| WO | 2005/049842 A2 | 6/2005 | |
| WO | 2007/025097 A2 | 3/2007 | |
| WO | WO-2007084294 A2 | 7/2007 | |
| WO | 2009/042164 A1 | 4/2009 | |
| WO | 2010/011961 A3 | 1/2010 | |
| WO | WO-2010011961 A2 | 1/2010 | |
| WO | WO-2010077319 A1 | 7/2010 | |
| WO | WO-2011143124 A2 | 11/2011 | |
| WO | 2012/129373 A2 | 9/2012 | |
| WO | WO-2012164565 A1 | 12/2012 | |
| WO | WO-2013019411 A1 | 2/2013 | |
| WO | WO-2013066423 A2 | 5/2013 | |
| WO | WO-2013066805 A1 | 5/2013 | |
| WO | WO-2013068845 A2 | 5/2013 | |
| WO | 2013/098244 A1 | 7/2013 | |
| WO | WO-2013112686 A1 | 8/2013 | |
| WO | 2013/142578 A1 | 9/2013 | |
| WO | WO-2013138363 A2 | 9/2013 | |
| WO | WO-2013141680 A1 | 9/2013 | |
| WO | WO-2013173535 A2 | 11/2013 | |
| WO | WO-2013176772 A1 | 11/2013 | |
| WO | WO-2014004487 A1 | 1/2014 | |
| WO | WO-2014018423 A2 | 1/2014 | |
| WO | WO-2014039872 A1 | 3/2014 | |
| WO | 2014/065596 A1 | 5/2014 | |
| WO | WO-2014071006 A1 | 5/2014 | |
| WO | 2014/093479 A1 | 6/2014 | |
| WO | 2014/093635 A1 | 6/2014 | |
| WO | WO-2014089290 A1 | 6/2014 | |
| WO | WO-2014093595 A1 | 6/2014 | |
| WO | WO-2014093694 A1 | 6/2014 | |
| WO | WO-2014093712 A1 | 6/2014 | |
| WO | WO-2014093768 A1 | 6/2014 | |
| WO | 2014/144155 A1 | 9/2014 | |
| WO | WO-2014144288 A1 | 9/2014 | |
| WO | WO-2014144761 A2 | 9/2014 | |
| WO | WO-2014150624 A1 | 9/2014 | |
| WO | WO-2014164466 A1 | 10/2014 | |
| WO | WO-2014165825 A2 | 10/2014 | |
| WO | 2014/186686 A2 | 11/2014 | |
| WO | WO-2014194190 A1 | 12/2014 | |
| WO | WO-2015006294 A2 | 1/2015 | |
| WO | WO-2015006747 A2 | 1/2015 | |
| WO | WO-2015026883 A1 | 2/2015 | |
| WO | WO-2015026885 A1 | 2/2015 | |
| WO | WO-2015026886 A1 | 2/2015 | |
| WO | WO-2015026887 A1 | 2/2015 | |
| WO | WO-2015070083 A1 | 5/2015 | |
| WO | WO-2015071474 A2 | 5/2015 | |
| WO | WO-2015112896 A2 | 7/2015 | |
| WO | WO-2015131101 A1 | 9/2015 | |
| WO | WO-2015112896 A9 | 11/2015 | |
| WO | WO-2015189693 A1 | 12/2015 | |
| WO | WO-2016007347 A1 | 1/2016 | |
| WO | WO-2016033298 A1 | 3/2016 | |
| WO | WO-2016040030 A1 | 3/2016 | |
| WO | WO-2016149352 A1 | 9/2016 | |
| WO | WO-2016186946 A1 | 11/2016 | |
| WO | WO-2017015015 A1 | 1/2017 | |
| WO | WO-2017034971 A1 | 3/2017 | |
| WO | WO-2017062855 A1 | 4/2017 | |
| WO | WO-2017066497 A2 | 4/2017 | |
| WO | WO-2017070032 A1 | 4/2017 | |
| WO | WO-2017117395 A1 | 7/2017 | |
| WO | WO-2017132239 A1 | 8/2017 | |
| WO | WO-2017155714 A1 | 9/2017 | |
| WO | WO-2017155715 A1 | 9/2017 | |
| WO | WO-2017155717 A1 | 9/2017 | |
| WO | WO-2017212264 A1 | 12/2017 | |
| WO | WO-2017218185 A1 | 12/2017 | |
| WO | WO-2018172556 A1 | 9/2018 | |
| WO | WO-2018197495 A1 | 11/2018 | |
| WO | WO-2018197520 A1 | 11/2018 | |
| WO | WO-2019074841 A1 | 4/2019 | |
| WO | WO-2019084148 A1 | 5/2019 | |
| WO | WO-2019089808 A1 | 5/2019 | |
| WO | WO-2019168953 A1 | 9/2019 | |
| WO | WO-2019177978 A1 | 9/2019 | |
| WO | WO-2019217354 A1 | 11/2019 | |
| WO | WO-2019217358 A1 | 11/2019 | |
| WO | WO-2019217816 A1 | 11/2019 | |

OTHER PUBLICATIONS

Srinivasan et al. Heterologous expression of the Baby Boom AP2/ERF transcription factor enhances the regeneration capacity of tobacco (*Nicotiana tabacum* L.). Planta. Jan. 2007;225(2):341-51. Epub Aug. 19, 2006. (Year: 2007).*

Wang et al. Genes controlling plant architecture. Curr. Opin. Biotechnol. Apr. 2006; 17(2):123-9. (Year: 2006).*

Farrell. The Regulation of Gene Expression in Plants and Animals. Chapter 1 pp. 1-38 In Regulation of Gene Expression in Plants, Edited by Carole L. Bassett., 2007, Springer. (Year: 2007).*

Zhiyong Mao et al., Comparison of nonhomologous end joining and homologous recombination in human cells, DNA Repair, 2008, 7:1765-1771.

Biserka Relic et al., Interaction of the DNA modifying proteins VirD1 and VirD2 of Agrobacterium tumefaciens: Analysis by subcellular localization in mammalian cells, Proc Natl Acad Sci, 2008, 95:9105-9110.

Alicja Ziemienowicz, Import of Agrobacterium T-DNA into plant nuclei: two distinct functions of VirD2 and VirE2 proteins, The Plant Cell, 2001, 13:369-383.

Bassett et al. Highly efficient targeted mutagenesis of Drosophila with the CRISPR/Cas9 system. Cell Rep. Jul. 11, 2013 ;4(1 ):220-8. Epub Jul. 1, 2013. (Year: 2013).

Cai et al. Optimizing the codon usage of synthetic gene with QPSO algorithm. J. Theor. Biol. Sep. 7, 2008;254(1):123-7. Epub May 17, 2008. (Year: 2008).

Dale et al. Intra- and intermolecular site-specific recombination in plant cells mediated by bacteriophage P1 recombinase. Gene. Jul. 2, 1990;91(1):79-85. (Year: 1990).

Damm et al. Efficient transformation of Arabidopsis thaliana using direct gene transfer to protoplasts. Mol. Gen. Genet. May 1989; 217(1):6-12. (Year: 1989).

Durai et al. Zinc finger nucleases: custom-designed molecular scissors for genome engineering of plant and mammalian cells. Nucleic Acids Res. 2005; 33(18): 5978-5990. (Year: 2005).

Dudas et al. DNA double-strand break repair by homologous recombination Mu tat. Res. Mar. 2004,566(2): 131-67. (Year: 2004).

Friedland et al. Heritable genome editing in C.elegans via a CRISPR-Cas9 system. Nat. Methods. Aug. 2013; 10 (8):741-3. Epub Jun. 3, 20130. (Year: 2013).

Gordon-Kamm et al. Transformation of Maize Cells and Regeneration of Fertile Transgenic Plants. The Plant Cell. Jul. 1990;2(7): 603-618. (Year: 1990).

Guerineau et al. Effect of two consensus sequences preceding the translation initiator codon on gene expression in blant protoplasts. Plant Mol. Biol. Feb. 1992;18(4):815-8. (Year: 1992).

Hiei et al. Efficient transformation of rice (*Oryza sativa* L.) mediated by Agrobacterium and sequence analysis of the boundaries of the T-DNA. The Plant Journal ( 1994) 6(2), 271-282. (Year: 1994).

Horsch et al. Inheritance of functional foreign genes in plants. Science. Feb. 3, 1984;223(4635):496-8. (Year: 1984).

Jiang et al. Successful transient expression of Cas9 and single guide RNA genes in Chlamydomonas reinhardtii. Eukaryot. Cell. Nov. 2014;13(11):1465-9. Epub Sep. 19, 2014. (Year: 2014).

Kilby et al. Plant J. FLP recombinase in transgenic plants: constitutive activity in stably transformed tobacco and generation of marked cell clones in *Arabidopsis*. PlantJ. Nov. 1995;8(5):637-52. (Year: 1995).

(56) References Cited

OTHER PUBLICATIONS

Klee et al. Agrobacterium-mediated plant transformation and its further applications to plant biology. Ann. Rev. Plant Physiol. 1987. 38:467-86. (Year: 1987).
Klein et al. High-velocity microprojectiles for delivering nucleic acids into living cells. Nature 327, 70-73 (1987). (Year: 1987).
Li et al. High-efficiency TALEN-based gene editing produces disease-resistant rice. Nat Biotechnol. May 7, 2012;30 (5):390-2, supplementary information. (Year: 2012).
Li et al. An improved rice transformation system using the biolistic method. Plant Cell Reports 12, 250-255 (1993). (Year: 1993).
Lloyd et al. Functional expression of the yeast FLP/FRT site-specific recombination system in Nicotiana tabacum. Mol. Gen Gent. Mar. 1994;242(6):653-7. (Year: 1994).
Luo et al. 'GM-gene-deletor': fused loxP-FRT recognition sequences dramatically improve the efficiency of FLP or CRE recombinase on transgene excision from pollen and seed of tobacco plants. Plant Biotechnol. J. Mar. 2007;5 (2):263-274. (Year: 2007).
Lyznik et al. Activity of yeast FLP recombinase in maize and rice protoplasts. Nucleic Acids Res. Feb. 25, 1993;21(4):969-75. (Year: 1993).
Maeser et al. The Gin recombinase of phage Mu can catalyse site-specific recombination in plant protoplasts. Mol. Gen. Genet. Nov. 1991;230(1-2):170-6. (Year: 1991).
Onouchi et al. Operation of an efficient site-specific recombination system of Zygosaccharomyces rouxii in tobacco cells. Nucleic Acids Res. Dec. 11, 1991;19(23):6373-8. (Year: 1991).
Puchta et al. Two different but related mechanisms are used in plants for the repair of genomic double-strand breaks by homologous recombination. Proc. Natl. Acad. Sci. U.S.A. May 14, 1996;93(10):5055-60. (Year: 1996).
Puchta et al. A transient assay in plant cells reveals a positive correlation between extrachromosomal recombination rates and length of homologous overlap. Nucleic Acids Research, vol. 19, Issue 10, May 11, 1991, pp. 2693-2700. (Year: 1991).
Puchta et al. Homologous recombination in plant cells is enhanced by in vivo induction of double strand breaks into DNA by a site-specific endonuclease. Nucleic Acids Res. Nov. 11, 1993 ;21 (22):5034-40. (Year: 1993).
Shukla et al. Precise genome modification in the crop species *Zea mays* using zinc-finger nucleases. Nature 459, 437-441 (2009). (Year: 2009).
Sugita et al. A transformation vector for the production of marker-free transgenic plants containing a single copy transgene at high frequency. Plant J. Jun. 2000;22(5):461-9. (Year: 2000).
Zhang et al. Transcription activator-like effector nucleases enable efficient plant genome engineering. Plant Physiol. Jan. 2013; 161 (1):20-7. Epub Nov. 2, 2012. (Year: 2013).
Zhang et al. A highly efficient rice green tissue protoplast system for transient gene expression and studying light/chloroplast-related processes. Plant Methods. Sep. 30, 2011;7(1):30. (Year: 2011).
Li, Xueyuan; et al.: "Efficient Protoplast Regeneration Protocol and CRISPR/Cas9-Mediated Editing of Glucosinolate Transporter (GTR) Genes in Rapeseed (*Brassica napus* L.)," Frontiers in Plant Science, Jul. 7, 2021 (Jul. 7, 2021), vol. 12, Article 680859.
Mao, et al.: "Letter to the Editor; Application of the CRISPR-Cas System for Efficient Genome Engineering in Plants," Molecular Plant, Nov. 2013 (Nov. 2013), vol. 6, No. 6, pp. 2008-2011.
Nekrasov, et al.: "Targeted mutagenesis in the model plant Nicotiana benthamiana using Cas9 RNA-guided endonuclease," Nature Biotechnology, Aug. 2013 (Aug. 2013), vol. 31, No. 8, pp. 691-693.
Rodolphe Barrangou et al., CRISPR PRovides Acquired Resistance Against Viruses in Prokaryotes, Science, 2007, pp. 1709-1712, vol. 315.
Rodolphe Barrangou et al., RNA-mediated programmable DNA cleavage, Nature Biotechnology, Sep. 2012, pp. 836-838, vol. 30, No. 9.
Rodolphe Barrangou et al., CRISPR-Cas sytems and RNA-guided interference, WIREs RNA, 2013, pp. 267-278, vol. 4.

Khaoula Belhaj et al., Plant genome editing made easy: targeted mutagenesis in model and crop plants using the CRISPR/Cas system, Plant Methods, 2013, pp. 39-48, vol. 9.
Nannan Chang et al., Genome editing with RNA-guided Cas9 nuclease in Zebrafish embryos, Cell Research, 2013, pp. 465-472, vol. 23.
Seung Woo Cho et al., Targeted genome engineering in human cells with the Cas9 RNA-guided endonuclease, Nature Biotechnology, Mar. 2013, pp. 230-232, vol. 31, No. 3.
Krzysztof Chylinski et al., The tracrRNA and Cas9 families of type II CRISPR-Cas immunity systems, RNA Biology, May 2013, pp. 726-737, vol. 10, No. 10.
Le Cong et al., Multiplex Genome Engineering Using CRISPR/Cas Systems, Sciencexpress Reports, Jan. 3, 2013, pp. 1-7, vol. 1.
Elitza Deltcheva et al., CRISPR RNA maturation by trans-encoded small RNA and host factor RNase III, Nature, Mar. 31, 2011, pp. 602-607, vol. 471.
Kathleen D'Halluin et al., Targeted molecular trait stacking in cotton through targeted double-strand break induction, Plant Biotechnology Journal, pp. 933-941, vol. 11.
James E. Dicarlo et al., Genome engineering in *Saccharomyces cerevisiae* using CRISPR-Cas systems, Nucleic Acids Research, Mar. 4, 2013, pp. 4336-4343, vol. 41, No. 7.
Zhengyan Feng et al., Efficient genome editing in plants using a CRISPR/Cas system, Cell Research, 2013, pp. 1229-1232, vol. 23.
Yanfang Fu et al., Improving CRISPR-Cas nuclease specificity using truncated guide RNAs, Nature Biotechnology, Mar. 2014, vol. 32, No. 3.
Todd Funke et al., Structural Basis of Glyphosate Resistance Resulting from the Double Mutation Thr$^{97}$ lle and Pro$^{101}$ Ser in 5-Enolpyruvylshikimate-e-phosphate Synthase from *Escherichia coli*, Journal of Biological Chemistry, Apr. 10, 2009, pp. 9864-9860, vol. 284, No. 15.
Thomas Gaj et al., ZFN, Talen and CRISPR/Cas-based methods for genome engineering, Trends Biotechnology, Jul. 2013, pp. 397-405, vol. 31(7).
Josiane E. Garneau et al., The CRISPR/Cas bacterial immune system cleaves bacteriophase and plasmid DNA, Nature, 2010, pp. 67-71, vol. 468.
Giedrius Gasiunas et al., Cas9-crRNA ribonucleoprotein complex mediates specific DNA cleavage for adaptive immunity in bacteria, PNAS, Sep. 4, 2012, e2579-2586.
Luke A Gilbert et al., CRISPR-Mediated Modular RNA-Guided Regulation of Transcription in Eukaryotes, Cell, Jul. 18, 2013, pp. 442-451, vol. 154(2).
Scott J. Gratz et al., Genome Engineering of Drosophila with the CRISPR RNA-Guided Cas9 Nuclease, Aug. 2013, Genetics, pp. 1029-1035, vol. 194.
Daniel H. Haft et al., A Guild of 45 CRISPR-Associated (Cas) Protein Families and Multiple CRISPR/Cas Subtypes Exist in Prokaryotic Genomes, PLoS Computational Biology, Nov. 2005, pp. 474-483, vol. 1, Issue 6.
Caryn R. Hale et al. , RNA-Guided RNA Cleavage by a CRISPR RNA-Cas Protein Complex, Cell, Nov. 25, 2009, pp. 945-956, vol. 139.
Rachel E. Haurwitz et al., Sequence- and Structure-Specific RNA Processing by a CRISPR Endonuclease, Science, Sep. 10, 2010, pp. 1355-1358, vol. 329.
Philippe Horvath et al., Diversity, Activity, and Evolution of CRISPR Loci in *Streptococcus thermophilus*, Journal of Bacteriology, Feb. 2008, pp. 1401-1412, vol. 190, No. 4.
Philippe Horvath et al., CRISPR/Cas, the Immune System of Bacteria and Archaea, Science, Jan. 8, 2010, pp. 167-170, vol. 327.
Zhonggang Hou et al., Efficient genome engineering in human pluripotent stem cells using Cas9 from Neisseria meningitides, PNAS, Sep. 24, 2013, pp. 15644-15649, vol. 110, No. 39.
Patrick D. Hsu et al., DNA targeting specificity of RNA-guided Cas9 nucleases, Nature Biotechnology, Sep. 2013, pp. 827-834, vol. 31, No. 9.
Woong Y. Hwang et al., Efficient In Vivo Genome Editing Using RNA-Guided Nucleases, Nature Biotech, Mar. 2013, pp. 227-229, vol. 31, No. 3.

(56) References Cited

OTHER PUBLICATIONS

Kyle Jacoby et al., Expanding LAGLIDADG endonuclease scaffold diversity by rapidly surveying evolutionary sequence space, Nucleic Acids Research, Feb. 2012, pp. 4954-4964, vol. 40, No. 11.

Wenyan Jiang et al., RNA-guided editing of bacterial genomes using CRISPR-Cas systems, Nature Biotechnology, Mar. 2013, pp. 233, vol. 31, No. 3.

Martin Jinek et al., A Programmable Dual-RNA-Guided DNA Endonuclease in Adaptive Bacterial Immunity, Science, Aug. 17, 2012, pp. 816-821, vol. 337.

Martin Jinek et al., RNA-programmed genome editing in human cells, eLife, 2013, e00471, pp. 1-9.

Ross A. Johnson et al., A rapid assay to quantify the cleavage efficiency of custom-designed nucleases in planta, Plant Mol Biol, 2013, pp. 207-221, vol. 82.

Eugene V. Koonin et al., CRISPR-CAS Evolution of an RNA-based adaptive immunity system in prokaryotes, RNA Biology, May 2013, pp. 679-686, vol. 10:5.

Jian-Feng Li et al., Multiplex and homologous recombination-mediated genome editing in Arabidopsis and Nicotiana benthamiana using guide RNA and Cas9, Nature Biotechnology, Aug. 2013, pp. 688-691, vol. 31, No. 8.

Michael R. Lieber et al., The Mechanism of Double-Strand DNA Break Repair by the Nonhomologous DNA End Joining Pathway, Annu Rev Biochem, 2010, pp. 181-211, vol. 79.

Ming Ma et al., A Guide RNA Sequence Design Platform for the CRISPR/Cas9 System for Model Organism Genomes, BioMed Research International, 2013, 4 pages, Article ID 270805.

Morgan L. Maeder et al., CRISPR RNA-guided activation of endogenous human genes, Nature Methods, Oct. 2013, pp. 977-979, vol. 10, No. 10.

Kira S. Makarova et al., Evolution and classification of the CRISPR-Cas systems, Nat Rev Microbiol, Jun. 2011, pp. 467-477, vol. 9(6).

Prashant Mali et al., RNA-Guided Human Genome Engineering via Cas9, Sciencexpress, Feb. 15, 2013, pp. 823-826, vol. 15, 339(6121).

Yanfei Mao et al., Application of the CRISPR-Cas System for Efficient Genome Engineering in Plants, Molecular Plant, Nov. 2013, pp. 2008-2011, vol. 6, No. 6.

Luciano A. Marraffini et al., CRISPR Interference Limits Horizontal Gene Transfer in Staphylococci by Targeting DNA, Science, Dec. 19, 2008, pp. 1843-1845, vol. 322(5909).

Luciano A. Marraffini et al., CRISPR interference: RNA-directed adaptive immunity in bacteria and archaea, Nat Rev Genet, Mar. 2010, pp. 181-190, vol. 11(3).

Jin Miao et al., Targeted mutagenesis in rice using CRISPR-Cas System, Cell Research, 2013, pp. 1233-1236, vol. 23.

Jeffrey C. Miller et al., A Tale nuclease architecture for efficient genome editing, Nature Biotechnology, Feb. 2011, pp. 143-148, vol. 29.

F. J. Mojica et al., Biological significance of a family of regularly spaced repeats in the genomes of Archaea, Bacteria and mitochondria, Molecular Microbiology, May 2000, pp. 244-246, vol. 36.

Vladimir Nekrasov et al., Targeted mutagenesis in the model plant Nicotiana benthamiana using Cas9 RNA-guided endonuclease, Nature Biotechnology, pp. 691-693, vol. 31, No. 8.

Nancy Podevin et al., Site-directed nucleases: a paradigm shift in predictable, knowledge-based plant breeding, Trends in Biotechnology, Jun. 2013, pp. 375-383, vol. 31, No. 6.

Lei S. Qi et al., Repurposing CRISPR as an RNA-Guided Platform for Sequence-Specific Control of Gene Expression, Cell, Feb. 28, 2013, pp. 1173-1183, vol. 152(5).

Sivaprakash Ramalingam et al., A CRISPR way to engineer the human genome, Genome Biology, 2013, 4 pages, vol. 14:107.

Paul D. Sadowski, Site-specific genetic recombination: hops, flips, and flops, FASEB, 1993, pp. 760-767, vol. 7.

Neville E. Sanjana et al., A Transcription Activator-Like Effector (TALE) Toolbox for Genome Engineering, Nat. Protoc, 2012, pp. 171-192, vol. 7(1).

Rimantas Sapranauskas et al., The *Streptococcus thermophilus* CRISPR/Cas system provides immunity in *Escherichia coli* Nucleic Acids Research, Aug. 2011, pp. 9275-9282, vol. 39, No. 21.

Brian Sauer, Site-specific recombination: developments and applications, Current Opinion in Biotechnology, 1994, pp. 521-527, vol. 5.

Qiwei Shan et al., Targeted genome modification of crop plants using a CRISPR-Cas system, Nature Biotechnology, Aug. 2013, pp. 686-688, vol. 31, No. 8.

Bin Shen et al., Generation of gene-modified mice via Cas9/RNA-mediated gene targeting, Cell Research, May 2013, pp. 720-723, vol. 23, No. 5.

Bruno Tinland et al., The T-DNA-linked VirD2 protein contains two distinct functional nuclear localization signals, Proc. Natl. Acad. Sci, Aug. 1992, pp. 7442-7446, vol. 89.

John Van Der Oost, New Tool for Genome Surgery, Science, Feb. 15, 2013, pp. 768-770, vol. 339.

Daniel F. Voytas, Plant Genome Engineering with Sequence-Specific Nucleases, Annual Review of Plant Biology, pp. 327-350, vol. 64.

Jianbin Wang et al., Targeted gene addition to a predetermined site in the human genome using a ZFN-based nicking enzyme, Genome Research, 2012, pp. 1316-1326.

Haoyi Wang et al., One-Step Generation of Mice Carrying Mutations in Multiple Genes by CRISPR/Cas-Mediated Genome Engineering, Cell, May 9, 2013, pp. 910-918, vol. 153(4).

Blake Wiedenheft et al., RNA-guided genetic silencing systems in bacteria and archaea, Nature, Feb. 16, 2012, pp. 331-338, vol. 482.

Kabin Xie et al., RNA-Guided Genome Editing in Plants Using a CRISPR-Cas System, Nov. 2013, Molecular Plant, pp. 1975-1983, vol. 6, No. 6.

Peter R. Beetham, A tool for functional plant genomics: Chimeric RNA/DNA oligonucleotides cause in vivo gene-specific mutations, Proc. Natl., Acad. Sci USA, Plant Biology, Jul. 1999, pp. 8774-8778, vol. 96.

Prashant Mali et al., CAS9 transcriptional activators for target specificity screening and paired nickases for cooperative genome engineering, Nat. Biotechnol., Sep. 2013, pp. 833-838, vol. 31(9).

International Search Report and Written Opinion—PCT/US2014/051778—mailed Dec. 3, 2014.

International Search Report and Written Opinion—PCT/US2014/051780—mailed Dec. 9, 2014.

Xu R., et al., "Gene Targeting Using the Agrobacterium Tumefaciens-Mediated CRISPR-Cas System in Rice," Rice, May 2014, vol. 7, No. 1, pp. 1-4.

Abler M.L., et al., "Control of mRNA Stability in Higher Plants," Plant Molecular Biology, 1996, vol. 32, pp. 63-78.

Ainley W.M., et al., "Trait Stacking via Targeted Genome Editing," Plant Biotechnology Journal, Aug. 19, 2013, vol. 11, No. 9, pp. 1126-1134, DOI:10.1111/pbi.12107, ISSN 1467-7644, XP055218224.

Ali Z., et al., "Efficient Virus-Mediated Genome Editing in Plants using the CRISPR/Cas9 system," Molecular Plant, Aug. 2015, vol. 8, pp. 1288-1291.

Anders C., et al., "Structural Basis of PAM-Dependent Target DNA Recognition by the Cas9 Endonuclease," Nature, Sep. 25, 2014, vol. 513, pp. 569-573.

Anonymous, "CRISPR-Cas9 Genome Engineering with Dharmacon Tm Edit-RTM Inducible Lentiviral Cas9 Nuclease," Horizon technical manual, Apr. 2014, pp. 1-18, XP055967783.

Anonymous: "Hypothetical Protein [Lactobacillus reuteri]: NCBI Reference Sequence: WP_019251774.1," Ncbi Protein, Jun. 29, 2013, 1 Page, XP055291687, [Retrieved on Jul. 27, 2016] Retrieved from URL: http://www.ncbi.nlm.nih.gov/protein/518081566?sat=21&satkey=43236412.

Anonymous: "Lactobacillus Reuteri TD1, Complete Genome, NCBI Reference Sequence: NC_021872.1," NCBI Nucleotide, Feb. 8, 2015, 592 Pages, XP055291935, [Retrieved on Jul. 28, 2016] Retrieved from URL: http://www.ncbi.nlm.nih.gov/nuccore/526230725?report=gb&sat=21&satkey=30378633.

Application Forum: "A Streamlined Method for the Production, Screening, and Application of sgRNAs for CRISPR/Cas9 Gene Editing," Sponsored Paper, BioTechniques, 2014, vol. 57, No. 3, p. 157.

(56) References Cited

OTHER PUBLICATIONS

Avila-Garcia W.V., et al., "Target site Mutation Associated with Glufosinate resistance in Italian Ryegrass (*Lolium perenne* L. ssp. Multiflorum)," Pest Management Science, Sep. 1, 2012, vol. 68, No. 9, pp. 1248-1254, DOI:10.1002/ps.3286, ISSN 1526498X, XP055978022.
Bae S., et al., "Cas-OFFinder: A Fast and Versatile Algorithm that Searches for Potential Off-Target sites of Cas9 RNA-Guided Endonucleases," Bioinformatics, 2014, vol. 30, No. 10, pp. 1473-1475.
Baltes N.J., et al., "DNA Replicons for Plant Genome Engineering," The Plant Cell, Jan. 2014, vol. 26, No. 1, pp. 151-163.
Barrangou R., et al., "CRISPR-Cas Systems: Prokaryotes Upgrade to Adaptive Immunity," Molecular Cell, Apr. 24, 2014, vol. 54, pp. 234-244.
Barrett C.M., et al., "Unlocking Access to DNA in Chromatin," Chemical Engineering Progress, Sep. 2018, vol. 114, No. 9, pp. 55-62.
Begemann M.B., et al., "Precise Insertion and Guided Editing of Higher Plant Genomes using Cpf1 CRISPR Nucleases," BioRxiv, 2017, 16 Pages, DOI: http://dx.doi.orgi/10.1101/109983.
Beurdeley M., et al., "Compact Designer TALENs for Efficient Genome Engineering," Nature Communications, Apr. 23, 2013, vol. 4, No. 1762, pp. 1-8.
Bollen Y., et al.: "How to Create State-of-The-Art Genetic Model Systems: Strategies for Optimal CRISPR-Mediated Genome Editing," Nucleic Acids Research, 2018, vol. 46, No., 13, pp. 6435-6454.
Bolotin A., et al., "Clustered Regularly Interspaced Short Palindrome Repeats (CRISPRs) have Spacers of Extrachromosomal Origin," Microbiology, Accepted on May 30, 2005, vol. 151, pp. 2551-2561.
Bolotin A., et al., "Complete Sequence and Comparative Genome Analysis of the Dairy Bacterium *Streptococcus thermophilus*," Nature Biotechnology, Dec. 2004, vol. 22, No. 12, pp. 1554-1558, 6 Pages.
Bondy-Denomy J., et al., "To Acquire or Resist: the Complex Biological Effects of CRISPR-Cas Systems," Trends in Microbiology, Epub Feb. 26, 2014, Apr. 2014, vol. 22, No. 4, pp. 218-225.
Bortesi L., et al., "The CRISPR/Cas9 System for Plant Genome Editing and Beyond," Biotechnology Advances, Jan. 1, 2015, vol. 33, No. 1, pp. 41-52, XP055217852.
Brief for Appellees for Appeal No. 2017-1907 submitted to the United States Court of Appeals for the Federal Circuit on Oct. 25, 2017, 80 pages.
Briner A.E., et al., "Guide RNA Functional Modules Direct Cas9 Activity and Orthogonality," Molecular Cell, Oct. 23, 2014, vol. 56, No. 2, 16, pp. 333-339, 17 Pages, Supplemental Information.
Briner A.E., et al., "Guide RNA Functional Modules Direct Cas9 Activity and Orthogonality," Molecular Cell, Oct. 23, 2014, vol. 56, No. 2, pp. 333-339.
Burstein D., et al., "New CRISPR-Cas Systems from Uncultivated Microbes," Nature, Feb. 9, 2017, vol. 542, pp. 237-241 (plus supplementary material).
Byrum J.R., et al., "N_Geneseq Database," Accession No. ARD65600, US 20070083945, Apr. 12, 2007, SEQ ID No. 147296.
Carte J., et al., "Cas6 is an Endoribonuclease that Generates Guide RNAs for Invader Defense in Prokaryotes," Genes and Development, 2008, vol. 22, pp. 3489-3496.
Cenik E.S., et al., "Argonaute Proteins," Current Biology, 2011, vol. 21, No. 12, pp. R446-R449.
Cermak T., et al., "A Multipurpose Toolkit to Enable Advanced Genome Engineering in Plants," The Plant Cell, Jun. 2017, vol. 29, pp. 1196-1217.
Chai R., et al., "B-Glucan Synthase Gene Overexpression and B-glucans Overproduction in Pleurotus Ostreatus Using Poromoter Swapping," PLoS One, Apr. 24, 2013, vol. 8, Issue 4, e61693.
Chang Y-J., et al., "Complete Genome Sequence of Acidaminococcus Fermentans Type Strain (VR4T)," Standards in Genomic Sciences, 2010, vol. 3, pp. 1-14.
Chen H., et al., "Promise and Issues of Genetically Modified Crops," Current Opinion in Plant Biology, May 1, 2013, vol. 16, No. 2, pp. 255-260, DOI:10.1016/j.pbi.2013.03.007, ISSN 1369-5266, XP055070912.
Chen J.S., et al., "CRISPR-Cas12a Target Binding Unleashes Indiscriminate Single-Stranded DNase Activity," Science, Apr. 27, 2018, vol. 360, pp. 436-439.
Chen S., et al., "Highly Efficient Mouse Genome Editing by CRISPR Ribonucleoprotein Electroporation of Zygotes," The Journal of Biological Chemistry, US, Jul. 8, 2016, vol. 291, No. 28, pp. 14457-14467, DOI:10.1074/jbc.M116.733154, ISSN 0021-9258, XP055363781.
Cheng A.W., et al., "Multiplexed Activation of Endogenous Genes by CRISPR-on, an RNA-Guided Transcriptional Activator System," Cell Research, Oct. 2013, vol. 23, No. 10, pp. 1163-1171.
Cho S.W., et al., "Analysis of Off-Target Effects of CRISPR/Cas-Derived RNA-Guided Endonucleases and Nickases," Genome Research, 2014, vol. 24, pp. 132-141.
Christou P., et al., "Stable Transformation of Soybean Callus by DNA-Coated Gold Particles," Plant Physiology, 1988, vol. 87, pp. 671-674.
Chylinski K., et al., "Classification and Evolution of Type II CRISPR-Cas Systems," Nucleic Acids Research, Published on Apr. 11, 2014, vol. 42, No. 10, pp. 6091-6105.
Claesson M.J., et al., "Multireplicon Genome Architecture of Lactobacillus Salivarius," Proceedings of the National Academy of Sciences, Apr. 25, 2006, vol. 103 No. 17, pp. 6718-6723.
Communication of a Notice of European Opposition & Opponents Submissions for European Application No. 14761478.8, Ref No. 417331 EPAXB/CX, dated Oct. 24, 2022, 31 Pages.
Database: "Cas9-CRISPR-Associated Endonuclease CAs9, Bacillus Cereus VD131—Cas9 Gene & Protein", UniProt Database Entry: R8LDU5, Apr. 15, 2019, 3 Pages.
Database: "CRISPR-Associated Endonuclease Cas9, Lactobacillus Salivarius (Strain UCC118): Q1WVK1_LACS1", UniProt, May 2, 2006, 2 Pages.
Database ENA: "Brevibacillus Laterosporus GI-9 Hnh Endonuclease Family Protein," Database Accession No. CCF15452, 2012, XP002788584, Retrieved from EBI.
Database: "Using Cpf1 for CRISPR," Benchling, Jan. 1, 2015, 4 Pages, Retrieved from URL: https://benchling.com/pub/cpf1, XP55396832.
Decision of EP Opposition Decision for EP3036327, Feb. 2020, 8 Pages.
Deyle D.R., et al., "Adeno-Associated Virus Vector Integration," Current Opinion in Molecular Therapeutics, Aug. 2009, vol. 11, No. 4, pp. 442-447.
Djukanovic V., et al.,"Male-Sterile Maize Plants Produced by Targeted Mutagenesis of the Cytochrome P450-like Gene (MS26) Using a Re-Designed I-CreI Homing Endonuclease," The Plant Journal, Nov. 5, 2013, vol. 76, No. 5, pp. 888-899.
Djukic M., et al., "Genome Seqence of Brevibacillus Laterosporus LMG 15441, a Pathogen of Invertebrates, "Journal of Bacteriology, American Society for Micorbiology, US, Oct. 2011, vol. 193, No. 19, pp. 5535-5536.
Dong D., et al., "The Crystal Structure of Cpf1 in complex with Crispr Rna," Nature, 2016, 16 pages, doi:10.1038/nature17944.
Dong O.X., et al., "Targeted DNA Insertion in Plants," The Proceedings of the National Academy of Sciences, Apr. 30, 2021, vol. 118 No. 22, e2004834117, 9 Pages.
Doudna J.A., et al., "The New Frontier of Genome Engineering with CRISPR-Cas9," Science, Nov. 24, 2014, vol. 346, No. 6213, 11 Pages.
Dow L.E., et al., "Inducible in Vivo Genome Editing with CRISPR-Cas9," Nature Biotechnology, Apr. 2005, vol. 33, No. 4, pp. 390-394, EPublished on Feb. 18, 2015.
Ellegaard K.M., et al., "Extensive Intra-phylotype Diversity in Lactobacilli and Bifidobacteria from the Honeybee Gut," BMC Genomics, Apr. 2015, vol. 16, No. 1, Article No. 284, 22 pages.
Endo A., et al., "Efficient Targeted Mutagenesis of Rice and Tobacco Genomes Using Cpf1 From Francisella Novicida," Nature Scientific Reports, 2016, vol. 6, 38169, 9 pages.

(56) References Cited

OTHER PUBLICATIONS

Endo M., et al., "Toward Establishing an Efficient and Versatile Gene Targeting System in Higher Plants," Biocatalysis and Agricultural Biotechnology, 2014, vol. 3, pp. 2-6.
EP Opposition EP3036327, Cited Documents List, 1 Page.
EP Opposition Response EP3036327.
EP Summons to Oral Proceedings EP3036327, Nov. 9, 2020, 12 Pages.
Esvelt K.M., et al., "Orthogonal Cas9 Proteins for RNA-guided Gene Regulation and Editing," Nature Methods, Sep. 29, 2013, vol. 10, No. 11, pp. 1116-1121.
Esvelt K.M., "Genome-Scale Engineering for Systems and Synthetic Biology," Molecular System Biology, Jan. 22, 2013, vol. 9, No. 641, pp. 1-17, XP055339996.
Extended European Search Report for European Application No. 18209296.5, mailed Feb. 12, 2019, 8 pages.
Extended European Search Report for European Application No. 19199945.7, mailed Jan. 14, 2020, 6 pages.
Fagerlund R.D., et al., "The Cpf1 CRISPR-Cas Protein Expands Genome-Editing tools," Genome Biology, 2015, vol. 16, pp. 251-253.
Fichtner F., et al., "Precision Genetic Modifications: a New Era in Molecular Biology and Crop Improvement," Planta, 2014, vol. 239, pp. 921-939.
Florez S.L., et al., "Enhanced Somatic Embryogenesis in Theobroma Cacao using the Homologous Baby Boom Transcription factor," BMC Plant Biology, 2015, vol. 15, No. 121, 13 pages.
Fonfara I., et al., "The CRISPR-Associated DNA-Cleaving Enzyme Cpf1 also Processes Precursor CRISPR RNA," Nature, Published: Apr. 20, 2016, Issue Date: Apr. 28, 2016, vol. 532, pp. 517-521, 19 pages.
Fraley R.T., et al., "Expression of Bacterial Genes in Plant Cells," Proceedings of the National Academy of Sciences of the United States of America, Aug. 1983, vol. 80, pp. 4803-4807.
Fujita J., et al., "The Point Mutation in the Promoter Region and the Single Nucleotide Polymorphism in Exon 1 of the Cytokeratin 19 Gene in Human Lung Cancer Cell Lines," Lung Cancer, Dec. 2001, vol. 34, No. 3, pp. 387-394.
Gabriel R., et al., "An Unbiased Genome-Wide Analysis of Zinc-Finger Nuclease Specificity," Nature Biotechnology, Sep. 2011, vol. 29, No. 9, pp. 816-823.
Ganal W.M., et al.; "A Large Maize (*Zea mays* L.) SNP Genotyping Array: Development and Germplasm Genotyping and Genetic Mapping to Compare with the B73 Reference Genome," PLOS One, Dec. 2011, vol. 6, Issue 12(e28334), 15 Pages.
Gao F., et al., "DNA-Guided Genome Editing Using the Natronobacterium Gregoryi Argonaute," Nature Biotechnology, Published on May 2, 2016, DOI:10.1038/nbt.3547, 7 Pages.
Gao H., et al., "Heritable Targeted Mutagenesis in Maize using a Designed Endonuclease," The Plant Journal, Epub Oct. 7, 2009, Jan. 2010, vol. 61 (1) pp. 176-187.
Gardlik R., et al., "Vectors and Delivery Systems in Gene Therapy," Medical Science Monitor, 2005, vol. 11, No. 4, pp. RA110-RA121, 13 Pages.
Garside E.L., et al., "Cas5d Processes Pre-crRNA and is a Member of a Larger Family of CRISPR RNA Endonucleases," RNA, 2012, vol. 18, No. 11, pp. 2020-2028.
Gil-Humanes J., et al., High-Efficiency Gene Targeting in Hexapioid Wheat Using DNA Replicons and CRISPR/Cas9, Plant Journal, Mar. 2017, vol. 89, No. 6, pp. 1251-1262.
Gilles A.F., et al., "Efficient CRISPR-mediated Gene Targeting and Transgene Replacement in the Beetle Tribolium Castaneum," The Company of Biologists Limited, Development, 2015, vol. 142, pp. 2832-2839.
Glenn T.C., et al., "Field Guide to Next-Generation DNA sequencers," Molecular Ecology Resources, 2011, vol. 11, pp. 759-769.
Gong S., et al., "DNA Unwinding is the Primary Determinant of CRISPR-Cas9 Activity," Cell Reports, Jan. 9, 2018, vol. 22, Issue 9, pp. 359-371.

Grissa I., et al., "CRISPRFinder: A Web Tool To Identify Clustered Regularly Interspaced Short Palindromic Repeats," Nucleic Acids Research, Information Retrieval Ltd, GB, Jul. 2007, vol. 35, pp. W52-W57, Epublished on May 30, 2007.
Guilinger J.P., et al., "Fusion of Catalytically Inactive Cas9 to FokI Nuclease Improves the Specificity of Genome Modification," Nature Biotechnology, Jun. 2014, vol. 32, No. 6, pp. 577-583.
Guilinger P., et al., "Broad Specificity Profiling of Talens Results In Engineered Nucleases With Improved DNA-Cleavage Specificity," Nature Methods, Apr. 2014, vol. 11, No. 4, pp. 429-435, (Published online on Feb. 16, 2014).
Habben J.E., et al., "Transgenic Alteration of Ethylene Biosynthesis Increases Grain Yield in Maize Under Field Drought-Stress Conditions," Plant Biotechnology Journal, 2014, vol. 12, pp. 685-693.
Haberer G., et al., "Structure and Architecture of the Maize Genome," Plant Physiology, Dec. 2005, vol. 139, pp. 1612-1624.
Harrington L.B., et al., "Programmed DNA Destruction by Miniature CRISPR-Cas14 Enzymes," Science, Nov. 16, 2018, vol. 362, pp. 839-842.
Heler R., et al., "Cas9 Specifies Functional Viral Targets During CRISPR-Cas Adaptation," Nature, Mar. 12, 2015, vol. 519, pp. 199-202, 16 Pages.
Hicks G.R., "Nuclear Import of Plant Proteins," Madame Curie Bioscience Database, Austin (TX), 2000-2013, pp. 61-82, Retrieved from URL: https://www.ncbi.nlm.nih.gov/books/NBK6124, XP055967787.
Hinchee M.A.W., et al., "Production of Transgenic Soybean Plants Using Agrobacterium- mediated DNA Transfer," Bio/Technology, Aug. 1988, vol. 6, pp. 915-922, DOI:10.1038/nbt0888-915, XP002045224.
Hink M.A., et al., "Structural Dynamics of Green Fluorescent Protein Alone and Fused with a Single Chain Fv Protein," The Journal of Biological Chemistry, Jun. 9, 2000, vol. 275, No. 23, pp. 17556-17560.
Hochstrasser M.L., et al., "Cutting it Close: CRISPR-Associated Endoribonuclease Structure and Function," Trends in Biochemical Sciences, Jan. 2014, vol. 40, No. 1, pp. 58-66.
Houdebine L-M., "The Methods to Generate Transgenic Animals and to Control Transgene Expression," Journal of Biotechnology, 2002, vol. 98, pp. 145-160.
Hsu P.D., et al., "Development and Applications of CRISPR-Cas9 for Genome Engineering," Cell, Jun. 5, 2014, vol. 157, pp. 1262-1278.
Huang T.P., et al., "Circularly Permuted and PAM-modified Cas9 Variants Broaden the Targeting Scope of Base Editors," Nature Biotechnology, Jun. 2019, vol. 37, pp. 626-631, 9 Pages.
Husaini A.M., et al., "Vehicles and ways for Efficient Nuclear Transformation in Plants," GMCrops, 2010, vol. 1, No. 5, pp. 276-287.
Hyun Y., et al., "Site-directed Mutagenesis in *Arabidopsis thaliana* Using Dividing Tissue-Targeted RGEN of the CRISPR/Cas System to Generate Heritable Null Alleles," Planta, Jan. 2015, vol. 241, No. 1, pp. 271-284.
International Preliminary Report on Patentability for International Application No. PCT/US2014/051778, mailed Mar. 3, 2016, 8 pages.
International Preliminary Report on Patentability for International Application No. PCT/US2014/051780, mailed Mar. 3, 2016, 9 pages.
International Preliminary Report on Patentability for International Application No. PCT/US2014/051781, mailed Mar. 3, 2016, 8 pages.
International Preliminary Report on Patentability for International Application No. PCT/US2014/051782, mailed Mar. 3, 2016, 6 pages.
International Preliminary Report on Patentability for International Application No. PCT/US2015/040143, mailed Jan. 26, 2017, 14 pages.
International Search Report and Written Opinion for International Application No. PCT/US2014/051781, mailed Dec. 3, 2014, 12 pages.

(56) References Cited

OTHER PUBLICATIONS

International Search Report and Written Opinion for International Application No. PCT/US2014/051782, mailed Dec. 3, 2014, 10 pages.
International Search Report and Written Opinion for International Application No. PCT/US2015/040143, mailed Oct. 28, 2015, 17 pages.
Jacobs T.B., et al., "Targeted Genome Modifications in Soybean with CRISPR/Cas9," BMC Biotechnology, Mar. 2015, vol. 15, No. 16, 10 pages.
Jiang W., et al., "CRISPR-Cas: New Tools for Genetic Manipulations of Bacterial Immunity Systems," Annual Review of Microbiology, vol. 69, No. 1, Jul. 22, 2015, pp. 209-228.
Jiang W., et al., "Demonstration of CRISPR/Cas9/sgRNA-Mediated Targeted Gene Modification in Arabidopsis, Tobacco, Sorghum and Rice," Nucleic Acids Research, Published Online Sep. 2, 2013, Nov. 1, 2013, vol. 41, No. 20, 12 pages, Oxford University Press, GB, doi:10.1093/nar/gkt780, ISSN 0305-1048, XP055219328.
Jiang W., et al., "Efficient CRISPR/Case9-Mediated Gene Editing in *Arabidopsis thaliana* and Inheritance of Modified Genes in the T2 and T3 Generations," PLOS ONE, Jun. 11, 2014, vol. 9, No. 6(e99225), pp. 1-10.
Jore M.M., et al., "Structural Basis for CRISPR RNA-guided DNA Recognition by Cascade," Nature Structural & Molecular Biology, May 2011, vol. 18, No. 5, pp. 529-537 (and Supplemental).
Jung J.H., et al., "Challenges in Wide Implementation of Genome Editing for Crop Improvement," Journal of Crop Science and Biotechnology, 2017, vol. 20, No. 2, pp. 129-135.
Kallimasioti-Pazi E.M., et al., "Heterochromatin Delays CRISPR-Cas9 Mutagenesis but does not Influence the Outcome of Mutagenic DNA Repair," PLOS Biology, Accepted: Nov. 21, 2018, Published: Dec. 12, 2018, vol. 16, No. 12, e2005595, 22 pages.
Kanchiswamy C.N., et al., "Non-GMO Genetically Edited Crop Plants," Trends in Biotechnology, Sep. 2015, vol. 33, No. 9, pp. 489-491, Doi: 10.1016/J.TIBTECH.2015.04.002, XP002765281.
Kartje, et al., "Chimeric Guides Probe and Enhance Cas9 Biochemical Activity," Biochemistry, 2018, vol. 57, No. 21, pp. 3027-3031.
Karvelis T., et al., "PAM Recognition by Miniature CRISPR-Cas14 Triggers Programmable Double-Stranded DNA Cleavage," bioRxiv, May 30, 2019, 10 Pages, DOI: http://dx.doi.org./10.101/654897.
Karvelis T., et al., "Rapid Characterization of CRISPR-Cas9 Protospacer Adjacent Motif Sequence Elements," Genome Biology, Nov. 19, 2015, vol. 16, No. 253, 13 Pages, DOI:10.1186/s13059-015-0818-7, XP055293242.
Keeler S.J., et al., "Regulation of Tobacco Acetolactate Synthase Gene Expression," Plant Physiology, Rockville, MD, USA, Jul. 1, 1993, vol. 102, No. 3, pp. 1009, 1018, DOI:10.1104/p. 102.3.1009, ISSN 00320889, XP055978016.
Kim G.B., et al., "Isolation and Characterization of Medicago Truncatula U6 Promoters for the Construction of Small Hairpin RNA-Mediated Gene Silencing Vectors," Plant Molecular Biology Reporter, Jun. 2014, 2013, vol. 31, No. 3, pp. 581-593.
Kim H., et al., "CRISPR/Cpf1-Mediated DNA-Free Plant Genome Editing," Nature Communications, Published Feb. 16, 2017, vol. 8, No. 14406, DOI: 10.1038/ncomms14406.
Kim H., et al., "Targeted Genome Editing for Crop Improvement, Plant Breeding And Biotechnology," Dec. 30, 2015, vol. 3, No. 4, pp. 283-290, (Published on Nov. 30, 2015).
Kim H.Y., et al., "Chimeric crRNAs with 19 DNA Residues in the Guide Region Show the Retained DNA Cleavage Activity of Cas9 with Potential to Improve the Specificity," Chemical Communications, Feb. 28, 2019, vol. 55, pp. 3552-3555.
Kim S., et al., "Highly Efficient RNA-Guided Genome Editing in Human Cells Via Delivery of Purified Cas9 Ribonucleoproteins," Genome Research, Apr. 2, 2014, vol. 24, pp. 1012-1019.
Kindle K.L., et al., "High-frequency Nuclear Transformation of Chlamydomonas Reinhardtii," Proceedings of the National Academy of Sciences of the United States of America, Feb. 1990, vol. 87, pp. 1228-1232.

Kocak D.D., et al., "Increasing the Specificity of CRISPR Systems with Engineered RNA Secondary Structures," Nature Biotechnology, Jun. 2019, vol. 37, pp. 657-666.
Kohli A., et al., "Transgene Organization in Rice Engineered Through Direct DNA Transfer Supports a Two-Phase Integration Mechanism Mediated by the Establishment of Integration Hot Spots," The Proceedings of the National Academy of Sciences, 1998, vol. 95, pp. 7203-7208.
Koo T., et al., "Measuring and Reducing Off-Target Activities of Programmable Nucleases Including CRISPR-Cas9," Molecules and Cells, 2015, vol. 38, No. 6, pp. 475-481.
Koonin E.V., et al., "Diversity, Classification and Evolution of CRISPR-Cas Systems," Current Opinion in Microbiology, 2017, vol. 37, pp. 67-78.
Kregten, et al., "Agrobacterium-Mediated T—DNA Transfer and Integration by Minimal VirD2 Consisting of the Relaxase Domain and a Type IV Secretion System Translocation Signal," Molecular Plant-Microbe Interactions, 2009, vol. 22, No. 11, pp. 1356-1365.
Kumar V., et al., "The CRISPR_Cas System for Plant Genome Editing: Advances and Opportunities," Journal of Experimental Botany, 2015, vol. 66, No. 1, pp. 47-57, Advance Access Publication Nov. 4, 2014.
Kuscu C., et al., "Genome-Wide Analysis Reveals Characteristics of Off-Target Sites Bound by the Cas9 Endonuclease," Nature Biotechnology, Jul. 2014, vol. 32, No. 7, pp. 677-683, (Published Online on May 18, 2014).
Leblanc C., et al., "Increased Efficiency of Targeted Mutagenesis by CRISPR/Cas9 in Plants Using Heat Stress," The Plant Journal, 2018, vol. 93, pp. 377-386, (Published online on Nov. 21, 2017).
Lee C.M., et al., "Nuclease Target Site Selection for Maximizing on-Target Activity and Minimizing Off-Target Effects in Genome Editing," Molecular Therapy: The Journal of the American Society of Gene Therapy, Mar. 1, 2016, vol. 24, No. 3, pp. 475-487.
Leenay R.T., et al., "Identifying and Visualizing Functional PAM Diversity across CRISPR-Cas Systems," Molecular Cell, Cell Press, Cambridge, MA, US, Apr. 7, 2016, vol. 62, No. 1, pp. 137-147 and Supplemental, Epublished on Mar. 31, 2016.
Leonard M.T., et al., "Complete Genome Sequences of Lactobacillus Johnsonii Strain N6.2 and Lactobacillus Reuteri Strain TD1," Genome Announcements, May 8, 2014, vol. 2, No. 3(e00397-14), 2 Pages, DOI:10.1128/genomeA.00397-14, XP055292032.
Li H., et al., "In Vivo Genome Editing Restores Haemostasis in a Mouse Model of Haemophilia," Nature, Jul. 14, 2011, vol. 475, No. 7355, pp. 217-221, 07 Pages.
Li J-F., et al., "Multiplex and Homologous Recombination-Mediated Plant Genome Editing in Arabidopsis and Nicotiana Benthamiana using Guide RNA and Cas9," Nature Biotechnology, Aug. 2013, vol. 31, No. 8(Supplemental), pp. 688-691, 15 Pages.
Li S., et al., "Synthesis-Dependent Repair of Cpf1-Induced Double Strand DNA Breaks Enables Targeted Gene Replacement in Rice," Journal of Experimental Botany, Jun. 28, 2018, vol. 69, No. 20, pp. 4715-4721.
Li X., et al., "Varied Transcriptional Efficiencies of Multiple Arabidopsis U6 Small Nuclear RNA Genes," Journal of Integrative Plant Biology, 2007, vol. 49, No. 2, pp. 222-229.
Li X-Q., "Comparative Analysis of the Base Compositions of the Pre-mRNA 3' Cleaved-Off Region and the mRNA 3' Untranslated Region Relative to the Genomic Base Composition in Animals and Plants," PLOS One, Jun. 18, 2014, vol. 9, Issue 6, e99928, 12 pages.
Li Z., et al., "Cas9-Guide RNA Directed Genome Editing in Soybean," Plant Physiology, Aug. 20, 2015, Oct. 2015, vol. 169, No. 2, pp. 960-970.
Li Z., et al., "Site-Specific Integration of Transgenes in Soybean via Recombinase-Mediated DNA Cassette Exchange," Plant Physiology, Nov. 1, 2009, vol. 151, No. 3, pp. 1087-1095.
Liang X., et al., "Rapid and Highly Efficient Mammalian Cell Engineering via Cas9 Protein Transfection," Journal of Biotechnology, May 21, 2015, vol. 208, pp. 44-53.
Liang Z., et al., "Efficient DNA-free Genome Editing of Bread Wheat Using CRISPR/Cas9 Ribonucleoprotein Complexes," Nature Communications, Jan. 18, 2017, vol. 8, No. 14261, 5 Pages.
Liang Z., et al., "Targeted Mutagenesis in Zea Mays using TALENs and the CRISPR/Cas System," Journal of Genetics and Genomics,

(56) References Cited

OTHER PUBLICATIONS

Elsevier, Bv, Nl, 2014, vol. 41, No. 2, pp. 63-68, (Published Online on Dec. 14, 2013), DOI: 10.1016/J.JGG.2013.12.001, ISSN 1673-8527, XP028661345.
Lin S., et al., "Enhanced Homology-directed Human Genome Engineering by Controlled Timing of CRISPR/Cas9 Delivery," ELIFE, Dec. 15, 2014, vol. 3, e04766, 32 pages.
Liu J., et al., "Nucleic Acid Molecules and Other Molecules Associated with Plants and Uses Thereof for Plant Improvement," US20040034888, Seq ID No. 17986, Sequence Alignment with Seq ID No. 9, Feb. 19, 2004, 1 Page.
Liu J-J., et al., "CasX Enzymes Comprise a Distinct Family of RNA-guided Genome Editors," Nature, Feb. 14, 2019, vol. 566, pp. 218-240 (Incl. Supplementary Material).
Luo S., et al., "Non-Transgenic Plant Genome Editing Using Purified Sequence-Specific Nucleases," Molecular Plant, Jun. 11, 2015, Sep. 2015, vol. 8, pp. 1425-1427.
Maier L-K., et al., "An Active Immune Defense with a Minimal CRISPR (Clustered Regularly Interspaced Short Palindromic Repeats) RNA and without the Cas6 Protein," The Journal of Biological Chemistry, Feb. 13, 2015, vol. 290, No. 7, pp. 4192-4201, 11 Pages.
Makarova K.S., et al., "An Updated Evolutionary Classification of CRISPR-Cas Systems," Nature Reviews Microbiology, Nov. 2015, vol. 13, 15 Pages, DOI: 10.1038/nrmicro3569.
Makarova K.S., et al., "The Basic Building Blocks and Evolution of CRISPR-CAS Systems," Biochemical Society Transactions, 2013, vol. 41, No. 6, pp. 1392-1400 (and Supplemental).
Malina A., et al., "Repurposing CRISPR/Cas9 for in Situ Functional Assays," Genes & Development, 2013, vol. 27, pp. 2602-2614 DOI:10.1101/gad.227132.113, XP055177303.
Mandal P.K., et al., "Efficient Ablation of Genes in Human Hematopoietic Stem and Effector Cells Using CRISPR/Cas9," Cell Stem Cell, Nov. 6, 2014, vol. 15, No. 5, pp. 643-652.
Martin-Ortigosa S., et al., "Mesoporous Silica Nanoparticle-Mediated Intracellular Cre Protein Delivery for Maize Genome Editing via loxP Site Excision 1'2[W][OPEN]," Plant Physiology, Feb. 2014, vol. 164, No. 2, pp. 537-547.
Martin-Ortigosa S., et al., "Proteolistics: A Biolistic Method for Intracellular Delivery of Proteins," Transgenic Resource, Oct. 2014, vol. 23, No. 5, pp. 743-756, DOI:10.1007/S11248-014-9807-Y, ISSN 0962-8819, XP035381272, (EPublished on Aug. 5, 2014).
Maruyama T., et al., "Corrigendum: Increasing the Efficiency of Precise Genome Editing with CRISPR-Cas9 by Inhibition of Non-homologous End Joining," Nature Biotechnology, May 2015, vol. 33, No. 5, pp. 538-542, 9 Pages.
Matsunaga T., et al., "Single-step Generation of Gene Knockout-Rescue System in Pluripotent Stem Cells by Promoter Insertion with CRISPR/Cas9," Biochemical and Biophysical Research Communications, 2014, vol. 444, pp. 158-163, DOI: 10.1016/j.bbrc.2014.01.037, XP028614859, (Published online on Jan. 22, 2014).
Miller W.A., et al., "The RNA World in Plants:Post-Transcriptional Control III," The Plant Cell, 2001, vol. 13, pp. 1710-1717.
Naito Y., et al., "CRISPRdirect: Software for Designing CRISPR/Cas Guide RNA with Reduced off-target Sites," Bioinformatics, 2015, vol. 31, No. 7, pp. 1120-1123, (Received, Revised, Accepted on 2014).
Nam K.H., et al., "Cas5d Protein Processes Pre-crRNA and Assembles into a Cascade-like Interference Complex in Subtype I-C/Dvulg CRISPR-Cas System," Structure, Sep. 5, 2012, vol. 20, pp. 1574-1584.
Natsume T., et al., "Hybridization Energies of Double Strands Composed of DNA, RNA, PNA and LNA," Chemical Physical Letters, 2007, vol. 434, pp. 133-138.
NCBI: "CRISPR-Associated Protein Cas9 [Prevotella Histicola JCM 15637 =DNF00424]," NCBIGenPept, Database Accession No. KGF29309, Jul. 9, 2014, 2 Pages. [Retrieved on 2019-06-09] Retrieved from the URL: https://www.ncbi.nlm.nih.gov/protein/690782330.
NCBI: "Type II CRISPR-RNA-Guided Endonuclease Cas9 [Enterococcus Faecalis]," Database RefSEQ NCBI, Database Accession No. WP_010710291.1, Oct. 7, 2015, 2 Pages.
NCBI: "Type II CRISPR-RNA-Guided Endonuclease Cas9 [Enterococcus Mundtii]," Database RefSEQ NCBI, Database Accession No. WP_023519017.1, Oct. 7, 2015, 2 Pages.
NCBI: "Type II CRISPR-RNA-Guided Endonuclease Cas9 [Flavobacterium chungangense]," Database RefSEQ NCBI, Database Accession No. WP_031455829.1, Oct. 7, 2015, 2 Pages.
NCBI: "Type II CRISPR-RNA-Guided Endonuclease Cas9 [Pseudomonas lini]," Database RefSEQ NCBI, Database Accession No. WP_048395223.1, Jul. 1, 2015, 2 Pages.
Nirenberg M., et al., "Historical Review: Deciphering the Genetic code—a Personal Account," Trends in Biochemical Sciences, 2003, Jan. 2004, vol. 29, No. 1, pp. 46-54.
Nishimasu H., et al., "Crystal Structure of Cas9 in Complex with Guide RNA and Target DNA," Cell, Elsevier, Amsterdam, NL, Feb. 13, 2014, vol. 156, No. 5, pp. 935-949, 23 Pages, (Accepted on Feb. 2, 2014), DOI: 10.1016/j.cell.2014.02.001, ISSN 0092-8674, S1-S8, XP055423859, (Includes Supplemental Information).
Nishimasu H., et al., "Structures and Mechanisms of CRISPR RNA-Guided Effector Nucleases," Current Opinion in Structural Biology, 2017, vol. 43, pp. 68-78.
O'Brien A., et al., "GT-Scan: Identifying Unique Genomic Targets," Bioinformatics, May 23, 2014, vol. 30, No. 18, pp. 2673-2675.
Oh J-H., et al., "CRISPR-Cas9-Assisted Recombineering in Lactobacillus Reuteri," Nucleic Acids Research, Sep. 29, 2014, vol. 42, No. 17(e131), pp. 1-4, 15 Pages, (and Supplemental), DOI:10.1093/nar/gku623, ISSN 0305-1048, XP055291625 and XP055190221, [Retrieved on Jul. 27, 2016] Retrieved from URL: http://nar.oxfordjournals.org/content/suppl/2014/07/29/gku623.DC1/nar-01438-met-h-2014-File007.pdf.
Opposition Notice for European Patent Application No. EP3036332, dated Mar. 2021.
Overbeek M.V., et al., "DNA Repair Profiling Reveals Nonrandom Outcomes at Cas9-Mediated Breaks," Molecular Cell, Elsevier, Amsterdam, NL, Aug. 18, 2016, vol. 63, No. 4, pp. 633-646, 15 Pages, Published Online Aug. 4, 2016, DOI: 10.1016/J.Molcel.2016.06.037, ISSN 1097-2765, XP029690136.
Ow D.W., "Recombinase-Mediated Gene Stacking as a Transformation Operating System," Journal of Integrative Plant Biology, 2011, vol. 53, No. 7, pp. 512-519.
P. Mali, Yang L., Esvelt K. M., Aach J., Guell M., Dicarlo J. E., Norville J. E., Church G. M., "Supplementary Materials for RNA Guided Human Genome Engineering via Cas9", Science, American Association for the Advancement of Science, US, US, (20130215), vol. 339, No. 6121, doi:10.1126/science.1232033, ISSN 00368075, pp. 1 36, XP055322657.
Pacher M., et al., "From Classical Mutagenesis to Nuclease-Based Breeding—Directing Natural DNA Repair for a Natural End-Product," The Plant Journal, Mar. 11, 2017, vol. 90, pp. 819-833, XP055650815.
Pattanayak V., et al., "High-Throughput Profiling of Off-Target DNA Cleavage Reveals RNA- Programmed Cas9 Nuclease Specificity," Nature Biotechnology, Published on Aug. 11, 2013, Sep. 2013, vol. 31, No. 9, pp. 839-843.
Paul J.W III., et al., "CRISPR/Cas9 for Plant Genome Editing: Accomplishments, Problems and Prospects," Plant Cell Reports, Springer International, DE, figure 4, Apr. 25, 2016, vol. 35, No. 7, pp. 1417-1427.
Peng N., et al., "A Synthetic Arabinose-Inducible Promoter Confers High Levels of Recombinant Protein Expression in Hyperthermophilic Archaean Sulfolobus Islandicus," Applied and Environmental Microbiology, Aug. 2012, vol. 78, No. 16, pp. 5630-5637.
Phillips A.J., "The Challenge of Gene Therapy and DNA Delivery," Journal of Pharmacy and Pharmacology, 2001, vol. 53, pp. 1169-1174.

SEQUENCE LISTING

```
Sequence total quantity: 567
SEQ ID NO: 1            moltype = DNA  length = 4107
FEATURE                 Location/Qualifiers
source                  1..4107
                        mol_type = unassigned DNA
                        organism = Streptococcus pyogenes
SEQUENCE: 1
atggataaga aatactcaat aggcttagat atcggcacaa atagcgtcgg atgggcggtg   60
atcactgatg aatataaggt tccgtctaaa aagttcaagg ttctgggaaa tacagaccgc  120
cacagtatca aaaaaatct tatagggct cttttatttg acagtggaga gacagcggaa   180
gcgactcgtc tcaaacggac agctcgtaga aggtatacac gtcggaagaa tcgtatttgt  240
```

```
tatctacagg agatttttc aaatgagatg gcgaaagtag atgatagttt ctttcatcga   300
cttgaagagt ctttttggt ggaagaagac aagaagcatg aacgtcatcc tattttgga    360
aatatagtag atgaagttgc ttatcatgag aaatatccaa ctatctatca tctgcgaaaa  420
aaattggtag attctactga taaagcggat ttgcgcttaa tctatttggc cttagcgcat  480
atgattaagt ttcgtggtca ttttttgatt gagggagatt taaatcctga taatagtgat  540
gtggacaaac tatttatcca gttggtacaa acctacaatc aattatttga agaaaaccct  600
attaacgcaa gtggagtaga tgctaaagcg attctttctg cacgattgag taaatcaaga  660
cgattagaaa atctcattgc tcagctcccc ggtgagaaga aaaatggctt atttgggaat  720
ctcattgctt tgtcattggg tttgacccct aattttaaat caaattttga tttggcagaa  780
gatgctaaat tacagctttc aaaagatact tacgatgatg atttagataa tttattggcg  840
caaattggag atcaatatgc tgatttgttt ttggcagcta agaatttatc agatgctatt  900
ttactttcag atatcctaag agtaaatact gaaataacta aggctcccct atcagcttca  960
atgattaaac gctacgatga acatcatcaa gacttgactc ttttaaaagc tttagttcga 1020
caacaacttc cagaaaagta taaagaaatc tttttgatc aatcaaaaaa cggatatgca 1080
ggttatattg atggggggagc tagccaagaa gaattttata aatttatcaa accaattta 1140
gaaaaaatgg atggtactga ggaattattg gtgaaactaa atcgtgaaga tttgctgcgc 1200
aagcaacgga cctttgacaa cggctctatt ccccatcaaa ttcacttggg tgagctgcat 1260
gctattttga gaagacaaga agactttat ccatttttaa aagacaatcg tgagaagatt 1320
gaaaaaatct tgacttttcg aattcctat tatgttggtc cattggcgcg tggcaatagt 1380
cgttttgcat ggatgactcg gaagtctgaa gaaacaatta ccccatggaa ttttgaagaa 1440
gttgtcgata aaggtgcttc agctcaatca tttattgaac gcatgacaaa ctttgataaa 1500
aatcttccaa atgaaaaagt actaccaaaa catgtttgc tttatgagta tttttacggtt 1560
tataacgaat tgacaaaggt caaatatgtt actgaaggaa tgcgaaaacc agcattctt 1620
tcaggtgaac agaagaaagc cattgttgat ttactcttca aaacaaatcg aaaagtaacc 1680
gttaagcaat taaagaaga ttatttcaaa aaatagaat gttttgatag tgttgaaatt 1740
tcaggagttg aagatagatt taatgcttca ttaggtacct accatgattt gctaaaaatt 1800
attaaagata aagatttttt ggataatgaa gaaaatgaag atatcttaga ggatattgtt 1860
ttaacattga ccttatttga agataggag atgattgagg aaagacttaa aacatatgct 1920
cacctctttg atgataaggt gatgaaacag cttaaacgtc gccgttatac tggttgggga 1980
cgtttgtctc gaaaattgat taatggtatt agggataagc aatctggcaa aacaatatta 2040
gatttttga aatcagatgg tttgccaat cgcaattta tgcagctgat ccatgatgat 2100
agtttgacat taaagaaga cattcaaaaa gcacaagtgt ctggacaagg cgatagttta 2160
catgaacata ttgcaaattt agctggtagc cctgctatta aaaaggtat ttacagact 2220
gtaaaagttg ttgatgaatt ggtcaaagta atggggcggc ataagccaga aaatatcgtt 2280
attgaaatgg cacgtgaaaa tcagacaact caaaagggcc agaaaattc gcgagagcgt 2340
atgaaacgaa tcgaagaagg tatcaaagaa ttaggaagtc agattcttaa agagcatcct 2400
gttgaaaata ctcaattgca aaatgaaaag ctctatctct attatctcca aaatggaaga 2460
gacatgtatg tggaccaaga attagatatt aatcgttaa gtgattatga tgtcgatcac 2520
attgttccac aaagttttcct taaagacgat tcaatagaca ataaggtctt aacgcgttct 2580
gataaaaatc gtggtaaatc ggataacgtt ccagtgaag aagtagtcaa aaagatgaaa 2640
aactattgga gacaacttct aaacgccaag ttaatcactc aacgtaagtt tgataattta 2700
acgaaagctg aacgtggagg tttgagtgaa cttgataaag ctggttttat caaacgccaa 2760
ttggttgaaa ctcgccaaat cactaagcat gtggcacaaa ttttggatag tcgcatgaat 2820
actaaatacg atgaaaatga taaacttatt cgagaggtta aagtgattac cttaaaatct 2880
aaattagttt ctgacttccg aaaagattc caattctata aagtacgtga gattaacaat 2940
taccatcatg cccatgatgc gtatctaaat gccgtcgttg gaactgcttt gattaagaaa 3000
tatccaaaac ttgaatcgga gttttgtctat ggtgattata aagttttatga tgttcgtaaa 3060
atgattgcta agtctgagca agaaataggc aaagcaaccg caaaatattt cttttactctt 3120
aatatcatga acttcttcaa aacagaaatt acacttgcaa atggagagat tcgcaaacgc 3180
cctctaatcg aaactaatgg ggaaactgga gaaattgtct gggataaagg gcgagatttt 3240
gccacagtgc gcaaagtatt gtccatgccc caagtcaagta ttgtcaagaa aacagaagta 3300
cagacaggcg gattctccaa ggagtcaatt ttaccaaaaa gaaattcgga caagcttatt 3360
gctcgtaaaa aagactggga tccaaaaaaa tatggtggtt ttgatagtcc aacggtagct 3420
tattcagtcc tagtggttgc taaggtgaaa aagggaaat cgaagaagtt aaaatccgtt 3480
aaagagttac tagggatcac aattatggaa agaagttcct ttgaaaaaaa tccgattgac 3540
tttttagaag ctaaaggata taaggaagtt aaaaaagact taatcattaa actacctaaa 3600
tatagtcttt ttgagttaga aaacggtcgt aacggatgc tggctagtgc cggagaatta 3660
caaaaaggaa atgagctggc tctgccaagc aaatatgtga atttttata tttagctagt 3720
cattatgaag agttgaaggg tagtccagaa gataacgaac aaaaacaatt gtttgtggag 3780
cagcataagc attatttaga tgagattatt gagcaaatca gtgaatttc taagcgtgtt 3840
attttagcag atgccaattt agataaagtt cttagtgcat ataacaaaca tagagacaaa 3900
ccaatacgtg aacaagcaga aaatattatt catttattta cgttgacgaa tcttggagct 3960
cccgctgctt ttaaatattt tgatacaaca attgatcgta aacgatatac gtctacaaaa 4020
gaagttttag atgccactct tatccatcaa tccatcactg tctttatga aacacgcatt 4080
gatttgagtc agctaggagg tgactga                                     4107

SEQ ID NO: 2           moltype = DNA  length = 189
FEATURE                Location/Qualifiers
source                 1..189
                       mol_type = unassigned DNA
                       organism = Solanum tuberosum
SEQUENCE: 2
gtaagttct gcttctacct ttgatatata tataataatt atcattaatt agtagtaata   60
taatattca aatatttttt tcaaaataaa agaatgtagt atatagcaat tgcttttctg  120
tagtttataa gtgtgtatat tttaatttat aacttttcta atatatgacc aaaacatggt  180
gatgtgcag                                                         189

SEQ ID NO: 3           moltype = AA  length = 9
FEATURE                Location/Qualifiers
```

```
source                  1..9
                        mol_type = protein
                        organism = Simian virus 40
SEQUENCE: 3
MAPKKKRKV                                                               9

SEQ ID NO: 4            moltype = AA  length = 18
FEATURE                 Location/Qualifiers
source                  1..18
                        mol_type = protein
                        organism = Agrobacterium tumefaciens
SEQUENCE: 4
KRPRDRHDGE LGGRKRAR                                                    18

SEQ ID NO: 5            moltype = DNA  length = 6717
FEATURE                 Location/Qualifiers
misc_feature            1..6717
                        note = synthesized sequence-Maize optimized Cas9 expression
                         cassette
source                  1..6717
                        mol_type = other DNA
                        organism = synthetic construct
SEQUENCE: 5
gtgcagcgtg acccggtcgt gccctctct agagataatg agcattgcat gtctaagtta       60
taaaaaatta ccacatattt tttttgtcac acttgtttga agtgcagttt atctatcttt     120
atacatatat ttaaactta ctctacgaat aatataatct atagtactac aataatatca      180
gtgttttaga gaatcatata aatgaacagt tagacatggt ctaaaggaca attgagtatt     240
ttgacaacag gactctacag ttttatcttt ttagtgtgca tgtgttctcc ttttttttg      300
caaatagctt cacctatata atacttcatc cattttatta gtacatccat ttagggttta    360
gggttaatgg ttttttataga ctaatttttt tagtacatct atttttattct attttagcct   420
ctaaattaag aaaactaaaa ctctatttta gttttttat ttaataattt agatatataaa    480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctggaccct tcgagagtt ccgctccacc gttggacttg      720
ctccgctgtc ggcatccaga aattgcgtgg cggagcggca gacgtgagcc ggcacggcag    780
gcggcctcct cctcctctca cggcaccggc agctacgggg gattcctttc ccaccgctcc    840
ttcgctttcc cttcctcgcc cgccgtaata aatagacacc ccctccccac cctctttccc   900
caacctcgtg ttgttcggag cgcacacaca cacaaccaga tctccccaa atccaccggt    960
cggcacctcc gcttcaaggt acgccgctcg tcctcccccc cccccctctc tacctttctct   1020
agatcggcgt tccggtccat gcatggttag ggcccggtag ttctacttct gttcatgttt   1080
gtgttagatc cgtgtttgtg ttagatccgt gctgctagcg ttcgtacacg gatgcgacct   1140
gtacgtcaga cacgttctga ttgctaactt gccagtgttt ctctttgggg aatcctggga   1200
tggctctagc cgttccgcag acgggatcga ttcatgatt ttttttgttt cgttgcatag    1260
ggtttggttt gccctttcc ttatttcaa tatatgccgt gcacttgttt gtcgggtcat    1320
cttttcatgc tttttttttgt cttggttgtg atgatgtggt ctggttgggc ggtcgttcta    1380
gatcggagta gaattctgtt tcaaactacc tggtggattt attaatttg gatctgtatg    1440
tgtgtgccat acatattcat agttacgaat tgaagatgat ggatggaaat atcgatctag   1500
gataggtata catgttgatg cgggttttac tgatgcatat acagagatgc ttttttgttcg   1560
cttggttgtg atgatgtggt gtggttgggc ggtcgttcat tcgttctaga tcggagtaga   1620
atactgtttc aaactacctg tgtatttat taattttga actgtatgtg tgtgtcatac      1680
atcttcatag ttacgagttt aagatggatg gaaatatcga tctaggatag gtacatgt     1740
tgatgtgggt tttactgatg catatacatg atggcatatg cagcatctat tcatatgctc    1800
taaccttgag tacctatcta ttaataaa caagtatgtt ttaattat tttgatcttg      1860
atatacttgg atgatggcat atgcagcagc tatatgtgga ttttttttag cctgccttca    1920
tacgctattt atttgcttgg tactgtttct tttgtcgatg ctcacccgt tgtttggtgt    1980
tacttctgca ggtcgactct agaggatcca tggcaccgaa gaagaagcgc aaggtgatgg   2040
acaagaagta cagcatcggc ctcgacatcg gcaccaactc ggtgggctgg gccgtcatca    2100
cggacgaata taaggtcccg tcgaagaagt tcaaggtcct cggcaatacca gaccgccaca   2160
gcatcaagaa aaacttgatc ggcgccctcc tgttcgatag cggcgagacc gcggaggcga   2220
ccaggctcaa gaggaccgcc aggagacggt tacactaggcg caagaacagg atctgctacc   2280
tgcaggagat cttcagcaac gagatggcga aggtggacga ctccttcttc acccgcctgg   2340
aggaatcatt cctggtggag gaggacaaga gcatgagcg gcacccaatc ttcggcaaca    2400
tcgtcgacga ggtaagtttc tgcttctacc ttgtatatat atataataat tatcattaat    2460
tagtagtaat ataatatttc aaatatttt tcaaaataa aagaatgtag tatatagcaa     2520
ttgctttct gtagtttata agtgtgtata ttttaattta taacttttct aatatatgac    2580
caaaacatgt tgatgtgcag gtggcctacc acgagaagta cccgacaatc taccacctcc    2640
ggaagaaact ggtggacagc acagacaagg cggacctccg gctcatctac cttgccctcg    2700
cgcatatgat caagttccgc ggccacttcc tcatcgagta gacctgaac ccggacaact     2760
ccgacgtgga caagctgttc atccagctcg tgcagacgta caatcaactg ttcgaggaga    2820
acccccataaa cgctagcggc gtgacgcca aggcaatcctt ctcggccagg ctctcgaaat    2880
caagaaggct ggagaacctt atcgcgcagt gccaggcga aagaagaac ggcctcttcg      2940
gcaacctttat tgcgctcagc ctcggcctga cgcccgaactt caaatcaaac ttcgacctcg   3000
cggaggacgc caagctccag ctctcaaagg acacctcagg cgacctcgac aacctcctc    3060
tggcccccagat aggagaccag tacgcggacc tcttcctcgc cgccaagaac ctctcgacg    3120
ctatcctgct cagcgacatc cttggggtca acaccgaaat taccaaggca ccgcgtccg     3180
ccagcatgat taaacgctac gacgagcacc atcaggacct cacgctgctc aaggcactcg     3240
tccgccagca gctccccgag aagtacaagg agatcttctt cgaccaatca aaaaacggct     3300
acgcgggata tatcgacggc ggtgccagcc aggaagagtt ctacaagttc atcaaaccaa    3360
```

```
tcctggagaa gatggacggc accgaggagt tgctggtcaa gctcaacagg gaggacctcc    3420
tcaggaagca gaggaccttc gacaacggct ccatcccgca tcagatccac ctgggcgaac    3480
tgcatgccat cctgcggcgc caggaggact tctacccgtt cctgaaggat aaccgggaga    3540
agatcgagaa gatcttgacg ttccgcatcc catactacgt gggcccgctg gctcgcggca    3600
actcccggtt cgcctggatg acccggaagt cggaggagac catcacaccc tggaactttg    3660
aggaggtggt cgataagggc gctagcgctc agagcttcat cgagcgcatg accaacttcg    3720
ataaaaacct gcccaatgaa aaagtcctcc ccaagcactc gctgctctac gagtacttca    3780
ccgtgtacaa cgagctcacc aaggtcaaat acgtcaccga gggcatgcgg aagccggcgt    3840
tcctgagcgg cgagcagaag aaggcgatag tggacctcct cttcaagacc aacaggaagg    3900
tgaccgtgaa gcaattaaaa gaggactact tcaagaaaat agagtgcttc gactccgtgg    3960
agatctcggg cgtggaggat cggttcaacg cctcactcgg cacgtatcac gacctcctca    4020
agatcattaa agacaaggac ttcctcgaca acgaggagaa cgaggacatc ctcgaggaca    4080
tcgtcctcac cctgacccct gttcgaggacc gcgaaatgat cgaggagagg ctgaagacct    4140
acgcgcacct gttcgacgac aaggtcatga aacagctcaa gaggcgccgc tacactggtt    4200
ggggaaggct gtcccgcaag ctcattaatg gcatcaggga caagcagagc ggcaagacca    4260
tcctggactt cctcaagtcc gacggggttcg ccaaccgcaa cttcatgcag ctcattcacg    4320
acgactcgct cacgttcaag gaagacatcc agaaggcaca ggtgagcggg cagggtgact    4380
ccctccacga acacatcgcc aacctggccg gctcgccggc cattaaaaag ggcatcctgc    4440
agacggtcaa ggtcgtcgac gagctcgtga aggtgatggg ccggcacaag cccgaaaata    4500
tcgtcatcga gatggccagg gagaaccaga ccacccaaaa agggcagaag aactcgcgcg    4560
agcggatgaa acggatcgag gagggcatta agagctcgg gtcccagatc ctgaaggagc    4620
accccgtgga aaataccccg ctccagaatg aaaagtctca cctctactac ctgcagaacg    4680
gccgcgacat gtacgtggac caggagctgg acattaatcg gctatcggac tacgacgtcg    4740
accacatcgt gccgcagtcg ttcctcaagg acgatagcat cgacaacaag gtgctcacccc    4800
ggtcggataa aaatcggggc aagagcgaca acgtgcccag cgaggaggtc gtgaagaaga    4860
tgaaaaacta ctggcgccag ctcctcaacg cgaaactgat cacccagcga aagttcgaca    4920
acctgacgaa ggcggaacgc ggtgcttga gcgaactcga taaggcgggc ttcataaaaa    4980
ggcagctggt cgagacgcgc cagatcacga agcatgtcgc ccagatcctg acagccgcca    5040
tgaatactaa gtacgatgaa aacgacaagc tgatccggga ggtgaaggtg atcacgctga    5100
agtccaagct cgtgtcggac ttccgcaagg acttccagtt ctacaaggtc cgcgagatca    5160
acaactacca ccacgcccac gacgcctacc tgaatgcggt ggtcgggacc gccctgatca    5220
agaagtaccc gaagctggag tcggagttcg tgtacggcga ctacaaggtc tacgacgtgc    5280
gcaaaatgat cgccaagtcc gagcaggaga tcggcaaggc cacggcaaaa tacttcttct    5340
actcgaacat catgaacttc ttcaagaccg agatcaccct cgcgaacggc gagatccgca    5400
agcgcccgct catcgaaacc aacggcgaga cgggcgagat cgtctgggat aagggccggg    5460
atttcgcgac ggtccgcaag gtgctctcca tgccgcaagt caatatcgtg aaaaagacgg    5520
aggtccagac gggcggggttc agcaaggagt ccatcctccc gaagcgcaac tccgacaagc    5580
tcatcgcgag gaagaaggat tgggaccccga aaaatatgg cggcttcgac agcccgaccg    5640
tcgcatacac cgtcctcgtc gtggcgaagg tggagaaggg caagtcaaag aagctcaagt    5700
ccgtgaagga gctgctcggg atcacgatta tggagcggtc ctccttcgag aagaacccga    5760
tcgacttcct agaggccaag ggatataagg aggtcaagaa ggacctgatt attaaactgc    5820
cgaagtactc gctcttcgag ctggaaaacg gccgcaagag gatgctcgcc tccgcaggcg    5880
agttgcagaa gggcaacgag ctcgcccctcc cgagcaaata cgtcaatttc ctgtacctcg    5940
ctagccacta tgaaaagctc aagggcagcc cggaggacaa cgagcagaag cagctctttcg    6000
tggagcagca caagcattac ctggacgaga tcatcgagca gatcagcgag ttctcgaagc    6060
gggtgatcct cgccgacgcg aacctggaca aggtgctgtc ggcatataac aagcaccgcg    6120
acaaaccaat acgcgagcag gccgaaaata tcatccacct cttcacccctc accaacctcg    6180
gcgctccggc agccttcaag tacttcgaca ccacgattga ccggaagcgg tacacgcagca    6240
cgaaggaggt gctcgatgcg acgctgatcc accagagcat cacagggctc tatgaaacac    6300
gcatcgacct gagccagctg ggcggagaca agagaccacg ggaccgccac gatggcgagc    6360
tgggaggccg caagcgggca aggtaggtac cgttaaccta gacttgtcca tcttctgatg    6420
tggccaactt aattaatgta tgaaataaaa ggatgcacac atagtgacat gctaatcact    6480
ataatgtggg catcaaagtt gtgtgttatg tgtaattact agttatctga ataaaagaga    6540
aagagatcat ccatatttct tatcctaaat gaatgtcacg tgtctttata attctttgat    6600
gaaccagatg catttcatta accaaatcca tatacatata aatattaatc atatataatt    6660
aatatcaatt gggttagcaa aacaaatcta gtctaggtgt gttttgcgaa tgcggcc      6717

SEQ ID NO: 6          moltype = RNA   length = 39
FEATURE               Location/Qualifiers
misc_feature          1..39
                      note = synthesized sequence-crRNA containing the LIGCas-3
                       target sequence in the variable targeting domain
source                1..39
                      mol_type = other RNA
                      organism = synthetic construct
SEQUENCE: 6
gcgtacgcgt acgtgtggtt ttagagctat gctgttttg                           39

SEQ ID NO: 7          moltype = RNA   length = 86
FEATURE               Location/Qualifiers
misc_feature          1..86
                      note = tracrRNA
source                1..86
                      mol_type = unassigned RNA
                      organism = Streptococcus pyogenes
SEQUENCE: 7
ggaaccattc aaaacagcat agcaagttaa aataaggcta gtccgttatc aacttgaaaa    60
agtggcaccg agtcggtgct tttttt                                          86
```

| SEQ ID NO: 8 | moltype = RNA length = 94 |
|---|---|
| FEATURE | Location/Qualifiers |
| misc_feature | 1..94 |
| | note = synthesized sequence- Long guide RNA containing the LIGCas-3 target sequence in the variable targeting domain |
| source | 1..94 |
| | mol_type = other RNA |
| | organism = synthetic construct |

SEQUENCE: 8

```
gcgtacgcgt acgtgtggtt ttagagctag aaatagcaag ttaaaataag gctagtccgt   60
tatcaacttg aaaaagtggc accgagtcgg tgct                               94
```

| SEQ ID NO: 9 | moltype = DNA length = 1000 |
|---|---|
| FEATURE | Location/Qualifiers |
| source | 1..1000 |
| | mol_type = unassigned DNA |
| | organism = Zea mays |

SEQUENCE: 9

```
tgagagtaca atgatgaacc tagattaatc aatgccaaag tctgaaaaat gcaccctcag   60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gttttgttagc gcatgtacaa ggaatgcaag ttttgagcga ggggggcatca 480
aagatctggc tgtgtttcca gctgttttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaatgct   660
attcgaattt ctactagcag taagtcgtgt ttagaaatta tttttttata tacctttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
agaaacatgg cccacggccc aatacgaagc accgcgacga agcccaaaca gcagtccgta  900
ggtggagcaa agcgctgggt aatacgcaaa cgttttgtcc caccttgact aatcacaaga  960
gtggagcgta ccttataaac cgagccgcaa gcaccgaatt                       1000
```

| SEQ ID NO: 10 | moltype = DNA length = 16 |
|---|---|
| FEATURE | Location/Qualifiers |
| source | 1..16 |
| | mol_type = unassigned DNA |
| | organism = Zea mays |

SEQUENCE: 10

```
tttttttttt tttttt                                                   16
```

| SEQ ID NO: 11 | moltype = RNA length = 59 |
|---|---|
| FEATURE | Location/Qualifiers |
| misc_feature | 1..59 |
| | note = synthesized sequence- Short guide RNA containing the LIGCas-3 variable targeting domain |
| source | 1..59 |
| | mol_type = other RNA |
| | organism = synthetic construct |

SEQUENCE: 11

```
gcgtacgcgt acgtgtggtt ttagagctag aaatagcaag ttaaaataag gctagtccg    59
```

| SEQ ID NO: 12 | moltype = DNA length = 1102 |
|---|---|
| FEATURE | Location/Qualifiers |
| misc_feature | 1..1102 |
| | note = synthesized sequence- Maize optimized long guide RNA expression cassette containing the LIGCas-3 variable targeting domain |
| source | 1..1102 |
| | mol_type = other DNA |
| | organism = synthetic construct |

SEQUENCE: 12

```
tgagagtaca atgatgaacc tagattaatc aatgccaaag tctgaaaaat gcaccctcag   60
tctatgatcc agaaaatcaa gattgcttga ggccctgttc ggttgttccg gattagagcc  120
ccggattaat tcctagccgg attacttctc taatttatat agattttgat gagctggaat  180
gaatcctggc ttattccggt acaaccgaac aggccctgaa ggataccagt aatcgctgag  240
ctaaattggc atgctgtcag agtgtcagta ttgcagcaag gtagtgagat aaccggcatc  300
atggtgccag tttgatggca ccattagggt tagagatggt ggccatgggc gcatgtcctg  360
gccaactttg tatgatatat ggcagggtga ataggaaagt aaaattgtat tgtaaaaagg  420
gatttcttct gttttgttagc gcatgtacaa ggaatgcaag ttttgagcga ggggggcatca 480
aagatctggc tgtgtttcca gctgttttttg ttagccccat cgaatccttg acataatgat  540
cccgcttaaa taagcaacct cgcttgtata gttccttgtg ctctaacaca cgatgatgat  600
aagtcgtaaa atagtggtgt ccaaagaatt tccaggccca gttgtaaaag ctaaatgct   660
attcgaattt ctactagcag taagtcgtgt ttagaaatta tttttttata tacctttttt  720
ccttctatgt acagtaggac acagtgtcag cgccgcgttg acggagaata tttgcaaaaa  780
agtaaaagag aaagtcatag cggcgtatgt gccaaaaact tcgtcacaga gagggccata  840
```

```
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gcgtacgcgt acgtgtggtt   1020
ttagagctag aaatagcaag ttaaaataag gctagtccgt tatcaacttg aaaaagtggc   1080
accgagtcgg tgctttttttt tt                                           1102

SEQ ID NO: 13          moltype = DNA   length = 27
FEATURE                Location/Qualifiers
source                 1..27
                       mol_type = unassigned DNA
                       organism = Zea mays
SEQUENCE: 13
gtactccatc cgccccatcg agtaggg                                         27

SEQ ID NO: 14          moltype = DNA   length = 24
FEATURE                Location/Qualifiers
source                 1..24
                       mol_type = unassigned DNA
                       organism = Zea mays
SEQUENCE: 14
gcacgtacgt caccatcccg ccgg                                            24

SEQ ID NO: 15          moltype = DNA   length = 24
FEATURE                Location/Qualifiers
source                 1..24
                       mol_type = unassigned DNA
                       organism = Zea mays
SEQUENCE: 15
gacgtacgtg ccctactcga tggg                                            24

SEQ ID NO: 16          moltype = DNA   length = 24
FEATURE                Location/Qualifiers
source                 1..24
                       mol_type = unassigned DNA
                       organism = Zea mays
SEQUENCE: 16
gtaccgtacg tgcccggcg gagg                                             24

SEQ ID NO: 17          moltype = DNA   length = 24
FEATURE                Location/Qualifiers
source                 1..24
                       mol_type = unassigned DNA
                       organism = Zea mays
SEQUENCE: 17
ggaattgtac cgtacgtgcc ccgg                                            24

SEQ ID NO: 18          moltype = DNA   length = 20
FEATURE                Location/Qualifiers
source                 1..20
                       mol_type = unassigned DNA
                       organism = Zea mays
SEQUENCE: 18
gcgtacgcgt acgtgtgagg                                                 20

SEQ ID NO: 19          moltype = DNA   length = 22
FEATURE                Location/Qualifiers
source                 1..22
                       mol_type = unassigned DNA
                       organism = Zea mays
SEQUENCE: 19
gctggccgag gtcgactacc gg                                              22

SEQ ID NO: 20          moltype = DNA   length = 23
FEATURE                Location/Qualifiers
source                 1..23
                       mol_type = unassigned DNA
                       organism = Zea mays
SEQUENCE: 20
ggccgaggtc gactaccggc cgg                                             23

SEQ ID NO: 21          moltype = DNA   length = 23
FEATURE                Location/Qualifiers
source                 1..23
                       mol_type = unassigned DNA
                       organism = Zea mays
SEQUENCE: 21
ggcgcgagct cgtgcttcac cgg                                             23

SEQ ID NO: 22          moltype = DNA   length = 21
```

```
FEATURE                 Location/Qualifiers
source                  1..21
                        mol_type = unassigned DNA
                        organism = Zea mays
SEQUENCE: 22
ggtgccaatc atgcgtcgcg g                                              21

SEQ ID NO: 23           moltype = DNA  length = 20
FEATURE                 Location/Qualifiers
source                  1..20
                        mol_type = unassigned DNA
                        organism = Zea mays
SEQUENCE: 23
ggtcgccatc acgggacagg                                                20

SEQ ID NO: 24           moltype = DNA  length = 24
FEATURE                 Location/Qualifiers
source                  1..24
                        mol_type = unassigned DNA
                        organism = Zea mays
SEQUENCE: 24
gtcgcggcac ctgtcccgtg atgg                                           24

SEQ ID NO: 25           moltype = DNA  length = 23
FEATURE                 Location/Qualifiers
source                  1..23
                        mol_type = unassigned DNA
                        organism = Zea mays
SEQUENCE: 25
ggaatgctgg aactgcaatg cgg                                            23

SEQ ID NO: 26           moltype = DNA  length = 24
FEATURE                 Location/Qualifiers
source                  1..24
                        mol_type = unassigned DNA
                        organism = Zea mays
SEQUENCE: 26
gcagctcttc ttggggaatg ctgg                                           24

SEQ ID NO: 27           moltype = DNA  length = 23
FEATURE                 Location/Qualifiers
source                  1..23
                        mol_type = unassigned DNA
                        organism = Zea mays
SEQUENCE: 27
gcagtaacag ctgctgtcaa tgg                                            23

SEQ ID NO: 28           moltype = DNA  length = 56
FEATURE                 Location/Qualifiers
misc_feature            1..56
                        note = synthesized sequence- MS26Cas-1 forward primer
source                  1..56
                        mol_type = other DNA
                        organism = synthetic construct
SEQUENCE: 28
ctacactctt tccctacacg acgctcttcc gatctaggac cggaagctcg ccgcgt        56

SEQ ID NO: 29           moltype = DNA  length = 54
FEATURE                 Location/Qualifiers
misc_feature            1..54
                        note = synthesized sequence- MS26Cas-1 and MS26Cas-3
                         reverse primer
source                  1..54
                        mol_type = other DNA
                        organism = synthetic construct
SEQUENCE: 29
caagcagaag acggcatacg agctcttccg atcttcctgg aggacgacgt gctg          54

SEQ ID NO: 30           moltype = DNA  length = 59
FEATURE                 Location/Qualifiers
misc_feature            1..59
                        note = synthesized sequence- MS26Cas-2 forward primer
source                  1..59
                        mol_type = other DNA
                        organism = synthetic construct
SEQUENCE: 30
ctacactctt tccctacacg acgctcttcc gatctaaggt cctggaggac gacgtgctg     59

SEQ ID NO: 31           moltype = DNA  length = 51
```

```
FEATURE                Location/Qualifiers
misc_feature           1..51
                       note = synthesized sequence- MS26Cas-2 and MS26
                        meganuclease reverse primer
source                 1..51
                       mol_type = other DNA
                       organism = synthetic construct
SEQUENCE: 31
caagcagaag acggcatacg agctcttccg atctccggaa gctcgccgcg t            51

SEQ ID NO: 32          moltype = DNA  length = 56
FEATURE                Location/Qualifiers
misc_feature           1..56
                       note = synthesized sequence- MS26Cas-3 forward primer
source                 1..56
                       mol_type = other DNA
                       organism = synthetic construct
SEQUENCE: 32
ctacactctt tccctacacg acgctcttcc gatcttcctc cggaagctcg ccgcgt       56

SEQ ID NO: 33          moltype = DNA  length = 59
FEATURE                Location/Qualifiers
misc_feature           1..59
                       note = synthesized sequence- MS26 Meganuclease forward
                        primer
source                 1..59
                       mol_type = other DNA
                       organism = synthetic construct
SEQUENCE: 33
ctacactctt tccctacacg acgctcttcc gatctttcct cctggaggac gacgtgctg   59

SEQ ID NO: 34          moltype = DNA  length = 63
FEATURE                Location/Qualifiers
misc_feature           1..63
                       note = synthesized sequence- LIGCas-1 forward primer
source                 1..63
                       mol_type = other DNA
                       organism = synthetic construct
SEQUENCE: 34
ctacactctt tccctacacg acgctcttcc gatctaggac tgtaacgatt tacgcacctg   60
ctg                                                                 63

SEQ ID NO: 35          moltype = DNA  length = 58
FEATURE                Location/Qualifiers
misc_feature           1..58
                       note = synthesized sequence- LIGCas-1 and LIGCas-2 reverse
                        primer
source                 1..58
                       mol_type = other DNA
                       organism = synthetic construct
SEQUENCE: 35
caagcagaag acggcatacg agctcttccg atctgcaaat gagtagcagc gcacgtat    58

SEQ ID NO: 36          moltype = DNA  length = 63
FEATURE                Location/Qualifiers
misc_feature           1..63
                       note = synthesized sequence- LIGCas-2 forward primer
source                 1..63
                       mol_type = other DNA
                       organism = synthetic construct
SEQUENCE: 36
ctacactctt tccctacacg acgctcttcc gatcttcctc tgtaacgatt tacgcacctg   60
ctg                                                                 63

SEQ ID NO: 37          moltype = DNA  length = 60
FEATURE                Location/Qualifiers
misc_feature           1..60
                       note = synthesized sequence- LIGCas-3 forward primer
source                 1..60
                       mol_type = other DNA
                       organism = synthetic construct
SEQUENCE: 37
ctacactctt tccctacacg acgctcttcc gatctaaggc gcaaatgagt agcagcgcac   60

SEQ ID NO: 38          moltype = DNA  length = 57
FEATURE                Location/Qualifiers
misc_feature           1..57
                       note = synthesized sequence- LIGCas-3 and LIG3-4
                        meganuclease reverse primer
```

```
source                  1..57
                        mol_type = other DNA
                        organism = synthetic construct
SEQUENCE: 38
caagcagaag acggcatacg agctcttccg atctcacctg ctgggaattg taccgta      57

SEQ ID NO: 39           moltype = DNA  length = 60
FEATURE                 Location/Qualifiers
misc_feature            1..60
                        note = synthesized sequence- LIG3-4 meganuclease forward
                         primer
source                  1..60
                        mol_type = other DNA
                        organism = synthetic construct
SEQUENCE: 39
ctacactctt tccctacacg acgctcttcc gatctccttc gcaaatgagt agcagcgcac    60

SEQ ID NO: 40           moltype = DNA  length = 58
FEATURE                 Location/Qualifiers
misc_feature            1..58
                        note = synthesized sequence- MS45Cas-1 forward primer
source                  1..58
                        mol_type = other DNA
                        organism = synthetic construct
SEQUENCE: 40
ctacactctt tccctacacg acgctcttcc gatctaggag gacccgttcg gcctcagt      58

SEQ ID NO: 41           moltype = DNA  length = 54
FEATURE                 Location/Qualifiers
misc_feature            1..54
                        note = synthesized sequence- MS45Cas-1, MS45Cas-2 and
                         MS45Cas-3 reverse primer
source                  1..54
                        mol_type = other DNA
                        organism = synthetic construct
SEQUENCE: 41
caagcagaag acggcatacg agctcttccg atctgccggc tggcattgtc tctg          54

SEQ ID NO: 42           moltype = DNA  length = 58
FEATURE                 Location/Qualifiers
misc_feature            1..58
                        note = synthesized sequence- MS45Cas-2 forward primer
source                  1..58
                        mol_type = other DNA
                        organism = synthetic construct
SEQUENCE: 42
ctacactctt tccctacacg acgctcttcc gatcttcctg gacccgttcg gcctcagt      58

SEQ ID NO: 43           moltype = DNA  length = 58
FEATURE                 Location/Qualifiers
misc_feature            1..58
                        note = synthesized sequence- MS45Cas-3 forward primer
source                  1..58
                        mol_type = other DNA
                        organism = synthetic construct
SEQUENCE: 43
ctacactctt tccctacacg acgctcttcc gatctgaagg gacccgttcg gcctcagt      58

SEQ ID NO: 44           moltype = DNA  length = 58
FEATURE                 Location/Qualifiers
misc_feature            1..58
                        note = synthesized sequence- ALSCas-1 forward primer
source                  1..58
                        mol_type = other DNA
                        organism = synthetic construct
SEQUENCE: 44
ctacactctt tccctacacg acgctcttcc gatctaaggc gacgatgggc gtctcctg      58

SEQ ID NO: 45           moltype = DNA  length = 53
FEATURE                 Location/Qualifiers
misc_feature            1..53
                        note = synthesized sequence- ALSCas-1, ALSCas-2 and
                         ALSCas-3 reverse primer
source                  1..53
                        mol_type = other DNA
                        organism = synthetic construct
SEQUENCE: 45
caagcagaag acggcatacg agctcttccg atctgcgtct gcatcgccac ctc           53
```

```
SEQ ID NO: 46            moltype = DNA   length = 58
FEATURE                  Location/Qualifiers
misc_feature             1..58
                         note = synthesized sequence- ALSCas-2 forward primer
source                   1..58
                         mol_type = other DNA
                         organism = synthetic construct
SEQUENCE: 46
ctacactctt tccctacacg acgctcttcc gatctttccc gacgatgggc gtctcctg      58

SEQ ID NO: 47            moltype = DNA   length = 58
FEATURE                  Location/Qualifiers
misc_feature             1..58
                         note = synthesized sequence- ALSCas-3 forward primer
source                   1..58
                         mol_type = other DNA
                         organism = synthetic construct
SEQUENCE: 47
ctacactctt tccctacacg acgctcttcc gatctggaac gacgatgggc gtctcctg      58

SEQ ID NO: 48            moltype = DNA   length = 63
FEATURE                  Location/Qualifiers
misc_feature             1..63
                         note = synthesized sequence- EPSPSCas-1 forward primer
source                   1..63
                         mol_type = other DNA
                         organism = synthetic construct
SEQUENCE: 48
ctacactctt tccctacacg acgctcttcc gatctggaag aggaaacata cgttgcattt     60
cca                                                                  63

SEQ ID NO: 49            moltype = DNA   length = 57
FEATURE                  Location/Qualifiers
misc_feature             1..57
                         note = synthesized sequence- PSPSCas-1 and EPSPSCas-3
                          reverse primer
source                   1..57
                         mol_type = other DNA
                         organism = synthetic construct
SEQUENCE: 49
caagcagaag acggcatacg agctcttccg atctggtgga aagttcccag ttgagga       57

SEQ ID NO: 50            moltype = DNA   length = 62
FEATURE                  Location/Qualifiers
misc_feature             1..62
                         note = synthesized sequence- PSPSCas-2 forward primer
source                   1..62
                         mol_type = other DNA
                         organism = synthetic construct
SEQUENCE: 50
ctacactctt tccctacacg acgctcttcc gatctaagcg gtggaaagtt cccagttgag    60
ga                                                                   62

SEQ ID NO: 51            moltype = DNA   length = 58
FEATURE                  Location/Qualifiers
misc_feature             1..58
                         note = synthesized sequence- EPSPSCas-2 reverse primer
source                   1..58
                         mol_type = other DNA
                         organism = synthetic construct
SEQUENCE: 51
caagcagaag acggcatacg agctcttccg atctgaggaa acatacgttg catttcca      58

SEQ ID NO: 52            moltype = DNA   length = 63
FEATURE                  Location/Qualifiers
misc_feature             1..63
                         note = synthesized sequence- EPSPSCas-3 forward primer
source                   1..63
                         mol_type = other DNA
                         organism = synthetic construct
SEQUENCE: 52
ctacactctt tccctacacg acgctcttcc gatctccttg aggaaacata cgttgcattt    60
cca                                                                  63

SEQ ID NO: 53            moltype = DNA   length = 43
FEATURE                  Location/Qualifiers
misc_feature             1..43
                         note = synthesized sequence- Forward primer for secondary
                          PCR
```

```
                                        159                                         160
                                                  -continued source                  1..43
                        mol_type = other DNA
                        organism = synthetic construct
SEQUENCE: 53
aatgatacgg cgaccaccga gatctacact ctttccctac acg                         43

SEQ ID NO: 54           moltype = DNA   length = 18
FEATURE                 Location/Qualifiers
misc_feature            1..18
                        note = synthesized sequence- Reverse primer for secondary
                         PCR
source                  1..18
                        mol_type = other DNA
                        organism = synthetic construct
SEQUENCE: 54
caagcagaag acggcata                                                     18

SEQ ID NO: 55           moltype = DNA   length = 93
FEATURE                 Location/Qualifiers
source                  1..93
                        mol_type = unassigned DNA
                        organism = Zea mays
SEQUENCE: 55
ctgtaacgat ttacgcacct gctgggaatt gtaccgtacg tgccccggcg gaggatatat       60
atacctcaca cgtacgcgta cgcgtatata tac                                    93

SEQ ID NO: 56           moltype = DNA   length = 98
FEATURE                 Location/Qualifiers
source                  1..98
                        mol_type = unassigned DNA
                        organism = Zea mays
SEQUENCE: 56
aggactgtaa cgatttacgc acctgctggg aattgtaccg tacgtgcccc ggtcggagga       60
tatatatacc tcacacgtac gcgtacgcgt atatatac                               98

SEQ ID NO: 57           moltype = DNA   length = 98
FEATURE                 Location/Qualifiers
source                  1..98
                        mol_type = unassigned DNA
                        organism = Zea mays
SEQUENCE: 57
aggactgtaa cgatttacgc acctgctggg aattgtaccg tacgtgcccc ggacggagga       60
tatatatacc tcacacgtac gcgtacgcgt atatatac                               98

SEQ ID NO: 58           moltype = DNA   length = 98
FEATURE                 Location/Qualifiers
source                  1..98
                        mol_type = unassigned DNA
                        organism = Zea mays
SEQUENCE: 58
aggactgtaa cgatttacgc acctgctggg aattgtaccg tacgtgcccc gggcggagga       60
tatatatacc tcacacgtac gcgtacgcgt atatatac                               98

SEQ ID NO: 59           moltype = DNA   length = 95
FEATURE                 Location/Qualifiers
source                  1..95
                        mol_type = unassigned DNA
                        organism = Zea mays
SEQUENCE: 59
aggactgtaa cgatttacgc acctgctggg aattgtaccg tacgtgcggt cggaggatat       60
atacctca cacgtacgcg tacgcgtata tatac                                    95

SEQ ID NO: 60           moltype = DNA   length = 98
FEATURE                 Location/Qualifiers
source                  1..98
                        mol_type = unassigned DNA
                        organism = Zea mays
SEQUENCE: 60
aggactgtaa cgatttacgc acctgctggg aattgtaccg tacgtgcccc ggccggagga       60
tatatatacc tcacacgtac gcgtacgcgt atatatac                               98

SEQ ID NO: 61           moltype = DNA   length = 96
FEATURE                 Location/Qualifiers
source                  1..96
                        mol_type = unassigned DNA
                        organism = Zea mays
SEQUENCE: 61
aggactgtaa cgatttacgc acctgctggg aattgtaccg tacgtgcccc gcggaggata       60
tatataccte acacgtacgc gtacgcgtat atac                                   96
```

```
SEQ ID NO: 62           moltype = DNA   length = 96
FEATURE                 Location/Qualifiers
source                  1..96
                        mol_type = unassigned DNA
                        organism = Zea mays
SEQUENCE: 62
aggactgtaa cgatttacgc acctgctggg aattgtaccg tacgtgcccc ggggaggata    60
tatataccte acacgtacgc gtacgcgtat atatac                              96

SEQ ID NO: 63           moltype = DNA   length = 94
FEATURE                 Location/Qualifiers
source                  1..94
                        mol_type = unassigned DNA
                        organism = Zea mays
SEQUENCE: 63
aggactgtaa cgatttacgc acctgctggg aattgtaccg tacgtgcccc ggaggatata    60
tatacctcac acgtacgcgt acgcgtatat atac                                94

SEQ ID NO: 64           moltype = DNA   length = 94
FEATURE                 Location/Qualifiers
source                  1..94
                        mol_type = unassigned DNA
                        organism = Zea mays
SEQUENCE: 64
aggactgtaa cgatttacgc acctgctggg aattgtaccg tacgtgcgtc ggaggatata    60
tatacctcac acgtacgcgt acgcgtatat atac                                94

SEQ ID NO: 65           moltype = DNA   length = 43
FEATURE                 Location/Qualifiers
source                  1..43
                        mol_type = unassigned DNA
                        organism = Zea mays
SEQUENCE: 65
aggactgtaa cgatttacgc acctgctggg aattgtaccg tac                      43

SEQ ID NO: 66           moltype = DNA   length = 98
FEATURE                 Location/Qualifiers
source                  1..98
                        mol_type = unassigned DNA
                        organism = Zea mays
SEQUENCE: 66
tcctctgtaa cgatttacgc acctgctggg aattgtaccg tacgtgaccc cggcggagga    60
tatatatacc tcacacgtac gcgtacgcgt atatatac                            98

SEQ ID NO: 67           moltype = DNA   length = 96
FEATURE                 Location/Qualifiers
source                  1..96
                        mol_type = unassigned DNA
                        organism = Zea mays
SEQUENCE: 67
tcctctgtaa cgatttacgc acctgctggg aattgtaccg tacgtccccg gcggaggata    60
tatataccte acacgtacgc gtacgcgtat atatac                              96

SEQ ID NO: 68           moltype = DNA   length = 98
FEATURE                 Location/Qualifiers
source                  1..98
                        mol_type = unassigned DNA
                        organism = Zea mays
SEQUENCE: 68
tcctctgtaa cgatttacgc acctgctggg aattgtaccg tacgtgtccc cggcggagga    60
tatatatacc tcacacgtac gcgtacgcgt atatatac                            98

SEQ ID NO: 69           moltype = DNA   length = 94
FEATURE                 Location/Qualifiers
source                  1..94
                        mol_type = unassigned DNA
                        organism = Zea mays
SEQUENCE: 69
tcctctgtaa cgatttacgc acctgctggg aattgtaccg taccccggc ggaggatata     60
tatacctcac acgtacgcgt acgcgtatat atac                                94

SEQ ID NO: 70           moltype = DNA   length = 93
FEATURE                 Location/Qualifiers
source                  1..93
                        mol_type = unassigned DNA
                        organism = Zea mays
SEQUENCE: 70
tcctctgtaa cgatttacgc acctgctggg aattgtaccg taccccggcg gaggatatat    60
```

```
atacctcaca cgtacgcgta cgcgtatata tac                              93

SEQ ID NO: 71           moltype = DNA   length = 98
FEATURE                 Location/Qualifiers
source                  1..98
                        mol_type = unassigned DNA
                        organism = Zea mays
SEQUENCE: 71
tcctctgtaa cgatttacgc acctgctggg aattgtaccg tacgtggccc cggcggagga  60
tatatatacc tcacacgtac gcgtacgcgt atatatac                         98

SEQ ID NO: 72           moltype = DNA   length = 92
FEATURE                 Location/Qualifiers
source                  1..92
                        mol_type = unassigned DNA
                        organism = Zea mays
SEQUENCE: 72
tcctctgtaa cgatttacgc acctgctggg aattgtaccg tacccggcgg aggatatata  60
tacctcacac gtacgcgtac gcgtatatat ac                               92

SEQ ID NO: 73           moltype = DNA   length = 99
FEATURE                 Location/Qualifiers
source                  1..99
                        mol_type = unassigned DNA
                        organism = Zea mays
SEQUENCE: 73
tcctctgtaa cgatttacgc acctgctggg aattgtaccg tacgtgaacc ccggcggagg  60
atatatatac ctcacacgta cgcgtacgcg tatatatac                        99

SEQ ID NO: 74           moltype = DNA   length = 61
FEATURE                 Location/Qualifiers
source                  1..61
                        mol_type = unassigned DNA
                        organism = Zea mays
SEQUENCE: 74
tcctctgtaa cgatttacgc acctgctggg aattgtaccg tacgtgtacg cgtatatata  60
c                                                                 61

SEQ ID NO: 75           moltype = DNA   length = 95
FEATURE                 Location/Qualifiers
source                  1..95
                        mol_type = unassigned DNA
                        organism = Zea mays
SEQUENCE: 75
tcctctgtaa cgatttacgc acctgctggg aattgtaccg tacgccccgg cggaggatat  60
atatacctca cacgtacgcg tacgcgtata tatac                            95

SEQ ID NO: 76           moltype = DNA   length = 93
FEATURE                 Location/Qualifiers
source                  1..93
                        mol_type = unassigned DNA
                        organism = Zea mays
SEQUENCE: 76
cgcaaatgag tagcagcgca cgtatatata cgcgtacgcg tacgtgtgag gtatatatat  60
cctccgccgg ggcacgtacg gtacaattcc cag                              93

SEQ ID NO: 77           moltype = DNA   length = 98
FEATURE                 Location/Qualifiers
source                  1..98
                        mol_type = unassigned DNA
                        organism = Zea mays
SEQUENCE: 77
aaggcgcaaa tgagtagcag cgcacgtata tacgcgtata cgcgtacgtt gtgaggtata  60
tatatcctcc gccggggcac gtacggtaca attcccag                         98

SEQ ID NO: 78           moltype = DNA   length = 96
FEATURE                 Location/Qualifiers
source                  1..96
                        mol_type = unassigned DNA
                        organism = Zea mays
SEQUENCE: 78
aaggcgcaaa tgagtagcag cgcacgtata tacgcgtata cgcgtacggt gaggtatata  60
tatcctccgc cggggcacgt acggtacaat tcccag                           96

SEQ ID NO: 79           moltype = DNA   length = 96
FEATURE                 Location/Qualifiers
source                  1..96
                        mol_type = unassigned DNA
                        organism = Zea mays
```

```
SEQUENCE: 79
aaggcgcaaa tgagtagcag cgcacgtata tatacgcgta cgcgtactgt gaggtatata    60
tatcctccgc cggggcacgt acggtacaat tcccag                              96

SEQ ID NO: 80          moltype = DNA  length = 95
FEATURE                Location/Qualifiers
source                 1..95
                       mol_type = unassigned DNA
                       organism = Zea mays
SEQUENCE: 80
aaggcgcaaa tgagtagcag cgcacgtata tatacgcgta cgcgtacgtg aggtatatat    60
atcctccgcc ggggcacgta cggtacaatt cccag                               95

SEQ ID NO: 81          moltype = DNA  length = 68
FEATURE                Location/Qualifiers
source                 1..68
                       mol_type = unassigned DNA
                       organism = Zea mays
SEQUENCE: 81
aaggcgcaaa tgagtagcag cgcacgtata tatcctcc gccggggcac gtacggtaca      60
attcccag                                                             68

SEQ ID NO: 82          moltype = DNA  length = 55
FEATURE                Location/Qualifiers
source                 1..55
                       mol_type = unassigned DNA
                       organism = Zea mays
SEQUENCE: 82
aaggcgcaaa tgagtagcag cgcacgtata tatacgcgta cggtacaatt cccag         55

SEQ ID NO: 83          moltype = DNA  length = 93
FEATURE                Location/Qualifiers
source                 1..93
                       mol_type = unassigned DNA
                       organism = Zea mays
SEQUENCE: 83
aaggcgcaaa tgagtagcag cgcacgtata tatacgcgta cgcgtgtgag gtatatatat    60
cctccgccgg ggcacgtacg gtacaattcc cag                                 93

SEQ ID NO: 84          moltype = DNA  length = 69
FEATURE                Location/Qualifiers
source                 1..69
                       mol_type = unassigned DNA
                       organism = Zea mays
SEQUENCE: 84
aaggcgcaaa tgagtagcag cgcacgtata tatacgcgta cgccggggca cgtacggtac    60
aattcccag                                                            69

SEQ ID NO: 85          moltype = DNA  length = 66
FEATURE                Location/Qualifiers
source                 1..66
                       mol_type = unassigned DNA
                       organism = Zea mays
SEQUENCE: 85
aaggcgcaaa tgagtagcag cgcacgtata tatcctccgc cggggcacgt acggtacaat    60
tcccag                                                               66

SEQ ID NO: 86          moltype = DNA  length = 95
FEATURE                Location/Qualifiers
source                 1..95
                       mol_type = unassigned DNA
                       organism = Zea mays
SEQUENCE: 86
aaggcgcaaa tgagtagcag cgcacgtata tatacgcgta cgcgtatgtg aggtatatat    60
atcctccgcc ggggcacgta cggtacaatt cccag                               95

SEQ ID NO: 87          moltype = DNA  length = 95
FEATURE                Location/Qualifiers
source                 1..95
                       mol_type = unassigned DNA
                       organism = Zea mays
SEQUENCE: 87
ccttcgcaaa tgagtagcag cgcacgtata tatacgcgta cgcgtacgtg aggtatatat    60
atcctccgcc ggggcacgta cggtacaatt cccag                               95

SEQ ID NO: 88          moltype = DNA  length = 68
FEATURE                Location/Qualifiers
source                 1..68
                       mol_type = unassigned DNA
```

```
                                    organism = Zea mays
SEQUENCE: 88
ccttcgcaaa tgagtagcag cgcacgtata tatatcctcc gccggggcac gtacggtaca    60
attcccag                                                             68

SEQ ID NO: 89           moltype = DNA   length = 65
FEATURE                 Location/Qualifiers
source                  1..65
                        mol_type = unassigned DNA
                        organism = Zea mays
SEQUENCE: 89
ccttcgcaaa tgagtagcag cgcacgtata tatacgcgta cgcgtacgta cggtacaatt    60
cccag                                                                65

SEQ ID NO: 90           moltype = DNA   length = 55
FEATURE                 Location/Qualifiers
source                  1..55
                        mol_type = unassigned DNA
                        organism = Zea mays
SEQUENCE: 90
ccttcgcaaa tgagtagcag cgcacgtata tatacgcgta cggtacaatt cccag         55

SEQ ID NO: 91           moltype = DNA   length = 69
FEATURE                 Location/Qualifiers
source                  1..69
                        mol_type = unassigned DNA
                        organism = Zea mays
SEQUENCE: 91
ccttcgcaaa tgagtagcag cgcacgtata tatacgcgta cgccggggca cgtacggtac    60
aattcccag                                                            69

SEQ ID NO: 92           moltype = DNA   length = 85
FEATURE                 Location/Qualifiers
source                  1..85
                        mol_type = unassigned DNA
                        organism = Zea mays
SEQUENCE: 92
ccttcgcaaa tgagtagcag cgcacgtata tatacgtgtg aggtatatat atcctccgcc    60
ggggcacgta cggtacaatt cccag                                          85

SEQ ID NO: 93           moltype = DNA   length = 93
FEATURE                 Location/Qualifiers
source                  1..93
                        mol_type = unassigned DNA
                        organism = Zea mays
SEQUENCE: 93
ccttcgcaaa tgagtagcag cgcacgtata tatacgcgta cgcgtgtgag gtatatatat    60
cctccgccgg ggcacgtacg gtacaattcc cag                                 93

SEQ ID NO: 94           moltype = DNA   length = 66
FEATURE                 Location/Qualifiers
source                  1..66
                        mol_type = unassigned DNA
                        organism = Zea mays
SEQUENCE: 94
ccttcgcaaa tgagtagcag cgcacgtata tatcctccgc cggggcacgt acgtacaat    60
tcccag                                                               66

SEQ ID NO: 95           moltype = DNA   length = 95
FEATURE                 Location/Qualifiers
source                  1..95
                        mol_type = unassigned DNA
                        organism = Zea mays
SEQUENCE: 95
ccttcgcaaa tgagtagcag cgcacgtata tatacgcgta cgcgtacgtg tggtatatat    60
atcctccgcc ggggcacgta cggtacaatt cccag                               95

SEQ ID NO: 96           moltype = DNA   length = 102
FEATURE                 Location/Qualifiers
source                  1..102
                        mol_type = unassigned DNA
                        organism = Zea mays
SEQUENCE: 96
ccttcgcaaa tgagtagcag cgcacgtata tatacgcgta cggtatatat acgtgtgagg    60
tatatatatc ctccgccggg gcacgtacgg tacaattccc ag                       102

SEQ ID NO: 97           moltype = DNA   length = 5424
FEATURE                 Location/Qualifiers
misc_feature            1..5424
```

```
                  note = synthesized sequence- donor DNA -HR Repair DNA
source            1..5424
                  mol_type = other DNA
                  organism = synthetic construct
SEQUENCE: 97
cccatagaaa actgtgtgct ataatacacc aaaaggaaag caaagtgaaa aggaaacttt    60
gaatagccaa gaagactcgg agtgcttcac gccttcacct atcccacata ggtgatgagc   120
taagagtaaa atgtagattc tctcgagtac tgaatattgc ctgcactttt ccttgcagta   180
aatacacctt taatccatga cgagagtcca ctctttgagt ccgtcttgag attcttccat   240
tgatcataca acatgacctc gaagtcctga tggagaacaa cttatataat taaaactaca   300
atacagaaag ttcctgacaa ttaaaacctt tggtggtggc atgccgtagg ttaaaaaaaa   360
tagataatga caacacaact ggagacacgc tctttgccga gtgctcacac gtttgctgag   420
agcgagcact cggcaaatat atgatttgcc gaataccacc ctcctcggca aaacaataca   480
ctaggcaaaa aggtagtttc ccatcaccat gatgcccgcc gttaatgtac cttctatgcc   540
gagtatgttg gcgctcagca aagagatcgt taccggcgtt tgtttcacca agagctcttt   600
gacgagtgtg gcacacgaca aaaccttttg ccgagtgtaa ttagtcgttt gccaagtgac   660
tggtgcagtt ggcaaaggag tcgtttatta tgtgtgggca aaatgatata tggtgccagt   720
tagggctagc aaattaaagg gggggggggg ggggttaggt tgaagaaggt gacgagtaat   780
aaggtctcgg acggccgcgc gcatatatat cagatccgat ccaatggcac acggtgcaaa   840
cgaaaagcac gaaatttcca ccagcttaat tagggagaga aaaatagagc accagctgat   900
gagtgaatga atgagataga cgggacacag agggtccagc aggctagcct actctggccg   960
ccctaaatag aagtcagtgc cgtgacgacg cgcaaacttc tttttgatcgg ctgcggaaat  1020
aatatactgt aacgatttac gcacctgctg ggaattgtac cgtacgtgcc ccggcggagg  1080
atatatatac ctcacacaag ggcgaattgt actagttagt tagctagtcg gtcctagatg  1140
ccgtaatcat tagctaatcg taagtgacgc ttggacacga gcggcttgag ctaggaacct  1200
acgaagtcat cggaatcagc tcaggtgtac agaagttcct atactttctg gagaatagga  1260
acttcggaat aggaacttcg tatacgctag ggccgcattc gcaaaacaca cctagactag  1320
atttgttttg ctaacccaat tgatattaat tatatatgat taatatttat atgtatatgg  1380
atttggttaa tgaaatgcat ctggttcatc aaagaattat aaagacacgt gacattcatt  1440
taggataaga aatatggatg atctctttct cttttattca gataactagt aattacacat  1500
aacacacaac tttgatgccc acattatagt gattagcatg tcactatgtg tgcatccttt  1560
tatttcatac attaattaag ttggccaatc cagaagatgg acaagtctag gtttcgactc  1620
agatctgcgt caccgggcgc accgggcgcg gcgggccgg cagctcgaag tcgcgctgcc   1680
agaagccgac gtcgtgccag ccgccgtgct tgtagccggc ggcgcggagg gtgccgcggg  1740
cggtgctagc gaggccctcg tggaggcgca cggacgggtc gttcgggagg ccgatcacgg  1800
ccaccacgga cttgaagccc tgggcctcca tgctcttgag gaggtgggtg tagagggtgg  1860
agccgaggcc gaggcgctgg tggcggtggg acacgtacac ggtggactcc acggtccagt  1920
cgtaggcgtt gcgggccttc cacgggccgg cgtaggcgat gccggccacc acgccctcca  1980
cctcggccac gagccacggg tagccgtcct ggaggcgctc caggtcgtcg atccactcct  2040
gcggggtctg cggctcggtg cggaagttca ccggtggaggt ctcgatgtag tggttcacga  2100
tgtcgcacac ggcggccatg tcggcggcgg tggccgggcg gatctcgacg gggcggcgct  2160
cggggggacat ggtgtcgtgt ggatcccggt ggatctgaag ttcctatact ttctagaaa   2220
taggaacttc ggaataggaa cttcgctagc gaattgatcc tctagagtcg acctgcagaa  2280
gtaacaccaa acaacagggt gagcatcgac aaaagaaaca gtaccaagca aataaatagc  2340
gtatgaaggc agggctaaaa aaatccacat atagctgctg catatgccat catccaagta  2400
tatcaagatc aaaataatta taaaacatac ttgtttatta taatagatag gtactcaagg  2460
ttagagcata tgaatagatg ctgcatatgc catcatgtat atgcatcagt aaaacccaca  2520
tcaacatgta tacctatcct agatcgatat ttccatccat cttaaactcg taactatgaa  2580
gatgtatgac acacacatac agttccaaaa ttaataaaata caccaggtag tttgaaacag  2640
tattctactc cgatctagaa cgaatgaacg accgcccaac cacaccacat catcacaacc  2700
aagcaacaa aaagcatctc tgtatatgca tcagtaaaac ccgcatcaac atgtataccct 2760
atcctagatc gatatttcca tccatcatct tcaattcgta actatgaata tgtatggcac  2820
acacatacag atccaaaatt aataaaatcca ccaggtagtt tgaaacagaa ttctactccg  2880
atctagaacg accgcccaac cagaccacat catcacaacc aagacaaaaa aaagcatgaa  2940
aagatgaccc acaaaacaag tgcacggcat atattgaaat aaaggaaaag ggcaaaccaa  3000
accctatgca acgaaacaaa aaaatcatg aaatcgatcc cgtctgcgga acggctagag  3060
ccatcccagg attccccaaa gagaaacact ggcaagttag caatcagaac gtgtctgacg  3120
tacaggtcgc atccgtgtac gaacgctagc agcacggatc taacacaaac acggatctaa  3180
cacaaacatg aacagaagta gaactaccgg gccctaacca tgcatggacc ggaacgccga  3240
tctagaaaag gtagagaggg ggggggggga ggacgagcgg cgtaccttga agcggaggtg  3300
ccgacgggtg gatttggggg agatctggtt gtgtgtgtgt gcgctccgaa caacacgagg  3360
ttggggaaag agggtgtgga ggggtgtct atttattacg gcgggcgagg aagggaaagc   3420
gaaggagcgg tgggaaagga atccccccgta gctgccggtg ccgtgagagg aggaggaggc  3480
cgcctgccgt gccggctcac gtctgccgct ccgccacgca atttctggat gggcggcgtg  3540
gagcaagtcc aacggtggag cggaactctc gagaggggtc cagaggcagc gacagagatg  3600
ccgtgccgtc tgcttcgctt ggcccgacgc gacgctgctg gttcgctggt tggtgtccgt  3660
tagactcgtc gacggcgttt aacaggctgg cattatctac tcgaaacaag aaaaatgttt  3720
ccttagtttt tttaatttct taaagggtat ttgttttaatt ttagtcctt ttattttatt  3780
ctattttata tctaaattat taaataaaaa aactaaaata gagttttagt tttcttaatt  3840
tagaggctaa aatagaataa aatagatgta ctaaaaaaat tagtctataa aaaccattaa  3900
ccctaaaccc taaatggatg tactaataaa atggatgaag tattatatag gtgaagctat  3960
ttgcaaaaaa aaggagaac acatgcacac taaaagata aaactgtaga gtcctgttgt   4020
caaaatactc aattgtcctt tagaccatgt ctaactgttc atttatatga ttctctaaaa  4080
cactgatatt attgtagtac tatagattat aaattattcgta taagtt tatatatatg   4140
tataaagata gataaactgc acttcaaaca agtgtgacaa aaaaaatatg tggtaatttt  4200
ttataactta gacatgcaat gctcattatc tctagagagg ggcacgaccg ggtcacgctg  4260
cactgcaggg tagcggcgaa ttcgcccttg tacgcgtacg cgtatatata cgtgcgctgc  4320
tactcatttg cgcgggaata cagctcagtc tgctgtgcgc tgcaggatgt acatacatac  4380
atgcgcaggt gcaaagtcta cgcgcgcggg caatgcaagc ccctggcgta gttgggccat  4440
```

```
gactgagatc acgcctcatg gtcatggaac gaaacaccgc gtccggccgg gctgccctg    4500
gcgtcacgcg ggaggcagct gctagcgtta gcgtacgtac ccaccgtctc gtacacacca    4560
ccgcagggag agagaagagc gatgcaatgc acatgtacag catccgcatc atgcatagat    4620
actcatatct tcaaggccac acatgcagca gtgtcgtacg ctacgttgtt caacggagg     4680
aggaggatac atacatagac acccacagcc agcctagcac atagcagata gcatacggac    4740
tcccgggtga ggaaaaatgg agggcgaacc aaaccaacca caaagaagca gcagcagcag    4800
cagcagcagc tgcggctgct atcaccactc accaactcca attaaagatc tctctctctc    4860
tctctactgg ccgccctgt cagtgccagc gcccggtttg ttgctagctg agctgcgggc     4920
gtcgctctta gatatagccc aaaactcact ccaccaccac tcgttccatg gaaccctaga    4980
ccaaaagtac tcgcgctctc ggccctcgct ctcgccctct ccctctccgc agcaaaagag    5040
atccggccgg ccgagaaggg cgcgcgctag ctgcccggct actagctggc gcccgccgc     5100
gcatatatct gtgtcatcgc catcacccac accatggccc ggccggccaa caccgccgta    5160
ttagctctgt ctgtcgctcg tccacctgcg accgactgag cgatcgatct ccaccgagct    5220
ctccgctaag cgctgtcctt gccgcgtcc tcccctccgt cccctacgca tccatttccg     5280
tgtgctcgtg tgtgcgcgcg cgggcactcc tgctcctgct ccctccgcc cctcctcccc     5340
tcccaggctc ccagctagcc gcgcccgccc gcgcgacctg cacctgcaca gatcgggcgg    5400
ccgggccgac cgatcgatcg agat                                            5424

SEQ ID NO: 98           moltype = DNA  length = 24
FEATURE                 Location/Qualifiers
misc_feature            1..24
                        note = synthesized sequence- Forward PCR primer
source                  1..24
                        mol_type = other DNA
                        organism = synthetic construct
SEQUENCE: 98
cccgttattg tatgaggtaa tgac                                            24

SEQ ID NO: 99           moltype = DNA  length = 31
FEATURE                 Location/Qualifiers
misc_feature            1..31
                        note = synthesized sequence- Reverse PCR primer for
                         site-specific transgene insertion at junction 1
source                  1..31
                        mol_type = other DNA
                        organism = synthetic construct
SEQUENCE: 99
gctcgtgtcc aagcgtcact tacgattagc t                                    31

SEQ ID NO: 100          moltype = DNA  length = 32
FEATURE                 Location/Qualifiers
misc_feature            1..32
                        note = synthesized sequence- Forward PCR primer for
                         site-specific transgene insertion at junction 2
source                  1..32
                        mol_type = other DNA
                        organism = synthetic construct
SEQUENCE: 100
ccatgtctaa ctgttcattt atatgattct ct                                   32

SEQ ID NO: 101          moltype = DNA  length = 24
FEATURE                 Location/Qualifiers
misc_feature            1..24
                        note = synthesized sequence- Reverse PCR primer for
                         site-specific transgene insertion at junction 2
source                  1..24
                        mol_type = other DNA
                        organism = synthetic construct
SEQUENCE: 101
gcagccgata ggttcatcat cttc                                            24

SEQ ID NO: 102          moltype = DNA  length = 7850
FEATURE                 Location/Qualifiers
misc_feature            1..7850
                        note = synthesized sequence- Linked Cas9 and LIGCas-3 long
                         guide RNA expression cassettes
source                  1..7850
                        mol_type = other DNA
                        organism = synthetic construct
SEQUENCE: 102
gtgcagcgtg acccggtcgt gcccctctct agagataatg agcattgcat gtctaagtta    60
taaaaaatta ccacatattt ttttgtcac acttgtttga agtgcagttt atctatcttt    120
atacatatat ttaaacttta ctctacgaat aatataatct atagtactac aataatatca    180
gtgttttaga gaatcatata aatgaacagt tagacatggt ctaaaggaca attgagtatt    240
ttgacaacag gactctacag ttttatcttt ttagtgtgca tgtgttctcc tttttttttg    300
caaatagctt cacctatata atacttcatc catttttatta gtacatccat ttagggttta    360
gggtaatgg ttttttataga ctaatttttt tagtacatct attttatctt attttagcct    420
ctaaattaag aaaactaaaa ctctatttta gttttttttat ttaataattt agatataaaa    480
tagaataaaa taaagtgact aaaaaattaaa caaatagccct ttaagaaatt aaaaaaacta    540
```

-continued

```
aggaaacatt tttcttgttt cgagtagata atgccagcct gttaaacgcc gtcgacgagt 600
ctaacggaca ccaaccagcg aaccagcagc gtcgcgtcgg gccaagcgaa gcagacggca 660
cggcatctct gtcgctgcct ctggacccct ctcgagagtt ccgctccacc gttggacttg 720
ctccgctgtc ggcatccaga aattgcgtgg cggagcggca gacgtgagcc ggcacggcag 780
gcggcctcct cctcctctca cggcaccggc agctacgggg gattcctttc ccaccgctcc 840
ttcgctttcc cttcctcgcc cgccgtaata aatagacacc ccctccacac cctctttccc 900
caacctcgtg ttgttcggag cgcacacaca cacaaccaga tctcccccaa atccaccgt 960
cggcacctcc gcttcaaggt acgccgctcg tcctcccccc cccccctctc taccttctct 1020
agatcggcgt tccggtccat gcatggttag ggcccggtag ttctacttct gttcatgttt 1080
gtgttagatc cgtgtttgtg ttagatccgt gctgctagcg ttcgtacacg gatgcgacct 1140
gtacgtcaga cacgttctga ttgctaactt gccagtgttt ctctttgggg aatcctggga 1200
tggctctagc cgttccgcag acgggatcga tttcatgatt tttttttgttt cgttgcatag 1260
ggtttggttt gcccttttcc tttatttcaa tatatgccgt gcacttgttt gtcgggtcat 1320
cttttcatgc tttttttttgt cttggttgtg atgatgtggt ctggttgggc ggtcgttcta 1380
gatcggagta gaattctgtt tcaaaactacc tggtggattt attaattttg gatctgtatg 1440
tgtgtgccat acatattcat agttacgaat gaagatgat ggatggaaat atcgatctag 1500
gataggtata catgttgatg cgggtttttac tgatgcatat acagagatgc tttttgttcg 1560
cttggttgtg atgatgtggt gtggttgggc ggtcgttcat tcgttctaga tcggagtaga 1620
atactgtttc aaactacctg gtgtatttat taattttgga actgtatgtg tgtgtcatac 1680
atcttcatag ttacgagttt aagatggatg gaaatatcga tctaggatag gtatacatgt 1740
tgatgtgggt tttactgatg catatacatg atggcatatg cagcatctat tcatatgctc 1800
taaccttgag tacctatcta ttataataaa caagtatgtt ttataattat tttgatcttg 1860
atatacttgg atgatggcat atgcagcagc tatatgtgta ttttttttagc cctgccttca 1920
tacgctattt atttgcttgg tactgttttct tttgtcgatg ctcaccctgt tgtttggtgt 1980
tacttctgca ggtcgactct agaggatcca tggcaccgaa gaagaagcgc aaggtgatgg 2040
acaagaagta cagcatcggc ctcgacatcg gcaccaactc ggtgggctgg gccgtcatca 2100
cggacgaata taaggtcccg tcgaagaagt tcaaggtcct cggcaataca gaccgccaca 2160
gcatcaagaa aaacttgatc ggcgccctcc tgttcgatag cggcgagacc gcggaggcga 2220
ccaggctcaa gaggaccgcc aggagacggt acactaggcg caagaacagg atctgctacc 2280
tgcaggagat cttcagcaac gagatggcga aggtggacga ctccttcttc caccgcctgg 2340
aggaatcatt cctggtggag gaggacaaga agcatgagcg gcacccaatc ttcggcaaca 2400
tcgtcgacga ggtaagtttc tgcttctacc tttgatatat atataataat tatcattaat 2460
tagtagtaat ataatatttc aaatattttt ttcaaaataa aagaatgtag tatatagcaa 2520
ttgcttttct gtagtttata agtgtgtata ttttaattta taacttttct aatatatgac 2580
caaaacatgg tgatgtgcag gtggcctacc acgagaagta cccgacaatc taccacctcc 2640
ggaagaaact ggtggacagc acagacaagg cggacctccg gctcatctac cttgccctcg 2700
cgcatatgat caagttccgc ggccacttcc tcatcgaggg cgacctgaac ccggacaact 2760
ccgacgtgga caagctgttc atccagctcg tgcagacgta caatcaactg ttcgaggaga 2820
acccataaa cgctagcggc gtggacgcca aggccatcct ctcggccagg ctctcgaaat 2880
caagaaggct ggagaacctt atcgcgcagt tgccaggcga aaagaagaac ggcctcttcg 2940
gcaaccttat tgcgctcagc ctcggcctga cgccgaactt caaatcaaac ttcgacctcg 3000
cggaggacgc caagctccag ctctcaaagg acacctacga cgacgacctc gacaacctcc 3060
tggcccagat aggagaccag tacgccgacc tcttcctcgc cgcaagaac ctctccgacg 3120
ctatcctgct cagcgacatc cttcgggtca acaccgaaat taccaaggca ccgctgtccc 3180
ccagcatgat taaacgctac gacgagcacc atcaggacct cacgctgctc aaggcactcg 3240
tccgccagca gctccccgag aagtacaagg agatcttctt cgaccaatca aaaaacggct 3300
acgcgggata tatcgacggc ggtgccagcc aggaagagtt ctacaagttc atcaaaccaa 3360
tcctggagaa gatggacggc accgaggagt tgctggtcaa gctcaacagg gaggacctcc 3420
tcaggaagca gaggaccttc gacaacggct ccatcccgca tcagatccac ctgggcgaac 3480
tgcatgccat cctgcggcgc caggaggact tctacccgtt cctgaaggat aaccgggaga 3540
agatcggaga gatcttgacg ttccgcatcc catactacgt gggcccgctg gctcgcggca 3600
actcccggtt cgcctggatg acccggaagt cggaggagac catcacaccc tggaactttg 3660
aggaggtggt cgataagggc gctagcgctc agagcttcat cgagcgcatg accaacttcg 3720
ataaaaacct gcccaatgaa aaagtcctcc ccaagcactc gctgctctac gagtacttca 3780
ccgtgtacaa cgagctcacc aaggtcaaat acgtcaccga ggcgcatgcgg aagccggcgt 3840
tcctgagcgg cgagcagaag aaggcgatag tggaccttcct cttcaagacc aacaggaagg 3900
tgaccgtgaa gcaattaaaa gaggactact tcaagaaaat agagtgcttc gactccgtgg 3960
agatctcggg cgtggaggat cggttcaacg cctcactcgg cacgtatcac gacctcctca 4020
agatcattaa agacaaggac ttcctcgaca acgaggagaa cgaggacatc ctcgaggaca 4080
tcgtcctcac cctgaccctg ttcgaggacc gcgaaatgat cgaggagagg ctgaagacct 4140
acgcgcacct gttcgacgac aaggtcatga aacagctcaa gaggcgccgc tacactggtt 4200
ggggaaggct gtcccgcaag ctcattaatg gcatcaggga caagcagagc ggcaagacca 4260
tcctggactt cctcaagtcc gacggggtccg ccaaccgcaa cttcatgcag ctcattcacg 4320
acgactcgct cacgttcaag gaagacatcc agaaggcaca ggtgagcggg cagggtgact 4380
ccctccacga acacatcgcc aacctggccg gctcgccggc cattaaaaag gcatcctgc 4440
agacggtcaa ggtcgtcgac gagtcgtgca aggtgatggg ccggcacaag cccgaaaata 4500
tcgtcataga gatggccagg gagaaccaga ccacccaaaa agggcagaag aactcgcgcg 4560
agcggatgaa acggatcgag gagggcatta aagagctcgg gtcccagatc ctgaaggagc 4620
accccgtgga aaataccag ctccagaatg aaaagctcta cctctactac ctgcagaagg 4680
gccgcgacat gtacgtggac caggagctgg acattaatcg gctatcggac tacgacgtcg 4740
accacatcgt gccgcagtcg ttcctcaagg acgatagcat cgacaacaag gtgctcaccc 4800
ggtcggataa aaatcgggc aagagcgaca acgtgcccag cgaggaggtc gtgaagaaga 4860
tgaaaaacta ctggcgccag ctcctcaacg cgaaactgat cacccagcgc aagttcgaca 4920
acctgacgga ggcgaacgc ggttgcttga gcgaactcga taaggcgggc ttcataaaaa 4980
ggcagctggt cgagacgcgc cagatcacga agcatgtcgc ccagatcctg gacagccgca 5040
tgaatactaa gtacgatgaa aacgacaagc tgatccggga ggtgaaggtg atcacgctga 5100
agtccaagct cgtgtcggac ttccgcaagg acttccagtt ctacaaggtc cgcgagatca 5160
acaactacca ccacgcccac gacgcctacc tgaatgcggt ggtcgggacc gccctgatca 5220
agaagtaccc gaagctggag tcggagttcg tgtacggcga ctacaaggtc tacgacgtgc 5280
```

```
gcaaaatgat cgccaagtcc gagcaggaga tcggcaaggc cacggcaaaa tacttcttct    5340
actcgaacat catgaacttc ttcaagaccg agatcaccct cgcgaacggc gagatccgca    5400
agcgcccgct catcgaaacc aacgcgaga  cgggcgagat cgtctgggat aagggccggg    5460
atttcgcgac ggtccgcaag gtgctctcca tgccgcaagt caatatcgtg aaaaagacgg    5520
aggtccagac gggcgggttc agcaaggagt ccatcctccc gaagcgcaac tccgacaagc    5580
tcatcgcgag gaagaaggat tgggacccga aaaaatatgg cggcttcgac agcccgaccg    5640
tcgcatacag cgtcctcgtc gtggcgaagg tggagaaggg caagtcaaag aagctcaagt    5700
ccgtgaagga gctgctcggg atcacgatta tggagcggtc ctccttcgag aagaacccga    5760
tcgacttcct agaggccaag ggatataagg aggtcaagaa ggacctgatt attaaactgc    5820
cgaagtactc gctcttcgag ctggaaaacg gccgcaagag gatgctcgcc tccgcaggcg    5880
agttgcagaa gggcaacgag ctcgcccgca cgagcaaata cgtcaatttc ctgtacctcg    5940
ctagccacta tgaaaagctc aagggcagcc cggaggacaa cgagcagaag cagctcttcg    6000
tggagcagca caagcattac ctggacgaga tcatcgagca gatcagcgag ttctcgaagc    6060
gggtgatcct cgccgacgcg aacctggaca aggtgctgtc ggcatataac aagcaccgcg    6120
acaaaccaat acgcgagcag gccgaaaata tcatccacct cttcaccctc accaacctcg    6180
gcgctccggc agccttcaag tacttcgaca ccacgattga ccggaagcgg tacacgagca    6240
cgaaggaggt gctcgatgcg acgctgatcc accagagcat cacagggctc tatgaaacac    6300
gcatcgacct gagccagctg ggcggagaca agagaccacg gaccgccac gatggcgagc    6360
tgggaggccg caagcgggca aggtaggtac cgttaaccta gacttgtcca tcttctggat    6420
tggccaactt aattaatgta tgaaataaaa ggatgcacac atagtgacat gctaatcact    6480
ataatgtggg catcaaagtt gtgtgttatg tgtaattact agttatctga ataaaagaga    6540
aagagatcat ccatatttct tatcctaaat gaatgtcaag tgtctttata ttctttgat    6600
gaaccagatg catttcatta accaaatcca tatacatata aatattaatc atatataatt    6660
aatatcaatt gggttagcaa aacaaatcta gtctaggtgt gttttgcgaa tgcggccccc    6720
cctcgaggtc gacggtatcg ataagctttg agagtacaat gatgaaccta gattaatcaa    6780
tgccaaagtc tgaaaaatgc accctcagtc tatgatccag aaaatcaaga ttgcttgagg    6840
ccctgttcgg ttgttccgga ttagagcccc ggattaattc ctagccggat tacttctcta    6900
atttatatag attttgatga gctggaatga atcctggctt attccggtac aaccgaacag    6960
gccctgaagg ataccagtaa tcgctgagct aaattggcat gctgtcagag tgtcagtatt    7020
gcagcaaggt agtgagtaa ccggcatcat ggtgccagtt tgatggcacc attagggtta    7080
gagatggtgg ccatgggcgc atgtcctggc caactttgta tgatatatgg cagggtgaat    7140
aggaaagtaa aattgtattg taaaaaggga tttcttctgt ttgttagcgc atgtacaagg    7200
aatgcaagtt ttgagcgagg gggcatcaaa gatctggctg tgtttccagc tgttttttgtt   7260
agcccccatcg aatccttgac ataatgatcc cgcttaaata agcaacctcg cttgtatagt    7320
tccttgtgct ctaacacacg atgatgataa gtcgtaaaat agtggtgtcc aaagaatttc    7380
caggcccagt tgtaaaagct aaaatgctat tcgaatttct actagcagta agtcgtgttt    7440
agaaattatt ttttttatata ccttttttcc ttctatgtac agtaggacac agtgtcagcg    7500
ccgcgttgac ggagaatatt tgcaaaaaag taaaagagaa agtcatagcg gcgtatgtgc    7560
caaaaacttc gtcacagaga gggccataag aaacatggcc cacggcccaa tacgaagcac    7620
cgcgacgaag cccaaacagc agtccgtagg tggagcaaag cgctgggtaa tacgcaaacg    7680
ttttgtccca ccttgactaa tcacaagagt ggagcgtacc ttataaaccg agccgcaagc    7740
accgaattgc gtacgcgtac gtgtggtttt agagctagaa atagcaagtt aaaataaggc    7800
tagtccgtta tcaacttgaa aaagtggcac cgagtcggtg cttttttttt               7850

SEQ ID NO: 103        moltype = DNA   length = 23
FEATURE               Location/Qualifiers
source                1..23
                      mol_type = unassigned DNA
                      organism = Zea mays
SEQUENCE: 103
tgggcaggtc tcacgacggt tgg                                              23

SEQ ID NO: 104        moltype = DNA   length = 91
FEATURE               Location/Qualifiers
source                1..91
                      mol_type = unassigned DNA
                      organism = Zea mays
SEQUENCE: 104
ccggtttcgc gtgctctggc tttacattac atgggcaggt ctcacgacgg ttgggctgga     60
gagccggctg gtaggggagg acctcaacgg c                                    91

SEQ ID NO: 105        moltype = DNA   length = 90
FEATURE               Location/Qualifiers
source                1..90
                      mol_type = unassigned DNA
                      organism = Zea mays
SEQUENCE: 105
ccggtttcgc gtgctctggc tttacattac atgggcaggt ctcacgaggt tgggctggag     60
agccggctgg taggggagga cctcaacggc                                      90

SEQ ID NO: 106        moltype = DNA   length = 90
FEATURE               Location/Qualifiers
source                1..90
                      mol_type = unassigned DNA
                      organism = Zea mays
SEQUENCE: 106
ccggtttcgc gtgctctggc tttacattac atgggcaggt ctcacacggt tgggctggag     60
agccggctgg taggggagga cctcaacggc                                      90
```

| SEQ ID NO: 107 | moltype = DNA length = 92 |
|---|---|
| FEATURE | Location/Qualifiers |
| source | 1..92 |
| | mol_type = unassigned DNA |
| | organism = Zea mays |

SEQUENCE: 107

| | | | | |
|---|---|---|---|---|
| ccggtttcgc gtgctctggc tttacattac atgggcaggt ctcacgacgg tttgggctgg | | | | 60 |
| agagccggct ggtaggggag gacctcaacg gc | | | | 92 |

| SEQ ID NO: 108 | moltype = DNA length = 89 |
|---|---|
| FEATURE | Location/Qualifiers |
| source | 1..89 |
| | mol_type = unassigned DNA |
| | organism = Zea mays |

SEQUENCE: 108

| | |
|---|---|
| ccggtttcgc gtgctctggc tttacattgc atgagcaggt cgtgacggtt gggctggaga | 60 |
| gccggctggt aggggaggac ctcaacggc | 89 |

| SEQ ID NO: 109 | moltype = DNA length = 57 |
|---|---|
| FEATURE | Location/Qualifiers |
| source | 1..57 |
| | mol_type = unassigned DNA |
| | organism = Zea mays |

SEQUENCE: 109

| | |
|---|---|
| gggcaggtct cgacggttgg gctggagagc cggctggtag gggaggacct caacggc | 57 |

| SEQ ID NO: 110 | moltype = DNA length = 57 |
|---|---|
| FEATURE | Location/Qualifiers |
| source | 1..57 |
| | mol_type = unassigned DNA |
| | organism = Zea mays |

SEQUENCE: 110

| | |
|---|---|
| ccggtttcgc gtgctcttgg gctggagagc cggctggtag gggaggacct caacggc | 57 |

| SEQ ID NO: 111 | moltype = DNA length = 22 |
|---|---|
| FEATURE | Location/Qualifiers |
| source | 1..22 |
| | mol_type = unassigned DNA |
| | organism = Zea mays |

SEQUENCE: 111

| | |
|---|---|
| atatacctca cacgtacgcg ta | 22 |

| SEQ ID NO: 112 | moltype = DNA length = 1053 |
|---|---|
| FEATURE | Location/Qualifiers |
| source | 1..1053 |
| | mol_type = unassigned DNA |
| | organism = Zea mays |

SEQUENCE: 112

| | |
|---|---|
| atgaacacca agtacaacaa ggagttcctg ctctacctgg ccggcttcgt ggacggcgac | 60 |
| ggctccatca aggcgcagat caagccgaac cagtcctgca agttcaagca ccagctctcc | 120 |
| ctgacccttcc aggtgaccca gaagacgcag aggcgctggt tcctcgacaa gctggtcgac | 180 |
| gagatcgggg tgggctacgt ctacgaccgc gggtcggtgt ccgactacga gctctcccag | 240 |
| atcaagcccc tgcacaactt cctcacccag ctccagccgt tcctcaagct gaagcagaag | 300 |
| caggcgaacc tcgtcctgaa gatcatcgag cagctcccct cggccaagga gtccccggac | 360 |
| aagttcctgg aggtgtgcac gtgggtcgac cagatccggg ccctcaacga cagcaagacc | 420 |
| cgcaagacga cctcggagac ggtgcgggcg tcctggact ccctcccagg atccgtggga | 480 |
| ggtctatcgc catctcaggc atccagcgcc gcatcctcgg cttcctcaag cccgggttca | 540 |
| gggatctccg aagcactcag agctggagca actaagtcca aggaattcct gctctacctg | 600 |
| gccggcttcg tggacggcga cggctccatc atcgcgttca tcaagccgcg ccagtgctac | 660 |
| aagttcaagc acgagctccg cctggagttc accgtgaccc agaagacgca gaggcgctac | 720 |
| ttcctcgaca agctggtcga cgagatcggg gtgggctacg tctacgaccg cgggtcggtg | 780 |
| tccgactacc gcctctccca gatcaagccc ctgcacaact tcctcaccca gctccagccg | 840 |
| ttcctcaagc tgaagcagaa gcaggcgaac ctcgtcctga agatcatcga gcagctcccc | 900 |
| tcggccaagg agtccccgga caagttcctg gaggtgtgca cgtgggtcga ccagatcgcg | 960 |
| gccctcaacg acagcaagac cgcaagacg acctcggaga cggtgcgggc ggtcctggac | 1020 |
| tccctcagcg agaagaagaa gtcgtcccccc tga | 1053 |

| SEQ ID NO: 113 | moltype = DNA length = 22 |
|---|---|
| FEATURE | Location/Qualifiers |
| source | 1..22 |
| | mol_type = unassigned DNA |
| | organism = Zea mays |

SEQUENCE: 113

| | |
|---|---|
| gatggtgacg tacgtgccct ac | 22 |

| SEQ ID NO: 114 | moltype = DNA length = 1053 |
|---|---|
| FEATURE | Location/Qualifiers |
| source | 1..1053 |
| | mol_type = unassigned DNA |

```
                        organism = Zea mays
SEQUENCE: 114
atgaacacca agtacaacaa ggagttcctc ctctacctgg caggtttcgt ggacggcgat    60
gggtctatca tcgcccagat tacccccgcaa cagtcctaca agttcaagca cgccctgcgg   120
ctgaggttca cggtcactca gaagacgcag cgcaggtggt tcctcgataa gctggtcgac   180
gaaatcggag tcggcaaggt gcgggacagg ggctctgtca gcgactacat cctctcccag   240
aagaagccgc tccacaactt cctgacccag ctgcagccct tcctcaagct caagcagaag   300
caggccaacc tggtgctcaa gatcatcgag cagctgccat ctgccaagga gtcaccagac   360
aagttccttg aggtctgcac ctgggtcgat cagatcgctg ccctgaacga ctccaagacg   420
aggaagacca cctccgagac cgtcagggct gtgctggact cactcccagg atccgttggc   480
ggtctcagcc cttctcaggc tagctcggct gcttcctcag ccagcagctc acctggctcc   540
ggtatcagcg aggctctcag agcaggtgcc accaagtcca aggagttcct cctgtacctg   600
gcaggcttcg ttgacggcga cggctcgatc atggcgtcca ttaccccgaa ccagtcgtgt   660
aagttcaagc atcagctgcg cctgcgcttt accgtcacgc agaagaccca gaggcgctgt   720
ttcctggaca aactggtgga cgagatcggg gtcgggaagg tgtacgacag agggagcgtt   780
agcgactacc ggctgtccca gaagaagccg ctccacaact tcctgacgca gctccaaccc   840
ttcctgaagc tgaagcagaa gcaggcgaac cttgtgctga gatcattga gcagctgccg   900
agcgccaagg agagccctga caagttcctg gaggtctgca cctgggtcga ccagatcgct   960
gccctcaacg actccaagac caggaagacc acgagcggaga ccgttcgggc tgtcctggac  1020
agcctctccg agaagaagaa gtcgagcccg tag                                1053

SEQ ID NO: 115         moltype = DNA  length = 4104
FEATURE                Location/Qualifiers
misc_feature           1..4104
                       note = synthesized sequence- soybean codon optimized Cas9
source                 1..4104
                       mol_type = other DNA
                       organism = synthetic construct
SEQUENCE: 115
atggacaaaa agtactcaat agggctcgac ataggggacta actccgttgg atgggccgtc    60
atcaccgacg agtacaaggt gccctccaag aagttcaagg tgttgggaaa caccgacagg   120
cacagcataa agaagaattt gatcggtgcc ctcctcttcg actccggaga gaccgctgag   180
gctaccaggc tcaagaggac cgctagaagg cgctacacca aggaagaaa cagaatctgc   240
tacctgcagg agatcttctc caacgagatg gccaaggtgg acgactcctt cttccaccgg   300
cttgaggaat cattcctggt ggaggaggat aaaaagcacg agagacaccc aatcttcggg   360
aacatcgtcg acgaggtggc ctaccatgaa aagtacccta ccatctacca cctgaggaag   420
aagctggtcg actctaccga caaggctgac ttgcgcttga tttacctggc tctcgctcac   480
atgataaagt tccgcggaca cttcctcatt gagggagacc tgaacccaga caactccgac   540
gtggacaagc tcttcatcca gctcgttcag acctacaacc agcttttcga ggagaaccca   600
atcaacgcca gtggagttga cgccaaggct atcctctctg ctcgtctgtc aaagtccagg   660
aggcttgaga acttgattgc ccagctgcct ggcgaaaaga gaacggact gttcggaaac   720
ttgatcgctc tctccctggg attgactccc aacttcaagt ccaacttcga cctcgccgag   780
gacgctaagt tgcagttgtc taaagacacc tacgacgatg acctcgacaa cttgctggcc   840
cagataggcg accaatacgc cgatctcttc ctcgccgcta gaacttgtc cgacgcaatc   900
ctgctgtccg acatcctgag agtcaacact gagattacca agctcctct gtctgcttcc   960
atgattaagc gctacgacga gcaccaccaa gatctgaccc tgctcaaggc cctggtgaga  1020
cagcagctgc ccgagaagta caaggagata tttttcgacc agtccaagaa cggctacgcc  1080
ggatacattg acggaggcgc ctcccaggaa gagttctaca gttcatcaa gccccatctt  1140
gagaagatga cggtaccga ggagctgttg gtgaagttga acagagagga cctgttgagg  1200
aagcagagaa ccttcgacaa cggaagcatc cctcaccaaa tccacctggg agagctccac  1260
gccatcttga ggaggcagga ggatttctat ccctcctgga aggacaaccg cgagaagatt  1320
gagaagatct tgaccttcag aattccttac tacgtcgggc cactcgccag aggaaactct  1380
aggttcgcct ggatgacccg caaatctgaa gagaccatta tcccctggaa cttcgaggaa  1440
gtcgtggaca agggcgcttc cgctcagtct ttcatcgaga ggatgaccaa cttcgataaa  1500
aatctgccca acgagaaggt gctgcccaag cactcccgta tgtacgagta tttcacagtg  1560
tacaacgagc tcaccaaggt gaagtacgtc acagagggaa tgaggaagcc tgccttcttg  1620
tccggagagc agaagaaggc catcgtcgac ctgctcttca agaccaacag gaaggtgact  1680
gtcaagcagc tgaaggagga ctacttcaag aagatcgagt gcttcgactc cgtcgagatc  1740
tctggtgtcg aggacaggtt caacgcctcc ctgggacttt accacgatct gctcaagatt  1800
attaaagaca aggacttcct ggacaacgag gaacgagg acatccttga ggacatcgtg  1860
ctcaccctga ccttgttcga agacaggaa atgatcgaag agaggctcaa gacctacgcc  1920
cacctcttcg acgacaaggt gatgaaacag ctgaagagac gcagatatac cggctgggga  1980
aggctctccc gcaaattgat caacgggatc agggacaagc agtcagggaa gactatactc  2040
gacttcctga gtccgacgg attcgccaac aggaacttca tgcagctcat tcacgacgac  2100
tccttgacct tcaaggagga catccagaag gctcaggtgt ctggacaggg tgactccttg  2160
catgagcaca ttgctaactt ggccggctct ccgctatta agaagggcat tttgcagacc  2220
gtgaaggtct tgacgagct cgtgaaggtg atgggacgcc acaagccaga gaacatcgtt  2280
attgagatgg ctcgcgagaa ccaaactacc cagaaagggc agaagaattc ccgcgagagg  2340
atgaagcgca ttgaggaggg cataaaagag cttggctctc agatcctcaa ggagcaccc  2400
gtcgagaaca ctcagctgca gaacgagaag ctgtacctgt actacctcca aaacggaagg  2460
gacatgtacg tggaccagga gctggacatc aacaggttgt ccgactacga cgtcgaccac  2520
atcgtgcctc agtccttcct gaaggatgac tccatcgaca taaagtgct gacacgctcc  2580
gataaaata gaggcaagtc cgacaacgtc ccctccgagg aggtcgtgaa gaagatgaaa  2640
aactactgga gacagctctt gaacgccaag ctgatcactc gcaagttt cgacaacctg  2700
actaaggctg agagaggagg attgtccgag ctcgataagg ccggattcat caagagacag  2760
ctcgtcgaaa cccgccaaat taccaagcac gtggcccaaa ttctggattc cgcatgaac  2820
accaagtacg atgaaaatga caagctgatc cgcgaggtca aggtgatcac cttgaagtcc  2880
aagctggtct ccgacttccg caaggacttc cagttctaca aggtgaggga gatcaacaac  2940
taccaccacg cacacgacgc ctacctcaac gctgtcgttg gaaccgccct catcaaaaaa  3000
```

-continued

```
tatcctaagc tggagtctga gttcgtctac ggcgactaca aggtgtacga cgtgaggaag    3060
atgatcgcta agtctgagca ggagatcggc aaggccaccg ccaagtactt cttctactcc    3120
aacatcatga acttcttcaa gaccgagatc actctcgcca acggtgagat caggaagcgc    3180
ccactgatcg agaccaacgg tgagactgga gagatcgtgt gggacaaagg gagggatttc    3240
gctactgtga ggaaggtgct ctccatgcct caggtgacat cgtcaagaa gaccgaagtt     3300
cagaccggag gattctccaa ggagtccatc ctccccaaga gaaactccga caagctgatc    3360
gctagaaaga aagactggga ccctaagaag tacggaggct cgattctcc taccgtggcc     3420
tactctgtgc tggtcgtggc caaggtggag aagggcaagt ccaagaagct gaaatccgtc    3480
aaggagctcc tcgggattac catcatggag aggagttcct tcgaagaaga ccctatcgac    3540
ttcctggagg ccaagggata taaagaggtg aagaaggacc tcatcatcaa gctgcccaag    3600
tactccctct tcgagttgga gaacggaagg aagaggatgc tggcttctgc cggagagttg    3660
cagaagggaa atgagctcgc ccttccctcc aagtacgtga acttcctgta cctcgcctct    3720
cactatgaaa agttgaaggg ctctcctgag gacaacgagc agaagcagct cttcgtggag    3780
cagcacaagc actacctgga cgaaattatc gagcagatct ctgagttcgc caagcgcgtg    3840
atattggccg acgccaacct cgacaaggtg ctgtccgcct acaacaagca cagggataag    3900
cccattcgcg agcaggctga aaacattatc cacctgttta ccctcacaaa cttgggagcc    3960
cctgctgcct tcaagtactt cgacaccacc attgacagga gagatacac ctccaccaag    4020
gaggtgctcg acgcaacact catccaccaa tccatcaccg gcctctatga aacaaggatt   4080
gacttgtccc agctgggagg cgac                                          4104
```

SEQ ID NO: 116           moltype = DNA  length = 1503
FEATURE                  Location/Qualifiers
source                   1..1503
                         mol_type = unassigned DNA
                         organism = Glycine max
SEQUENCE: 116
```
ccgggtttac ttattttgtg ggtatctata cttttattag attttaatc aggctcctga     60
tttcttttta tttcgattga attcctgaac ttgtattatt cagtagatcg aataaattat    120
aaaaagataa aatcataaaa taatatttta tcctatcaat catattaaag caatgaatat    180
gtaaaattaa tcttatcttt attttaaaaa atcatatagg tttagtattt ttttaaaaat    240
aaagatagga ttagttttac tattcactgc ttattacttt taaaaaaatc ataaggtttt    300
agtatttttt taaaataaat ataggaatag tttactatt cactgcttta atagaaaaat    360
agtttaaaat ttaagatagt tttaatccca gcatttgcca cgtttgaacg tgagccgaaa    420
cgatgtcgtt acattatctt aacctagctg aaacgatgtc gtcataatat cgccaaatgc    480
caactggact acgtcgaacc cacaaatccc acaaagcgcg tgaaatcaaa tcgctcaaac    540
cacaaaaaag aacaacgcgt tgttacacg ctcaatccca cgcgagtaga gcacagtaac     600
cttcaaataa gcgaatgggg cataatcaga aatccgaaat aaacctaggg gcattatcgg    660
aaatgaaaag tagctcactc aatataaaaa tctaggaacc ctagttttcg ttatcactct    720
gtgctccctc gctctatttc tcagtctctg tgtttgcggc tgaggattcc gaacgagtga    780
ccttcttcgt ttctcgcaaa ggtaacagcc tctgctcttg tctcttcgat tcgatctatg    840
cctgtctctt atttacgatg atgtttcttc ggttatgttt ttttatttat gctttatgct    900
gttgatgttc ggttgtttgt ttcgcttttgt ttttgtggtt cagttttta ggattctttt    960
ggttttttgaa tcgattaatc ggaagagatt ttcgagttat ttggtggtat ggtggtaaat    1020
cttttttttg aggtcataga tctgttgtat ttgtgttata aacatgcgac tttgtatgat    1080
ttttacgag gttatgatgt tctggttgtt ttattatgaa tctgttgaga cagaaccatg      1140
atttttgttg atgttcgttt acactattaa aggtttgttt taacaggatt aaaagttttt    1200
taagcatgtt gaaggagtct tgtagatatg taaccgtcga tgttttttt gtgggttttgt   1260
tcacatgtta tcaagcttaa tcttttacta tgtatgcgac catatctgga tccagcaaag    1320
gcgatttttt aattccttgt gaaacttttg taatatgaag ttgaaatttt gttattggta    1380
aactataaat gtgtgaagtt ggagtatacc tttaccttct tatttggctt tgtgatagtt    1440
taatttatat gtatttgag ttctgacttg tatttctttg aattgattct agtttaagta     1500
atc                                                                  1503
```

SEQ ID NO: 117           moltype = DNA  length = 33
FEATURE                  Location/Qualifiers
misc_feature             1..33
                         note = synthesized sequence- inker SV40 NLS
source                   1..33
                         mol_type = other DNA
                         organism = synthetic construct
SEQUENCE: 117
```
tctagagccg atcccaagaa gaagagaaag gtg                                  33
```

SEQ ID NO: 118           moltype = AA  length = 1379
FEATURE                  Location/Qualifiers
REGION                   1..1379
                         note = synthesized sequence- Cas9 with a SV40 NLS
source                   1..1379
                         mol_type = protein
                         organism = synthetic construct
SEQUENCE: 118
```
MDKKYSIGLD IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG    120
NIVDEVAYHE KYPTIYHLRK KLVDSTDKAD LRLIYLALAH MIKFRGHFLI EGDLNPDNSD    180
VDKLFIQLVQ TYNQLFEENP INASGVDAKA ILSARLSKSR RLENLIAQLP GEKKNGLFGN    240
LIALSLGLTP NFKSNFDLAE DAKLQLSKDT YDDDLDNLLA QIGDQYADLF LAAKNLSDAI    300
LLSDILRVNT EITKAPLSAS MIKRYDEHHQ DLTLLKALVR QQLPEKYKEI FFDQSKNGYA    360
GYIDGGASQE EFYKFIKPIL EKMDGTEELL VKLNREDLLR KQRTFDNGSI PHQIHLGELH    420
AILRRQEDFY PFLKDNREKI EKILTFRIPY YVGPLARGNS RFAWMTRKSE ETITPWNFEE    480
```

```
VVDKGASAQS FIERMTNFDK NLPNEKVLPK HSLLYEYFTV YNELTKVKYV TEGMRKPAFL  540
SGEQKKAIVD LLFKTNRKVT VKQLKEDYFK KIECFDSVEI SGVEDRFNAS LGTYHDLLKI  600
IKDKDFLDNE ENEDILEDIV LTLTLFEDRE MIEERLKTYA HLFDDKVMKQ LKRRRYTGWG  660
RLSRKLINGI RDKQSGKTIL DFLKSDGFAN RNFMQLIHDD SLTFKEDIQK AQVSGQGDSL  720
HEHIANLAGS PAIKKGILQT VKVVDELVKV MGRHKPENIV IEMARENQTT QKGQKNSRER  780
MKRIEEGIKE LGSQILKEHP VENTQLQNEK LYLYYLQNGR DMYVDQELDI NRLSDYDVDH  840
IVPQSFLKDD SIDNKVLTRS DKNRGKSDNV PSEEVVKKMK NYWRQLLNAK LITQRKFDNL  900
TKAERGGLSE LDKAGFIKRQ LVETRQITKH VAQILDSRMN TKYDENDKLI REVKVITLKS  960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKHYLDEII EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGDSR ADPKKKRKV  1379

SEQ ID NO: 119            moltype = DNA   length = 8519
FEATURE                   Location/Qualifiers
misc_feature              1..8519
                          note = synthesized sequence- QC782
source                    1..8519
                          mol_type = other DNA
                          organism = synthetic construct
SEQUENCE: 119
ccgggtttac ttattttgtg ggtatctata ctttttattag attttttaatc aggctcctga   60
tttcttttta tttcgattga attcctgaac ttgtattatt cagtagatcg aataaattat  120
aaaaagataa aatcataaaa taatatttta tcctatcaat catattaaag caatgaatat  180
gtaaaattaa tcttatcttt attttaaaaa atcatatagg tttagtattt ttttaaaaat  240
aaagatagga ttagtttttac tattcactgc ttattacttt taaaaaaatc ataaaggttt  300
agtatttttt taaaataaat ataggaatag ttttactatt cactgcttta atagaaaaat  360
agtttaaaat ttaagatagt tttaatccca gcatttgcca cgtttgaacg tgagccgaaa  420
cgatgtcgtt acattatctt aacctagctg aaacgatgtc gtcataatat cgccaaatgc  480
caactggact acgtcgaacc cacaaatccc acaaagcgcg tgaaatcaaa tcgctcaaac  540
cacaaaaaag aacaacgcgt tgttacacg ctcaatccca cgcagtaga gcacagtaga  600
cttcaaataa gcgaatgggg cataatcaga aatccgaaat aaacctaggg gcattatcgg  660
aaatgaaaag tagctcactc aatataaaaa tctaggaacc ctagttttcg ttatcactct  720
gtgctccctc gctctatttc tcagtctctg tgtttgcggc tgaggattcc gaacgagtga  780
ccttcttcgt ttctcgcaaa ggtaacagcc tctgctcttg tctcttcgat tcgatctatg  840
cctgtctctt atttacgatg atgtttcttc ggttatgttt tttatttat gctttatgct  900
gttgatgttc ggttgtttgt ttcgctttgt ttttgtggtt cagttttta ggattctttt  960
ggttttttgaa tcgattaatc ggaagagatt tcgagttat ttggtgtgtt ggaggtgaat 1020
ctttttttg aggtcatagga tctgttgtat ttgtgttata acatgcgac tttgtatgat 1080
ttttacgag gttgatgt tctggttgtt ttattatgaa tctgttgaga cagaaccatg 1140
attttttgttg atgttcgttt acactattaa aggtttgttt taacaggatt aaaagttttt 1200
taagcatgtt gaaggagtct tgtagatatg taaccgtcga tagtttttt gtgggtttgt 1260
tcacatgtta tcaagcttaa tcttttacta tgtatgcgac catatctgga tccagcaaag 1320
gcgattttttt aattccttgt gaaacttttg taatatgaag ttgaaatttt gttattggta 1380
aactataaat gtgtgaagtt ggagtatacc tttaccttct tatttggctt tgtgatagtt 1440
taatttatat gtattttgag ttctgacttg tattctcttg aattgattct agtttaagta 1500
atccatggac aaaaagtact caatagggct cgacatagg actaactccg ttggatgggc 1560
cgtcatcacc gacgagtaca aggtgccctc caagaagttc aaggtgttgg gaaacaccga 1620
caggcacagc ataaagaaga attttgatcgg tgccctcctc ttcgactccg gagagaccgc 1680
tgaggctacc aggctcaaga ggaccgctag aaggcgctac accagaagga agaacagaat 1740
ctgctacctg caggagatct tctccaacga gatggccaag gtggacgact ccttcttcca 1800
ccgccttgag gaatcattcc tggtggagga ggataaaaag cacgagagac acccaatcct 1860
cgggaacatc gtcgacgagg tggcctacca tgaaaagtac cctaccatct accacctgag 1920
gaagaagctg gtcgactcta ccgacaaggc tgacttgcgc ttgatttacc tggctctcgc 1980
tcacatgata aagttccgcg gacacttcct cattgaggga gacctgaacc cagacaactc 2040
cgacgtggac aagctcttca tccagctcgt tcagacctac aaccagcttt tcgaggagaa 2100
cccaatcaac gccagtggag ttgacgccaa ggctatcctc tctgctcgtc tgtcaaagtc 2160
caggaggctt gagaacttga ttgcccagct gcctggcgaa aagaagaacg gactgttcgg 2220
aaacttgatc gctctctccc tgggattgac tccaacttc aagtccaact cgacctcgc 2280
cgaggacgct aagttgcagt tgtctaaaga cacctacgac gatgacctcg acaacttgct 2340
ggcccagata ggcgaccaat acgccgatct cttcctcgcc gctaagaact tgtccgacgc 2400
aatcctgctg tccgacatcc tgagagtcaa cactgagatt accaaagctc ctctgtctgt 2460
ttccatgatt aagcgctacg acgagcacca ccaagatctg accctgctca ggccctggt 2520
gagacagcag ctgccgaga agtacaagga gatctttttc gaccagtcca gaacggcta 2580
cgccggatac attgacggag gcgcctccca ggaagagttc tacaagttca tcaagccat 2640
ccttgacaca atggacggta ccgaggagct gttggtgaag ttgaacagag aggacctgtt 2700
gaggaagcag agaaccttcg acaacggaag catccctcac caaatccacc tgggagagct 2760
ccacgccatc ttgaggaggc aggaggattt ctatccttc ctgaaggaca accgcgagaa 2820
gattgagaag atcttgacct tcagaattcc ttactacgtc gggccactcg ccagaggaaa 2880
ctcctaggttc gcctggatga cccgcaaatc tgaagagacc attactccct ggaacttcga 2940
ggaagtcgtg gacaaggcgc cttccgctca gtctttcatc gaggatggga ccaacttgga 3000
taaaaatctg cccaacgaga aggtgctgcc caagcactcc ctgttgtacg agtatttcac 3060
agtgtacaac gagctcacca aggtgaagta cgtcacagag ggaatgagga agcctgcctt 3120
cttgtccgga gagcagaaga aggccatcgt cgacctgctc ttcaagacca caggaaggt 3180
gactgtcaag cagctgaagg aggactactt caagaagatc gagtgcttcg actccgtcga 3240
gatctctggt gtcgaggaca ggttcaacgc ctcccttggg acttaccacg atctgctcaa 3300
```

```
gattattaaa gacaaggact tcctggacaa cgaggagaac gaggacatcc ttgaggacat    3360
cgtgctcacc ctgaccttgt tcgaagacag ggaaatgatc gaagagaggc tcaagaccta    3420
cgcccacctc ttcgacgaca aggtgatgaa acagctgaag agacgcagat ataccggctg    3480
gggaaggctc tcccgcaaat tgatcaacgg gatcaggac aagcagtcag ggaagactat     3540
actcgacttc ctgaagtccg acggattcgc caacaggaac ttcatgcagc tcattcacga    3600
cgactccttg accttcaagg aggacatcca gaaggctcag gtgtctggac agggtgactc    3660
cttgcatgag cacattgcta acttggccgg ctctcccgct attaagaagg gcattttgca    3720
gaccgtgaag gtcgttgacg agctcgtgaa ggtgatggga cgccacaagc cagagaacat    3780
cgttattgag atggctcgcg agaaccaaac tacccagaaa gggcagaaga attcccgcgc    3840
gaggatgaag cgcattgagg agggcataaa agagcttggc tctcagatcc tcaaggagca    3900
ccccgtcgag aacactcagc tgcagaacga gaagctgtac ctgtactacc tccaaaacgg    3960
aagggacatg tacgtggacc aggagctgga catcaacagg ttgtccgact acgacgtcga    4020
ccacatcgtg cctcagtcct tcctgaagga tgactccatc gacaataaag tgctgacacg    4080
ctccgataaa aatagaggca gtccgacaa cgtcccctcc gaggaggtcg tgaagaagat     4140
gaaaaactac tggagacagc tcttgaacgc caagctcatc acccagcgta agttcgacaa    4200
cctgactaag gctgagagag gaggattgtc cgagctcgat aaggccggat tcatcaagag    4260
acagctcgtc gaaacccgcc aaattaccaa gcacgtggcc caaattctgg attcccgcat    4320
gaacaccaag tacgatgaaa atgacaagct gatccgcgag gtcaaggtga tcacctttgaa   4380
gtccaagctg gtctccgact tccgcaagga cttccagttc tacaaggtga gggagatcaa    4440
caactaccac cacgcacacg acgcctacct caacgctgtc gttggaaccg ccctcatcaa    4500
aaaatatcct aagctggagt ctgagttcgt ctacggcgac tacaaggtgt acgacgtgag    4560
gaagatgatc gctaagtctg agcaggagat cggcaaggcc accgccaagt acttcttcta    4620
ctccaacatc atgaacttct tcaagaccga gatcactctc gccaacgtg agatcaggaa     4680
gcgcccactg atcgagacca acggtgagac tggagagatc gtgtgggaca aaggaggga    4740
tttcgctact gtgaggaagg tgctctccat gcctcaggtg aacatcgtca agaagaccga    4800
agttcagacc ggaggattct ccaaggagtc catcctcccc aagagaaact ccgacaagct    4860
gatcgctaga aagaaagact gggacctaa gaagtacgga ggcttcgatt ctcctaccgt     4920
ggcctactct gtgctggtcg tggccaaggt ggagaagggc aagtccaaga agctgaaatc    4980
cgtcaaggag ctcctcggga ttaccatcat ggagaggagt tccttcgaga agaaccctat    5040
cgacttcctg gaggccaagg gatataaaga ggtgaagaag gacctcatca tcaagctgcc    5100
caagtactcc ctcttcgagt tggagaacgg aaggaagagg atgctggctt ctgccggaga    5160
gttgcagaag ggaaatgagc tcgcccttcc ctccaagtac gtgaacttcc tgtacctcgc    5220
ctctcactat gaaaagttga agggctctcc tgaggacaac gagcagaagc agctcttcgt    5280
ggagcagcac aagcactacc tggacgaaat tatcgagcag atctctgagt tctccaagcg    5340
cgtgatattg gccgacgcca acctcgacaa ggtgctgtcc gcctacaaca agcacaggga    5400
taagcccatt cgcgagcagg ctgaaaacat tatccacctg tttacccctca caaacttggg    5460
agcccctgct gccttcaagt acttcgacac caccattgac aggaagagat acacctccac    5520
caaggaggtg ctcgacgcaa cactcatcca ccaatccatc accggcctct atgaaacaag    5580
gattgcttc tcccagctgg gaggcgactc tagagccgat cccaagagaa agagaaaggt     5640
gtaggttaac ctagacttgt ccatcttctg gattggccaa cttaattaat gtatgaaata    5700
aaaggatgca cacatagtga catgctaatc actataatgt gggcatcaaa gttgtgtgtt    5760
atgtgtaatt actagttatc tgaataaaag agaaagagat catccatatt tcttatccta    5820
aatgaatgtc acgtgtcttt ataattcttt gatgaaccag atgcatttca ttaaccaaat    5880
ccatatacat ataaatatta atcatatata attaatatca attgggttag caaaacaaat    5940
ctagtctagg tgtgttttgc gaatgcggcc gctcgagggg gggcccgta ccggcgcgcc     6000
gttctatagt gtcacctaaa tcgtatgtgt atgatacata aggttatgta ttaattgtag    6060
ccgcgttcta acgacaatat gtccatatgg tgcactctca gtacaatctg ctctgatgcc    6120
gcatagttaa gccagccccg acacccgcca cacccgctg acgcgccctg acgggcttgt     6180
ctgctcccgg catccgctta cagacaagct gtgaccgtct ccgggagctg catgtgtcag    6240
aggttttcac cgtcatcacc gaaacgcgcg agacgaaagg gcctcgtgat acgcctattt    6300
ttataggtta atgtcatgac caaaatccct taacgtgagt tttcgttcca ctgacgtca    6360
gaccccgtag aaaagatcaa aggatcttct tgagatcctt ttttctgcg cgtaatctgc     6420
tgcttgcaaa caaaaaaacc accgctacca gcggtggttt gtttgccgga tcaagagcta    6480
ccaactcttt ttccgaaggt aactggcttc agcagagcgc agataccaaa tactgtcctt    6540
ctagtgtagc cgtagttagg ccaccacttc aagaactctg tagcaccgcc tacatacctc    6600
gctctgctaa tcctgttacc agtggctgct gccagtggcg ataagtcgtg tcttaccggg    6660
ttggactcaa gacgatagtt accggataag gcgcagcggt cgggctgaac ggggggttcg    6720
tgcacacagc ccagcttgga gcgaacgacc tacaccgaac tgagatacct acagcgtgag    6780
cattgagaaa gcgccacgct tcccgaaggg agaaaggcgg acaggtatcc ggtaagcggc    6840
agggtcggaa caggagagcg cacgagggag cttccaggg gaaacgcctg gtatctttat     6900
agtcctgtcg ggtttcgcca cctctgactt gagcgtcgat ttttgtgatg ctcgtcaggg    6960
gggcggagcc tatggaaaaa cgccagcaac gcggccttttt acggttcct ggcctttgc     7020
tggccttttg ctcacatgtt ctttcctgcg ttatcccctg attctgtgga taaccgtatt    7080
accgcctttg agtgagctga taccgctcgc cgcagccgaa cgaccgagcg cagcgagtca    7140
gtgagcgagg aagcggaaga gcgcccaata cgcaaaccgc ctctccccgc gcgttggccg    7200
attcattaat gcaggttgat cagatctcga tcccgcgaaa ttaatacgac tcactatagg    7260
gagaccacac cggtttccct ctagaaataa ttttgtttaa cttaagaag gagatatacc     7320
catggaaaag cctgaactca ccgcgacgtc tgtcgagaag tttctgatcg aaaagttcga    7380
cagcgtctcc gacctgatgc agctctcgga gggcgaagaa tctcgtgctt tcagcttcga    7440
tgtaggaggg cgtggatatg tcctgcgggt aaatagctgc gccgatggtt tctacaaaga    7500
tcgttatgtt tatcggcact ttgcatcggc cgcgctcccg attccggaag tgcttgacat    7560
tggggaattc agcgagagcc tgacctattg catctcccgc cgtgcacagg gtgtcacgtt    7620
gcaagacctg cctgaaaccg aactgcccgc tgttctgcag ccggtcgcgg aggctatgga    7680
tgcgatcgct gcggccgatc ttagccagac gagcgggttc ggcccattcg gaccgcaagg    7740
aatcggtcaa tacactacat ggcgtgattt catatgcgcg attgctgatc ccatgtgta    7800
tcactggcaa actgtgatgg acgacaccgt cagtgcgtcc gtcgcgcagg ctctcgatga    7860
gctgatgctt tgggccgagg actgccccga agtccggcac ctcgtgcacg cggatttcgg    7920
ctccaacaat gtcctgacgg acaatggccg cataacagcg gtcattgact ggagcgaggc    7980
gatgttcggg gattcccaat acgaggtcgc caacatcttc ttctgaggc cgtggttggc     8040
```

```
ttgtatggag cagcagacgc gctacttcga gcggaggcat ccggagcttg caggatcgcc  8100
gcggctccgg gcgtatatgc tccgcattgg tcttgaccaa ctctatcaga gcttggttga  8160
cggcaatttc gatgatgcag cttgggcgca gggtcgatgc gacgcaatcg tccgatccgg  8220
agccgggact gtcgggcgta cacaaatcgc ccgcagaagc gcggccgtct ggaccgatgg  8280
ctgtgtagaa gtactcgccg atagtggaaa ccgacgccgc agcactcgtc cgagggcaaa  8340
ggaatagtga ggtacagctt ggatcgatcc ggctgctaac aaagcccgaa aggaagctga  8400
gttggctgct gccaccgctg agcataacct agcataaccc cttggggcct ctaaacgggt  8460
cttgagggggt ttttgctga aaggaggaac tatatccgga tgatcgggcg cgccggtac   8519
```

```
SEQ ID NO: 120          moltype = DNA   length = 434
FEATURE                 Location/Qualifiers
source                  1..434
                        mol_type = unassigned DNA
                        organism = Glycine max
SEQUENCE: 120
ccgggtgtga tttagtataa agtgaagtaa tggtcaaaag aaaaagtgta aaacgaagta   60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaa                                                    434
```

```
SEQ ID NO: 121          moltype = DNA   length = 104
FEATURE                 Location/Qualifiers
misc_feature            1..104
                        note = synthesized sequence- Guide RNA for DD43CR1
source                  1..104
                        mol_type = other DNA
                        organism = synthetic construct
SEQUENCE: 121
gtcccttgta cttgtacgta gttttagagc tagaaatagc aagttaaaat aaggctagtc   60
cgttatcaac ttgaaaaagt ggcaccgagt cggtgctttt tttt                   104
```

```
SEQ ID NO: 122          moltype = DNA   length = 3098
FEATURE                 Location/Qualifiers
misc_feature            1..3098
                        note = synthesized sequence- QC783
source                  1..3098
                        mol_type = other DNA
                        organism = synthetic construct
SEQUENCE: 122
ccgggtgtga tttagtataa agtgaagtaa tggtcaaaag aaaaagtgta aaacgaagta   60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat ctttctctta ccctgtttat attgagacct gaaacttgag agagatacac  300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg tcccttgtac ttgtacgtag ttttagagct agaaatagca  480
agttaaaata aggctagtcc gttatcaact tgaaaaagtg caccgagtc ggtgcttttt  540
tttgcggccg ctcgaggggg ggcccggtac cggcgcgccg ttctatagtg tcacctaaat  600
cgtatgtgta tgatacataa ggttatgtat taattgtagc cgcgttctaa cgacaatatg  660
tccatatggt gcactctcag tacaatctgc tctgatgcg catagttaag ccagcccccga  720
cacccgccaa cacccgctga cgcgccctga cgggcttgtc tgctcccggc atccgcttac  780
agacaagctg tgaccgtctc cgggagctgc atgtgtcaga ggttttcacc gtcatcaccg  840
aaacgcgcga gacgaaaggg cctcgtgata cgcctatttt tataggttaa tgtcatgacc  900
aaaatccctt aacgtgagtt ttcgttccac tgagcgtcag accccgtaga aaagatcaaa  960
ggatcttctt gagatccttt ttttctgcgc gtaatctgct gcttgcaaac aaaaaaacca 1020
ccgctaccag cggtggtttg tttgccggat caagagctac caactctttt tccgaaggta 1080
actggcttca gcagagcgca gataccaaat actgtcctctc tagtgtagcc gtagttaggc 1140
caccacttca agaactctgt agcaccgcct acatacctcg ctctgctaat cctgttacca 1200
gtggctgctg ccagtggcga taagtcgtgt cttaccgggt tggactcaag acgatagtta 1260
ccggataagg cgcagcggtc gggctgaacg ggggggtttcgt gcacacagcc cagcttggag 1320
cgaacgacct acaccgaact gagataccta cagcgtgagc attgagaaag cgccacgctt 1380
cccgaaggga gaaaggcgga caggtatccg gtaagcggca gggtcggaac aggagagcgc 1440
acgagggagc ttccaggggg aaacgcctgg tatctttata gtcctgtcgg gtttcgccac 1500
ctctgacttg agcgtcgatt tttgtgatgc tcgtcagggg gcggagcct atggaaaaac 1560
gccagcaacg cggccttttt acggttcctg gccttttgct ggccttttgc tcacatgttc 1620
tttcctgcgt tatcccctga ttctgtggat aaccgtatta ccgcctttga gtgagctgat 1680
accgctcgcc gcagccgaac gaccgagcgc agcgagtcag tgagcgagga gcggaagag 1740
cgcccaatac gcaaaccgcc tctccccgcg cgttggccga ttcattaatg caggttgatc 1800
agatctcgat ccgcgaaat taatacgact cactataggg agaccacaac ggtttccctc 1860
tagaaataat tttgtttaac tttaagaagg agatatacccc atggaaagc ctgaactcac 1920
cgcgacgtct gtcgagaagt ttctgatcga aaagttcgac agcgtctccg acctgatgca 1980
gctctcggag ggcgaagaat ctcgtgcttt cagcttcgat gtaggagggc gtggatatgt 2040
cctgcgggta aatagctgcg ccgatggttt ctacaaagat cgttatgttt atcggcactt 2100
tgcatcggcc gcgctcccga ttccggaagt gcttgacatt ggggaattca gcgagagcct 2160
```

```
gacctattgc atctcccgcc gtgcacaggg tgtcacgttg caagacctgc ctgaaaccga    2220
actgcccgct gttctgcagc cggtcgcgga ggctatggat gcgatcgctg cggccgatct    2280
tagccagacg agcgggttcg gcccattcgg accgcaagga atcggtcaat acactacatg    2340
gcgtgatttc atatgcgcga ttgctgatcc ccatgtgtat cactggcaaa ctgtgatgga    2400
cgacaccgtc agtgcgtccg tcgcgcaggc tctcgatgag ctgatgcttt gggccgagga    2460
ctgccccgaa gtccggcacc tcgtgcacgc ggatttcggc tccaacaatg tcctgacgga    2520
caatggccgc ataacagcgg tcattgactg gagcgaggcg atgttcgggg attcccaata    2580
cgaggtcgcc aacatcttct tctgaggcc gtggttggct tgtatggagc agcagacgcg    2640
ctacttcgag cggaggcatc cggagcttgc aggatcgccg cggctccggg cgtatatgct    2700
ccgcattggt cttgaccaac tctatcagag cttggttgac ggcaatttcg atgatgcagc    2760
ttgggcgcag ggtcgatgcg acgcaatcgt ccgatccgga gccggactg tcgggcgtac    2820
acaaatcgcc cgcagaagcg cggccgtctg accgatggc tgtgtagaag tactcgccga    2880
tagtggaaac cgacgcccca gcactcgtcc gagggcaaag gaatagtgag gtacagcttg    2940
gatcgatccg gctgctaaca aagcccgaaa ggaagctgga ttggctgctg ccaccgctga    3000
gcaataacta gcataacccc ttggggcctc taaacgggtc ttgaggggtt ttttgctgaa    3060
aggaggaact atatccggat gatcgggcgc gccggtac                          3098

SEQ ID NO: 123         moltype = DNA   length = 9093
FEATURE                Location/Qualifiers
misc_feature           1..9093
                       note = synthesized sequence- QC815
source                 1..9093
                       mol_type = other DNA
                       organism = synthetic construct
SEQUENCE: 123
ccgggtgtga tttagtataa agtgaagtaa tggtcaaaag aaaaagtgta aaacgaagta    60
cctagtaata agtaatattg aacaaaataa atggtaaagt gtcagatata taaaataggc   120
tttaataaaa ggaagaaaaa aaacaaacaa aaaataggtt gcaatgggc agagcagagt    180
catcatgaag ctagaaaggc taccgataga taaactatag ttaattaaat acattaaaaa   240
atacttggat cttttctctta ccctgtttat attgagacct gaaacttgag aggagatacac  300
taatcttgcc ttgttgtttc attccctaac ttacaggact cagcgcatgt catgtggtct   360
cgttccccat ttaagtccca caccgtctaa acttattaaa ttattaatgt ttataactag   420
atgcacaaca acaaagcttg tccccttgtac ttgtacgtag ttttagagct agaaatagca   480
agttaaaata aggctagtcc gttatcaact tgaaaaagtg gcaacgagtc ggtgcttttt   540
tttgcggccg caattggatc ggggttactt attttgtggg tatctatact tttattagat   600
ttttaatcag gctcctgatt tcttttttatt tcgattgaat tcctgaactt gtattattca   660
gtagatcgaa taaattataa aaagataaaa tcataaaata atatttttatc ctatcaatca   720
tattaaagca atgaatatgt aaaattaatc ttatcttttat tttaaaaaat catataggtt   780
tagtatttttt ttaaaataa agataggatt agttttacta ttccactgctt attacttttca  840
aaaaaatcat aaaggtttag tatttttttta aaataaat aggaatagtt ttactattca   900
ctgctttaat agaaaaatag tttaaaattt aagatagttt taatcccagc atttgccacg   960
tttgaacgtg agccgaaacg atgtcgttac attatcttaa cctagctgaa acgatgtcgt  1020
cataatatcg ccaaatgcca actgactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctagggc attatcggaa atgaaagta gctcactcaa tataaaaatc taggaaccct   1260
agttttcgtt atcactctgt gctccctcgc tctatttctc agtctctgtg tttgcggctg   1320
aggattccga acgagtgacc ttcttcgttt ctcgcaaagg taacagcctc tgctcttgtc   1380
tcttcgattc gatctatgcc tgtctcttat ttacgatgat gtttcttcgg ttatgtttttt   1440
ttattttatgc tttatgctgt tgatgttcgg ttgtttgttt cgctttgttt ttgtggttca   1500
gttttttagg attctttttgg ttttttgaatc gattaatcgg aagagatttc cgagttattt  1560
ggtgtgttgg aggtgaatct ttttttttgag gtcatagatc tgttgtattt gtgttataaa   1620
catgcgactt tgtatgattt tttacgaggt tatgatgttc tggttgtttt attatgaatc   1680
tgttgagaca gaaccatgat ttttgttgat gttcgtttac actattaaag gtttgtttta   1740
acaggattaa aagttttta agcatgttga aggagtcttg tagatatgta accgtcgata   1800
gtttttttgt gggtttgttc acatgttatc aagcttaatc ttttactatg tatgcgacca   1860
tatctggatc cagcaaaggc gattttttaa ttccttgtga aacttttgta atatgaagtt   1920
gaaatttgt tattggtaaa ctaaaatgt gtgaagttgg agtataccttt accttctta    1980
tttggcttttg tgatagttta attatatgt attttgagtt ctgacttgta ttcttttgaa    2040
ttgattctag tttaagtaat ccatggacaa aaagtactca ataggggctcg acataggac    2100
taactccgtt ggatgggccg tcatcaccga cgagtacaag gtgccctcca agaagttcaa    2160
ggtgttggga aacaccgaca ggcacagcat aaagaagaat ttgatcggtg cctcctctt    2220
cgactccgga gagaccgctg aggctaccag gctcaagagg accgctagaa ggcgctacac    2280
cagaaggaag aacagaatct gctacctgca ggagatcttc tccaacgaaa tggccaaggt   2340
ggacgactcc ttcttccacc gccttgagga atcattcctg gtggaggagg ataaaaagca    2400
cgacgagaca ccaatcttcg gaacatcgt cgacgaggtg gcctaccatg aaaagtaccc    2460
taccatctac cacctgagga gaagctggt cgactctacc gacaaggctg acttgcgctt    2520
gatttacctg gctctcgctc acatgataaa gttccgcgga cacttcctca ttgagggaga    2580
cctgaaccca gacaactccg acgtggacaa gctcttcatc cagctcgttc agacctacaa    2640
ccagctttc gaggagaacc caatcaacgc cagtggagtt gacgccaagg ctatcctctc    2700
tgctcgtctg tcaaagtcca ggaggcttga gaacttgatt gccagctgc tggcgaaaa    2760
gaagaacgga ctgttcggaa acttgatcgc tctctcctg ggattgactc ccaacttcaa    2820
gtccaacttc gacctcgccg aggacgctaa gttgcagttg tctaaagaca cctacgacga    2880
tgacctcgac aacttgctgg cccagatagg gaccaaatc tcctccgcg aactcgtcct    2940
taagaacttg tccgacgcaa tcctgctgtc cgacatcctg agagtcaaca ctgagattac    3000
caaagctcct ctgtctgctt ccatgattaa gcgctacgac gagcaccacc aagatctgac    3060
cctgctcaag gccctggtga gacagcagct gcccgagaag tacaaggaga tcttttcgaa    3120
ccagtccaag aacggctacg ccggatacat tgacggagc gcctcccagg aagagttcta    3180
caagttcatc aagcccatcc ttgagaagat ggacggtacc gaggagctgt tggtgaagtt    3240
```

```
gaacagagag gacctgttga ggaagcagag aaccttcgac aacggaagca tccctcacca  3300
aatccacctg ggagagctcc acgccatctt gaggaggcag gaggatttct atcccttcct  3360
gaaggacaac cgcgagaaga ttgagaagat cttgaccttc agaattcctt actacgtcgg  3420
gccactcgcc agaggaaact ctaggttcgc ctggatgacc cgcaaatctg aagagaccat  3480
tactccctgg aacttcgagg aagtcgtgga caagggcgct tccgctcagt cttttcatcga  3540
gaggatgacc aacttcgata aaaatctgcc caacgagaag gtgctgccca agcactccct  3600
gttgtacgag tatttcacag tgtacaacga gctcaccaag gtgaagtacg tcacagaggg  3660
aatgaggaag cctgccttct tgtccggaga gcagaagaag gccatcgtcg acctgctctt  3720
caagaccaac aggaaggtga ctgtcaagca gctgaaggag gactacttca agaagatcga  3780
gtgcttcgac tccgtcgaga tctctggtgt cgaggacagg ttcaacgcct cccttgggac  3840
ttaccacgat ctgctcaaga ttattaaaga caaggacttc ctggacaacg aggagaacga  3900
ggacatcctt gaggacatcg tgctcaccct gaccttgttc gaagacaggg aaatgatcga  3960
agagaggctc aagacctacg cccacctctt cgacgacaag gtgatgaaac agctgaagag  4020
acgagatat accggctggg gaaggctctc ccgcaaattg atcaacggga tcagggacag  4080
gcagtcaggg aagactatac tcgacttcct gaagtccgac ggattcgcca acaggaactt  4140
catgcagctc attcacgacg actccttgac cttcaaggag gacatccaga aggctcaggt  4200
gtctggacag ggtgactcct tgcatgagca cattgctaac ttggccggct ctcccgctat  4260
taagaaggge attttgcaga ccgtgaaggt cgttgacgag ctcgtgaagg tgatgggacg  4320
ccacaagcca gagaacatcg ttattgagat ggctcgcgag aaccaaacta cccagaaagg  4380
gcagaagaat tcccgcgaga ggattgaagcg cattgcagag ggcataaaag agcttggctc  4440
tcagatcctc aaggagcacc ccgtcgagaa cactcagctg cagaacgaga agctgtacct  4500
gtactacctc caaaacggaa gggacatgta cgtggaccag gagctggaca tcaacaggtt  4560
gtccgactac gacgtcgacc acatcgtgcc tcagtccttc ctgaaggatg actccatcga  4620
caataaagtg ctgacacgct ccgataaaaa tagaggcaag tccgacaacg tccctccga  4680
ggaggtcgtg aagaagatga aaaactactg gagacagctc ttgaacgcca agctcatcac  4740
ccagcgtaag ttcgacaacc tgactaaggc tgagagggga ggattgtccg agctcgataa  4800
ggccggattc atcaagagac agctcgtcga aacccgccaa attaccaagc acgtggccca  4860
aattctggat tcccgcatga acaccaagta cgatgaaaat gacaagctga tccgcgaggt  4920
caaggtgatc accttgaagt ccaagctggt ctccgacttc cgcaaggact tccagttcta  4980
caaggtgagg gagatcaaca actaccacca cgcacacgac gcctacctca acgctgtcgt  5040
tggaaccgcc ctcatcaaaa aatatcctaa gctggagtct gagttcgtct acggcgacta  5100
caaggtgtac gacgtgagga agatgatcgc taagtctgag caggagatcg gcaaggccac  5160
cgccaagtac ttcttctact ccaacatcat gaacttcttc aagaccgaga tcactctcgc  5220
caacggtgag atcaggaagc gcccactgat cgagaccaac ggtgagactg gagagatcgt  5280
gtgggacaaa gggagggatt tcgctactgt gaggaaggtg ctctccatgc ctcaggtgaa  5340
catctcaag aagaccgaag ttcagaccgg aggattctcc aaggagtcca tcctcccaa  5400
gagaaactcc gacaagctga tcgctagaaa gaaagactgg gaccctaaga agtacgagg  5460
cttcgattct cctaccgtgg cctactctgt gctggtcgtg gccaaggtgg agagggcaa  5520
gtccaagaag ctgaaatccg tcaaggagct cctcgggatt accatcatgg aggagttc   5580
cttcgagaag aacccatcg acttcctgga ggccaaggga tataaagagg tgaagaagga  5640
cctcatcatc aagctgccca gtactcccct cttcgagttg gagaacggaa ggaagaggat  5700
gctggcttct gccggagagt tgcagaaggg aaatgagctc gcccttccct ccaagtacgt  5760
gaacttcctg tacctcgcct ctcactatga aagttgaag tgctctcctg aggacaacga  5820
gcagaagcag ctcttcgtgg agcagcacaa gcactacctg gacgaaatta tcgagcagat  5880
ctctgagttc tccaagcgcg tgatattggc cgacgccaac ctcgacaagg tgctgtccgc  5940
ctacaacaag cacagggata agcccattcg cgagcaggct gaaaacatta tccacctgtt  6000
taccctcaca aacttgggag ccctgctgc cttcaagtac ttcgacacca ccattgacag  6060
gaagagatac acctccacca aggaggtgct cgacgcaaca ctcatccacc aatccatcac  6120
cggcctctat gaaacaagga ttgacttgtc ccagctggga ggcgactcta gagccgatcc  6180
caagaagaag agaaaggtgt aggttaacct agacttgtcc atcttctgga ttggccaact  6240
taattaatgt atgaaataaa aggatgcaca catagtgaca tgctaatcac tataatgtgg  6300
gcatcaaagt tgtgtgttat gtgtaattac tagttatctg aataaaagag aaagagatca  6360
tccatattc ttatcctaaa tgaatgtcac gtgtctttat aattctttga tgaaccagat  6420
gcattcatt aaccaaatcc atatacatat aaatattaat catatataat taatatcaat  6480
tgggttagca aaacaaatct agtctaggtg tgttttgcga attcgatatc aagcttatcg  6540
ataccgtcga ggggggccc ggtaccggcg cgccgttcta tagtgtcacc taaatcgtat  6600
gtgtatgata cataaggtta tgtattaatt gtagccgcgt tctaacgaca atatgtccat  6660
atggtgcact ctcagtacaa tctgctctga tgccgcatag ttaagccagc cccgacaccc  6720
gccaacaccc gctgacgcgc cctgacgggc ttgtcgctcc ccgcatccg cttacagaca  6780
agctgtgacc gtctccggga gctgcatgtg tcagaggttt tcaccgtcat caccgaaacg  6840
cgcgagacga aagggcctcg tgatacgcct atttttatag gttaatgtca tgaccaaaat  6900
cccttaacgt gagttttcgt tccactgagc gtcagacccc gtagaaaaga tcaaaggatc  6960
ttcttgagat cctttttttc tgcgcgtaat ctgctgcttg caaacaaaaa aaccaccgct  7020
accagcgtg gtttgtttgc cggatcaaga gctaccaact ctttttccga aggtaactgg  7080
cttcagcaga gcgcagatac caaatactgt ccttctagtg tagccgtagt taggccacca  7140
cttcaagaac tctgtagcac cgcctacata cctcgctctg ctaatcctgt taccagtggc  7200
tgctgccagt ggcgataagt cgtgtcttac cgggttggac tcaagacgat agttaccgga  7260
taaggcgcag cggtcgggct gaacgggggg ttcgtgcaca gcccagct tggagcgaac  7320
gacctacacc gaactgagat acctacagcg tgagcattga gaaagcgcca cgcttcccga  7380
agggagaaag gcggacaggt atccggtaag cggcagggtc ggaacaggag agcgcacgag  7440
ggagcttcca ggggggaaacg cctggtatct ttatagtcct gtcgggtttc gccacctctg  7500
acttgagcgt cgatttttgt gatgctcgtc aggggggcgg agcctatgga aaaacgccag  7560
caacgcggcc tttttacggt tcctggcctt ttgctggcct tttgctcaca tgttctttcc  7620
tgcgttatcc cctgattctg tggataaccg tattaccgcc tttgagtgag ctgataccgc  7680
tcgccgcagc cgaacgaccg agcgcagcga gtcagtgagc gaggaagcgg aagagcgccc  7740
aatacgcaaa ccgcctctcc ccgcgcgttg gccgattcat taatgcaggt tgatcagatc  7800
tcgatcccgc gaaattaata cgactcacta tagggagacc acaacggttt ccctctagaa  7860
ataatttgt ttaactttaa gaaggagata tacccatgga aaagcctgaa ctcaccgcga  7920
cgtctgtcga gaagtttctg atcgaaaagt tcgacagcgt ctccgacctg atgcagctct  7980
```

```
cggagggcga agaatctcgt gctttcagct tcgatgtagg agggcgtgga tatgtcctgc    8040
gggtaaatag ctgcgccgat ggtttctaca aagatcgtta tgtttatcgg cactttgcat    8100
cggccgcgct cccgattccg gaagtgcttg acattgggga attcagcgag agcctgacct    8160
attgcatctc ccgccgtgca cagggtgtca cgttgcaaga cctgcctgaa accgaactgc    8220
ccgctgttct gcagccggtc gcggaggcta tggatgcgat cgctgcggcc gatcttagcc    8280
agacgagcgg gttcggccca ttcggaccgc aaggaatcgg tcaatacact acatggcgtg    8340
atttcatatg cgcgattgct gatccccatg tgtatcactg gcaaactgtg atggacgaca    8400
ccgtcagtgc gtccgtcgcg caggctctcg atgagctgat gctttgggcc gaggactgcc    8460
ccgaagtccg gcacctcgtg cacgcggatt tcggctccaa caatgtcctg acggacaatg    8520
gccgcataac agcggtcatt gactggagcg aggcgatgtt cggggattcc caatacgagg    8580
tcgccaacat cttcttctgg aggccgtggt tggcttgtat ggagcagcag acgcgctact    8640
tcgagcggag gcatccggag cttgcaggat cgccgcggct ccgggcgtat atgctccgca    8700
ttggtcttga ccaactctat cagagcttgg ttgacgcaa tttcgatgat gcagcttggg    8760
cgcagggtcg atgcgacgca atcgtccgat ccggagccgg gactgtcggg cgtacacaaa    8820
tcgcccgcag aagcgcggcc gtctggaccg atggctgtgt agaagtactc gccgatagtg    8880
gaaaccgacg ccccagcact cgtccgaggg caaaggaata gtgaggtaca gcttggatcg    8940
atccggctgc taacaaagcc cgaaaggaag ctgagttggc tgctgccacc gctgagcaat    9000
aactagcata accccttggg gcctctaaac gggtcttgag gggtttttg ctgaaaggag     9060
gaactatatc cggatgatcg ggcgcgccgg tac                                  9093

SEQ ID NO: 124          moltype = DNA  length = 4107
FEATURE                 Location/Qualifiers
source                  1..4107
                        mol_type = unassigned DNA
                        organism = Streptococcus pyogenes
SEQUENCE: 124
atggataaga aatactcaat aggcttagat atcggcacaa atagcgtcgg atgggcggtg      60
atcactgatg attataaggt tccgtctaaa aagctcaagg gtctgggaaa tacagaccgc     120
cacggtatca aaaaaaatct tataggggct cttttatttg acagtggaga gacagcggaa     180
gcgactcgtc tcaaacggac agctcgtaga aggtatacga gtcggaagaa tcgtatttgt     240
tatctacaga agatttttc aaatgagatg gcgaaagtag atgatagttt ctttcatcga     300
cttgaagagt ctttttggt ggaagaagac aagaagcatg aacgtcatcc tatttttgga     360
aatatagtag atgaagttgc ttatcatgag aaatatccaa ctatctatca tctgcgaaaa     420
aaattggcag attctactga taaagtggat ttgcgcttaa tctatttggc cttagcgcat     480
atgattaagt ttcgtggtca ttttttgatt gagggagatt taaatcctga taatagtagt     540
gtggacaaac tatttatcca gttggtacaa acctacaatc aattatttga agaaaaccct     600
attaacgcaa gtagagtaga tgctaaagcg attcttctg cacgattgag taaatcaaga     660
cgattagaaa atctcattgc tcagctcccc ggtgagaaga aaaatggatt gtttgggaat     720
ctcattgctt tgtcattggg attgacccct aattttaaat caattttga ttgggcagaa     780
gatgctaaat tacagctttc aaaagatact tacgatgatg atttagataa tttattggcg     840
caaattggag atcaatatgc tgatttgttt ttggcagcta agaattttat agatgctact     900
ttactttcag atatcctaag agtaaatagt gaaaaactaa aggctcccct atcagcttca     960
atgattaagc gctacgatga acatcatcaa gacttgactc tttttaaagc tttagttcga    1020
caacaacttc cagaaaagta taaagaaatc ttttttgatc aatcaaaaaa cggatatgca    1080
ggttatattg atggggagc tagccaagaa gaatttata aattatcaa accaatttta      1140
gaaaaaatgg atggtactga ggaattattg gcgaaactaa atcgtgaaga tttgctgcgc    1200
aagcaagaca cctttgacaa cggctctatt ccctatcaaa ttcacttggg tgagctgcat    1260
gctattttga aagacaaga agacttttat ccattttaa aagacaatcg tgagaagatt    1320
gaaaaaatct tgacttttcg aattccttat tatgttggtc cattggcgcg tggcaatagt    1380
cgttttgcat ggatgactcg gaagtctgaa gaaacaatta ccccatgaa ttttgaagaa     1440
gttgtcgata aaggtgcttc agctcaatca tttattgaac gcatgacaaa ctttgataag     1500
aatcttccaa atgaaaaagt actaccaaaa catagtttgc tttatgagta ttttacggtt     1560
tataacgaat tgacaaaagt caaatatgtt actgagggaa tgcgaaaacc agcatttctt     1620
tcaggtgaac agaagaaagc cattgttgat ttactcttca aaacaaatcg aaaagtaacc     1680
gttaagcaat taaaagaaga ttatttcaaa aaatagaat gttttgatag tgttgaaatt     1740
tcaggagttg aagatagatt taatgcttca ttaggtacct accatgattt gctaaaaatt     1800
attaaagata aagattttt ggataatgaa gaaacgaag atatcttaga ggatattgtt     1860
ttaacattga cctatttga agatagggag atgattgagg aaagacttaa acatatgct     1920
cacctcttg atgataaggt gaaacag cttaaacgtc gccgttatac tggttgggga     1980
cgtttgtctc gaaaattgat taatggtatt agggataagc aatctggcaa aacaatatta     2040
gatttttga atcagatgg ttttgccaat cgcaatttta tgcagctgat ccatgatgat     2100
agtttgacat ttaagaaga cattcaaaaa gcacaagtgt ctggacaagg cgatagttta     2160
catgaacata ttgcaaattt agctggtagc cctgctatta aaaaggtat tttacagact     2220
gtaaagttg ttgatgaatt ggtcaaagta atgggcggc ataagccaga aaatatcgtt     2280
attgaaatgg cacgtgaaaa tcagacaact caaaagggcc agaaaaattc gcgtgagcgt     2340
atgaaacgta ttgaagaagg aataaaagaa ctaggaagtg atattctaaa ggagtatcct     2400
gttgaaaaca ctcaattaca aaatgaaaag ctctatctct attatctcca aaatggaaga     2460
gacatgtatg tggaccaaga attagatatt aatcgtttaa gtgattacga tgtcgatcac     2520
attgttccac aaagtttcct taaagacgat tcaatagaca ataaggtctt aacgcgttct     2580
gataaaaatc gtggtaaatc ggataacgtt ccaagtgaag aagtagtcaa aaagatgaaa     2640
aactattgga gacaacttct aaacgccaag ttaatcactc aacgtaagtt tgataattta     2700
acaaaagctg aacgtggagg tttgagtgaa cttgataaag ttggttttat caacgccaa     2760
ttggtggaa ctgccaaat cactaagcat gtggcacaaa ttttggatag tcgcatgaat     2820
actaaatacg atgaaaatga taaacttatt cgagaggtta aagtgattac cttaaaatct     2880
aaattagttt ctgacttccg aaaagatttt caattctata agtacgtga ttaacaat     2940
taccatcatg cccatgatgc gtatcttaat gccgtcgttg gaactgcttt gattaagaaa     3000
tatccaaaac ttgaatcgga gtttgtctat ggtgattata aagtttatga tgttcgtaaa     3060
atgattgcta agtctgagca ggaaatagc aaagcaaccg caaatattt cttttactct     3120
aatatcatga acttcttcaa aacagaaatt acacttgcaa atgagagat cgcaaacgc     3180
```

```
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aataatggaa agaagctctt ttgaaaaaga tccgattgac    3540
ttttttagaag ctaaaggata taaggaagtt agaaaagact taatcattaa actacctaaa    3600
tatagtcttt ttgagttaga aaacggtcgt aacggatgc tggctagtgc cggagaattg    3660
caaaaaggaa atgactagc tctgccaagc aaatatgtga atttttata tttagctagt    3720
cattatgaaa agttgaaggg tagtccagaa gataacgaac aaaaacaatt gtttgtggag    3780
cagcataagc attatttaga tgagattatt gagcaaatca gtgaattttc taagcgtgtt    3840
atttttagcag atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta aacgatatac gtctacaaaa    4020
gaagttttag atgccactct tatccatcaa tccatcactg gtctttatga aacacgcatt    4080
gatttgagtc agctaggagg tgactga                                        4107

SEQ ID NO: 125           moltype = DNA  length = 20
FEATURE                  Location/Qualifiers
source                   1..20
                         mol_type = unassigned DNA
                         organism = Glycine max
SEQUENCE: 125
ggaactgaca cacgacatga                                                20

SEQ ID NO: 126           moltype = DNA  length = 20
FEATURE                  Location/Qualifiers
source                   1..20
                         mol_type = unassigned DNA
                         organism = Glycine max
SEQUENCE: 126
gacatgatgg aacgtgacta                                                20

SEQ ID NO: 127           moltype = DNA  length = 20
FEATURE                  Location/Qualifiers
source                   1..20
                         mol_type = unassigned DNA
                         organism = Glycine max
SEQUENCE: 127
gtcccttgta cttgtacgta                                                20

SEQ ID NO: 128           moltype = DNA  length = 20
FEATURE                  Location/Qualifiers
source                   1..20
                         mol_type = unassigned DNA
                         organism = Glycine max
SEQUENCE: 128
gtattctaga aaagaggaat                                                20

SEQ ID NO: 129           moltype = DNA  length = 70
FEATURE                  Location/Qualifiers
source                   1..70
                         mol_type = unassigned DNA
                         organism = Glycine max
SEQUENCE: 129
atcaaaattc ggaactgaca cacgacatga tggaacgtga ctaaggtggg ttttgactt     60
tgcatgtcga                                                           70

SEQ ID NO: 130           moltype = DNA  length = 70
FEATURE                  Location/Qualifiers
source                   1..70
                         mol_type = unassigned DNA
                         organism = Glycine max
SEQUENCE: 130
tcgacatgca aagtcaaaaa cccaccttag tcacgttcca tcatgtcgtg tgtcagttcc     60
gaattttgat                                                           70

SEQ ID NO: 131           moltype = DNA  length = 70
FEATURE                  Location/Qualifiers
source                   1..70
                         mol_type = unassigned DNA
                         organism = Glycine max
SEQUENCE: 131
ggcagactcc aattcctctt ttctagaata ccctccgtac gtacaagtac aagggacttg     60
tgagttgtaa                                                           70

SEQ ID NO: 132           moltype = DNA  length = 70
FEATURE                  Location/Qualifiers
source                   1..70
```

```
                              mol_type = unassigned DNA
                              organism = Glycine max
SEQUENCE: 132
ttacaactca caagtcccctt gtacttgtac gtacggaggg tattctagaa aagaggaatt    60
ggagtctgcc                                                             70

SEQ ID NO: 133              moltype = DNA   length = 71
FEATURE                     Location/Qualifiers
misc_feature                1..71
                              note = synthesized sequence-primer DD20-S3
source                      1..71
                              mol_type = other DNA
                              organism = synthetic construct
SEQUENCE: 133
ctacactctt tccctacacg acgctcttcc gatctggaat ttacagcaca agtagatcac    60
ttgtacttat c                                                           71

SEQ ID NO: 134              moltype = DNA   length = 59
FEATURE                     Location/Qualifiers
misc_feature                1..59
                              note = synthesized sequence-primer DD20-A
source                      1..59
                              mol_type = other DNA
                              organism = synthetic construct
SEQUENCE: 134
caagcagaag acggcatacg agctcttccg atctaaatca ctctcacttc gacatgcaa     59

SEQ ID NO: 135              moltype = DNA   length = 71
FEATURE                     Location/Qualifiers
misc_feature                1..71
                              note = synthesized sequence-primer DD20-S4
source                      1..71
                              mol_type = other DNA
                              organism = synthetic construct
SEQUENCE: 135
ctacactctt tccctacacg acgctcttcc gatctttcct ttacagcaca agtagatcac    60
ttgtacttat c                                                           71

SEQ ID NO: 136              moltype = DNA   length = 68
FEATURE                     Location/Qualifiers
misc_feature                1..68
                              note = synthesized sequence-primer DD43-S3
source                      1..68
                              mol_type = other DNA
                              organism = synthetic construct
SEQUENCE: 136
ctacactctt tccctacacg acgctcttcc gatctagctg taaatacagc cttacaactc    60
acaagtcc                                                               68

SEQ ID NO: 137              moltype = DNA   length = 63
FEATURE                     Location/Qualifiers
misc_feature                1..63
                              note = synthesized sequence-Primer, DD43-A
source                      1..63
                              mol_type = other DNA
                              organism = synthetic construct
SEQUENCE: 137
caagcagaag acggcatacg agctcttccg atctttaatt taggactaaa agaagaggca    60
gac                                                                    63

SEQ ID NO: 138              moltype = DNA   length = 68
FEATURE                     Location/Qualifiers
misc_feature                1..68
                              note = synthesized sequence- Primer, DD43-S4
source                      1..68
                              mol_type = other DNA
                              organism = synthetic construct
SEQUENCE: 138
ctacactctt tccctacacg acgctcttcc gatctctagg taaatacagc cttacaactc    60
acaagtcc                                                               68

SEQ ID NO: 139              moltype = DNA   length = 68
FEATURE                     Location/Qualifiers
misc_feature                1..68
                              note = synthesized sequence- Primer, DD43-S5
source                      1..68
                              mol_type = other DNA
                              organism = synthetic construct
SEQUENCE: 139
```

```
ctacactctt tccctacacg acgctcttcc gatctgatcg taaatacagc cttacaactc   60
acaagtcc                                                            68

SEQ ID NO: 140           moltype = DNA   length = 43
FEATURE                  Location/Qualifiers
misc_feature             1..43
                         note = synthesized sequence- Primer, JKY557
source                   1..43
                         mol_type = other DNA
                         organism = synthetic construct
SEQUENCE: 140
aatgatacgg cgaccaccga gatctacact ctttccctac acg                     43

SEQ ID NO: 141           moltype = DNA   length = 18
FEATURE                  Location/Qualifiers
misc_feature             1..18
                         note = synthesized sequence- primer, JKY558
source                   1..18
                         mol_type = other DNA
                         organism = synthetic construct
SEQUENCE: 141
caagcagaag acggcata                                                 18

SEQ ID NO: 142           moltype = DNA   length = 117
FEATURE                  Location/Qualifiers
misc_feature             1..117
                         note = synthesized sequence- DD20CR1 PCR amplicon
source                   1..117
                         mol_type = other DNA
                         organism = synthetic construct
SEQUENCE: 142
ggaatttaca gcacaagtag atcacttgta cttatcaaaa ttcggaactg acacacgaca   60
tgatggaacg tgactaaggt gggtttttga ctttgcatgt cgaagtgaga gtgattt     117

SEQ ID NO: 143           moltype = DNA   length = 117
FEATURE                  Location/Qualifiers
misc_feature             1..117
                         note = synthesized sequence- DD20CR2 PCR amplicon
source                   1..117
                         mol_type = other DNA
                         organism = synthetic construct
SEQUENCE: 143
ttcctttaca gcacaagtag atcacttgta cttatcaaaa ttcggaactg acacacgaca   60
tgatggaacg tgactaaggt gggtttttga ctttgcatgt cgaagtgaga gtgattt     117

SEQ ID NO: 144           moltype = DNA   length = 108
FEATURE                  Location/Qualifiers
misc_feature             1..108
                         note = synthesized sequence- DD43CR1 PCR amplicon
source                   1..108
                         mol_type = other DNA
                         organism = synthetic construct
SEQUENCE: 144
agctgtaaat acagccttac aactcacaag tcccttgtac ttgtacgtac ggagggtatt   60
ctagaaaaga ggaattggag tctgcctctt cttttagtcc taaattaa               108

SEQ ID NO: 145           moltype = DNA   length = 108
FEATURE                  Location/Qualifiers
misc_feature             1..108
                         note = synthesized sequence- DD43CR2 PCR amplicon
source                   1..108
                         mol_type = other DNA
                         organism = synthetic construct
SEQUENCE: 145
ctaggtaaat acagccttac aactcacaag tcccttgtac ttgtacgtac ggagggtatt   60
ctagaaaaga ggaattggag tctgcctctt cttttagtcc taaattaa               108

SEQ ID NO: 146           moltype = DNA   length = 108
FEATURE                  Location/Qualifiers
misc_feature             1..108
                         note = synthesized sequence- amplicon
source                   1..108
                         mol_type = other DNA
                         organism = synthetic construct
SEQUENCE: 146
ctaggtaaat acagccttac aactcacaag tcccttgtac ttgtacgtac ggagggtatt   60
ctagaaaaga ggaattggag tctgcctctt cttttagtcc taaattaa               108

SEQ ID NO: 147           moltype = DNA   length = 101
```

```
FEATURE                 Location/Qualifiers
source                  1..101
                        mol_type = unassigned DNA
                        organism = Glycine max
SEQUENCE: 147
ggaatttaca gcacaagtag atcacttgta cttatcaaaa ttcggaactg acacacgatg    60
atggaacgtg actaaggtgg gttttttgact ttgcatgtcg a                      101

SEQ ID NO: 148          moltype = DNA   length = 101
FEATURE                 Location/Qualifiers
source                  1..101
                        mol_type = unassigned DNA
                        organism = Glycine max
SEQUENCE: 148
ggaatttaca gcacaagtag atcacttgta cttatcaaaa ttcggaactg acacacgatg    60
gaacgtgact aaggtgggtt tttgactttg catgtcgaag t                       101

SEQ ID NO: 149          moltype = DNA   length = 101
FEATURE                 Location/Qualifiers
source                  1..101
                        mol_type = unassigned DNA
                        organism = Glycine max
SEQUENCE: 149
ggaatttaca gcacaagtag atcacttgta cttatcaaaa ttcggaactg acacacgact    60
gatggaacgt gactaaggtg ggttttttgac tttgcatgtc g                      101

SEQ ID NO: 150          moltype = DNA   length = 101
FEATURE                 Location/Qualifiers
source                  1..101
                        mol_type = unassigned DNA
                        organism = Glycine max
SEQUENCE: 150
ggaatttaca gcacaagtag atcacttgta cttatcaaaa ttcggaactg acacacatgg    60
aacgtgacta aggtgggttt ttgactttgc atgtcgaagt g                       101

SEQ ID NO: 151          moltype = DNA   length = 101
FEATURE                 Location/Qualifiers
source                  1..101
                        mol_type = unassigned DNA
                        organism = Glycine max
SEQUENCE: 151
ggaatttaca gcacaagtag atcacttgta cttatcaaaa ttcggaactg acacatgatg    60
gaacgtgact aaggtgggtt tttgactttg catgtcgaag t                       101

SEQ ID NO: 152          moltype = DNA   length = 101
FEATURE                 Location/Qualifiers
source                  1..101
                        mol_type = unassigned DNA
                        organism = Glycine max
SEQUENCE: 152
ggaatttaca gcacaagtag atcacttgta cttatcaaaa ttcggaactg acacagacat    60
gatggaacgt gactaaggtg ggttttttgac tttgcatgtc g                      101

SEQ ID NO: 153          moltype = DNA   length = 101
FEATURE                 Location/Qualifiers
source                  1..101
                        mol_type = unassigned DNA
                        organism = Glycine max
SEQUENCE: 153
ggaatttaca gcacaagtag atcacttgta cttatcaaaa ttcggaactg acacgacatg    60
atggaacgtg actaaggtgg gttttttgact ttgcatgtcg a                      101

SEQ ID NO: 154          moltype = DNA   length = 101
FEATURE                 Location/Qualifiers
source                  1..101
                        mol_type = unassigned DNA
                        organism = Glycine max
SEQUENCE: 154
ggaatttaca gcacaagtag atcacttgta cttatcaaaa ttcggaactg acacaagaaa    60
tgatggaacg tgactaaggt gggttttttga ctttgcatgt c                      101

SEQ ID NO: 155          moltype = DNA   length = 101
FEATURE                 Location/Qualifiers
source                  1..101
                        mol_type = unassigned DNA
                        organism = Glycine max
SEQUENCE: 155
ggaatttaca gcacaagtag atcacttgta cttatcaaaa ttcggaactg acacacgatt    60
gaacgtgact aaggtgggtt tttgactttg catgtcgaag t                       101
```

```
SEQ ID NO: 156         moltype = DNA  length = 101
FEATURE                Location/Qualifiers
source                 1..101
                       mol_type = unassigned DNA
                       organism = Glycine max
SEQUENCE: 156
ggaatttaca gcacaagtag atcacttgta cttatcaaaa ttcggaactg acacacattg    60
aacgtgacta aggtgggttt ttgactttgc atgtcgaagt g                       101

SEQ ID NO: 157         moltype = DNA  length = 101
FEATURE                Location/Qualifiers
source                 1..101
                       mol_type = unassigned DNA
                       organism = Glycine max
SEQUENCE: 157
ttcctttaca gcacaagtag atcacttgta cttatcaaaa ttcggaactg acacacgaca    60
tgatggaacg tctaaggtgg gttttttgact ttgcatgtcg a                      101

SEQ ID NO: 158         moltype = DNA  length = 101
FEATURE                Location/Qualifiers
source                 1..101
                       mol_type = unassigned DNA
                       organism = Glycine max
SEQUENCE: 158
ttcctttaca gcacaagtag atcacttgta cttatcaaaa ttcggaactg acacacgaca    60
tgatggaacc taaggtgggt ttttgacttt gcatgtcgaa g                       101

SEQ ID NO: 159         moltype = DNA  length = 101
FEATURE                Location/Qualifiers
source                 1..101
                       mol_type = unassigned DNA
                       organism = Glycine max
SEQUENCE: 159
ttcctttaca gcacaagtag atcacttgta cttatcaaaa ttcggaactg acacacgaca    60
tgatggaacg tgactaggtg ggttttttgac tttgcatgtc g                      101

SEQ ID NO: 160         moltype = DNA  length = 101
FEATURE                Location/Qualifiers
source                 1..101
                       mol_type = unassigned DNA
                       organism = Glycine max
SEQUENCE: 160
ttcctttaca gcacaagtag atcacttgta cttatcaaaa ttcggaactg acacacgaca    60
tgatggaact aaggtgggtt tttgactttg catgtcgaag t                       101

SEQ ID NO: 161         moltype = DNA  length = 101
FEATURE                Location/Qualifiers
source                 1..101
                       mol_type = unassigned DNA
                       organism = Glycine max
SEQUENCE: 161
ttcctttaca gcacaagtag atcacttgta cttatcaaaa ttcggaactg acacacgaca    60
tgatggaacg aaggtgggtt tttgactttg catgtcgaag t                       101

SEQ ID NO: 162         moltype = DNA  length = 101
FEATURE                Location/Qualifiers
source                 1..101
                       mol_type = unassigned DNA
                       organism = Glycine max
SEQUENCE: 162
ttcctttaca gcacaagtag atcacttgta cttatcaaaa ttcggaactg acacacgaca    60
tgatggaagg tgggtttttg actttgcatg tcgaagtgag a                       101

SEQ ID NO: 163         moltype = DNA  length = 101
FEATURE                Location/Qualifiers
source                 1..101
                       mol_type = unassigned DNA
                       organism = Glycine max
SEQUENCE: 163
ttcctttaca gcacaagtag atcacttgta cttatcaaaa ttcggaactg acacacgaca    60
tgatggacgt gactaaggtg ggttttttgac tttgcatgtc g                      101

SEQ ID NO: 164         moltype = DNA  length = 101
FEATURE                Location/Qualifiers
source                 1..101
                       mol_type = unassigned DNA
                       organism = Glycine max
SEQUENCE: 164
```

```
ttcctttaca gcacaagtag atcacttgta cttatcaaaa ttcggaactg acacacgaca    60
tgatggaact ttactaaggt gggttttga ctttgcatgt c                        101

SEQ ID NO: 165         moltype = DNA  length = 101
FEATURE                Location/Qualifiers
source                 1..101
                       mol_type = unassigned DNA
                       organism = Glycine max
SEQUENCE: 165
ttcctttaca gcacaagtag atcacttgta cttatcaaaa ttcggaactg acacacgaca    60
tgatggaacg tgacaaggtg ggttttgac tttgcatgtc g                        101

SEQ ID NO: 166         moltype = DNA  length = 101
FEATURE                Location/Qualifiers
source                 1..101
                       mol_type = unassigned DNA
                       organism = Glycine max
SEQUENCE: 166
ttcctttaca gcacaagtag atcacttgta cttatcaaaa ttcggaactg acacactaca    60
ttatttaact ttactaaggt gggttttga ctttgcatgt c                        101

SEQ ID NO: 167         moltype = DNA  length = 108
FEATURE                Location/Qualifiers
source                 1..108
                       mol_type = unassigned DNA
                       organism = Glycine max
SEQUENCE: 167
agctgtaaat acagccttac aactcacaag tcccttgtac ttgtacgtac ggagggtatt    60
ctagaaaaga ggaattggag tctgcctctt cttttagtcc taaattaa                108

SEQ ID NO: 168         moltype = DNA  length = 101
FEATURE                Location/Qualifiers
source                 1..101
                       mol_type = unassigned DNA
                       organism = Glycine max
SEQUENCE: 168
agctgtaaat acagccttac aactcacaag tcccttgtac ggagggtatt ctagaaaaga    60
ggaattggag tctgcctctt cttttagtcc taaattaaag a                       101

SEQ ID NO: 169         moltype = DNA  length = 101
FEATURE                Location/Qualifiers
source                 1..101
                       mol_type = unassigned DNA
                       organism = Glycine max
SEQUENCE: 169
agctgtaaat acagccttac aactcacaag tcccttgtac ttgtacggag ggtattctag    60
aaaagaggaa ttggagtctg cctcttcttt tagtcctaaa t                       101

SEQ ID NO: 170         moltype = DNA  length = 101
FEATURE                Location/Qualifiers
source                 1..101
                       mol_type = unassigned DNA
                       organism = Glycine max
SEQUENCE: 170
agctgtaaat acagccttac aactcacaag tcccttacgg agggtattct agaaaagagg    60
aattggagtc tgcctcttct tttagtccta aattaaagat c                       101

SEQ ID NO: 171         moltype = DNA  length = 101
FEATURE                Location/Qualifiers
source                 1..101
                       mol_type = unassigned DNA
                       organism = Glycine max
SEQUENCE: 171
agctgtaaat acagccttac aactcacaag tcccttgtac ttgtaccgta cggagggtat    60
tctagaaaag aggaattgga gtctgcctct tcttttagtc c                       101

SEQ ID NO: 172         moltype = DNA  length = 101
FEATURE                Location/Qualifiers
source                 1..101
                       mol_type = unassigned DNA
                       organism = Glycine max
SEQUENCE: 172
agctgtaaat acagccttac aactcacaag tcccttgtac tgtacggagg gtattctaga    60
aaagaggaat tggagtctgc ctcttctttt agtcctaaat t                       101

SEQ ID NO: 173         moltype = DNA  length = 101
FEATURE                Location/Qualifiers
source                 1..101
                       mol_type = unassigned DNA
```

```
                        organism = Glycine max
SEQUENCE: 173
agctgtaaat acagccttac aactcacaag tcccttgtag tacggagggt attctagaaa    60
agaggaattg gagtctgcct cttcttttag tcctaaatta a                       101

SEQ ID NO: 174          moltype = DNA   length = 101
FEATURE                 Location/Qualifiers
source                  1..101
                        mol_type = unassigned DNA
                        organism = Glycine max
SEQUENCE: 174
agctgtaaat acagccttac aactcacaag tcccttgtac ttgtacgtag ggtattctag    60
aaaagaggaa ttggagtctg cctcttcttt tagtcctaaa t                       101

SEQ ID NO: 175          moltype = DNA   length = 100
FEATURE                 Location/Qualifiers
source                  1..100
                        mol_type = unassigned DNA
                        organism = Glycine max
SEQUENCE: 175
agctgtaaat acagccttac aactcacaag tcctacactc tttccctaca cgacgctctt    60
cttttagtcc taaattaaag atcggaagat ctcgtatgcc                         100

SEQ ID NO: 176          moltype = DNA   length = 101
FEATURE                 Location/Qualifiers
source                  1..101
                        mol_type = unassigned DNA
                        organism = Glycine max
SEQUENCE: 176
agctgtaaat acagccttac aactcacaag tcccttgtac ttgtacctta cggagggtat    60
tctagaaaag aggaattgga gtctgcctct tcttttagtc c                       101

SEQ ID NO: 177          moltype = DNA   length = 101
FEATURE                 Location/Qualifiers
source                  1..101
                        mol_type = unassigned DNA
                        organism = Glycine max
SEQUENCE: 177
ctaggtaaat acagccttac aactcacaag tcccttgtac ttgtacgtac ggagggtatt    60
ctagaaaatt ggagtctgcc tcttcttta gtcctaaatt a                        101

SEQ ID NO: 178          moltype = DNA   length = 101
FEATURE                 Location/Qualifiers
source                  1..101
                        mol_type = unassigned DNA
                        organism = Glycine max
SEQUENCE: 178
ctaggtaaat acagccttac aactcacaag tcccttgtac ttgtacgtac ggagggtatt    60
ctagaaaaga attggagtct gcctcttctt ttagtcctaa a                       101

SEQ ID NO: 179          moltype = DNA   length = 101
FEATURE                 Location/Qualifiers
source                  1..101
                        mol_type = unassigned DNA
                        organism = Glycine max
SEQUENCE: 179
ctaggtaaat acagccttac aactcacaag tcccttgtac ttgtacgtac ggagggtatt    60
ctagaattgg agtctgcctc ttcttttagt cctaaattaa a                       101

SEQ ID NO: 180          moltype = DNA   length = 101
FEATURE                 Location/Qualifiers
source                  1..101
                        mol_type = unassigned DNA
                        organism = Glycine max
SEQUENCE: 180
ctaggtaaat acagccttac aactcacaag tcccttgtac ttgtacgtac ggagggtatt    60
ctagaaaaga aattggagtc tgcctcttct tttagtccta a                       101

SEQ ID NO: 181          moltype = DNA   length = 101
FEATURE                 Location/Qualifiers
source                  1..101
                        mol_type = unassigned DNA
                        organism = Glycine max
SEQUENCE: 181
ctaggtaaat acagccttac aactcacaag tcccttgtac ttgtacgtac ggagggtatt    60
ctagaaaaat tggagtctgc ctcttctttt agtcctaaat t                       101

SEQ ID NO: 182          moltype = DNA   length = 101
FEATURE                 Location/Qualifiers
```

```
source                  1..101
                        mol_type = unassigned DNA
                        organism = Glycine max
SEQUENCE: 182
ctaggtaaat acagccttac aactcacaag tcccttgtac ttgtacgtac ggagggtatt    60
ctagaaaaga ggattggagt ctgcctcttc ttttagtcct a                      101

SEQ ID NO: 183          moltype = DNA  length = 101
FEATURE                 Location/Qualifiers
source                  1..101
                        mol_type = unassigned DNA
                        organism = Glycine max
SEQUENCE: 183
ctaggtaaat acagccttac aactcacaag tcccttgtac ttgtacgtac ggagggtatt    60
ctagaaattg gagtctgcct cttctttttag tcctaaatta a                     101

SEQ ID NO: 184          moltype = DNA  length = 101
FEATURE                 Location/Qualifiers
source                  1..101
                        mol_type = unassigned DNA
                        organism = Glycine max
SEQUENCE: 184
ctaggtaaat acagccttac aactcacaag tcccttgtac ttgtacgtac ggagggtatt    60
ctattggagt ctgcctcttc ttttagtcct aaattaaaga t                      101

SEQ ID NO: 185          moltype = DNA  length = 101
FEATURE                 Location/Qualifiers
source                  1..101
                        mol_type = unassigned DNA
                        organism = Glycine max
SEQUENCE: 185
ctaggtaaat acagccttac aactcacaag tcccttgtac ttgtacgtac ggagggtatt    60
ctagtctgcc tcttctttta gtcctaaatt aaagatcgga a                      101

SEQ ID NO: 186          moltype = DNA  length = 101
FEATURE                 Location/Qualifiers
source                  1..101
                        mol_type = unassigned DNA
                        organism = Glycine max
SEQUENCE: 186
ctaggtaaat acagccttac aactcacaag tcccttgtac ttgtacgtac ggagggtatt    60
ctagaaaagt ctgcctcttc ttttagtcct aaattaaaga t                      101

SEQ ID NO: 187          moltype = DNA  length = 101
FEATURE                 Location/Qualifiers
source                  1..101
                        mol_type = unassigned DNA
                        organism = Glycine max
SEQUENCE: 187
ctaggtaaat acagccttac aactcacaag tcccttgtac ttgtacgtac ggagggtatt    60
ctagaaaaga gaattggagt ctgcctcttc ttttagtcct a                      101

SEQ ID NO: 188          moltype = DNA  length = 101
FEATURE                 Location/Qualifiers
source                  1..101
                        mol_type = unassigned DNA
                        organism = Glycine max
SEQUENCE: 188
ctaggtaaat acagccttac aactcacaag tcccttgtac ttgtacgtac ggagggtatt    60
ctagaaaaga ggagtctgcc tcttctttta gtcctaaatt a                      101

SEQ ID NO: 189          moltype = DNA  length = 101
FEATURE                 Location/Qualifiers
source                  1..101
                        mol_type = unassigned DNA
                        organism = Glycine max
SEQUENCE: 189
ctaggtaaat acagccttac aactcacaag tcccttgtac ttgtacgtac ggagggtatt    60
ctaattggag tctgcctctt cttttagtcc taaattaaag a                      101

SEQ ID NO: 190          moltype = DNA  length = 101
FEATURE                 Location/Qualifiers
source                  1..101
                        mol_type = unassigned DNA
                        organism = Glycine max
SEQUENCE: 190
ctaggtaaat acagccttac aactcacaag tcccttgtac ttgtacgtac ggagggtatt    60
ctagaaaaga ggaaattgga gtctgcctct tcttttagtc c                      101
```

```
SEQ ID NO: 191        moltype = DNA  length = 101
FEATURE               Location/Qualifiers
source                1..101
                      mol_type = unassigned DNA
                      organism = Glycine max
SEQUENCE: 191
ctaggtaaat acagccttac aactcacaag tcccttgtac ttgtacgtac ggagggtatt    60
ctagaaagag gaattggagt ctgcctcttc ttttagtcct a                      101

SEQ ID NO: 192        moltype = AA  length = 1377
FEATURE               Location/Qualifiers
REGION                1..1377
                      note = synthesized sequence- maize optimized moCAS9
                       endonuclease
source                1..1377
                      mol_type = protein
                      organism = synthetic construct
SEQUENCE: 192
MAPKKKRKVM DKKYSIGLDI GTNSVGWAVI TDEYKVPSKK FKVLGNTDRH SIKKNLIGAL    60
LFDSGETAEA TRLKRTARRR YTRRKNRICY LQEIFSNEMA KVDDSFFHRL EESFLVEEDK   120
KHERHPIFGN IVDEVAYHEK YPTIYHLRKK LVDSTDKADL RLIYLALAHM IKFRGHFLIE   180
GDLNPDNSDV DKLFIQLVQT YNQLFEENPI NASGVDAKAI LSARLSKSRR LENLIAQLPG   240
EKKNGLFGNL IALSLGLTPN FKSNFDLAED AKLQLSKDTY DDDLDNLLAQ IGDQYADLFL   300
AAKNLSDAIL LSDILRVNTE ITKAPLSASM IKRYDEHHQD LTLLKALVRQ QLPEKYKEIF   360
FDQSKNGYAG YIDGGASQEE FYKFIKPILE KMDGTEELLV KLNREDLLRK QRTFDNGSIP   420
HQIHLGELHA ILRRQEDFYP FLKDNREKIE KILTFRIPYY VGPLARGNSR FAWMTRKSEE   480
TITPWNFEEV VDKGASAQSF IERMTNFDKN LPNEKVLPKH SLLYEYFTVY NELTKVKYVT   540
EGMRKPAFLS GEQKKAIVDL LFKTNRKVTV KQLKEDYFKK IECFDSVEIS GVEDRFNASL   600
GTYHDLLKII KDKDFLDNEE NEDILEDIVL TLTLFEDREM IEERLKTYAH LFDDKVMKQL   660
KRRRYTGWGR LSRKLINGIR DKQSGKTILD FLKSDGFANR NFMQLIHDDS LTFKEDIQKA   720
QVSGQGDSLH EHIANLAGSP AIKKGILQTV KVVDELVKVM GRHKPENIVI EMARENQTTQ   780
KGQKNSRERM KRIEEGIKEL GSQILKEHPV ENTQLQNEKL YLYYLQNGRD MYVDQELDIN   840
RLSDYDVDHI VPQSFLKDDS IDNKVLTRSD KNRGKSDNVP SEEVVKKMKN YWRQLLNAKL   900
ITQRKFDNLT KAERGGLSEL DKAGFIKRQL VETRQITKHV AQILDSRMNT KYDENDKLIR   960
EVKVITLKSK LVSDFRKDFQ FYKVREINNY HHAHDAYLNA VVGTALIKKY PKLESEFVYG  1020
DYKVYDVRKM IAKSEQEIGK ATAKYFFYSN IMNFFKTEIT LANGEIRKRP LIETNGETGE  1080
IVWDKGRDFA TVRKVLSMPQ VNIVKKTEVQ TGGFSKESIL PKRNSDKLIA RKKDWDPKKY  1140
GGFDSPTVAY SVLVVAKVEK GKSKKLKSVK ELLGITIMER SSFEKNPIDF LEAKGYKEVK  1200
KDLIIKLPKY SLFELENGRK RMLASAGELQ KGNELALPSK YVNFLYLASH YEKLKGSPED  1260
NEQKQLFVEQ HKHYLDEIIE QISEFSKRVI LADANLDKVL SAYNKHRDKP IREQAENIIH  1320
LFTLTNLGAP AAFKYFDTTI DRKRYTSTKE VLDATLIHQS ITGLYETRID LSQLGGD     1377

SEQ ID NO: 193        moltype = DNA  length = 6677
FEATURE               Location/Qualifiers
misc_feature          1..6677
                      note = synthesized sequence- maize optimized moCAS9
                       endonuclease
source                1..6677
                      mol_type = other DNA
                      organism = synthetic construct
SEQUENCE: 193
ctgcagtgca gcgtgacccg gtcgtgcccc tctctagaga taatgagcat tgcatgtcta    60
agttataaaa aattaccaca tatttttttt gtcacacttg tttgaagtgc agtttatcta   120
tctttataca tatatttaaa cttactctca cgaataatat aatctatagt actacaataa   180
tatcatgtt ttagagaatc atataaatga acagttagac atggtctaaa ggacaattga   240
gtattttgac aacaggactc tacagtttta tcttttttagt gtgcatgtgt tctcctttt   300
ttttgcaaat agcttcacct atataatact tcatccattt tattagtaca tccatttagg   360
gtttagggtt aatggttttt atagactaat ttttttagta catctatttt attctattt   420
agcctctaaa ttaagaaaac taaaactcta ttttagtttt tttatttaat aatttagata   480
taaaatagaa taaaataaag tgactaaaaa ttaaacaaat acccttaag  aaattaaaaa   540
aactaaggaa acatttttct tgtttcgagt agataatgcc agcctgttaa acgccgtcga   600
cgagtctaac ggacaccaac cagcgaacca gcagcgtcgc gtcgggccaa gcgaagcaga   660
cggcacggca tctctgtcgc tgcctctgga cccctctcga gagttccgct ccaccgttgg   720
acttgctccg ctgtcggcat ccagaaattg cgtggcggaa cggcagacgt gagccggcac   780
ggcaggcggc ctcctcctcc tctcacggca cggcagctac gggggattcc tttcccaccg   840
ctccttcgct ttcccttcct cgcccgccgt aataaataga caccccctcc acaccctctt   900
tccccaacct cgtgttgttc ggagcgcaca cacacacaac cagatctccc ccaaatccac   960
ccgtcggcac ctccgcttca aggtacgccg ctcgtcctcc ccccccccc  tctctacctt  1020
ctctagatcg gcgttccggt ccatgcatgg tagggcccg gtagttctac ttctgttcat  1080
gtttgtgtta gatccgtgtt tgtgttagat ccgtgctgct agcgttcgta cacgggatgcg  1140
acctgtacgt cagacacgtt ctgattgcta acttgccagt gtttctcttt ggggaatcct  1200
gggatggctc tagccgttcc gcagacggga tcgatttcat gatttttttt gtttcgttgc  1260
ataggggtttg gtttgccctt ttcctttatt tcaatatatg ccgtgcactt gtttgtcggg  1320
tcatctttcc atgcttttt  ttgtcttggt tgtgatgatg ttgctgctggt  1380
tctagatcgg agtagaattc tgtttcaaac tacctggtgg atttattaat tttggatctg  1440
tatgtgtgtg ccatacatat tcatagttac gaattgaaga tgatggatgg aaatatcgat  1500
ctaggatagg tatacatgtt gatgcgggt tactgatgc atatacagag atgctttttg    1560
ttcgcttggt tgtgatgatg tggtgtggtt gggcggtcgt tcattcgttc agatcggag   1620
tagaatactg tttcaaacta cctggtgtat ttattaattt tggaactgta tgtgtgtgtc  1680
```

```
atacatcttc atagttacga gtttaagatg gatggaaata tcgatctagg ataggtatac  1740
atgttgatgt gggttttact gatgcatata catgatggca tatgcagcat ctattcatat  1800
gctctaacct tgagtaccta tctattataa taaacaagta tgttttataa ttattttgat  1860
cttgatatac ttggatgatg gcatatgcag cagctatatg tggattttt tagccctgcc   1920
ttcatacgct atttatttgc ttggtactgt ttcttttgct gatgctcacc ctgttgtttg  1980
gtgttacttc tgcaggtcga ctctagagga tccccatggc cccgaagaag aagaggaagg  2040
tgcacatgga taagaagtac agcatcggcc tcgacatcgg gaccaacagc gtcggctggg  2100
ccgtcatcac cgacgaatat aaggtgccca gcaagaagtt caaggtgctc gggaatacag  2160
accgccacag catcaagaag aacctgatcg gcgccctcct gttcgactcg ggcgagaccg  2220
ctgaggccac cagactaaag aggaccgctc gccgccgcta cacccgccgc aagaaccgca  2280
tatgctacct ccaggagatc ttcagcaacg agatggccaa ggtggacgac agcttcttcc  2340
accgccttga ggagtcgttc ctcgtggagg aggacaagaa gcatgagagg cacccgatct  2400
tcgggaacat cgtggacgag gtaagttct gcttctacct ttgatatata tataatatt   2460
atcattaatt agtagtaata taatatttca aatattttt tcaaaataaa agaatgtagt   2520
atatagcaat tgcttttctg tagtttataa gtgtgtatat tttaatttat aacttttcta  2580
atatatgacc aaaacatggt gatgtgcagg tggcgtacca cgagaagtac ccgacgatct  2640
accacctccg caagaagctg gtcgactcca cagacaaggc cgacctcaga ctgatctacc  2700
tggcctcgc gcacatgatc aagttccgcg gcacttcct catcgagggc gacctgaacc    2760
cggacaactc cgacgtcgac aagctcttca tccagctggt ccagacctac aatcaactgt  2820
tcgaggagaa cccgatcaac gcgtccgcg tggacgcgaa ggccatcctc agcgcgaggc   2880
tcagcaaatc aagacggctg gagaacctga tcgcccagct cccaggcgag aagaaaaacg  2940
gcttgttcgg caacctgatc gcgctctcgc tcggcctcac ccccaacttc aaatcaaact  3000
tcgacctggc cgaggacgcg aaactgcagc tgtccaagga cacttacgac gacgacctcg  3060
acaacctgct ggcgcaaatc ggtgaccagt acgcagacct cttcctggcc gccaagaacc  3120
tctcggacgc catcctgctg tccgatatcc tgagagtgaa tacggagatc accaaggcgc  3180
cgctcagcgc ctccatgatt aaaaggtacg acgagcacca ccaggacctg acgctgctca  3240
aggcctggt gcgccagcag ctccccgaga agtacaagga gatcttcttc gaccaatcaa   3300
aaaacggcta cgccggctac atcgacgggg gcgcctccca ggaggagttc tacaagttca  3360
tcaaaccaat tctcgagaag atggacggca cggaggagct tctcgtgaag ctcaaccggg  3420
aggacctcct gaggaagcag aggacgttcg acaacggctc gatacccgcat cagatccacc  3480
tgggcgagct ccacgccatc ctgcgccggc aggaggattt ctatccgttc ctcaaggaca  3540
acagggagaa gatcgagaaa attctgacgt tccgcatccc gtactacgtg ggccctctcg  3600
cgcgcgggaa cagccggttc gcctggatga ctcggaagtc ggaggagacg atcacgccgt  3660
ggaacttcga ggaggtggtg gacaagggcg cctccgccca gtcgttcatc gagcgcatga  3720
cgaacttcga taaaaatctg cccaatgaaa aagtgctccc gaagcacagc ctcctctacg  3780
agtacttcac ggtgtacaac gagctcacga aggtgaagta cgtgaccgag ggtatgcgga  3840
agccggcgtt cctgagcggc gagcagaaga aggccatcgt ggacctcctc ttcaagacga  3900
accggaaagt caccgtgaag caattaaagg aggactactt caagaaaata gagtgcttcg  3960
acagcgtcga gatctcgggc gtcgaggaca ggttcaacgc gctgctgggc acataccacg  4020
acctcctcaa gatcattaaa gacaaggact tcctggacaa cgaggagaac gaggacatcc  4080
tcgaggacat cgtgctgacc ctcaccctgt ttgaggaccg ggagatgatc gaggagcgcc  4140
tcaagacgta cgctcacctt ttcgacgaca aggtgatgaa acagctgaag cggcgccgct  4200
acaccggatg gggccggctc tcccgcaagc tcattaatgg gatcagggac aagcagtccg  4260
gcaagaccat actcgatttc ctgaagagcg acggcttcgc caaccggaac ttcatgcagc  4320
tcatccacga cgactccctc actttcaagg aggacatcca gaaggcccag gtcagcggac  4380
agggcgactc gctccacgaa cacatcgcca acctggccgg gtcgcctgcg attaaaaagg  4440
gaatccttca gaccgtcaag gtcgtggacg agctggtgaa ggtgatgggc aggcacaagc  4500
ccgaaaatat cgtcattgag atggcccggg agaaccagac cacgcagaaa ggccagaaga  4560
acagccggga gcgcatgaaa cggatcgagg agggtatcaa ggagctgggc tcgcagatcc  4620
tcaaggagca ccctgtggaa atacccagc tgcagaatga aaagctctac ctctactacc   4680
tccagaacgg ccgcgacatg tacgtggacc aggagctgga cattaatcgc ctctcggact  4740
acgacgtcga ccacatcgtc ccgcagtcct tcctgaagga cgacagcatc gacaacaagg  4800
tcttgacccg ctccgataaa aatcgcggga agtccgacaa cgtgccgtcg gaggaggtgg  4860
tcaagaagat gaaaaactac tggcgccagc tgctcaacgc caagctaatc acgcagcgca  4920
agttcgacaa cctcaccaag gccgaacgcg gcggtctctc cgagcttgat aaggctgggt  4980
tcatcaagag acagctggtg gagacccagc agatcaccaa gcatgtcgcc cagatcctga  5040
actcgcgcat gaatactaag tacgatgaaa acgacaagct catccgcgag gtgaaggtga  5100
tcaccctgaa gagcaagctg gtctcggact tccggaagga cttccagttc tacaaggtcc  5160
gggagatcaa caactaccac cacgcgcacg acgcctacct gaacgcggtg gtgggcacag  5220
ccccttataaa gaagtaccct aagctcgagt ccgagttcgt gtacggcgac tacaaggtgt  5280
acgacgtccg caagatgatc gcgaagagcg agcaggagat cgggaaggcc accgcaaaat  5340
acttcttcta ctccaacatc atgaacttct tcaagaccga gatcaccctg gccaacgggg  5400
agatccgcaa gcgcccgctg attgagacga cggagagac aggcgagata gtctgggaca   5460
agggcaggga cttcgccacc gtgcgcaagg ttctgtccat gccgcaggtg aacatcgtga  5520
agaagactga ggtgcagaca ggcggcttct cgaaggagtc catcctgccc aagcggaaca  5580
gcgacaagct catcgcgcgg aagaaggact gggaccctaa aaaatatggc gggttcgact  5640
cgcccaccgt ggcttactcg gtcctcgtgg tggccaaggt cgagaagggc aaaagcaaga  5700
agctgaagag cgtcaaggag ctcctcggca tcaccatcat ggagcggtcc agcttcgaga  5760
agaacccgat cgacttcctc gaggcgaagg gatataaga ggtgaagaag gacctcatca   5820
ttaaactgcc gaagtactcg ctattcgaac tggagaatgg tcgcaagagg atgctcgcga  5880
gcgctgcga gctgcagaaa gggaacagc tggctctccc gagcaagtac gtcaacttcc   5940
tctacctggc ctcccactat gaaaagctca agggctcgcc ggaggacaac gagcagaagc  6000
agctgttcgt cgagcagcac aagcattacc tcgacgagat catcgagcag atctcggagt  6060
tcagcaagcg tgtcgatcct gccgacgcca acctgcacgg tgctgtcc gcatataaca    6120
agcaccgcga caaaccaata cgggagcagg ccgaaaatat catccacctg ttcaccctca  6180
cgaacctggg cgccccgcc gcgttcaagt acttcgacac aaccatcgac cgcaagcggt   6240
acacgagcac gaaggaggtg ctggacgcca cgttgattca ccagtccatc acgggcctgt  6300
atgaaacaag gatcgatctc agccagctcg gcggcgacta ggtaccacat ggttaaccta  6360
gacttgtcca tcttctggat tggccaactt aattaatgta tgaaataaaa ggatgcacac  6420
```

```
atagtgacat gctaatcact ataatgtggg catcaaagtt gtgtgttatg tgtaattact    6480
agttatctga ataaaagaga aagagatcat ccatatttct tatcctaaat gaatgtcacg    6540
tgtcttttata attctttgat gaaccagatg catttcatta accaaatcca tatacatata   6600
aatattaatc atatataatt aatatcaatt gggttagcaa aacaaatcta gtctaggtgt    6660
gttttgcgaa ttgcggc                                                   6677

SEQ ID NO: 194            moltype = DNA  length = 100
FEATURE                   Location/Qualifiers
misc_feature              1..100
                          note = synthesized sequence- DNA version of guide RNA
                          (EPSPS sgRNA)
source                    1..100
                          mol_type = other DNA
                          organism = synthetic construct
SEQUENCE: 194
gcagtaacag ctgctgtcaa gttttagagc tagaaatagc aagttaaaat aaggctagtc     60
cgttatcaac ttgaaaaagt ggcaccgagt cggtgctttt                          100

SEQ ID NO: 195            moltype = DNA  length = 3708
FEATURE                   Location/Qualifiers
misc_feature              1..3708
                          note = synthesized sequence- EPSPS polynucleotide template
source                    1..3708
                          mol_type = other DNA
                          organism = synthetic construct
SEQUENCE: 195
ctgcagccca tcaaggagat ctccggcacc gtcaagctgc cggggtccaa gtcgcttttcc    60
aacaggatcc tcctgctcgc cgccctgtcc gaggtgagcg attttggtgc ttgctgcgct   120
gccctgtctc actgctacct aaatgttttg cctgtcgaat accatggatt ctcggtgtaa   180
tccatctcac gatcagatgc accgcatgtc gcatgcctag ctctctctaa tttgtctagt   240
agtttgtata cggattaaga ttgataaatc ggtaccgcaa aagctaggtg taaataaaca   300
ctacaaaatt ggatgttccc ctatcggcct gtactcggct actcgttctt gtgatggcat   360
gttatttctt cttggtgttt ggtgaactcc cttatgaaat ttgggcgcaa agaaatcgcc   420
ctcaagggtt gatcttatgc catcgtcatg ataaacagtg aagcacggat gatcctttac   480
gttgttttta acaaactttg tcagaaaact agcaatgtta acttcttaat gatgatttca   540
caacaaaaaa ggtaaccttg ctactaacat aacaaaagac ttgttgctta ttaattatat   600
gttttttttaa tctttgatca ggggacaaca gtggttgata acctgttgaa cagtgaggat   660
gtccactaca tgctcggggc cttgaggact cttggtctct ctgtcgaagc ggacaaagct   720
gccaaaagag ctgtagttgt tggctgtggt ggaaagttcc cagttgagga tgctaaagag   780
gaagtgcagc tcttcttggg gaatgctgga atcgcaatgc ggtcattgac agcagctgtt   840
actgctgctg gtgaaatgc aacgtatgtt cctctctct ctctacaata cttgttggag    900
ttagtatgaa acccatgtgt atgtctagtg gcttatggtg tattggtttt tgaacttcag   960
ttacgtgctt gatggagtac caagaatgag ggagagaccc attggcgact tggttgtcag  1020
attgaagcag cttggtgcag atgttgattg tttccttggc actgactgcc cacctgttcg  1080
tgtcaatgga atcggagggc tacctggtgg caaggttagt tactaagggc cacatgttac  1140
attcttctgt aaatggtaca actattgtcg agcttttgca tttgtaagga aaacattgat  1200
tgatctgaat ttgatgctac accacaaaat atctacaaat ggtcatccct aactagcaaa  1260
ccatgtctcc attaagctca atgaagtaat acttggcatg tgtttatcaa cttaatttcc  1320
atcttctggg gtattgcctg ttttctagtc taatagcatt tgttttaaga attagctctt  1380
acaactgtta tgttctacag gtcaagctgt ctggctccat cagcagtcag tacttgagtg  1440
ccttgctgat ggctgctcct ttggctcttg gggatgtgga gattgaaatc attgataaat  1500
taatctccat tccctacgtc gaaatgacat tgagattgat ggagcgtttt ggtgtgaaag  1560
cagagcattc tgatagctgg gacagattct acattaaggg aggtcaaaaa tacaagtaag  1620
ctctgtaatg tatttcacta ctttgatgcc aatgtttcag ttttcagttt tccaaacagt  1680
cgcatcaata tttgaataga tgcactgtag aaaaaaatca ttgcagggaa aaactagtac  1740
tgagtatttt gactgtaaat tatttaacca gtcggaatat agtcagtcta ttggagtcaa  1800
gagcgtgaac cgaaatagcc agttaattat cccattatac agaggacaac catgtatact  1860
attgaaactt ggtttaagag aatctaggta gctggactcg tagctgcttg gcatggatac  1920
cttcttatct ttaggaaaag acacttgatt ttttttctgt ggccctctat gatgtgtgaa  1980
cctgcttctc tattgcttta gaaggatata tctatgtcgt tatgcaacat gcttccctta  2040
gtcatttgta ctgaaatcag tttcataagt tcgttagtgg ttccctaaac gaaaccttgt  2100
ttttctttgc aatcaacagg tcccctaaaa atgccatgt tgaaggtgat gcctcaagcg   2160
caagctattt cttggctggt gctgcaatta ctggagggac tgtgactgtg aaggttgtg   2220
gcaccaccag tttgcaggta aagatttctt ggctggtgct acgataactg cttttgtctt  2280
tttggtttca gcattgttct cagagtcact aaataacatt atcatctgca aacgtcaaat  2340
agacatactt aggtgaatgg atattcatgt aaccgtttcc ttacaaattt gctgaaacct  2400
cagggtgatg tgaagtttgc tgaggtactg gagatgatgg gagcgaaggt tacatggacc  2460
gagactagcg taactgttac tggcccaccg cgggagccat ttgggaggaa acacctcaag  2520
gcgattgatg tcaacatgaa caagatgcct gatgtcgcca acgataactg cttttgtgcc  2580
ctctttgccg atggcccgac agccatcaga gacggtaaaa cattctcagc cctacaacca  2640
tgcctcttct acatcactac ttgacaagac taaaaactat ggctcgttg gcagtggctt  2700
cctggagagt aaaggagacc gagaggatgg ttgcgatccg gacggagcta accaaggtaa  2760
ggctacatac ttcacatgtc tcacgtcgtc tttccatagc tcgctgcctc ttagcggctt  2820
gcctgcggtc gctccatcct cggttgctgt ctgtgtttct cacacgctggg agcatctgtt  2880
gaggaagggc cggactactg catcatcacg ccgccggaga agctgaacgt gacggcgatc  2940
gacacgtacg acgaccacag gatggccatg gccttctccc ttgccgcctg tgccgaggtc  3000
cccgtgacca tccgggaccc tgggtgcacc cggaagacct tccccgacta cttcgatgtg  3060
ctgagcactt tcgtcaagaa ttaataaagc gtgcgatact accacgcagc ttgattgaag  3120
tgataggctt gtgctgagga aatacatttc ttttgttctg tttttttctct ttcacgggat  3180
```

```
taagttttga gtctgtaacg ttagttgttt gtagcaagtt tctatttcgg atcttaagtt    3240
tgtgcactgt aagccaaatt tcatttcaag agtggttcgt tggaataata agaataataa    3300
attacgtttc agtggctgtc aagcctgctg ctacgtttta ggagatggca ttagacattc    3360
atcatcaaca acaataaaac cttttagcct caaacaataa tagtgaagtt atttttttagt   3420
cctaaacaag ttgcattagg atatagttaa aacacaaaag aagctaaagt tagggtttag    3480
acatgtggat attgttttcc atgtatagta tgttctttct ttgagtctca tttaactacc    3540
tctacacata ccaactttag tttttttttct acctcttcat gttactatgg tgccttctta   3600
tcccactgag cattggtata tttagaggtt tttgttgaac atgcctaaat catctcaatc    3660
aacgatggac aatcttttct tcgattgagc tgaggtacgc catctaga                 3708
```

```
SEQ ID NO: 196          moltype = DNA   length = 15
FEATURE                 Location/Qualifiers
misc_feature            1..15
                        note = synthesized sequence- TIPS nucleotide modifications
source                  1..15
                        mol_type = other DNA
                        organism = synthetic construct
SEQUENCE: 196
atcgcaatgc ggtca                                                       15

SEQ ID NO: 197          moltype = DNA   length = 19
FEATURE                 Location/Qualifiers
misc_feature            1..19
                        note = synthesized sequence- Primer Seqeunce-1 F-E2
source                  1..19
                        mol_type = other DNA
                        organism = synthetic construct
SEQUENCE: 197
ccgaggagat cgtgctgca                                                   19

SEQ ID NO: 198          moltype = DNA   length = 20
FEATURE                 Location/Qualifiers
misc_feature            1..20
                        note = synthesized sequence- Primer Seqeunce-2 F-E2
source                  1..20
                        mol_type = other DNA
                        organism = synthetic construct
SEQUENCE: 198
caatggccgc attgcagttc                                                  20

SEQ ID NO: 199          moltype = DNA   length = 19
FEATURE                 Location/Qualifiers
misc_feature            1..19
                        note = synthesized sequence- Primer Seqeunce-1 F-T
source                  1..19
                        mol_type = other DNA
                        organism = synthetic construct
SEQUENCE: 199
ccgaggagat cgtgctgca                                                   19

SEQ ID NO: 200          moltype = DNA   length = 20
FEATURE                 Location/Qualifiers
misc_feature            1..20
                        note = synthesized sequence- Primer Seqeunce-2 F-T
source                  1..20
                        mol_type = other DNA
                        organism = synthetic construct
SEQUENCE: 200
tgaccgcatt gcgattccag                                                  20

SEQ ID NO: 201          moltype = DNA   length = 24
FEATURE                 Location/Qualifiers
misc_feature            1..24
                        note = synthesized sequence- Primer Seqeunce-1 H-T
source                  1..24
                        mol_type = other DNA
                        organism = synthetic construct
SEQUENCE: 201
tccaagtcgc tttccaacag gatc                                             24

SEQ ID NO: 202          moltype = DNA   length = 20
FEATURE                 Location/Qualifiers
misc_feature            1..20
                        note = synthesized sequence- Primer Seqeunce-2 H-T
source                  1..20
                        mol_type = other DNA
                        organism = synthetic construct
SEQUENCE: 202
tgaccgcatt gcgattccag                                                  20
```

```
SEQ ID NO: 203          moltype = DNA   length = 19
FEATURE                 Location/Qualifiers
misc_feature            1..19
                        note = synthesized sequence- Primer Seqeunce-1 F-E3
source                  1..19
                        mol_type = other DNA
                        organism = synthetic construct
SEQUENCE: 203
ccgaggagat cgtgctgca                                                    19

SEQ ID NO: 204          moltype = DNA   length = 24
FEATURE                 Location/Qualifiers
misc_feature            1..24
                        note = synthesized sequence- Primer Seqeunce-2 F-E3
source                  1..24
                        mol_type = other DNA
                        organism = synthetic construct
SEQUENCE: 204
accaagctgc ttcaatccga caac                                              24

SEQ ID NO: 205          moltype = DNA   length = 63
FEATURE                 Location/Qualifiers
source                  1..63
                        mol_type = unassigned DNA
                        organism = Zea mays
SEQUENCE: 205
ggggaatgct ggaactgcaa tgcggccatt gacagcagct gttactgctg ctggtggaaa       60
tgc                                                                     63

SEQ ID NO: 206          moltype = DNA   length = 60
FEATURE                 Location/Qualifiers
source                  1..60
                        mol_type = unassigned DNA
                        organism = Zea mays
SEQUENCE: 206
ggggaatgct ggaactgcaa tgcggccatt ggcagctgtt actgctgctg gtggaaatgc       60

SEQ ID NO: 207          moltype = DNA   length = 50
FEATURE                 Location/Qualifiers
source                  1..50
                        mol_type = unassigned DNA
                        organism = Zea mays
SEQUENCE: 207
ggggaatgct ggaactgcac agcagctgtt actgctgctg gtggaaatgc                  50

SEQ ID NO: 208          moltype = DNA   length = 33
FEATURE                 Location/Qualifiers
source                  1..33
                        mol_type = unassigned DNA
                        organism = Zea mays
SEQUENCE: 208
ggggaatgct gttactgctg ctggtggaaa tgc                                    33

SEQ ID NO: 209          moltype = DNA   length = 51
FEATURE                 Location/Qualifiers
source                  1..51
                        mol_type = unassigned DNA
                        organism = Zea mays
SEQUENCE: 209
aatgctggaa tcgcaatgcg gtcattgaca gcagctgtta ctgctgctgg t                51

SEQ ID NO: 210          moltype = DNA   length = 51
FEATURE                 Location/Qualifiers
source                  1..51
                        mol_type = unassigned DNA
                        organism = Zea mays
SEQUENCE: 210
aatgctggaa ctgcaatgcg gccattgaca gcagctgtta ctgctgctgg t                51

SEQ ID NO: 211          moltype = DNA   length = 5124
FEATURE                 Location/Qualifiers
source                  1..5124
                        mol_type = unassigned DNA
                        organism = Zea mays
SEQUENCE: 211
atggcggcca tggcgaccaa ggccgccgcg ggcaccgtgt cgctggacct cgccgcgccg       60
ccggcggcgg cagcggcggc ggcggtgcag gcgggtgccg aggagatcgt gctgcagccc      120
atcaaggaga tctccggcac cgtcaagctg ccggggtcca gtcgctttc caacaggatc       180
```

```
ctcctgctcg ccgccctgtc cgaggtgagc gattttggtg cttgctgcgc tgccctgtct   240
cactgctacc taaatgtttt gcctgtcgaa taccatggat tctcggtgta atccatctca   300
cgatcagatg caccgcatgt cgcatgccta gctctctcta atttgtctag tagtttgtat   360
acggattaag attgataaat cggtaccgca aaagctaggt gtaaataaac actacaaaat   420
tggatgttcc cctatcggcc tgtactcggc tactcgttct tgtgatggca tgttatttct   480
tcttggtgtt tggtgaactc ccttatgaaa tttgggcgca aagaaatcgc cctcaagggt   540
tgatcttatg ccatcgtcat gataaacagt gaagcacgga tgatccttta cgttgttttt   600
aacaaacttt gtcagaaaac tagcaatgtt aacttcttaa tgatgatttc acaacaaaaa   660
aggtaacctt gctactaaca taacaaaaga cttgttgctt attaattata tgttttttta   720
atctttgatc aggggacaac agtggttgat aacctgttga acagtgagga tgtccactac   780
atgctcgggg ccttgaggac tcttggtctc tctgtcgaag cggacaaagc tgccaaaaga   840
gctgtagttg ttggctgtgg tggaaagttc ccagttgagg atgctaaaga ggaagtgcag   900
ctcttcttgg ggaatgctgg aactgcaatg cggccattga cagcagctgt tactgctgct   960
ggtggaaatg caacgtatgt ttcctctctc tctctacaat acttgttgga gttagtatga  1020
aacccatgtg tatgtctagt ggcttatggt gtattggttt ttgaacttca gttacgtgct  1080
tgatggagta ccaagaatga gggagagacc cattggcgac ttggttgtcg gattgaagca  1140
gcttggtgca gatgttgatt gtttccttgg cactgactgc ccacctgttc gtgtcaatgg  1200
aatcggaggg ctacctggtg gcaaggttag ttactaaggg ccacatgtta cattcttctg  1260
taaatggtac aactattgtc gagcttttgc atttgtaagg aaaacattga ttgatctgaa  1320
tttgatgcta caccacaaaa tatctacaaa tggtcatccc taactagcaa accatgtctc  1380
cattaagctc aatgaagtaa tacttggcat gtgtttatca acttaatttc catcttctgg  1440
ggtattgcct gttttctagt ctaatagcat ttgtttttag aattagctct tacaactgtt  1500
atgttctaca ggtcaagctg tctggctcca tcagcagtca gtacttgagt gccttgctga  1560
tggctgctcc tttggctctt gggatgtgg agattgaaat cattgataaa ttaatctcca  1620
ttccctacgt cgaaatgaca ttgagattga tggagcgttt tggtgtgaaa gcagagcatt  1680
ctgatagctg ggacagattc tacattaagg gaggtcaaaa atacaagtaa gctctgtaat  1740
gtatttcact actttgatgc caatgtttca gttttcagtt tccaaacag tcgcatcaat  1800
atttgaatag atgcactgta gaaaaaaatc attgcaggga aaaactagta ctgagtattt  1860
tgactgtaaa ttatttaacc agtcggaata tagtcagtct attggagtca agagcgtgaa  1920
ccgaaatagc cagttaatta tcccattata cagaggacaa ccatgtatac tattgaaact  1980
tggtttaaga gaatctaggt agctggactc gtagctgctt ggcatggata ccttcttatc  2040
tttaggaaaa gacacttgat tttttttctg tggccctcta tgatgtgtga acctgcttct  2100
ctattgcttt agaaggatat atctatgtcg ttatgcaaca tgcttccctt agtcatttgt  2160
actgaaatca gtttcataag ttcgttagtg gttccctaaa cgaaaccttg ttttctcttg  2220
caatcaacag gtccctaaa aatgcctatg ttgaaggtga tgcctcaagc gcaagctatt  2280
tcttggctgg tgctgcaatt actggaggga ctgtgactgt ggaaggttgt ggcaccacca  2340
gtttgcaggt aaagatttct tggctggtgc tacgataact gcttttgtct ttttggtttc  2400
agcattgttc tcagagtcac taaataacat tatcatctgc aaacgtcaaa tagacatact  2460
taggtgaatg gatattcatg taaccgtttc cttacaaatt tgctgaaacc tcagggtagt  2520
gtgaagtttg ctgaggtact ggagatgatg ggagcgaagg ttacatggac cgagactagc  2580
gtaactgtta ctggcccacc gcgggagcca tttgggagga aacacctcaa ggcgattgat  2640
gtcaacatga acaagatgcc tgatgtcgcc atgactcttg ctgtggttgc cctctttgcc  2700
gatgccccga cagccatcag agacggtaaa acattcctaa caaccc atgcctcttc  2760
tacatcacta cttgacaaga ctaaaaacta ttggctcgtt ggcagtggct tcctggagag  2820
taaaggagac cgagaggatg gttgcgatcc ggacggagct aaccaaggta aggctacata  2880
cttcacatgt ctcacgtcgt cttttccatag ctcgctgcct cttagcggct tgcctgcggt  2940
cgctccatcc tcggttgctg tctgtgtttt ccacagctgg gatcatgtct tgaggaaggg  3000
ccggactact gcatcatcac gccgccgag aagctgaacg tgacggcgat cgacacgtac  3060
gacgaccaca ggatggccat ggccttctcc cttgccgcct gtgccgaggt ccccgtgacc  3120
atccgggacc ctgggtgcac ccggaagacc ttccccgact acttcgatgt gctgagcact  3180
ttcgtcaaga attaataaag cgtgcgatca taccacgcag cttgattgaa gtgataggct  3240
tgtgctgagg aaatacattt cttttgttct gttttttctc tttcacggga ttaagtttg  3300
agtctgtaac gttagttgtt tgtagcaagt ttctatttcg gatcttaagt ttgtgcactg  3360
taagccaaat ttcatttcaa gagtggttcg ttggaataat aagaataata aattacgttt  3420
cagtggctgt caagcctgct gctacgtttt aggagatggc attagacatt catcatcaac  3480
aacaataaaa ccttttagcc tcaaacaata atagtgaagt tatttttag tcctaaacaa  3540
gttgcattag gatatagtta aaacacaaaa gaagctaaag ttagggttta gacatgtgga  3600
tattgttttc catgtatagt atgttctttc tttgagtctc atttaactac ctctacacat  3660
accaacttta gtttttttttc tacctcttca tgttactatg gtgccttctt atcccactga  3720
gcattggtat atttagaggt ttttgttgaa catgcctaaa tcatctcaat caacgatgga  3780
caatcttttc ttcgattgag ctgaggtacg tcatctagag gataggacct tgagaatatg  3840
tgtccgtcaa tagctaaccc tctactaatt ttttcaatca agcaacctat ggcttgact  3900
ttaattcgta ccggcttcta ctacttctac agtattttgt ctcataaat tgcagctaca  3960
acagtcagaa cggctggctt taaaatcaaa tggccaatgga atcattgaaa ggcatcttga  4020
caatgtctaa aattattacc ttctctagac gttgatatct ttgctccgga ttcgatccct  4080
tgttgtatga ccacaaatcc aacaccaaat acgcatttct gcaacacacc caaacacccc  4140
ttccaaataa gtgaatggt tgagaaattt gctattttga ttaaatattg gtgaaggggc  4200
aaggctgagg aaacgagacg aaggttcctt gacacgtgaaa aaatggaaca ctctagaggc  4260
ggagggagcg aggcgagctg tgtgaattgc cacccattga ttaagaatcc aacaacttga  4320
ctagcaaatg ccgacatggg tagcctacaa aggcgagttt ggagctggt ttcgtaataa  4380
ggaaatttct caaccaacta ctttccttag aaaagagttg cttgaccgga tcaacatctc  4440
cccctaaacc ccttggaggg ggaggggct aagatttaa tctacaagtt agatctaact  4500
gtccacctca atcccctca aggaggtttt tgtattattt gttagtgtag aatgataaag  4560
tggatgtatt gataggagat ggggtacaca tatttatagg gactcaaacc taaccctaat  4620
gggtcggcag cccaacagtg gtgtccggcc cacacacaca ctcacacaca cagtctaaca  4680
tccccccgcag tcgcaaacggg gacaccacac acgatgagac tggagtagag gccgaaggta  4740
ggagccgacg ggttgaaatc cccctagtc gcagcgtcgt gatagtacga atgttgcggc  4800
tggagtagag accggtgtgt gctccaagaa gacgatagcc cctagatgcc gaggtagccg  4860
aagtcgaggt ggtcgcggtc ggaagacgcg cagcaaaagc ctgatcttcg ggatggtcga  4920
```

```
cgttcgagcg tcaacgatcg gtagggcgac acaataaaag ggcaccagca ggtcgacctt   4980
cctgcttctt cgatcgtcca gacgtcaagg agcctcgcta gggaggccga cggcagcgca   5040
cgcggctacg ccggtcatgg tgtcctcacc cgcggcagaa aagaagggga atgtcggatc   5100
cgaccgagaa ggccacggca gcga                                          5124

SEQ ID NO: 212           moltype = DNA   length = 3387
FEATURE                  Location/Qualifiers
source                   1..3387
                         mol_type = unassigned DNA
                         organism = Streptococcus thermophilus
SEQUENCE: 212
atgagtgact tagttttagg acttgatatc ggtataggtt ctgttggtgt aggtatcctt     60
aacaaagtga caggagaaat tatccataaa aactcacgca tcttcccagc agctcaagca    120
gaaaataacc tagtacgtag aacgaatcgt caaggaagac gcttgacacg acgtaaaaaa    180
catcgtatag ttcgtttaaa tcgtctattt gaggaaagtg gattaatcac cgattttacg    240
aagatttcaa ttaatcttaa cccatatcaa ttacgagtta agggcttgac cgatgaattg    300
tctaatgaag aactgtttat cgctcttaaa aatatggtga acaccgtgg gattagttac    360
ctcgatgatg ctagtgatga cggaaattca tcagtaggag actatgcaca aattgttaag    420
gaaaatagta aacaattaga aactaagaca ccgggacaga tacagttgga acgctaccaa    480
acatatggtc aattacgtgg tgattttact gttgagaaag atggcaaaaa acatcgcttg    540
attaatgtct ttccaacatc agcttatcgt tcagaagcct taaggatact gcaaactcaa    600
caagaattta atccacagat tacagatgaa tttattaatc gttatctcga aattttaact    660
ggaaaacgga aatattatca tggacccgga aatgaaaagt cacggactga ttatggtcgt    720
tacagaacga gtgagaaaac tttagacaat attttttggaa ttctaattgg gaaatgtaca   780
ttttatccag aagagtttag agcagcaaaa gcttcctaca cggctcaaga attcaatttg    840
ctaaatgatt tgaacaatct aaacagttcct actgaaacca aaaagttgac caaagaacag    900
aagaatcaaa tcattaatta tgtcaaaaat gaaaaggcaa tggggccagc gaaacttttt    960
aaatatatcg ctaagttact ttcttgtgat gttgcagata tcaagggata ccgtatcgac   1020
aaatcaggta aggctgagat tcatactttc gaagcctatc gaaaaatgaa aacgcttgaa   1080
accttagata ttgaacaaat ggatagagaa acgcttgata aattagccta tgtcttaaca   1140
ttaaacactg agagggaagg tattcaagaa gccttagaac atgaatttgc tgatggtagc   1200
tttagccaga agcaagttga cgaattggtt caattccgca agcaaatag ttccattttt    1260
ggaaaaggat ggcataattt ttctgtcaaa ctgatgatgg agtaattcc agaattgtat    1320
gagacgtcag aagagcaaat gactatcctg acacgacttg gaaaacaaaa acgacttcgt   1380
cttcaaataa aacaaaatat ttcaaataaa acaaaatata tagatgagaa actattaact   1440
gaagaaatct ataatcctgt tgttgctaag tctgttcgcc aggctataaa aatcgtaaat   1500
gcggcgatta agaatacgg agactttgac aatattgtca tcgaaatggc tcgtgaaaca   1560
aatgaagatg atgaaaagaa agctattcaa aagattcaaa aagccaacaa agatgaaaaa   1620
gatgcagcaa tgcttaaggc tgctaaccaa tataatggaa aggctgaatt accacatagt   1680
gttttccacg gtcataagca attagcgact aaaatccgcc tttggcatca gcaaggagaa   1740
cgttgccttt atactggtaa gacaatctca atccatgatt tgataaataa tcctaatcag   1800
tttgaagtag atcatatttt acctcttttct atcacattcg atgatagcct tgcaaataag   1860
gttttggttt atgcaactgc taaccaagaa aaaggacaac gaacaccttta tcaggcttta   1920
gatagtatgg atgatgcgtg gtctttccgt gaattaaaag cttttgtacg tgagtcaaaa   1980
acactttcaa acaagaaaaa agaataccte cttacgaaga agatatttc aaagtttgat   2040
gttcgaaaga aatttattga acgaaatctt gtagatacaa gatacgcttc aagagttgtc   2100
ctcaatgccc ttcaagaaca cttttagagct cacaagattg atacaaaagt ttccgtggtt   2160
cgtggccaat ttcatctca attgagacgc cattgggggaa ttgagaagac tcgtgatact   2220
tatcatcacc atgctgtcga tgcattgatt attgccgcct caagtcagtt gaatttgtgg   2280
aaaaaacaaa agaatacccet tgtaagttat tcagaagaac aactccttga tattgaaaca   2340
ggtaacttca ttagtgatga tgagtacaag aatctgtgt tcaaagccce ttatcaacat   2400
tttgttgata cattgaagag taaagaattt gaagacagta tcttattctc atatcaagtg   2460
gattctaagt taatcgtaa aatatcagat gccactattt atgcgacaag acaggctaaa   2520
gtgggaaaag ataagaagga tgaaacttat gtcttaggga aaatcaaaga tatctatact   2580
caggatggtt atgatgcctt tatgaagatt tataagaagg ataagtcaaa attcctcatg   2640
tatcgtcacg acccacaaac ctttgagaaa gttatcgagc caattttaga gaactatcct   2700
aataagcaaa tgaatgaaaa aggaaaagag gtaccatgta atcctttcct aaaatataaa   2760
gaagaacatg gctatattcg taaatatagt aaaaaaggca atggtcctga aatcaagagt   2820
cttaaatact atgatagtaa gcttttaggt aatcctattg atattactcc agagaatagt   2880
aaaaaataaag ttgtcttaca gtcattaaaa ccttggagaa cagatgtcta tttcaataag   2940
gctactggaa aatacgaaat ccttggatta aaatatgctg atctacaatt tgagaaaggg   3000
acaggaacat ataagatttc ccaggaaaaa tacaatgaca ttaagaaaaa agagggtgta   3060
gattctgatt cagaattcaa gtttacactt tataaaatg atttgttact cgttaaagat   3120
acagaaacaa aagaacaaca gcttttccgt tttcttttctc gaacttttacc taaacaaaaa   3180
cattatgttg aattaaaacc ttatgataaa cagaaatttg aaggaggtga ggcgttaatt   3240
aaagtgttgg gtaacgttgc taatggtggt caatgcataa aaggactagc aaaatcaaat   3300
atttctattt ataagtaag aacagatgtc ctaggaaatc agcatatcat caaaaatgag   3360
ggtgataagc ctaagctaga ttttttaa                                       3387

SEQ ID NO: 213           moltype = DNA   length = 3369
FEATURE                  Location/Qualifiers
source                   1..3369
                         mol_type = unassigned DNA
                         organism = Streptococcus thermophilus
SEQUENCE: 213
atgagtgact tagttttagg acttgatatc ggtataggtt ctgttggtgt aggtatcctt     60
aacaaagtga caggagaaat tatccataaa aactcacgca tcttcccagc agctcaagca    120
gaaaataacc tagtacgtag aacgaatcgt caaggaagac gcttgacacg acgtaaaaaa    180
catcgtatag ttcgtttaaa tcgtctattt gaggaaagtg gattaatcac cgattttacg    240
```

```
aagatttcaa ttaatcttaa cccatatcaa ttacgagtta agggcttgac cgatgaattg    300
tctaatgaag aactgtttat cgctcttaaa aatatggtga acaccgtgg  gattagttac    360
ctcgatgatg ctagtgatga cggaaattca tcagtaggag actatgcaca aattgttaag    420
gaaaatagta acaattaga  aactaagaca ccgggacaga tacagttgga acgctaccaa    480
acatatggtc aattacgtgg tgattttact gttgagaaag atggcaaaaa acatcgcttg    540
attaatgtct ttccaacatc agcttatcgt tcagaagcct taaggatact gcaaactcaa    600
caagaattta attcacagat tacagatgaa tttattaatc gttatctcga aattttaact    660
ggaaaacgaa aatattatca tggacccgga aatgaaaagt cacggactga ttatggtcgt    720
tacagaacga atggagaaac tttagacaat attttggaa  ttctaattgg gaaatgtaca    780
ttttatccag acgagtttag agcagcaaaa gcttcctaca cggctcagaa attcaatttg    840
ctaaatgatt tgaacaatct aacagttcct actgaaacca aaagttgag  caaagaacag    900
aagaatcaaa tcattaatta tgtcaaaaat gaaaaggtaa tggggccagc gaaacttttt    960
aaatatatcg ctaaattact ttcttgtgat gttgcagata tcaagggaca ccgtatcgac   1020
aaatcaggta aggctgagat tcatactttc gaagcctatc gaaaaatgaa aacgcttgaa   1080
accttagata ttgagcaaat ggatagaaa  acgcttgata aattagccta tgtcttaaca   1140
ttaaacactg agagggaagg tattcaagaa gctttagaac atgaatttgc tgatggtagc   1200
tttagccaga agcaagttga cgaattggtt caattccgca aagcaaatag ttccattttt   1260
ggaaaaggat ggcataattt ttctgtcaaa ctgatgatga agttaattcc agaattgtat   1320
gagacgtcag aagagcaaat gactatcctg acacgacttg gaaaacaaaa aacaacttcg   1380
tcttcaaata aacaaaata  tatagatgag aaactattaa ctgaagaaat ctataatcct   1440
gttgttgcta agtctgttcg ccaggctata aaaatcgtaa atgcggcgat taagaatac    1500
ggagactttg acaatattgt catcgaaatg gctcgtgaaa caagtgaagt tgatgaaaag   1560
aaagctattc aaaagattca aaagccaac  aagatgaaa  aagatgcagc aatgcttaag   1620
gctgctaacc aatataatgg aaaggctgaa ttaccacata tgtgttttcca cggtcataag   1680
caattagcga ctaaaatccg cctttggcat cagcaaggaa acgttgcct  ttatactggt   1740
aagacaatct caatccatga tttgataaat aatcctaatc agtttgaagt agatcatatt   1800
ttacctcttt ctatcacatt cgatgatagc cttgcaaata aggttttggt ttatgcaact   1860
gctaaccaag aaaaaggaca cgaacacct  tatcaggctt tagatagtat ggatgatgcg   1920
tggtcttttcc gtgaattaaa agcttttgta cgtgagtcaa aaacactttc aaacaagaaa   1980
aaagaatacc tccttacaga agaagatatt tcaaagtttg atgttcgaaa gaaatttatt   2040
gaacgaaatc ttgtagatac aagatacgct tcaagagttg tcctcaatgc ccttcaagaa   2100
cactttgagc tcacaagat  tgatacaaaa gtttccgtgg ttcgtggcca atttacatct   2160
caattgagac gccattgggg aattgagaag actcgtgata cttatcatca ccatgctgtc   2220
gatgcattga ttattgccgc ctcaagtcag ttgaatttgt ggaaaaaaca aaagaatacc   2280
cttgtaagtt attcagaaga acaactcctt gatattgaa  caggtgaact tattagtgat   2340
gatgagtaca aggaatctgt gttcaaagcc cctatcaac  attttgttga tacattgaag   2400
agtaaagaat ttgaagacag tatcttattc tcatatcaag tggattctaa gtttaatcgt   2460
aaaatatcag atgccactat ttatgcgaca agacaggcta aagtgggaaa agataagaag   2520
gatgaaactt atgtcttagg gaaaatcaaa gatatctata ctcaggatgg ttatgatgcc   2580
tttatgaaga tttataagaa ggataagtca aaattcctca tgtatcgtca cgacccacaa   2640
acctttgaga aagttatcga gccaattta  gagaactatc ctaataagga aatgaatgaa   2700
aaagggaaag aagtaccatg taatcctttc ctaaaatata aagaagaaca tggctatatt   2760
cgtaaatata gtaaaaaagg caatggtcct gaaatcaaa  gtcttaaata ctatgatagt   2820
aagcttttag gtaatcctat tgatattact ccagagaata gtaaaaataa agttgtctta   2880
cagtcattaa aacttggag  aacagatgtc tatttcaata aaaatactgg taaatatgaa   2940
attttaggac tgaaatatgc tgatttacaa tttgaaaaga agacaggaac atataagatt   3000
tcccaggaaa aatacaatgg ccattatgaa gaagaggtg  tagattctga ttcagaattc   3060
aagtttacac tttataaaaa tgatttgtta ctcgttaaag atacagaaac aaaagaacaa   3120
cagcttttcc gttttctttc tcgaactatg cctaatgtga aatattatgt agagttaaag   3180
ccttattcaa aagataaatt tgagaagaat gagtcactta ttgaaatttt aggttctgca   3240
gataagtcag gacgatgtat aaaagggcta ggaaaatcaa atatttctat ttataaggta   3300
agaacagatg tccataggaaa tcagcatatc atcaaaaatg agggtgataa gcctaagcta   3360
gatttttaa                                                           3369
```

| SEQ ID NO: 214 | moltype = DNA length = 4113 |
|---|---|
| FEATURE | Location/Qualifiers |
| source | 1..4113 |
| | mol_type = unassigned DNA |
| | organism = Streptococcus agalactiae |

SEQUENCE: 214

```
atgaataagc catattcaat aggccttgac atcggtacta attccgtcgg atggagcatt     60
attacagatg attataaagt acctgctaag aagatgagag ttttagggaa cactgataaa    120
gaatatatta agaagaatct cataggtgct ctgcttttg  atggcgggaa tactgctgca    180
gatacgcgct tgaagcgaac tgctcgtcgt cgttattcaa tcagaatca  tcgtattcta    240
tatttacaag aaatttttgc agaggaaatg agtaaagttg atgatagttt ctttcatcga    300
ttagaggatt cttttctagt tgaggaagat aagagaggga gcaagtatcc tatctttgca    360
acattgcagg aagagaaaga ttatcatgaa aaattttcga caatctatca tttgagaaaa    420
gaattagctg acaagaaga  aaaagcagac cttcgtctta tttatattga tctagctcat    480
atcattaaat ttagagggca tttcctaatt gaggatgata gctttgatgt caggaataca    540
gacatttcaa aacaatatca agattttta  gaaatcttta atacaacttt tgaaaataat    600
gatttgttat ctcaaaacgt tgacgtagag gcaatactaa cagataagat tagcaagtct    660
gcgaagaaag atcgtatttt agcgcagtat cctaaccaaa aatctactgg catttttgca    720
gaattttga  aattgattgt cggaaatcaa gctgacttca agaaatattt caatttggag    780
gataaaaacgc cgcttcaatt cgctaaggat agctacgatg aagatttaga aaatcttctt    840
ggacagattg gtgatgaatt tgcagactta ttctcagcag cgaaaaagtt atatgatagt    900
gtccttttgt ctggcattct tacagtaatc gacctcagta ccaaggcgcc actttcagct    960
tctatgattc agcgttatga tgaacataga gaggacttga aacagttaaa acaattcgta   1020
aaagcttcat tgccggaaaa atatcaagaa atatttgctg attcatcaaa agatggctac   1080
gctggttata ttgaaggtaa aactaatcaa gaagcttttt ataaataccct gtcaaaattg   1140
```

```
ttgaccaagc aagaagatag cgagaattt cttgaaaaaa tcaagaatga agatttcttg   1200
agaaaacaaa ggacctttga taatggctca attccacacc aagtccattt gacagagctg   1260
aaagctatta tccgccgtca atcagaatac tatcccttct tgaaagagaa tcaagatagg   1320
attgaaaaaa tccttacctt tagaattcct tattatatcg ggccactagc acgtgagaag   1380
agtgattttg catggatgac tcgcaaaaca gatgacagta ttcgaccttg gaatttttgaa   1440
gacttggttg ataaagaaaa atctgcggaa gcttttatcc atcgtatgac caacaatgat   1500
ttttatcttc ctgaagaaaa agttttacca aagcatagtc ttatttatga aaaatttacg   1560
gtctataatg agttgactaa ggttagatat aaaaatgagc aaggtgagac ttatttttttt   1620
gatagcaata ttaaacaaga aatctttgat ggagtattca aggaacatcg taaggtatcc   1680
aagaagaagt tgctagattt tctggctaaa gaatatgagg agtttaggat agtagatgtt   1740
attggtctag ataaagaaaa taaagctttc aacgcctcat tgggaactta ccacgatctc   1800
gaaaaaatac tagacaaaga ttttctagat aatccagata atgagtctat tctggaagat   1860
atcgtccaaa ctctaacatt atttgaagac agagaaatga ttaagaagcg tcttgaaaac   1920
tataaagatc tttttacaga gtcacaacta aaaaaactct atcgtcgtca ctatactggc   1980
tggggacgat tgtctgctaa gttaatcaat ggtattcgag ataaagagag tcaaaaaaca   2040
atcttggact atcttattga tgatggtaga tctaatcgca actttatgca gttgataaat   2100
gatgatggtc tatctttcaa atcaattatc agtaaggcac aggctggtag tcattcagat   2160
aatctaaaag aagttgtagg tgagcttgca ggtagccctg ctattaaaaa gggaattca   2220
caaagtttga aaattgttga tgagcttgtt aaagtcatgg gatacgaacc tgaacaaatt   2280
gtggttgaga tggcgcgtga gaatcaaaca acaaatcaag gtcgtcgtaa ctctcgacaa   2340
cgctataaac ttcttgatga tggcgttaag aatctagcta gtgacttgaa tggcaatatt   2400
ttgaaagaat atcctacgga taatcaagcg ttgcaaaatg aaagactttt cctttactac   2460
ttacaaaacg gaagagatat gtataccggg gaagctctag atattgacaa tttaagtcaa   2520
tatgatattg accacattat tcctcaagct ttcataaaag atgattctat tgataatcgt   2580
gtttttggtat catctgctaa aaatcgtgga aagtcagatg atgttcctag ccttgaaatt   2640
gtaaaagatt gtaaagttttt ctggaaaaaa ttacttgatg ctaagttaat gagtcagcag   2700
aagtatgata atttgactaa ggcagagcgc ggaggcctaa cttccgatga taggcaaga   2760
tttatccaac gtcagttggt tgagacacga caaattacca agcatgttgc ccgtatcttg   2820
gatgaacgct taataatga gcttgatagt aaaggtagaa ggatccgcaa agttaaaatt   2880
gtaaccttga agtcaaattt ggtttcaaat ttccgaaaag aatttggatt ctataaatt   2940
cgtgaagtta acaattatca ccatgcacat gatgcctatc ttaatgcagt agttgctaaa   3000
gctattctaa ccaaatatcc tcagttagag ccagaatttg tctacggcga ctatccaaaa   3060
tataatagtt acaaacgcg taatccgct acagaaaagc tattttttcta ttcaaatatt   3120
atgaacttct ttaaaactaa ggtaacttta gcggatggaa ccgttgttgt aaaagatgat   3180
attgaagtta ataatgatac gggtgaaatt gtttgggata aaaagaaaca ctttgcgaca   3240
gttagaaaag tcttgtcata ccctcagaac aatatcgtga agaacagaa gattcagaca   3300
ggtggtttct ctaaggaatc aatcttggcg catggtaact cagataagtt gattccaaga   3360
aaacgaaagg atatttattt agatcctaag aaatatggag gttttgatag tccgatagta   3420
gcttactctg ttttagttgt agctgatatc aaaaaggta aagcacaaaa actaaaaaca   3480
gttacggaac ttttaggaat taccatcatg gagaggtcca gatttgagaa aaatccatca   3540
gctttccttg aatcaaaagg ctatttaaat attagggctg ataaactaat tattttgccc   3600
aagtatagtc tgttcgaatt agaaaatggg cgtcgtcgat tacttgctag tgctggtgaa   3660
ttacaaaaag gtaatgagct agccttacca acacaatta tgaagttctt ataccttga   3720
agtcgttata atgagtcaaa aggtaaacca gaggagattg agaagaaaca agaatttgta   3780
aatcaacatg tctcttattt tgatgacatc cttcaattaa ttaatgattt tcaaaacga   3840
gttattctag cagatgctaa tttagagaaa atcaataagc tttaccaaga taataaggaa   3900
aaatatatcag tagatgaact tgctaataat attatccttt tatttacttt taccagtcta   3960
ggagctccag cagcttttaa attttttgat aaaatagttg atagaaaacg ctatacatca   4020
actaaagaag tacttaattc taccctaatt catcaatcta ttactggact ttatgaaaca   4080
cgtattgatt tgggtaagtt aggagaagat tga                               4113
```

SEQ ID NO: 215    moltype = DNA   length = 4134
FEATURE           Location/Qualifiers
source            1..4134
                  mol_type = unassigned DNA
                  organism = Streptococcus agalactiae
SEQUENCE: 215

```
atgaataagc catattcaat aggccttgac atcggtacta attccgtcgg atggagcatt     60
attacagatg attataaagt acctgctaag aagatgagag tttagggaa cactgataaa    120
gaatatatta agaagaatct cataggtgct ctgcttttttg atggcgggaa tactgctgca    180
gatagacgct tgaagcgaac tgctcgtcgt cgttatacac gtcgtagaaa tcgtattcta    240
tatttacaag aaatttttgc agaggaaatg agtaaagttg atgatagttt ctttcatcga    300
ttagaggatt cttttctagt tgaggaagat aagagaggta gcaagtatcc tatctttgca    360
acaatgcagg aggagaaata ttatcatgaa aaatttccga caatctatca tttgagaaaa    420
gaattggctg acaagaaaga aaagcagac cttcgtcttg tttatctggc tctagctcat    480
atcattaaat tcagagggca tttcctaatt gaggatgata gatttgatgt gaggaatacc    540
gatattcaaa acaatatca agcctttta gaaattttg atactacctt tgaaaataat    600
catttgttat ctcaaaatgt agatgtagaa gcaattctaa cagataagt tagcaagtct    660
gcgaagaagt atcgcatctt agcgcagtat cctaaccaaa aatctactgg tatttttgca    720
gaattttga aattgattgt cggaaatcaa gctgacttca agaacatttt caatttggag    780
gataaaacac cgcttcaatt cgctaaggat agctacgatg aagattttaga aaatcttctt    840
ggacagattg gtgatgaatt tgcagactta ttctcagtag cgaaaagct atatgatagt    900
gttctttttat ctggcattct tacagtaact gatctcagta ccaggcgcc actttctgcc    960
tctatgattc agcgtttatga tgaacatcat gaggacttaa agcatctaaa acaattcgta   1020
aaagcttcat tacctgaaaa ttatcggaa gtatttgctg attcatcaaa agatggctac   1080
gctggctata ttgaaggcaa aactaatcaa gaagcttttt ataaatatct gttaaaattg   1140
ttgaccaaac aagaaggtag cgagtatttt cttgagaaaa ttaagaatga agatttttg   1200
agaaaacaga gaacctttga taatggctca atcccgcatc aagtccattt gacagaattg   1260
agggctatta ttcgacgtca atcagaatac tatccattct tgaaagagaa tcaagatagg   1320
```

```
attgaaaaaa tccttacctt tagaattcct tattatgtcg ggccactagc acgtgagaag  1380
agtgattttg catggatgac tcgcaaaaca gatgacagta ttcgaccttg aattttgaa   1440
gacttggttg ataaagaaaa atctgcggaa gcttttatcc atcgcatgac caacaatgac  1500
ctctatcttc cagaagaaaa agttttacca aagcatagtc ttatttatga aaaatttact  1560
gtttacaatg aattaacgaa ggttagattt ttggcagaag gcttaaaga ttttcaattt    1620
ttaaatagga agcaaaaaga aactatcttt aacagcttgt ttaaggaaaa acgtaaagta  1680
actgaaaagt atattattag ttttttgaat aaagttgatg gatatgaagg aattgcaatc  1740
aaaggaattg agaaacagtt taacgctagc ctttcaacct atcatgatct taaaaaaata  1800
cttggcaagg atttccttga taatacagat aacgagctta ttttggaaga tatcgtccaa  1860
actctaacct tatttgaaga tagagaaatg attaagaagt gtcttgacat ctataaagat  1920
ttttttacag agtcacagct taaaaagtc tatcgccgtc actatactgg ctggggacga    1980
ttgtctgcta agctaataaa tggcatccga aataaagaga atcaaaaaac aatcttggac  2040
tatcttattg atgatggaag tgcaaaccga aacttcatgc agttgataaa tgatgatgat  2100
ctatcattta aaccaattat tgacaaggca cgaactggta gtcattcgga taatctgaaa  2160
gaagttgtag gtgaacttgc tggtagccct gctattaaaa aagggattct acaaagtttg  2220
aaaatagttg atgagctggt taaagtcatg ggctatgaac ctgaacaaat cgtggttgaa  2280
atggcacgtg agaaccaaac gacagcaaaa ggattaagtc gttcacgaca acgcttgaca  2340
accttgagag aatctcttgc taatttgaag agtaatattt ggaagagaa aaagcctaag   2400
tatgtgaaag atcaagttga aaatcatcat ttatctgatg accgtctttt cctttactac  2460
ttacaaaacg gaagagatat gtatacaaaa aaggctctgg atattgataa tttaagtcaa  2520
tatgatattg accacattat tcctcaagct ttcataaaag atgattctat tgataatcgt  2580
gttttggtat catctgctaa aaatcgtgga aaatcagatg atgttcctag cattgaaatt  2640
gtaaaagctc gcaaaatgtt ctggaaaaat ttactggatg ctaagttaat gagtcagcgt  2700
aagtatgata atttgactaa ggcagagcgc ggaggcctaa cttccgatga taaggcaaga  2760
tttatccaac gtcagttggt tgagactcga caaattacca agcatgtagc tcgtatcttg  2820
gatgaacgct tcaataatga agttgataat ggtaaaaaga tttgcaaggt taaaattgga  2880
accttgaagt caaatttggt ttcaaatttc cgaaaagaat ttggattcta taaaattcgt  2940
gaagttaatg attatcacca tgcacacgat gcttatctta atgcagtagt tgccaaagct  3000
attctaacca aatatccaca gttagagcca gagtttgtct acggaatgta tagacagaaa  3060
aaactttcga aaatcgttca tgaggataag gaagaaaaat atagtgaagc aaccaggaaa  3120
atgttttttct actccaactt gatgaatatg ttcaaaagag ttgtgaggtt agcagatggt  3180
tctattgttg taagaccagt aatagaaact ggtagatata tgagaaaaac tgcatgggat  3240
aaaaagaaac actttgcgac agttagaaaa gtcttgtcat accctcagaa caatatcgtg  3300
aagaagacag agattcagac aggtggttc tctaaggaat caatcttggc gcatggtaac    3360
tcagataagt tgattccaag aaaaacgaag gatatttatt tagatcctaa gaaatatgga  3420
ggttttgata gtccgatagt agcttactct gttttagttg tagctgatat caaaaaaggt  3480
aaagcacaaa aactaaaaac agttacggaa cttttaggaa ttaccatcat ggagaggtcc  3540
agatttgaga aaaatccatc agctttcctt gaatcaaaag gttatttaaa tattagggac  3600
gataaattaa tgattttacc gaagtatagt ctgttcgaat tagaaaatgg gcgtcgtcga  3660
ttacttgcta gtgctggtga attacaaaaa ggtaacgagc tagccttacc aacacaattt  3720
atgaagttct tataccttgc aagtcgttat aatgagtcaa aagtaaacc agaggagatt   3780
gagaagaaac aagaatttgt aaatcaacat gtctcttatt ttgatgacat ccttcaatta  3840
attaatgatt tttcaaaacg agttattcta gcagtgcta atttagaaga aatcaataag   3900
ctttaccagg ataataagga aaatatacca gtagatgaac ttgctaataa tattatcaat  3960
ctatttactt ttaccagtct aggagctcca gcagctttta aatttttga taaaaatagtt  4020
gatagaaaac gctatacatc aactaaagaa gtacttaatt ctactctaat ccatcaatct  4080
attactggac tttatgaaac acgtattgat ttgggtaaat taggagaaga ttga         4134

SEQ ID NO: 216          moltype = DNA   length = 4038
FEATURE                 Location/Qualifiers
source                  1..4038
                        mol_type = unassigned DNA
                        organism = Streptococcus mutans
SEQUENCE: 216
atgaaaaaac cttactctat tggacttgat attggaacca attctgttgg ttgggctgtt  60
gtgacagatg actacaaagt tcctgctaag aagatgaagg ttctgggaaa tacagataaa  120
agtcatatcg agaaaaattt gcttggcgct ttattatttg atagcgggaa tactgcagaa  180
gacagacggt aaagagaac tgctcgccgt cgttacacac gtcgcagaaa tcgtattta    240
tatttgcaag agatttttc agaagaaatg ggcaaggtag atgatagttc ctttcatcgt  300
ttagaggatt cttttcttgt tactgaggat aaacgaggag agcgccatcc catttttggg  360
aatcttgaag aagaagttaa gtatcatgaa aattttccaa ccatttatca tttgcggcaa  420
tatcttgcgg ataatccaga aaagttgat ttgcgtttag tttatttggc tttggcacat   480
ataattaagt ttagaggtca ttttttaatt gaaggaaagt tgatacacg caataatgat    540
gtacaaagac tgtttcaaga atcttttagca gtctatgata atactttga gaatagttcg   600
cttcaggagc aaaatgttca agttgaagaa attctgactg ataaaatcag taaatctgct  660
aagaaagata gagttttgaa actttttcct aatgaaaagt ctaatggccg ctttgcagaa  720
tttctaaaac taattgttgg taatcaagct gattttaaaa agcattttga attagaagag  780
aaagcaccat tgcaattttc taaagatact tatgaagaag agttagaagt actattagct  840
caaattggag ataattacgc agagctcttt ttatcagcaa agaaactgta tgatagtatc  900
cttttatcag ggattttaac agttactgat gttggtacca aagcgccttt atctgcttcg  960
atgattcagc gatataatga acatcagatg gatttagctc agcttaaaca attcattcgt  1020
cagaaattat cagataaata taacgaagtt ttttctgatg tttcaaaaga cggctatgcg  1080
ggttatattg atgggaaaac aaatcaagaa gcttttttata aataccttaa aggtctatta  1140
aataagattg agggaagtgg ctatttcctt gataaaattg agcgtgaagtt tttctaaga   1200
aagcaacgta cctttgacaa tggctctatt ccacatcaga ttcatcttca agaaatgcgt  1260
gctatcattc gtagacaggc tgaatttat ccgtttttag cagacaatca agataggatt    1320
gagaaattat tgacttccg tattcctac tatgttggtc cattagcgcg cggaaaaagt     1380
gattttgctt ggttaagtcg gaaatcggct gataaaatta caccatggaa ttttgatgaa  1440
atcgttgata aagaatcctc tgcagaagct tttatcaatc gtatgacaaa ttatgatttg  1500
```

```
tacttgccaa atcaaaaagt tcttcctaaa catagtttat tatacgaaaa atttactgtt 1560
tacaatgaat taacaaaggt taaatataaa acagagcaag gaaaaacagc atttttgat  1620
gccaatatga agcaagaaat ctttgatggc gtatttaagg tttatcgaaa agtaactaaa 1680
gataaattaa tggatttcct tgaaaaagaa tttgatgaat tcgtattgt tgatttaaca  1740
ggtctggata aagaaaataa agtatttaac gcttcttatg gaacttatca tgtttgtgt  1800
aaaattttag ataaagattt tctcgataat tcaaagaatg aaaagatttt agaagatatt 1860
gtgttgacct taacgttatt tgaagataga gaaatgatta gaaacgtct agaaaattac  1920
agtgattat tgaccaaaga acaagtgaaa aagctggaaa gacgtcatta tactggttgg  1980
ggaagattat cagctgagtt aattcatggt attcgcaata aagaaagcag aaaaacaatt  2040
cttgattatc tcattgatga tggcaatagc aatcggaact ttatgcaact gattaacgat  2100
gatgctcttt ctttcaaaga agagattgct aaggcacaag ttattggaga aacagacaat  2160
ctaaatcaag ttgttagtga tattgctggc agccctgcta ttaaaaaagg aatttttacaa 2220
agcttgaaga ttgttgatga gcttgtcaaa attatgggac atcaacctga aaatatcgtt  2280
gtggagatgg cgcgtgaaaa ccagtttacc aatcaggaac gacgaaattc acagcaacgt  2340
ttgaaaggtt tgacagattc tattaaagaa tttggaagtc aaattcttaa agaacatccg  2400
gttgagaatt cacagttaca aaatgataga ttgtttctat attatttaca aaacggcaga  2460
gatatgtata ctggagaaga attggatatt gattatctaa gccagtatga tatagaccat  2520
attatcccgc aagcttttat aaaggataat tctattgata atagagtatt gactagctca  2580
aaggaaaatc gtgaaaatc ggatgatgta ccaagtaaag atgttgttcg taaaatgaaa   2640
tcctattgga gtaagctact tcggcaaag cttattacac aacgtaaatt tgataatttg  2700
acaaaagctg aacgaggtgg attgaccgac gatgataaag ctggattcat caagcgtcaa  2760
ttagtagaaa cacgacaaat taccaaacat gtagcacgta ttctgacgaa acgatttaat  2820
acagaaacag atgaaaacaa caagaaaatt cgtcaagtaa aaattgtgac cttgaaatca  2880
aatcttgttt ccaatttccg taaagagttt gaactctaca aagtgcgtga aattaatgac  2940
tatcatcatg cacatgatgc ctatctcaat gctgtaattg gaaaggcttt actaggtgtt  3000
taccacaat tggaacctga atttgtttat ggtgattatc ctcatttca tggacataaa  3060
gaaaataaag caactgctaa gaattttttc tattcaaata ttatgaactt ctttaaaaaa  3120
gatgatgtcc gtactgataa aaatggtgaa attatctgga aaaagatga gcatatttct  3180
aatattaaaa aagtgctttc ttatccacaa gttaatattg ttaagaaagt agaggagcaa  3240
acgggaggat tttctaaaga atctatcttg ccgaaaagta attctgacaa attcttattcct 3300
cgaaaaacga agaaatttta ttgggatacc aagaaatatg gaggatttga tagcccgatt  3360
gttgctatt ctatttttagt tattgctgat attgaaaaag gtaaatcaa aaaattgaaa  3420
acagtcaaag ccttagttgg tgtcactatt atggaaaaga tgacttttga aagggatcca  3480
gttgcttttc ttgagcgaaa aggctatcga aatgttcaag aagaaaatat tataaagtta  3540
ccaaaatata gtttatttaa actagaaaac ggacgaaaaa ggctattggc aagtgctagg  3600
gaacttcaaa agggaaatga aatcgttttg ccaaatcatt taggaacctt gctttatcac  3660
gctaaaaata ttcataaagt tgatgaacca agcatttgg actatgttga taaacataaa  3720
gatgaattta aggagttgct agatgttgtg tcaaacttttt ctaaaaaata tactttagca  3780
gaaggaaatt tagaaaaaat caaagaatta tatgcacaaa ataatggtga agatcttaaa  3840
gaattagcaa gttcatttat caacttatta acatttactg ctataggagc accggctact  3900
tttaaattct ttgataaaaa tattgatcga aaacgtatata cttcaactac tgaaattctc  3960
aacgctaccc tcatccacca atccatcacc ggtctttatg aaacgcggat tgatctcaat  4020
aagttaggag gagactaa                                                 4038

SEQ ID NO: 217        moltype = DNA  length = 20
FEATURE               Location/Qualifiers
misc_feature          1..20
                      note = synthesized sequence- Mprimer qADH-F
source                1..20
                      mol_type = other DNA
                      organism = synthetic construct
SEQUENCE: 217
caagtcgcgg tttcaatca                                                20

SEQ ID NO: 218        moltype = DNA  length = 21
FEATURE               Location/Qualifiers
misc_feature          1..21
                      note = synthesized sequence- Primer qADH-R
source                1..21
                      mol_type = other DNA
                      organism = synthetic construct
SEQUENCE: 218
tgaaggtgga agtcccaaca a                                             21

SEQ ID NO: 219        moltype = DNA  length = 19
FEATURE               Location/Qualifiers
misc_feature          1..19
                      note = synthesized sequence- probe ADH-VIC
source                1..19
                      mol_type = other DNA
                      organism = synthetic construct
SEQUENCE: 219
tgggaagcct atctaccac                                                19

SEQ ID NO: 220        moltype = DNA  length = 15
FEATURE               Location/Qualifiers
misc_feature          1..15
                      note = synthesized sequence- Probe wtEPSPS
source                1..15
```

```
                          mol_type = other DNA
                          organism = synthetic construct
SEQUENCE: 220
cggccattga cagca                                                    15

SEQ ID NO: 221            moltype = DNA   length = 20
FEATURE                   Location/Qualifiers
misc_feature              1..20
                          note = synthesized sequence- Forward primer qEPSPS-F
source                    1..20
                          mol_type = other DNA
                          organism = synthetic construct
SEQUENCE: 221
tcttggggaa tgctggaact                                               20

SEQ ID NO: 222            moltype = DNA   length = 21
FEATURE                   Location/Qualifiers
misc_feature              1..21
                          note = synthesized sequence- reverse primer qEPSPSR
source                    1..21
                          mol_type = other DNA
                          organism = synthetic construct
SEQUENCE: 222
caccagcagc agtaacagct g                                             21

SEQ ID NO: 223            moltype = DNA   length = 17
FEATURE                   Location/Qualifiers
misc_feature              1..17
                          note = synthesized sequence- FAM-wtEPSPS R probe
source                    1..17
                          mol_type = other DNA
                          organism = synthetic construct
SEQUENCE: 223
tgctgtcaat ggccgca                                                  17

SEQ ID NO: 224            moltype = DNA   length = 20
FEATURE                   Location/Qualifiers
misc_feature              1..20
                          note = synthesized sequence- forward primer qEPSPS-F
source                    1..20
                          mol_type = other DNA
                          organism = synthetic construct
SEQUENCE: 224
tcttggggaa tgctggaact                                               20

SEQ ID NO: 225            moltype = DNA   length = 20
FEATURE                   Location/Qualifiers
misc_feature              1..20
                          note = synthesized sequence- reverse primer q wtEPSPS RA
source                    1..20
                          mol_type = other DNA
                          organism = synthetic construct
SEQUENCE: 225
ccaccagcag cagtaacagc                                               20

SEQ ID NO: 226            moltype = DNA   length = 21
FEATURE                   Location/Qualifiers
misc_feature              1..21
                          note = synthesized sequence- forward primer q epTIPS F
source                    1..21
                          mol_type = other DNA
                          organism = synthetic construct
SEQUENCE: 226
ggaagtgcag ctcttcttgg g                                             21

SEQ ID NO: 227            moltype = DNA   length = 19
FEATURE                   Location/Qualifiers
misc_feature              1..19
                          note = synthesized sequence- reverse primer q epTIPS R
source                    1..19
                          mol_type = other DNA
                          organism = synthetic construct
SEQUENCE: 227
agctgctgtc aatgaccgc                                                19

SEQ ID NO: 228            moltype = DNA   length = 15
FEATURE                   Location/Qualifiers
misc_feature              1..15
                          note = synthesized sequence- TIPS probe
```

```
source                  1..15
                        mol_type = other DNA
                        organism = synthetic construct
SEQUENCE: 228
aatgctggaa tcgca                                                       15

SEQ ID NO: 229          moltype = DNA  length = 23
FEATURE                 Location/Qualifiers
misc_feature            1..23
                        note = MHP14Cas1 target site
source                  1..23
                        mol_type = unassigned DNA
                        organism = Zea mays
SEQUENCE: 229
gttaaatctg acgtgaatct gtt                                              23

SEQ ID NO: 230          moltype = DNA  length = 21
FEATURE                 Location/Qualifiers
misc_feature            1..21
                        note = MHP14Cas3 target site
source                  1..21
                        mol_type = unassigned DNA
                        organism = Zea mays
SEQUENCE: 230
acaaacattg aagcgacata g                                                21

SEQ ID NO: 231          moltype = DNA  length = 18
FEATURE                 Location/Qualifiers
misc_feature            1..18
                        note = TS8Cas1 target site
source                  1..18
                        mol_type = unassigned DNA
                        organism = Zea mays
SEQUENCE: 231
gtacgtaacg tgcagtac                                                    18

SEQ ID NO: 232          moltype = DNA  length = 20
FEATURE                 Location/Qualifiers
misc_feature            1..20
                        note = TS8Cas2 target site
source                  1..20
                        mol_type = unassigned DNA
                        organism = Zea mays
SEQUENCE: 232
gctcatcagt gatcagctgg                                                  20

SEQ ID NO: 233          moltype = DNA  length = 17
FEATURE                 Location/Qualifiers
misc_feature            1..17
                        note = TS9Cas2 target site
source                  1..17
                        mol_type = unassigned DNA
                        organism = Zea mays
SEQUENCE: 233
ggctgtttgc ggcctcg                                                     17

SEQ ID NO: 234          moltype = DNA  length = 21
FEATURE                 Location/Qualifiers
misc_feature            1..21
                        note = TS9Cas3 target site
source                  1..21
                        mol_type = unassigned DNA
                        organism = Zea mays
SEQUENCE: 234
gcctcgaggt tgcacgcacg t                                                21

SEQ ID NO: 235          moltype = DNA  length = 20
FEATURE                 Location/Qualifiers
misc_feature            1..20
                        note = TS10Cas1 target site
source                  1..20
                        mol_type = unassigned DNA
                        organism = Zea mays
SEQUENCE: 235
gcctcgcctt cgctagttaa                                                  20

SEQ ID NO: 236          moltype = DNA  length = 18
FEATURE                 Location/Qualifiers
misc_feature            1..18
```

```
                        note = TS10Cas3 target site
source                  1..18
                        mol_type = unassigned DNA
                        organism = Zea mays
SEQUENCE: 236
gctcgtgttg gagataca                                                      18

SEQ ID NO: 237          moltype = DNA  length = 80
FEATURE                 Location/Qualifiers
source                  1..80
                        mol_type = unassigned DNA
                        organism = Zea mays
SEQUENCE: 237
gttaaatctg acgtgaatct gtttggaatt gaaaacaag tgcttccttt catacaccac          60
tatgtcgctt caatgtttgt                                                    80

SEQ ID NO: 238          moltype = DNA  length = 80
FEATURE                 Location/Qualifiers
source                  1..80
                        mol_type = unassigned DNA
                        organism = Zea mays
SEQUENCE: 238
acaaacattg aagcgacata gtggtgtatg aaaggaagca cttgttttc aattccaaac          60
agattcacgt cagatttaac                                                    80

SEQ ID NO: 239          moltype = DNA  length = 66
FEATURE                 Location/Qualifiers
source                  1..66
                        mol_type = unassigned DNA
                        organism = Zea mays
SEQUENCE: 239
ccagtactgc acgttacgta cgtacgaact aatatactcc accagctgat cactgatgag        60
ccgagc                                                                   66

SEQ ID NO: 240          moltype = DNA  length = 66
FEATURE                 Location/Qualifiers
source                  1..66
                        mol_type = unassigned DNA
                        organism = Zea mays
SEQUENCE: 240
gctcggctca tcagtgatca gctggtggag tatattagtt cgtacgtacg taacgtgcag        60
tactgg                                                                   66

SEQ ID NO: 241          moltype = DNA  length = 35
FEATURE                 Location/Qualifiers
source                  1..35
                        mol_type = unassigned DNA
                        organism = Zea mays
SEQUENCE: 241
ccgacgtgcg tgcaacctcg aggccgcaaa cagcc                                   35

SEQ ID NO: 242          moltype = DNA  length = 35
FEATURE                 Location/Qualifiers
source                  1..35
                        mol_type = unassigned DNA
                        organism = Zea mays
SEQUENCE: 242
ggctgtttgc ggcctcgagg ttgcacgcac gtcgg                                   35

SEQ ID NO: 243          moltype = DNA  length = 68
FEATURE                 Location/Qualifiers
source                  1..68
                        mol_type = unassigned DNA
                        organism = Zea mays
SEQUENCE: 243
gctcgtgttg gagatacagg gacagcaagt acttggccct taactagcga aggcgaggcg        60
gccatgga                                                                 68

SEQ ID NO: 244          moltype = DNA  length = 68
FEATURE                 Location/Qualifiers
source                  1..68
                        mol_type = unassigned DNA
                        organism = Zea mays
SEQUENCE: 244
tccatggccg cctcgccttc gctagttaag gccaagtac ttgctgtccc tgtatctcca         60
acacgagc                                                                 68

SEQ ID NO: 245          moltype = DNA  length = 1108
FEATURE                 Location/Qualifiers
```

```
misc_feature            1..1108
                        note = synthesized sequence- MHP14Cas-1 guideRNA cassette
source                  1..1108
                        mol_type = other DNA
                        organism = synthetic construct
SEQUENCE: 245
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta ttttttttata tacctttttt    720
ccttctatgt acagtaggac acagtgtcag cgccgcgttg acggagaata tttgcaaaaa   780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc cacccttgact aatcacaaga    960
gtggagcgta ccttataaac cgagccgcaa gcaccgaatt gttaaatctg acgtgaatct   1020
gttgttttag agctagaaat agcaagttaa aataaggcta gtccgttatc aacttgaaaa   1080
agtggcaccg agtcggtgct ttttttt                                     1108

SEQ ID NO: 246         moltype = DNA  length = 1106
FEATURE                Location/Qualifiers
misc_feature           1..1106
                       note = synthesized sequence- MHP14Cas-3 gRNA cassette
source                 1..1106
                       mol_type = other DNA
                       organism = synthetic construct
SEQUENCE: 246
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta ttttttttata tacctttttt    720
ccttctatgt acagtaggac acagtgtcag cgccgcgttg acggagaata tttgcaaaaa   780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc cacccttgact aatcacaaga    960
gtggagcgta ccttataaac cgagccgcaa gcaccgaatt gcaaacattg aagcgacata   1020
ggttttagag ctagaaatag caagttaaaa taaggctagt ccgttatcaa cttgaaaaag   1080
tggcaccgag tcggtgcttt tttttt                                      1106

SEQ ID NO: 247         moltype = DNA  length = 1103
FEATURE                Location/Qualifiers
misc_feature           1..1103
                       note = synthesized sequence- TS8Cas-1 guideRNA cassette
source                 1..1103
                       mol_type = other DNA
                       organism = synthetic construct
SEQUENCE: 247
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta ttttttttata tacctttttt    720
ccttctatgt acagtaggac acagtgtcag cgccgcgttg acggagaata tttgcaaaaa   780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc cacccttgact aatcacaaga    960
gtggagcgta ccttataaac cgagccgcaa gcaccgaatt gtacgtaacg tgcagtacgt   1020
```

```
tttagagcta gaaatagcaa gttaaaataa ggctagtccg ttatcaactt gaaaaagtgg   1080
caccgagtcg gtgctttttt ttt                                           1103

SEQ ID NO: 248          moltype = DNA  length = 1105
FEATURE                 Location/Qualifiers
misc_feature            1..1105
                        note = synthesized sequence- TS8Cas-2 guideRNA cassette
source                  1..1105
                        mol_type = other DNA
                        organism = synthetic construct
SEQUENCE: 248
tgagagtaca atgatgaacc tagattaatc aatgccaaag tctgaaaaat gcaccctcag   60
tctatgatcc agaaaatcaa gattgcttga ggccctgttc ggttgttccg gattagagcc   120
ccggattaat tcctagccgg attacttctc taatttatat gagcttgaat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga ggggcatca    480
aagatctggc tgtgtttcca gctgtttttg ttagccccat cgaatcctg acataatgat    540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta tttttttata tacctttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
gtggagcgta ccttataaac cgagccgcaa gcaccgaatt gctcatcagt gatcagctgg  1020
gttttagagc tagaaatagc aagttaaaat aaggctagtc cgttatcaac ttgaaaaagt  1080
ggcaccgagt cggtgctttt ttttt                                        1105

SEQ ID NO: 249          moltype = DNA  length = 1102
FEATURE                 Location/Qualifiers
misc_feature            1..1102
                        note = synthesized sequence- TS9Cas-2 guideRNA cassette
source                  1..1102
                        mol_type = other DNA
                        organism = synthetic construct
SEQUENCE: 249
tgagagtaca atgatgaacc tagattaatc aatgccaaag tctgaaaaat gcaccctcag   60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga ggggcatca    480
aagatctggc tgtgtttcca gctgtttttg ttagccccat cgaatcctg acataatgat    540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta tttttttata tacctttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
gtggagcgta ccttataaac cgagccgcaa gcaccgaatt ggctgtttgc ggcctcggtt  1020
ttagagctag aaatagcaag ttaaaataag ctagtccgt tatcaacttg aaaaagtggc   1080
accgagtcgg tgcttttttt tt                                           1102

SEQ ID NO: 250          moltype = DNA  length = 1106
FEATURE                 Location/Qualifiers
misc_feature            1..1106
                        note = synthesized sequence- TS9Cas-3 guideRNA cassette
source                  1..1106
                        mol_type = other DNA
                        organism = synthetic construct
SEQUENCE: 250
tgagagtaca atgatgaacc tagattaatc aatgccaaag tctgaaaaat gcaccctcag   60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga ggggcatca    480
aagatctggc tgtgtttcca gctgtttttg ttagccccat cgaatcctg acataatgat    540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta tttttttata tacctttttt   720
```

```
cettctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gcctcgaggt tgcacgcacg   1020
tgttttagag ctagaaatag caagttaaaa taaggctagt ccgttatcaa cttgaaaaag   1080
tggcaccgag tcggtgcttt tttttt                                        1106

SEQ ID NO: 251           moltype = DNA  length = 1105
FEATURE                  Location/Qualifiers
misc_feature             1..1105
                         note = synthesized sequence- TS10Cas-1 guideRNA cassette
source                   1..1105
                         mol_type = other DNA
                         organism = synthetic construct
SEQUENCE: 251
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga ggggcatca    480
aagatcggc tgtgtttcca gctgtttttg ttagccccat cgaatcctg acataatgat    540
cccgcttaaa taagcaacct cgcttgtata gttccttgtg ctctaacaca cgatgatgat    600
aagtcgtaaa atagtggtgt ccaaagaatt tccaggccca gttgtaaaag ctaaatgct    660
attcgaattt ctactagcag taagtcgtgt ttagaaatta ttttttttata tacctttttt    720
cettctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gcctcgcctt cgctagttaa   1020
gttttagagc tagaaatagc aagttaaaat aaggctagtc cgttatcaac ttgaaaagt   1080
ggcaccgagt cggtgctttt ttttt                                         1105

SEQ ID NO: 252           moltype = DNA  length = 1103
FEATURE                  Location/Qualifiers
misc_feature             1..1103
                         note = synthesized sequence- TSCas-3 guideRNA cassette
source                   1..1103
                         mol_type = other DNA
                         organism = synthetic construct
SEQUENCE: 252
tgagagtaca atgatgaacc tagattaatc aatgccaaag tctgaaaaat gcaccctcag     60
tctatgatcc agaaaatcaa gattgcttga ggccctgttc ggttgttccg gattagagcc    120
ccggattaat tcctagccgg attacttctc taatttatat agattttgat gagctggaat    180
gaatcctggc ttattccggt acaaccgaac aggccctgaa ggataccagt aatcgctgag    240
ctaaattggc atgctgtcag agtgtcagta ttgcagcaag gtagtgagat aaccggcatc    300
atggtgccag tttgatggca ccattagggt tagagatggt ggccatgggc gcatgtcctg    360
gccaactttg tatgatatat ggcagggtga ataggaaagt aaaattgtat tgtaaaaagg    420
gatttcttct gtttgttagc gcatgtacaa ggaatgcaag ttttgagcga ggggcatca    480
aagatcggc tgtgtttcca gctgtttttg ttagccccat cgaatcctg acataatgat    540
cccgcttaaa taagcaacct cgcttgtata gttccttgtg ctctaacaca cgatgatgat    600
aagtcgtaaa atagtggtgt ccaaagaatt tccaggccca gttgtaaaag ctaaatgct    660
attcgaattt ctactagcag taagtcgtgt ttagaaatta ttttttttata tacctttttt    720
cettctatgt acagtaggac acagtgtcag cgccgcgttg acggagaata tttgcaaaaa    780
agtaaaagag aaagtcatag cggcgtatgt gccaaaaact tcgtcacaga gagggccata    840
agaaacatgg cccacggccc aatacgaagc accgcgacga agcccaaaca gcagtccgta    900
ggtggagcaa agcgctgggt aatacgcaaa cgttttgtcc caccttgact aatcacaaga    960
gtggagcgta ccttataaac cgagccgcaa gcaccgaatt gctcgtgttg gagatacagt   1020
tttagagcta gaaatagcaa gttaaaataa ggctagtccg ttatcaactt gaaaagtgg   1080
caccgagtcg gtgcttttttt ttt                                          1103

SEQ ID NO: 253           moltype = DNA  length = 4928
FEATURE                  Location/Qualifiers
misc_feature             1..4928
                         note = synthesized sequence- MHP14Cas1 donor
source                   1..4928
                         mol_type = other DNA
                         organism = synthetic construct
SEQUENCE: 253
gccatgtcat cttgtagtta gggcttggag ctagtcgacc gttggaggct ttgtcctcat     60
gcggcaccgg acagtctggt gctacaccgg gccctctga ccatctgctc                120
tgacatctga attgcactgt tcactttgca gagtcgacca ttgcgtgcag gtagccattg    180
ctccgctggt gcaccggaca gtccagtggc acaccggaca gtcgatgaa ttatagcgga   240
gctgcgcctg ggaaacccga agctgaggag tttgagctga ttcaccctgg tgcaccggac    300
actgtccggt ggcacactgg acagtccggt gcgccggacc agggcacact tcggtttcct    360
ttttgctcct ttctttgaa gctaacttg ttctttgat tggtttgtgt tgaacccttta    420
```

```
gcacctgtag aatgtatgat ctagagcaaa ctagttagtc caattatttg tgttgggcaa    480
ttcaaccacc aaaaacattt aggaaaatgt ttgatcttat ttcccttttca tattctctta   540
ttgctagttg tcggggtgaa gttgagctct tgcttaggtt ttaattagtg ttgatttta    600
gaaaaaccca attcaccccc ctcttgggca tcgtgatcct tttagcaaca aaatgtgcac   660
acatcaaaac aagcgcttct accatatgta gttgttgcac aataatggtc ctccttagga   720
tttgcaaccg tttaacaata gctatgtgac cacagattta tgtcggatgc acgaaaattg   780
taggattttta catttcttta ccttggttca caaacattga agcgacatag tggtgtatga   840
aaggaagcac ttgttttttca attccaaacc gcggtaccat ttaaatctta agcctaggat   900
aacttcgtat agcatacatt atacgaagtt atggcgccgc tagcctgcag tgcagcgtga   960
cccggtcgtg ccctctcta gagataatga gcattgcatg tctaagttat aaaaaattac    1020
cacatatttt ttttgtcaca cttgtttgaa gtgcagttta tctatcttta tacatatatt   1080
taaactttac tctacgaata atataatcta tagtactaca ataatatcag tgttttagag   1140
aatcatataa atgaacagtt agacatggtc taaaggacaa ttgagtattt tgacaacagg   1200
actctacagt tttatctttt tagtgtgcat gtgttctcct tttttttgc aaatagctc    1260
acctatataa tacttcatcc attttattag tacatccatt tagggtttag ggttaatggt   1320
ttttatagac taatttttttt agtacatcta ttttattcta ttttagcctc taaattaaga   1380
aaactaaaac tctatttag tttttttattt taataattta gatataaaat agaataaaat   1440
aaagtgacta aaaattaaac aaataccctt taagaaatta aaaaaactaa ggaaacatttt  1500
ttcttgtttc gagtagataa tgccagcctg ttaaacgccg tcgacagtc taacggacac    1560
caaccagcga accagcagcg tcgcgtcggg ccaagcgaag cagacggcac ggcatctctg   1620
tcgctgcctc tggaccccctc tcgagagttc cgctccaccg ttggacttgc tccgctgtcg   1680
gcatccagaa attgcgtggc ggagcggcag acgtgagcgg cacggcagg cggcctcctc   1740
ctcctctcac ggcaccggca gctacggggg attccttttcc caccgctcct tcgctttccc   1800
ttcctcgccc gccgtaataa atagacacc cctccacacc ctcttttcccc aacctcgtgt   1860
tgttcggagc gcacacacac acaaccagat ctcccccaaa tccaccccgtc ggcacctccg   1920
cttcaaggta cgccgctcgt cctccccccccc ccccctctct accttctcta gatcggcgtt  1980
ccggtccatg catggttagg gcccggtagt tctacttctg ttcatgtttg tgttagatcc   2040
gtgtttgtgt tagatccgtg ctgctagcgt tcgtacacgg atgcgacctg tacgtcagac   2100
acgttctgat tgctaacttg ccagtgtttc tctttgggga atcctgggat ggctctagcc   2160
gttccgcaga cgggatcgat ttcatgattt tttttgtttc gttgcatagg gtttggtttg    2220
cccttttcct ttatttcaat atatgccgtg cacttgtttg tcgggtcatc ttttcatgct   2280
ttttttttgtc ttggttgtga tgatgtggtc tggttgggcg gtcgttctag atcggagtag  2340
aattctgttt caaactacct ggtggattta ttaattttgg atctgtatgt gtgtgccata    2400
catattcata gttacgaatt gaagatgatg gatggaaata tcgatctagg ataggtatac   2460
atgttgatgc gggttttact gatgcatata cagagatgct tttttgttcgc ttggttgtga  2520
tgatgtggtg tggttgggcg gtcgttcatt cgttctagat cggagtagaa tactgtttca   2580
aactacctgg tgtatttatt aattttggaa ctgtatgtgt gtgtcataca tcttcatagt   2640
tacgagttta agatggatgg aaatatcgat ctaggataga tatacatgtt gatgtgggtt   2700
ttactgatgc atatacatga tggcatatgc agcatctatt catatgctct aaccttgagt   2760
acctatctat tataataaac aagtatgttt tataattatt ttgatcttga tacttggaa   2820
tgatggcata tgcagcagct atatgtggat ttttttagcc ctgccttcat acgctattta   2880
tttgcttggt actgtttctt ttgtcgatgc tcaccctgtt gtttggtgtt acttctgcag   2940
gtcgactcta gaggatcaat tcgctagcga agttcctatt ccgaagttcc tattctcag   3000
aaagtatagg aacttcagat ccaccgggat ccccgatcat gcaaaaactc attaactcag   3060
tgcaaaacta tgcctggggc agcaaaacgg cgttgactga actttatggt atggaaaatc   3120
cgtccagcca gccgatggcc gagctgtgga tgggcgcaca tccgaaaagc agttcacgag   3180
tgcagaatgc cgccggagat atcgtttcac tgcgtgatgt gattgagagt gataaatcga   3240
ctctgctcgg agaggccgtt gccaaacgct ttggcgaact gccttttcctg ttcaaagtat  3300
tatgcgcagc acagccactc tccattcagg ttcatccaaa caaacacaat tctgaaatcg   3360
gttttgccaa agaaaatgcc gcaggtatcc cgatggatgc cgccgagcgt aactataaag   3420
atcctaacca caagccggag ctggtttttg cgctgacgcc tttccttgcg atgaacgtgt   3480
ttcgtgaatt ttccgagatt gtctccctac tccagccggt cgcaggtgca catccggcga   3540
ttgctcactt tttacaacag cctgatgccg aacgtttaag cgaactgttc gccagcctgt   3600
tgaatatgca gggtgaagaa aaatcccgcg cgctggcgat tttaaaatcg ccctcgata   3660
gccacagggg tgaacctgg caaacgattc gtttaatttc tgaattttac ccggaagaca   3720
gcggtctgtt ctccccgcta ttgctgaatg tggtgaaatt gaaccctggc gaagcgatgt   3780
tcctgttcgc tgaacaccg cacgcttacc tgcaaggcgt ggcgctggaa gtgatggcaa   3840
actccgataa cgtgctgcgt gcgggtctga cgcctaaata cattgatatt ccggaactgg   3900
ttgccaatgt gaaattcgaa gccaaaccgg ctaaccagtt gttgacccag ccggtgaaac   3960
aaggtgcaga actggacttc ccgattccag tggatgattt tgccttctcg ctgcatgacc   4020
ttagtgataa agaaaccacc attagccagc agagtgccgc catttgttc tgcgtcgaag   4080
gcgatgcaac gttgtggaaa ggtctcagc agttacagct taaacgggt gaatcagcgt   4140
ttattgccgc caacgaatca ccggtgactg tcaaggcca cggccgttta gcgcgtgttt   4200
acaacaagct gtaagagctt actgaaaaaa ttaacatctc ttgctaagct gggggtggaa   4260
cctagacttg tccatcttct ggattggcca acttaattaa tgtatgaaat aaaaggatgc   4320
acacatagtg acatgctaat cactataatg tgggcatcaa agttgtgtgt tatgtgtaat   4380
tactagttat ctgaataaaa gagaaagaga tcatccatat ttcttatcct aaatgaatgt   4440
cacgtgtctt tataattctt tgatgaacca gatgcatttc attaaccaaa tccatataca   4500
tataaatatt aatcatatat aattaatatc aatgggtta gcaaaacaaa tctagtctag   4560
gtgtgttttg cgaatgcggc cctagcgtat acgaagttcc tattccgaag ttcctattct   4620
ccagaaagta taggaacttc tgtacacctg agctgattcc gatgacttcg taggttccta   4680
gctcaagcct ctcgtgtcca agcgtcactt acgattagct aatgattacg gcatctagga   4740
ccgactagct aactaactag taccgaggcc ggccccgcgg gagctcggcg cgccagattc   4800
acgtcagatt taaccaaaac tatattatga ggtacacata ttacaatcca aaatgaatta   4860
tctagttctc gagttgtaca cagtttatca cgtgttttac acattccaac cctaaactcc   4920
aaccgtgg                                                            4928

SEQ ID NO: 254     moltype = DNA  length = 4570
FEATURE            Location/Qualifiers
```

```
misc_feature         1..4570
                     note = synthesized sequence- MHP14Cas3 donor
source               1..4570
                     mol_type = other DNA
                     organism = synthetic construct
SEQUENCE: 254
acacttcggt ttccttttg ctcctttctt ttgaagccta acttgttctt ttgattggtt    60
tgtgttgaac cttagcacc tgtagaatgt atgatctaga gcaaactagt tagtccaatt   120
atttgtgttg ggcaattcaa ccaccaaaaa catttaggaa aatgtttgat cttatttccc   180
tttcatattc tcttattgct agttgtcggg gtgaagttga gctcttgctt aggttttaat   240
tagtgttgat ttttagaaaa acccaattca ccccccctctt gggcatcgtg atccttttag   300
caacaaaatg tgcacacatc aaaacaagcg cttctaccat atgtagttgt tgcacaataa   360
tggtcctcct taggatttgc aaccgtttaa caatagctat gtgaccacag atttatgtcg   420
gatgcacgaa aattgtagga ttttacattt ctttaccttg gttcacaaac attgaagcga   480
caggtaccat ttaaatctta agcctaggat aacttcgtat agcatacatt atacgaagtt   540
atggcgccgc tagcctgcag tgcagcgtga cccggtcgtg cccctctcta gagataatga   600
gcattgcatg tctaagttat aaaaaattac acatatttt ttttgtcaca cttgtttgaa   660
gtgcagttta tctatcttta tacatatatt taaactttac tctacgaata atataatcta   720
tagtactaca ataatatcag tgtttagag aatcatataa atgaacagtt agacatggtc   780
taaaggacaa ttgagtattt tgacaacagg actctacagt tttatctttt tagtgtgcat   840
gtgttctcct ttttttttgc aaatagcttc acctatataa tacttcatcc attttattag   900
tacatccatt tagggtttag ggtaatggt tttataga taatttttt agtacatcta   960
ttttattcta tttagcctc taaattaaga aaactaaaac tctattttag tttttttatt  1020
taataattta gatataaaat agaataaat aaagtgacta aaaattaaac aaataccctt  1080
taagaaatta aaaaaactaa ggaaacattt ttccttgttc gagtagataa tgccagcctg  1140
ttaaacgccg tcgacgagtc taacggacac caaccagcga accagcagcg tcgcgtcgga  1200
ccaagcgaag cagacggcac ggcatcctg tcgctgcctc tggaccccctc tcgagagttc  1260
cgctccaccg ttggacttgc tccgctgtcg gcatccagaa attgcgtggc ggagcggcag  1320
acgtgagccg gcacggcagg cggcctcctc ctcctctcac ggcaccggca gctacggggg  1380
attcctttcc caccgctcct tcgctttccc ttcctcgccc gccgtaataa atagacaccc  1440
cctccacacc ctcttttcccc aacctcgtgt tgttcggagc gcacacacac acaaccagat  1500
ctccccccaaa tccacccgtc ggcacctccg cttcaaggta cgccgctcgt cctccccccc  1560
cccctctct accttctcta gatcggcgtt ccggtccatg catggttagg gcccggtagt  1620
tctacttctg ttcatgtttg tgttagatcc gtgtttgtgt tagatccgtg ctgctagcgt  1680
tcgtacacgg atgcgacctg tacgtcagac acgttctgat tgctaacttg ccagtgttc  1740
tctttgggga atcctgggat ggctctagcc gttccgcaga cgggatcgat ttcatgattt  1800
ttttttgtttc gttgcatagg gtttggtttg ccctttttcct ttatttcaat atatgccgtg  1860
cacttgtttg tcgggtcatc ttttcatgct tttttttgtc ttggttgtga tgatgtggtc  1920
tggttgggcg gtcgttctag atcggagtag aattctgttt caaactacct ggtggattta  1980
ttaattttgg atctgtatgt gtgtgccata catattcata gttacgaatt gaagatgatg  2040
gatgaaaata tcgatctagg ataggtatac atgttgatgc gggttttact gatgcatata  2100
cagagatgct ttttgttcgc ttggttgtga tgatgtggtg tggttgggcg gtcgttcatt  2160
cgttctagat cggagtagaa tactgtttca aactacctg tgtattatt aattttggaa  2220
ctgtatgtgt gtgtcataca tcttcatagt tacgagttta agatggatgg aaatatcgat  2280
ctaggatagg tatacatgtt gatgtgggtt ttactgatgc atatacatga tggcatatgc  2340
agcatctatt catatgctct aaccttgagt acctatctat tataataaac aagtatgttt  2400
tataattatt ttgatcttga tatacttgga tgatggcagt gcagcagct atatgtggat  2460
ttttttagcc ctgccttcat acgctattta tttgcttggt actgtttctt ttgtcgatgt  2520
tcaccctgtt gtttggtgtt acttctgcag gtcgactcta gaggatcaat tcgctagcga  2580
agttcctatt ccgaagttcc tattctctag aaagtatagg aacttcagat ccaccgggat  2640
cccgatcat gcaaaaactc attaactcag tgcaaaacta tgcctgggc agcaaaacgg  2700
cgttgactga actttatggt atggaaaatc cgtccagcca gccgatggcc gagctgtgga  2760
tgggcgcaca tccgaaaagc agttcacgag tgcagaatgc cgccggagat atcgtttcac  2820
tgcgtgatgt gattgagagt gataaatcga ctctgctcgg agaggccgtt gccaaacgct  2880
ttggcgaact gcctttcctg ttcaaagtat tatgcgcagc acagccactc tccattcagg  2940
ttcatccaaa caaacacaat tctgaaatcg gttttgccaa agaaaatgcc gcaggtatcc  3000
cgatggatgc cgccgagcgt aactataaag atcctaacca caagccggag ctggttttg  3060
cgctgacgcc tttccttgcg atgaacgcgt ttcgtgaatt ttccgagatt gtctccctac  3120
tccagccggt cgcaggtgca catccggcga ttgctcactt tttacaacag cctgatgccg  3180
aacgtttaag cgaactgttc gccagcctgt tgaatatgca gggtgaagaa aaatcccgcg  3240
cgctggcgat tttaaaatcg gccctcgata gccagcaggg tgaaccgtgg caaacgattc  3300
gtttaatttc tgaattttac ccggaagaca gcggtctgtt ctcccgcta ttgctgaatg  3360
tggtgaaatt gaaccctggc gaagcgatgt tcctgttcgc tgaaacaccg cacgcttacc  3420
tgcaaggcgt ggcgctgaaa gtgatggcaa actccgataa cgtgctgcgt gcgggtctga  3480
cgcctaaata cattgatatt ccggaactgg ttgccaatgt gaaattcgaa gccaaaccgg  3540
ctaaccagtt gttgacccag ccggtgaaac aaggtcagaa actggacttc ccgattccag  3600
tggatgattt tgccttctcg ctgcatgacc ttagtgataa agaaaccacc attagccagc  3660
agagtgccgc cattttgttc tgcgtcgaag gcgatgcaac gttgtggaaa ggttctcagc  3720
agttacaagc tgaaaccggg gaatcagcgt ttattgccgc caacgaatca ccggtgactg  3780
tcaaaggcca cggccgttta cgcgcgtgttt acaacaagct gtaagagctt actgaaaaaa  3840
ttaacatctc ttgctaagct gggggtgaa cctagacttg tccatcttct ggattggcca  3900
acttaattaa tgtatgaaat aaaaggatgc acacatagtg acatgctaat cactataatg  3960
tgggcatcaa agttgtgtgt tatgtgtaat tactagttat ctgaataaaa gagaaagaga  4020
tcatccatat ttccttatcct aaatgaatgt cacgtgtctt tataatttct tgatgaacca  4080
gatgcatttc attaaccaaa tccatataca tataaatatt aatcatatat aattaatatc  4140
aattgggtta gcaaaacaaa tctagtctag gtgtgttttg cgaatgcggc cctagctat   4200
acgaagttcc tattccgaag ttcctattct ccagaaagta taggaacttc tgtacacctg  4260
agctgattcc gatgacttcg taggttccta gctcaagccg ctcgtgtcca agcgtcactt  4320
acgattagct aatgattacg gcatctagga ccgactagca aactaactag taccgaggcc  4380
```

```
ggccccgcgg gagctcggcg cgcctagtgg tgtatgaaag gaagcacttg ttttcaatt    4440
ccaaacagat tcacgtcaga tttaaccaaa actatattat gaggtacaca tattacaatc    4500
caaaatgaat tatctagttc tcgagttgta cacagtttat cacgtgtttt acacattcca    4560
accctaaact                                                            4570
```

| SEQ ID NO: 255 | moltype = DNA  length = 5091 |
|---|---|
| FEATURE | Location/Qualifiers |
| misc_feature | 1..5091 |
| | note = synthesized sequence- TS8Cas-1 donor |
| source | 1..5091 |
| | mol_type = other DNA |
| | organism = synthetic construct |

SEQUENCE: 255
```
cacacatgac tgcctgagaa tctgctgccg ttgcctctca tattatattc gatccctga     60
ctaaaaaaac tcgggccgg ctaatacgta ctgtacgtac gcagaattta cggtccagca    120
cgggcatgcc gcgcgggctg actttgctcc actgactcga tcatgtgcgg attccatcgc    180
ggcgtagcgt agccaaccgc aacgcaaacc gacttcatct ttttttttta ttatgaacaa    240
aaggagatcg agagaaacgt gaacggtaaa taatatatct gatcccatgc atgcacgctg    300
cctgggtcga tctcgctctc gctccgccca gacgaacatg catgctggtc aggctcaacg    360
ctcaggcggg caagctgtgg gaggacatgg gatgggagag gaggacacat gcatgctggc    420
cagtcaggca ctgtgctggc acatgaggta gggatagggg ggccctcggc cagtgtccag    480
gccgcatgca tgcatgcccc ccctgctgct cgaccgaaca cgttggatg cctggattga    540
tgcaacagtt tggacggacg gaccatacgt tatgtaccag taggtaccat ttaaatctta    600
agcctaggat aacttcgtat agcatacatt atacgaagtt atggcgccgc tagcctgcag    660
tgcagcgtga cccggtcgtg cccctctcta gatataatga gcattgcatg tctaagttat    720
aaaaaattac cacatatttt ttttgtcaca cttgtttgaa gtgcagttta tctatcttta    780
tacatatatt taaactttac tctacgaata atataatcta tagtactaca ataatatcag    840
tgttttagag aatcatataa atgaacagtt agacatggtc taaaggacaa ttgagtattt    900
tgacaacagg actctacagt tttatctttt tagtgtgcat gtgttctcct tttttttgc    960
aaatagcttc acctatataa tacttcatcc attttattag tacatccatt tagggtttag   1020
ggttaatggt ttttatagac taattttttt agtacatcta ttttattcta tttagcctc   1080
taaattaaga aaactaaaac tctattttag tttttttatt taataattta gatataaaat   1140
agaataaaat aaagtgacta aaattaaac aaatacccctt taagaaatta aaaaaactaa   1200
ggaaacattt ttcttgttc gagtagataa tgccagcctg ttaaacgccg tcgacgagtc   1260
taacggacac caaccagcga accagcagcg tcgcgtcggg ccaagcgaag cagacggcac   1320
ggcatctctg tcgctgcctc tggacccctc tcgagagttc cgctccaccg ttggacttgc   1380
tccgctgtcg gcatccagaa attgcgtggc ggagcggcag acgtgagccg gcacggcagg   1440
cggcctcctc ctcctctcac ggcaccggca gctacggggg attccttttcc caccgctcct   1500
tcgcttttccc ttcctcgccc gccgtaataa atagacaccc cctccacacc ctctttcccc   1560
aacctcgtgt tgttcggagc gcacacacac acaaccagat ctcccccaaa tccaccccgtc   1620
ggcacctccg cttcaaggta cgccgctcgt cctccccccc cccctctct acctctctcta   1680
gatcggcgtt ccgtccatg catggttagg gcccggtagt tctacttctg ttcatgtttg   1740
tgttagatcc gtgtttgtgt tagatccgtg ctgctagcgt tcgtacacgg atgcgacctg   1800
tacgtcagac acgttctgat tgctaacttg ccagtgtttc tcttttgggga atcctgggat   1860
ggctctagcc gttccgcaga cgggatcgat ttcatgattt tttttgttc gttgcatagg   1920
gtttggtttg cccttttcct ttattcaat atatgccgtg cacttgtttg tcgggtcatc   1980
ttttcatgct tttttttgtc ttggttgtga tgatgtggtct ggtttgggcg tcgttctag   2040
atcggagtag aattctgttt caaactacct ggtggatta ttaattttgg atctgtatgt   2100
gtgtgccata catattcata gttacgaatt gaagatgatg gatggaaata tcgatctagg   2160
ataggtatac atgttgatgc gggtttttact gatgcatata cagagatgct tttttgttcgc   2220
ttggttgtga tgatgtggtg tggttgggcg gtcgttcatt cgttctagat cggagtacaa   2280
tactgttctca aactacctgg tgtatttatt aatttttggaa ctgtatgtgt gtgtcataca   2340
tcttcatagt tacgagttta agatggatgg aaatatcgat ctaggatagg tatacatgtt   2400
gatgtgggtt ttactgatgc atatacatga tggcatatgc agcatctatt catatgctct   2460
aaccttgagt acctatctat tataataaac aagtatgttt tataattatt ttgatcttga   2520
tatacttgga tgatggcata tgcagcagct atatgtggat tttttttagcc ctgccttcat   2580
acgctattta tttgcttggt actgtttctt ttgtcgatgc tcacctcgtt gtttggtgtt   2640
acttctgcag gtcgactcta gaggatcaat tcgctagcga agttcctatt ccgaagttcc   2700
tattctctag aaagtatagg aacttcagat ccaccgggat ccccgatcat gcaaaaactc   2760
attaactcag tgcaaaacta tgcctggggc agcaaaacgg cgttgactga actttatggt   2820
atggaaaatc cgtccagcca gccgatggcc gagctgtgga tgggcgcaca tccgaaaagc   2880
agttcacgag tgcagaatgc cgccggagat atcgtttcac tgcgtgatgt gattgagagt   2940
gataaaatcg actctgctcg gagaggccgtt gccaaacgct ttggcgaact gccttttcctg   3000
ttcaaagtat tatgcgcagc acagccactc tccattcagg ttcatccaaa caaacacaat   3060
tctgaaatcg gttttgccaa agaaaatgcc gcaggtatcc cgatggatgc cgccgagcgt   3120
aactataaag atcctaaacca caagccgag ctggtttttg cgctgacgcc tttccttgcg   3180
atgaacgcgt ttcgtgaatt ttccgagatt gtctccctac tccagccggt cgcaggtgca   3240
catccggcga ttgctcactt tttacaacag cctgatgccg aacgtttaag cgaactgttc   3300
gccagcctgt tgaatatgca gggtgaagaa aaatcccgc gctggcgat tttaaaatcg   3360
gccctcgata gccagcaggg tgaaccgtgg caaacgattc gtttaatttc tgaattttac   3420
ccggaagaca gcggtctgtt ctccccgcta tgctgaatg tggtgaaatt gaaccctggc   3480
gaagcgatgt tcctgttcgc tgaaacaccg cacgcttacc tgcaaggcgt ggcgctgaa   3540
gtgatggcaa actccgataa cgtgctgcgt gcgggtctga cgcctaaata cattgatatt   3600
ccggaactgg ttgccaatgt gaaattcgaa gccaaactgg ctaaccagtt gttgaccag   3660
ccggtgaaac aaggtgcaga actggacttc ccgattccag tggatgattt tgccttctcg   3720
ctgcatgacc ttagtgataa agaaaccacc attagccagc agagtgccgc catttttgttc   3780
tgcgtcgaag gcgatgcaac gttgtggaaa ggttctcagc agttacagct taaaccgggt   3840
gaatcagcgt ttattgccgc caacgaatca ccggtgactg tcaaaggcca cggccgttta   3900
gcgcgtgttt acaacaagct gtaagagctt actgaaaaaa ttaacatctc ttgctaagct   3960
```

```
gggggtggaa cctagacttg tccatcttct ggattggcca acttaattaa tgtatgaaat 4020
aaaaggatgc acacatagtg acatgctaat cactataatg tgggcatcaa agttgtgtgt 4080
tatgtgtaat tactagttat ctgaataaaa gagaaagaga tcatccatat ttcttatcct 4140
aaatgaatgt cacgtgtctt tataattctt tgatgaacca gatgcatttc attaaccaaa 4200
tccatataca tataaatatt aatcatatat aattaatatc aattgggtta gcaaaacaaa 4260
tctagtctag gtgtgttttg cgaatgcggc cctagcgtat acgaagttcc tattccgaag 4320
ttcctattct ccagaaagta taggaacttc tgtacacctg agctgattcc gatgacttcg 4380
taggttccta gctcaagccg ctcgtgtcca agcgtcactt acgattagct aatgattacg 4440
gcatctagga ccgactagct aactaactag taccgaggcc ggccccgcgg actgcacgtt 4500
acgtacgtac gaactaatat actccaccag ctgatcactg atgagccgag ccgccatgca 4560
ttgtaattta taacatgtgc ggctgtacgc ttccatctca aatacctttt tatatatata 4620
ttgtacttta tagtctacga cataatctgc catggtaatt tataagatgt gctttattgc 4680
tcgttgttct gttctcatct gtgtccatgg catggcatgg atacaaaatg tatgtatggc 4740
cacgcatcca atctgtgacg ttgtcaaggc agaggtccaa ccgtccaaga ccctcttgtg 4800
ccgccctgta cttgcagtca gtgacgttgt gagaaaaagc tgtgggtggt ctccgcagag 4860
cgcgcgggcc acgagaggga gccccatctc tcggccgagg ggtacggggg ctccagacac 4920
ggtcctttgg tttcttctgc ctgtagcgag cggccccgcc ccccaccgcg ctgctagcct 4980
agccgatgct gatccatcca ccacccacaa gggattgttc cacgacttgt ggacctgacc 5040
atgacgtgac ttcacgccat gtacgctcag ccgctcacta gctttttttt c 5091

SEQ ID NO: 256          moltype = DNA  length = 5237
FEATURE                 Location/Qualifiers
misc_feature            1..5237
                        note = synthesized sequence- TS8Cas-2 donor
source                  1..5237
                        mol_type = other DNA
                        organism = synthetic construct
SEQUENCE: 256
tctctttcag ggcttgttcg tttacgttgg attgcacccg gaatcgttac agctaatcaa 60
agtttatata aattagaaa gcaaccggat aggaatcgtt ccgacccacc aattcgacac 120
aaacgaacaa ggcctcaatc cttctcaatc cacctccaac ccaataagct cttggaggcg 180
gcggcgggag agcagccaca cacatgactg cctgagaatc tgctgccgtt gcctctcata 240
ttatattcga tccctgact aaaaaaactc ggggccggct aatacgtact gtacgtacgc 300
agaattacg gtccagcacg ggcatgccgc gcgggctgac tttgctccac tgactcgatc 360
atgtgcggat tccatcgcgg cgtagcgtag ccaaccgcaa cgcaaaccga cttcatcttt 420
tttttttatt atgaacaaaa ggagatcgag agaaacgtga acgtaaaata atatatctga 480
tcccatgcat gcacgctgcc tgggtcgatc tcgctctcgc tccgcccaga cgaacatgca 540
tgctggtcag gctcaacgct caggcgggca agctgtggga ggacatggga tgggagagga 600
ggacacatgc atgctggcca gtcaggcact gtgctggcac atgaggtagg gatagggggg 660
ccctcggcca gtgtccaggc cgcatgcatg catgccccc ctgctgctcg accgaacaac 720
gttggatgcc tggattgatg caacagtttg gacggacgga ccatacgtta tgtaccagta 780
ctgcacgtta cgtacgtacg aactaatata ctccaccagg tacattttaa atcttaagcc 840
taggtaact tcgtatagca tacattatac gaagttatgc cgcgcgctagc ctgcagtgca 900
gcgtgacccg gtcgtgcccc tctctagaga taatgagcat tgcatgtcta agttataaaa 960
aattaccaca tatttttttt gtcacacttg tttgaagtgc agtttatcta tctttataca 1020
tatatttaaa ctttactcta cgaataatat aatctatagt actacaataa tatcagtgtt 1080
ttagagaatc atataaaatga acagttagac atggtctaaa ggacaattga gtattttgac 1140
aacaggactc tacagtttta tctttttagt gtgcatgtgt tctccttttt ttttgcaaat 1200
agcttcacct atataatact tcatccattt tattagtaca tccatttagg gtttagggtt 1260
aatggttttt atagactaat tttttttagta catctatttt attctatttt agcctctaaa 1320
ttaagaaaac taaaactcta aattttagtttt tttattttaat aatttagata taaaatagaa 1380
taaaataaag tgactaaaaa ttaaacaaat acccttaag aaattaaaaa aactaaggaa 1440
acatttttct tgtttcgagt agataatgcc agcctgttaa acgccgtcga cgagtctaac 1500
ggacaccaac cagcgaacca gcagcgtcgc gtcgggccaa gcgaagcaga cggcacggca 1560
tctctgtcgc tgcctctgga cccctctcga gagttccgct ccaccgttgg acttgctccg 1620
ctgtcggcat ccagaaattg cgtggcggag cggcagacgt gagccggcac ggcaggcggc 1680
ctcctcctcc tctcacggca ccggcagcta cggggatttc ctttcccacc gctccttcgc 1740
tttccctccc tcgccgccg taataaatag acaccccctc cacaccctct ttccccaacc 1800
tcgtgttgtt cggagcgcac acacacacaa ccagatctcc cccaaatcca cccgtcggca 1860
cctccgcttc aaggtacgcc gtcgtcctc ccccccccc ctctctacct tctctagatc 1920
ggcgttccgg tccatgcatg gttagggccc ggtagttcta cttctgttca tgtttgtgtt 1980
agatccgtgt ttgtgttaga tccgtgctgc tagcgttcgt acacggatgc gacctgtacg 2040
tcagacacgt tctgattgct aacttgccag tgttctctt tggggaatcc tgggatggct 2100
ctagccgttc cgcagacggg atcgatttca tgattttttt tgttcgttg cataggtta 2160
ggtttgccct tttccttat ttcaatatat gccgtgcact tgtttgtcgg gtcatctttt 2220
catgcttttt tttgtcttgg ttgtgatgat gtggtctggt tgggcggtcg ttctagatcg 2280
gagtagaatt ctgtttcaaa ctacctggtg gatttattaa ttttgatct gtatgtgtgt 2340
gccatacata ttcatagtta cgaattgaag atgatggatg gaaatatcga tctaggatag 2400
gtatacatgt tgatgcgggt tttactgatg catatacaga gatgctttt gttcgcttga 2460
ttgtgatgat gtggtgtggt tgggcggtcg ttcattcgtt ctagatcgga gtagaatact 2520
gtttcaaact acctggtgta tttattaatt ttggaactgt atgtgtgtgt catacatctt 2580
catagttacg agtttaagat ggatggaaat atcgatctag gataggtata catgttgatg 2640
tggggtttac tgatgcatat acatgatggc atatgcagca tctattcata tgctctaacc 2700
ttgagtaccct atcattata ataaacaagt atgttttata attatttga tcttgatata 2760
cttggatgat ggcatatgca gcagctatat gtggatttt ttagccctgc cttcatacgc 2820
tatttatttg cttggtactg tttctttgt cgatgctcac cctgttgttt ggtgttactt 2880
ctgcaggtcg actctagagg atcaattcgc tagcgaagtt cctattccga agttcctatt 2940
ctctagaaag tataggaact tcagatccac cgggatcccc gatcatgcaa aaactcatta 3000
actcagtgca aaactatgcc tggggcagca aaacggcgtt gactgaactt tatggtatgg 3060
```

```
aaaatccgtc cagccagccg atggccgagc tgtggatggg cgcacatccg aaaagcagtt  3120
cacgagtgca gaatgccgcc ggagatatcg tttcactgcg tgatgtgatt gagagtgata  3180
aatcgactct gctcggagag gccgttgcca aacgctttgg cgaactgcct ttcctgttca  3240
aagtattatg cgcagcacag ccactctcca ttcaggttca tccaaacaaa cacaattctg  3300
aaatcggttt tgccaaagaa aatgccgcag gtatcccgat ggctgccgcc gagcgtaact  3360
ataaagatcc taaccacaag ccggagctgg tttttgcgct gacgcctttc cttgcgatga  3420
acgcgtttcg tgaattttcc gagattgtct ccctactcca gccggtcgca ggtgcacatc  3480
cggcgattgc tcactttta caacagcctg atgccgaacg tttaagcgaa ctgttcgcca  3540
gcctgttgaa tatgcagggt gaagaaaaat cccgcgcgct ggcgatttta aaatcggccc  3600
tcgatagcca gcagggtgaa ccgtggcaaa cgattcgttt aatttctgaa ttttaccgg  3660
aagacagcgt tctgttctcc ccgctattgc tgaatgtggt gaaattgaac cctggcgaag  3720
cgatgttcct gttcgctgaa acaccgcacg cttacctgca aggcgtggcg ctggaagtga  3780
tggcaaactc cgataacgtg ctgcgtgcgg gtctgacgcc taaatacatt gatattccgg  3840
aactggttgc caatgtgaaa ttcgaagcca aaccggctaa ccagttgttg acccagccgg  3900
tgaaacaagg tgcagaactg gacttccga ttccagtgga tgattttgcc ttctcgctgc  3960
atgaccttag tgataaagaa accaccatta gccagcagag tgccgccatt ttgttctgcg  4020
tcgaaggcga tgcaacgttg tggaaggtt ctcagcagtt acagcttaaa ccgggtgaat  4080
cagcgtttat tgccgccaac gaatcaccgg tgactgtcaa aggccacggc cgtttagcgc  4140
gtgtttacaa caagctgtaa gagcttactg aaaaaattaa catctcttgc taagctgggg  4200
gtggaaccta gacttgtcca tcttctggat tggccaactt aattaatgta tgaaataaaa  4260
ggatgcacac atagtgacat gctaatcact ataatgtggg catcaaagtt gtgtgttatg  4320
tgtaattact agttatctga ataaaagaga aagagatcat ccatatttct tatcctaaat  4380
gaatgtcacg tgtctttata attctttgat gaaccagatg catttcatta accaaatcca  4440
tatacatata aatattaatc atatataatt aatatcaatt gggttagcaa aacaaatcta  4500
gtctaggtgt gttttgcgaa tgcggcccta gcgtatacga agttcctatt ccgaagttcc  4560
tattctccag aaagtatagg aacttctgta cacctgagct gattccgatg acttcgtagg  4620
ttcctagctc aagccgctcg tgtccaagcc tcacttacga ttagctaatg attacgcat  4680
ctaggaccga ctagctaact aactagtacc gaggccggcc ccgcgggagc tcgctgatca  4740
ctgatgagcc gagccgccat gcattgtaat ttataacatg tgcggctgta cgcttccatc  4800
tcaaataccct ttttatatat atattgtact ttatagtcta cgacataatc tgccatggta  4860
atttataaga tgtgctttat tgctcgttgt tctgttctca tctgtgtcca tggcatggca  4920
tggatacaaa atgtatgtat ggccacgcat ccaatctgtg acgttgtcaa ggcagaggtc  4980
caaccgtcca agaccctctt gtgccgccct gtacttgcag tcagtgacgt tgtgagaaaa  5040
agctgtgggt ggtctccgca gagcgcgcgg gccacgagag ggagcccat ctctcggccg  5100
aggggtacgg gggctccaga cacggtcctt tggtttcttc tgcctgtagc gagcggcccc  5160
gcccccacc gcgctgctag cctagccgat gctgatccat ccaccaccca caaggattg  5220
ttccacgact tgtggac                                                  5237

SEQ ID NO: 257          moltype = DNA  length = 5427
FEATURE                 Location/Qualifiers
misc_feature            1..5427
                        note = synthesized sequence- TS9Cas-2 donor
source                  1..5427
                        mol_type = other DNA
                        organism = synthetic construct
SEQUENCE: 257
agcaaggaac taaactgtta ttggacgcta agtttagta ctttatcttt aacatctttc    60
agcatttcta tgtagatatt taagggctaa attttagcaa gtgtgctgat aaattttagc  120
ctaaatgttt ctgttgggct aaatttagc aagtgtactg ttaaatttta gcatattcct   180
tttagagtgg tatgggtgtg catagactaa atgtttccgt tgggcccctaa tttaacgatg  240
tgtacgcagg cctgtttaga tgacttggta ccggcatatg gcctcgtact gtttcattg    300
atgacgcgag cgtgcggccc atgcagcagc agcacgccgg gaaggcagcg gattttgaag  360
tactattgga cagcgcggcg cggggaccgg gtcgttggcg cgcggtggag tgggggtggg  420
tggtcctggc gtcctgccct gcgcgatggt cgatggatgc cccatgcgcg tgtaaccgcc  480
cagccgtcgc catccgacca ggtgggcaga cgtacgtacg gtggcacgcc cacggcccat  540
cggccatcgc gatcgcgttc gtatcgtgtc ctcaataacg aaagcgccaa cggaaggcgc  600
tgtcgtcgtc agttcaccgc gcgccggcgc cctgtgtcct cgtccctctc gacttctcga  660
ccagtaagaa ctctcgcgag ctgcggagct gctggcgatg gccggccggt gggatccgac  720
gtgcgtgcaa cctcgaattt aaatcttaag cctaggataa cttcgtatag catacattat  780
acgaagttat ggcgccgcta gcctgcagtg cagcgtgacc cggtcgtgcc cctctctaga  840
gataatgagc attgcatgtc taagttataa aaaattacca catatttttt ttgtcacact  900
tgtttgaagt gcagtttatc tatctttata catatattta aactttactc tacgaataat  960
ataatctata gtactacaat aatatcagtg ttttagaaga tcatataat gaacagttag  1020
acatggtcta aaggacaatt gagtattttg acaacaggac tctacagttt tatctttta   1080
gtgtgcatgt gttctccttt ttttttgcaa atagcttcac ctatataata cttcatccat  1140
tttattagta catccattta gggtttaggg ttaatggttt ttatagacta atttttttag  1200
tacatctatt ttattctatt ttagcctcta aattaagaaa actaaaactc tatttttagt  1260
ttttattta ataatttaga tataaaatag aataaaataa agtgactaaa aattaaacaa   1320
ataccctta agaaattaaa aaaactaagg aaacattttt cttgtttcga gtagataatg  1380
ccagcctgtt aaacgccgtc gacgagtcta acgacacca accagcgaac cagcagcgtc  1440
gcgtcgggcc aagcgaagca gacggcacgg catctctgtc gctgcctctg gaccctctc   1500
gagagttccg ctccaccgtt ggacttgctc cgctgtcggc atcagaaat tgcgtggcgg   1560
agcggcagac gtgagccggc acggcaggcg gcctcctcct cctctcacgg caccggcagc  1620
tacgggggat tcctttccca ccgctccttc gctttccctt cgtcgcccgc cgtaataaat  1680
agacaccccc tccacaccct cttttcccaa cctcgtgttg ttcggagcgc acacacacac  1740
aaccagatct cccccaaatc caccccgtcgg cacctccgct tcaaggtacg ccgctcgtcc  1800
tccccccccc ccctctctac cttctctaga tcggcgttcc ggtccatgca tggttagggc  1860
ccggtagttc tacttctgtt catgtttgtg ttagatccgt gtttgtgtta gatccgtgct  1920
gctagcgttc gtacacggat gcgacctgta cgtcagacac gttctgattg ctaacttgcc  1980
```

-continued

```
agtgtttctc tttggggaat cctgggatgg ctctagccgt tccgcagacg ggatcgattt  2040
catgatttttt tttgtttcgt tgcatagggt ttggtttgcc cttttccttt atttcaatat  2100
atgccgtgca cttgtttgtc gggtcatctt ttcatgcttt tttttgtctt ggttgtgatg  2160
atgtggtctg gttgggcggt cgttctagat cggagtagaa ttctgtttca aactacctgg  2220
tggatttatt aattttggat ctgtatgtgt gtgccataca tattcatagt tacgaattga  2280
agatgatgga tggaaatatc gatctaggat aggtatacat gttgatgcgg gttttactga  2340
tgcatataca gagatgcttt ttgttcgctt ggttgtgatg atgtggtgtg gttgggcggt  2400
cgttcattcg ttctagatcg gagtagaata ctgtttcaaa ctacctggtg tatttattaa  2460
ttttggaact gtatgtgtgt gtcatacatc ttcatagtta cgagtttaag atggatggaa  2520
atatcgatct aggataggta tacatgttga tgtgggtttt actgatgcat atacatgatg  2580
gcatatgcag catctattca tatgctctaa ccttgagtac ctatctatta taataaacaa  2640
gtatgtttta taattatttt gatcttgata tacttggatg atggcatatg cagcagctat  2700
atgtggattt ttttagccct gccttcatac gctattttatt tgcttggtac tgtttcttt   2760
gtcgatgctc accctgttgt ttggtgttac ttctgcaggt cgactctaga ggatcaattc  2820
gctagcgaag ttcctattcc gaagttccta ttctctagaa agtataggaa cttcagatcc  2880
accgggatcc ccgatcatgc aaaaactcat taactcagtg caaaactatg cctggggcag  2940
caaaacggcg ttgactgaac tttatggtat ggaaaatccg tccagccagc cgatggccga  3000
gctgtggatg ggcgcacatc cgaaaagcag ttcacgagtg cagaatgccg ccggagatat  3060
cgtttcactg cgtgatgtga ttgagagtga taaatcgact ctgctcggag aggccgttgc  3120
caaacgcttt ggcgaactgc ctttcctgtt caaagtatta tgcgcagcac agccactctc  3180
cattcaggtt catccaaaca aacacaattc tgaaatcggt tttgccaaag aaaatgccgc  3240
aggtatcccg atggatgccg ccgagcgtaa ctataaagat cctaaccaca gccggagct   3300
ggtttttgcg ctgacgcctt tccttgcgat gaacgcgttt cgtgaatttt ccgagattgt  3360
ctccctactc cagccggtcg caggtgcaca tccggcgatt gctcactttt tacaacagcc  3420
tgatgccgaa cgtttaagcg aactgttcgc cagcctgttg aatatgcagg gtgaagaaaa  3480
atcccgcgcg ctggcgattt taaaatcggc cctgatagc cagcagggtg aaccgttggca  3540
aacgattcgt ttaattctgt aatttttaccc ggaagacagc ggtctgttct ccccgctatt  3600
gctgaatgtg gtgaaattga acccctggcga agcgatgttc ctgttcgctg aaacaccgca  3660
cgcttacctg caaggcgtgg cgctggaagt gatggcaaac tccgataacg tgctgcgtgc  3720
gggtctgacg cctaaataca ttgatattcc ggaactggtt gccaatgtga aattcgaagc  3780
caaaccggct aaccagttgt tgacccagcc ggtgaaacaa ggtgcagaac tggacttccc  3840
gattccagtg gatgattttg ccttctcgct gcatgacctt agtgataaag aaaccaccat  3900
tagccagcag agtgccgcca ttttgttctg cgtcgaaggc gatgcaacgt tgtggaaagg  3960
ttctcagcag ttacagctta aaccgggtga atcagccgtt attgccgcca acgaatcacc  4020
ggtgactgtc aaaggccacg gccgttagc gcgtgtttac aacaagctgt aagagcttac  4080
tgaaaaaatt aacatctctt gctaagctgg gggtggaacc tagacttgtc catcttctgg  4140
attggccaac ttaattaatg tatgaaataa aaggatgcac acatagtgac atgctaatca  4200
ctataatgtg ggcatcaaag ttgtgtgtta tgtgtaatta ctagttatct gaataaaaga  4260
gaaagagatc atccatattt cttatccctaa atgaatgtca cgtgtctttta taattctttg  4320
atgaaccaga tgcatttcat taaccaaatc catatacata taaatattaa tcatatataa  4380
ttaatatcaa ttgggttagc aaaacaaatc tagtctaggt gtgtttttgcg aatgcggccc  4440
tagcgtatac gaagttccta ttccgaagtt cctattctcc agaaagtata ggaacttctg  4500
tacacctgag ctgattccga tgacttcgta ggttcctagc tcaagccgct cgtgtccaag  4560
cgtcacttac gattagctaa tgattacggc atctaggacc gactagctaa ctaactagta  4620
ccgaggccgg ccccgcggga gctcggccgc aaacagcctg gtgacagacg aagccagcaa  4680
gcacgtacgt acgcacgtct ctgctggtct ggatgtgtat ggatatggac gtctcacgtc  4740
tggacctcgt cgtcgccgtt gtattgtatc atgccaacca cttccgtacc gtaccccctc  4800
gcgtgccaac atgaccaccg ccggtacgtc tccatcgtcg gccgtcgcg tctcaggcag  4860
ctctcaatta agcggacgtg ttttggtaat ctggtggaac ccgcgcgca ctgagggttt  4920
gggggccccg gcggacgagc gagcgagaga cggtgcatgc atgccaaatg caacgaggg   4980
cccgccgcc catccaataa ccaacccaga cgtagcgcaa ccaacgtacg agtcctgtgc  5040
tggcgcgtac gactaccacg ctagctgccg cgacatgcga actacggtcc accaggcacc  5100
agccatgaca atatatactg tatatatatt tttcttcttc tttttgtttc cgtctctctca  5160
agttcctgct ctgctcctgc ctgtccgcgg tgccgatcgg cgagagagca tgcatggaca  5220
tggaccacgc gagatccagg aaccggcacg ggcccatgcg tggcaggcgg ccgtttcgtc  5280
aggttccccg aaatgccccca actgcgcggc tgcaggatgg ctcatggctg gctgcctagc  5340
tggcccgtga caccgatcga tcggtaacga cgacgcacgc acctgaagca caggaaggag  5400
cctcccctctc gcatgcacgt tagtact                                      5427
```

SEQ ID NO: 258  moltype = DNA   length = 5426
FEATURE         Location/Qualifiers
misc_feature    1..5426
                note = synthesized sequence- TS9Cas-3 donor
source          1..5426
                mol_type = other DNA
                organism = synthetic construct
SEQUENCE: 258

```
agcaaggaac taaactgtta ttggacgcaa agtttagtac tttatctttta acatctttca   60
gcatttctat gtagatattt aagggctaaa ttttagcaag tgtgctgata aattttagcc  120
taaatgtttc tgtttgggcta aattttagca agtgtactgt taaattttag catattcctt  180
ttagagtggt atgggtgtgc atagactaaa tgtttccgtt gggccctaat ttaacgatgt  240
gtacgcaggc ctgtttagat gacttggtac cggcatatgg cctcgtactg tttcatttga  300
tgacgcgagc gtgcggccca tgcagcagca gcacgccggg aaggcagcgg attttgaagt  360
actattggac agcgcggcgc ggggaccggg tcgttggcgt ggttgggagt gggggtgggt  420
ggtcctggcg tcctgccctg cgcgatggtc gatggatgcc ccatgcgcgt gtaaccgccc  480
agccgtcgcc atccgaccag gtgggcagac gtacgtacgg tggcacgccc acggccatc   540
ggccatcgcg atcgcgttcg tatcgtgtcc tcaataacga aagcgccaac ggaaggcgct  600
gtcgtcgtca gttcaccgcg cgccggcgcc ctgtgtcctc gtccctctcg acttctcgac  660
cagtaagaac tctcgcgagc tgcggagctg ctggcgatgg ccggccggtg ggatccgacg  720
```

```
atttaaatct taagcctagg ataacttcgt atagcataca ttatacgaag ttatggcgcc   780
gctagcctgc agtgcagcgt gacccggtcg tgccctctc tagagataat gagcattgca    840
tgtctaagtt ataaaaaatt accacatatt tttttgtca cacttgtttg aagtgcagtt    900
tatctatctt tatacatata tttaaacttt actctacgaa taatataatc tatagtacta   960
caataatatc agtgttttag agaatcatat aaatgaacga ttagacatgg tctaaaggac  1020
aattgagtat tttgacaaca ggactctaca gttttatctt tttagtgtgc atgtgttctc  1080
cttttttttt gcaaatagct tcacctatat aatacttcat ccattttatt agtacatcca  1140
tttagggttt agggttaatg gttttttatag actaattttt ttagtacatc tattttattc  1200
tattttagcc tctaaattaa gaaaactaaa actctatttt agttttttta tttaataatt  1260
tagatataaa atagaataaa ataagtgac taaaaattaa acaaataccc tttaagaaat    1320
taaaaaaact aaggaaacat ttttcttgtt tcgagtagat aatgccagcc tgttaaacgc  1380
cgtcgacgag tctaacggac accaaccagc gaaccagcag cgtcgcgtcg ggccaagcga  1440
agcagacggc acggcatctc tgtcgctgcc tctggacccc tctcgagagt tccgctccac  1500
cgttggactt gctccgctgt cggcatccag aaattgcgga ggagcggc agacgtgagc    1560
cggcacggca ggcggcctcc tcctcctctc acggcaccgg cagctacggg ggattccttt  1620
cccaccgctc cttcgctttc ccttcctcgc ccgccgtaat aaatagacac cccctccaca  1680
ccctcttttcc ccaacctcgt gttgttcgga gcgcacacac acacaaccag atctcccca   1740
aatccacccg tcggcacctc cgcttcaagg tacgccgctc gtcctccccc cccccctct    1800
ctaccttctc tagatcggcg ttccggtcca tgcatggtta gggcccggta gttctacttc  1860
tgttcatgtt tgtgttagat ccgtgtttgt gttagatccg tgctgctagc gttcgtacac  1920
ggatgcgacc tgtacgtcag acacgttctg attgctaact tgccagtgtt tctctttggg  1980
gaatcctggg atggctctag ccgttccgca gacgggatcg atttcatgat ttttttttgtt  2040
tcgttgcata gggtttggtt tgcccttttc ctttatttca atatatgccg tgcacttgtt  2100
tgtcgggtca tcttttcatg cttttttttg tcttggttgt gatgatgtgg tctggttggg  2160
cggtcgttct agatcggagt agaattcgt ttcaaactac ctggtggatt tattaatttt   2220
ggatcgtgat gtgtgtgcca tacatattca tagttacgaa ttgaagatga tggatggaaa  2280
tatcgatcta ggataggtat acatgttgat gcgggtttta ctgatgcata tacagagatg  2340
cttttttgttc gcttggttgt gatgatgtgg tgtggttggg cggtcgttca ttcgttctag  2400
atcggagtag aatactgttt caaactacct ggtgtattta ttaatttggg aactgtatgt  2460
gtgtgtcata catcttcata gttacgagtt taagatggat ggaaatatcg atctaggata  2520
ggtacatg ttgatgtggg tttttactgat gcatatacat gatggcatat gcagcatcta   2580
ttcatatgct ctaaccttga gtaccatctc attataataa acaagtatgt tttataatta  2640
ttttgatctt gatatacttg gatgatggca tatgcagcag ctatatgtgg attttttttag 2700
ccctgccttc atacgctatt tatttgcttg gtactgtttc ttttgtcgat gctcaccctg  2760
ttgtttggtg ttacttctgc aggtcgactc tagaggatca attcgctagc gaagttccta  2820
ttccgaagtt cctattctct agaaagtata ggaactcag atccaccggg atccccgatc    2880
atgcaaaaac tcattaactc agtgcaaaac tatgcctggg gcagcaaaac ggcgttgact  2940
gaactttatg gtatggaaaa tccgtccagc cagccgatgg ccgagctgtg gatgggcgca  3000
catccgaaaa gcagttcacg agtgcaagat gccgccgaga atatcgtttc actgcgtgat  3060
gtgattgaga gtgataaatc gactctgctc ggagaggccg ttgccaaacg ctttggcgaa  3120
ctgccttttcc tgttcaaagt attatgcgca gcacagccac tctccattca ggttcatcca  3180
aacaaacaca attctgaaat cggttttgcc aaagaaaatg ccgcaggtat cccgatggat  3240
gccgccgagc gtaactataa agatcctaac cacaagccgg agtggttttt tgcgctgacg  3300
cctttccttg cgatgaacgc gtttcgtgaa ttttccgaga ttgtctccct actccagccg  3360
gtcgcaggtg cacatccggc gattgctcac ttttttacaac agcctgatgc cgaacgttta  3420
agcgaactgt tcgccagcct gttgaatatg cagggtgaag aaaaatcccg cgcgctggcg  3480
attttaaaat cggccctcga tagccagcag ggtgaaccgt ggcaaacgat tcgttttaatt  3540
tctgaatttt acccggaaga cagcggtctg ttctccccgc tattgctgaa tgtggtgaaa  3600
ttgaaccctg cgaagcgat gttcctgttc gctgaaacac cgcacgctta cctgcaaggc  3660
gtggcgctga agtgatggc aaactccgat aacgtgctgc gtgcgggtct gacgcctaaa  3720
tacattgata ttccggaact ggttgccaat gtgaaattgc aagccaaacc ggctaaccag  3780
ttgttgaccc agccggtgaa acaaggtgca gaactggact tcccgattcc agtggatgat  3840
tttgccttct cgctgcatga ccttagtgat aaagaaacca ccattagcca gcagagtgcc  3900
gccatttgt tctgcgtcga aggcgatgca acgttgtgga aaggttctca gcagttacag  3960
cttaaaccgg gtgaatcagc gttattgcc gccaacgaat caccggtgac tgtcaaaggc  4020
cacggccgtt tagcgcgtgt ttacaacaag ctgtaagagc ttactgaaaa aattaacatc  4080
tcttgctaag ctggggtgg aacctagact tgtccatctt ctggattggc caacttaatt  4140
aatgtatgaa ataaaaggat gcacacatag tgacatgcta atcactataa tgtgggcatc  4200
aaagttgtgt gttatgtgta attactagtt atctgaataa aagagaaaga gatcatccat  4260
atttcttatc ctaaatgaat gtcacgtgtc tttataattc tttgatgaac cagatgcatt  4320
tcattaacca aatccatata catataaata ttaatcatat ataattaata tcaattgggt  4380
tagcaaaaca aatctagtct aggtgtgttt tgcgaatgcg ccctagcgt atacgaagtt    4440
cctattccga agttccatt ctccagaaag tataggaact tctgtacacc tgagctgatt     4500
ccgatgactt cgtaggttcc tagctcaagc cgctcgtgtc caagcgtcac ttacgattag  4560
ctaatgatta cggcatctag gaccgactag ctaactaact agtaccgagg ccggccccgc  4620
gggagctctg cgtgcaacct cgaggccgca aacagcctgg tgacagacga agccagcaag  4680
cacgtacgta cgcacgtctc tgctggtctg gatgtgtatg gatatggacg tctcacgtct  4740
ggacgtcgtc gtcgccgttg tatttgtatca tgccaaccac ttccgtaccg taccccctcg  4800
cgtgccaaca tgaccaccgc cggtacgtct ccatcgtcgc ccgtcggcgt ctcaggcagc  4860
tctcaattaa gcggacgtgt tttggtaatc tggtggaacg ccgcgcgcac tgagggtttg  4920
ggggcccgg cggacgagcg agcgagagac ggtgcatgca tgccaaatgg caacgagggc    4980
ccgcccgccc atccaataac caacccagac gtagcgcaac caacgtacga gtcctgtgct  5040
ggcgcgtacg actaccacgc tagctgccgc gacatgcgaa ctaccgtcca ccaggcacca  5100
gccatgacaa tatatactt ttcttcttct ttttgttttcc gctctctcaa                5160
gttcctgctc tgctcctgcc tgtccgcggt gccgatcggc gagagagcat gcatggacat  5220
ggaccacgcg agatccagga accggacagg gcccatgcgt ggcaggcggc cgtttcgtca  5280
ggttccccga aatgccccaa ctgcgcggct gcaggatggc tcatggctgg ctgcctagct  5340
ggcccgtgac accgatcgat cggtaacgac gacgcacgca cctgaagcac aggaaggagc  5400
ctccctctcg catgcacgtt agtact                                         5426
```

```
SEQ ID NO: 259          moltype = DNA  length = 5152
FEATURE                 Location/Qualifiers
misc_feature            1..5152
                        note = synthesized sequence- TS10Cas-1 donor
source                  1..5152
                        mol_type = other DNA
                        organism = synthetic construct
SEQUENCE: 259
ggtaccaaat agtaaacggg aggggaggtc gctagtagta aacgctaggt agctaggata   60
atccgtctcg tgttggacgg aaggttttgg acgcatctgc gtgcacagcc cgctgataca  120
gatctgatcg actagctagc tagatgccga ggcccagag caaggccgg atactcctgc   180
acagtccctg agatttcagc acagcaggtg ctgttgcatc aatatataaa tccctgcttt  240
attaatttaa tctctgtgca tgtatccata catcgtcagc ggctcagcgc tatcacactg  300
cagtgcacgc agctagttga gcgcctgggt cagtatatat atagctagta gggacaaagg  360
ggggcactgt acgttggttt ggtttggcac gcacgcgatc gagagtggtg gaatggactg  420
cagatcatcg atcgctgcac tgtacgcacg cgcaccggac tgcatttgca tgcccctgaa  480
ggaggaaagg ggaaggaaag aaaagaaata ggagaaagaa ggaagaagcag agaaatacgt  540
cacagtccaa gaagagtgag ccgccctagc tagcttcaac cctgacgaac ccggcagcca  600
cacttccggc catgtatgca tgcatgcatg gcttagcttc agatgtccaa tcgaatccat  660
caagacctgg ccgttttcc atggccgcct cgccttcgct agtggtacca tttaaatctt  720
aagcctagga taacttcgta tagcatacat tatacgaagt tatggcgcg ctagcctgca   780
gtgcagcgtg accggtcgt gcccctctct agagataatg agcattgcat gtctaagtta   840
taaaaaatta ccacatattt tttttgtcac acttgtttga agtgcagttt atctatcttt  900
atacatatat ttaaacttta ctctacgaat aatataatct atagtactac aataatatca  960
gtgttttaga gaatcatata aatgaacagt tcaaaggaca attgagtatt              1020
ttgacaacag gactctacag ttttatcttt ttagtgtgca tgtgttctcc ttttttttg   1080
caaatagctt cacctatata atacttcatc cattttatta gtacatccat ttagggttta  1140
gggttaatgg ttttttataga ctaatttttt tagtacatct attttattct attttagcct  1200
ctaaattaag aaaactaaaa ctctatttta gtttttttat ttaataattt agatataaaa  1260
tagaataaaa taaagtgact aaaaattaaa caaatacccct ttaagaaatt aaaaaaacta  1320
aggaaacatt tttcttgttt cgagtagata atgccagcct gttaaacgcc gtcgacgagt  1380
ctaacgggaca ccaaccagcg aaccagcagc gtcgcgtcgg gccaagcgaa gcagacggca  1440
cggcatctct gtcgctgcct ctggaccct ctcgagagt ccgctccac gttggacttg    1500
ctccgctgtc ggcatccaga aattgcgtgg cggagcggca gacgtgagcc ggcacggcag  1560
gcggcctcct cctcctctca cggcaccggc agctacgggg gattcctttc ccaccgctcc  1620
ttcgcttttcc cttcctcgcc cgccgtaata aatagacacc cctccacac cctctttccc   1680
caacctcgtg ttgttcggag cgcacacaca caaccaga tctccccaa atccaccccgt    1740
cggcacctcc gcttcaaggt acgccgctcg tcctcccccc ccccctctc tacctctct   1800
agatcggcgt tccggtccat gcatggttag ggcccggtag ttctacttct gttcatgttt  1860
gtgttagatc cgtgttttgtg ttagatccgt gctgctagcg ttcgtacacg gatgcgacct  1920
gtacgtcaga cacgttctga ttgctaactt gccagtgttt ctctttgggg aatcctggga  1980
tggctctagc cgttccgcag acgggatcga tttcatgatt tttttttgtt cgttgcatag  2040
ggtttggttt gcccttttcc tttatttcaa tatatgccgt gcacttgttt gtcgggtcat  2100
cttttcatgc tttttttgt cttggttgtg atgatgtggt ctggttgggc ggtcgttcta  2160
gatcggagta gaattctgtt tcaaactacc tggtggattt attaattttg gatctgtatg  2220
tgtgtgccat acatattcat agttacgaat tgaagatgat ggatgaaat atcgatctag  2280
gataggtata catgttgatg cgggtttac tgatgcatat acagagatgc ttttttgttcg  2340
cttggttgtg atgatgtggt gtggttgggc ggtcgttcat tcgttctaga tcggagtaga  2400
atactgtttc aaactacctg gtgtatttat taattttgga actgtatgtg tgtgtcatac  2460
atcttcatag ttacgagttt aagatggatg gaaatatcga tctaggatag gtatacatgt  2520
tgatgtgggt tttactgatg catatacatg atgcatatg cagcatctat tcatatgctc   2580
taaccttgag tacctatcta ttataataaa caagtatgtt ttataattat tttgatcttg  2640
atatacttgg atgatggcat atgcagcagc tatatgtgga tttttttagc cctgccttca  2700
tacgctattt atttgcttgg tactgtttct tttgtcgatg ctcaccctgt tgtttggtgt  2760
tacttctgca ggtcgactct agaggatcaa ttcgctagcg aagttcctat tccgagttc   2820
ctattctcta gaaagtatag gaacttcaga tccaccggga tccccgatca tgcaaaaact  2880
cattaactca gtgcaaaact atgcctgggg cagcaaaacg gcgttgactg aactttatgg  2940
tatggaaaat ccgtccagcc agccgatggc cgagctgtgg atgggcgcac atccgaaaag  3000
cagttcacga gtgcagaatg ccgccggaga tatcgtttca ctgcgtgatg tgattgagag  3060
tgataaatcg actctgctcg gagaggccgt tgccaaacgc tttggcgaac tgcctttcct  3120
gttcaaagta ttatgcgcag cacagccact ctccattcag gttcatccaa acaaacacaa  3180
ttctgaaatc ggtttttgcca agaaaatgc cgcaggtatc ccgatggatg ccgccgagcg  3240
taactataaa gatcctaacc acaagccgga gctggtttt gcgctgacgc cttttcctgc  3300
gatgaacgcg tttcgtgaat tttccgagat tgtctcccta ctccagccgg tcgcaggtga  3360
acatccggcg attgctcact ttttacaaca gcctgatgcc gaacgtttaa gcgaactgtt  3420
cgccagcctg ttgaatatgc agggtgaaga aaaatcccgc gcgctggcga ttttaaaatc  3480
ggccctcgat agccagcagg gtgaaccgtg gcaaacgatt cgtttaattt ctgaatttta  3540
cccggaagac agccggtctgt tctccccgct attgctgaat gtggtgaaat tgaacctgag  3600
cgaagcgatg ttcctgttcg ctgaaacacc gcacgcttac ctgcaaggcg tggcgctgga  3660
agtgatggca aactccgata acgtgctgcg tgcgggtctg acgctaaat acattgatat  3720
tccgaactg gttgccaatg tgaaattcga agccaaaccg gctaaccagt tgttgaccca  3780
gccggtgaaa caaggtgcag aactggactt cccgattcca gtggatgatt tgccttctc    3840
gctgcatgac gtcagtgata aagaaccac cattagcgag tcagtgccg tcattttgtt  3900
ctgcgtcgaa ggcgatgcaa cgttgtgaa aggttctcag cagttacagc ttaaaccgga  3960
tgaatcagca tttattgccg ccaacgaatc accggtgact gtcaaaggcc acggccgttt  4020
agcgcgtgtt tacaacaagc tgtaagagct tactgaaaaa attaacatct cttgctaagc  4080
tgggggtgga acctagactt gtccatcttc tggattggcc aacttaatta atgtatgaaa  4140
taaaaggatg cacacatagt gacatgctaa tcactataat gtgggcatca aagttgtgtg  4200
```

```
ttatgtgtaa ttactagtta tctgaataaa agagaaagag atcatccata tttcttatcc   4260
taaatgaatg tcacgtgtct ttataattct ttgatgaacc agatgcattt cattaaccaa   4320
atccatatac atataaatat taatcatata taattaatat caattgggtt agcaaaacaa   4380
atctagtcta ggtgtgtttt gcgaatgcgg ccctagcgta tacgaagttc ctattccgaa   4440
gttcctattc tccagaaagt ataggaactt ctgtacacct gagctgattc cgatgacttc   4500
gtaggttcct agctcaagcc gctcgtgtcc aagcgtcact tacgattagc taatgattac   4560
ggcatctagg accgactagc taactaacta gtaccgaggc cggccccgcg ggagctcggc   4620
gcgcctaagg gccaagtact tgctgtccct gtatctccaa cacgagcctt gattcctgcc   4680
ggccggtgat ggcaatggcc gctagtagtc tccgctagct agggagcggc gatccgacgc   4740
gacgccacca tgtgtctaga aaagaagttt cttgctttgc atgcagactt attagcgcgg   4800
tcgacacctg tggggacccc gtgtcttgag acaatgagac tgcctgtccg cccaagacac   4860
tacttgtagc catgaagcca tcgactcctc tccttgctct ccagtaatcc agtggatgga   4920
tccatcatcg atagtttagt ttatcagtct tcttgaggcc gggtgtcccc atgcataatg   4980
atgacagaaa gcctgggcca ggtaaaagcc aaaagtttg accctctagg tactggggcg   5040
agccctggcg tttgaacaaa aaaaaaatc gagcgtgtcg ccccggcctg ttttcgaact   5100
cctaaacgac gtcgcaactt tttttataca cacactaccg gtacatggct tt          5152
```

SEQ ID NO: 260         moltype = DNA   length = 5146
FEATURE              Location/Qualifiers
misc_feature       1..5146
                       note = synthesized sequence- TS10Cas-3 donor
source               1..5146
                       mol_type = other DNA
                       organism = synthetic construct SEQUENCE: 260
```
aaatagtaaa cgggagggga ggtcgctagt agtaaacgct aggtagctag gataatccgt     60
ctcgtgttgg acggaaggtt ttggacgcat ctgcgtgcac agcccgctga tacagatctg    120
atcgactagc tagctagatg ccgaggcccc agagcaaggc ccggatactc ctgcacagtc    180
cctgagattt cagcacagca ggtgctgttg catcaatata taaatccctg ctttattaat    240
ttaatctctg tgcatgtatc catacatcgt cagcggctca gcgctatcac actgcagtgc    300
acgcagctag ttgagcgcct gggtcagtat atatatagct agtagggaca aaggggggca    360
ctgtacgttg gtttggtttg gcacgcacgc gatcgagagt ggtggaatgg actgcagatc    420
atcgatcgct gcactgtacg cacgcgcacc ggactgcatt tgcatgcccc tgaaggagga    480
aaggggaagg aaaagaaaga aataggagaa agaagaagaa gcagagaaat acgtcacagt    540
ccaagaagag tgagccgccc tagctagctt caaccctgac gaacccggca gccacacttc    600
cggccatgta tgcatgcatg catggcttag cttcagatgt ccaatcgaat ccatcaagac    660
ctggccggtt ttccatggcc gcctcgcctt cgctagttaa gggccaagta cttgctgtcc    720
ctgtggtacc atttaaatct taagcctagg ataacttcgt atagcataca tttacgaag     780
ttatgcgcgc gctagcctgc agtgcagcgt gacccggtcg tgccctctc tagagataat    840
gagcattgca tgtctaagtt ataaaaaatt accacatatt ttttttgtca cacttgtttg    900
aagtgcagtt tatctatctt tatacatata tttaaacttt actctacgaa taatataatc    960
tatagtacta caataataatc agtgtttag agaatcatat aaatgaacag ttagacatgg   1020
tctaaaggac aattgagtat tttgacaaca ggactctaca gtttatctt tttagtgtga   1080
atgtgttctc cttttttttt gcaaatagct tcacctatat aatacttcat ccattttatt   1140
agtacatcca tttagggttt agggttaatg gtttttatag actaattttt ttagtacatc   1200
tattttattc tattttagcc tctaaattaa gaaaactaaa actctatttt agttttttta   1260
tttaataatt tagatataaa ataaatata ataaagtgac taaaaattaa acaaatacc     1320
tttaagaaat taaaaaaact aaggaaacat ttttctgtt tcgagtagat aatgccagcc   1380
tgttaaacgc cgtcgacgag tctaacggac accaaccagc gaaccagcag cgtcgcgtcg   1440
ggccaagcga agcagacggc acggcatctc tgtcgctgcc tctggacccc tctcgagagt   1500
tccgctccac cgttggactt gctccgctgt cggcatccag aaattgcgtg gcggagcggc   1560
agacgtgagc cggcacggca ggcggcctcc tcctcctctc acggcaccgg cagctacggg   1620
ggattccttt cccaccgctc cttcgctttc ccttcctcgc ccgccgtaat aaatagacac   1680
cccctccaca ccctctttcc ccaacctcgt gttgttcgga gcgcacacac acacaaccag   1740
atctccccca aatccaccg tcggcacctc cgcttcaagg tacgccgtc gtcctccccc    1800
ccccccctct ctaccttctc tagatcggcg ttccggtcca tgcatggtta gggcccggta   1860
gttctacttc tgttcatgtt tgtgttagat ccgtgtttgt gttagatccg tgctgctagc   1920
gttcgtacac ggatgcgacc tgtacgtcag acacgttctg attgctaact tgccagtgtt   1980
tctcttttggg gaatcctggg atggctctag ccgttccgca gacggggatcg atttcatgat   2040
ttttttgtt tcgttgcata gggtttggtt tgcccttttc ctttatttca atatatgccg   2100
tgcacttgtt tgtcgggtca tcttttcatg ctttttttg tcttggttgt gatgatgtgg   2160
tctggttggg cggtcgttct agatcggagt agaattctgt ttcaaactac ctggtggatt   2220
tattaatttt ggatctgtat gtgtgtgcca tacatattca tagttacgaa ttgaagatga   2280
tggatggaaa tatcgatcta ggataggtat acatgttagt gcgggtttta ctgatgcata   2340
tacagagatg ctttttgttc gcttggttgt gatgatgtgg tgtggttggg cggtcgttca   2400
ttcgttctag atcggagtag aatactgttt caaactacct ggtgtattta ttaatttgg    2460
aactgtatgt gtgtgtcata catcttcata gttacgagtt taagatggat ggaaatatcg   2520
atctaggata ggtatacatg ttgatgtggg ttttactgat gcatatacat gatggcatat   2580
gcagcatcta ttcatatgct ctaaccttga gtacctatct attataataa acaagtatgt   2640
tttataatta ttttgatctt gatatacttg gatgatggca tatgcagcag ctatatgtgt   2700
atttttttag ccctgccttc atacgctatt tatttgcttg gtactgtttc ttttgtcgat   2760
gctcaccctg ttgtttggtg ttacttctgc aggtcgactc tagaggatca attcgctagc   2820
gaagttccta ttccgaagtt cctattctct agaaagtata ggaacttcag atccaccggg   2880
atcccgatc atgcaaaaac tcattaactc agtgcataac tatgcctggg ggcagcaaaaac   2940
ggcgttgact gaactttatg gtatggaaaa tccgtccagc cagccgatgg ccgagctgtg   3000
gatgggcgca catccgaaaa gcagttcacg agtgcagaat gccgccggag atatcgtttc   3060
actgcgtgat gtgattgaga gtgataaatc gactctgctc ggagaggccg ttgccaaacg   3120
ctttggccgaa ctgcctttcc tgttcaaagt attatgcgca gcacagccac tctccattca   3180
ggttcatcca aacaaacaca attctgaaat cggttttgcc aagaaaatg ccgcaggtat   3240
```

```
cccgatggat gccgccgagc gtaactataa agatcctaac cacaagccgg agctggtttt   3300
tgcgctgacg cctttccttg cgatgaacgc gtttcgtgaa ttttccgaga ttgtctccct   3360
actccagccg gtcgcaggtg cacatccggc gattgctcac tttttacaac agcctgatgc   3420
cgaacgttta agcgaactgt tcgccagcct gttgaatatg cagggtgaag aaaaatcccg   3480
cgcgctggcg attttaaaat cggccctcga tagccgcag ggtgaaccgt ggcaaacgat    3540
tcgtttaatt tctgaatttt acccggaaga cagcggtctg ttctccccgc tattgctgaa   3600
tgtggtgaaa ttgaaccctg gcgaagcgat gttcctgttc gctgaaacac cgcacgctta   3660
cctgcaaggc gtggcgctgg aagtgatggc aaactccgat aacgtgctgc gtgcgggtct   3720
gacgcctaaa tacattgata ttccggaact ggttgccaat gtgaaattcg aagccaaacc   3780
ggctaaccag ttgttgaccc agccggtgaa acaaggtgca gaactggact tcccgattcc   3840
agtggatgat tttgccttct cgctgcatga ccttagtgat aaagaaacca ccattagcca   3900
gcagagtgcc gccattttgt tctgcgtcga aggcgatgca acgttgtgga aaggttctca   3960
gcagttacag cttaaaccgg gtgaatcagc gtttattgcc gccaacgaat caccggtgac   4020
tgtcaaaggc cacggccgtt tagcgcgtgt ttacaacaag ctgtaagagc ttactgaaaa   4080
aattaacatc tcttgctaag ctgggggtgg aacctagact tgtccatctt ctggattggc   4140
caacttaatt aatgtatgaa ataaaaggat gcacacatag tgacatgcta atcactataa   4200
tgtgggcatc aaagttgtgt gttatgtgta attactagtg atctgaataa aagagaaaga   4260
gatcatccat atttcttatc ctaaatgaat gtcacgtgtc tttataattc tttgatgaac   4320
cagatgcatt tcattaacca aatccatata catataaata ttaatcatat ataattaata   4380
tcaattgggt tagcaaaaca aatctagtct aggtgtgttt tgcgaatgcg gcccctagcgt  4440
atacgaagtt cctattccga agttcctatt ctccagaaaa tataggaact tctgtacacc   4500
tgagctgatt ccgatgactt cgtaggttcc tagctcaagc cgctcgtgtc caagcgtcac   4560
ttacgattag ctaatgatta cggcatctag gaccgactag ctaactaact agtaccgagg   4620
ccggcccccgc gggagctcgg cgcgccatct ccaacacgag ccttgattcc tgccggccgg   4680
tgatggcaat ggccgctagt agtctccgct agctagggag cggcgatccg acgcgacgcc   4740
accatgtgtc tagaaaagaa gtttcttgct ttgcatgcag acttattagc gcggtcgaca   4800
cctgtgggga ccccgtgtct tgagacaatg agactgcctg tccgcccaag cactacttgg   4860
tagccatgaa gccatcgact cctctccttg ctctccagta atccagtgga tggatccatc   4920
atcgatagtt tagtttatca gtcttcttga ggccggtgtc ccccatgcat aatgatgaca   4980
gaaagcctgg gccaggtaaa agccaaaaag tttgaccctc taggtactgg ggccagccct   5040
ggcgtttgaa caaaaaaaaa atctgagcgt gtcgccccgg cctgttttcg aactcctaaa   5100
cgacgtcgca actttttttta tacacacact accggtacat ggcttt                5146
```

SEQ ID NO: 261       moltype = DNA  length = 32
FEATURE                Location/Qualifiers
misc_feature       1..32
                        note = synthesized sequence- ubir primer from donor
source                 1..32
                        mol_type = other DNA
                        organism = synthetic construct
SEQUENCE: 261
ccatgtctaa ctgttcattt atatgattct ct                              32

SEQ ID NO: 262       moltype = DNA  length = 31
FEATURE                Location/Qualifiers
misc_feature       1..31
                        note = synthesized sequence- psbf primer from dono
source                 1..31
                        mol_type = other DNA
                        organism = synthetic construct
SEQUENCE: 262
gctcgtgtcc aagcgtcact tacgattagc t                               31

SEQ ID NO: 263       moltype = DNA  length = 27
FEATURE                Location/Qualifiers
misc_feature       1..27
                        note = synthesized sequence- MHP14 14-1HR1f primer
source                 1..27
                        mol_type = other DNA
                        organism = synthetic construct
SEQUENCE: 263
ctcacatgag gctcttcttt gcttgct                                     27

SEQ ID NO: 264       moltype = DNA  length = 26
FEATURE                Location/Qualifiers
misc_feature       1..26
                        note = synthesized sequence- MHP14 14-1HR2r primer
source                 1..26
                        mol_type = other DNA
                        organism = synthetic construct
SEQUENCE: 264
aggatcctat tccccaattt gtagat                                      26

SEQ ID NO: 265       moltype = DNA  length = 21
FEATURE                Location/Qualifiers
misc_feature       1..21
                        note = synthesized sequence- CHR1-8 8HR1f primer
source                 1..21
                        mol_type = other DNA

```
                        organism = synthetic construct
SEQUENCE: 265
cagtccgtgg attgaagcca t                                              21

SEQ ID NO: 266          moltype = DNA  length = 22
FEATURE                 Location/Qualifiers
misc_feature            1..22
                        note = synthesized sequence- CHR1-8 8HR2r primer
source                  1..22
                        mol_type = other DNA
                        organism = synthetic construct
SEQUENCE: 266
ctctgtctcc gagacgtgct ta                                             22

SEQ ID NO: 267          moltype = DNA  length = 26
FEATURE                 Location/Qualifiers
misc_feature            1..26
                        note = synthesized sequence- CHR1-9 9HR1f primer
source                  1..26
                        mol_type = other DNA
                        organism = synthetic construct
SEQUENCE: 267
ggagcaaatg ttttaggtat gaaatg                                         26

SEQ ID NO: 268          moltype = DNA  length = 28
FEATURE                 Location/Qualifiers
misc_feature            1..28
                        note = synthesized sequence- CHR1-9 9HR2r primer
source                  1..28
                        mol_type = other DNA
                        organism = synthetic construct
SEQUENCE: 268
cggattctaa agatcatacg taaatgaa                                       28

SEQ ID NO: 269          moltype = DNA  length = 21
FEATURE                 Location/Qualifiers
misc_feature            1..21
                        note = synthesized sequence- CHR1-10 10HR1f primer
source                  1..21
                        mol_type = other DNA
                        organism = synthetic construct
SEQUENCE: 269
tggcttgtct atgcgcatct c                                              21

SEQ ID NO: 270          moltype = DNA  length = 20
FEATURE                 Location/Qualifiers
misc_feature            1..20
                        note = synthesized sequence- CHR1-10 10HR2r primer
source                  1..20
                        mol_type = other DNA
                        organism = synthetic construct
SEQUENCE: 270
ccagacccaa acagcaggtt                                                20

SEQ ID NO: 271          moltype = DNA  length = 18
FEATURE                 Location/Qualifiers
misc_feature            1..18
                        note = synthesized sequence- MHP14Cas-1 probe
source                  1..18
                        mol_type = other DNA
                        organism = synthetic construct
SEQUENCE: 271
cagattcacg tcagattt                                                  18

SEQ ID NO: 272          moltype = DNA  length = 27
FEATURE                 Location/Qualifiers
misc_feature            1..27
                        note = synthesized sequence- MHP14cas-1 forward primer
source                  1..27
                        mol_type = other DNA
                        organism = synthetic construct
SEQUENCE: 272
catagtggtg tatgaaagga agcactt                                        27

SEQ ID NO: 273          moltype = DNA  length = 30
FEATURE                 Location/Qualifiers
misc_feature            1..30
                        note = synthesized sequence- MHP14cas-1 reverse primer
source                  1..30
```

```
                            mol_type = other DNA
                            organism = synthetic construct
SEQUENCE: 273
cattttggat tgtaatatgt gtacctcata                                            30

SEQ ID NO: 274           moltype = DNA  length = 17
FEATURE                  Location/Qualifiers
misc_feature             1..17
                         note = synthesized sequence- MHP14Cas-3 probe
source                   1..17
                         mol_type = other DNA
                         organism = synthetic construct
SEQUENCE: 274
caccactatg tcgcttc                                                          17

SEQ ID NO: 275           moltype = DNA  length = 22
FEATURE                  Location/Qualifiers
misc_feature             1..22
                         note = synthesized sequence- MHP14Cas-3 forward primer
source                   1..22
                         mol_type = other DNA
                         organism = synthetic construct
SEQUENCE: 275
cggatgcacg aaaattgtag ga                                                    22

SEQ ID NO: 276           moltype = DNA  length = 24
FEATURE                  Location/Qualifiers
misc_feature             1..24
                         note = synthesized sequence- MHP14Cas-3 reverse primer
source                   1..24
                         mol_type = other DNA
                         organism = synthetic construct
SEQUENCE: 276
ctgacgtgaa tctgtttgga attg                                                  24

SEQ ID NO: 277           moltype = DNA  length = 18
FEATURE                  Location/Qualifiers
misc_feature             1..18
                         note = synthesized sequence- TS8Cas-1 probe
source                   1..18
                         mol_type = other DNA
                         organism = synthetic construct
SEQUENCE: 277
tacgtaacgt gcagtact                                                         18

SEQ ID NO: 278           moltype = DNA  length = 21
FEATURE                  Location/Qualifiers
misc_feature             1..21
                         note = synthesized sequence- TS8Cas-1 forward primer
source                   1..21
                         mol_type = other DNA
                         organism = synthetic construct
SEQUENCE: 278
acggacggac catacgttat g                                                     21

SEQ ID NO: 279           moltype = DNA  length = 26
FEATURE                  Location/Qualifiers
misc_feature             1..26
                         note = synthesized sequence- TS8Cas-1 reverse primer
source                   1..26
                         mol_type = other DNA
                         organism = synthetic construct
SEQUENCE: 279
tcagctggtg gagtatatta gttcgt                                                26

SEQ ID NO: 280           moltype = DNA  length = 18
FEATURE                  Location/Qualifiers
misc_feature             1..18
                         note = synthesized sequence- TS8Cas-2 probe
source                   1..18
                         mol_type = other DNA
                         organism = synthetic construct
SEQUENCE: 280
ccagctgatc actgatga                                                         18

SEQ ID NO: 281           moltype = DNA  length = 21
FEATURE                  Location/Qualifiers
misc_feature             1..21
                         note = synthesized sequence- TS8Cas-2 forward primer
```

```
                        source               1..21
                                             mol_type = other DNA
                                             organism = synthetic construct
                        SEQUENCE: 281
                        acggacggac catacgttat g                                                  21

SEQ ID NO: 282       moltype = DNA   length = 26
                        FEATURE              Location/Qualifiers
                        misc_feature         1..26
                                             note = synthesized sequence- TS8Cas-2 reverse primer
                        source               1..26
                                             mol_type = other DNA
                                             organism = synthetic construct
                        SEQUENCE: 282
                        cgcacatgtt ataaattaca atgcat                                             26

SEQ ID NO: 283       moltype = DNA   length = 14
                        FEATURE              Location/Qualifiers
                        misc_feature         1..14
                                             note = synthesized sequence- TS9Cas-2 probe
                        source               1..14
                                             mol_type = other DNA
                                             organism = synthetic construct
                        SEQUENCE: 283
                        ctgtttgcgg cctc                                                          14

SEQ ID NO: 284       moltype = DNA   length = 19
                        FEATURE              Location/Qualifiers
                        misc_feature         1..19
                                             note = synthesized sequence- TS9Cas-2 forward primer
                        source               1..19
                                             mol_type = other DNA
                                             organism = synthetic construct
                        SEQUENCE: 284
                        ctgcggagct gctggcgat                                                     19

SEQ ID NO: 285       moltype = DNA   length = 20
                        FEATURE              Location/Qualifiers
                        misc_feature         1..20
                                             note = synthesized sequence- TS9Cas-2 reverse primer
                        source               1..20
                                             mol_type = other DNA
                                             organism = synthetic construct
                        SEQUENCE: 285
                        cttgctggct tcgtctgtca                                                    20

SEQ ID NO: 286       moltype = DNA   length = 15
                        FEATURE              Location/Qualifiers
                        misc_feature         1..15
                                             note = synthesized sequence- TS9Cas-3 probe
                        source               1..15
                                             mol_type = other DNA
                                             organism = synthetic construct
                        SEQUENCE: 286
                        ccgacgtgcg tgcaa                                                         15

SEQ ID NO: 287       moltype = DNA   length = 19
                        FEATURE              Location/Qualifiers
                        misc_feature         1..19
                                             note = synthesized sequence- TS9Cas-3 forward primer
                        source               1..19
                                             mol_type = other DNA
                                             organism = synthetic construct
                        SEQUENCE: 287
                        ctgcggagct gctggcgat                                                     19

SEQ ID NO: 288       moltype = DNA   length = 20
                        FEATURE              Location/Qualifiers
                        misc_feature         1..20
                                             note = synthesized sequence- TS9Cas-3 reverse primer
                        source               1..20
                                             mol_type = other DNA
                                             organism = synthetic construct
                        SEQUENCE: 288
                        cttgctggct tcgtctgtca                                                    20

SEQ ID NO: 289       moltype = DNA   length = 17
                        FEATURE              Location/Qualifiers
                        misc_feature         1..17
```

```
                   note = synthesized sequence- TS10Cas-1 probe
source             1..17
                   mol_type = other DNA
                   organism = synthetic construct
SEQUENCE: 289
tcgccttcgc tagttaa                                                         17

SEQ ID NO: 290     moltype = DNA   length = 20
FEATURE            Location/Qualifiers
misc_feature       1..20
                   note = synthesized sequence- TS10Cas-1 forward primer
source             1..20
                   mol_type = other DNA
                   organism = synthetic construct
SEQUENCE: 290
aagacctggc cggttttcca                                                      20

SEQ ID NO: 291     moltype = DNA   length = 18
FEATURE            Location/Qualifiers
misc_feature       1..18
                   note = synthesized sequence- TS10Cas-1 reverse primer
source             1..18
                   mol_type = other DNA
                   organism = synthetic construct
SEQUENCE: 291
tagcggccat tgccatca                                                        18

SEQ ID NO: 292     moltype = DNA   length = 19
FEATURE            Location/Qualifiers
misc_feature       1..19
                   note = synthesized sequence- TS10Cas-3 probe
source             1..19
                   mol_type = other DNA
                   organism = synthetic construct
SEQUENCE: 292
ctgtatctcc aacacgagc                                                       19

SEQ ID NO: 293     moltype = DNA   length = 20
FEATURE            Location/Qualifiers
misc_feature       1..20
                   note = synthesized sequence- TS10Cas-3 forward primer
source             1..20
                   mol_type = other DNA
                   organism = synthetic construct
SEQUENCE: 293
aagacctggc cggttttcca                                                      20

SEQ ID NO: 294     moltype = DNA   length = 18
FEATURE            Location/Qualifiers
misc_feature       1..18
                   note = synthesized sequence- TS10Cas-3 reverse primer
source             1..18
                   mol_type = other DNA
                   organism = synthetic construct
SEQUENCE: 294
tagcggccat tgccatca                                                        18

SEQ ID NO: 295     moltype = DNA   length = 472
FEATURE            Location/Qualifiers
misc_feature       1..472
                   note = GM-U6-9.1 promoter
source             1..472
                   mol_type = unassigned DNA
                   organism = Glycine max
SEQUENCE: 295
cccgggttaa gagaattgta agtgtgcttt tatatattta aaattaatat attttgaaat     60
gttaaaatat aaagaaaat tcaatgtaaa ttaaaaataa ataaatgttt aataagata      120
aattttaaaa cataaaagaa aatgtctaac aagaggatta agatcctgtg ctcttaaatt    180
tttaggtgtt gaaatcttag ccatacaaaa tatattttat taaaaccaag catgaaaaaa    240
gtcactaaag agctatataa ctcatgcagc tagaaatgaa gtgaagggaa tccagtttgt    300
tctcagtcga aagagtgtct atctttgttc ttttctgcaa ccgagttaag caaaatggga    360
atgcgaggta tcttcctttc gttaggggag caccagatgc atagttagtc ccacattgat    420
gaatataaca agagcttcac agaatatata gcccaggcca cagtaaaagc tt            472

SEQ ID NO: 296     moltype = DNA   length = 5958
FEATURE            Location/Qualifiers
misc_feature       1..5958
                   note = synthesized sequence- EF1A2-CAS9
source             1..5958
``` mol_type = other DNA
organism = synthetic construct

SEQUENCE: 296

```
gggtttactt attttgtggg tatctatact tttattagat ttttaatcag gctcctgatt   60
tcttttatt tcgattgaat tcctgaactt gtattattca gtagatcgaa taaattataa  120
aaagataaaa tcataaaata atattttatc ctatcaatca tattaaagca atgaatatgt  180
aaaattaatc ttatctttat tttaaaaaat catataggtt tagtatttt ttaaaaataa  240
agataggatt agttttacta ttcactgctt attacttta aaaaaatcat aaaggtttag  300
tattttttta aaataaatat aggaatagtt ttactattca ctgctttaat agaaaaatag  360
tttaaaattt aagatagttt taatcccagc atttgccacg tttgaacgtg agccgaaacg  420
atgtcgttac attatcttaa cctagctgaa acgatgtcgt cataatatcg ccaaatgcca  480
actggactac gtcgaaccca caaatcccac aaagcgcgtg aaatcaaatc gctcaaacca  540
caaaaaagaa caacgcgttt gttacacgct caatcccacg cgagtagagc acagtaacct  600
tcaaataagc gaatggggca taatcagaaa tccgaaataa acctaggggc attatcggaa  660
atgaaaagta gctcactcaa tataaaaatc taggaaccct agttttcgtt atcactctgt  720
gctccctcgc tctatttctc agtctctgtg tttgcggctg aggattccga acgagtgacc  780
ttcttcgttt ctcgcaaagg taacagcctc tgctcttgtc tcttcgattc gatctatgcc  840
tgtctcttat ttacgatgat gtttcttcgg ttatgttttt ttatttatgc tttatgctgt  900
tgatgttcgg ttgtttgttt cgctttgttt ttgtggttca gttttttagg attcttttgg  960
tttttgaatc gattaatcgg aagagatttt cgagttattt ggtgtgttgg aggtgaatct 1020
ttttttttgag gtcatagatc tgttgtattt gtgttataaa catgcgactt tgtatgattt 1080
tttacgaggt tatgatgttc tggttgtttt attatgaatc tgttgagaca gaaccatgat 1140
ttttgttgat gttcgtttac actattaaag gtttgttta acaggattaa aagtttttta 1200
agcatgttga aggagtcttg tagatatgta accgtcgata gtttttttgt gggtttgttc 1260
acatgttatc aagcttaatc ttttactatg tatgcgacca tatctggatc cagcaaaggc 1320
gattttttaa ttccttgtga aacttttgta atatgaagtt gaaattttgt tattggtaaa 1380
ctataaatgt gtgaagttgg agtataccat taccttctta tttggctttg tgatagttta 1440
atttatatgt attttgagtt ctgacttgta tttctttgaa ttgattctag tttaagtaat 1500
ccatggacaa aaagtactca ataggggctcg acataggggac taactccgtt ggatgggccg 1560
tcatcaccga cgagtacaag gtgccctcca agaagttcaa ggtgttggga aacaccgaca 1620
ggcacagcat aaagaagaat ttgatccggtg ccctcctctt cgactccgga gagaccgctg 1680
aggctaccag gctcaagagg accgctagaa ggcgctacac cagaaggaag aacagaatct 1740
gctacctgca ggagatcttc tccaacgaga tggccaaggt ggacgactcc ttcttccacc 1800
gccttgagga atcattcctg gtggaggagg ataaaaagca cgagagacac ccaatcttcg 1860
ggaacatcgt cgacgaggtg gcctaccatg aaaagtaccc taccatctac cacctgagga 1920
agaagctggt cgactctacc gacaaggctg acttgcgctt gatttacctg gctctcgctc 1980
acatgataaa gttccgcgga cacttcctca ttgagggaga cctgaaccca gacaactccg 2040
acgtggacaa gctcttcatc cagctcgttc agacctacaa ccagctttc gaggagaacc 2100
caatcaacgc cagtggagtt gacgccaagg ctatcctctc tgctcgtctg tcaaagtcca 2160
ggaggcttga gaacttgatt gcccagctgc ctggcgaaaa gaagaacgga ctgttcggaa 2220
acttgatcgc tctctcctg ggattgactc ccaacttcaa gtccaactc gacctcgccg 2280
aggacgctaa gttgcagttg tctaaagaca cctacgacga tgacctcgac aacttgctgg 2340
cccagatagg cgaccaatac gccgatctct tcctcgccgc taagaacttg tccgacgcaa 2400
tcctgctgtc cgacatcctg agagtcaaca ctgagattac caaagctcct ctgtctgctt 2460
ccatgattaa gcgctacgac gagcaccacc aagatctgac cctgctcaag gccctggtga 2520
gacagcagct gcccgagaag tacaaggaga tcttttttcga ccagtccaag aacggctacg 2580
ccggatacat tgacggaggc gcctcccagg aagagttcta caagttcatc aagcccatcc 2640
ttgagaagat ggacggtacc gaggagctgt tggtgaagtt aacagagaca gacctgttga 2700
ggaagcagag aaccttcgac aacggaagca tccctcacca aatccacctg ggagagctcc 2760
acgccatctc gaggaggcag gaggatttct atcccttcct gaaggacaac cgcgagaaga 2820
ttgagaagat cttgacccttc agaattcctt actacgtcgg gccactcgcc agaggaaact 2880
ctaggttcgc ctggatgacc cgcaaatctg aagagaccat tactccctgg aacttcgagg 2940
aagtcgtgga caagggcgct tccgctcagt ctttcatcga gaggatgacc aacttcgata 3000
aaaatctgcc caacgagaag gtgctgccca agcactccct gttgtacgag tatttcacag 3060
tgtacaacga gctcaccaag gtgaagtacg tcacagagga aatgaggaag cctgccttct 3120
tgtccggaga gcaagaagaag gccatcgtcg acctgctctt caagaccaac aggaaggtga 3180
ctgtcaagca gctgaaggag gactacttca agaagatcga gtgcttcgac tccgtcgaga 3240
tctctggtgt cgaggacagg ttcaacgcct cccttgggac ttaccacgat ctgctcaaga 3300
ttattaaaga caaggacttc ctggacaacg aggagaacga ggacatcctt gaggacatcg 3360
tgctcacccct gaccttgttc gaagacaggg aaatgatcga agagaggctc aagacctacg 3420
cccacctctt cgacgacaag gtgatgaaac agctgaagag acgcagatat accggctggg 3480
gaaggctctc ccgcaaattg atcaacggga tcagggacaa gcagtcaggg aagactatac 3540
tcgacttcct gaagtccgac ggattcgcca acaggaactt catgcagctc attcacgacg 3600
actccttgac cttcaaggag gacatccaga aggctcaggt gtctggacag ggtgactcct 3660
tgcatgagca cattgctaac ttggccggct ctcccgctat taagaagggc attttgcaga 3720
ccgtgaaggt cgttgacgag ctcgtgaagg tgatggacgcc cacaagcca gagaacatcg 3780
ttattgagat ggctcgcgag aaccaaacta cccagaaagg gcaagaat tcccgcgaga 3840
ggatgaagcg cattgaggag ggcataaaag agcttggctc tcagatcctc aaggagcacc 3900
ccgtcgagaa cactcagctg cagaacgaga agctgtacct gtactacctc caaaacggaa 3960
gggacatgta cgtggaccag gagctggaca tcaacaggtt gtccgactac gacgtcgacc 4020
acatcgtgcc tcagtccttc ctgaaggatg actccatcga caataaagtg ctgacacgct 4080
ccgataaaaa tagaggcaag tccgacaacg tcccctccga ggaggtcgtg aagaagatga 4140
aaaactactg gagacagctc ttgaacgcca agctcatcac ccagcgtaag ttcgacaacc 4200
tgactaaggc tgagagagga ggattgtccg agctcgataa ggccgattc atcaagagac 4260
agctcgtcga aacccgccaa attaccaagc acgtggccca aattctggat tcccgcatga 4320
acaccaagta cgatgaaaat gacaagctga tccgcgaggt caaggtgatc accttgaagt 4380
ccaagctggt ctccgacttc cgcaaggact ccagttctca aaggtgagg gagatcaaca 4440
actaccacca cgcacacgac gcctacctca acgctgtcgt tggaaccgcc ctcatcaaaa 4500
aatatcctaa gctggagtct gagttcgtct acggcgacta caaggtgtac gacgtgaggga 4560
```

```
agatgatcgc taagtctgag caggagatcg gcaaggccac cgccaagtac ttcttctact    4620
ccaacatcat gaacttcttc aagaccgaga tcactctcgc caacggtgag atcaggaagc    4680
gcccactgat cgagaccaac ggtgagactg gagagatcgt gtgggacaaa ggggagggatt   4740
tcgctactgt gaggaaggtg ctctccatgc ctcaggtgaa catcgtcaag aagaccgaag    4800
ttcagaccgg aggattctcc aaggagtcca tcctccccaa gagaaactcc gacaagctga    4860
tcgctagaaa gaaagactgg gaccctaaga agtacggagg cttcgattct cctaccgtga    4920
cctactctgt gctggtcgtg gccaaggtgg agaagggcaa gtccaagaag ctgaaatccg    4980
tcaaggagct cctcgggatt accatcatgg agaggagttc cttcgagaag aaccctatcg    5040
acttcctgga ggccaaggga tataaagagg tgaagaagga cctcatcatc aagctgccca    5100
agtactccct cttcgagttg gagaacgaaa ggaagaggat gctggcttct gccggagagt    5160
tgcagaaggg aaatgagctc gcccttccct ccaagtacgt gaacttcctg tacctcgcct    5220
ctcactatga aagttgaag ggctctcctg aggacaacga gcagaagcag ctcttcgtgg     5280
agcagcacaa gcactacctg gacgaaatta tcgagcagat ctctgagttc tccaagcgcg    5340
tgatattggc cgacgccaac ctcgacaagg tgctgtccgc ctacaacaag cacagggata    5400
agcccattcg cgagcaggct gaaaacatta tccacctgtt taccctcaca aacttgggag    5460
cccctgctgc cttcaagtac ttcgacacca ccattgacag gaagagatac acctccacca    5520
aggaggtgct cgacgcaaca ctcatccacc aatccatcac cggcctctat gaaacaagga    5580
ttgacttgtc ccagctggga ggcgactcta gagccgatcc caagaagaag agaaaggtgt    5640
aggttaacct agacttgtcc atcttctgga ttggccaact taattaatgt atgaaataaa    5700
aggatgcaca catagtgaca tgctaatcac tataatgtgg gcatcaaagt tgtgtgttat    5760
gtgtaattac tagttatctg aataaaagag aaagagatca tccatatttc ttatcctaaa    5820
tgaatgtcac gtgtctttat aattctttga tgaaccagat gcatttcatt aaccaaatcc    5880
atatacatat aaatattaat catatataat taatatcaat tgggttagca aaacaaatct    5940
agtctaggtg tgttttgc                                                  5958

SEQ ID NO: 297           moltype = DNA  length = 573
FEATURE                  Location/Qualifiers
misc_feature             1..573
                         note = synthesized sequence- U6-9.1-DD20CR1
source                   1..573
                         mol_type = other DNA
                         organism = synthetic construct
SEQUENCE: 297
ccgggttaag agaattgtaa gtgtgctttt atatatttaa aattaatata ttttgaaatg     60
ttaaatata aagaaaatt caatgtaaat taaaaataaa taaatgttta ataagataa       120
attttaaaac ataaaagaaa atgtctaaca agaggattaa gatcctgtgc tcttaaattt    180
ttaggtgttg aaatcttagc catacaaaat atattttatt aaaaccaagc atgaaaaaag    240
tcactaaaga gctatataac tcatgcagct agaaatgaag tgaagggaat ccagtttgtt    300
ctcagtcgaa agagtgtcta tctttgttct tttctgcaa cgagttaagc aaaatgggaa    360
tgcgaggtat cttcctttcg ttaggggagc accagatgca tagttagtcc cacattgatg    420
aatataacaa gagcttcaca gaatatatag cccaggccac agtaaaagct tggaactgac    480
acacgacatg agttttagag ctagaaatag caagttaaaa taaggctagt ccgttatcaa    540
cttgaaaaag tggcaccgag tcggtgcttt ttt                                 573

SEQ ID NO: 298           moltype = DNA  length = 6611
FEATURE                  Location/Qualifiers
misc_feature             1..6611
                         note = synthesized sequence- U6-9.1-DD20CR1+EF1A2-CAS9
source                   1..6611
                         mol_type = other DNA
                         organism = synthetic construct
SEQUENCE: 298
cgcgccggta cccgggttaa gagaattgta agtgtgcttt tatatattta aaattaatat     60
attttgaaat gttaaaatat aaagaaaat tcaatgtaaa ttaaaaataa ataaatgttt    120
aataagata aattttaaaa cataaaagaa aatgtctaac aagaggatta agatcctgtg    180
ctcttaaatt tttaggtgtt gaaatcttag ccatacaaaa tatattttat aaaaccaag    240
catgaaaaaa gtcactaaag agctatataa ctcatgcagc tagaaatgaa gtgaagggaa    300
tccagtttgt tctcagtcga aagagtgtct atctttgttc ttttctgcaa ccgagttaag    360
caaaatggga atgcgaggta tcttcctttc gttaggggag caccagatgc atagttagtc    420
ccacattgat gaatataaca agagcttcac agaatatata gcccaggcca cagtaaaagc    480
ttggaactga cacacgacat gagttttaga gctagaaata gcaagttaaa ataaggctag    540
tccgttatca acttgaaaaa gtggcaccga gtcggtgctt tttttgcgg ccgcaattgg     600
atcgggttta cttatttgt gggtatctat acttttatta gatttttaat caggctcctg    660
atttcttttt atttcgattg aattcctgaa cttgtatagc tcagtagatc gaataaatta    720
taaaagata aaatcataaa ataatatttt atcctatcaa tcatattaaa gcaatgaata    780
tgtaaaatta atcttatctt tatttttaaaa aatcatatag gtttagtatt ttttttaaaaa   840
taaagatagg attagttttta ctattcactg cttattactt ttaaaaaaat cataaaggtt    900
tagtattttt ttaaaataaa tataggaata gttttactat tcactgcttt aatagaaaaa    960
tagtttaaaa tttaagatag ttttaatccc agcatttgcc acgtttgaac gtgagccgaa    1020
acgatgtcgt tacattatct taacctagct gaaacgatgt cgtcataata tcgccaaatg    1080
ccaactggac tacgtcgaac ccacaaatcc cacaaagcgc gtgaaatcaa atcgctcaaa    1140
ccacaaaaaa gaacaacgcg tttgttacac gctcaatccc acgcgagtag agcacagtaa    1200
ccttcaaata agcgaatggg gcataatcag aaatccgaaa taaacctagg ggcattatcg    1260
gaaaatgaaa gtagctcact caatatataaa cctaggtatc gttatcactc                1320
tgtgctccct cgctctattt ctcagtctct gtgtttgcgg ctgaggattc cgaacgagtg    1380
accttcttcg tttctcgcaa aggtaacagc ctctgctctt gtctcttcga ttcgatctat    1440
gcctgtctct tatttacgat gatgtttctt cggttatgtt tttttattta tgctttatgc    1500
tgttgatgtt cggttgtttg tttgctttg ttttttggt tcagtttttt aggattcttt     1560
tggttttga atcgattaat cggaagagat tttcgagtta tttggtgtgt tggaggtgaa    1620
```

```
tctttttttt gaggtcatag atctgttgta tttgtgttat aaacatgcga ctttgtatga    1680
tttttttacga ggttatgatg ttctggttgt tttattatga atctgttgag acagaaccat  1740
gattttgtt gatgttcgtt tacactatta aaggtttgtt ttaacaggat taaaagtttt    1800
ttaagcatgt tgaaggagtc ttgtagatat gtaaccgtcg atagtttttt tgtgggtttg   1860
ttcacatgtt atcaagctta atctttact atgtatgcga ccatatctgg atccagcaaa    1920
ggcgatttt taattccttg tgaaacttttt gtaatatgaa gttgaaattt tgttattggt   1980
aaactataaa tgtgtgaagt tggagtatac ctttaccttc ttatttggct ttgtgatagt   2040
ttaatttata tgtatttga gttctgactt gtatttcttt gaattgattc tagtttaagt   2100
aatccatgga caaaaagtac tcaataggc tcgacataggg gactaactcc gttggatggg   2160
ccgtcatcac cgacgagtac aaggtgccct ccaagaagtt caaggtgttg ggaaacaccg   2220
acaggcacag cataaagaag aatttgatcg gtgccctcct cttcgactcc ggagagaccg   2280
ctgaggctac caggctcaag aggaccgcta gaaggcgcta caccgaaagg aagaacagaa   2340
tctgctacct gcaggagatc ttctccaacg agatggccaa ggtggacgac tccttcttcc   2400
accgccttga ggaatcattc ctggtggagg aggataaaaa gcacgagaga cacccaatct   2460
tcggaaacat cgtcgacgag gtggcctacc atgaaaagta ccctaccatc taccacctga   2520
ggaagaagct ggtcgactct accgacaagg ctgacttgcg cttgatttac ctggctctcg   2580
ctcacatgat aaagttccgc ggacacttcc tcattgaggg agacctgaac ccagacaact   2640
ccgacgtgga caagctcttc atccagctcg ttcagaccta caaccagctt ttcgaggaga   2700
acccaatcaa cgccagtgga gttgacgcca aggctatcct ctctgctcgt ctgtcaaagt   2760
ccaggaggct tgagaacttg attgcccagc tgcctggcga aaagaagaac ggactgttcg   2820
gaaacttgat cgctctctcc ctgggattga ctcccaactt caagtccaac ttcgacctcg   2880
ccgaggacgc taagttgcag ttgtctaaag acacctacgc cgatcaactt gacaacttgc   2940
tggcccagat aggcgaccaa tacgccgatc tcttcctcgc cgctaagaac ttgtccgacg   3000
caatcctgct gtccgacatc ctgagagtca acactgagat taccaaagct cctctgtctg   3060
cttccatgat taagcgctac gacgagcacc accaagatct gaccctgctc aaggcctctg   3120
tgagacagca gctgcccgac aagtacaagg agatcttttt cgaccagtcc aagaacgct   3180
acgccggata cattgacgga ggcgcctccc aggaagagtt ctacaagttc atcaagccca   3240
tccttgagaa gatggacggt accgaggagc tgttggtgaa gttgaacaga gaggacctgt   3300
tgaggaagca gagaaccttc gacaacgaaa gcatccctca ccaaatccac ctgggagagc   3360
tccacgccat cttgaggagg caggaggatt tctatccctt cctgaaggac aaccgcagga   3420
agattgagaa gatcttgacc ttcagaattc cttactacgt cgggccactc gccagaggaa   3480
actctaggtt cgcctggatg acccgcaaat ctgaagagac cattactccc tggaacttcg   3540
aggaagtcgt ggacaagggc gcttccgctc agtcttttcat cgagaggatg accaacttcg   3600
ataaaaatct gcccaacgag aaggtgctgc ccaagcactc cctgttgtac gagtatttca   3660
cagtgtacaa cgagctcacc aaggtgaagt acgtcacaga gggaatgagg aagcctgcct   3720
tcttgtccgg agagcagaag aaggccatcg tcgacctgct cttcaagacc aacaggaagg   3780
tgactgtcaa gcagctgaag gaggactact tcaagaagat cgagtgcttc gactccgtcg   3840
agatctctgg tgtcgaggac aggttcaacg cctcccttgg gacttaccac gatctgctca   3900
agattattaa agacaaggac ttcctggaca acggaggaga cgaggacatc cttgaggaca   3960
tcgtgctcac cctgaccttg ttcgaagaca gggaaatgat cgaagagagg ctcaagacct   4020
acgcccacct cttcgacgac aaggtgatga acagctgaa gagacgcaga tataccggct   4080
ggggaaggct ctcccgcaaa ttgatcaacg ggatcaggga caagcagtca gggaagacta   4140
tactcgatcgt cctgaagtcc gacggattcg ccaacaggaa cttcatgcag ctcattcacg   4200
acgactcctt gaccttcaag gaggacatcc agaaggctca ggtgtctgga cagggtgact   4260
ccttgcatga gcacattgct aacttggccg gctctcccgc tattaagaag gcatttgc    4320
agaccgtgaa ggtcgttgac gagctcgtga aggtgatggg acgccacaag ccagagaaca   4380
tcgttattga gatggctcgc gagaaccaaa ctacccagaa agggcagaag aattcccgcg   4440
agaggatgaa gcgcattgag gagggcataa aagagcttgg ctctcagatc ctcaaggagc   4500
accccgtcga gaacactcag ctgcagaacg agaagctgta cctgtactac ctccaaaacg   4560
gaagggacat gtacgtggac caggagctgg acatcaacag gttgtccgac tacgacgtcg   4620
accacatcgt gcctcagtcc ttcctgaagg atgactccat cgacaataaa gtgctgacac   4680
gctccgataa aaatagaggc aagtccgaca acgtccccctc cgaggaggtc gtgaagaaga   4740
tgaaaaacta ctgttgaacag ctcttgaacg ccaagctcat cacccagcgt aagttcgaca   4800
acctgactaa ggctgagaga ggaggattgt ccgagctcga taaggccgga ttcatcaaga   4860
gacagctcgt cgaaacccgc caaattacca agcacgtggc ccaaattctg gattcccgca   4920
tgaacaccaa gtacgatgaa aatgacaagc tgatcgcga ggtcaaggtg atcaccttga   4980
agtccaagct ggtctccgac ttcgcaagg acttccagtt ctacaaggtg agggagatca   5040
acaactacca ccacgcacac gacgcctacc tcaacgctgt cgttggaacc gccctcatca   5100
aaaaatatcc taagctggag tctgatttcg tctacgcga ctacaaggtg tacgacgtga   5160
ggaagatgat cgctaagtct gagcaggaga tcggcaaggc caccgccaag tacttcttct   5220
actccaacat catgaacttc ttcaagaccg agatcactct cgccaacggt gagatcagga   5280
agcgcccact gatcgagacc aacggtgaga ctggagagat cgtgtgggac aaagggaggg   5340
atttcgctac tgtgaggaag gtgctctcca tgcctcaggt gaacatcgtc aagaagaccg   5400
aagttcagac cggaggattc tccaaggagt ccatcctcca agagaaaact tccgacaagg   5460
tgatcgctag aaagaaagac tgggaccta agaagtacgg aggcttcgat tctcctaccg   5520
tggcctactc tgtgctggtc gtggccaagg tggagaaggg caagtccaag aagctgaaat   5580
ccgtcaagga gctcctcggg attaccatca tggagaggag ttccttcgag aagaaccta   5640
tcgactttcct ggaggccaag ggatataaag aggtgaagaa ggacctcatc atcaagctgc   5700
ccaagtactc cctcttcgag ttggaaacg gaaggaagg gatgctggct tctgccggag   5760
agttgcagaa gggaaatgag ctcgccctcc cctccaagta cgtgaacttc ctgtacctcg   5820
cctctcacta tgaaaagttg aagggctctc ctgaggacaa cgagcagaag cagctcttcg   5880
tggagcagca caagcactac ctggacgaaa ttatcgagca gatctctgag ttctccaagc   5940
gcgtgatatt ggccgacgcc aacctcgaca aggtgctgtc cgcctacaac aagcacaggg   6000
ataagccat tcgcgagcag gctgaaaaca ttatcaccct gtttacctc acaaacttgg   6060
gagccctgc tgccttcaag tacttcgaca ccaccattga caggaagaga tacacctcca   6120
ccaaggaggt gctcgacgca acactcatcc accaatccat caccggcctc tatgaaacaa   6180
ggattgactt gtcccagctg ggaggcgact ctagagccga tcccaagaag aagagaaagg   6240
tgtaggttaa cctagacttg tccatcttct ggattggcca acttaattaa tgtatgaaat   6300
aaaaggatgc acacatagtg acatgctaat cactataatg tgggcatcaa agttgtgtgt   6360
```

```
tatgtgtaat tactagttat ctgaataaaa gagaaagaga tcatccatat ttcttatcct   6420
aaatgaatgt cacgtgtctt tataattctt tgatgaacca gatgcatttc attaaccaaa   6480
tccatataca tataaatatt aatcatatat aattaatatc aattgggtta gcaaaacaaa   6540
tctagtctag gtgtgttttg cgaattcgat atcaagctta tcgataccgt cgaggggggg   6600
cccggtaccg g                                                        6611
```

| | | |
|---|---|---|
| SEQ ID NO: 299 | moltype = DNA length = 5686 | |
| FEATURE | Location/Qualifiers | |
| misc_feature | 1..5686 | |
| | note = synthesized sequence- DD20HR1-SAMS:HPT-DD20HR2 | |
| source | 1..5686 | |
| | mol_type = other DNA | |
| | organism = synthetic construct | |

SEQUENCE: 299

```
cgcgcctcta gttgaagaca cgttcatgtc ttcatcgtaa gaagacactc agtagtcttc   60
ggccagaatg gccatctgga ttcagcaggc ctagaaggcc atttaaatcc tgaggatctg   120
gtcttcctaa ggacccggga tatcgctatc aactttgtat agaaaagttg ggccgaattc   180
gagctcggta cggccagaat ccggtaagtg actagggtca cgtgacccta gtcacttaaa   240
ttcggccaga atggccatct ggattcagca ggcctagaag gcccggaccg attaaacttt   300
aattcggtcc gggttacctc gagcctagta ataattacac atctaagata tcccctttctt  360
tttcaagtaa aataatatca tatgatctca tttttagtgaa acaatactat ttccctgata   420
actctcttca acattaggga cttcatctaa tcatctactt tcaaggtata actagacgta   480
tttgttcttt taaaaaaaac actagatgta ctcgtcaact caaaattcat cgttcatgca   540
ttttaattaa actttaatta gctaatgagt agaaaaagat catacgagta aaatagaaga   600
atcttcctag attttggaag aatggattgg agtgtaagtg aattgatcca ttagtggaag   660
atgctctttta caatggccaa acttgttctaa ttgttagagc acatttgaga tgaaacactt   720
cagtagtgga ggtaacctac aatcctagga tctgtatcct ctatcactaa tggagcaatg   780
ggtttgagat tgacttactc cttccttgt ctctcgtagt gcatatgcgc actttcaaag   840
gctacacaaa agccgttaac ttttgttta tttaagttac gaaagatagt tgaattagag   900
taaatggtga tattgaatta ggattttaaa taattttaaa agaatttttt taataaaaaa   960
aatattgtgt tgttggatca aaattttta ataacatgaa taaggaaatg gattgcaatg   1020
aggttttaaa caattatttt aacatatagg atttttagaaa gacttttata atattttgtt   1080
gaagtttaga ttttaatata tttatgtttt aaaatttaa aaaaaacttc atgaatttat   1140
aatatttgaa aaagcacgt gaatatttag aaaaacattta aaaatacaat aataaatcat   1200
aatgagatag ggtgtattca tgtgtagacg agacaccaag tatatggttc acaagtgaat   1260
catctttttt ttttacagca caagtagatc acttgtactt atcaaaattc ggaactgaca   1320
cacactagtg gtcacctaag tgactagggt cacgtgaccc tagtcactta ttcccaaaca   1380
ctagtaacgg ccgccagtgt gctggaattc gcccttccca agcttgctc tagatcaaac   1440
tcacatccaa acataacatg gatatcttcc ttaccaatca tactaattat tttgggttaa   1500
atattaatca ttatttttaa gatattaatt aagaaattaa aagatttttt aaaaaaatgt   1560
ataaaattat attattcatg atttttcata catttgattt tgataataaa tatatttttt   1620
ttaatttctt aaaaaatgtt gcaagacact tattagacat agtcttgttc tgtttacaaa   1680
agcattcatc atttaatca ttaaaaaata tttaatacta acagtagaat ttcttgtga   1740
gtggtgtggg agtaggcaac ctggcattga aacgagagaa agagagtcag aaccagaaga   1800
caaataaaaa gtatgcaaca aacaaatcaa aatcaaaggg caaaggctgg ggttggctca   1860
attggttgct acattcaatt tcaactcag tcaacggttg agattcactc tgacttcccc   1920
aatctaagcc gcggatgcaa acggttgaat ctaacccaca atccaatctc gttacttagg   1980
ggcttttccg tcattaactc acccctgcca cccggtttcc ctataaattg gaactcaatg   2040
ctccctctca aactcgtatc gcttcagagt tgagaccaag acacactcgt tcatatatct   2100
ctctgctctt ctcttctctt ctacctctca aggtactttt cttctccctc taccaaatcc   2160
tagattccgt ggttccaattt cggatcttgc acttctggtt tgctttgcct tgctttttcc   2220
tcaactgggt ccatctagga tccatgtgaa actctactct ttctttaata tctgcggaat   2280
acgcgtttga ctttcagatc tagtcgaaat catttcataa ttgcctttct ttcttttagc   2340
ttatgagaaa taaaatcact tttttttttat ttcaaaataa accttgggcc ttgtgctgac   2400
tgagatgggg tttggtgatt acagaatttt agcgaatttt gtaattgtac ttgtttgtct   2460
gtagttttgt tttgtttct tgtttctcat acattcctta ggcttcaatt ttattcgagt   2520
ataggtcaca ataggaattc aaactttgag caggggaatt aatccccttcc ttcaaatcca   2580
gtttgtttgt atatatgttt aaaaaatgaa actttttgctt taaattctat tataacttt   2640
tttatggctg aaattttgc atgtgtcttt gctctctgtt gtaaatttac tgtttaggta   2700
ctaactctag gcttgttgtg cagttttga agtataacaa cagaagttcc tattccgaag   2760
ttcctattct ctagaaagta taggaacttc cactagtcca tgaaaaagcc tgaactcacc   2820
gcgacgtctg tcgagaagtt tctgatcgaa agttcgaca gcgtctccga cctgatgcag   2880
ctctcggagg gcgaagaatc tcgtgctttc agcttcgatg taggagggcg tggatatgtc   2940
ctgcgggtaa atagctgcgc cgatggtttc tacaaagatc gttatgttta tcggcacttt   3000
gcatcggccg cgctcccgat tccggaagtg cttgacattg ggaattcag cgagagcctg   3060
acctattgca tctcccgccg tgcacagggt gtcacgttgc aagacctgcc tgaaaccgaa   3120
ctgcccgctg ttctgcagcc ggtcgcggag gccatggatg cgatcgctgc ggccgatctt   3180
agccagacga gcgggttcgg cccattcgga ccgcaaggaa tcggtcgaata cactacatgg   3240
cgtgatttca tatgcgcgat tgctgatccc catgtgtatc acctcggcaaac tgtgatggc   3300
gacaccgtca gtgcgtccgt cgcgcaggct ctcgatgagc tgatgctttg gccgaggac   3360
tgcccccgaag tccggcacct cgtgcacgcg gatttcggct ccaacaatgt cctgacggac   3420
aatgccgcga taacagcggt cattgactgg agcgaggcga tgttcgggga ttcccaatac   3480
gaggtcgcca acatcttctt ctggaggccg tggttggctt gtatggagca gcagacgcgc   3540
tacttcgagc ggaggcatcc ggagcttgca ggatcgccgc ggctccgggc gtatctgctc   3600
cgcattggtc ttgaccaact ctatcagagc ttggttgacg gcaatttcga tgatgcagct   3660
tgggcgcagg gtcgatgcga cgcaatcgtc cgatccggag ccgggactgt cgggcgtaca   3720
caaatcgccc gcagaagcgc ggccgtctgg accgatggct gtgtagaagt actcgccgat   3780
agtggaaacc gacgccccag cactcgtccg agggcaaagg aatagtgagg tacctaaaga   3840
aggagtgcgt cgaagcagat cgttcaaaca tttggcaata aagtttctta agattgaatc   3900
```

```
ctgttgccgg tcttgcgatg attatcatat aatttctgtt gaattacgtt aagcatgtaa    3960
taattaacat gtaatgcatg acgttattta tgagatgggt ttttatgatt agagtcccgc    4020
aattatacat ttaatacgcg atagaaaaca aaatatagcg cgcaaactag gataaattat    4080
cgcgcgcggt gtcatctatg ttactagatc gatgtcgacc cgggcccctag gaggccggcc   4140
cagctgatga tcccggtgaa gttcctattc cgaagttcct attctccaga aagtatagga    4200
acttcactag agcttgcggc cgcgcatgct gacttaatca gctaacgcca ctcgacctgc    4260
aggcatgccc gcggatatcg atgggccccg gccgaagctt caagtttgta caaaaaagca    4320
ggctggcgcc ggaaccaatt cagtcgactg gatccggtac cgaattgcgc gccgcactcg    4380
agatatctag acccagcttt cttgtacaaa gtggccgtta acggatcggc cagaatccgg    4440
taagtgacta gggtcacgtg accctagtca cttaaattcg gccagaatgg ccatctggat    4500
tcagcaggcc tagaaggccc ggaccgatta aactttaatt cggtccgggt tacctctaga    4560
aagcttgtcg acctgcagac acgacatgat ggaacgtgac taaggtgggt ttttgacttt    4620
gcatgtcgaa gtgagagtga tttttattgag agaaataatag aagacctaca aacaaaatga   4680
tcccgacgct aaagtaagta cgagagttaa gagaataaat gggaaaatat gcatacatga    4740
ttaggtgtgt gttcgtctca agaaagtacg aatgaatatg gtgtgtttgt agtacatgaa    4800
tgatgtgttt tgagggttca agggaaattg atatttatg agtgaaatgg aaccagaggt     4860
ctttgttgac aaggggttgtt atgactcttg caaataatta atagcttata aataatagcc    4920
aataacttat tatagataga gttagaata atatatagct aaatttgaac aaggcataca     4980
aaacaaaaat gctaaatatg aataagacaa tcaaaattgt agtcgatgtt caactctttg    5040
tcgttgaaga acttgtttgc agtggtatag taaatgggtg tgagtgcagt gtctcaccca    5100
tctcacacca cacaaccaac ttcatatcta aagatattgt cgctgaatac aaaattgagt    5160
tatggaatat acaattcata atatagatac gaaaaatcat ttcttacaaa acattcaatc    5220
aaaaattatt caaacataat tctagattaa gtaatccgaa gtacaagtta gtatcctaga    5280
tccgttaatt taaaattatg tttgcataat ttggatttg gtgttctata agggcacaat     5340
tttgttcatt cttacaagtt tgtcaattct aaaatatatg caaatttgaa gaaaaaaaat    5400
ttacgaatgt gtctcaaaca ataacttaat gggaggaaga tagggggatga agaagctcaa   5460
aattaccaac gccttctacc tcaagaagct acttcacaca aaatatgact ggcggaagga    5520
taggggacaa ccgataacga gaaggagata cataaggtaa tgtacgttgt tgtgtgaggg    5580
atccggtcac ctaagtgact agggtcacgt gaccctagtc acttattccc gggcaacttt    5640
attatacaaa gttgatagat ctcgaattca ttccgattaa tcgtgg                   5686
```

```
SEQ ID NO: 300           moltype = DNA   length = 6611
FEATURE                  Location/Qualifiers
misc_feature             1..6611
                         note = synthesized sequence- U6-9.1-DD20CR2+EF1A2-CAS9
source                   1..6611
                         mol_type = other DNA
                         organism = synthetic construct
SEQUENCE: 300
cgcgccggta cccgggttaa gagaattgta agtgtgcttt tatatattta aaattaatat      60
attttgaaat gttaaaatat aaaagaaaat tcaatgtaaa ttaaaaataa ataaatgttt    120
aataagata  aattttaaaa cataaaagaa aatgtctaac aagaggatta agatcctgtg   180
ctcttaaatt tttaggtgtt gaaatcttag ccatacaaaa taattttat  taaaaccaag    240
catgaaaaaa gtcactaaag agctatataa ctcatgcagc tagaaatgaa gtgaagggaa    300
tccagtttgt tctcagtcga aagagtgtct atctttgttc ttttctgcaa ccgagttaag    360
caaaatggga atgcgaggta tcttcctttc gttaggggag caccagatgc atagttagtc    420
ccacattgga gaatataaca agagcttcac agaatatata gcccaggcca cagtaaaagc    480
ttgacatgat ggaacgtgac tagttttaga gctagaaata gcaagttaaa ataaggctag    540
tccgttatca acttgaaaaa gtggcaccga gtcggtgctt ttttgcgg ccgcaattgg      600
atcgggttta cttatttgt gggtatctat acttttatta gattttaat caggctcctg      660
atttcttttt atttcgattg aattcctgaa cttgtattat tcagtagatc gaataaatta    720
taaaagata  aaatcataaa ataatatttt atcctatcaa tcatattaaa gcaatgaata    780
tgtaaaatta atcttatctt tatttttaaaa aatcatatag gttagtatt tttttaaaaa   840
taaagatagg attagtttta ctattcactg cttattactt ttaaaaaat cataaggtt     900
tagtattttt ttaaaataaa tataggaata gttttactat tcactgcttt aatagaaaaa    960
tagtttaaaa tttaagatag ttttaatccc agcatttgcc acgtttgaac gtgagccgaa   1020
acgatgtcgt tacattatct taacctagct gaaacgatgt cgtcataata tcgccaaatg   1080
ccaactggac tacgtcgaac ccacaaatcc cacaaagcgc gtgaaatcaa atcgctcaaa    1140
ccacaaaaaa gaacaacgcg tttgttacac gctcaatccc acgcgagtag agcacagtaa    1200
ccttcaaata agcgaatggg gcataatcag aaatccgaaa taaacctagg ggcattatcg    1260
gaaatgaaaa gtagctcact caatatcaaa atctaggaac cctagttttc gttatcactc    1320
tgtgctccct cgctctattt ctcagtctct gtgtttgcgg ctgaggattc cgaacgagtg    1380
accttcttcg tttctcgcaa aggtaacagc ctctgctctt gtctcttcga ttcgatctat    1440
gcctgtctct tatttacgat gatgttctctt cggttatgtc ttttattta tgcttttatga   1500
tgttgatgtt cggttgtttg tttcgctttg tttttgtggt tcagtttttt aggattcttt    1560
tggttttga atcgattaat cggaagagat tttcgagtta tttggtgtgt tggaggtgaa    1620
tctttttttt gaggtcatag atctgttgta tttgtgttat aaacatgcga ctttgtatga    1680
tttttacga ggttatgatg ttctggttgt tttattatga atctgttgag acagaaccat     1740
gattttgtt gatgttcgtt tacactatta aaggttttgt ttaacaggat taaaagtttt    1800
ttaagcatgt tgaaggagtc ttgtagatat gtaaccgtcg atagtttttt tgtgggtttg    1860
ttcacatgtt atcaagctta atctttact atgtatgcga ccatatctgg atccagcaaa    1920
ggcgattttt taattccttg tgaaactttt gtaatatgaa gttgaatttt tgttattggt    1980
aaactataaa tgtgtgaagt tggagtatac ctttaccttc ttatttggct ttgtgatagt    2040
ttaatttata tgtatttttga gttctgactt gtatttcttt tgattgatc tagtttaagt    2100
aatccatgaa caaaagtac tcaatagggc tcgacatagg gactaactcc gttggatggg    2160
ccgtcatcac cgacgagtac aaggtgccct ccaagaagtt caaggtgttg ggaaacaccg    2220
acaggcacag cataaagaag aatttgatcg gtgccctcct cttcgactcc ggagagaccg    2280
ctgaggctac caggctcaag aggaccgcta gaaggcgcta caccagaagg aagaacgaga    2340
tctgctacct gcaggagatc ttctccaacg agatggccaa ggtggacgac tccttcttcc    2400
```

```
accgccttga ggaatcattc ctggtggagg aggataaaaa gcacgagaga cacccaatct  2460
tcgggaacat cgtcgacgag gtggcctacc atgaaaagta ccctaccatc taccacctga  2520
ggaagaagct ggtcgactct accgacaagg ctgacttgcg cttgatttac ctggctctcg  2580
ctcacatgat aaagttccgc ggacacttcc tcattgaggg agacctgaac ccagacaact  2640
ccgacgtgga caagctcttc atccgactcg ttcagaccta caaccagctt ttcgaggaga  2700
acccaatcaa cgccagtgga gttgacgcca aggctatcct ctctgctcgt ctgtcaaagt  2760
ccaggaggct tgagaacttg attgcccagc tgcctggcga aaagaagaac ggactgttcg  2820
gaaacttgat cgctctctcc ctgggattga ctcccaactt caagtccaac ttcgacctcg  2880
ccgaggacgc taagttgcag ttgtctaaag acacctacga cgatgacctc gacaacttgc  2940
tggcccagat aggcgaccaa tacgccgatc tcttcctcgc cgctaagaac ttgtccgacg  3000
caatcctgct gtccgacatc ctgagagtca cactgagat taccaaagct cctctgtctg  3060
cttccatgat taagcgctac gacgagcacc accaagatct gaccctgctc aaggccctgg  3120
tgagacagca gctgcccgag aagtacaagg agatcttttt cgaccagtcc aagaacggct  3180
acgccggata cattgacgga ggcgcctccc aggaagagtt ctacaagttc atcaagccca  3240
tccttgagaa gatggacggt accgaggagc tgttggtgga gttgaacaga gaggacctgt  3300
tgaggaagca gagaaccttc gacaacggaa gcatccctca ccaaatccac ctgggagagc  3360
tccacgccat cttgaggagg caggaggatt tctatccctt cctgaaggac aaccgcgaga  3420
agattgagaa gatcttgacc ttcagaattc cttactacgt cgggccactc gccagaggaa  3480
actctaggtt cgcctggatg acccgcaaat ctgaagagac cattactccc tggaacttcg  3540
aggaagtcgt ggacaagggc gcttccgctc agtctttcat cgagaggatg accaacttcg  3600
ataaaaatct gcccaacgag aaggtgctgc ccaagcactc cctgttgtac gagtatttca  3660
cagtgtacaa cgagctcacc aaggtgaagt acgtcacaga gggaatgagg aagcctgcct  3720
tcttgtccgg agagcagaag aaggccatcg tcgacctgct cttcaagacc aacaggaagg  3780
tgactgtcaa gcagctgaag gaggactact tcaagaagat cgagtgcttc gactccgtcg  3840
agatctctgg tgtcgaggac aggttcaacg cctcccttgg gacttaccac gatctgctca  3900
agattattaa agacaaggac ttcctggaca acgaggagaa cgaggacatc cttgaggaca  3960
tcgtgctcac cctgaccttg ttcgaagaca gggaaatgat cgaagagagg ctcaagacct  4020
acgcccacct cttcgacgac aaggtgatga acagctgaa gagacgcaga tataccggct  4080
ggggaaggct ctcccgcaaa ttgatcaacg ggatcaggga caagcagtca gggaagacta  4140
tactcgactt cctgaagtcc gacggattcg ccaacagaaa cttcatgcag ctcattcacg  4200
acgactcctt gaccttcaag gaggacatcc agaaggctca ggtgtctgga cagggtgact  4260
ccttgcatga gcacattgct aacttggccg gctctcccgc tattaagaag ggcattttgc  4320
agaccgtgaa ggtcgttgac gagctcgtga aggtgatggg acgccacaag ccagagaaca  4380
tcgttattga gatggctcgc gagaaccaaa ctacccagaa agggcagaag aattcccgcg  4440
agaggatgaa gcgcattgag gagggcataa aagagcttgg ctctcagatc ctcaaggagc  4500
accccgtcga gaacactcag ctgcagaacg agagctgta cctgtactac ctccaaaacg  4560
gaagggacat gtacgtggac caggagctgg acatcaacag gttgtccgac tacgacgtcg  4620
accacatcgt gcctcagtcc ttcctgaagg atgactccat cgacaataaa gtgctgacac  4680
gctccgataa aaatagaggc aagtccgaca acgtccccctc cgaggaggtc gtgaagaaga  4740
tgaaaaacta ctggagacag ctcttgaacg ccaagctcat cacccagcgt aagttcgaca  4800
acctgactaa ggctgagaga ggaggattgt ccgagtcga taaggccgga ttcatcaaga  4860
gacagctcgt cgaaacccgc caaattacca agcacgtggc ccaaattctg gattcccgca  4920
tgaacaccaa gtacgatgaa aatgacaagc tgatccgcga ggtcaaggtg atcaccttga  4980
agtccaagct ggtctccgac ttccgcaagg acttccagtt ctacaaggtg agggagatca  5040
acaactacca ccacgcacac gacgcctacc tcaacgctgt cgttggaacc gccctcatca  5100
aaaaatatcc taagctggag tctgagttcg tctacgcgca ctacaaggtg tacgacgtga  5160
ggaagatgat cgctaagtct gagcaggaga tcggcaaggc caccgccaag tacttcttct  5220
actccaacat catgaacttc ttcaagaccg agatcactct cgccaacggt gagatcagga  5280
agcgccact gatcgagacc aacggtgaga ctggagagat cgtgtgggac aaagggaggg  5340
atttcgctac tgtgaggaag gtgctctcca tgcctcaggt gaacatcgtc aagaagaccg  5400
aagttcagac cggaggattc tccaaggagt ccatctccc caagagaaac tccgacaagc  5460
tgatcgctag aaagaaagac tgggacccta agaagtacgg aggcttcgat tctcctaccg  5520
tggcctactc tgtgctggtc gtggccaagg tggagaaggg caagtccaag aagctgaaat  5580
ccgtcaagga gctcctcggg attaccatca tggagaggag ttccttcgag aagaacccta  5640
tcgacttcct ggaggccaaa ggatataaag aggtgaagaa ggacctcatc atcaagctgc  5700
ccaagtactc cctcttcgag ttggagaacg gaaggaagag gatgctggct tctgccggaa  5760
agttgcagaa gggaaatgag ctcgcccttc cctccaagta cgtgaacttc ctgtacctcg  5820
cctctcacta tgaaaagttg aagggctctc ctgaggacaa cgagcagaag cagctcttcg  5880
tggagcagca caagcactac ctggacgaaa ttatcgagca gatctctgag ttctccaagc  5940
gcgtgatatt ggccgacgcc aacctcgaca aggtgctgtc cgcctacaac aagcacaggg  6000
ataagcccat tcgcgagcag gctgaaaaca ttatccacct gtttaccctc acaaacttgg  6060
gagcccctgc tgccttcaag tacttcgaca ccaccattga caggaagaga tacacctcca  6120
ccaaggaggt gctcgacgca acactcatcc accaatccat caccggcctc tatgaaacaa  6180
ggattacttt gtcccagctg ggaggcgact ctagaccgaa aagagaaagg tgtaggttaa  6240
cctagacttg tccatcttct ggattggcca acttaattaa tgtatgaaat  6300
aaaaggatgc acacatagtg acatgctaat cactataatg tgggcatcaa agttgtgtgt  6360
tatgtgtaat tactagttat ctgaataaaa gagaaagaga tcatccatat ttcttatcct  6420
aaatgaatgt cacgtgtctt tataattctt tgatgaacca gatgcatttc attaaccaaa  6480
tccatataca tataaatatt aatcatatat aattaatatc aattgggtta gcaaaacaaa  6540
tctagtctag gtgtgttttg cgaattcgat atcaagctta tcgataccgt cgaggggggg  6600
cccggtaccg g                                                         6611

SEQ ID NO: 301       moltype = DNA  length = 6611
FEATURE              Location/Qualifiers
misc_feature         1..6611
                     note = synthesized sequence- U6-9.1:DD43CR1+EF1A2:CAS9
source               1..6611
                     mol_type = other DNA
                     organism = synthetic construct
```

```
SEQUENCE: 301
cgcgccggta cccgggttaa gagaattgta agtgtgcttt tatatattta aaattaatat   60
attttgaaat gttaaaatat aaaagaaaat tcaatgtaaa ttaaaaataa ataaatgttt  120
aataaagata aattttaaaa cataaaagaa aatgtctaac aagaggatta agatcctgtg  180
ctcttaaatt tttaggtgtt gaaatccttag ccatacaaaa tatattttat taaaaccaag  240
catgaaaaaa gtcactaaag agctatataa ctcatgcagc tagaaatgaa gtgaagggaa  300
tccagtttgt tctcagtcga aagagtgtct atctttgttc ttttctgcaa ccgagttaag  360
caaaatggga atgcgaggta tcttcctttc gttaggggag caccagatgc atagttagtc  420
ccacattgat gaatataaca agagcttcac agaatatata gcccaggcca cagtaaaagc  480
ttgtcccttg tacttgtacg tagttttaga gctagaaata gcaagttaaa ataaggctag  540
tccgttatca acttgaaaaa gtggcaccga gtcggtgctt ttttttgcgg ccgcaattgg  600
atcgggttta cttattttgt gggtatctat acttttatta gattttaat caggctcctg  660
atttctttt atttcgattg aattcctgaa cttgtattat tcagtagatc gaataaatta  720
taaaaagata aaatcataaa ataatatttt atcctatcaa tcatattaaa gcaatgaata  780
tgtaaaatta atcttatctt tattttaaaa aatcatatag gtttagtatt tttttaaaaa  840
taaagatagg attagttta ctattcactg cttattactt ttaaaaaaat cataaaggtt  900
tagtatttt ttaaaataaa tataggaata gttttactat tcactgcttt aatagaaaaa  960
tagtttaaaa tttaagatag ttttaatccc agcatttgcc acgtttgaac gtgagccgaa 1020
acgatgtcgt tacattatct taacctagct gaaacgatgt cgtcataata tcgccaaatg 1080
ccaactggac tacgtcgaac ccacaaatcc cacaaagcgc gtgaaatcaa atcgctcaaa 1140
ccacaaaaaa gaacaacgcg tttgttacac gctcaatccc acgcgagtag agcacagtaa 1200
ccttcaaata agcgaatggg gctaaatcag aaatccgaaa taaacctagg ggcattatcg 1260
gaaatgaaaa gtagctcact caatatataaa atctaggaac cctagttttc gttatcactc 1320
tgtgctccct cgctcatttt ctcagtctct gtgtttgcgg ctgaggattc cgaacgagtg 1380
accttcttcg tttctcgcaa aggtaacagc ctctgctctt gtctcttcga ttcgatctat 1440
gcctgtctct tatttacgat gatgtttctt cggttatgtt tttttattta tgctttatgc 1500
tgttgatgtt cggttgtttg tttcgctttg ttttttgtggt tcagtttttt aggattcttt 1560
tggttttttga atcgattaat cggaagagat tttcgagtta tttggtgtgt tggaggtgaa 1620
tctttttttt gaggtcatag atctgttgta tttgtgttat aaacatgcga ctttgtatga 1680
ttttttacga ggttatgatg ttctggttgt tttattatga atctgttgag acagaaccat 1740
gatttttgtt gatgttcgtt tacactatta aaggtttgtt ttaacaggat taaaagtttt 1800
ttaagcatgt tgaaggagtc ttgtagatat gtaaccgtcg atagttttt tgtgggtttg 1860
ttcacatgtt atcaagctta atcttttact atgtatgcga ccatatctgg atccagcaaa 1920
ggcgatttt taattccttg tgaaactttt gtaatatgaa gttgaaattt tgttattggt 1980
aaactataaa tgtgtgaagt tggagtatac ctttaccttc ttatttggct ttgtgatagt 2040
ttaatttata tgtattttga gttctgactt gtatttcttt gaattgattc tagtttaagt 2100
aatccatgga caaaaagtac tcaataggggc tcgacatagg gactaactcc gttggatggg 2160
ccgtcatcac cgacgagtac aaggtgccct ccaagaagtt caaggtgttg ggaaacaccg 2220
acaggcacag cataaagaag aatttgatcg gtgccctcct cttcgactcc ggagagccg 2280
ctgaggctac caggctcaag aggaccgcta gaaggcgcta caccagaagg aagaacagaa 2340
tctgctacct gcaggagatc ttctccaacg agatggccaa ggtggacgac tccttcttcc 2400
accgccttga ggaatcattc ctggtggagg aggataaaaa gcacgagaga cacccaatct 2460
tcgggaacat cgtcgacgag gtggcctacc atgaaaagta ccctaccatc taccacctga 2520
ggaagaagct ggtcgactct accgacaagg ctgacttgcg cttgatttac ctggctctcg 2580
ctcacatgat aaagttccgc ggacacttcc tcattgaggg agacctgaac ccagacaact 2640
ccgacgtgga caagctcttc atccagctcg ttcagaccta caaccagctt ttcgaggaga 2700
acccaatcaa cgccagtgga gttgacgcca aggctatcct ctctgctcgt ctgtcaaagt 2760
ccaggaggct tgagaacttg attgcccagc tgcctggcga aaagaagaac ggactgttcg 2820
gaaacttgat cgctctctcc ctgggattga ctcccaactt caagtccaac ttcgacctcg 2880
ccgaggacgc taagttgcag ttgtctaaag acacctacga cgatgacctc gacaacttgc 2940
tggcccagat aggcgaccaa tacgccgatc tcttcctcgc gctaagaac ttgtccgaca 3000
caatcctgct gtccgacatc ctgagagtca cactgagat taccaaagct cctctgtctg 3060
cttccatgat taagcgctac gacgagcacc accaagatct gaccctgctc aaggcccctgg 3120
tgagacagca gctgcccgag aagtacaagg agatctttt cgaccagtcc aagaacggct 3180
acgccggata cattgacgga ggcgcctccc aggaagagtt ctacaagttc atcaagccca 3240
tccttgagaa gatggacggt accgaggagc tgttggtgaa gttgaacaga gaggacctgt 3300
tgaggaagca gagaaccttc gacaacggaa gcatccctca ccaaatccac ctgggagagc 3360
tccacgccat cttgaggagg caggaggatt tctatccctt cctgaaggac aaccgcgaga 3420
agattgagaa gatcttgacc ttcagaattc cttactacgt cgggccactc gccagaggaa 3480
actctaggtt cgcctggatg acccgcaaat ctgaagagac cattactccc tggaacttcg 3540
aggaagtcgt ggacaagggc gcttccgctc agtctttcat cgagaggatg accaacttcg 3600
ataaaaatct gcccaacgag aaggtgctgc caagcactc cctgttgtac gagtatttca 3660
cagtgtacaa cgagctcacc aaggtgaagt acgtcacaga gggaatgagg aagcctgcct 3720
tcttgtccgg agagcagaag aaggccatcg tcgacctgct cttcaagacc aacaggaagg 3780
tgactgtcaa gcagctgaag gaggactact tcaagaagat cgagtgcttc gactccgtcg 3840
agatctctgg tgtcgaggac aggttcaacg cctcccttgg gacttaccac gatctgctca 3900
agattattaa agacaaggac ttcctggaca acgaggagaa cgaggacatc cttgaggaca 3960
tcgtgctcac cctgaccttg ttcgaagaca gggaaatgat cgaagagagg ctcaagacct 4020
acgcccacct cttcgacgac aaggtgatga aacagctgaa gagacgcaga tataccggct 4080
ggggaaggct ctcccgcaaa ttgatcaacg gatcaggga caagcagtca gggaagacta 4140
tactcgactt cctgaagtcc gacggattcg ccaacaggaa cttcatgcag ctcattcacg 4200
acgactcctt gaccttcaag gaggacatcc agaaggctca ggtgtctgga cagggtgact 4260
ccttgcatga gcacatttgct aacttggccg gctctcccgc tattaagaag gcatttttgc 4320
agaccgtgaa ggtcgttgac gagctcgtga aggtgatgag ccagagaaca 4380
tcgttattga gatggctcgc gagaaccaaa ctacccagaa agggcagaag aattcccgcg 4440
agaggatgaa gcgcattgag gagggcataa aagagcttgg ctctcagatc ctcaaggagc 4500
accccgtcga gaacactcag ctgcagaacg agaagctgta cctgtactac ctccaaaacg 4560
gaagggacat gtacgtggac caggagctgg acatcaacag gttgtccgac tacgacgtcg 4620
accacatcgt gcctcagtcc ttcctgaagg atgactccat cgacaataaa gtgctgacac 4680
```

```
gctccgataa aaatagaggc aagtccgaca acgtccccctc cgaggaggtc gtgaagaaga  4740
tgaaaaacta ctggagacag ctcttgaacg ccaagctcat cacccagcgt aagttcgaca  4800
acctgactaa ggctgagaga ggaggattgt ccgagctcga taaggccgga ttcatcaaga  4860
gacagctcgt cgaaacccgc caaattacca agcacgtggc ccaaattctg gattcccgca  4920
tgaacaccaa gtacgatgaa aatgacaagc tgatccgcga ggtcaaggtg atcaccttga  4980
agtccaagct ggtctccgac ttccgcaagg acttccagtt ctacaaggtg agggagatca  5040
acaactacca ccacgcacac gacgcctacc tcaacgctgt cgttggaacc gccctcatca  5100
aaaaatatcc taagctggag tctgagttcg tctacggcga ctacaaggtg tacgacgtga  5160
ggaagatgat cgctaagtct gagcaggaga tcggcaaggc caccgccaag tacttcttct  5220
actccaacat catgaacttc ttcaagaccg agatcactct cgccaacggt gagatcagga  5280
agcgcccact gatcgagacc aacggtgaga ctggagagat cgtgtgggac aaagggaggg  5340
atttcgctac tgtgaggaag gtgctctcca tgcctcaggt gaacatcgtc aagaagaccg  5400
aagttcgagac cggaggattc tccaaggagt ccatcctccc caagagaaac tccgacaagc  5460
tgatcgctag aaagaaagac tgggaccccta agaagtacgg aggcttcgat tctcctaccg  5520
tggcctactc tgtgctggtc gtggccaagg tggagaaggg caagtccaag aagctgaaat  5580
ccgtcaagga gctcctcggg attaccatca tggagaggag ttccttcgag aagaacccta  5640
tcgacttcct ggaggccaag ggatataaag aggtgaagaa ggacctcatc atcaagctgc  5700
ccaagtactc cctcttcgag ttggagaacg gaaggaagga gatgctggct tctgccggag  5760
agttgcagaa gggaaatgag ctcgcccttc cctccaagta cgtgaacttc ctgtacctcg  5820
cctctcacta tgaaaagttg aagggctctc ctgaggacaa cgagcagaag cagctcttcg  5880
tggagcagca caagcactac ctggacgaaa ttatcgagca gatctctgag ttctccaagc  5940
gcgtgatatt ggccgacgcc aacctcgaca aggtgctgtc cgcctacaac aagcacaggg  6000
ataagcccat tcgcgagcag gctgaaaaca ttatccacct gtttaccctc acaaacttgg  6060
gagcccctgc tgccttcaag tacttcgaca ccaccattga caggaagaga tacacctcca  6120
ccaaggaggt gctcgacgca acactcatcc accaatccat caccggcctc tatgaaacaa  6180
ggattgactt gtcccagctg ggaggcgact ctagagccga tcccaagaag aagagaaagg  6240
tgtaggttaa cctagacttg tccatcttct ggattggcca acttaattaa tgtatgaaat  6300
aaaaggatgc acacatagtg acatgctaat cactataatg tgggcatcaa agttgtgtgt  6360
tatgtgtaat tactagttat ctgaataaaa gagaaagaga tcatccatat ttcttatcct  6420
aaatgaatgt cacgtgtctt tataattctt tgatgaacca gatgcatttc attaaccaaa  6480
tccatataca tataaatatt aatcatatat aattaatatc aattgggtta gcaaaacaaa  6540
tctagtctag gtgtgttttg cgaattcgat atcaagctta tcgataccgt cgaggggggg  6600
cccggtaccg g                                                       6611

SEQ ID NO: 302       moltype = DNA   length = 5719
FEATURE              Location/Qualifiers
misc_feature         1..5719
                     note = synthesized sequence- DD43HR1-SAMS:HPT-DD43HR2
source               1..5719
                     mol_type = other DNA
                     organism = synthetic construct
SEQUENCE: 302
cgcgcctcta gttgaagaca cgttcatgtc ttcatcgtaa gaagacactc agtagtcttc   60
ggccagaatg gccatctgga ttcagcaggc ctagaaggcc atttaaatcc tgaggatctg  120
gtcttcctaa ggacccggga tatcgctatc aactttgtat agaaaagttg ggccgaattc  180
gagctcggta cggccagaat ccggtaagtg actaggtca cgtgacccta gtcacttaaa  240
ttcggccaga atggccatct ggattcagca ggcctagaag gcccggaccg attaaacttt  300
aattcggtcc gggttacctc gagatcttgt tcccctcctt ggtttggcat aaattgattt  360
tcatggctct tctcggtcga aactggagct aattcacccct tagtctctct taaaattctg  420
gctgtaagaa acaccacaga acacataaat tataaactaa ttataatttg aagagtaaaa  480
tatgttttta ctcttatgat ttaattagtg tagtttttaat ttctccttt ttttaaaaaa  540
ttttggtatt cataaatttc aatttttttaa aaataattgt tgttaccgt taatgataac  600
gggatatgtt atgttaccac taaatcggac aaaaaaaatt caaaactttt ataaggatta  660
aaattaacaa aaatattta aaaaaatcta acctcaataa agttaaattt ataagcacaa  720
aataactctt ttaagcctaa tttggcaaga cacaagcaag ctcacctgta gcattaatag  780
aaaggaagca aagcaagaga aaagcaacca gaaggaagcg tttgcttggt gacacagcca  840
tcttacttga atttatggta ttactgagaa acctgatct tgcttcaaaa tcttctagtt  900
accctctttt tataggcaga aagagaacta gctagttgcc aataggatat gaggacatgt  960
ggtgcaatgc actcactctt caaggacaag aaaaacaatg gctacaattg tggttcaaat 1020
caatgtctcc tgctctgtcc gcctgaaaa tgacacccctt ttgcttggaa aagaggatca 1080
aagctaagaa caggagtggc ttcattccct tcatgtaacc aaaacttttc gcattctgtc 1140
attcgtgaat cagcaaaatc tgcaaccaaa atatatggt gcctaaataa agaaataaa  1200
ataatttaga gttgcggact aaaataataa acaaagaaa tatattataa tctagaatta 1260
atttaggact aaaagaagag gcagactcca attcctcttt tctagaatac cctccgtacg 1320
tacactagtg gtcacctaag tgactagggt cacgtgaccc tagtcactta ttcccaaaca 1380
ctagtaacgg ccgccagtgt gctggaattc gcccttccca agctttgctc tagatcaaac 1440
tcacatccaa acataacatg gatatcttcc ttaccaatca tactaattat ttggggttaa 1500
atattaatca ttattttaa gatattaatt aagaaattaa aagattttt aaaaaaatgt 1560
ataaaattat attattcatg attttttcata catttgattt tgataataaa tatatttttt 1620
ttaatttctt aaaaaatgtt gcaagacact tattagacat agtcttgttc tgtttacaaa 1680
agcattcatc atttaataca ttaaaaaata tttaatacta acagtagaat cttcttgtga 1740
gtggtgtggg agtaggcaac ctggcattga acgagagaa agagagtcag aaccagaaga 1800
caaataaaaa gtatgcaaca aacaaatcaa aatcaaaggg caaggctggg gttggctca  1860
attgttgct acattcaatt ttcaactcag ttcaaggttg agattcactc tgacttccca 1920
aatctaagcc gcggatgcaa acggttgaat ctaacccaca atccaatctc gttacttagg 1980
ggcttttccg tcattaactc accccctgcca cccggtttcc ctataaattg gaactcaatg 2040
ctcccctcta aactcgtatc gcttcagagt tgagaccaag acacactcgt tcatatatct 2100
ctctgctctt ctcttctctt ctacctctca aggtacttt cttctccctc taccaaatcc 2160
tagattccgt ggttcaattt cggatcttgc acttctggtt tgctttgcct tgcttttcc  2220
```

```
tcaactgggt ccatctagga tccatgtgaa actctactct ttctttaata tctgcggaat  2280
acgcgtttga ctttcagatc tagtcgaaat catttcataa ttgcctttct ttcttttagc  2340
ttatgagaaa taaaatcact tttttttat ttcaaaataa accttgggcc ttgtgctgac  2400
tgagatgggg tttggtgatt acagaatttt agcgaatttt gtaattgtac ttgtttgtct  2460
gtagttttgt tttgttttct tgtttctcat acattcctta ggcttcaatt ttattcgagt  2520
ataggtcaca ataggaattc aaactttgag caggggaatt aatcccttcc ttcaaatcca  2580
gtttgtttgt atatatgttt aaaaaatgaa acttttgctt taaattctat tataactttt  2640
tttatgcgta aaattttgc atgtgtcttt gctctctgtt gtaaattac tgtttaggta    2700
ctaactctag gcttgttgtg cagttttga agtataacaa cagaagttcc tattccgaag   2760
ttcctattct ctagaaagta taggaacttc cactagtcca tgaaaaagcc tgaactcacc  2820
gcgacgtctg tcgagaagtt tctgatcgaa aagttcgaca gcgtctccga cctgatgcag  2880
ctctcggagg gcgaagaatc tcgtgctttc agcttgatg taggagggcg tggatatgtc   2940
ctgcgggtaa atagctgcgc cgatggtttc tacaaagatc gttatgttta tcggcacttt  3000
gcatcggccg cgctcccgat tccggaagtg cttgacattg gggaattcag cgagagcctg  3060
acctattgca tctcccgccg tgcacagggt gtcacgttgc aagacctgcc tgaaaccgaa  3120
ctgccccgtg ttctgcagcc ggtcgcggag gccatggatg cgatcgctgc ggccgatctt  3180
agccagacga gcgggttcgg cccattcgga ccgcaaggaa tcggtcaata cactacatgg  3240
cgtgatttca tatgcgcgat tgctgatccc catgtgtatc actggcaaac tgtgatggac  3300
gacaccgtca gtgcgtccgt cgcgcaggct ctcgatgagc tgatgctttg ggccgaggac  3360
tgccccgaag tccggcacct cgtgcacgcg gatttcggct ccaacaatgt cctgacggac  3420
aatggccgca taacagcggt cattgactgg agcgaggcga tgttcgggga ttcccaatac  3480
gaggtcgcca acatcttctt ctggaggccg tggttggctt gtatggagca gcagacgcgc  3540
tacttcgagc ggaggcatcc ggagcttgca ggatcgccgc ggctccgggc gtatatgctc  3600
cgcattggtc ttgaccaact ctatcagagc ttggttgacg gcaatttcga tgatgcagct  3660
tgggcgcagg gtcgatgcga cgcaatcgtc cgatccggag ccgggactgt cggcgtaca   3720
caaatcgccc gcagaagcgc ggccgtctgg accgatggct gtgtagaagt actcgccgat  3780
agtggaaacc gacgcccag cactcgtccg agggcaaagg aatagtgagg tacctaaaga   3840
aggagtgcgt cgaagcagat cgttcaaaca tttggcaata aagttcttta agattgaatc  3900
ctgttgccga tcttgcgatg attatcatat aatttctgtt gaattacgtt aagcatgtaa  3960
taattaacat gtaatgcatg acgttattta tgagatgggt tttatgatt agagtcccgc   4020
aattatacat ttaatacgcg ataaaaaca aaatatacg cgcaaactag gataaattat    4080
cgcgcgcggt gtcatctatg ttactagatc gatgtcgacc cgggcccctag gaggccggcc  4140
cagctgatga tcccggtgaa gttcctattc cgaagttcct attctccaga agtataggga  4200
acttcactag agcttgcggc cgcgcatgct gacttaatca gctaacgcca ctcgacctcg  4260
aggcatgccc gcggatatcg atgggccccg gccgaagctt caagtttgta caaaaaagca  4320
ggctggcgcc ggaaccaatt cagtcgactg gatccggtac cgaattgcg gccgcactcg   4380
agatatctag acccagcttt cttgtacaaa gtggccgtta acggatcggc cagaatccgg  4440
taagtgacta gggtcacgtg accctagtca cttaaattcg gccagaatgg ccatctggat  4500
tcagcaggtc tagaaggccc ggaccgatta aactttaatt cggtccggtt tacctctaga  4560
aagcttgtcg acctgcaggt acaagtacaa gggacttgtg agttgtaagg ctgtatttac  4620
aatagtgaaa agagaatcat ctgggtgatt gggtttttag tccccagtga cgaattaaag  4680
gtttgaattc ttagtatgtt tgggaatcaa ttaggaattt cgttttggac tttccaaagc  4740
aattattcac tttttcattc attaaatgtg actaaaaaat tttattct ccattggcca    4800
ggatgcatcg tttatataaa cataacctta gtgaaagcag tgttttcatg tgacagcggc   4860
agactatatc ttaaacaaaa ttacttgtaa agaaagatac cgttaggaaa aaatgaaaa   4920
gaaaattgaa gctatcactt gtttactttc ctaatatctt tcaagaatac aatgtggtga  4980
atttcaattt tccctacata tgtataccgt cagcctgacg caacttatga aacttctctt   5040
tctttcattt gatgtatata taagacaca ttatatataa agaaacttta tatatatctc   5100
catcatattt tagtacttgc tactatgtaa aattagctgt tggaagtatc tcaagaaaca  5160
tttaatttat tgaccaagc attaaccatt catctacatt tgagttctaa aataaatctt   5220
aaatgatgtg gaggaaggaa aattgttaat tatttccctc ttctccctaca tggatatacc  5280
tgaaacatgc aatggatgga ttagatttta acatttgcag cctgagaagt tcactgactt  5340
tcctccagct attttatgtg tgcccgccac catttatagc tcatgattgt agctgaactg  5400
caaaaactgc atcgattgca aactgaaatt gagaatctct tttcaacttt atatgctgat  5460
tgatgcatgc tgagcatgct atactagtac tcgaagttcc tatatgtaga ctttgttact  5520
gcctaatata ctttgtgttt gttctcaagt tcttatttta tttcatattt tttcctaaa   5580
aaggttaatg gctctataaa ggttgagtga cggatccggt cacctaagtg actagggtca   5640
cgtgacccta gtcacttatt cccgggcaac tttattatac aaagttgata gatctcgaat   5700
tcattccgat taatcgtgg                                                5719
SEQ ID NO: 303         moltype = DNA   length = 6611
FEATURE                Location/Qualifiers
misc_feature           1..6611
                       note = synthesized sequence- U6-9.1:DD43CR2+EF1A2:CAS9
source                 1..6611
                       mol_type = other DNA
                       organism = synthetic construct
SEQUENCE: 303
cgcgccggta cccggggttaa gagaattgta agtgtgcttt tatatattta aaattaatat   60
attttgaaat gttaaaatat aaaagaaaat tcaatgtaaa ttaaaaataa ataaatgttt  120
aataaagata aattttaaaa cataaaagaa aatgtctaac aagaggatta agatcctgtg  180
ctcttaaatt tttaggtgtt gaaatcttag ccatacaaaa tatatttat taaaaccaag    240
catgaaaaaa gtcactaaag agctatataa ctcatgcagc tagaaatgaa gtgaagggaa   300
tccagtttgt tctcagtcga aagagtgtct atcttttgtt ttctgcaa ccgagttaga    360
caaaatggga atgcgaggta tcttcctttc gttaggggag caccagatgc atagttagtc  420
ccacattgat gaatataaca agagcttcac agaatatata gcccaggcca cagtaaaagc  480
ttgtattcta gaaagagga atgttttaga gctagaaata gcaagttaaa ataaggctag   540
tccgttatca acttgaaaaa gtggaccga gtcggtgctt ttttttgcgg ccgcaattgg   600
atcgggttta cttatttgtg gggtatctat acttttatta gattttaat caggctcctg   660
```

```
atttcttttt atttcgattg aattcctgaa cttgtattat tcagtagatc gaataaatta   720
taaaaagata aaatcataaa ataatatttt atcctatcaa tcatattaaa gcaatgaata   780
tgtaaaatta atcttatctt tattttaaaa aatcatatag gtttagtatt tttttaaaaa   840
taaagatagg attagtttta ctattcactg cttattactt ttaaaaaaat cataaaggtt   900
tagtattttt ttaaaataaa tataggaata gtttactat tcactgcttt aatagaaaaa   960
tagtttaaaa tttaagatag ttttaatccc agcatttgcc acgtttgaac gtgagccgaa  1020
acgatgtcgt tacattatct taacctagct gaaacgatgt cgtcataata tcgccaaatg  1080
ccaactggac tacgtcgaac ccacaaatcc cacaaagcgc gtgaaatcaa atcgctcaaa  1140
ccacaaaaaa gaacaacgcg tttgttacac gctcaatccc acgcgagtag agcacagtaa  1200
ccttcaaata agcgaatggg gcataatcag aaatccgaaa taaacctagg ggcattatcg  1260
gaaatgaaaa gtagctcact caatataaaa atctaggaac cctagttttc gttatcactc  1320
tgtgctccct cgctctattt ctcagtctct gtgtttgcgg ctgaggattc cgaacgagtg  1380
accttcttcg tttctcgcaa aggtaacagc ctctgctctt gtctcttcga ttcgatctat  1440
gcctgtctct tatttacgat gatgtttctt cggttatgct tttttattta tgctttatgc  1500
tgttgatgtt cggttgtttg tttcgctttg tttttgtggt tcagtttttt aggattcttt  1560
tggttttga atcgattaat cggaagagat tttcgagtta tttggtgtgt tggaggtgaa  1620
tctttttttt gaggtcatag atctgttgta tttgtgttat aaacatgcga ctttgtatga  1680
ttttttacga ggttatgatg ttctggttgt tttattatga atctgttgag acagaaccat  1740
gattttttgtt gatgttcgtt tacactatta aaggtttgtt ttaacaggat taaaagtttt  1800
ttaagcatgt tgaaggagtc ttgtagatat gtaaccgtcg atagtttttt tgtgggtttg  1860
ttcacatgtt atcaagctta atcttttact atgtatgcga ccatatctgg atccagcaaa  1920
ggcgattttt taattccttg tgaaacttttt gtaatatgaa gttgaaattt tgttattggt  1980
aaactataaa tgtgtgaagt tggagtatac ctttaccttc ttatttggct ttgtgatagt  2040
ttaatttata tgtattttga gttctgactt gtatttcttt gaattgattc tagtttaagt  2100
aatccatgga caaaaagtac tcaataggc tcgacatagg gactaactcc gttggatggg  2160
ccgtcatcac cgacgagtca aaggtgccct ccaagaagtt caaggtgttg ggaaacaccg  2220
acaggcacag cataaagaag aatttgatcg gtgcccctcct cttcgactcc ggagagaccg  2280
ctgaggctac caggctcaag aggaccgcta gaaggcgcta caccagaagg aagaacagaa  2340
tctgctacct gcaggagatc ttctccaacg agatggccaa ggtggacgac tccttcttcc  2400
accgccttga ggaatcattc ctggtggagg aggataaaaa gcacgagaga cacccaatct  2460
tcgggaacat cgtcgacgag gtggcctacc atgaaaagta ccctaccatc taccacctga  2520
ggaagaagct ggtcgactct accgacaagg ctgacttgcg cttgatttac ctggctctcg  2580
ctcacatgat aaagttccgc ggacacttcc tcattgaggg agacctgaac ccagacaact  2640
ccgacgtgga caagctcttc atccagctcg ttcagaccta caaccagctt ttcgaggaga  2700
acccaatcaa cgccagtgga gttgacgcca aggctatcct ctctgctcgt ctgtcaaagt  2760
ccaggaggct tgagaacttg attgcccagc tgcctggcga aaagaagaac ggactgttcg  2820
gaaacttgat cgctctctcc ctgggattga ctcccaactt caagtccaac ttcgacctcg  2880
ccgaggacgc taagttgcag ttgtctaaag acacctacga cgatgacctc gacaacttgc  2940
tggcccagat aggcgaccaa tacgccgatc tcttcctcgc cgctaagaac ttgtccgacg  3000
caatcctgct gtccgacatc ctgagagtca cactgagat taccaaagct cctctgtctg  3060
cttccatgat taagcgctac gacgagcacc accaagatct gaccctgctc aaggccctgg  3120
tgagacagca gctgccgag aagtacaagg agatcttttt cgaccagtcc aagaacggct  3180
acgccggata cattgacgga ggcgcctccc aggaagagt ctacaagttc atcaagccga  3240
tccttgagaa gatggacggt accgaggagc tgttggtgaa gttgaacaga gaggacctgt  3300
tgaggaagca gagaaccttc gacaacggaa gcatccctca ccaaatccac ctgggagagc  3360
tccacgccat cttgaggagg caggaggatt tctatcccct cctgaaggac aaccgcgaga  3420
agattagaaa gatcttgacc ttcagaattc cttactacgt cgggccactc gccagaggaa  3480
actctaggtt cgcctggatg acccgcaaat ctgaagagac cattactccc tggaacttcg  3540
aggaagtcgt ggacaagggc gcttccgctc agtctttcat cgagaggatg accaacttcg  3600
ataaaaatct gcccaacgag aaggtgctgc ccaagcactc cctgttgtac gagtatttca  3660
cagtgtacaa cgagctcacc aaggtgaagt acgtcacaga gggaatgagg aagcctgctt  3720
tcttgtccgg agagcagaag aaggccatcg tcgacctgct cttcaagacc aacaggaagg  3780
tgactgtcaa gcagctgaag gaggactact tcaagaagat cgagtgcttc gactccgtcg  3840
agatctctgt tgtcgaggac aggttcaacg cctcccttgg gacttaccac gatctgctca  3900
agattattaa agacaaggac ttcctggaca acgaggagaa cgaggacatc cttgaggaca  3960
tcgtgctcac cctgaccttg ttcgaagaca gggaaatgat cgaagagagg ctcaagacct  4020
acgcccacct cttcgacgac aaggtgatga acagctgaaa gagacgcaga tataccggct  4080
ggggaaggct ctcccgcaaa ttgatcaacg ggatcaggga caagcagtca gggaagacta  4140
tactcgactt cctgaagtcc gacggattcg ccaacaggaa cttcatgcag ctcattcacg  4200
acgactcctt gaccttcaag gaggacatcc agaaggctca ggtgtctgga cagggtgact  4260
ccttgcatga gcacattgct aacttggccg gctctcccgc tattaagaag ggcattttgc  4320
agaccgtgaa ggtcgttgac gagctcgtga aggtgatggg acgccacaag ccagagaaca  4380
tcgttattga gatggctcgc gagaaccaaa ctacccagaa agggcagaag aattcccgcg  4440
agaggataga gcgcattgag gagggcataa aagagctttgg ctctcagatc ctcaaggagc  4500
accccgtcga gaacactcag ctgcagaacg agaagctgta cctgtactac ctccaaaacg  4560
gaagggacat gtacgtggac caggagctgg acatcaacag gttgtccgac tacgacgtcg  4620
accacatcgt gcctcagtcc ttcctgaagg atgactccat cgacaataaa gtgctgacac  4680
gctccgataa aaatagaggc aagtccgaca acgtcccctc cgaggaggtc gtgaagaaga  4740
tgaaaaacta ctggagacag ctcttgaacg ccaagctcat cacccagctc aagttcgaca  4800
acctgactaa ggctgagaga ggaggattgt ccgagctcga taaggccgga ttcatcaaga  4860
gacagctcgt cgaaacccgc caaattacca agcacgtggc ccaaattctg gattcccgca  4920
tgaacaccaa gtacgatgaa aatgacaagc tgatccgcga ggtcaaggtg atcaccttga  4980
agtccaagct ggtctccgac ttccgcaagg acttccagtt ctacaaggtg agggagatca  5040
acaactacca ccacgcacac gacgcctacc tcaacgctgt cgttgaaacc gcccttcatca  5100
aaaaatatcc taagctggag tctgagttcg tctacgcgca ctacaaggtg tacgacgtga  5160
ggaagatgat cgctaagtct gagcaggaga tcggcaaggc caccgccaag tacttcttct  5220
actccaaacat catgaacttc ttcaagaccg agatcactct cgccaacggt gagatcagga  5280
agcgcccact gatcgagacc aacggtgaga ctggagagat cgtgtgggac aaagggaggg  5340
atttcgctac tgtgaggaag gtgctctcca tgcctcaggt gaacatcgtc aagaagaccg  5400
```

```
aagttcagac cggaggattc tccaaggagt ccatcctccc caagagaaac tccgacaagc    5460
tgatcgctag aaagaaagac tgggacccta agaagtacgg aggcttcgat tctcctaccg    5520
tggcctactc tgtgctggtc gtggccaagg tggagaaggg caagtccaag aagctgaaat    5580
ccgtcaagga gctcctcggg attaccatca tggagaggag ttccttcgag aagaacccta    5640
tcgacttcct ggaggccaag ggatataaag aggtgaagaa ggacctcatc atcaagctgc    5700
ccaagtactc cctcttcgag ttggagaacg aaggaagag gatgctggct tctgccggaa    5760
agttgcagaa gggaaatgag ctcgcccttc cctccaagta cgtgaacttc ctgtacctcg    5820
cctctcacta tgaaaagttg aagggctctc ctgaggacaa cgagcagaag cagctcttcg    5880
tggagcagca caagcactac ctggacgaaa ttatcgaga gatctctgag ttctccaagc    5940
gcgtgatatt ggccgacgcc aacctcgaca aggtgctgtc cgcctacaac aagcacaggg    6000
ataagcccat tcgcgagcag gctgaaaaca ttatccacct gtttaccctc acaaacttgg    6060
gagcccctgc tgccttcaag tacttcgaca ccaccattga caggaagaga tacacctcca    6120
ccaaggaggt gctcgacgca acactcatcc accaatccat caccggcctc tatgaaacaa    6180
ggattgactt gtcccagctg ggaggcgact ctagagccga tccaagaag aagagaaagg    6240
tgtaggttaa cctagacttg tccatcttct ggattggcca acttaattaa tgtatgaaat    6300
aaaaggatgc acacatagtg acatgctaat cactataatg tgggcatcaa agttgtgtgt    6360
tatgtgtaat tactagttat ctgaataaaa gagaaagaga tcatccatat ttcttatcct    6420
aaatgaatgt cacgtgtctt tataattctt tgatgaacca agtgcatttc attaaccaaa    6480
tccatataca tataaatatt aatcatatat aattaatatc aattgggtta gcaaaacaaa    6540
tctagtctag gtgtgttttg cgaattcgat atcaagctta tcgataccgt cgaggggggg    6600
cccggtaccg g                                                         6611

SEQ ID NO: 304          moltype = DNA   length = 64
FEATURE                 Location/Qualifiers
misc_feature            1..64
                        note = synthesized sequence- DD20 qPCR amplicon
source                  1..64
                        mol_type = other DNA
                        organism = synthetic construct
SEQUENCE: 304
attcggaact gacacacgac atgatggaac gtgactaagg tgggttttg actttgcatg     60
tcga                                                                 64

SEQ ID NO: 305          moltype = DNA   length = 115
FEATURE                 Location/Qualifiers
misc_feature            1..115
                        note = synthesized sequence- DD43 qPCR amplicon
source                  1..115
                        mol_type = other DNA
                        organism = synthetic construct
SEQUENCE: 305
aaagaagagg cagactccaa ttcctctttt ctagaatacc ctccgtacgt acaagtacaa    60
gggacttgtg agttgtaagg ctgtatttac aatagtgaaa agagaatcat ctggg         115

SEQ ID NO: 306          moltype = DNA   length = 20
FEATURE                 Location/Qualifiers
misc_feature            1..20
                        note = synthesized sequence- primer, DD20-CR1
source                  1..20
                        mol_type = other DNA
                        organism = synthetic construct
SEQUENCE: 306
ggaactgaca cacgacatga                                                20

SEQ ID NO: 307          moltype = DNA   length = 20
FEATURE                 Location/Qualifiers
misc_feature            1..20
                        note = synthesized sequence- primer, DD20-CR2
source                  1..20
                        mol_type = other DNA
                        organism = synthetic construct
SEQUENCE: 307
gacatgatgg aacgtgacta                                                20

SEQ ID NO: 308          moltype = DNA   length = 22
FEATURE                 Location/Qualifiers
misc_feature            1..22
                        note = synthesized sequence- primer, DD20-F
source                  1..22
                        mol_type = other DNA
                        organism = synthetic construct
SEQUENCE: 308
attcggaact gacacacgac at                                             22

SEQ ID NO: 309          moltype = DNA   length = 17
FEATURE                 Location/Qualifiers
misc_feature            1..17
                        note = synthesized sequence- FAM-MGB probe, DD20-T
source                  1..17
```

```
                            mol_type = other DNA
                            organism = synthetic construct
SEQUENCE: 309
atggaacgtg actaagg                                                          17

SEQ ID NO: 310          moltype = DNA   length = 22
FEATURE                 Location/Qualifiers
misc_feature            1..22
                        note = synthesized sequence- primer, DD20-R
source                  1..22
                        mol_type = other DNA
                        organism = synthetic construct
SEQUENCE: 310
tcgacatgca aagtcaaaaa cc                                                    22

SEQ ID NO: 311          moltype = DNA   length = 20
FEATURE                 Location/Qualifiers
misc_feature            1..20
                        note = synthesized sequence- primer, DD43CR1
source                  1..20
                        mol_type = other DNA
                        organism = synthetic construct
SEQUENCE: 311
gtcccttgta cttgtacgta                                                       20

SEQ ID NO: 312          moltype = DNA   length = 20
FEATURE                 Location/Qualifiers
misc_feature            1..20
                        note = synthesized sequence- primer, DD43CR2
source                  1..20
                        mol_type = other DNA
                        organism = synthetic construct
SEQUENCE: 312
gtattctaga aaagaggaat                                                       20

SEQ ID NO: 313          moltype = DNA   length = 26
FEATURE                 Location/Qualifiers
misc_feature            1..26
                        note = synthesized sequence- primer, DD43-F
source                  1..26
                        mol_type = other DNA
                        organism = synthetic construct
SEQUENCE: 313
ttctagaata ccctccgtac gtacaa                                                26

SEQ ID NO: 314          moltype = DNA   length = 26
FEATURE                 Location/Qualifiers
misc_feature            1..26
                        note = synthesized sequence- primer, DD43-F2
source                  1..26
                        mol_type = other DNA
                        organism = synthetic construct
SEQUENCE: 314
aaagaagagg cagactccaa ttcctc                                                26

SEQ ID NO: 315          moltype = DNA   length = 19
FEATURE                 Location/Qualifiers
misc_feature            1..19
                        note = synthesized sequence- FAM-MGB probe, DD43-T
source                  1..19
                        mol_type = other DNA
                        organism = synthetic construct
SEQUENCE: 315
caagggactt gtgagttgt                                                        19

SEQ ID NO: 316          moltype = DNA   length = 26
FEATURE                 Location/Qualifiers
misc_feature            1..26
                        note = synthesized sequence- primer, DD43-R
source                  1..26
                        mol_type = other DNA
                        organism = synthetic construct
SEQUENCE: 316
cccagatgat tctcttttca ctattg                                                26

SEQ ID NO: 317          moltype = DNA   length = 19
FEATURE                 Location/Qualifiers
misc_feature            1..19
                        note = synthesized sequence- primer, Cas9-F
```

```
source                    1..19
                          mol_type = other DNA
                          organism = synthetic construct
SEQUENCE: 317
ccttcttcca ccgccttga                                                  19

SEQ ID NO: 318            moltype = DNA   length = 19
FEATURE                   Location/Qualifiers
misc_feature              1..19
                          note = synthesized sequence- FAM-MGB probe, Cas9-T
source                    1..19
                          mol_type = other DNA
                          organism = synthetic construct
SEQUENCE: 318
aatcattcct ggtggagga                                                  19

SEQ ID NO: 319            moltype = DNA   length = 21
FEATURE                   Location/Qualifiers
misc_feature              1..21
                          note = synthesized sequence- primer, Cas9-R
source                    1..21
                          mol_type = other DNA
                          organism = synthetic construct
SEQUENCE: 319
tgggtgtctc tcgtgctttt t                                               21

SEQ ID NO: 320            moltype = DNA   length = 22
FEATURE                   Location/Qualifiers
misc_feature              1..22
                          note = synthesized sequence- primer, Sams-76F
source                    1..22
                          mol_type = other DNA
                          organism = synthetic construct
SEQUENCE: 320
aggcttgttg tgcagttttt ga                                              22

SEQ ID NO: 321            moltype = DNA   length = 22
FEATURE                   Location/Qualifiers
misc_feature              1..22
                          note = synthesized sequence- FAM-MGB probe, FRT1I-63T
source                    1..22
                          mol_type = other DNA
                          organism = synthetic construct
SEQUENCE: 321
tggactagtg gaagttccta ta                                              22

SEQ ID NO: 322            moltype = DNA   length = 21
FEATURE                   Location/Qualifiers
misc_feature              1..21
                          note = synthesized sequence- primer, FRT1I-41F
source                    1..21
                          mol_type = other DNA
                          organism = synthetic construct
SEQUENCE: 322
gcggtgagtt caggcttttt c                                               21

SEQ ID NO: 323            moltype = DNA   length = 31
FEATURE                   Location/Qualifiers
misc_feature              1..31
                          note = synthesized sequence- primer, DD20-LB
source                    1..31
                          mol_type = other DNA
                          organism = synthetic construct
SEQUENCE: 323
ggttataccT tcttcttagt gtggtctatc c                                    31

SEQ ID NO: 324            moltype = DNA   length = 31
FEATURE                   Location/Qualifiers
misc_feature              1..31
                          note = synthesized sequence- primer, Sams-A1
source                    1..31
                          mol_type = other DNA
                          organism = synthetic construct
SEQUENCE: 324
cccaaaataa ttagtatgat tggtaaggaa g                                    31

SEQ ID NO: 325            moltype = DNA   length = 23
FEATURE                   Location/Qualifiers
misc_feature              1..23
```

```
                        note = synthesized sequence- primer, QC498A-S1
source                  1..23
                        mol_type = other DNA
                        organism = synthetic construct
SEQUENCE: 325
ggaacttcac tagagcttgc ggc                                               23

SEQ ID NO: 326          moltype = DNA   length = 28
FEATURE                 Location/Qualifiers
misc_feature            1..28
                        note = synthesized sequence- primer, DD20-RB
source                  1..28
                        mol_type = other DNA
                        organism = synthetic construct
SEQUENCE: 326
gccattacat tcttcataag ttcctctc                                          28

SEQ ID NO: 327          moltype = DNA   length = 26
FEATURE                 Location/Qualifiers
misc_feature            1..26
                        note = synthesized sequence- primer, DD43-LB
source                  1..26
                        mol_type = other DNA
                        organism = synthetic construct
SEQUENCE: 327
gtgtagtcca ttgtagccaa gtcacc                                            26

SEQ ID NO: 328          moltype = DNA   length = 24
FEATURE                 Location/Qualifiers
misc_feature            1..24
                        note = synthesized sequence- primer, DD43-RB
source                  1..24
                        mol_type = other DNA
                        organism = synthetic construct
SEQUENCE: 328
caaaccggag agagaggaag aacc                                              24

SEQ ID NO: 329          moltype = DNA   length = 2105
FEATURE                 Location/Qualifiers
misc_feature            1..2105
                        note = synthesized sequence- DD20 HR1-HR2 PCR amplicon
source                  1..2105
                        mol_type = other DNA
                        organism = synthetic construct
SEQUENCE: 329
ggttatacct tcttcttagt gtggtctatc ccctagtaat aattacacat ctaagatatc   60
cccttctttt tcaagtaaaa taatatcata tgatctcatt ttagtgaaac aatactattt  120
ccctgataac tctcttcaac attagggact tcatctaatc atctactttc aaggtataac  180
tagacgtatt tgttctttta aaaaaaacac tagatgtact cgtcaactca aaattcatcg  240
ttcatgcatt ttaattaaac tttaattagc taatgagtag aaaaagatca tacgagtaaa  300
atagaagaat cttcctagat tttggaagaa tggattggga tgtaagtgaa ttgatccatt  360
agtggaagat gctctcttaca atggccaaac tgttctaatt gttagagcac atttgagatg  420
aaacacttca gtagtggagg taacctacaa tcctaggatc tgtatcctct atcactaatg  480
gagcaatggg tttgagattg acttactcct ttccttgtct ctcgtagtgc atatgcgcac  540
tttcaaaggc tacacaaaag ccgttaactt ttgttttatt taagttacga aagatagttg  600
aattagagta aatggtgata ttgaattagg atttttaaata attttaaaag aattttttta  660
ataaaaaaaa tattgtgttg ttggatcaaa attttttaaat aacatgaata aggaaatgga  720
ttgcaatgag gttttaaaca attattttaa catataggat tttagaaaga cttttataat  780
attttgttga agtttagatt ttaatatatt tatgttttaa aattttaaaa aaaacttcat  840
gaatttataa tatttgaaaa agacacgtga atatttagaa aacatttaaa attacaataa  900
taaatcataa tgagataggg tgtattcatg tgtagacgag acaccaagta tatggttcac  960
aagtgaatca tcttttttttt ttacagcaca agtagatcac ttgtacttat caaaattcgg 1020
aactgacaca cgacatgatg gaacgtgact aaggtgggtt tttgactttg catgtcgaag 1080
tgagagtgat tttattgaga gaataataga agacctacaa aacaaatgat cccgacgcta 1140
aagtaagtac gagagttaag agaataaatg ggaaaatatg catacatgat taggtgtgtg 1200
ttcgtctcaa gaaagtacga atgaaatatgg tgtgtttgta gtacatgaat gatgtgtttt 1260
gagggttcaa gggaaattga tatttataga gtgaaatgga accagaggtc tttgttgaca 1320
agggttgtta tgactcttgc aaataattaa tagcttataa ataatagcca ataacttatt 1380
atagatagag ttagagataa tatatagcta aatttgaaca aggcatacaa aacaaaaatg 1440
ctaaatatga ataagacaat caaaattgta gtcgatgttc aactctttgt cgttgaagaa 1500
cttgtttgca gtggtatagt aaatgggtgt gagtgcagtg tctcacccat ctcacaccac 1560
acaaccaact tcatatctaa agatattgtc gctgaataca aaattgagtt atggaatata 1620
caattcataa tatagatacg aaaaatcatt tcttacaaaa cattcaatca aaaattattc 1680
aaacataatt ctagattaag taatccgaag tacaagttag tatcctagat ccgttaattt 1740
aaaattatgt ttgcataatt ttggatttgg tgttctataa gggcacaatt tgttcattc  1800
ttacaagttt gtcaattcta aaatatatgc aaatttgaag aaaaaaaatt tacgaatgtg 1860
tctcaaacaa taacttaatg ggaggagaat gagggatgaa gaagctcaaa attaccaacg 1920
ccttctacct caagaagcta cttcacacaa aatatgactg gcggaaggat aggggacaac 1980
cgataacgag aaggagatac ataaggtaat gtacgttgtt gtgtgaggta cacaattatg 2040
```

```
gggatgaaga agttcaactt tagtcgaaaa aatgtttgag aggaacttat gaagaatgta    2100
atggc                                                               2105

SEQ ID NO: 330          moltype = DNA  length = 1204
FEATURE                 Location/Qualifiers
misc_feature            1..1204
                        note = synthesized sequence- DD20 HR1-SAMS PCR amplicon
source                  1..1204
                        mol_type = other DNA
                        organism = synthetic construct
SEQUENCE: 330
ggttatacct tcttcttagt gtggtctatc ccctagtaat aattcacat  ctaagatatc    60
cccttctttt tcaagtaaaa taatatcata tgatctcatt ttagtgaaac aatactattt   120
ccctgataac tctcttcaac attagggact tcatctaatc atctactttc aaggtataac   180
tagacgtatt tgttctttta aaaaaaacac tagatgtact cgtcaactca aaattcatcg   240
ttcatgcatt ttaattaaac tttaattagc taatgagtag aaaagatca tacgagtaaa    300
atagaagaat cttcctagat tttggaagaa tggattggag tgtaagtgaa ttgatccatt   360
agtggaagat gctctttaca atggccaaac tgttctaatt gttagagcac atttgagatg   420
aaacacttca gtagtggagg taacctacaa tcctaggatc tgtatcctct atcactaatg   480
gagcaatggg tttgagattg acttactcct ttccttgtct ctcgtagtgc atatgcgcac   540
tttcaaaggc tacacaaaag ccgttaactt tttgtttatt taagttacga aagatagttg   600
aattagagta aatggtgata ttgaattagg attttaaata attttaaaag aattttttta   660
ataaaaaaaa tattgtgttg ttggatcaaa attttttaaat aacatgaata aggaaatgga   720
ttgcaatgag gttttaaaca attatttttaa catataggat tttagaaaga cttttataat   780
attttgttga agtttagatt ttaatatatt tatgttttaa aattttaaaa aaacttcat    840
gaatttataa tatttgaaaa agacacgtga atattttaag aacattttaaa attacaataa   900
taaatcataa tgagataggg tgtattcatg tgtagacgag acaccaagta tatggttcac    960
aagtgaatca tctttttttt ttacagcaca agtagatcac ttgtacttat caaaaattcgg  1020
aactgacaca cactagtggt cacctaagtg actagggtca cgtgacccta gtcacttatt  1080
cccaaacact agtaacggcc gccagtgtgc tggaattcgc cctcccaag ctttgctcta   1140
gatcaaactc acatccaaac ataacatgga tatcttcctt accaatcata ctaattattt  1200
tggg                                                               1204

SEQ ID NO: 331          moltype = DNA  length = 1459
FEATURE                 Location/Qualifiers
misc_feature            1..1459
                        note = synthesized sequence- DD20 NOS-HR2 PCR amplicon
source                  1..1459
                        mol_type = other DNA
                        organism = synthetic construct
SEQUENCE: 331
ggaacttcac tagagcttgc ggccgcgcat gctgacttaa tcagctaacg ccactcgacc    60
tgcaggcatg cccgcggata tcgatgggcc ccggccgaag cttcaagttt gtacaaaaaa   120
gcaggctggc gccggaacca attcagtcga ctgatccgg taccgaattc gcggccgcac   180
tcgagatatc tagacccagc tttcttgtac aaagtggccg ttaacggatc ggccagaatc   240
cggtaagtga ctagggtcac gtgacccctag tcacttaaat tcggcagaa tggccatctg   300
gattcagcag gcctagaagg cccggaccga ttaaacttta attggtccg ggttacctct   360
agaaagcttg tcgacctgca gacacgacat gatggaacgt gactaaggtg ggttttgac    420
tttgcatgtc gaagtgagag tgatttatt gagagaataa tagaagacct acaaaacaaa    480
tgatcccgac gctaaagtaa gtacgagagt taagagaata aatgggaaaa tatgcataca    540
tgattaggtg tgtgttcgtc tcaagaaagt acgaatgaat atggtgtgtt tgtagtacat    600
gaatgatgtg ttttgagggt tcaagggaaa ttgatattta tagagtgaaa tggaaccaga    660
ggtctttgtt gacaagggtt gttatgactc ttgcaaataa ttaatagctt ataaataata    720
gccaataact tattatagat agagttagag ataatatata gctaaatttg aacaaggcat    780
acaaaacaaa aatgctaaat atgaataaga caatcaaaat tgtatgtcgt gttcaactct    840
ttgtcgttga agaacttgtt tgcagtggta tagtaaatgc gtgtgagtgc agtgtctcac    900
ccatctcaca ccacacaacc aacttcatat ctaaagatat tgtcgctgaa tacaaaattg    960
agttatggaa tatacaattc ataatataga tacgaaaaat catttcttac aaaacattca   1020
atcaaaaatt attcaaacat aattctagat taagtaatcc gaagtacaag ttagtatcct  1080
agatccgtta atttaaaatt atgtttgcat aattttggat ttggtgttct ataagggcac  1140
aattttgttc attcttacaa gtttgtcaat tctaaaatat atgcaaattt gaagaaaaaa  1200
aatttacgaa tgtgtctcaa acaataactt aatgggagga aatgaggga tgaagaagct   1260
caaaattacc aacgccttct acctcaagaa gctacttcac acaaaatatg actggcgaa   1320
ggataggga caaccgataa cgagaaggag atacataagg taatgtacgt tgttgtgtga   1380
ggtacacaat tatggggatg aagaagttca actttagtcg aaaaaatgtt tgagaggaac  1440
ttatgaagaa tgtaatggc                                                1459

SEQ ID NO: 332          moltype = DNA  length = 2098
FEATURE                 Location/Qualifiers
misc_feature            1..2098
                        note = synthesized sequence- DD43 HR1-HR2 PCR amplicon
source                  1..2098
                        mol_type = other DNA
                        organism = synthetic construct
SEQUENCE: 332
gtgtagtcca ttgtagccaa gtcaccaata tcttgttccc ctccttggtt tggcataaat    60
tgattttcat ggctcttctc ggtcgaaact ggagctaatt cacccttagt ctctcttaaa   120
attctggctg taagaaacac cacagaacac ataaattata aactaattat aatttgaaga   180
gtaaaatatg tttttactct tatgatttaa ttagtgtagt tttaatttc tccttttttt   240
```

```
aaaaaatttt ggtattcata aatttcaatt ttttaaaaat aattgttgtt acccgttaat  300
gataacggga tatgttatgt taccactaaa tcggacaaaa aaaattcaaa acttttataa  360
ggattaaaat taacaaaaat attttaaaaa aatctaacct caataaagtt aaatttataa  420
gcacaaaata atacttttaa gcctaatttg gcaagacaca agcaagctca cctgtagcat  480
taatagaaag gaagcaaagc aagagaaaag caaccagaag gaagcgtttg cttggtgaca  540
cagccatctt acttgaattt atggtattac tgagaaacct tgatcttgct tcaaaatctt  600
ctagttaccc tcttttata ggcagaaaga gaactagcta gttgccaata ggatatgagg  660
acatgtggtg caatgcactc actcttcaag gacaagaaaa acaatggcta caattgtggt  720
tcaaatcaat gtctcctgct ctgtcctgcc tgaaaatgac acccttttgc ttggaaaaga  780
ggatcaaagc taagaacagg agtggcttca ttcccttcat gtaaccaaac actttcgcat  840
tctgtcattc gtgaatcagc aaaatctgca accaaaaata tatggtgcct aaataaaaga  900
aataaaaataa tttagagttg cggactaaaa taataaacaa aagaaatata ttataatcta  960
gaattaattt aggactaaaa gaagaggcag actccaattc ctcttttcta gaataccctc  1020
cgtacgtaca agtacaaggg acttgtgagt tgtaaggctg tatttacaat agtgaaaaga  1080
gaatcatctg ggtgattggg ttttagtcc ccagtgacga attaaaggtt tgaattctta  1140
gtatgtttgg gaatcaatta ggaatttcgt tttggacttt ccaaagcaat tattcacttt  1200
ttcattcatt aaatgtgact aaaaaattgt tatttctcca ttggccagga tgcatcgttt  1260
atataaacat aaccttagtg aaagcagtgt tttcatgtga cagcggcaga ctatatctta  1320
aacaaaatta cttgtaaaga aagataccgt taggaaaaaa atgaaaagaa aattgaagct  1380
atcacttgtt tactttccta atatctttca agaatacaat gtggtgaatt tcaattttcc  1440
ctacatatgt ataccgtcag cctgacgcaa cttatgaaac ttctctttct ttcatttgat  1500
gtatatataa agacacatta tatataaaga aactttatat atatctccat catattttag  1560
tacttgctac tatgtaaaat tagctgttgg aagtatctca agaaacatt aatttattga  1620
accaagcatt aaccattcat ctacatttga gttctaaaat aaatcttaaa tgatgtggag  1680
gaagggaaat tgttaattat ttccctcttc tcctacatgg atatacctga aacatgcaat  1740
ggatggatta gattttaaca tttgcagcct gagaagttca ctgacttttcc tccagctatt  1800
ttatgtgtgc ccgccaccat ttatagctca tgattgtagc tgaactgcaa aaactgcatc  1860
gattgcaaac tgaaattgag aatctctttt caacttttata tgctgattga tgcatgctga  1920
gcatgctata ctagtactcg aagttcctat atgtagactt tgttactgcc taatatactt  1980
tgtgtttgtt ctcaagttct tatttattt catattttt cctataaaag gttaatggct  2040
ctataaaggt tgagtgacat atatatacta taaaggttcc tcctctctct ccggttttg  2098

SEQ ID NO: 333        moltype = DNA  length = 1202
FEATURE               Location/Qualifiers
misc_feature          1..1202
                      note = synthesized sequence- DD43 HR1-SAMS PCR PCR amplicon
source                1..1202
                      mol_type = other DNA
                      organism = synthetic construct
SEQUENCE: 333
gtgtagtcca ttgtagccaa gtcaccaata tcttgttccc ctccttggtt tggcataaat  60
tgattttcat ggctcttctc ggtcgaaact ggagctaatt caccccttagt ctctcttaaa  120
attctggctg taagaaacac cacagaacac ataaattata aactaattat aatttgaaga  180
gtaaaatatg ttttactct tatgatttaa ttagtgtagt tttaatttc tccttttttt  240
aaaaaatttt ggtattcata aatttcaatt ttttaaaaat aattgttgtt acccgttaat  300
gataacggga tatgttatgt taccactaaa tcggacaaaa aaaattcaaa acttttataa  360
ggattaaaat taacaaaaat attttaaaaa aatctaacct caataaagtt aaatttataa  420
gcacaaaata atacttttaa gcctaatttg gcaagacaca agcaagctca cctgtagcat  480
taatagaaag gaagcaaagc aagagaaaag caaccagaag gaagcgtttg cttggtgaca  540
cagccatctt acttgaattt atggtattac tgagaaacct tgatcttgct tcaaaatctt  600
ctagttaccc tcttttata ggcagaaaga gaactagcta gttgccaata ggatatgagg  660
acatgtggtg caatgcactc actcttcaag gacaagaaaa acaatggcta caattgtggt  720
tcaaatcaat gtctcctgct ctgtcctgcc tgaaaatgac acccttttgc ttggaaaaga  780
ggatcaaagc taagaacagg agtggcttca ttcccttcat gtaaccaaac actttcgcat  840
tctgtcattc gtgaatcagc aaaatctgca accaaaaata tatggtgcct aaataaaaga  900
aataaaaataa tttagagttg cggactaaaa taataaacaa aagaaatata ttataatcta  960
gaattaattt aggactaaaa gaagaggcag actccaattc ctcttttcta gaataccctc  1020
cgtacgtaca ctagtggtca cctaagtgac tagggtcacg tgaccctagt cacttattcc  1080
caaacactag taacggccgc cagtgtgctg gaattcgccc ttcccaagct tgctctaga  1140
tcaaactcac atccaaacat aacatggata tcttccttac caatcatact aattattttg  1200
gg                                                                 1202

SEQ ID NO: 334        moltype = DNA  length = 1454
FEATURE               Location/Qualifiers
misc_feature          1..1454
                      note = synthesized sequence- DD43 NOS-HR2 PCR PCR amplicon
source                1..1454
                      mol_type = other DNA
                      organism = synthetic construct
SEQUENCE: 334
ggaacttcac tagagcttgc ggccgcgcat gctgacttaa tcagctaacg ccactcgacc  60
tgcaggcatg cccgcggata tcgatgggcc cggccgaag cttcaagttt gtacaaaaaa  120
gcaggctggc gccggaacca attcagtcga ctggatccgg taccgaattc gcggccgcac  180
tcgagatatc tagacccagc tttcttgtac aaagtggcc ttaacgaagc ggccagaatc  240
cggtaagtga ctagggtcac gtgaccctag tcacttaaat tcggccagaa tggccatctg  300
gattcagcag gcctagaagg cccggaccga ttaaacttta attcggtccg gttacctct  360
agaaagcttg tcgacctgca ggtacaagta caagggactt tgagttgta aggctgtatt  420
tacaatagtg aaaagagaat catctgggtg attgggtttt tagtccccag tgacgaatta  480
aaggtttgaa ttcttagtat gtttgggaat caattaggaa tttcgtttg gactttccaa  540
```

```
agcaattatt cacttttca ttcattaaat gtgactaaaa aattgttatt tctccattgg      600
ccaggatgca tcgtttatat aaacataacc ttagtgaaag cagtgttttc atgtgacagc      660
ggcagactat atcttaaaca aaattacttg taaagaaaga taccgttagg aaaaaaatga      720
aaagaaaatt gaagctatca cttgtttact ttcctaatat ctttcaagaa tacaatgtgg      780
tgaatttcaa ttttccctac atatgtatac cgtcagcctg acgcaactta tgaaacttct      840
ctttctttca tttgatgtat atataaagac acattatata taagaaaact ttatatatat      900
ctccatcata ttttagtact tgctactatg taaaattagc tgttggaagt atctcaagaa      960
acatttaatt tattgaacca agcattaacc attcatctac atttgagttc taaaataaat     1020
cttaaatgat gtggaggaag ggaaattgtt aattatttcc ctcttctcct acatggatat     1080
acctgaaaca tgcaatggat ggattagatt ttaacatttg cagcctgaga agttcactga     1140
cttttcctcca gctattttat gtgtgcccgc caccatttat agctcatgat tgtagctgaa     1200
ctgcaaaaac tgcatcgatt gcaaactgaa attgagaatc tcttttcaac tttatatgct     1260
gattgatgca tgctgagcat gctatactag tactcgaagt tcctatatgt agactttgtt     1320
actgcctaat atactttgtg tttgttctca agttcttatt ttatttcata tttttcctta     1380
taaaaggtta atggctctat aaaaggttgag tgacatatat atactataaa ggttcttcct     1440
ctctctccgg tttg                                                         1454

SEQ ID NO: 335          moltype = DNA   length = 60
FEATURE                 Location/Qualifiers
misc_feature            1..60
                        note = soybean genomic DD20CR1 target region
source                  1..60
                        mol_type = unassigned DNA
                        organism = Glycine max
SEQUENCE: 335
acttgtactt atcaaaattc ggaactgaca cacgacatga tggaacgtga ctaaggtggg       60

SEQ ID NO: 336          moltype = DNA   length = 59
FEATURE                 Location/Qualifiers
source                  1..59
                        mol_type = unassigned DNA
                        organism = Glycine max
SEQUENCE: 336
acttgtactt atcaaaattc ggaactgaca cacgactgat ggaacgtgac taaggtggg        59

SEQ ID NO: 337          moltype = DNA   length = 59
FEATURE                 Location/Qualifiers
source                  1..59
                        mol_type = unassigned DNA
                        organism = Glycine max
SEQUENCE: 337
acttgtactt atcaaaattc ggaactgaca cacgaatgat ggaacgtgac taaggtggg        59

SEQ ID NO: 338          moltype = DNA   length = 58
FEATURE                 Location/Qualifiers
source                  1..58
                        mol_type = unassigned DNA
                        organism = Glycine max
SEQUENCE: 338
acttgtactt atcaaaattc ggaactgaca cacgatgatg gaacgtgact aaggtggg         58

SEQ ID NO: 339          moltype = DNA   length = 58
FEATURE                 Location/Qualifiers
source                  1..58
                        mol_type = unassigned DNA
                        organism = Glycine max
SEQUENCE: 339
acttgtactt atcaaaattc ggaactgaca cacgacgatg gaacgtgact aaggtggg         58

SEQ ID NO: 340          moltype = DNA   length = 58
FEATURE                 Location/Qualifiers
source                  1..58
                        mol_type = unassigned DNA
                        organism = Glycine max
SEQUENCE: 340
acttgtactt atcaaaattc ggaactgaca cacggtgatg gaacgtgact aaggtggg         58

SEQ ID NO: 341          moltype = DNA   length = 57
FEATURE                 Location/Qualifiers
source                  1..57
                        mol_type = unassigned DNA
                        organism = Glycine max
SEQUENCE: 341
acttgtactt atcaaaattc ggaactgaca cacatgatgg aacgtgacta aggtggg          57

SEQ ID NO: 342          moltype = DNA   length = 57
FEATURE                 Location/Qualifiers
source                  1..57
                        mol_type = unassigned DNA
```

```
                         organism = Glycine max
SEQUENCE: 342
acttgtactt atcaaaattc ggaactgaca cacgtgatgg aacgtgacta aggtggg        57

SEQ ID NO: 343           moltype = DNA  length = 56
FEATURE                  Location/Qualifiers
source                   1..56
                         mol_type = unassigned DNA
                         organism = Glycine max
SEQUENCE: 343
acttgtactt atcaaaattc ggaactgaca cactgatgga acgtgactaa ggtggg         56

SEQ ID NO: 344           moltype = DNA  length = 56
FEATURE                  Location/Qualifiers
source                   1..56
                         mol_type = unassigned DNA
                         organism = Glycine max
SEQUENCE: 344
acttgtactt atcaaaattc ggaactgaca cacggatgga acgtgactaa ggtggg         56

SEQ ID NO: 345           moltype = DNA  length = 55
FEATURE                  Location/Qualifiers
source                   1..55
                         mol_type = unassigned DNA
                         organism = Glycine max
SEQUENCE: 345
acttgtactt atcaaaattc ggaactgaca cacgatggaa cgtgactaag gtggg          55

SEQ ID NO: 346           moltype = DNA  length = 55
FEATURE                  Location/Qualifiers
source                   1..55
                         mol_type = unassigned DNA
                         organism = Glycine max
SEQUENCE: 346
acttgtactt atcaaaattc ggaactgaca catgatggaa cgtgactaag gtggg          55

SEQ ID NO: 347           moltype = DNA  length = 54
FEATURE                  Location/Qualifiers
source                   1..54
                         mol_type = unassigned DNA
                         organism = Glycine max
SEQUENCE: 347
acttgtactt atcaaaattc ggaactgaca cacatggaac gtgactaagg tggg           54

SEQ ID NO: 348           moltype = DNA  length = 54
FEATURE                  Location/Qualifiers
source                   1..54
                         mol_type = unassigned DNA
                         organism = Glycine max
SEQUENCE: 348
acttgtactt atcaaaattc ggaactgaca ctgatggaac gtgactaagg tggg           54

SEQ ID NO: 349           moltype = DNA  length = 53
FEATURE                  Location/Qualifiers
source                   1..53
                         mol_type = unassigned DNA
                         organism = Glycine max
SEQUENCE: 349
acttgtactt atcaaaattc ggaactgaca cgatggaacg tgactaaggt ggg            53

SEQ ID NO: 350           moltype = DNA  length = 51
FEATURE                  Location/Qualifiers
source                   1..51
                         mol_type = unassigned DNA
                         organism = Glycine max
SEQUENCE: 350
acttgtactt atcaaaattc ggaactgatg atggaacgtg actaaggtgg g              51

SEQ ID NO: 351           moltype = DNA  length = 50
FEATURE                  Location/Qualifiers
source                   1..50
                         mol_type = unassigned DNA
                         organism = Glycine max
SEQUENCE: 351
acttgtactt atcaaaattc ggaactgaca tggaacgtga ctaaggtggg                50

SEQ ID NO: 352           moltype = DNA  length = 50
FEATURE                  Location/Qualifiers
source                   1..50
```

```
                    mol_type = unassigned DNA
                    organism = Glycine max
SEQUENCE: 352
acttgtactt atcaaaattc ggaactgtga tggaacgtga ctaaggtggg           50

SEQ ID NO: 353      moltype = DNA   length = 51
FEATURE             Location/Qualifiers
source              1..51
                    mol_type = unassigned DNA
                    organism = Glycine max
SEQUENCE: 353
acttgtactt atcaaaattc ggaactgaca cacgaacgtg actaaggtgg g         51

SEQ ID NO: 354      moltype = DNA   length = 50
FEATURE             Location/Qualifiers
source              1..50
                    mol_type = unassigned DNA
                    organism = Glycine max
SEQUENCE: 354
acttgtactt atcaaaattc ggaactgaca cggaacgtga ctaaggtggg           50

SEQ ID NO: 355      moltype = DNA   length = 49
FEATURE             Location/Qualifiers
source              1..49
                    mol_type = unassigned DNA
                    organism = Glycine max
SEQUENCE: 355
acttgtacct atcaaaattc ggaactgaat ggaacgtgac taaggtggg            49

SEQ ID NO: 356      moltype = DNA   length = 48
FEATURE             Location/Qualifiers
source              1..48
                    mol_type = unassigned DNA
                    organism = Glycine max
SEQUENCE: 356
acttgtactt atcaaaattc ggaactgatg gaacgtgact aaggtggg             48

SEQ ID NO: 357      moltype = DNA   length = 46
FEATURE             Location/Qualifiers
source              1..46
                    mol_type = unassigned DNA
                    organism = Glycine max
SEQUENCE: 357
acttgtactt atcaaaattc ggaactgaga acgtgactaa ggtggg               46

SEQ ID NO: 358      moltype = DNA   length = 38
FEATURE             Location/Qualifiers
source              1..38
                    mol_type = unassigned DNA
                    organism = Glycine max
SEQUENCE: 358
acttgtactt atcaaaattc ggaactgaca cacgacat                        38

SEQ ID NO: 359      moltype = DNA   length = 38
FEATURE             Location/Qualifiers
source              1..38
                    mol_type = unassigned DNA
                    organism = Glycine max
SEQUENCE: 359
acttgtactt atcaaaattc ggaactgaca aggtggg                         38

SEQ ID NO: 360      moltype = DNA   length = 39
FEATURE             Location/Qualifiers
source              1..39
                    mol_type = unassigned DNA
                    organism = Glycine max
SEQUENCE: 360
acttgtactt atcaaaattc ggaacgtgac taaggtggg                       39

SEQ ID NO: 361      moltype = DNA   length = 24
FEATURE             Location/Qualifiers
source              1..24
                    mol_type = unassigned DNA
                    organism = Glycine max
SEQUENCE: 361
actatggaac gtgactaagg tggg                                       24

SEQ ID NO: 362      moltype = DNA   length = 211
FEATURE             Location/Qualifiers
```

```
source                  1..211
                        mol_type = unassigned DNA
                        organism = Glycine max
SEQUENCE: 362
acttgtactt atcaaaattc ggaactgaca cacggccggt gatggattgg tggatgagtg    60
ttgcgtcgag cacctccttg gtggaggtgt atctcttcct gtcaatggtg gtgtcgaagt   120
acttgaaggc agcaggggct cccaagtttg tgagggtaaa caggtggata atgttttcag   180
cctgctcgcg atggaacgtg actaaggtgg g                                  211

SEQ ID NO: 363          moltype = DNA  length = 90
FEATURE                 Location/Qualifiers
source                  1..90
                        mol_type = unassigned DNA
                        organism = Glycine max
SEQUENCE: 363
acttgtactt atcaaaaact acttgtgctg taaaaaaaaa gaggaacaat cttcactcat    60
caataagtga tggaacgcga ctaaggtggg                                     90

SEQ ID NO: 364          moltype = DNA  length = 57
FEATURE                 Location/Qualifiers
misc_feature            1..57
                        note = soybean genomic DD20CR2 target region
source                  1..57
                        mol_type = unassigned DNA
                        organism = Glycine max
SEQUENCE: 364
gacacacgac atgatggaac gtgactaagg tgggttttg actttgcatg tcgaagt        57

SEQ ID NO: 365          moltype = DNA  length = 61
FEATURE                 Location/Qualifiers
source                  1..61
                        mol_type = unassigned DNA
                        organism = Glycine max
SEQUENCE: 365
actgacacac gacatgatgg aacgtgaact aaggtgggtt tttgactttg catgtcgaag    60
t                                                                    61

SEQ ID NO: 366          moltype = DNA  length = 59
FEATURE                 Location/Qualifiers
source                  1..59
                        mol_type = unassigned DNA
                        organism = Glycine max
SEQUENCE: 366
actgacacac gacatgatgg aacgtactaa ggtgggtttt tgactttgca tgtcgaagt     59

SEQ ID NO: 367          moltype = DNA  length = 58
FEATURE                 Location/Qualifiers
source                  1..58
                        mol_type = unassigned DNA
                        organism = Glycine max
SEQUENCE: 367
actgacacac gacatgatgg aacgtctaag gtgggttttt gactttgcat gtcgaagt      58

SEQ ID NO: 368          moltype = DNA  length = 58
FEATURE                 Location/Qualifiers
source                  1..58
                        mol_type = unassigned DNA
                        organism = Glycine max
SEQUENCE: 368
actgacacac gacatgatgg aacgtgaaag gtgggttttt gactttgcat gtcgaagt      58

SEQ ID NO: 369          moltype = DNA  length = 57
FEATURE                 Location/Qualifiers
source                  1..57
                        mol_type = unassigned DNA
                        organism = Glycine max
SEQUENCE: 369
actgacacac gacatgatgg aacgctaagg tgggttttg actttgcatg tcgaagt        57

SEQ ID NO: 370          moltype = DNA  length = 57
FEATURE                 Location/Qualifiers
source                  1..57
                        mol_type = unassigned DNA
                        organism = Glycine max
SEQUENCE: 370
actgacacac gacatgatgg aacgtgaagg tgggttttg actttgcatg tcgaagt        57

SEQ ID NO: 371          moltype = DNA  length = 56
FEATURE                 Location/Qualifiers
```

```
source                  1..56
                        mol_type = unassigned DNA
                        organism = Glycine max
SEQUENCE: 371
actgacacac gacatgatgg aacgtgaggt gggttttga ctttgcatgt cgaagt        56

SEQ ID NO: 372          moltype = DNA   length = 56
FEATURE                 Location/Qualifiers
source                  1..56
                        mol_type = unassigned DNA
                        organism = Glycine max
SEQUENCE: 372
actgacacac gacatgatgg aacgtaaggt gggttttga ctttgcatgt cgaagt        56

SEQ ID NO: 373          moltype = DNA   length = 56
FEATURE                 Location/Qualifiers
source                  1..56
                        mol_type = unassigned DNA
                        organism = Glycine max
SEQUENCE: 373
actgacacac gacatgatgg aacctaaggt gggttttga ctttgcatgt cgaagt        56

SEQ ID NO: 374          moltype = DNA   length = 56
FEATURE                 Location/Qualifiers
source                  1..56
                        mol_type = unassigned DNA
                        organism = Glycine max
SEQUENCE: 374
actgacacac gacatgatgg aacgtgaggt gggttttga ctttgcatgt cgaagt        56

SEQ ID NO: 375          moltype = DNA   length = 55
FEATURE                 Location/Qualifiers
source                  1..55
                        mol_type = unassigned DNA
                        organism = Glycine max
SEQUENCE: 375
actgacacac gacatgatgg aactaaggtg gttttttgac tttgcatgtc gaagt         55

SEQ ID NO: 376          moltype = DNA   length = 54
FEATURE                 Location/Qualifiers
source                  1..54
                        mol_type = unassigned DNA
                        organism = Glycine max
SEQUENCE: 376
actgacacac gacatgatgg aataaggtgg gttttgact tgcatgtcg aagt            54

SEQ ID NO: 377          moltype = DNA   length = 53
FEATURE                 Location/Qualifiers
source                  1..53
                        mol_type = unassigned DNA
                        organism = Glycine max
SEQUENCE: 377
actgacacac gacatgatgg ctaaggtggg ttttgactt tgcatgtcga agt            53

SEQ ID NO: 378          moltype = DNA   length = 53
FEATURE                 Location/Qualifiers
source                  1..53
                        mol_type = unassigned DNA
                        organism = Glycine max
SEQUENCE: 378
actgacacac gacatgatgg ataaggtggg ttttgactt tgcatgtcga agt            53

SEQ ID NO: 379          moltype = DNA   length = 51
FEATURE                 Location/Qualifiers
source                  1..51
                        mol_type = unassigned DNA
                        organism = Glycine max
SEQUENCE: 379
actgacacac gacatgatgg aaggtgggtt tttgactttg catgtcgaag t             51

SEQ ID NO: 380          moltype = DNA   length = 50
FEATURE                 Location/Qualifiers
source                  1..50
                        mol_type = unassigned DNA
                        organism = Glycine max
SEQUENCE: 380
actgacacac gacatgatgg aggtgggttt tgactttgc atgtcgaagt                50

SEQ ID NO: 381          moltype = DNA   length = 44
```

```
FEATURE                 Location/Qualifiers
source                  1..44
                        mol_type = unassigned DNA
                        organism = Glycine max
SEQUENCE: 381
actgacacac gacatgatgg gtttttgact ttgcatgtcg aagt              44

SEQ ID NO: 382          moltype = DNA  length = 43
FEATURE                 Location/Qualifiers
source                  1..43
                        mol_type = unassigned DNA
                        organism = Glycine max
SEQUENCE: 382
actgacacac gacaggtggg tttttgactt tgcatgtcga agt               43

SEQ ID NO: 383          moltype = DNA  length = 40
FEATURE                 Location/Qualifiers
source                  1..40
                        mol_type = unassigned DNA
                        organism = Glycine max
SEQUENCE: 383
actgacacta aggtgggttt ttgactttgc atgtcgaagt                   40

SEQ ID NO: 384          moltype = DNA  length = 25
FEATURE                 Location/Qualifiers
source                  1..25
                        mol_type = unassigned DNA
                        organism = Glycine max
SEQUENCE: 384
actgacacac gacatgatgg aacgt                                   25

SEQ ID NO: 385          moltype = DNA  length = 20
FEATURE                 Location/Qualifiers
source                  1..20
                        mol_type = unassigned DNA
                        organism = Glycine max
SEQUENCE: 385
actgacacac gacatgatgg                                         20

SEQ ID NO: 386          moltype = DNA  length = 60
FEATURE                 Location/Qualifiers
misc_feature            1..60
                        note = soybean genomic DD43CR1 target region
source                  1..60
                        mol_type = unassigned DNA
                        organism = Glycine max
SEQUENCE: 386
agccttacaa ctcacaagtc ccttgtactt gtacgtacgg agggtattct agaaaagagg  60

SEQ ID NO: 387          moltype = DNA  length = 59
FEATURE                 Location/Qualifiers
source                  1..59
                        mol_type = unassigned DNA
                        organism = Glycine max
SEQUENCE: 387
agccttacaa ctcacaagtc ccttgtactt gtactacgga gggtattcta gaaaagagg   59

SEQ ID NO: 388          moltype = DNA  length = 59
FEATURE                 Location/Qualifiers
source                  1..59
                        mol_type = unassigned DNA
                        organism = Glycine max
SEQUENCE: 388
agccttacaa ctcacaagtc ccttgtactt gtagtacgga gggtattcta gaaaagagg   59

SEQ ID NO: 389          moltype = DNA  length = 58
FEATURE                 Location/Qualifiers
source                  1..58
                        mol_type = unassigned DNA
                        organism = Glycine max
SEQUENCE: 389
agccttacaa ctcacaagtc ccttgtactt gtgtacggag ggtattctag aaaagagg    58

SEQ ID NO: 390          moltype = DNA  length = 58
FEATURE                 Location/Qualifiers
source                  1..58
                        mol_type = unassigned DNA
                        organism = Glycine max
SEQUENCE: 390
```

```
agccttacaa ctcacaagtc ccttgtactt gcgtacggag ggtattctag aaaagagg          58

SEQ ID NO: 391            moltype = DNA   length = 57
FEATURE                   Location/Qualifiers
source                    1..57
                          mol_type = unassigned DNA
                          organism = Glycine max
SEQUENCE: 391
agccttacaa ctcacaagtc ccttgtactt ggtacggagg gtattctaga aaagagg            57

SEQ ID NO: 392            moltype = DNA   length = 57
FEATURE                   Location/Qualifiers
source                    1..57
                          mol_type = unassigned DNA
                          organism = Glycine max
SEQUENCE: 392
agccttacaa ctcacaagtc ccttgtactt gttacggagg gtattctaga aaagagg            57

SEQ ID NO: 393            moltype = DNA   length = 56
FEATURE                   Location/Qualifiers
source                    1..56
                          mol_type = unassigned DNA
                          organism = Glycine max
SEQUENCE: 393
agccttacaa ctcacaagtc ccttgtactt gtacggaggg tattctagaa aagagg             56

SEQ ID NO: 394            moltype = DNA   length = 55
FEATURE                   Location/Qualifiers
source                    1..55
                          mol_type = unassigned DNA
                          organism = Glycine max
SEQUENCE: 394
agccttacaa ctcacaagtc ccttgtactt tacggaggt attctagaaa agagg               55

SEQ ID NO: 395            moltype = DNA   length = 55
FEATURE                   Location/Qualifiers
source                    1..55
                          mol_type = unassigned DNA
                          organism = Glycine max
SEQUENCE: 395
agccttacaa ctcacaagtc ccttgtactg tacggaggt attctagaaa agagg               55

SEQ ID NO: 396            moltype = DNA   length = 54
FEATURE                   Location/Qualifiers
source                    1..54
                          mol_type = unassigned DNA
                          organism = Glycine max
SEQUENCE: 396
agccttacaa ctcacaagcc ccttgtactt acggaggta ttctagaaaa gagg                54

SEQ ID NO: 397            moltype = DNA   length = 52
FEATURE                   Location/Qualifiers
source                    1..52
                          mol_type = unassigned DNA
                          organism = Glycine max
SEQUENCE: 397
agccttacaa ctcacaagtc ccttgtatac ggagggtatt ctagaaaaga gg                 52

SEQ ID NO: 398            moltype = DNA   length = 52
FEATURE                   Location/Qualifiers
source                    1..52
                          mol_type = unassigned DNA
                          organism = Glycine max
SEQUENCE: 398
agccttacaa ctcacaagtc ccttgtgtac ggagggtatt ctagaaaaga gg                 52

SEQ ID NO: 399            moltype = DNA   length = 50
FEATURE                   Location/Qualifiers
source                    1..50
                          mol_type = unassigned DNA
                          organism = Glycine max
SEQUENCE: 399
agccttacaa ctcacaagtc ccttgtacgg agggtattct agaaaagagg                    50

SEQ ID NO: 400            moltype = DNA   length = 49
FEATURE                   Location/Qualifiers
source                    1..49
                          mol_type = unassigned DNA
                          organism = Glycine max
```

```
SEQUENCE: 400
agccttacaa ctcacaagtc cctttacgga gggtattcta gaaaagagg               49

SEQ ID NO: 401         moltype = DNA   length = 48
FEATURE                Location/Qualifiers
source                 1..48
                       mol_type = unassigned DNA
                       organism = Glycine max
SEQUENCE: 401
agccttacaa ctcacaagtc ccttacggag ggtattctag aaaagagg                48

SEQ ID NO: 402         moltype = DNA   length = 47
FEATURE                Location/Qualifiers
source                 1..47
                       mol_type = unassigned DNA
                       organism = Glycine max
SEQUENCE: 402
agccttacaa ctcacaagtc cctacggagg gtattctaga aaagagg                 47

SEQ ID NO: 403         moltype = DNA   length = 43
FEATURE                Location/Qualifiers
source                 1..43
                       mol_type = unassigned DNA
                       organism = Glycine max
SEQUENCE: 403
agccttacaa ctcacaagtc ccttgtactt gtaagaaaag agg                     43

SEQ ID NO: 404         moltype = DNA   length = 49
FEATURE                Location/Qualifiers
source                 1..49
                       mol_type = unassigned DNA
                       organism = Glycine max
SEQUENCE: 404
agccttacaa ctcacaagtc ctaaattaaa ggttattcta gaaaagagg               49

SEQ ID NO: 405         moltype = DNA   length = 227
FEATURE                Location/Qualifiers
source                 1..227
                       mol_type = unassigned DNA
                       organism = Glycine max
SEQUENCE: 405
agccttacaa ctcacaagtc ccttgtactt gtagaatcca gttcataaaa caagtgacac   60
acaacagata tgaactggac tacgtcgaac ccacaaatcc cacaaagcgc gtgaaatcaa  120
atcgctcaaa ccacaaaaaa gaacaacgcg tttgttacac gctaatacca aaattatacc  180
caaatcttaa gctatttatg cgtacggagg gtattctaga aaagagg                227

SEQ ID NO: 406         moltype = DNA   length = 97
FEATURE                Location/Qualifiers
source                 1..97
                       mol_type = unassigned DNA
                       organism = Glycine max
SEQUENCE: 406
agccttacaa ctcacaagtc ccttgtactt gtaatgctcc cctctaaact cgtatcgctt   60
cagagttgag agtacggagg gtattctaga aaagagg                            97

SEQ ID NO: 407         moltype = DNA   length = 183
FEATURE                Location/Qualifiers
source                 1..183
                       mol_type = unassigned DNA
                       organism = Glycine max
SEQUENCE: 407
agccttacaa ctcacaagtc ccttgtatat agatacccac aaaataagta aacccgatcc   60
aaaatcttaa atgatgtgga ggaagggaaa ttgttaatta ttcccctctt ctcctacatg  120
gatataccTg aaacatgcaa tggatggatt agattttgta cggagggtat tctagaaaag  180
agg                                                                183

SEQ ID NO: 408         moltype = DNA   length = 234
FEATURE                Location/Qualifiers
source                 1..234
                       mol_type = unassigned DNA
                       organism = Glycine max
SEQUENCE: 408
agccttacaa ctcacaagtc ccttgtactt gtaccagggg atgtttttta tttacattca   60
cgtcttttgg aaagagccgc taaattaagt tctcagttag gcgaaggaag tatgactgct  120
ttaccaatag ttgaaactca atcgggagat gtttcagctt atattcctac taatgtaatt  180
tccattacag atggccaaat attcttacgt acggaggggta ttctagaaaa gagg       234

SEQ ID NO: 409         moltype = DNA   length = 280
FEATURE                Location/Qualifiers
```

| | | |
|---|---|---|
| source | 1..280 | |
| | mol_type = unassigned DNA | |
| | organism = Glycine max | |

SEQUENCE: 409

```
agccttacaa ctcacaagtc ccttgtactt gtaccgaaaa tttcagccat aaaaaaagtt    60
ataatagaat ttaaagcaaa agtttcattt tttaaacata tatactgaca cgctccgata   120
aaaatagagg caagtccgac aacgtccct ccgaggaggt cgtgaagaag atgaaaaact    180
actggagaca gctcttgaac gccaagctca tcacccagcg taagctcgac aacctgacta   240
aggctgagag aggtgtacgg agggtattct agaaaagagg                          280
```

| | | |
|---|---|---|
| SEQ ID NO: 410 | moltype = DNA   length = 250 | |
| FEATURE | Location/Qualifiers | |
| source | 1..250 | |
| | mol_type = unassigned DNA | |
| | organism = Glycine max | |

SEQUENCE: 410

```
agccttacaa ctcacaagtc ccttgtactt gtactggatt tggtgaggga tgcttccgtt    60
gtcgaaggtt ctctgcttcc tcaacaggtc ctctctgttc aacttcacca acagctcctc   120
ggtaccgtcc atcttctcaa ggatgaagat cgagtgcttc gactccgtcg agatctctgg   180
tgtcgaggac aggttcaacg cctcccttgg gacttgccac gatcgtacgg agggtattct   240
agaaaagagg                                                            250
```

| | | |
|---|---|---|
| SEQ ID NO: 411 | moltype = DNA   length = 161 | |
| FEATURE | Location/Qualifiers | |
| source | 1..161 | |
| | mol_type = unassigned DNA | |
| | organism = Glycine max | |

SEQUENCE: 411

```
agccttacaa ctcacaagtc ccttatgacc tcaaaaaaaa gattcacctc caacacacca    60
aataactcga aaatctcttt cctattctct agaaagtata ggaacttcca ctagtccatg   120
aaaaagcctg aactcgtacg agggtattc tagaaaagag g                         161
```

| | | |
|---|---|---|
| SEQ ID NO: 412 | moltype = DNA   length = 185 | |
| FEATURE | Location/Qualifiers | |
| source | 1..185 | |
| | mol_type = unassigned DNA | |
| | organism = Glycine max | |

SEQUENCE: 412

```
agccttacaa ctcacaagtc ccttgtactt gtacacctgg ggcatggaga gcaccttcct    60
cacagtagcg aaatccctcc ctttgtccca cacgatctct ccagtctcac cgttggtctc   120
gatcagtggg cgcttcctga tctcaccgtt ggcgagagtg tacggagggt attctagaaa   180
agagg                                                                 185
```

| | | |
|---|---|---|
| SEQ ID NO: 413 | moltype = DNA   length = 212 | |
| FEATURE | Location/Qualifiers | |
| source | 1..212 | |
| | mol_type = unassigned DNA | |
| | organism = Glycine max | |

SEQUENCE: 413

```
agccttacaa ctcacaagtc ccttgtactt gtgctaggtt agccgaaaga tggttatcgg    60
ttcaaggacg caaggtgccc ctgcttttc agggtaataa ggggtagaga aaatgcctcg   120
agccaaagtt cgagtaccag gcgctacagc gctgaagtaa tccatgccat actcccagga   180
aaagccgtac ggagggtatt ctagaaaaga gg                                  212
```

| | | |
|---|---|---|
| SEQ ID NO: 414 | moltype = DNA   length = 231 | |
| FEATURE | Location/Qualifiers | |
| source | 1..231 | |
| | mol_type = unassigned DNA | |
| | organism = Glycine max | |

SEQUENCE: 414

```
agccttacaa ctcacaagtc ccttgtactt gtactcaagt tcttatttta tttcatattt    60
tttcctataa aaggttaatg gctctataaa ggttgagtga cggatccggt cacctaagtg   120
actagggtca cgtgaccctaa gtcacttatt cccgggcaac tttattatac aaagttgata  180
gatctcgaat tcattccgat taatcgtggc gagggtattc tagaaaagag g             231
```

| | | |
|---|---|---|
| SEQ ID NO: 415 | moltype = DNA   length = 98 | |
| FEATURE | Location/Qualifiers | |
| source | 1..98 | |
| | mol_type = unassigned DNA | |
| | organism = Zea mays | |

SEQUENCE: 415

```
tcctctgtaa cgatttacgc acctgctggg aattgtaccg tacgtgcccc ggtcggagga    60
tatatatacc tcacacgtac gcgtacgcgt atatatac                             98
```

| | | |
|---|---|---|
| SEQ ID NO: 416 | moltype = DNA   length = 98 | |
| FEATURE | Location/Qualifiers | |
| source | 1..98 | |
| | mol_type = unassigned DNA | |
| | organism = Zea mays | |

```
SEQUENCE: 416
tcctctgtaa cgatttacgc acctgctggg aattgtaccg tacgtgcccc ggacggagga    60
tatatatacc tcacacgtac gcgtacgcgt atatatac                            98

SEQ ID NO: 417          moltype = DNA   length = 98
FEATURE                 Location/Qualifiers
source                  1..98
                        mol_type = unassigned DNA
                        organism = Zea mays
SEQUENCE: 417
tcctctgtaa cgatttacgc acctgctggg aattgtaccg tacgtgcccc gggcggagga    60
tatatatacc tcacacgtac gcgtacgcgt atatatac                            98

SEQ ID NO: 418          moltype = DNA   length = 98
FEATURE                 Location/Qualifiers
source                  1..98
                        mol_type = unassigned DNA
                        organism = Zea mays
SEQUENCE: 418
tcctctgtaa cgatttacgc acctgctggg aattgtaccg tacgtgcccc ggccggagga    60
tatatatacc tcacacgtac gcgtacgcgt atatatac                            98

SEQ ID NO: 419          moltype = DNA   length = 99
FEATURE                 Location/Qualifiers
source                  1..99
                        mol_type = unassigned DNA
                        organism = Zea mays
SEQUENCE: 419
tcctctgtaa cgatttacgc acctgctggg aattgtaccg tacgtgcccc ggatcggagg    60
atatatatac ctcacacgta cgcgtacgcg tatatatac                           99

SEQ ID NO: 420          moltype = DNA   length = 94
FEATURE                 Location/Qualifiers
source                  1..94
                        mol_type = unassigned DNA
                        organism = Zea mays
SEQUENCE: 420
tcctctgtaa cgatttacgc acctgctggg aattgtaccg tacgtgcccc ggaggatata    60
tataccctcac acgtacgcgt acgcgtatat atac                               94

SEQ ID NO: 421          moltype = DNA   length = 81
FEATURE                 Location/Qualifiers
source                  1..81
                        mol_type = unassigned DNA
                        organism = Zea mays
SEQUENCE: 421
tcctctgtaa cgatttacgc acctgctggg aattgtaccg tacgtgcccc ggttcacacg    60
tacgcgtacg cgtatatata c                                              81

SEQ ID NO: 422          moltype = DNA   length = 65
FEATURE                 Location/Qualifiers
source                  1..65
                        mol_type = unassigned DNA
                        organism = Zea mays
SEQUENCE: 422
tcctctgtaa cgatttacgc acctgctggg aattgtaccg tacgtacgcg tacgcgtata    60
tatac                                                                65

SEQ ID NO: 423          moltype = DNA   length = 99
FEATURE                 Location/Qualifiers
source                  1..99
                        mol_type = unassigned DNA
                        organism = Zea mays
SEQUENCE: 423
tcctctgtaa cgatttacgc acctgctggg aattgtaccg tacgtgcccc ggttcggagg    60
atatatatac ctcacacgta cgcgtacgcg tatatatac                           99

SEQ ID NO: 424          moltype = DNA   length = 95
FEATURE                 Location/Qualifiers
source                  1..95
                        mol_type = unassigned DNA
                        organism = Zea mays
SEQUENCE: 424
tcctctgtaa cgatttacgc acctgctggg aattgtaccg tacgtgcccc cggaggatat    60
atatacctca cacgtacgcg tacgcgtata tatac                               95

SEQ ID NO: 425          moltype = DNA   length = 98
FEATURE                 Location/Qualifiers
source                  1..98
```

```
                            mol_type = unassigned DNA
                            organism = Zea mays
SEQUENCE: 425
gaagctgtaa cgatttacgc acctgctggg aattgtaccg tacgtgaccc cggcggagga    60
tatatatacc tcacacgtac gcgtacgcgt atatatac                            98

SEQ ID NO: 426              moltype = DNA   length = 98
FEATURE                     Location/Qualifiers
source                      1..98
                            mol_type = unassigned DNA
                            organism = Zea mays
SEQUENCE: 426
gaagctgtaa cgatttacgc acctgctggg aattgtaccg tacgtgtccc cggcggagga    60
tatatatacc tcacacgtac gcgtacgcgt atatatac                            98

SEQ ID NO: 427              moltype = DNA   length = 96
FEATURE                     Location/Qualifiers
source                      1..96
                            mol_type = unassigned DNA
                            organism = Zea mays
SEQUENCE: 427
gaagctgtaa cgatttacgc acctgctggg aattgtaccg tacgtccccg gcggaggata    60
tatatacctc acacgtacgc gtacgcgtat atatac                              96

SEQ ID NO: 428              moltype = DNA   length = 98
FEATURE                     Location/Qualifiers
source                      1..98
                            mol_type = unassigned DNA
                            organism = Zea mays
SEQUENCE: 428
gaagctgtaa cgatttacgc acctgctggg aattgtaccg tacgtggccc cggcggagga    60
tatatatacc tcacacgtac gcgtacgcgt atatatac                            98

SEQ ID NO: 429              moltype = DNA   length = 99
FEATURE                     Location/Qualifiers
source                      1..99
                            mol_type = unassigned DNA
                            organism = Zea mays
SEQUENCE: 429
gaagctgtaa cgatttacgc acctgctggg aattgtaccg tacgtgcacc ccggcggagg    60
atatatatac ctcacacgta cgcgtacgcg tatatatac                           99

SEQ ID NO: 430              moltype = DNA   length = 87
FEATURE                     Location/Qualifiers
source                      1..87
                            mol_type = unassigned DNA
                            organism = Zea mays
SEQUENCE: 430
gaagctgtaa cgatttacgc acctgctggg aattgtaccc ggcggaggat atatatacct    60
cacacgtacg cgtacgcgta tatatac                                        87

SEQ ID NO: 431              moltype = DNA   length = 92
FEATURE                     Location/Qualifiers
source                      1..92
                            mol_type = unassigned DNA
                            organism = Zea mays
SEQUENCE: 431
gaagctgtaa cgatttacgc acctgctggg aattgtaccg tccccggcgg aggatatata    60
tacctcacac gtacgcgtac gcgtatatat ac                                  92

SEQ ID NO: 432              moltype = DNA   length = 94
FEATURE                     Location/Qualifiers
source                      1..94
                            mol_type = unassigned DNA
                            organism = Zea mays
SEQUENCE: 432
gaagctgtaa cgatttacgc acctgctggg aattgtaccg taccccggc ggaggatata    60
tatacctcac acgtacgcgt acgcgtatat atac                                94

SEQ ID NO: 433              moltype = DNA   length = 95
FEATURE                     Location/Qualifiers
source                      1..95
                            mol_type = unassigned DNA
                            organism = Zea mays
SEQUENCE: 433
gaagctgtaa cgatttacgc acctgctggg aattgtaccg tacgcccgg cggaggatat    60
atacctcaca cgtacgcg tacgcgtata tatac                                 95

SEQ ID NO: 434              moltype = DNA   length = 88
```

```
FEATURE                 Location/Qualifiers
source                  1..88
                        mol_type = unassigned DNA
                        organism = Zea mays
SEQUENCE: 434
gaagctgtaa cgatttacgc acctgctggg aattgtaccc cggcggagga tatatatacc    60
tcacacgtac gcgtacgcgt atatatac                                       88

SEQ ID NO: 435          moltype = DNA   length = 98
FEATURE                 Location/Qualifiers
source                  1..98
                        mol_type = unassigned DNA
                        organism = Zea mays
SEQUENCE: 435
aaggcgcaaa tgagtagcag cgcacgtata tatacgcgta cgcgtacgtt gtgaggtata    60
tatatcctcc gccggggcac gtacggtaca attcccag                            98

SEQ ID NO: 436          moltype = DNA   length = 96
FEATURE                 Location/Qualifiers
source                  1..96
                        mol_type = unassigned DNA
                        organism = Zea mays
SEQUENCE: 436
aaggcgcaaa tgagtagcag cgcacgtata tatacgcgta cgcgtacggt gaggtatata    60
tatcctccgc cggggcacgt acggtacaat tcccag                              96

SEQ ID NO: 437          moltype = DNA   length = 95
FEATURE                 Location/Qualifiers
source                  1..95
                        mol_type = unassigned DNA
                        organism = Zea mays
SEQUENCE: 437
aaggcgcaaa tgagtagcag cgcacgtata tatacgcgta cgcgtacgtg aggtatatat    60
atcctccgcc ggggcacgta cggtacaatt cccag                               95

SEQ ID NO: 438          moltype = DNA   length = 96
FEATURE                 Location/Qualifiers
source                  1..96
                        mol_type = unassigned DNA
                        organism = Zea mays
SEQUENCE: 438
aaggcgcaaa tgagtagcag cgcacgtata tatacgcgta cgcgtactgt gaggtatata    60
tatcctccgc cggggcacgt acggtacaat tcccag                              96

SEQ ID NO: 439          moltype = DNA   length = 68
FEATURE                 Location/Qualifiers
source                  1..68
                        mol_type = unassigned DNA
                        organism = Zea mays
SEQUENCE: 439
aaggcgcaaa tgagtagcag cgcacgtata tatatcctcc gccggggcac gtacggtaca    60
attcccag                                                             68

SEQ ID NO: 440          moltype = DNA   length = 93
FEATURE                 Location/Qualifiers
source                  1..93
                        mol_type = unassigned DNA
                        organism = Zea mays
SEQUENCE: 440
aaggcgcaaa tgagtagcag cgcacgtata tatacgcgta cgcgtgtgag gtatatatat    60
cctccgccgg ggcacgtacg gtacaattcc cag                                 93

SEQ ID NO: 441          moltype = DNA   length = 89
FEATURE                 Location/Qualifiers
source                  1..89
                        mol_type = unassigned DNA
                        organism = Zea mays
SEQUENCE: 441
aaggcgcaaa tgagtagcag cgcacgtata tatacgcgta cgtgaggtat atatatcctc    60
cgccggggca cgtacggtac aattcccag                                      89

SEQ ID NO: 442          moltype = DNA   length = 89
FEATURE                 Location/Qualifiers
source                  1..89
                        mol_type = unassigned DNA
                        organism = Zea mays
SEQUENCE: 442
aaggcgcaaa tgagtagcag cgcacgtata tatacgcgta cgcgtactat atatatcctc    60
cgccggggca cgtacggtac aattcccag                                      89
```

```
SEQ ID NO: 443           moltype = DNA  length = 94
FEATURE                  Location/Qualifiers
source                   1..94
                         mol_type = unassigned DNA
                         organism = Zea mays
SEQUENCE: 443
aaggcgcaaa tgagtagcag cgcacgtata tatacgcgta cgcgtacgga ggtatatata    60
tcctccgccg gggcacgtac ggtacaattc ccag                                94

SEQ ID NO: 444           moltype = DNA  length = 96
FEATURE                  Location/Qualifiers
source                   1..96
                         mol_type = unassigned DNA
                         organism = Zea mays
SEQUENCE: 444
aaggcgcaaa tgagtagcag cgcacgtata tatacgcgta cgcgtacgat gaggtatata    60
tatcctccgc cggggcacgt acggtacaat tcccag                              96

SEQ ID NO: 445           moltype = DNA  length = 1051
FEATURE                  Location/Qualifiers
misc_feature             1..1051
                         note = synthesized sequence-
                         LIGCas-1_crRNA_Expression_Cassette
source                   1..1051
                         mol_type = other DNA
                         organism = synthetic construct
SEQUENCE: 445
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta ttttttttata taccttttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga gcccaaaca gcagtccgta    900
ggtggagcaa agcgctgggt aatacgcaaa cgttttgtcc caccttgact aatcacaaga   960
gtggagcgta cctttataaac cgagccgcaa gcaccgaatt gtaccgtacg tgccccggcg  1020
ggttttagag ctatgctgtt ttgttttttt t                                 1051

SEQ ID NO: 446           moltype = DNA  length = 1051
FEATURE                  Location/Qualifiers
misc_feature             1..1051
                         note = synthesized sequence-
                         LIGCas-2_crRNA_Expression_Cassette
source                   1..1051
                         mol_type = other DNA
                         organism = synthetic construct
SEQUENCE: 446
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgtttttg ttagccccat cgaatccttg acataatgat   540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta ttttttttata taccttttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga gcccaaaca gcagtccgta    900
ggtggagcaa agcgctgggt aatacgcaaa cgttttgtcc caccttgact aatcacaaga   960
gtggagcgta cctttataaac cgagccgcaa gcaccgaatt ggaattgtac cgtacgtgcc  1020
cgttttagag ctatgctgtt ttgttttttt t                                 1051

SEQ ID NO: 447           moltype = DNA  length = 1047
FEATURE                  Location/Qualifiers
misc_feature             1..1047
                         note = synthesized sequence-
```

|  |  |
|---|---|
|  | LIGCas-3_crRNA_Expression_Cassette |
| source | 1..1047 |
|  | mol_type = other DNA |
|  | organism = synthetic construct |

SEQUENCE: 447

```
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgttttg ttagccccat cgaatccttg acataatgat    540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta tttttttata tacctttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
gtggagcgta cctataaaac cgagccgcaa gcaccgaatt gcgtacgcgt acgtgtggtt  1020
ttagagctat gctgttttgt ttttttt                                     1047
```

|  |  |
|---|---|
| SEQ ID NO: 448 | moltype = DNA length = 1087 |
| FEATURE | Location/Qualifiers |
| misc_feature | 1..1087 |
|  | note = synthesized sequence- tracrRNA_Expression_Cassette |
| source | 1..1087 |
|  | mol_type = other DNA |
|  | organism = synthetic construct |

SEQUENCE: 448

```
tgagagtaca atgatgaacc tagattaatc aatgccaaag tctgaaaaat gcaccctcag    60
tctatgatcc agaaaatcaa gattgcttga ggccctgttc ggttgttccg gattagagcc   120
ccggattaat tcctagccgg attacttctc taatttatat agattttgat gagctggaat   180
gaatcctggc ttattccggt acaaccgaac aggccctgaa ggataccagt aatcgctgag   240
ctaaattggc atgctgtcag agtgtcagta ttgcagcaag gtagtgagat aaccggcatc   300
atggtgccag tttgatggca ccattagggt tagagatggt ggccatgggc gcatgtcctg   360
gccaactttg tatgatatat ggcagggtga ataggaaagt aaaattgtat tgtaaaaagg   420
gatttcttct gtttgttagc gcatgtacaa ggaatgcaag ttttgagcga gggggcatca   480
aagatctggc tgtgtttcca gctgttttg ttagccccat cgaatccttg acataatgat    540
cccgcttaaa taagcaacct cgcttgtata gttccttgtg ctctaacaca cgatgatgat   600
aagtcgtaaa atagtggtgt ccaaagaatt tccaggccca gttgtaaaag ctaaaatgct   660
attcgaattt ctactagcag taagtcgtgt ttagaaatta tttttttata tacctttttt   720
ccttctatgt acagtaggac acagtgtcag cgccgcgttg acggagaata tttgcaaaaa   780
agtaaaagag aaagtcatag cggcgtatgt gccaaaaact tcgtcacaga gagggccata   840
agaaacatgg cccacggccc aatacgaagc accgcgacga agcccaaaca gcagtccgta   900
ggtggagcaa agcgctgggt aatacgcaaa cgttttgtcc caccttgact aatcacaaga   960
gtggagcgta cctataaaac cgagccgcaa gcaccgaatt ggaaccattc aaaacagcat  1020
agcaagttaa aataaggcta gtccgttatc aacttgaaaa agtggcaccg agtcggtgct  1080
tttttt                                                            1087
```

|  |  |
|---|---|
| SEQ ID NO: 449 | moltype = DNA length = 63 |
| FEATURE | Location/Qualifiers |
| misc_feature | 1..63 |
|  | note = synthesized sequence- LIGCas-2 forward primer for primary |
| source | 1..63 |
|  | mol_type = other DNA |
|  | organism = synthetic construct |

SEQUENCE: 449

```
ctacactctt tccctacacg acgctcttcc gatctgaagc tgtaacgatt tacgcacctg    60
ctg                                                                 63
```

|  |  |
|---|---|
| SEQ ID NO: 450 | moltype = DNA length = 60 |
| FEATURE | Location/Qualifiers |
| misc_feature | 1..60 |
|  | note = synthesized sequence- LIGCas-3 forward primer for primary PCR |
| source | 1..60 |
|  | mol_type = other DNA |
|  | organism = synthetic construct |

SEQUENCE: 450

```
ctacactctt tccctacacg acgctcttcc gatctttccc gcaaatgagt agcagcgcac    60
```

|  |  |
|---|---|
| SEQ ID NO: 451 | moltype = DNA length = 19 |
| FEATURE | Location/Qualifiers |
| source | 1..19 |
|  | mol_type = unassigned DNA |

```
                            organism = Zea mays
SEQUENCE: 451
gcgtgcatcg atccatcgc                                                    19

SEQ ID NO: 452          moltype = DNA  length = 21
FEATURE                 Location/Qualifiers
source                  1..21
                        mol_type = unassigned DNA
                        organism = Zea mays
SEQUENCE: 452
ggctacggat agatatgatg c                                                 21

SEQ ID NO: 453          moltype = DNA  length = 20
FEATURE                 Location/Qualifiers
source                  1..20
                        mol_type = unassigned DNA
                        organism = Zea mays
SEQUENCE: 453
gttacttctc taagcacggc                                                   20

SEQ ID NO: 454          moltype = DNA  length = 21
FEATURE                 Location/Qualifiers
misc_feature            1..21
                        note = synthesized sequence- P1, Forward_primer
source                  1..21
                        mol_type = other DNA
                        organism = synthetic construct
SEQUENCE: 454
gcgccattcc ctaaaggtaa c                                                 21

SEQ ID NO: 455          moltype = DNA  length = 23
FEATURE                 Location/Qualifiers
misc_feature            1..23
                        note = synthesized sequence- P2, Reverse_primer
source                  1..23
                        mol_type = other DNA
                        organism = synthetic construct
SEQUENCE: 455
gctaatcgta agtgacgctt gga                                               23

SEQ ID NO: 456          moltype = DNA  length = 31
FEATURE                 Location/Qualifiers
misc_feature            1..31
                        note = synthesized sequence- P3, Forward_primer
source                  1..31
                        mol_type = other DNA
                        organism = synthetic construct
SEQUENCE: 456
gctcgtgtcc aagcgtcact tacgattagc t                                      31

SEQ ID NO: 457          moltype = DNA  length = 20
FEATURE                 Location/Qualifiers
misc_feature            1..20
                        note = synthesized sequence- P4, Reverse_primer
source                  1..20
                        mol_type = other DNA
                        organism = synthetic construct
SEQUENCE: 457
ctgcgaactg cttgattccg                                                   20

SEQ ID NO: 458          moltype = DNA  length = 24
FEATURE                 Location/Qualifiers
misc_feature            1..24
                        note = synthesized sequence- P5, Forward_primer
source                  1..24
                        mol_type = other DNA
                        organism = synthetic construct
SEQUENCE: 458
accgtcctta tctctgcatc atct                                              24

SEQ ID NO: 459          moltype = DNA  length = 31
FEATURE                 Location/Qualifiers
misc_feature            1..31
                        note = synthesized sequence- PBS, Primer Binding Site
source                  1..31
                        mol_type = other DNA
                        organism = synthetic construct
SEQUENCE: 459
gctcgtgtcc aagcgtcact tacgattagc t                                      31
```

```
SEQ ID NO: 460          moltype = DNA  length = 1823
FEATURE                 Location/Qualifiers
misc_feature            1..1823
                        note = Zm-GOS2 PRO-GOS2 INTRON, maize GOS2 promoter and
                         GOS2 intron1 including the promoter, 5'-UTR1, INTRON1 and
                         5'-UTR2 sequence
source                  1..1823
                        mol_type = unassigned DNA
                        organism = Zea mays
SEQUENCE: 460
taattattgg ctgtaggatt ctaaacagag cctaaatagc tggaatagct ctagccctca    60
atccaaacta atgatatcta tacttatgca actctaaatt tttattctaa aagtaatatt   120
tcattttgt caacgagatt ctctactcta ttccacaatc ttttgaagct atatttacct   180
taaatctgta ctctatacca ataatcatat attctattat ttattttat ctctctccta   240
aggagcatcc ctctatgtct gcatggcccc cgcctcgggt cccaatctct tgctctgcta   300
gtagcacaga agaaaacact agaaatgact tgcttgactt agagtatcag ataaacatca   360
tgtttactta actttaattt gtatcggttt ctactattt tataatattt ttgtctctaa   420
agatactacg tgcaacagta taatcaacct agtttaatcc agagcgaagg attttttact   480
aagtacgtga ctccatatgc acagcgttcc ttttatggtt cctcactggg cacagcataa   540
acgaaccctg tccaatgttt tcagcgcgaa caaacagaaa ttccatcagc gaacaaacaa   600
catacatgcg agatgaaaat aaataataaa aaaagctccg tctcgatagg ccggcacgaa   660
tcgagagcct ccatagccag ttttttccat cggaacggcg gttcgcgcac ctaattatat   720
gcaccacacg cctataaagc caaccaaccc gtcggagggg cgcaagccag acagaagaca   780
gcccgtcagc ccctctcgtt tttcatccgc cttcgcctcc aaccgcgtgc gctccacgcc   840
tcctccagga aagcgagagg tgagcgcagt ccccttcc ctccttccaa ttcaattcgt   900
cttctcgttc gcagccctag gatttgggggg tctggagggg tttgatcgtt tctcgccgtg   960
aatctgcttt ggtgtaaacc aacgatctc ggatcgtagt cttcagaaga tcccggattt  1020
tgcggtttgg ccctcctgg attcaattcg tcgtatcgtt cgcagcccta ggatttgggg  1080
atctggaggg gtttgatcgt ttctcgccgc gaatctgctc tggtgtaaac caacggatct  1140
cgggtcgtag tcttcagaag gtcccggatt ttgcggtttg gccctcctg gattcaattc  1200
gtcgtatcgt tcgcagccct aggatttggg gatcgtggaggg gtttgatcc tttctcgccg  1260
cgaatctgct ctggtataac caacggatct cgggtcgtag tcttcagaag gtcccggatt  1320
ttgcggttg gtggttcttg ctctatgaat cagagggatg gttcttcccg gatttatgcc  1380
ttgcggccac tctgtcgaat catggggttt cgaccgatt cgtaggcgtg ctccctgttt  1440
tggatgggaa gtaggcgtgt ttgtagtatt cgtgcttcga ttcgtcaacg gagattagaa  1500
gacctgggat gggatttgag gaatctagg tatctgtcta gcacgtttct agatctattc  1560
ttcagctgtt atatgagagt aattttgaa ccctggtggg gtatgtttga ccagtattc  1620
tgtagattat tgtccgtgac ttgctggctg ttaccgtcct tatctctgca tcatctatct  1680
gtgctagttt ctgcgtgctt ctcaaatatt tccggcctgt gtagcatgtg actgataata  1740
tgatttggc agcttctgca taagaacaac aaatcaaaag cttgatcagc tcggtgccta  1800
caaaacctca acaaccaagt ttc                                         1823

SEQ ID NO: 461          moltype = DNA  length = 556
FEATURE                 Location/Qualifiers
misc_feature            1..556
                        note = Zm-ARGOS8 promoter
source                  1..556
                        mol_type = unassigned DNA
                        organism = Zea mays
SEQUENCE: 461
gttacttctc taagcacggc tggatttcag gcctctagtc ctctactagt actagctaca    60
cgacgtgcac gcatgcatca cagcatcaac aactagacac gcacacgctg cacgcggccg   120
gggaacccca tgattccccc cttccccgcg cgcggtttga tttcctttcc tggtacggat   180
ccatatctga gggcttgttc ggttattccc aacacacatg tattggatgg gattgaaaaa   240
aaaatgagaa gaagtttgac ttgtttggga ttcaaaccca tccaatccca ctcaatccaa   300
atggattgag agctaaccga acaagccctc atagtacata cctggtacgg atccatatca   360
tagtacatag atccagtaga atagaaggtg atccgaccgc cggcgcttgc gttgttttcc   420
ccggtccatt gaacctgcca accctcctaa ccacaggcac gccaaaccgc gggctccggc   480
caccaccgcc accgccacct gccctgccgc acctctccaa ccccaaatcc agggggggg   540
gggggcacca tgcgtg                                                   556

SEQ ID NO: 462          moltype = DNA  length = 155
FEATURE                 Location/Qualifiers
misc_feature            1..155
                        note = Zm-ARGOS8 5'-UTR
source                  1..155
                        mol_type = unassigned DNA
                        organism = Zea mays
SEQUENCE: 462
catcgatcca tcgctggcgc gcgggtccgg cggggcggtc tgtgagggca aatttatata    60
ggtctagtgg gtacccggct acggatagat atgatgctgc actgcacatt ggctatatct   120
gaggctcctc cgcgcgcctt ggccaggtgt ctgtc                              155

SEQ ID NO: 463          moltype = DNA  length = 285
FEATURE                 Location/Qualifiers
source                  1..285
                        mol_type = unassigned DNA
                        organism = Zea mays
```

```
SEQUENCE: 463
atgcgggcga tgccgcagga agaggaagcc gcggtggcga cgacgaccat ggccgggggc    60
aaggtggcgg cgctgctggc cacggcggcc gcgctgctgc tgctgctccc gctggcgctg   120
ccgccgctgc cgccgccgcc cacgcagctg ttgttcgtcc ccgtggtctt gctgctcctc   180
gtggcgtccc tcgcgttctg ccccgccgcg acccctcgc cgtcgccgat gcatgccgcc    240
gaccacgggt cgttcgggac cactggatca ccgcacctat gttga                   285

SEQ ID NO: 464          moltype = DNA  length = 2843
FEATURE                 Location/Qualifiers
misc_feature            1..2843
                        note = Zm-GOS2 gene, including promoter, 5'-UTR, CDS,
                        3'-UTR and introns sequence
source                  1..2843
                        mol_type = unassigned DNA
                        organism = Zea mays
SEQUENCE: 464
taattattgg ctgtaggatt ctaaacagag cctaaatagc tggaatagct ctagccctca    60
atccaaacta atgatatcta tacttatgca actctaaatt tttattctaa aagtaatatt   120
tcattttgt caacgagatt ctctactcta ttccacaatc ttttgaagct atatttacct    180
taaatctgta ctctatacca ataatcatat attctattat ttattttat ctctctccta    240
aggagcatcc ctctatgtct gcatggcccc cgcctcgggt cccaatctct tgctctgcta   300
gtagcacaga agaaaacact agaaatgact tgcttgactt agagtatcag ataaacatca   360
tgtttactta actttaattt gtatcggttt ctactatttt tataatattt ttgtctctat   420
agatactacg tgcaacagta taatcaacct agtttaatcc agagcgaagg atttttact    480
aagtacgtga ctccatatgc acagcgttcc ttttatggtt cctcactggg cacagcataa   540
acgaaccctg tccaatgttt tcagcgcgaa caaacagaaa ttccatcagc gaacaaacaa   600
catacatgcg agatgaaaat aaataataaa aaaagctccg tctcgatagg ccggcacgaa   660
tcgagagcct ccatagccag tttttttccat cggaacggcg gttcgcgcac ctaattatat   720
gcaccacacg cctataaagc caaccaaccc gtcggagggg cgcaagccag acagaagaca   780
gcccgtcagc ccctctcgtt tttcatccgc cttcgcctcc aaccgcgtgc gctccacgcc   840
tcctccagga aagcgagagg tgagcgcagt ccccttccc ctccttccaa ttcaattcgt    900
cttctcgttc gcagccctag gatttgggg tctggagggg tttgatcgtt tctgccgtg    960
aatctgcttt ggtgtaaacc aacggatctc ggatcgtagt cttcagaaga tcccggattt  1020
tgcggtttgg cccctcctgg attcaattcg tcgtatcgtt cgcagcccta ggatttgggg  1080
atctggaggg gtttgatcgt ttctcgccgc gaatctgctc tggtgtaaac caacggatct  1140
cgggtcgtag tcttcagaag gtcccggatt ttgcggttg ccccctcctg gattcaattc   1200
gtcgtatcgt tcgcagccct aggatttggg gatctggagg ggtttgatcc tttctcgccg  1260
cgaatctgct ctggtataac caacggatct cgggtcgtag tcttcagaag gtcccggatt  1320
ttgcggtttg gtggttcttg ctctatgaat cagagggatg gttcttcccg gtgtttatgcc  1380
ttgcggccac tctgtcgaat catgggttt cgacccgatt cgtaggcgtg ctccctgttt   1440
tggatgggaa gtaggcgtgt tgtagtatt cgtgcttcga ttcgtcaacg gagattagaa   1500
gacctgggat gggatttgag gaaatctagg tatctgtcta gcacgtttct agatctattc   1560
ttcagctgtt atatgagagt aattttgaa ccctggtggg gtatgtttga ccgagtattc   1620
tgtagattat tgtccgtgac ttgctggctg ttaccgtcct tatctctgca tcatctatct   1680
gtgctagttt ctgcgtgctt ctcaaatatt tccggcctgt gtagcatgtg actgataata   1740
tgatttggc agcttctgca taagaacaac aaatcaaaag cttgatcagc tcggtgccta   1800
caaaacctca acaaccaagt ttcatgtctg atctcgaccg ccagcttcca tctgccttg   1860
gtatggctac ttctcaattc atgatgccat gttttttttt atattgtggt tttacataat   1920
acatagcatc ttccagcttc ctgaaagta ttactgaata gattgataac atcatacaca    1980
cgaagttcat cttgaacatg cttattagtg ttctgtttgc atctgatggt atggcatcat   2040
ctttgataga tccgtttgct gaggcaaatg ctggaggctc tggtgctggt cctggaacga   2100
aggattatgt gcatgtgcgc atccagcagc gcaacggcag aaagagtctg actacagtcc   2160
agggtctgaa gaaagagttc agctataaca agatcctcaa ggatctgaag aaggaattct   2220
gctgcaatgg tactgtagtt caggacccag agctaggcca ggtaagatac gagaacaatg   2280
catttcaagc ttgtaaaaat ggtatctgcc ggttggtgga tatactgatc tgttttgtccg   2340
ctgcaggtca ttcagctcca aggtgaccag cgcaagaatg ttgctacttt cctagttcag   2400
gtattcagaa tcttcagacc tggccagctg aatactgttt taccataccg atagatgttc   2460
aatctgttaa tactgatcgt gcaattatta cttgtcttgg taggctggga ttgcgaagaa   2520
agagaacatc aagattcacg ggttctaagg gacctgtaaa tgcttgtgcc ctatattgg   2580
tgcctccaca tattggggag cttgaagcat cgacagttac tagtcattgc ttacttatat   2640
aagaacataa gtagtatttg ctattgtcaa gtgtgccttg cttgatgcaa gttgtgtttt   2700
cgtatcatta ttattatgca cggccatcgt acgtgtatgg cttgtatggg ttattgccaa   2760
cttaataaaa gcaacactctg tttgcctata agcactgatg tttgcctcgt catgcacatg   2820
ttgagtcggg tttatttgt att                                           2843

SEQ ID NO: 465          moltype = DNA  length = 800
FEATURE                 Location/Qualifiers
misc_feature            1..800
                        note = Zm-GOS2 PRO, maize GOS2 promoter
source                  1..800
                        mol_type = unassigned DNA
                        organism = Zea mays
SEQUENCE: 465
taattattgg ctgtaggatt ctaaacagag cctaaatagc tggaatagct ctagccctca    60
atccaaacta atgatatcta tacttatgca actctaaatt tttattctaa aagtaatatt   120
tcattttgt caacgagatt ctctactcta ttccacaatc ttttgaagct atatttacct    180
taaatctgta ctctatacca ataatcatat attctattat ttattttat ctctctccta    240
aggagcatcc ctctatgtct gcatggcccc cgcctcgggt cccaatctct tgctctgcta   300
gtagcacaga agaaaacact agaaatgact tgcttgactt agagtatcag ataaacatca   360
```

```
tgtttactta actttaattt gtatcggttt ctactatttt tataatattt ttgtctctat    420
agatactacg tgcaacagta taatcaacct agtttaatcc agagcgaagg attttttact    480
aagtacgtga ctccatatgc acagcgttcc tttatggtt cctcactggg cacagcataa     540
acgaaccctg tccaatgttt tcagcgcgaa caaacagaaa ttccatcagc gaacaaacaa    600
catacatgcg agatgaaaat aaataataaa aaaagctccg tctcgatagg ccggcacgaa    660
tcgagagcct ccatagccag ttttttccat cggaacggcg gttcgcgcac ctaattatat    720
gcaccacacg cctataaagc caaccaaccc gtcggagggg cgcaagccag acagaagaca    780
gcccgtcagc ccctctcgtt                                                800

SEQ ID NO: 466          moltype = DNA   length = 1023
FEATURE                 Location/Qualifiers
misc_feature            1..1023
                        note = GOS2 INTRON, maize GOS2 5'-UTR1 and intron1 and
                        5'-UTR2 sequence
source                  1..1023
                        mol_type = unassigned DNA
                        organism = Zea mays
SEQUENCE: 466
tttcatccgc cttcgcctcc aaccgcgtgc gctccacgcc tcctccagga aagcgagagg    60
tgagcgcagt cccctttccc ctccttccaa ttcaattcgt cttctcgttc gcagccctag    120
gatttggggg tctggagggg tttgatcgtt tctcgccgtg aatctgcttt ggtgtaaacc    180
aacggatctc ggatcgtagt cttcagaaga tcccggattt tgcggtttgg ccctcctgg    240
attcaattcg tcgtatcgtt cgcagcccta ggatttgggg atctggaggg gtttgatcgt    300
ttctcgccgc gaatctgctc tggtgtaaac caacggatct cggtcgtag tcttcagaag     360
gtcccggatt ttgcggtttg gcccctcctg gattcaattc gtcgtatcgt tcgcagccct    420
aggatttggg gatctggagg ggtttgatcc tttctcgccg cgaatctgct ccggtataac    480
caacggatct cggtcgtag tcttcagaag gtcccggatt ttgcggtttg gtggttcttg     540
ctctatgaat cagagggatg gttcttcccg gatttatgcc ttgcggccac tctgtcgaat    600
catgggggttt cgacccgatt cgtaggcgtg ctccctgttt tggatgggaa gtaggcgtgt   660
ttgtagtatt cgtgcttcga ttcgtcaacg gagattagaa cccatggga t gggatttgag   720
gaaatctagg tatctgtcta gcacgtttct agatctattc ttcagctgtt atatgagagt    780
aattttggaa ccctggtggg gtatgtttga ccgagtattc tgtagattat tgtccgtgac    840
ttgctggctg ttaccgtcct tatctctgca tcatctatct gtgctagttt ctgcgtgctt    900
ctcaaatatt tccggcctgt gtagcatgtg actgataata tgattttggc agcttctgca    960
taagaacaac aaatcaaaag cttgatcagc tcggtgccta caaaacctca acaaccaagt   1020
ttc                                                                 1023

SEQ ID NO: 467          moltype = DNA   length = 23
FEATURE                 Location/Qualifiers
source                  1..23
                        mol_type = unassigned DNA
                        organism = Glycine max
SEQUENCE: 467
gcgtcctttg acagcagctg tgg                                            23

SEQ ID NO: 468          moltype = DNA   length = 23
FEATURE                 Location/Qualifiers
source                  1..23
                        mol_type = unassigned DNA
                        organism = Glycine max
SEQUENCE: 468
gcaaccacag ctgctgtcaa agg                                            23

SEQ ID NO: 469          moltype = DNA   length = 434
FEATURE                 Location/Qualifiers
source                  1..434
                        mol_type = unassigned DNA
                        organism = Glycine max
SEQUENCE: 469
ccgggtgtga tttagtataa agtgaagtaa tggtcaaaag aaaaagtgta aaacgaagta    60
cctagtaata agtaatattg aacaaaataa atggtaaagt gtcagatata taaaataggc    120
tttaataaaa ggaagaaaaa aaacaaacaa aaaataggtt gcaatggggc agagcagagt    180
catcatgaag ctagaaaggc taccgataga taaactatag ttaattaaat acattaaaaa    240
atacttggat ctttctctta ccctgtttat attgagacct gaaacttgag agagcacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaa                                                     434

SEQ ID NO: 470          moltype = DNA   length = 9093
FEATURE                 Location/Qualifiers
misc_feature            1..9093
                        note = synthesized sequence- QC878
source                  1..9093
                        mol_type = other DNA
                        organism = synthetic construct
SEQUENCE: 470
ccgggtgtga tttagtataa agtgaagtaa tggtcaaaag aaaaagtgta aaacgaagta    60
cctagtaata agtaatattg aacaaaataa atggtaaagt gtcagatata taaaataggc    120
tttaataaaa ggaagaaaaa aaacaaacaa aaaataggtt gcaatggggc agagcagagt    180
```

```
catcatgaag ctagaaaggc taccgataga taaactatag ttaattaaat acattaaaaa    240
atacttggat cttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaaagcttg cgtccttga cagcagctgg ttttagagct agaaatagca    480
agttaaaata aggctagtcc gttatcaact tgaaaagtg gcaccgagtc ggtgcttttt    540
tttgcggccg caattggatc gggtttactt attttgtggg tatctatact tttattagat    600
ttttaatcag gctcctgatt tcttttatt tcgattgaat tcctgaactt gtattattca    660
gtagatcgaa taaattataa aaagatataa tcataaaata atatttttatc ctatcaatca    720
tattaaagca atgaatatgt aaaattaatc ttatctttat tttaaaaaat catataggtt    780
tagtattttt ttaaaaataa agataggatt agttttacta ttcactgctt attacttta    840
aaaaaatcat aaaggtttag tatttttta aaataaatat aggaatagtt ttactattca    900
ctgctttaat agaaaaatag tttaaaattt aagatagttt taatcccagc atttgccacg    960
tttgaacgtg agccgaaacg atgtcgttac attatcttaa cctagctgaa acgatgtcgt   1020
cataatatcg ccaaatgcca actgactac gtcgaaccca caaatcccac aaagcgcgtg   1080
aaatcaaatc gctcaaacca caaaaaagaa caacgcgttt gttacacgct caatcccacg   1140
cgagtagagc acagtaacct tcaataagc gaatggggca taatcagaaa tccgaaataa   1200
acctaggggc attatcggaa atgaaaagta gctcactcaa tataaaaatc taggaaccct   1260
agttttcgtt atcactctgt gctccctcgc tctatttctc agtctctgtg tttgcggctg   1320
aggattccga acgagtgacc ttcttcgttt ctcgcaaagg taacagcctc tgctcttgtc   1380
tcttcgattc gatctatgcc tgtctcttat ttacgatgat gtttcttcgg ttatgttttt   1440
ttatttatgc tttatgctgt tgatgttcgg ttgtttgatt cgcttttgtt ttgtggttca   1500
gttttttagg attcttttgg ttttttgaatc gattaatcgg aagagatttt cgagttattt   1560
ggtgtgttgg aggtgaatct ttttttgag gtcatagatc tgttgtattt gtgttataaa   1620
catgcgactt tgtatgattt tttacgaggt tatgatgttc tggttgtttt attatgaatc   1680
tgttgagaca gaaccatgat ttttgttgat gttcgtttac actattaaag gtttgtttta   1740
acaggattaa aagttttta agcatgttga aggagtcttg tagatatgta accgtcgata   1800
gttttttttgt gggtttgttc acatgttatc aagcttaatc ttttactatg tatgcgacca   1860
tatctggatc cagcaaaggc gatttttaa ttccttgtga aacttttgta atatgaagtt   1920
gaaattttgt tattggtaaa ctataaatgt gtgaagttgg agtatacctt taccttccta   1980
tttggctttg tgatagttta atttatatgt attttgagtt ctgacttgta tttctttgaa   2040
ttgattctag tttaagtaat ccatggacaa aaagtactca ataggctcg acatagggac   2100
taactccgtt ggatgggccg tcatcaccga cgagtacaag gtgccctcca agaagttcaa   2160
ggtgttggga aacaccgaca ggcacagcat aaagaagaat ttgatcggtg ccctcctctc   2220
cgactccgga gagaccgctg aggctaccag gctcaagagg accgtactaga ggcgctacac   2280
cagaaggaag aacagaatct gctacctgca ggagatcttc tccaacgaga tggccaaggt   2340
ggacgactcc ttcttccacc gccttgagga atcattcctg gtggaggagg ataaaaagca   2400
cgagagacac ccaatcttcg ggaacatcgt cgacgaggtg gcctaccatg aaaagtaccc   2460
taccatctac cacctgagga agaagctggt cgactctac gacaaggctg acttgcgctt   2520
gatttacctg gctctcgctc acatgataaa gttccgcgga cacttcctca ttgagggaga   2580
cctgaaccca gacaactccg acgtggacaa gctcttcatc cagctcgttc agacctacaa   2640
ccagcttttt gaggagaacc caatcaacgc cagtggagtt gacgccaagg ctatcctctc   2700
tgctcgtctg tcaaagtcca ggaggcttga gaacttgatt ccagctcgtg ctggcgaaaa   2760
gaagaacgga ctgttcggaa acttgatcgc tctctccctg ggattgactc ccaacttcaa   2820
gtccaacttc gacctcgccg aggacgctaa gttgcagttg tctaaagaca cctacgacga   2880
tgacctcgac aacttgctgg cccagatagg cgaccaatac gccgatctct tcctcgccgc   2940
taagaacttg tccgacgcaa tcctgctgtc cgacatccta agagtcaaca ctgagattac   3000
caaagctcct ctgtctgctt tccatgattaa gcgctacgac gagcaccacc aagatctgac   3060
cctgctcaag gccctggtga acagcagct gcccgagaag tacaaggaga tcttttcga   3120
ccagtccaag aacggctacg ccggatacat tgacggaggc gcctcccagg aagagttcta   3180
caagttcatc aagcccatcc ttgagaagat ggacggtacc gaggagctgt tggtgaagtt   3240
gaacagagag gacctgttga ggaagcagag aaccttcgac aacggaagca tccctcacca   3300
aatccacctg ggagagctcc acgccatctt gaggaggcag gaggatttct atcccttcct   3360
gaaggacaac cgcgagaaga ttgagaagat cttgaccttc agaattcctt actacgtcgg   3420
gccactcgcc agaggaaact ctaggttcgc ctggatgacc cgcaaatctg aagagaccat   3480
tactccctgg aacttcgagg aagtcgtgga caaggcgct tccgtcagt cttttcatcga   3540
gaggatgacc aacttcgata aaaatctgcc caacgagaag gtgctgccca gcactccct   3600
gttgtacgag tatttcacag tgtacaacga gctcaccaag gtgaagtacg tcacagaggg   3660
aatgaggaag cctgccttct tgtccggaga gcagaagaag gccatcgtcg acctgctctt   3720
caagaccaac aggaaggtga ctgtcaagca gctgaaggag gactacttca agaagatcga   3780
gtgcttcgac tccgtcgaga tctctggtgt cgaggacagg ttcaacgcct cccttgggac   3840
ttaccacgat ctgctcaaga ttattaaaga caaggacttc ctggacaacg aggagaacga   3900
ggacatcctt gaggacatcg tgctcaccct gaccttgttc gaagacaggg aaatgatcga   3960
agagaggctc aagacctacg cccaccttct cgacgacaag gtgataaagc agcttaagag   4020
acgcagatat accggctggg gaaggctctc ccgcaaattg atcaacggga tcaggacaa   4080
gcagtcaggg aagactatac tcgacttcct gaagtccgac ggattcgcca caggaactt   4140
catgcagctc attcacgacg actccttgac cttcaaggag acatccaga aggctcaggt   4200
gtctggacag ggtgactcct tgcatgagca cattgctaac ttggccggct ctcccgctat   4260
taagaaggga atttttgcaga ccgtgaaggt cgttgacgag ctcgtgaagg tgatgggacg   4320
ccacaagcca gagaacatcg ttattgagat ggctcgcgaa aaccaaacta cccagaaagg   4380
gcagaagaat tccgcgcaga ggatgaagcg cattgaggag gcataaaag agcttggctc   4440
tcagatcctc aaggagcacc ccgtcgaaa cactcagctg cagaacgaga gctgtacct   4500
gtactacctac caaaacggaa gggacatgta cgtggaccaa gagctggaca tcaacaggtt   4560
gtccgactac gacgtcgacc acatcgtgcc tcagtccttc ctgaaggatg actccatcga   4620
caataaagtg ctgacacgct ccgataaaaa tagaggcaag tccgacaacg tccctccga   4680
ggaggtcgtg aagaagatga aaaactctg gagacagctc ttgaacgcca agctcatcac   4740
ccagcgtaag ttcgacaacc tgactaaggc tgagagagga ggattgtccg agctcgataa   4800
ggccggattc atcaagagac agctcgtcga aaccgccaa attccaagc acgtggccca   4860
aattctggat tcccgcatga acaccaagta cgatgaaaat gacaagctga tccgcgaggt   4920
```

```
caaggtgatc accttgaagt ccaagctggt ctccgacttc cgcaaggact tccagttcta    4980
caaggtgagg gagatcaaca actaccacca cgcacacgac gcctacctca acgctgtcgt    5040
tggaaccgcc ctcatcaaaa aatatcctaa gctggagtct gagttcgtct acggcgacta    5100
caaggtgtac gacgtgagga agatgatcgc taagtctgag caggagatcg gcaaggccac    5160
cgccaagtac ttcttctact ccaacatcat gaacttcttc aagaccgaga tcactctcgc    5220
caacggtgag atcaggaagc gcccactgat cgagaccaac ggtgagactg gagagatcgt    5280
gtgggacaaa gggagggatt tcgctactgt gaggaaggtg ctctccatgc ctcaggtgaa    5340
catcgtcaag aagaccgaag ttcagaccgg aggattctcc aaggagtcca tcctccccaa    5400
gagaaactcc gacaagctga tcgctagaaa gaaagactgg gaccctaaga agtacggagg    5460
cttcgattct cctaccgtgg cctactctgt gctggtcgtg gccaaggtgg agaagggcaa    5520
gtccaagaag ctgaaatccg tcaaggagct cctcggcatt accatcatgg agaggagttc    5580
cttcgagaag aaccctatcg acttcctgga ggccaaggga tataagaggg tgaagaagga    5640
cctcatcatc aagctgccca agtactccct cttcgagttg gagaacggaa ggaagaggat    5700
gctggcttct gccggagagt tgcagaaggg aaatgagctc gcccttccct ccaagtacgt    5760
gaacttcctg tacctcgcct ctcactatga aaagttgaag ggctctcctg aggacaacga    5820
gcagaagcag ctcttcgtgg agcagcacaa gcactacctg gacgaaatta tcgagcagat    5880
ctctgagttc tccaagcgcg tgatattggc cgacgccaac ctcgacaagg tgctgtccgc    5940
ctacaacaag cacagggata agcccattcg cgagcaggct gaaacatta tccacctgtt    6000
taccctcaca aacttgggag cccctgctgc cttcaagtac ttcgacacca ccattgacag    6060
gaagagatac acctccacca aggaggtgct cgacgcaaca ctcatccacc aatccatcac    6120
cggcctctat gaaacaagga ttgacttgtc ccagctggga ggcgactcta gagccgatcc    6180
caagaagaag agaaaggtgt aggttaacct agacttgtcc atcttctgga ttggccaact    6240
taattaatgt atgaaataaa aggatgcaca catagtgaca tgctaatcac tataatgtgg    6300
gcatcaaagt tgtgtgttat gtgtaattac tagttatctg aataaaagag aaagagatca    6360
tccatatttc ttatcctaaa tgaatgtcac gtgtctttat aatctttga tgaaccagat    6420
gcatttcatt aaccaaatcc catatacatat aaatattaat catatatcaat    6480
tgggttagca aaacaaatct agtctaggtg tgttttgcga attcgatatc aagcttatcg    6540
ataccgtcga gggggggccc ggtaccggcg cgccgttcta tagtgtcacc taaatcgtat    6600
gtgtatgata cataaggtta tgtattaatt gtagccgcgt tctaacgaca atatgtccat    6660
atggtgcact ctcagtacaa tctgctctga tgccgcatag ttaagccagc cccgacaccc    6720
gccaacaccc gctgacgcgc cctgacgggc ttgtctgctc ccggcatccg cttacagaca    6780
agctgtgacc gtctccggga gctgcatgtg tcagaggttt tcaccgtcat caccgaaacg    6840
cgcgagacga aagggcctcg tgatacgcct atttttatag gttaatgtca tgaccaaaat    6900
cccttaacgt gagttttcgt tccactgagc gtcagacccc gtagaaaaga tcaaaggatc    6960
ttcttgagat ccttttttttc tgcgcgtaat ctgctgcttg caaacaaaaa aaccaccgct    7020
accagcggtg gtttgtttgc cggatcaaga gctaccaact cttttttccga aggtaactgg    7080
cttcagcaga gcgcagatac caaatactgt ccttctagtg tagccgtagt taggccacca    7140
cttcaagaac tctgtagcac cgcctacata cctcgctctg ctaatcctgt taccagtggc    7200
tgctgccagt ggcgataagt cgtgtcttac cgggttggac tcaagacgat agttaccgga    7260
taaggcgcag cggtcgggct gaacgggggg ttcgtgcaca cagcccagct tggagcgaac    7320
gacctacacc gaactgagat acctacacgcg tgagcattga aaagcgcca cgcttcccga    7380
agggagaaag gcggacaggt atccggtaag cggcagggtc ggaacaggag agcgcacgag    7440
ggagcttcca gggggaaacg cctggtatct ttatagtcct gtcgggtttc gccacctctg    7500
acttgagcgt cgatttttgt gatgctcgtc agggggggcgg agcctatgga aaaacgccag    7560
caacgcggcc tttttacggt tcctggcctt ttgctggcct tttgctcaca tgttctttcc    7620
tgcgttatcc cctgattctg tggataaccg tattaccgcc tttgagtgag ctgataccgc    7680
tcgccgcagc cgaacgaccg agcgcagcga gtcagtgagc gaggaagcgg aagagcgccc    7740
aatacgcaaa ccgcctctcc ccgcgcgttg gccgattcat taatgcaggt tgatcagatc    7800
tcgatcccgc gaaattaata cgactcacta tagggagacc acaacggttt ccctctagaa    7860
ataatttttgt ttaactttaa gaaggagata tacccatgga aaagcctgaa ctcaccgcga    7920
cgtctgtcga gaagtttctg atcgaaaagt tcgacacgct ctccgacctg atgcagctct    7980
cggagggcga agaatctcgt gctttcagct tcgatgtagg agggcgtgga tatgtcctgc    8040
gggtaaatag ctgcgccgat ggtttctaca agatcgtta tgtttatcgg cactttgcat    8100
cggccgcgct cccgattccg gaagtgcttg acattgggga attcagcgag agcctgacct    8160
attgcatctc ccgccgtgca caggggtgtca cgttgcaaga cctgcctgaa accgaactgc    8220
ccgctgttct gcagccggtc gcggaggcta tggatgcgat cgctgcggcc gatcttagcc    8280
agacgagcgg gttcggccca ttcggaccgc aaggaatcgg tcaatacact acatggcgtg    8340
atttcatatg cgcgattgct gatccccatg tgtatcactg gcaaactgtg atggacgaca    8400
ccgtcagtgc gtccgtcgcg caggctctcg atgagctgat gctttgggcc gaggactgcc    8460
ccgaagtccg gcacctcgtg cacgcggatt tcggctccaa caatgtcctg acggacaatg    8520
gccgcataac agcggtcatt gactggagcg aggcgatgtt cggggattcc caatacgagg    8580
tcgccaacat cttcttctgg aggccgtggt tggcttgtat ggagcagcag acgcgctact    8640
tcgagcggag gcatccggag cttgcaggat cgccgcggct ccgggcgtat atgctccgca    8700
ttggtcttga ccaactctat cagagcttgg ttgacggcaa tttcgatgat gcagcttggg    8760
cgcagggtcg atgcgacgca atcgtccgat ccggagccgg gactgtcggg cgtacacaaa    8820
tcgcccgcag aagcgcggcc gtctggaccg atggctgtgt agaagtactc gccgatagtg    8880
gaaaccgacg ccccagcact cgtccgaggg caaaggaata gtgaggtaca gcttggatcg    8940
atccggctgc taacaaagcc cgaaaggaag ctgagttggc tgctgccacc gctgagcaat    9000
aactagcata acccccttggg gcctctaaac gggtcttgag ggggttttg ctgaaaggag    9060
gaactatatc cggatgatcg ggcgcgccgg tac                                9093
```

SEQ ID NO: 471        moltype = DNA   length = 9093
FEATURE               Location/Qualifiers
misc_feature       1..9093
                       note = synthesized sequence- QC879
source                1..9093
                       mol_type = other DNA
                       organism = synthetic construct
SEQUENCE: 471

```
ccgggtgtga tttagtataa agtgaagtaa tggtcaaaag aaaaagtgta aaacgaagta    60
cctagtaata agtaatattg aacaaaataa atggtaaagt gtcagatata taaaataggc   120
tttaataaaa ggaagaaaaa aaacaaacaa aaaataggtt gcaatggggc agagcagagt   180
catcatgaag ctagaaaggc taccgataga taaactatag ttaattaaat acattaaaaa   240
atacttggat cttttctctta ccctgtttat attgagacct gaaacttgag agagatacac   300
taatcttgcc ttgttgtttc attccctaac ttacaggact cagcgcatgt catgtggtct   360
cgttccccat ttaagtccca caccgtctaa acttattaaa ttattaatgt ttataactag   420
atgcacaaca acaaagcttg caaccacagc tgctgtcaag ttttagagct agaaatagca   480
agttaaaata aggctagtcc gttatcaact tgaaaaagtg gcaccgagtc ggtgcttttt   540
tttgcggccg caattggatc gggtttactt attttgtggg tatctatact tttattagat   600
ttttaatcag gctcctgatt tcttttttatt tcgattgaat tcctgaactt gtattattca   660
gtagatcgaa taaattataa aaagataaaa tcataaaata atatttttatc ctatcaatca   720
tattaaagca atgaatatgt aaaattaatc ttatctttat tttaaaaaat catataggtt   780
tagtatttt ttaaaaataa agataggatt agttttacta ttcactgctt attacttta   840
aaaaaatcat aaaggtttag tatttttta aaataaatat aggaatagtt ttactattca   900
ctgctttaat agaaaaatag tttaaaattt aagatagttt taatcccagc atttgccacg   960
tttgaacgtg agccgaaacg atgtcgttac attatcttaa cctagctgaa acgatgtcgt  1020
cataatatcg ccaaatgcca actgactac gtcgaaccca caaatcccac aaagcgcgtg  1080
aaatcaaatc gctcaaacca caaaaagaa caacgcgttt gttacacgct caatcccacg  1140
cgagtagagc acagtaacct tcaaataagc gaatggggca taatcagaaa tccgaaataa  1200
acctagggc attatcggaa atgaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgg ttgtttgttt cgctttgttt ttgtggttca  1500
gttttttagg attctttttgg ttttgaatc gattaatcgg aagagatttt cgagttattt  1560
ggtgtgttgg aggtgaatct tttttttgag gtcatagatc tgttgtattt gtgttataaa  1620
catgcgactt tgtatgattt tttacgaggt tatgatgttc tggttgtttt attatgaatc  1680
tgttgagaca gaaccatgat ttttgttgat gttcgtttac actattaaag gtttgtttta  1740
acaggattaa aagttttta agcatgttga aggagtcttg tagatatgta accgtcgata  1800
gttttttgt gggtttgttc acatgttatc aagcttaatc ttttactatg tatgcgacca  1860
tatctggatc cagcaaaggc gattttttaa ttccttgtga aacttttgta atatgaagtt  1920
gaaatttgt tattggtaaa ctaaaatgt gtgaagttgg agtataccttc taccttcttca  1980
tttggctttg tgatagttta atttatatgt atttgagtt ctgactttgta tttcttgaa  2040
ttgattctag tttaagtaat ccatggacaa aaagtactca ataggggctcg acataggggac  2100
taactccgtt ggatgggccg tcatcaccga cgagtacaag gtgccctcca agaagttcaa  2160
ggtgttggga aacaccgaca ggcacagcat aagaagaat ttgatcggtg ccctcctctt  2220
cgactccgga gagaccgctg aggctaccag gctcaagagg accgctagaa ggcgctacac  2280
cagaaggaag aacagaatct gctacctgca ggagatcttc tccaacgaca tggccaaggt  2340
ggacgactcc ttcttccacc gccttgagga atcattcctg gtggaggagg ataaaaagca  2400
cgagagacac ccaatcttcg ggaacatcgt cgacgaggtg gctaccatg aaaagtaccc  2460
taccatctac cacctgagga gaagctggt cgactctacc gacaaggctg acttgcgctt  2520
gatttacctg gctctcgctc acatgataaa gttccgcgaa cactcctca ttgagggaga  2580
cctgaaccca gacaactccg acgtggacaa gctcttcatc cagctcgttc agacctacaa  2640
ccagcttttc gaggagaacc caatcaacgc cagtggagtt gacgccaagg ctatcctctc  2700
tgctcgtctg tcaaagtcca ggaggcttga gaacttgatt gcccagctgc ctggcgaaaa  2760
gaagaacgga ctgttcggaa acttgatcgc tctctcccctg ggattgactc ccaacttcaa  2820
gtccaacttc gacctcgccg aggacgctaa gttgcagttg tctaaagaca cctacgacga  2880
tgacctcgac aacttgctgg cccagatagg cgaccaatac gccgatctct tcctcgccgc  2940
taagaacttg tccgacgcaa tcctgctgtc cgacatcctg agagtcaaca ctgagattac  3000
caaagctcct ctgtctgctt ccatgattaa gcgctacgac gagcaccacc aagatctgac  3060
cctgctcaag gccctggtga gacagcagct gcccgagaag tacaaggaga tctttttcga  3120
ccagtccaag aacggctacg ccggatacat tgacggaggc gcctcccagg aagagttcta  3180
caagttcatc aagcccatcc ttgagaagat ggacggtacc gaggagctgt ggtgaagtt  3240
gaacagagag gacctgttga ggaagcagag aaccttcgac aacggaagca tccctcacca  3300
aatccacctg ggagagctcc acgccatctt gaggaggcag gaggatttct atccttcct  3360
gaaggacaac cgcgagaaga ttgagaagat cttgaccttc agaattccctt actacgtcgg  3420
gccactcgcc agaggaaact ctaggttcgc ctggatgacc cgcaaatctg aagagaccat  3480
tactccctgg aacttcgagg aagtcgttga caagggcgct tccgctcagt ctttcatcga  3540
gaggatgacc aacttcgata aaaatctgcc caacgagag gtgctgccca agcactccct  3600
gttgtacgag tatttcacag tgtacaacga gctcaccaag gtgaagtacg tcacagaggg  3660
aatgaggaag cctgccttct tgtccggaga gcagaagaag gccatcgtcg acctgctctt  3720
caagaccaac aggaaggtga ctgtcaagca gctgaaggag gactacttca gaagatcga  3780
gtgcttcgac tccgtcgaga tctctggtgt cgaggacgag ttcaacgct cccttggaca  3840
ttaccacgat ctgctcaaga ttattaaaga caaggacttc ctggacaacg aggaacgaa  3900
ggacatcctt gaggacatcg tgctcaccct gaccttgttc gaagacaggg aaatgatcga  3960
agagaggctc aagacctacg cccacctctt cgacgacaag gtgatgaaac agctgaagag  4020
acgcagatat accggctggg gaaggctctc ccgcaaattg atcaacggga tcagggacaa  4080
gcagtcaggg aagactatac tcgacttcct gaagtccgac ggattcgcca acagaaactt  4140
catgcagctc attcacgacg actccttgac cttcaaggag gacatccaga aggctcaggt  4200
gtctggacag ggtgactcct tgcatgagca cattgctaac ttggccggct ctcccgctat  4260
taagaagggc attttgcaga ccgtgaaggt cgttgacgag ctcgtgaagg tgatgggacg  4320
ccacaagcca gagaacatcg ttattgagat ggctcgcgag aacccaaacta cccagaaagg  4380
gcagaagaat tccgcgaga ggatgaagcg cattgaggag ggcataaaag agcttggtgc  4440
tcagatcctc aaggagcacc cgtcgagaa cactcagctg cagaacgaga agctgtacct  4500
gtactacctc caaaacggaa gggacatgta cgtggaccag gagctggaca tcaacaggtt  4560
gtccgactac gacgtcgacc acatcgtgcc tcagtccttc ctgaaggatg actccatcga  4620
caataaagtg ctgacacgct ccgataaaaa tagaggcaag tccgacaacg tcccctccga  4680
ggaggtcgtg aagaagatga aaaactactg gagacagctc ttgaacgcca agctcatcac  4740
```

```
ccagcgtaag ttcgacaacc tgactaaggc tgagagagga ggattgtccg agctcgataa   4800
ggccggattc atcaagagac agctcgtcga aacccgccaa attaccaagc acgtggccca   4860
aattctggat tcccgcatga acaccaagta cgatgaaaat gacaagctga tccgcgaggt   4920
caaggtgatc accttgaagt ccaagctggt ctccgacttc cgcaaggact tccagttcta   4980
caaggtgagg gagatcaaca actaccacca cgcacacgag gcctacctca acgctgtcgt   5040
tggaaccgcc ctcatcaaaa aatatcctaa gctggagtct gagttcgtct acggcgacta   5100
caaggtgtac gacgtgagga agatgatcgc taagtctgag caggagatcg gcaaggccac   5160
cgccaagtac ttcttctact ccaacatcat gaacttcttc aagaccgaga tcactctcgc   5220
caacggtgag atcaggaagc gcccactgat cgagaccaac ggtgagactg gagagatcgt   5280
gtgggacaaa gggagggatt tcgctactgt gaggaaggtg ctctccatgc ctcaggtgaa   5340
catcgtcaag aagaccgaag ttcagaccgg aggattctcc aaggagtcca tcctccccaa   5400
gagaaactcc gacaagctga tcgctagaaa gaaagactgg gacctaaga agtacggagg    5460
cttcgattct cctaccgtgg cctactctgt gctggtcgtg gccaaggtgg agaagggcaa   5520
gtccaagaag ctgaaatccg tcaaggagct cctcgggatt accatcatgg agaggagttc   5580
cttcgagaag aacccatcg acttcctgga ggccaaggga tataaagagg tgaagaagga    5640
cctcatcatc aagctgccca agtactccct cttcgagttg gagaacggaa ggaagaggat   5700
gctggcttct gccggagagt tgcagaaggg aaatgagctc gcccttccct ccaagtacgt   5760
gaacttcctg tacctcgcct ctcactatga aagttgaag ggctctcctg aggacaacga    5820
gcagaagcag ctcttcgtgg agcagcacaa gcactacctg gacgaaatta tcgagcagat   5880
ctctgagttc tccaagcgcg tgatattggc cgacgccaac ctcgacaagg tgctgtccgc   5940
ctacaacaag cacagggata agcccattcg cgagcaggct gaaaacatta tccacctgtt   6000
taccctcaca aacttgggag cccctgctgc cttcaagtac ttcgacacca ccattgacag   6060
gaagagatac acctccacca aggaggtgct cgacgcaaca ctcatccacc aatccatcac   6120
cggcctctat gaaacaagga ttgacttgtc ccagctggga ggcgactcta gagccgatcc   6180
caagaagaag agaaaggtgt aggttaacct agacttgtcc atcttctgga ttggccaact   6240
taattaatgt atgaaataaa aggatgcaca catagtgcac ttgctaatcac tataatgtgg    6300
gcatcaaagt tgtgtgttat gtgtaattac tagttatctg aataaaagag aaagagatca   6360
tccatatttc ttatcctaaa tgaatgtcac gtgtctttat aatctttga tgaaccagat    6420
gcatttcatt aaccaaatcc atatacatat aaatattaat catatataat taatatcaat   6480
tgggttagca aaacaaatct agtctaggtg tgttttgcga attcgatatc aagcttatcg   6540
ataccgtcga gggggggccc ggtaccggcg cgccgttcta tagtgtcacc taaatcgtat   6600
gtgtatgata cataaggtta tgtattaatt gtagccgcgt tctaacgaca atatgtccat   6660
atggtgcact ctcagtacaa tctgctctga tgccgcatag ttaagccagc ccgacaccc    6720
gccaacaccc gctgacgcgc cctgacgggc ttgtctgctc ccggcatccg cttacagaca   6780
agctgtgacc gtctccggga gctgcatgtg tcagaggttt tcaccgtcat caccgaaacg   6840
cgcgagacga aagggcctcg tgatacgcct atttttatag gttaatgtca tgaccaaaat   6900
cccttaacgt gagttttcgt tccactgagc gtcagacccc gtagaaaaga tcaaaggatc   6960
ttcttgagat ccttttttttc tgcgcgtaat ctgctgcttg caaacaaaaa aaccaccgct   7020
accagcggtg gtttgtttgc cggatcaaga gctaccaact cttttccga aggtaactgg    7080
cttcagcaga gcgcagatac caaatactgt ccttctagtg tagccgtagt taggccacca   7140
cttcaagaac tctgtagcac cgcctacata cctcgctctg ctaatcctgt taccagtggc   7200
tgctgccagt ggcgataagt cgtgtcttac cgggttggac tcaagacgat agttaccgga   7260
taaggcgcag cggtcgggct gaacggggggg ttcgtgcaca cagcccagct tggagcgaac   7320
gacctacacc gaactgagat acctacagcg tgagcattga gaaagcgcca cgcttcccga   7380
agggagaaag gcggacaggt atccggtaag cggcagggtc ggaacaggag agcgcacgag   7440
ggagcttcca gggggaaacg cctggtatct ttatagtcct gtcgggtttc gccacctctg   7500
acttgagcgt cgatttttgt gatgctcgtc agggggggg agcctatgga aaaacgccag   7560
caacgcggcc tttttacggt tcctggcctt ttgctggcct tttgctcaca tgttctttcc   7620
tgcgttatcc cctgattctg tggataaccg tattaccgcc tttgagtgag ctgataccgc   7680
tcgccgcagc cgaacgaccg agcgcagcga gtcagtgagc gaggaagcgg aagagcgccc   7740
aatacgcaaa ccgcctctcc ccgcgcgttg gccgattcat taatgcaggt tgatcagatc   7800
tcgatcccgc gaaattaata cgactcacta tagggagacc acaacggttt ccctctagaa   7860
ataattttgt ttaactttaa gaaggagata tacccatgga aaagcctgaa ctcaccgcga   7920
cgtcgtcga agtttctg atcgaaaagt tcgacagcgt ctccgacctg atgcagctct     7980
cggagggcga agaatctcgt gctttcagct tcgatgtagg agggcgtgga tatgtcctgc   8040
gggtaaatag ctgcgccgat ggtttctaca aagatcgtta tgtttatcgg cactttgcat   8100
cggccgcgct cccgattccg gaagtgcttg acattgggga attcagcgag agcctgacct   8160
attgcatctc ccgccgtgca cagggtgtca cgttgcaaga cctgcctgaa accgaactgc   8220
ccgctgttct gcagccggtc gcggaggcta tggatgcgat cgctgcggcc gatcttagcc   8280
agacgagcgg gttcggccca ttcggaccgc aaggaatcgg tcaatacact acatggcgtg   8340
atttcatatg cgcgattgct gatccccatg tgtatcactg gcaaactgtg atggacgaca   8400
ccgtcagtgc gtccgtcgcg caggctctcg atgagctgat gctttgggcc gaggactgcc   8460
ccgaagtccg gcacctcgtg cacgcggatt tcggctccaa caatgtcctg acggacaatg   8520
gccgcataac agcggtcatt gactggagcg aggcgatgtt cggggattcc caatacgagg   8580
tcgccaacat cttcttctgg aggccgtggt tggcttgtat ggagcagcag acgcgctact   8640
tcgagcggag gcatccggag cttgcaggat cgccgcggct ccgggcgtat atgctccgca   8700
ttggtcttga ccaactctat cagagcttgg ttgacggcaa tttcgatgat gcagcttggg   8760
cgcagggtcg atgcgacgca atcgtccgat ccggagccgg gactgtcggg cgtacacaaa   8820
tcgcccgcag aagcgcggcc gtctggaccg atggctgtgt agaagtactc gccgatagtg   8880
gaaaccgacg ccccagcact cgtccgaggg caaaggaata gtgaggtaca gcttggatcg   8940
atccggctgc taacaaagcc cgaaaggaag ctgagttggc tgctgccacc gctgagcaat   9000
aactagcata accccttggg gcctctaaac gggtcttgag gggttttttg ctgaaaggag   9060
gaactatatc cggatgatcg ggcgcgccgg tac                                9093
```

SEQ ID NO: 472  moltype = DNA length = 1357
FEATURE    Location/Qualifiers
misc_feature  1..1357
       note = synthesized sequence- RTW1013A
source     1..1357

```
                        mol_type = other DNA
                        organism = synthetic construct
SEQUENCE: 472
ctagaagata aaccctcccc caaaacacaa attagaatga catttcaagt tccatgtatg    60
tcactttcat tctattattt ttacaacttt tagttactta acagatgtct tgttcagcat   120
aaattataat ttattctgtt ttttttttagg gaacaactgt tgtagacaac ttgttgtata   180
gtgaggatat tcattacatg cttggtgcat taaggaccct tggactgcgt gtggaagatg   240
acaaaacaac caaacaagca attgttgaag gctgtggggg attgtttccc actagtaagg   300
aatctaaaga tgaaatcaat ttattccttg gaaatgctgg tattgcaatg agatctttga   360
cagcagctgt tgttgctgca ggtggaaatg caaggtctgt tttttttttt tttgttcagc   420
ataatctttg aattgttcct cgtataacta atcacaacag agtacgtgtt cttcttcctg   480
ttataatcta aaaatctcat ccagattagt catcctttct tcttaaaagg aacctttaat   540
tatcaatgta tttatttaat atttaaatta gcttgtcaaa gtctagcata tacatatttt   600
gattatattc tgagaaatgc acctgagggt gttcctcatg atctacttca acctctgtta   660
ttattagatt ttctatcatg attactggtt tgagtctcta agtagaccat cttgatgttc   720
aaaatatttc agctacgtac ttgatggggt gccccgaatg agagagaggc caattgggga   780
tttggttgct ggtcttaagc aacttggtgc agatgttgat tgcttctctg gcacaaactg   840
tccacctgtt cgtgtaaatg ggaagggagg acttcctggc ggaaaggtat ggtttggatt   900
tcatttagaa taaggtggag taactttcct ggatcaaaat tctaatttaa gaagcctccc   960
tgttttcctc tctttagaat aagactaagg gtaggtttag gagttgggtt ttggagagaa  1020
atggaaggga gagcaatttt tttcttcttc taataaaatat tctttaattt gatacatttt  1080
ttaagtaaaa gaatataaag atagattagc ataacttaat gttttaatct tttatttatt  1140
tttataaaata ttatataccct gtctatttaa aaatcaaata tttgtcctcc attccctttc  1200
ccttcaaaac ctcagttcca aatataccgt agttgaatta tattttggaa ggcctattgg  1260
ttggagactt ttccttttca gagattatcc ctcaccttta ttatagccctt tctattttta  1320
aacttcatat agacgccatt cttggggcgg ccgcgat                            1357

SEQ ID NO: 473         moltype = DNA  length = 1357
FEATURE                Location/Qualifiers
misc_feature           1..1357
                        note = synthesized sequence- RTW1012A
source                 1..1357
                        mol_type = other DNA
                        organism = synthetic construct
SEQUENCE: 473
ctagaagata aaccctcccc caaaacacaa attagaatga catttcaagt tccatgtatg    60
tcactttcat tctattattt ttacaacttt tagttactta acagatgtct tgttcagcat   120
aaattataat ttattctgtt ttttttttagg gaacaactgt tgtagacaac ttgttgtata   180
gtgaggatat tcattacatg cttggtgcat taaggaccct tggactgcgt gtggaagatg   240
acaaaacaac caaacaagca attgttgaag gctgtggggg attgtttccc actagtaagg   300
aatctaaaga tgaaatcaat ttattccttg gaaatgctgg tattgcaatg agatctttga   360
cagcagctgt ggttgctgca ggtggaaatg caaggtctgt tttttttttt tttgttcagc   420
ataatctttg aattgttcct cgtataacta atcacaacag agtacgtgtt cttcttcctg   480
ttataatcta aaaatctcat ccagattagt catcctttct tcttaaaagg aacctttaat   540
tatcaatgta tttatttaat atttaaatta gcttgtcaaa gtctagcata tacatatttt   600
gattatattc tgagaaatgc acctgagggt gttcctcatg atctacttca acctctgtta   660
ttattagatt ttctatcatg attactggtt tgagtctcta agtagaccat cttgatgttc   720
aaaatatttc agctacgtac ttgatggggt gccccgaatg agagagaggc caattgggga   780
tttggttgct ggtcttaagc aacttggtgc agatgttgat tgcttctctg gcacaaactg   840
tccacctgtt cgtgtaaatg ggaagggagg acttcctggc ggaaaggtat ggtttggatt   900
tcatttagaa taaggtggag taactttcct ggatcaaaat tctaatttaa gaagcctccc   960
tgttttcctc tctttagaat aagactaagg gtaggtttag gagttgggtt ttggagagaa  1020
atggaaggga gagcaatttt tttcttcttc taataaaatat tctttaattt gatacatttt  1080
ttaagtaaaa gaatataaag atagattagc ataacttaat gttttaatct tttatttatt  1140
tttataaaata ttatataccct gtctatttaa aaatcaaata tttgtcctcc attccctttc  1200
ccttcaaaac ctcagttcca aatataccgt agttgaatta tattttggaa ggcctattgg  1260
ttggagactt ttccttttca gagattatcc ctcaccttta ttatagccctt tctattttta  1320
aacttcatat agacgccatt cttggggcgg ccgcgat                            1357

SEQ ID NO: 474         moltype = DNA  length = 30
FEATURE                Location/Qualifiers
misc_feature           1..30
                        note = synthesized sequence- primer, soy1-F1
source                 1..30
                        mol_type = other DNA
                        organism = synthetic construct
SEQUENCE: 474
ccactagtaa ggaatctaaa gatgaaatca                                     30

SEQ ID NO: 475         moltype = DNA  length = 24
FEATURE                Location/Qualifiers
misc_feature           1..24
                        note = synthesized sequence- primer, soy1-R2
source                 1..24
                        mol_type = other DNA
                        organism = synthetic construct
SEQUENCE: 475
cctgcagcaa ccacagctgc tgtc                                           24
```

```
SEQ ID NO: 476          moltype = DNA  length = 15
FEATURE                 Location/Qualifiers
misc_feature            1..15
                        note = synthesized sequence- probe, soy1-T1(FAM-MGB
source                  1..15
                        mol_type = other DNA
                        organism = synthetic construct
SEQUENCE: 476
ctgcaatgcg tcctt                                                         15

SEQ ID NO: 477          moltype = DNA  length = 19
FEATURE                 Location/Qualifiers
misc_feature            1..19
                        note = synthesized sequence- primer, cas9-F
source                  1..19
                        mol_type = other DNA
                        organism = synthetic construct
SEQUENCE: 477
ccttcttcca ccgccttga                                                     19

SEQ ID NO: 478          moltype = DNA  length = 21
FEATURE                 Location/Qualifiers
misc_feature            1..21
                        note = synthesized sequence- primer, Cas9-R
source                  1..21
                        mol_type = other DNA
                        organism = synthetic construct
SEQUENCE: 478
tgggtgtctc tcgtgctttt t                                                  21

SEQ ID NO: 479          moltype = DNA  length = 19
FEATURE                 Location/Qualifiers
misc_feature            1..19
                        note = synthesized sequence- probe, Cas9-T(FAM-MGB)
source                  1..19
                        mol_type = other DNA
                        organism = synthetic construct
SEQUENCE: 479
aatcattcct ggtggagga                                                     19

SEQ ID NO: 480          moltype = DNA  length = 25
FEATURE                 Location/Qualifiers
misc_feature            1..25
                        note = synthesized sequence- primer, pINII-99F
source                  1..25
                        mol_type = other DNA
                        organism = synthetic construct
SEQUENCE: 480
tgatgcccac attatagtga ttagc                                              25

SEQ ID NO: 481          moltype = DNA  length = 22
FEATURE                 Location/Qualifiers
misc_feature            1..22
                        note = synthesized sequence- primer, pINII-13R
source                  1..22
                        mol_type = other DNA
                        organism = synthetic construct
SEQUENCE: 481
catcttctgg attggccaac tt                                                 22

SEQ ID NO: 482          moltype = DNA  length = 17
FEATURE                 Location/Qualifiers
misc_feature            1..17
                        note = synthesized sequence- probe, pINII-69T(FAM-MGB)
source                  1..17
                        mol_type = other DNA
                        organism = synthetic construct
SEQUENCE: 482
actatgtgtg catcctt                                                       17

SEQ ID NO: 483          moltype = DNA  length = 23
FEATURE                 Location/Qualifiers
misc_feature            1..23
                        note = synthesized sequence- primer, SIP-130F
source                  1..23
                        mol_type = other DNA
                        organism = synthetic construct
SEQUENCE: 483
ttcaagttgg gcttttcag aag                                                 23
```

```
SEQ ID NO: 484          moltype = DNA  length = 22
FEATURE                 Location/Qualifiers
misc_feature            1..22
                        note = synthesized sequence- primer, SIP-198R
source                  1..22
                        mol_type = other DNA
                        organism = synthetic construct
SEQUENCE: 484
tctccttggt gctctcatca ca                                            22

SEQ ID NO: 485          moltype = DNA  length = 15
FEATURE                 Location/Qualifiers
misc_feature            1..15
                        note = synthesized sequence- probe, SIP-170T(VIC-MGB)
source                  1..15
                        mol_type = other DNA
                        organism = synthetic construct
SEQUENCE: 485
ctgcagcaga accaa                                                    15

SEQ ID NO: 486          moltype = DNA  length = 24
FEATURE                 Location/Qualifiers
misc_feature            1..24
                        note = synthesized sequence- WOL569, Forward_primer
source                  1..24
                        mol_type = other DNA
                        organism = synthetic construct
SEQUENCE: 486
ggacccatta ggtgagagcg tggg                                          24

SEQ ID NO: 487          moltype = DNA  length = 19
FEATURE                 Location/Qualifiers
misc_feature            1..19
                        note = synthesized sequence- WOL876, Reverse_primer
source                  1..19
                        mol_type = other DNA
                        organism = synthetic construct
SEQUENCE: 487
cagctgctgt caaagatct                                                19

SEQ ID NO: 488          moltype = DNA  length = 29
FEATURE                 Location/Qualifiers
misc_feature            1..29
                        note = synthesized sequence- WOL570, Reverse_primer
source                  1..29
                        mol_type = other DNA
                        organism = synthetic construct
SEQUENCE: 488
tctaataata acagaggttg aagtagatc                                     29

SEQ ID NO: 489          moltype = DNA  length = 4104
FEATURE                 Location/Qualifiers
source                  1..4104
                        mol_type = unassigned DNA
                        organism = Glycine max
SEQUENCE: 489
atggacaaaa agtactcaat agggctcgac atagggacta actccgttgg atgggccgtc   60
atcaccgacg agtacaaggt gccctccaag aagttcaagg tgttgggaaa caccgacagg  120
cacagcataa agaagaattt gatcggtgcc ctcctcttcg actccggaga gaccgctgag  180
gctaccaggc tcaagaggac cgctagaagg cgctacacca gaaggaagaa cagaatctgc  240
tacctgcagg agatcttctc caacgagatg gccaaggtgg acgactcctt cttccaccgc  300
cttgaggaat cattcctggt ggaggaggat aaaaagcacg agacaccc  aatcttcggg  360
aacatcgtcg acgaggtggc ctaccatgaa aagtacccca ccatctacca cctgaggaag  420
aagctggtcg actctaccga caaggctgac ttgcgcttga tttacctggc tctcgctcac  480
atgataaagt tccgcggaca cttcctcatt gaggagacc tgaacccaga caactccgac  540
gtggacaagc tcttcatcca gctcgttcag acctacaacc agcttttcga ggagaaccca  600
atcaacgcca gtggagttga cgccaaggct atcctctcgc tcgtctgtc  aaagtccagg  660
aggcttgaga acttgattgc ccagctgcct ggcgaaaaga  agaacggact gttcggaaac  720
ttgatcgctc tctcccctgg gattgactcc aacttcaagt ccaacttcga cctcgccgag  780
gacgctaagt tgcagttgtc taaagacacc tacgacgatg acctcgacaa cttgctggcc  840
cagataggcg accaatacgc cgatctcttc ctcgccgcta gaacttgtc  cgacgcaatc  900
ctgctgtccg acatcctgag agtcaacact gagattacca agctcctct  gtctgcttcc  960
atgattaagc gctacgacga gcaccaccaa gatctgaccc tgctcaaggc cttggtgaga 1020
cagcagctgc ccgagaagta caaggagatc tttttcgacc agtccaagaa cggctacgcc 1080
ggatacattg acgaggcgc  ctcccaggaa gagttctaca gttcatcaa  gcccatcctt 1140
gagaagatga acggtaccga ggagctgttg gtgaagttga acagagagga cctgttgagg 1200
aagcagagaa ccttcgacaa cggaagcatc cctcaccaaa tccacctggg agagctccac 1260
gccatcttga ggaggcagga ggatttctat ccccttcctg aggacaaccg cgagaagatt 1320
```

```
gagaagatct tgaccttcag aattccttac tacgtcgggc cactcgccag aggaaactct    1380
aggttcgcct ggatgacccg caaatctgaa gagaccatta ctccctggaa cttcgaggaa    1440
gtcgtggaca agggcgcttc cgctcagtct ttcatcgaga ggatgaccaa cttcgataaa    1500
aatctgccca acgagaaggt gctgcccaag cactccctgt tgtacgagta tttcacagtg    1560
tacaacgagc tcaccaaggt gaagtacgtc acagagggaa tggaagcc tgccttcttg     1620
tccggagagc agaagaaggc catcgtcgac ctgctcttca agaccaacag gaaggtgact    1680
gtcaagcagc tgaaggagga ctacttcaag aagatcgagt gcttcgactc cgtcgagatc    1740
tctggtgtcg aggacaggtt caacgcctcc cttgggactt accacgatct gctcaagatt    1800
attaaagaca aggacttcct ggacaacgag gagaacgagg acatccttga ggacatcgtg    1860
ctcaccctga ccttgttcga agacagggaa atgatcgaag agaggctcaa gacctacgcc    1920
cacctcttcg acgacaaggt gatgaaacag ctgaagagac gcagatatac cggctgggga    1980
aggctctccc gcaaattgat caacgggatc agggacaagc agtcaggaa gactatactc     2040
gacttcctga agtccgacgg attcgccaac aggaacttca tgcagtccat tcacgacgac    2100
tccttgacct tcaaggagga catccagaag gctcaggtgt ctggacaggg tgactccttg    2160
catgagcaca ttgctaactt ggccggtctc cccgctatta agaagggcat tttgcagacc    2220
gtgaaggtcg ttgacgagct cgtgaaggtg atgggacgcc acaagccaga gaacatcgtt    2280
attgagatgg ctcgcgagaa ccaaactacc cagaaagggc agaagaattc ccgcgagagg    2340
atgaagcgca ttgaggaggg cataaaagag cttggctctc agatcctcaa ggagcacccc    2400
gtcgagaaca ctcagctgca gaacgagaag ctgtacctgt actacctcca aaacggaagg    2460
gacatgtacg tggaccagga gctggacatc aacaggttgt ccgactacga cgtcgaccac    2520
atcgtgcctc agtccttcct gaaggatgac tccatcgaca taaagtgct gacacgctcc     2580
gataaaaata gaggcaagtc cgacaacgtc ccctccgagg aggtcgtgaa aagatgaaa    2640
aactactgga gacagctctt gaacgccaag ctcatcaccc agcgtaagtt cgacaacctg    2700
actaaggctc agagaggagg attgtccgag ctcgataagg ccggattcat caagagacag    2760
ctcgtcgaaa cccgccaaat taccaagcac gtggcccaaa ttctggattc ccgcatgaac    2820
accaagtacg atgaaaatga caagctgatc cgcgaggtca aggtgatcac cttgaagtcc    2880
aagctggtct ccgacttccg caaggacttc cagttctaca aggtgaggga gatcaacaac    2940
taccaccacg cacacgacgc ctacctcaac gctgtcgttg gaaccgccct catcaaaaaa    3000
tatcctaagc tggagtctga gttcgtctac ggcgactaca aggtgtacga cgtgaggaag    3060
atgatcgcta agtctgagca ggagatcggc aaggccaccg ccaagtactt cttctactcc    3120
aacatcatga acttcttcaa gaccgagatc actctcgcca acggtgagat caggaagcgc    3180
ccactgatcg agaccaacgg tgagactgga gagatcgtgt gggacaaagg gagggatttc    3240
gctactgtga ggaaggtgct ctccatgcct caggtgaaca tcgtcaagaa gaccgaagtt    3300
cagaccggag gattctccaa ggagtccatc ctccccaaga gaaactccga caagctgatc    3360
gctagaaaga aagactggga ccctaagaag tacggaggct tcgattctcc taccgtggcc    3420
tactctgtgc tggtcgtggc caaggtggag aagggcaagt ccaagaagct gaaatccgtc    3480
aaggagctcc tcgggattac catcatggag aggagttcct tcgagaagaa ccctatcgac    3540
ttcctggagg ccaagggata taagaggtg aagaaggacc tcatcatcaa gctgcccaag    3600
tactccctct tcgagttgga gaacggaagg aagaggatgc tggcttctgc cggagagttg    3660
cagaagggaa atgagctcgc ccttccctcc aagtacgtga acttcctgta cctgcctct    3720
cactatgaaa agttgaaggg ctccctgag gacaacgagc gaagcagct cttcgtggag    3780
cagcacaagc actacctgga cgaaattatc gagcagatct ctgagttctc caagcgcgtg    3840
atattggccg acgccaacct cgacaaggtg ctgtccgcct acaacaagca cagggataag    3900
cccattcgcg agcaggctga aaacattatc cacctgtttta ccctcacaaa cttgggagcc    3960
cctgctgcct tcaagtactt cgacaccacc attgacagga gagatacac ctccaccaag    4020
gaggtgctcg acgcaacact catccaccaa tccatcaccg gcctctatga aacaaggatt    4080
gacttgtccc agctgggagg cgac                                          4104

SEQ ID NO: 490        moltype = DNA   length = 23
FEATURE               Location/Qualifiers
source                1..23
                      mol_type = unassigned DNA
                      organism = Glycine max
SEQUENCE: 490
gtttgtttgt tgttgggtgt ggg                                              23

SEQ ID NO: 491        moltype = DNA   length = 22
FEATURE               Location/Qualifiers
source                1..22
                      mol_type = unassigned DNA
                      organism = Glycine max
SEQUENCE: 491
tgttgttggg tgtgggaata gg                                               22

SEQ ID NO: 492        moltype = DNA   length = 9174
FEATURE               Location/Qualifiers
misc_feature          1..9174
                      note = synthesized sequence- RTW1199
source                1..9174
                      mol_type = other DNA
                      organism = synthetic construct
SEQUENCE: 492
ccgggtgtga tttagtataa agtgaagtaa tggtcaaaag aaaaagtgta aaacgaagta     60
cctagtaata agtaatattg aacaaaataa atggtaaagt gtcagatata taaaataggc    120
tttaataaaa ggaagaaaaa aaacaaacaa aaaataggtt gcaatggggc agagcagagt    180
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
```

```
atgcacaaca acaaagcttg tttgtttgtt gttgggtgtg ttttagagct agaaatagca    480
agttaaaata aggctagtcc gttatcaact tgaaaaagtg gcaccgagtc ggtgctttt     540
tttgcggccg caattggatc gggtttactt attttgtggg tatctatact tttattagat    600
ttttaatcag gctcctgatt tctttttatt tcgattgaat tcctgaactt gtattattca    660
gtagatcgaa taaattataa aaagataaaa tcataaaata atattttatc ctatcaatca    720
tattaaagca atgaatatgt aaaattaatc ttatcttat tttaaaaaat catataggtt     780
tagtattttt ttaaaaataa agataggatt agttttacta ttcactgctt attactttta    840
aaaaaatcat aaaggtttag tattttttta aaataaatat aggaatagtt ttactattca    900
ctgctttaat agaaaaatag tttaaaattt aagatagttt taatcccagc atttgccacg    960
tttgaacgtg agccgaaacg atgtcgttac attatcttaa cctagctgaa acgatgtcgt    1020
cataatatcg ccaaatgcca actgactac gtcgaaccca caaatcccac aaagcgcgtg     1080
aaatcaaatc gctcaaacca caaaaaagaa caacgcgttt gttacacgct caatcccacg    1140
cgagtagagc acagtaacct tcaaataagc gaatggggca taatcagaaa tccgaaataa    1200
acctaggggc attatcggaa atgaaaagta gctcactcaa tataaaaatc taggaaccct    1260
agttttcgtt atcactctgt gctccctcgc tctatttctc agtctctgtg tttgcggctg    1320
aggattccga acgagtgacc ttcttcgttt ctcgcaaagg taacagcctc tgctcttgtc    1380
tcttcgattc gatctatgcc tgtctcttat ttacgatgat gtttcttcgg ttatgttttt    1440
ttatttatgc tttatgctgt tgatgttcgg ttgtttgttt cgctttgttt ttgtggttca    1500
gttttttagg attcttttgg tttttgaatc gattaatcgg aagagatttt cgagttattt    1560
ggtgtgttgg aggtgaatct tttttttgag gtcatagatc tgttgtattt gtgttataaa    1620
catgcgactt tgtatgattt tttacgaggt tatgatgttc tggttgtttt attatgaatc    1680
tgttgagaca gaaccatgat ttttgttgat gttcgtttac actattaaag gtttgtttta    1740
acaggattaa aagttttta agcatgttga aggagtcttg tagatatgta accgtcgata     1800
gtttttttgt gggtttgttc acatgttatc aagcttaatc ttttactatg tatgcgacca    1860
tatctggatc cagcaaaggc gatttttaa ttccttgtga aacttttgta atatgaagtt     1920
gaaattttgt tattggtaaa ctataaatgt gtgaagttgg agtataccttt taccttctta    1980
tttggctttg tgatagttta atttatatgt attttgagtt ctgacttgta tttctttgaa    2040
ttgattctag tttaagtaat ccatggcacc gaagaagaag cgcaaggtga tggacaaaaa    2100
gtactcaata gggctcgaca tagggactaa ctccgttgga tgggccgtca tcaccgacga    2160
gtacaaggtg ccctccaaga agttcaaggt gttgggaaac accgacaggc acagcataaa    2220
gaagaatttg atcggtgccc tcctcttcga ctccggagag accgctgagg ctaccaggct    2280
caagaggacc gctagaaggc gctacaccag aaggaagaac agaatctgct acctgcagga    2340
gatcttctcc aacgagatgg ccaaggtgga cgactccttc ttccaccgcc ttgaggaatc    2400
attcctggtg gaggaggata aaaagcacga gagacacga atcttcggga acatcgtcga    2460
cgaggtggcc taccatgaaa agtaccctac catctaccac ctgaggaaga agctggtcga    2520
ctctaccgac aaggctgact tgcgcttgat ttacctggct ctcgctcaca tgataaagtt    2580
ccgcggacac ttcctcattg agggagacct gaacccagac aactccgacg tggacaagct    2640
cttcatccag ctcgttcaga cctacaacca gcttttcgag gagaacccaa tcaacgccag    2700
tggagttgac gccaaggcta tcctctctgc tcgtctgtca aagtccagga ggcttgagaa    2760
cttgattgcc cagctgcctg gcgaaaagaa gaacggactg ttcggaaact tgatcgctct    2820
ctccctggga ttgactccca acttcaagtc caacttcgac ctcgccgagg acgctaagtt    2880
gcagttgtct aaagacacct acgacgatga cctcgacaac ttgctggccc agataggcga    2940
ccaatacgcc gatctcttcc tcgccgctaa gaacttgtcc gacgcaatcc tgctgtccga    3000
catcctgaga gtcaacactg agattaccaa agctcctctg tctgcttcca tgattaagcg    3060
ctacgacgag caccaccaag atctgaccct gctcaaggcc ctggtgagac agcagctgcc    3120
cgagaagtac aaggagatct ttttcgacca gtccaagaac ggctacgccg atacattgga    3180
cggaggcgcc tcccaggaag agttctacaa gttcatcaag cccatccttg agaagatgga    3240
cggtaccgag gagctgttgg tgaagttgaa cagagaggac ctgttgagga agcagagaac    3300
cttcgacaac ggaagcatcc ctcaccaaat ccacctggga gagctccacg ccatcttgag    3360
gaggcaggag gatttctatc ccttcctgaa ggacaaccgc gagaagattg agaagatctt    3420
gaccttcaga attccttact acgtcgggcc actcgccaga ggaaactcta ggttcgcctg    3480
gatgacccgc aaatctgaag agaccattac tccctggaac ttcgaggaag tcgtggacaa    3540
gggcgcttcc gctcagtctt tcatcgagag gatgaccaac ttcgataaaa atctgcccaa    3600
cgagaaggtg ctgcccaagc actccctgtt gtacgagtat ttcacagtgt acaacgagct    3660
caccaaggtg aagtacgtca cagagggaat gaggaagcct gccttcttgt ccggagagca    3720
gaagaaggcc atcgtcgacc tgctcttcaa gaccaacagg aaggtgactg tcaagcagct    3780
gaaggaggac tacttcaaga agatcgagtg cttcgactcc gtcgagatct ctggtgtcga    3840
ggacaggttc aacgcctccc ttgggactta ccacgatctg ctcaagatta ttaaagacaa    3900
ggacttcctg gacaacgagg agaacgagga catccttgag gacatcgtgc tcacccctga    3960
cttgttcgaa gacagggaaa tgatcgaaga gaggctcaag acctacgccc accttcttga    4020
cgacaaggtg atgaaacagc tgaagagacg cagatatacc ggctgggaa ggctctcccg     4080
caaattgatc aacgggatca gggacaagca gtcaggaaag actatactcg acttcctgaa    4140
gtccgacgga ttcgccaaca ggaacttcat gcagctcatt cacgacgact ccttgacctt    4200
caaggaggac atccagaagg ctcaggtgtc tggacaggtc gatccttgc atgagcacat     4260
tgctaacttg gccggctctc ccgctattaa gaagggcatt ttgcagaccg tgaaggtcgt    4320
tgacgagctc gtgaaggtga tgggacgcca aagccagag aacatcgtta ttgagatggc     4380
tcgcgagaac caaactaccc agaaagggca gaagaattcc cgcgagagga tgaagcgcat    4440
tgaggagggc ataaaagagc ttggctctca gatcctcaag gagcaccccg tcgagaacac    4500
tcagctgcag aacgagaagc tgtacctgta ctacctccaa acgaaggg acatgtacgt     4560
ggaccaggag ctggacatca acaggttgtc cgactacgac gtcgaccaca tcgtgcctca    4620
gtccttcctg aaggatgact ccatcgacaa taaagtgctg acacgctccg ataaaaatag    4680
aggcaagtcc gacaacgtcc cctccgagga ggtcgtgaag aagatgaaaa actactggag    4740
acagctcttg aacgccaagc tcatcaccca gcgtaagttc gacaacctga ctaaggctga    4800
gagagggaga ttgtccgagc tcgataaggc tggattcatc aagagacagc tcgtcgaaac    4860
ccgccaaatt accaagcacg tggcccaaat tctggattcc cgcatgaaca ccaagtacga    4920
tgaaaatgac aagctgatcc gcgaggtcaa ggtgatcacc ttgaagtcca agctggtctc    4980
cgacttccgc aaggacttcc agttctacaa ggtgagggag atcaacaact accaccacgc    5040
acacgacgcc tacctcaacg ctgtcgttgg aaccgccctc atcaaaaat atcctaagct     5100
ggagtctgag ttcgtctacg gcgactacaa ggtgtacgac gtgaggaaga tgatcgctaa    5160
```

```
gtctgagcag gagatcggca aggccaccgc caagtacttc ttctactcca acatcatgaa    5220
cttcttcaag accgagatca ctctcgccaa cggtgagatc aggaagcgcc cactgatcga    5280
gaccaacggt gagactggag agatcgtgtg ggacaaaggg agggatttcg ctactgtgag    5340
gaaggtgctc tccatgcctc aggtgaacat cgtcaagaag accgaagttc agaccggagg    5400
attctccaag gagtccatcc tccccaagag aaactccgac aagctgatcg ctagaaagaa    5460
agactgggac cctaagaagt acggaggctt cgattctcct accgtggcct actctgtgct    5520
ggtcgtggcc aaggtggaga agggcaagtc caagaagctg aaatccgtca aggagctcct    5580
cgggattacc atcatggaga ggagttcctt cgagaagaac cctatcgact tcctggaggc    5640
caagggatat aaagaggtga agaaggacct catcatcaag ctgcccaagt actccctctt    5700
cgagttggag aacggaagga agaggatgct ggcttctgcc ggagagttgc agaagggaaa    5760
tgagctcgcc cttccctcca agtacgtgaa cttcctgtac ctcgcctctc actatgaaaa    5820
gttgaagggc tctcctgagg acaacgagca gaagcagctc ttcgtggagc agcacaagca    5880
ctacctggac gaaattatcg agcagatctc tgagttctcc aagcgcgtga tattggccga    5940
cgccaacctc gacaaggtgc tgtccgccta caacaagcac agggataagc ccattcgcga    6000
gcaggctgaa aacattatcc acctgtttac cctcacaaac ttgggagccc ctgctgcctt    6060
caagtacttc gacaccacca ttgacaggaa gagatacacc tccaccaagg aggtgctcga    6120
cgcaacactc atccaccaat ccatcaccgg cctctatgaa acaaggattg acttgtccca    6180
gctgggaggc gactctagag ccgatcccaa gaagaagaga aaggtgaaga gaccacggga    6240
ccgccacgat ggcgagctgg gaggccgcaa gcgggcaagg taggttaacc tagacttgtc    6300
catcttctgg attggccaac ttaattaatg tatgaaataa aaggatgcac acatagtgac    6360
atgctaatca ctataatgtg ggcatcaaag ttgtgtgtta tgtgtaatta ctagttatct    6420
gaataaaaga gaaagagatc atccatattt ctttatcctaa gtaatgtca cgtgtcttta    6480
taattctttg atgaaccaga tgcatttcat taaccaaatc catatacata taaatattaa    6540
tcatatataa ttaatatcaa ttgggttagc aaaacaaatc tagtctaggt gtgttttgcg    6600
aattcgatat caagcttatc gataccgtcg agggggggcc cggtaccggc gcgccgttct    6660
atagtgtcac ctaaatcgta tgtgtatgat acataaggtt atgtattaat tgtagccgcg    6720
ttctaacgac aatatgtcca tatggtgcac tctcagtaca atctgctctg atgccgcata    6780
gttaagccag ccccgacacc cgccaacacc cgctgacgcg ccctgacggg cttgtctgct    6840
cccggcatcc gcttacagac aagctgtgac cgtctccggg agctgcatgt gtcagaggtt    6900
ttcaccgtca tcaccgaaac gcgcgagacg aaagggcctc gtgatacgcc tatttttata    6960
ggttaatgtc atgaccaaaa tcccttaacg tgagttttcg ttccactgag cgtcagaccc    7020
cgtagaaaag atcaaaggat cttcttgaga tccttttttt ctgcgcgtaa tctgctgctt    7080
gcaaacaaaa aaaccaccgc taccagcggt ggtttgtttg ccggatcaag agctaccaac    7140
tcttttttcg aaggtaactg gcttcagcag agcgcagata ccaaatactg ttcttctagt    7200
gtagccgtag ttaggccacc acttcaagaa ctctgtagca ccgcctacat acctcgctct    7260
gctaatcctg ttaccagtgg ctgctgccag tggcgataag tcgtgtctta ccgggttgga    7320
ctcaagacga tagttaccgg ataaggcgca gcggtcgggc tgaacggggg gttcgtgcac    7380
acagcccagc ttggagcgaa cgacctacac cgaactgaga tacctacagc gtgagctatg    7440
agaaagcgcc acgcttcccg aagggagaaa ggcggacagg tatccggtaa gcggcagggt    7500
cggaacagga gagcgcacga gggagcttcc aggggaaac gcctggtatc tttatagtcc    7560
tgtcgggttt cgccacctct gacttgagcg tcgatttttg tgatgctcgt caggggggcg    7620
gagcctatgg aaaaacgcca gcaacgcggc cttttttacgg ttcctggcct tttgctggcc    7680
ttttgctcac atgttctttc ctgcgttatc ccctgattct gtggataacc gtattaccgc    7740
ctttgagtga gctgataccg ctcgccgcag ccgaacgacc gagcgcagcg agtcagtgag    7800
cgaggaagcg gaagagcgcc caatacgcaa accgcctctc cccgcgcgtt ggccgattca    7860
ttaatgcagg ttgatcagat ctcgatcccg cgaaattaat acgactcact ataggggagac    7920
cacaacggtt tccctctaga aataattttg tttaacttta agaaggagat atacccatgg    7980
aaaagcctga actcaccgcg acgtctgtcg agaagtttct gatcgaaaag ttcgacagcg    8040
tctccgacct gatgcagctc tcggaggcg aagaatctcg tgctttcagc ttcgatgtag    8100
gagggcgtgg atatgtcctg cgggtaaata gctgcgccga tggtttctac aaagatcgtt    8160
atgtttatcg gcactttgca tcggccgcgc tcccgattc ggaagtgctt gacattgggga    8220
aattcagcga gagcctgacc tattgcatct cccgccgtgc acagggtgtc acgttgcaag    8280
acctgcctga aaccgaactg cccgctgttc tgcagccggt cgcggaggct atggatgcga    8340
tcgctgcggc cgatcttagc cagacgagcg ggttcggccc attcggaccg caaggaatcg    8400
gtcaatacac tacatggcgt gatttcatat gcgcgattgc tgatccccat gtgtatcact    8460
ggcaaactgt gatggacgac accgtcagtg cgtccgtcgc gcaggctctc gatgagctga    8520
tgctttgggc cgaggactgc cccgaagtcc ggcacctcgt gcacgcggat ttcggctcca    8580
acaatgtcct gacggacaat ggccgcataa cagcggtcat tgactggagc gaggcgatgt    8640
tcggggattc ccaatacgag gtcgccaaca tcttcttctg gaggccgtgg ttggcttgta    8700
tggagcagca gacgcgctac ttcgagcgga ggcatccgga gcttgcagga tcgccgcggc    8760
tccgggcgta tatgctccgc attggtcttg accaactcta tcagagcttg gttgacggca    8820
atttcgatga tgcagcttgg gcgcagggtc gatgcgacgc aatcgtccga tccggagccg    8880
ggactgtcgg gcgtacacaa atcgcccgca gaagcgcggc cgtctggacc gatggctgtg    8940
tagaagtact cgccgatagt ggaaaccgac gccccagcac tcgtccgagg gcaaaggaat    9000
agtgaggtac agcttggatc gatccggctg ctaacaaagc ccgaaaggaa gctgagttgg    9060
ctgctgccac cgctgagcaa taactagcat aaccccttgg ggcctctaaa cgggtcttga    9120
ggggttttt gctgaaagga ggaactatat ccggatgctc gggcgcgccg gtac           9174
```

SEQ ID NO: 493       moltype = DNA  length = 9174
FEATURE              Location/Qualifiers
misc_feature      1..9174
                        note = synthesized sequence- RTW1200
source              1..9174
                        mol_type = other DNA
                        organism = synthetic construct
SEQUENCE: 493
```
ccgggtgtga tttagtataa agtgaagtaa tggtcaaaag aaaaagtgta aaacgaagta    60
cctagtaata agtaatattg aacaaaataa atggtaaagt gtcagatata taaaataggc   120
tttaataaaa ggaagaaaaa aaacaaacaa aaaataggtt gcaatgggc agagcagagt   180
```

```
catcatgaag ctagaaaggc taccgataga taaactatag ttaattaaat acattaaaaa    240
atacttggat ctttctctta ccctgtttat attgagacct gaaacttgag agagatacac    300
taatcttgcc ttgttgtttc attccctaac ttacaggact cagcgcatgt catgtggtct    360
cgttccccat ttaagtccca caccgtctaa acttattaaa ttattaatgt ttataactag    420
atgcacaaca acaaagcttg tgttgttggg tgtgggaatg ttttagagct agaaatagca    480
agttaaaata aggctagtcc gttatcaact tgaaaaagtg gcaccgagtc ggtgcttttt    540
tttgcggccg caattggatc gggtttactt attttgtggg tatctatact tttattagat    600
ttttaatcag gctcctgatt tctttttatt tcgattgaat tcctgaactt gtattattca    660
gtagatcgaa taaattataa aaagataaaa tcataaaata atattttatc ctatcaatca    720
tattaaagca atgaatatgt aaaattaatc ttatctttat tttaaaaaat catataggtt    780
tagtattttt ttaaaaataa agataggatt agttttacta ttcactgctt attacttttt    840
aaaaaatcat aaaggtttag tattttttta aaataaatat aggaatagtt ttactattca    900
ctgctttaat agaaaaatag tttaaaattt aagatagttt taatcccagc atttgccacg    960
tttgaacgtg agccgaaacg atgtcgttac attatcttaa cctagctgaa acgatgtgct   1020
cataatatcg ccaaatgcca actgactac gtcgaaccca caaatcccac aaagcgcgtg    1080
aaatcaaatc gctcaaacca caaaaaagaa caacgcgttt gttacacgct caatcccacg   1140
cgagtagagc acagtaacct tcaaataagc gaatggggca taatcagaaa tccgaaataa   1200
acctaggggc attatcggaa atgaaaagta gctcactcaa tataaaaatc taggaaccct   1260
agttttcgtt atcactctgt gctccctcgc tctatttctc agtctctgtg tttgcggctg   1320
aggattccga acgagtgacc ttcttcgttt ctcgcaaagg taacagcctc tgctcttgtc   1380
tcttcgattc gatctatgcc tgtctcttat ttacgatgat gtttcttcgg ttatgttttt   1440
ttatttatgc tttatgctgt tgatgttcgg ttgtttgttt cgcttttgtt ttgtggttca   1500
gtttttttagg attctttttgg tttttgaatc gattaatcgg aagagatttt cgagttattt   1560
ggtgtgttgg aggtgaatct tttttttgag gtcatagatc tgttgtattt gtgttataaa   1620
catgcgactt tgtatgattt tttacgaggt tatgatgttc tggttgtttt attatgaatc   1680
tgttgagaca gaaccatgat tttttgttgat gttcgtttac actattaaag gtttgttttta  1740
acaggattaa aagttttttta agcatgttga aggagtcttg tagatatgta accgtcgata   1800
gttttttttgt gggtttgttc acatgttatc aagcttaatc ttttactatg tatgcgacca   1860
tatctggatc cagcaaaggc gatttttttaa ttccttgtga aacttttgta atatgaagtt   1920
gaaattttgt tattggtaaa ctataaatgt gtgaagttgg agtatacctt taccttctta   1980
tttggctttg tgatagttta atttatatgt attttgagtt ctgacttgta tttctttgaa   2040
ttgattctag tttaagtaat ccatggcacc gaagaagaag cgcaaggtga tggacaaaaa   2100
gtactcaata gggctcgaca tagggactaa ctccgttgga tgggccgtca tcaccgacga   2160
gtacaaggtg ccctccaaga agttcaaggt gttgggagag accgacagga acagcataaa   2220
gaagaatttg atcggtgccc tcctcttcga ctccggagag accgctgagg ctaccaggct   2280
caagaggacc gctagaaggc gctacaccag aaggaagaac agaatctgct acctgcagga   2340
gatcttctcc aacgagatgg ccaaggtgga cgactccttc ttccaccgcc ttgaggaatc   2400
attcctggtg gaggaggata aaaagcacga gagacaccca atcttcggga acatcgtcga   2460
cgaggtggcc taccatgaaa agtacccctac catctaccac ctgaggaaga agctggtcga   2520
ctctaccgac aaggctgact gcgcttgat ttacctggct ctcgctcaca tgataaagtt   2580
ccgcggacac ttcctcattg agggagacct gaacccagac aactccgacg tggacaagct   2640
cttcatccag ctcgttcaga cctacaacca gcttttcgag gagaacccaa tcaacgccag   2700
tggagttgac gccaaggcta tcctctctgc tcgtctgtca aagtccagga ggcttgagaa   2760
cttgattgcc cagctgcctg gcgaaaagaa gaacggactg ttcggaaact tgatcgctct   2820
ctccctggga ttgactccca acttcaagtc caacttcgac ctcgccgagg acgctaagtt   2880
gcagttgtct aaagacacct acgacgatga cctcgacaac ttgctggccc agataggcga   2940
ccaatacgcc gatctcttcc tcgccgctaa gaacttgtcc gacgcaatcc tgctgtccga   3000
catcctgaga gtcaacactg agattaccaa agctcctctg tctgcttcca tgattaagcg   3060
ctacgacgag caccaccaag atctgaccct gctcaaggcc ctggtgagac agcagctgcc   3120
cgagaagtac aaggagatct ttttcgacca gtccaagaac ggctacgccg atacattgga   3180
cggaggcgcc tcccaggaag agttctacaa gttcatcaag cccatccttg agaagatgga   3240
cggtaccgag gagctgttgg tgaagttgaa cagagaggac ctgttgagga agcagagaac   3300
cttcgacaac ggaagcatcc ctcaccaaat ccacctggga gagctccacg ccatcttgag   3360
gaggcaggag gatttctatc ccttcctgaa ggacaaccgc gagaagattg agaagatctt   3420
gaccttcaga attccttact acgtcgggcc actcgccagg ggaaactcta ggttcgcctg   3480
gatgacccgc aaatctgaag agaccattac tccctggaac ttcgaggaag tcgtggacaa   3540
gggcgcttcc gctcagtctt tcatcgagag gatgaccaac ttcgataaaa atctgcccaa   3600
cgagaaggtg ctgcccaagc actccctgtt gtacgagtat ttcacagtgt acaacgagct   3660
caccaaggtg aagtacgtca cagagggaat gaggaagcct gccttcttgt ccggagagca   3720
gaagaaggcc atcgtcgacc tgctcttcaa gaccaacagg aaggtgactg tcaagcagct   3780
gaaggaggac tacttcaaga agatcgagtg cttcgactcc gtcgagatct ctggtgtcga   3840
ggacaggttc aacgcctccc ttgggactta ccacgatctg ctcaagatta ttaaagacaa   3900
ggacttcctg gacaacgagg agaacgagga catccttgag gacatcgtgc tcaccctgac   3960
cttgttcgaa gacagggaaa tgatcgaaga gaggctcaag acctacgccc acctcttcga   4020
cgacaaggtg atgaaacagc tgaagagacg cagatatacc ggctggggaa ggctctcccg   4080
caaattgatc aacgggatca gggacaagca gtcaggaag actatactcg acttcctgaa   4140
gtccgacgga ttcgccaaca ggaacttcat gcagctcatt cacgacgact ccttgacctt   4200
caaggaggac atccagaagg ctcaggtgtc tggacagggt gactccttgc atgagcacat   4260
tgctaacttg gccggctctc ccgctattaa gaagggcatt ttgcagaccg tgaaggtcgt   4320
tgacgagctc gtgaaggtga tgggacgcca caagccagag aacatcgtta ttgagatggc   4380
tcgcgagaac caaactaccc agaaaggca gaagaattcc cgcgagagga tgaagcgcat   4440
tgaggagggc ataaaagagc ttggctctca gatcctcaag gagcaccccg tcgagaacac   4500
tcagctgcag aacgagaagc tgtacctgta ctacctccaa aacggaaggg acatgtacgt   4560
ggaccaggag ctgacctca acggttgtc cgactacgag gtcgaccaca tcgtgcctca   4620
gtccttcctg aaggatgact ccatcgacaa taaagtgctg acacgctccg ataaaaatag   4680
aggcaagtcc gacaacgtcc cctccgagga ggtcgtgaag aagatgaaaa actactggag   4740
acagctcttg aacgccaagc tcatcaccca gcgtaagttc gacaacctga ctaaggctga   4800
gagaggagga ttgtccgagc tcgataaggc cggattcatc aagagacagc tcgtcgaaac   4860
ccgccaaatt accaagcacg tggcccaaat tctggattcc cgcatgaaca ccaagtacga   4920
```

```
tgaaaatgac aagctgatcc gcgaggtcaa ggtgatcacc ttgaagtcca agctggtctc   4980
cgacttccgc aaggacttcc agttctacaa ggtgagggag atcaacaact accaccacgc   5040
acacgacgcc tacctcaacg ctgtcgttgg aaccgccctc atcaaaaaat atcctaagct   5100
ggagtctgag ttcgtctacg gcgactacaa ggtgtacgac gtgaggaaga tgatcgctaa   5160
gtctgagcag gagatcggca aggccaccgc caagtacttc ttctactcca acatcatgaa   5220
cttcttcaag accgagatca ctctcgccaa cggtgagatc aggaagcgcc cactgatcga   5280
gaccaacggt gagactggag agatcgtgtg ggacaaaggg agggatttcg ctactgtgag   5340
gaaggtgctc tccatgcctc aggtgaacat cgtcaagaag accgaagttc agaccggagg   5400
attctccaag gagtccatcc tccccaagag aaactccgac aagctgatcg ctagaaagaa   5460
agactgggac cctaagaagt acgaggcttt cgattctcct accgtggcct actctgtgct   5520
ggtcgtggcc aaggtggaga agggcaagtc caagaagctg aaatccgtca aggagctcct   5580
cgggattacc atcatggaga ggagttcctt cgagaagaac cctatcgact tcctggaggc   5640
caagggatat aaagaggtga agaaggacct catcatcaag ctgcccaagt actccctctt   5700
cgagttggag aacgaaagga agaggatgct ggcttctgcc agagagttgc agaagggaaa   5760
tgagctcgcc cttccctcca agtacgtgaa cttcctgtac ctcgcctctc actatgaaaa   5820
gttgaagggc tctcctgagg acaacgtagca gaagcagctc ttcgtggagc agcacaagca   5880
ctacctggac gaaattatcg agcagatctc tgagttctcc aagcgcgtga tattggccga   5940
cgccaacctc gacaaggtgc tgtccgccta caacaagcac agggataagc ccattcgcga   6000
gcaggctgaa aacattatcc acctgtttac cctcacaaac ttgggagccc tgctgccttt   6060
caagtacttc gacaccacca ttgacaggaa gagatacacc tccaccaagg aggtgctcga   6120
cgcaacactc atccaccaat ccatcaccgg cctctatgaa acaaggattg acttgtccca   6180
gctgggaggc gactctagag ccgatcccaa gaagaagaa aaggtgaaga gaccacggga   6240
ccgccacgat ggcgagctgg gaggccgcaa gcgggcaagg taggttaacc tagacttgtc   6300
catcttctgg attggccaac ttaattaatg tatgaaataa aaggatgcac acatagtgac   6360
atgctaatca ctataatgtg ggcatcaaag ttgtgtgtta tgtgtaatta ctagttatct   6420
gaataaaaga gaaagagatc atccatattt cttatcctaa atgaatgtca cgtgtcttta   6480
taattctttg atgaaccaga tgcatttcat taaccaaatc catatacata taaattattaa   6540
tcatatataa ttaatatcaa ttgggttagc aaaacaaatc tagtctaggt gtgttttgcg   6600
aattcgatat caagcttatc gataccgtcg aggggggggcc cggtaccggc gcgccgttct   6660
atagtgtcac ctaaatcgta tgtgtatgat acataaggtt atgtattaat tgtagccgcg   6720
ttctaacgac aatatgtcca tatggtgcac tctcagtaca atctgctctg atgccgcata   6780
gttaagccag ccccgacacc cgccaacacc cgctgacgcg ccctgacggg cttgtctgct   6840
cccggcatcc gcttacagac aagctgtgac cgtctccggg agctgcatgt gtcagaggtt   6900
ttcaccgtca tcaccgaaac gcgcgagacg aaagggcctc gtgatacgcc tatttttata   6960
ggttaatgtc atgaccaaaa tcccttaacg tgagttttcg ttccactgag cgtcagaccc   7020
cgtagaaaag atcaaaggat cttcttgaga tccttttttt ctgcgcgtaa tctgctgctt   7080
gcaaacaaaa aaccaccgc taccagcggt ggtttgtttg ccggatcaag agctaccaac   7140
tctttttccg aaggtaactg gcttcagcag agcgcagata ccaaatactg ttcttctagt   7200
gtagccgtag ttaggccacc acttcaagaa ctctgtagca ccgcctacat acctcgctct   7260
gctaatcctg ttaccagtgg ctgctgccag tggcgataag tcgtgtctta ccgggttgga   7320
ctcaagacga tagttaccgg ataaggcgca gcggtcgggc tgaacggggg gttcgtgcac   7380
acagcccagc ttggagcgaa cgacctacac cgaactgaga tacctacagc gtgagctatg   7440
agaaagcgcc acgcttcccg aagggagaaa ggcggacagg tatccggtaa gcggcagggt   7500
cggaacagga gagcgcacga gggagcttcc agggggaaac gcctggtatc tttatagtcc   7560
tgtcgggttt cgccacctct gacttgagcg tcgatttttg tgatgctcgt cagggggggcg   7620
gagcctatgg aaaaacgcca gcaacgcggc ctttttacgg ttcctggcct tttgctggcc   7680
ttttgctcac atgttctttc ctgcgttatc ccctgattct gtggataaac gtattaccgc   7740
ctttgagtga gctgataccg ctcgccgcag ccgaacgacc gagcgcagcg agtcagtgag   7800
cgaggaagcg gaagagcgcc caatacgcaa accgcctctc cccgcgcgtt ggccgattca   7860
ttaatgcagg ttgatcagat ctcgatcccg cgaaattaat acgactcact ataggggac   7920
cacaacggtt tccctctaga aataatttg tttaacttta agaaggagat atacccatgg   7980
aaaagcctga actcaccgcg acgtctgtcg agaagtttct gatcgaaaag ttcgacagcg   8040
tctccgacct gatgcagctc tcggagggcg aagaatctcg tgctttcagc ttcgatgtag   8100
gagggcgtgg atatgtcctg cgggtaaata gctgcgccga tggtttctac aaagatcgtt   8160
atgtttatcg gcactttgca tcggccgcgc tcccgatcc ggaagtgctt gacattgggg   8220
aattcagcga gagcctgacc tattgcatct cccgccgtgc acagggtgtc acgttgcaag   8280
acctgcctga aaccgaactg cccgctgttc tgcagccggt cgcggaggct atggatgcga   8340
tcgctgcggc cgatcttagc cagacgagcg gttcggccc attcggaccg caaggaatcg   8400
gtcaatacac tacatggcgt gatttcatat gcgcgattgc tgatccccat gtgtatcact   8460
ggcaaactgt gatggacgac accgtcagtg cgtccgtcgc gcaggctctc gatgagctga   8520
tgctttgggc cgaggactgc cccgaagtcc ggcaccgcgt gcacgcggat tcggctcca   8580
acaatgtcct gacggacaat ggccgcataa cagcggtcat tgactggagc gaggcgatgt   8640
tcggggattc ccaatacgag gtcgccaaca tcttcttctg gaggccgtgg ttggcttgta   8700
tggagcagca gacgcgctac ttcgagcgga ggcatccgga gcttgcagga tcgccgcggc   8760
tccgggcgta tatgctccgc attggtcttg accaactcta tcagagcttg gttgacggca   8820
atttcgatga tgcagcttgg gcgcagggtc gatgcgacgc aatcgtccga tccggagccg   8880
ggactgtcgg gcgtacacaa atcgcccgca gaagcgcggc cgtctggacc gatggctgtg   8940
tagaagtact cgccgatagt ggaaaccgac gccccagcac tcgtccgagg gcaaaggaat   9000
agtgagttag agcttggatc gatccggctg ctaacaaagc ccgaaaggaa gctgagttgg   9060
ctgctgccac cgctgagcaa taactagcat aaccccttgg ggcctctaaa cgggtcttga   9120
ggggtttttt gctgaaagga ggaactatat ccgatgctc gggcgcgccg gtac         9174

SEQ ID NO: 494        molType = DNA    length = 3175
FEATURE               Location/Qualifiers
misc_feature          1..3175
                      note = synthesized sequence- RTW1190A
source                1..3175
                      mol_type = other DNA
                      organism = synthetic construct
```

```
SEQUENCE: 494
cgaattctac aggtcactaa taccatctaa gtagttggtt catagtgact gcatatgtaa    60
aaattatcct tattttaagg aaattaaaaa ttatcatata tatataagtt ttaaattaat   120
tatcttatat atgtaccaaa aagttttaaa gcaattatta taaaaattaa taaatttatc   180
atataaaata atttataatt aaattttaaa ttatcaattc attaaattaa attatttaaa   240
attttgaat gataatataa taatttttatc ctctactaag tcccaacgtt tcctatttta   300
ttccactttt agcaataaat tttgtcataa acacttataa caaaaaagt aagtaaaaaa   360
taaaaaaaag tttttcaata aagtataaac taatttgtat aaacttttag aaaaaatata   420
gttatacatt gataatataa attttttaca taattatccg atcaactcat tatatatgat   480
aaatttattg atttttttaaa ataattatct taaaataatt taaacaatga tttgcaatta   540
gatgataata taaaattatt ttacacacta catgtattaa actcaaactt ttatatatta   600
gtttttctaa aaactaattt ttaactcaaa aaaaatgtta cttataattt tcttatcttc   660
tttttttata agtattttt aagaaattta ttgaaacatg accatgcttg ggtcaataat   720
actactctct tagacaccaa acaacccttc ccaaactata atctaatcca aaagccatca   780
ttcatttttcc ttggtaggta aagttccaag accttcacca acttttttcac tcaattgttt   840
tggtgtaagc aattcgacat gtgttagtgt tagttggcaa ccaaaaatcc ctttatgtga   900
ctcaatccaa caaccactca caccaccaac ccccataacc atttctcaca ataccctttca   960
tttacacatt atcatcacca aaaataaata aaaaaaacct ctcatttcag agagagagag  1020
agagacttca cagaccaaag tgcagagaac aacaaagttc acaactttaa ggaaaattga  1080
aatggcccaa gtgagcagag tgcacaatct tgctcaaagc actcaaattt ttggccattc  1140
ttccaactcc aacaaactca aatcggtgaa ttcggtttca ttgaggccac gcctttgggg  1200
ggcctcaaaa tctcgcatcc cgatgcataa aatgggaa atttaatgt                1260
ggggaaggga aattccggcg tgtttaaggt ttctgcatcg gtcgccgccg cagagaagcc  1320
gtcaacgtcg ccggagatcg tgttggaacc catcaaagac ttctcgggta ccatcacatt  1380
gccagggtcc aagtctctgt ccaatcgaat tttgcttctt gctgctctct ctgaggttcg  1440
tagatttctt ccgttttttt ttcttcttct ttattgtttt ttctacatcg gcatgatgtt  1500
gatttgattg tgttttctat cgtttcatcg attataaatt ttcataatca gaagattcag  1560
ctttttattaa tgcaagaacg tccttaattg atgattttat aaccgtaaat taggtctaat  1620
tagagttttt ttcataaaga ttttcagatc cgttacaac aagccttaat tgttgattct  1680
gtagtcgtag attaaggttt ttttcatgaa ctacttcaga tccgttaaac acagccttta  1740
tttgttgata cttcagtcgt ttttcaagaa attgttcaga tccgttgata aaagccttat  1800
tcgttgattc tgtatggtat ttcaagagat attgctcagg tcctttagca actacccttat  1860
ttgttgattc tgtggccata gattaggatt ttttttcacg aaattgcttc ttgaaattac  1920
gtgatggatt ttgattctga tttatcttgt gattgttgac tctacaggga caactgttg   1980
tagacaactt gttgtatagt gaggatattc attacatgct tggtcatta aggacccttg  2040
gactgcgtgt ggaagatgac aaaacaacca aacaagcaat tgttgaaggc tgtgggggat  2100
tgtttcccac tagtaaggaa tctaaagatg aaatcaattt attccttgga aatgctggta  2160
ttgcaatgag atctttgaca gcagctgttg ttgctgcagg tggaaatgca aggtctgttt  2220
ttttttttt tgttcagcat aatctttgaa ttgttcctcg tataactaat cacaacagag  2280
tacgtgttct tcttcctgtt ataatctaaa aatctcatcc agattagtca tcctttcttc  2340
ttaaaggaa ccttttaatta tcaatgtatt tatttaatat ttaaattagc ttgtcaaagt   2400
ctagcatata catatttga ttatattctg agaaatgcac ctgagggtgt tcctcatgat  2460
ctacttcaac ctctgttatt attagatttt ctatcatgat tactggtttg agtctctaag  2520
tagaccatct tgatgttcaa aatatttcag ctacgtactt gatggggtgc cccgaatgag  2580
agagaggcca attgggggatt tggttgctgg tcttaagcaa cttggtgcag atgttgattg  2640
cttttcttggc acaaactgtc cacctgttcg tgtaaatggg aagggaggac ttcctggcgg  2700
aaaggtatgg tttggatttc actttagaata aggtggagta acttcctgg atcaaaattc  2760
taatttaaga agcctccctg ttttcctctc tttagaataa gactaaggggt aggtttagga  2820
gttgggtttt ggagagaaat ggaagggaga gcaatttttt tcttcttcta ataaatattc  2880
tttaatttga tacatttttt aagtaaaga atataaagat agattagcat aacttaatgt  2940
tttaatcttt tatttatttt tataaatatt atataccgtg ctatttaaaa atcaaatatt  3000
tgtcctccat tcccttttccc ttcaaacct cagttccaaa tataccgtag ttgaattata  3060
ttttggaagg cctattggtt ggagacttttt cctttcaga gattatccct cacctttatt  3120
atagcctttc tattttaaa cttcatatag acgccattct tggggcggcc gcgat        3175

SEQ ID NO: 495          moltype = DNA   length = 23
FEATURE                 Location/Qualifiers
misc_feature            1..23
                        note = synthesized sequence- primer, soy1-F3
source                  1..23
                        mol_type = other DNA
                        organism = synthetic construct
SEQUENCE: 495
gtttgtttgt tgttgggtgt ggg                                            23

SEQ ID NO: 496          moltype = DNA   length = 25
FEATURE                 Location/Qualifiers
misc_feature            1..25
                        note = synthesized sequence- primer, soy1-R3
source                  1..25
                        mol_type = other DNA
                        organism = synthetic construct
SEQUENCE: 496
gacatgatgc ttcattttca cagaa                                          25

SEQ ID NO: 497          moltype = DNA   length = 18
FEATURE                 Location/Qualifiers
misc_feature            1..18
                        note = synthesized sequence- probe, soy1-T2(FAM-MGB)
```

```
source                   1..18
                         mol_type = other DNA
                         organism = synthetic construct
SEQUENCE: 497
tgtgtagagt ggattttg                                                    18

SEQ ID NO: 498           moltype = DNA  length = 22
FEATURE                  Location/Qualifiers
misc_feature             1..22
                         note = synthesized sequence- primer, soy1-F2
source                   1..22
                         mol_type = other DNA
                         organism = synthetic construct
SEQUENCE: 498
tgttgttggg tgtgggaata gg                                               22

SEQ ID NO: 499           moltype = DNA  length = 31
FEATURE                  Location/Qualifiers
misc_feature             1..31
                         note = synthesized sequence- WOL1001, Forward_primer
source                   1..31
                         mol_type = other DNA
                         organism = synthetic construct
SEQUENCE: 499
aggtttaatt ttatataatg ttagcataca g                                     31

SEQ ID NO: 500           moltype = DNA  length = 28
FEATURE                  Location/Qualifiers
misc_feature             1..28
                         note = synthesized sequence- 500 WOL1002, Reverse_primer
source                   1..28
                         mol_type = other DNA
                         organism = synthetic construct
SEQUENCE: 500
atcaacatca tgctgatgta gaacaaac                                         28

SEQ ID NO: 501           moltype = DNA  length = 29
FEATURE                  Location/Qualifiers
misc_feature             1..29
                         note = synthesized sequence- 501 WOL1003, Forward_primer
source                   1..29
                         mol_type = other DNA
                         organism = synthetic construct
SEQUENCE: 501
attctgattt atcttgtgat tgttgactc                                        29

SEQ ID NO: 502           moltype = DNA  length = 27
FEATURE                  Location/Qualifiers
misc_feature             1..27
                         note = synthesized sequence- WOL1004, Reverse_primer
source                   1..27
                         mol_type = other DNA
                         organism = synthetic construct
SEQUENCE: 502
atttactttg gagagaataa ggagggg                                          27

SEQ ID NO: 503           moltype = DNA  length = 23
FEATURE                  Location/Qualifiers
source                   1..23
                         mol_type = unassigned DNA
                         organism = Glycine max
SEQUENCE: 503
gaaacgttgg gacttagtag agg                                              23

SEQ ID NO: 504           moltype = DNA  length = 23
FEATURE                  Location/Qualifiers
source                   1..23
                         mol_type = unassigned DNA
                         organism = Glycine max
SEQUENCE: 504
ggaataaaat aggaaacgtt ggg                                              23

SEQ ID NO: 505           moltype = DNA  length = 9174
FEATURE                  Location/Qualifiers
misc_feature             1..9174
                         note = synthesized sequence- RTW1201
source                   1..9174
                         mol_type = other DNA
                         organism = synthetic construct
```

```
SEQUENCE: 505
ccgggtgtga tttagtataa agtgaagtaa tggtcaaaag aaaaagtgta aaacgaagta   60
cctagtaata agtaatattg aacaaaataa atggtaaagt gtcagatata taaaataggc  120
tttaataaaa ggaagaaaaa aaacaaacaa aaaataggtt gcaatggggc agagcagagt  180
catcatgaag ctagaaaggc taccgataga taaactatag ttaattaaat acattaaaaa  240
atacttggat cttctctta ccctgtttat attgagacct gaaacttgag agagatacac   300
taatcttgcc ttgttgtttc attccctaac ttacaggact cagcgcatgt catgtggtct  360
cgttccccat ttaagtccca caccgtctaa acttattaaa ttattaatgt ttataactag  420
atgcacaaca acaaagcttg aaacgtttggg acttagtagg ttttagagct agaaatagca  480
agttaaaata aggctagtcc gttatcaact tgaaaaagtg gcaccgagtc ggtgctttt   540
tttgcggccg caattggatc gggtttactt attttgtggg tatctatact tttattagat  600
ttttaatcag gctcctgatt tcttttatt tcgattgaat tcctgaactt gtattattca   660
gtagatcgaa taaattataa aaagataaaa tcataaaata atattttatc ctatcaatca  720
tattaaagca atgaatatgt aaaattaatc ttatctttat tttaaaaaat catataggtt  780
tagtattttt ttaaaaataa agataggatt agtttactaa ttcactgctt attacttta   840
aaaaaatcat aaaggtttag tattttttta aaatataat aggaatagtt ttactattca   900
ctgctttaat agaaaatag tttaaaattt aagatagtt taatcccagc atttgccacg    960
tttgaacgtg agccgaaacg atgtcgttac attatcttaa cctagctgaa acgatgtcgt 1020
cataatatcg ccaaatgcca actgactac gtcgaaccca caaatcccac aaagcgcgtg  1080
aaatcaaatc gctcaaacca caaaaagaa caacgcgttt gttacacgct caatcccacg   1140
cgagtagagc acagtaacct tcaaataagc gaatggggca taatcagaaa tccgaaataa 1200
acctaggcga attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc tttatgctgt tgatgttcgt ttgttttgtt cgcttttgtt ttgtggttca  1500
gttttttagg attcttttgg ttttgaatc gattaatcgg aagagatttt cgagttattt  1560
ggtgtgttgg aggtgaatct ttttttgag gtcatagatc tgttgtattt gtgttataaa  1620
catgcgactt tgtatgattt tttacgaggt tatgatgttc tggttgtttt attatgaatc  1680
tgttgagaca gaaccatgat tttttgtgat gttcgtttac actattaaag gtttgttta   1740
acaggattaa aagttttta agcatgttga aggagtcttg tagatatgta accgtcgata   1800
gtttttttgt gggtttgttc acatgttatc aagcttaatc ttttactatg tatgcgacca  1860
tatctggatc cagcaaaggc gatttttaa ttccttgtga aacttttgta atatgaagtt   1920
gaaattttgt tattggtaaa ctataaatgt gtgaagttgg agtatacctt taccttctta  1980
tttggctttg tgatagttta atttatatgt attttgagtt ctgacttgta tttcttgaa   2040
ttgattctag tttaagtaat ccatggcacc gaagaagaag cgcaaggtga tggacaaaaa 2100
gtactcaata gggctcgaca tagggactaa ctccgttgga tgggccgtca tcaccgacga  2160
gtacaaggtg ccctccaaga agttcaaggt gttgggaaac accgacaggc acagcataaa  2220
gaagaatttg atcggtgccc tcctcttcga ctccggagag accgctgagg ctaccaggct  2280
caagaggacc gctagaaggc gctacaccag aaggaagaac agaatctgct acctgcagga  2340
gatcttctcc aacgagatgg ccaaggtgga cgactccttc ttccaccgcc ttgaggaatc  2400
attcctggtg gaggaggata aaaagcacga gagacaccca atcttcggga acatcgtcga  2460
cgaggtggcc taccatgaaa agtacccta catctaccac ctgaggaaga agctggtcga  2520
ctctaccgac aaggctgact gcgcttgat ttacctggct ctcgctcaca tgataaagtt   2580
ccgcggacac ttcctcattg agggagacct gaacccagac aactccgacg tggacaagct  2640
cttcatccag ctcgttcaga cctacaacca gcttttcgag gagaacccaa tcaacgccag  2700
tggagttgac gccaaggcta tcctctctgc tcgtctgtca aagtccagga ggcttgagaa  2760
cttgattgcc cagctgcctg gcgaaaagaa gaacggactg ttcggaaact tgatcgctct  2820
ctccctggga ttgactccca acttcaagtc caacttcgac ctcgccgagg acgctaagtt  2880
gcagttgtct aaagacacct acgacgatga cctcgacaac ttgctggccc agataggcga  2940
ccaatacgcc gatctcttcc tcgccgctaa gaacttgtcc gacgcaatcc tgctgtccga  3000
catcctgaga gtcaacactg agattaccaa agctcctctg tctgcttcca tgattaagcg  3060
ctacgacgag caccaccaag atctgaccct gctcaaggcc ctggtgagac agcagctgcc  3120
cgagaagtac aaggagatct ttttcgacca gtccaagaac ggctacgccg gatacattga  3180
cggaggcgcc tcccaggaag agttctacaa gttcatcaag cccatccttg agaagatgga  3240
cggtaccgag gagctgttgg tgaagttgaa cagagaggac ctgttgagga agagagaac   3300
cttcgacaac ggaagcatcc ctcaccaaat ccacctggga gagctccacg ccatcttgag  3360
gaggcaggag gatttctatc ccttcctgaa ggacaaccgc gagaagattg agaagatctt  3420
gaccttcaga attccttact acgtcgggcc actcgccaga ggaaactcta ggttcgcctg  3480
gatgaccccgc aaatctgaag agaccattac tccctggaac ttcgaggaag tcgtggacaa  3540
gggcgcttcc gctcagtctt tcatcgagag gatgaccaac ttcgataaaa atctgcccaa  3600
cgagaaggtc ctgcccaagc actccctgtt gtacgagtat ttcacagtgt acaacgagct  3660
caccaaggtg aagtacgtca cagagggaat gaggaagcct gccttcttgt ccggagagca  3720
gaagaaggcc atcgtcgacc tgctcttcaa gaccaacagg aagtgactg tcaagcagct   3780
gaaggaggac tacttcaaga gatcgagtc cttcgactcc gtcgagatct ctggtgtcga  3840
ggacaggttc aacgctcccc ttgggactta ccacgatctg ctcaagatta ttaaagacaa  3900
ggacttcctg gacaacgagg agaacgagga catccttgag gacatcgtgc tcaccctgac  3960
cttgttcgaa gacagggaaa tgatcgaaga gaggctcaag acctacgcc acctcttcga   4020
cgacaaggtg atgaaacagc tgaagacacg cagatataac ggctgggaa ggctctcccg   4080
caaattgatc aacgggatca gggacaagca gtcaggaag actatactcg acttcctgaa   4140
gtccgacgga ttcgcaaaca ggaacttcat gcagctcatt cacgacgact ccttgacctt  4200
caaggaggac atccagaagg ctcaggtgtc tggacagggt gactccttgc atgagcacat  4260
tgctaacttg gccggctctc ccgctattaa gaagggcatt ttgcagaccg tgaaggtcgt  4320
tgacgagctc gtgaaggtga tgggacgcca caagccagaa aacatcgtta ttgagatgcg  4380
tcgcgagaac caaactaccc agaaagggca gaagaattcc cgcgagagga tgaagcgcat  4440
tgaggagggc ataaaagagc ttggctctca gatcctcaag gagcacccg tcgaacacac   4500
tcagctgcag aacgagaagc tgtacctgta ctacctccaa aacggaaggg acatgtacgt  4560
ggaccaggag ctggacatca acaggttgtc cgactacgac gtcgaccaca tcgtgcctca  4620
gtccttcctg aaggatgact ccatcgacaa taaagtgctg acacgctccg ataaaaatag  4680
```

```
aggcaagtcc gacaacgtcc cctccgagga ggtcgtgaag aagatgaaaa actactggag   4740
acagctcttg aacgccaagc tcatcaccca gcgtaagttc gacaacctga ctaaggctga   4800
gagaggagga ttgtccgagc tcgataaggc cggattcatc aagagacagc tcgtcgaaac   4860
ccgccaaatt accaagcacg tggcccaaat tctggattcc cgcatgaaca ccaagtacga   4920
tgaaaatgac aagctgatcc gcgaggtcaa ggtgatcaac ttgaagtcca agctggtctc   4980
cgacttccgc aaggacttcc agttctacaa ggtgagggag atcaacaact accaccacgc   5040
acacgacgcc tacctcaacg ctgtcgttgg aaccgccctc atcaaaaaat atcctaagct   5100
ggagtctgag ttcgtctacg gcgactacaa ggtgtacgac gtgaggaaga tgatcgctaa   5160
gtctgagcag gagatcggca aggccaccgc caagtacttc ttctactcca acatcatgaa   5220
cttcttcaag accgagatca ctctccgccaa cggtgagatc aggaagcgcc cactgatcga   5280
gaccaacggt gagactggag agatcgtgtg ggacaaaggg agggatttcg ctactgtgag   5340
gaaggtgctc tccatgcctc aggtgaacat cgtcaagaag accgaagttc agaccggagg   5400
attctccaag gagtccatcc tccccaagag aaactccgac aagctgatcg ctagaaagaa   5460
agactgggac cctaagaagt acggaggctt cgattctcct accgtggcct actctgtgct   5520
ggtcgtggcc aaggtggaga agggcaagtc caagaagctg aaatccgtca aggagctcct   5580
cgggattacc atcatggaga ggagttcctt cgagaagaac cctatcgact tcctggaggc   5640
caagggatat aaagaggtga agaaggacct catcatcaag ctgcccaagt actccctctt   5700
ccgagttggag aacggaagga agaggatgct ggcttctgcc ggagagttgc agaagggaaa   5760
tgagctcgcc cttccctcca agtacgtgaa cttcctgtac ctcgcctctc actatgaaaa   5820
gttgaagggc tctcctgagg acaacgagca gaagcagctc ttcgtggagc agcacaagca   5880
ctacctggac gaaattatcg agcagatctc tgagttctcc aagcgcgtga tattggccga   5940
cgccaacctc gacaaggtgc tgtccgccta caacaagcag agggataagc ccattcgcga   6000
gcaggctgaa aacattatcc acctgtttac cctcacaaac ttgggagccc tgctgccttt   6060
caagtacttc gacaccacca ttgacaggaa gagatacacc tccaccaagg aggtgctcga   6120
cgcaacactc atccaccaat ccatcaccgg cctctatgaa acaaggattg acttgtccca   6180
gctgggaggc gactctagag ccgatcccaa gaagaagaga aagtgaaga gaccacggga   6240
ccgccacgat ggcgagctgg gaggccgcaa gcgggcaagg taggttaacc tagacttgtc   6300
catcttctgg attggccaac ttaattaatg tatgaaataa aaggatgcac acatagtgac   6360
atgctaatca ctataatgtg ggcatcaaag ttgtgtgtta tgtgtaatta ctagttatct   6420
gaataaaaga gaaagagatc atccatattt cttatcctaa atgaatgtca cgtgtcttta   6480
taattctttg atgaaccaga tgcatttcat taaccaaatc catatacata taaatattaa   6540
tcatatataa ttaatatcaa ttgggttagc aaaacaaatc tagtctaggt gtgttttgcg   6600
aattcgatat caagcttatc gataccgtcg agggggggcc cggtaccggc gcgccgttct   6660
atagtgtcac ctaaatcgta tgtgtatgat acataaggtt atgtattaat tgtagccgcg   6720
ttctaacgac aatatgtcca tatggtgcac tctcagtaca atctgctctg atgccgcata   6780
gttaagccag ccccgacacc cgccaacacc cgctgacgcg ccctgacggg cttgtctgct   6840
cccggcatcc gcttacagac aagctgtgac cgtctccggg agctgcatgt gtcagaggtt   6900
ttcaccgtca tcaccgaaac gcgcgagacg aaagggcctc gtgatacgcc tatttttata   6960
ggttaatgtc atgaccaaaa tcccttaacg tgagttttcg ttccactgag cgtcagaccc   7020
cgtagaaaag atcaaaggat cttcttgaga tccttttttt ctgcgcgtaa tctgctgctt   7080
gcaaacaaaa aaaccaccgc taccagcggt ggtttgtttg ccggatcaag agctaccaac   7140
tcttttttccg aaggtaactg gcttcagcag agcgcagata ccaaatactg ttcttctagt   7200
gtagccgtag ttaggccacc acttcaagaa ctctgtagca ccgcctacat acctcgctct   7260
gctaatcctg ttaccagtgg ctgctgccaa tggcgataag tcgtgtctta ccgggttgga   7320
ctcaagacga tagttaccgg ataaggcgca gcggtcgggc tgaacggggg gttcgtgcac   7380
acagcccagc ttggagcgaa cgacctacac cgaactgaga tacctacagc gtgagctatg   7440
agaaagcgcc acgcttcccg aagggagaaa ggcggacagg tatccggtaa gcggcagggt   7500
cggaacagga gagcgcacga gggagcttcc agggggaaac gcctggtatc tttatagtcc   7560
tgtcgggttt cgccacctct gacttgagcg tcgatttttg tgatgctcgt caggggggcg   7620
gagcctatgg aaaaacgcca gcaacgcggc ctttttacgg ttcctggcct tttgctggcc   7680
ttttgctcac atgttctttc ctgcgttatc ccctgattct gtggataacc gtattaccgc   7740
ctttgagtga gctgataccg ctcgccgcag ccgaacgacc gagcgcagcg agtcagtgag   7800
cgaggaagcg gaagagcgcc caatacgcaa accgcctctc cccgcgcgtt ggccgattca   7860
ttaatgcagg ttgatcagat ctcgatcccg cgaaattaat acgactcact atagggagac   7920
cacaacggtt tccctctaga aataattttg tttaacttta agaaggagat atacccatgg   7980
aaaagcctga actcaccgcg acgtctgtcg agaagtttct gatcgaaaag ttcgacagcg   8040
tctccgacct gatgcagctc tcggagggcg aagaatctcg tgctttcagc ttcgatgtag   8100
gagggcgtgg atatgtcctg cgggtaaata gctgcgccga tggtttctac aaagatcgtt   8160
atgtttatcg gcactttgca tcggccgcgc tcccgattcc ggaagtgctt gacattgggg   8220
aattcagcga gagcctgacc tattgcatct cccgccgtgc acagggtgtc acgttgcaag   8280
acctgcctga aaccgaactg cccgctgttc tgcagccggt cgcggaggct atggatgcga   8340
tcgctgcggc cgatcttagc cagacgagcg ggttcggccc attcggaccg caaggaatcg   8400
gtcaatacac tacatggcgt gatttcatat gcgcgattgc tgatccccat gtgtatcact   8460
ggcaaactgt gatggacgac accgtcagtg cgtccgtcgc gcaggctctc gatgagctga   8520
tgctttgggc cgaggactgc cccgaagtcc ggcacctcgt gcacgcggat ttcggctcca   8580
acaatgtcct gacggacaat ggccgcataa cagcggtcat tgactggagc gaggcgatgt   8640
tcggggattc ccaatacgag gtcgccaaca tcttcttctg gaggccgtgg ttggcttgta   8700
tggagcagca gacgcgctac ttcgagcgga ggcatccgga gcttgcagga tcgccgcggc   8760
tccgggatca tatgctccgc attggtcttg accaactcta tcagagcttg gttgacggca   8820
atttcgatga tgcagcttgg gcgcagggtc gatgcgacgc aatcgtccga tccggagccg   8880
ggactgtcgg cgctacacaa atcgcccgca agcgcggc cgtctggacc gatggctgtg   8940
tagaagtact cgccgatagt ggaaaccgac gccccagcac tcgtccgagg gcaaaggaat   9000
agtgaggtac agcttggatc gatccggctg ctaacaaagc ccgaaaggaa gctgagttgg   9060
ctgctgccac cgctgagcaa taactagcat aaccccttgg ggcctctaaa cgggtcttga   9120
ggggttttttt gctgaaagga ggaactatat ccggatgctc gggcgcgccg gtac         9174

SEQ ID NO: 506         moltype = DNA   length = 9174
FEATURE                Location/Qualifiers
misc_feature           1..9174
```

|  | note = synthesized sequence- RTW1202 |  |
|---|---|---|
| source | 1..9174 |  |
|  | mol_type = other DNA |  |
|  | organism = synthetic construct |  |

SEQUENCE: 506

```
ccgggtgtga tttagtataa agtgaagtaa tggtcaaaag aaaaagtgta aaacgaagta    60
cctagtaata agtaatattg aacaaaataa atggtaaagt gtcagatata taaaataggc   120
tttaataaaa ggaagaaaaa aaacaaacaa aaaataggtt gcaatggggc agagcagagt   180
catcatgaag ctagaaaggc taccgataga taaactatag ttaattaaat acattaaaaa   240
atacttggat ctttctctta ccctgtttat attgagacct gaaacttgag agagatacac   300
taatcttgcc ttgttgtttc attccctaac ttacaggact cagcgcatgt catgtggtct   360
cgttccccat ttaagtccca caccgtctaa acttattaaa ttattaatgt ttataactag   420
atgcacaaca acaaagcttg gaataaaata ggaaacgttg ttttagagct agaaatagca   480
agttaaaata aggctagtcc gttatcaact tgaaaaagtg gcaccgagtc ggtgcttttt   540
tttgcggccg caattggatc gggtttactt attttgtggg tatctatact tttattagat   600
ttttaatcag gctcctgatt tcttttttat tcgattgaat tcctgaactt gtattattca   660
gtagatcgaa taaattataa aaagataaaa tcataaaata atattttatc ctatcaatca   720
tattaaagca atgaatatgt aaaattaatc ttatctttat tttaaaaaat catataggtt   780
tagtattttt ttaaaaataa agataggatt agttttacta ttcactgctt attacttta   840
aaaaaatcat aaaggtttag tattttttta aaataaatat aggaatagtt ttactattca   900
ctgctttaat agaaaaatag tttaaatttt aagatagttt taatcccagc atttgccacg   960
tttgaacgtg agccgaaacg atgtcgttac attatcttaa cctagctgaa acgatgtcgt  1020
cataatatcg ccaaatgcca actgactac gtcgaaccca caaatcccac aaagcgcgtg  1080
aaatcaaatc gctcaaacca caaaaaagaa caacgcgttt gttacacgct caatcccacg  1140
cgagtagagc acagtaacct tcaaataagc gaatggggca taatcagaaa tccgaaataa  1200
acctagggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgatgat gtttcttcgg ttatgttttt  1440
ttatttatgc ttttatgctgt tgatgttcgg ttgtttgttt cgctttgttt ttgtggttca  1500
gttttttagg attctttttgg tttttgaatc gattaatcgg aagagatttt cgagttattt  1560
ggtgtgttgg aggtgaatct ttttttgag gtcatagatc tgttgtattt gtgttataaa  1620
catgcgactt tgtatgattt tttacgaggt tatgatgttc tggttgtttt attatgaatc  1680
tgttgagaca gaaccatgat tcttttgtgat gttcgtttac actattaaag gtttgttta  1740
acaggattaa aagtttttta agcatgttga aggagtcttg tagatatgta accgtcgata  1800
gttttttttgt gggtttgttc acatgttatc aagcttaatc ttttactatg tatgcgacca  1860
tatctggatc cagcaaaggc gatttttaa ttccttgtga aacttttgta atatgaagtt  1920
gaaattttgt tattggtaaa ctataaatgt gtgaagttgg agtatacctt taccttctta  1980
tttggcttttg tgatagttta atttatatgt attttgctt ctgacttgta tttctttgaa  2040
ttgattctag tttaagtaat ccatggcacc gaagaagaag cgcaaggtga tggacaaaaa  2100
gtactcaata gggctcgaca tagggactaa ctccgttgga tgggccgtca tcaccgacga  2160
gtacaaggtg ccctccaaga agttcaaggt gttgggaaac accgacggcc acagcataaa  2220
gaagaatttg atcggtgccc tcctcttcga ctccggagag acgctgagg tctaccaggct  2280
caagaggacc gctagaaggc gctacaccag aaggaagaac agaatctgct acctgcagga  2340
gatcttctcc aacgagatgg ccaaggtgga cgactcctc ttccaccgcc ttgaggaatc  2400
attcctggtg gaggaggata aaaagcacga gagacaccca atcttcggga acatcgtcga  2460
cgaggtgccc taccatgaaa agtaccctac catctaccac ctgaggaaga agctggtcga  2520
ctctaccgac aaggctgact gcgcttgat ttacctggct ctcgctcaca tgataaagtt  2580
ccgcggacac ttcctcattg agggagacct gaacccagac aactccgacg tggacaagct  2640
cttcatccga ctcgttcaga cctacaacca gcttttcgag gagaacccaa tcaacgccag  2700
tggagttgac gccaaggcta tcctctctgc tcgtctgtca aagtccagga ggcttgagaa  2760
cttgattgcc cagctgcctg cgcgaaaagaa gaacggactg ttcggaaact tgatcgctct  2820
ctccctggga ttgactccca acttcaagtc aacttcgac ctcgccgagg acgctaagtt  2880
gcagttgtct aaagacacct acgacgatga cctcgacaac ttgctggccc agataggcga  2940
ccaatacgcc gatctcttcc tcgccgctaa gaacttgtcc gacgcaatcc tgctgtccga  3000
catcctgaga gtcaacactg agattaccaa agctcctctg tctgcttcca tgattaagcg  3060
ctacgacgag caccaccaag atctgaccct gctcaaggcc ctggtgagac agcagctgcc  3120
cgagaagtac aaggagatct ttttcgacca gtccaagaac ggctacgccg gatacattga  3180
cggaggcgcc tccagggaag agttctacaa gttcatcaag cccatccttg agaagatgga  3240
cggtaccgag gagctgttgg tgaagttgaa cagagaggac ctgttgagga agcagagaac  3300
cttcgacaac ggaagcatcc ctcaccaaat ccacctggga gagctccacg ccatcttgag  3360
gaggcaggag gatttctatc ccttcctgaa ggacaaccgc gagaagattg agaagatctt  3420
gaccttcaga attccttact acgtcgggcc actcgccaga ggaaactcta ggttcgcctg  3480
gatgacccgc aaatctgaag agaccattac tccctggaac ttcgaggaag tcgtggacaa  3540
gggcgcttcc gctcagtctt tcatcgagag gatgaccaac ttcgataaaa atctgcccaa  3600
cgagaaggtg ctgcccaagc actccctgtt gtacgagtat ttcacagtgt acaacgagct  3660
caccaaggtg aagtacgtca cagagggaat gaggaagcct gccttcttgt ccggagagca  3720
gaagaaggcc atcgtcgacc tgctcttcaa gaccaacagg aaggtgactg tcaagcgctt  3780
gaaggaggac tacttcaaga agatcgagtg cttcgactcc gtcgagatct ctggtgtcga  3840
ggacaggttc aacgcctccc ttgggactta ccacgatctg ctcaagatta ttaaagacaa  3900
ggacttcctg gacaacgagg agaacgagga catccttgag gacatcgtgc tcaccctgac  3960
cttgttcgaa gacagggaaa tgatcgaaga gaggctcaag acctacgccc acctcttcga  4020
cgacaaggtg atgaaacagc tgaagagacg cagatatacc ggctggggaa ggctctcccg  4080
caaattgatc aacgggatca gggacaagca gtcagggaag actatactcg acttcctgaa  4140
gtccgacgga ttcgcaacaa ggaacttcat gcagctcatt cacgacgact ccttgacctt  4200
caaggaggac atccagaagg ctcaggtgtc tggacagggt gactccttgc atgagcacat  4260
tgctaacttg gccggctctc cgctattaa gaagggcatt ttgcagaccg tgaaggtcgt  4320
tgacgagctc gtgaaggtga tgggacgcca caagccagag aacatcgtta ttgagatggc  4380
tcgcgagaac caaactaccc agaaagggca gaagaattcc cgcgagagga tgaagcgcat  4440
```

```
tgaggagggc ataaaagagc ttggctctca gatcctcaag gagcacccccg tcgagaacac  4500
tcagctgcag aacgagaagc tgtacctgta ctacctccaa aacggaaggg acatgtacgt  4560
ggaccaggag ctggacatca acaggttgtc cgactacgac gtcgaccaca tcgtgcctca  4620
gtccttcctg aaggatgact ccatcgacaa taaagtgctg acacgctccg ataaaaatag  4680
aggcaagtcc gacaacgtcc cctccgagga ggtcgtgaag aagatgaaaa actactggag  4740
acagctcttg aacgccaagc tcatcaccca gcgtaagttc gacaacctga ctaaggctga  4800
gagaggagga ttgtccgagc tcgataaggc cggattcatc aagagacagc tcgtcgaaac  4860
ccgccaaatt accaagcacg tggcccaaat tctggattcc cgcatgaaca ccaagtacga  4920
tgaaaatgac aagctgatcc gcgaggtcaa ggtgatcaac ttgaagtcca agctggtctc  4980
cgacttccgc aaggacttcc agttctacaa ggtgagggag atcaacaact accaccacgc  5040
acacgacgcc tacctcaacg ctgtcgttgg aaccgccctc atcaaaaaat atcctaagct  5100
ggagtctgag ttcgtctacg gcgactacaa ggtgtacgac gtgaggaaga tgatcgctaa  5160
gtctgagcag gagatcggca aggccaccgc caagtacttc ttctactcca acatcatgaa  5220
cttcttcaag accgagatca ctctccgcaa cggtgagatc aggaagcgcc cactgatcga  5280
gaccaacggt gagactggag agatcgtgtg ggacaaaggg agggatttcg ctactgtgag  5340
gaaggtgctc tccatgcctc aggtgaacat cgtcaagaag accgaagttc agaccggagg  5400
attctccaag gagtccatcc tccccaagag aaactccgac aagctgatcg ctagaaagaa  5460
agactgggac cctaagaagt acggaggctt cgattctcct accgtggcct actctgtgct  5520
ggtcgtggcc aagtggagag agggcaagtc caagaagctg aaatccgtca aggagctcct  5580
cgggattacc atcatggaga ggagttcctt cgagaagaac cctatcgact tcctggaggc  5640
caagggatat aaagaggtga agaaggacct catcatcaag ctgcccaagt actccctctt  5700
cgagttggag aacggaagga gagagttgc ggcttctgct ggagagttgc agaagggaaa  5760
tgagctcgcc cttccctcca gtacgtgaaa cttcctgtac ctcgcctctc actatgaaaa  5820
gttgaagggc tctcctgagg acaacgagca aagcagctc ttcgtggagc agcacaagca  5880
ctacctggac gaaattatcg agcagatctc tgagttctcc aagcgcgtga tattggccga  5940
cgccaacctc gacaaggtgc tgtccgccta caacaagcag agggataagc ccattcgcga  6000
gcaggctgaa aacattatcc acctgtttac cctcacaaac ttgggagccc ctgctgcctt  6060
caagtacttc gacaccacca ttgacaggaa gagatacacc tccaccaagg aggtgctcga  6120
cgcaacactc atccaccaat ccatcaccgg cctctatgaa acaaggattg acttgtccca  6180
gctgggaggc gactctagag ccgatcccaa gaagaagaga aagtgaaga gaccacgga  6240
ccgccacgat ggcgagctgg gaggccgcaa gcgggcaagg taggttaacc tagacttgtc  6300
catcttctgg attggccaac ttaattaatg tatgaaataa aaggatgcac acatagtgac  6360
atgctaatca ctataatgtg ggcatcaaag ttgtgtgtta tgtgtaatta ctagttatct  6420
gaataaaaga gaaagagatc atccatattt ctttatcctaa atgaatgtca cgtgtcttta  6480
taattctttg atgaaccaga tgcatttcat taaccaaatc catatacata taaatattaa  6540
tcatatataa ttaatatcaa ttgggttagc aaaacaaatc tagtctaggt gtgttttgcg  6600
aattcgatat caagcttatc gataccgtcg agggggggcc cggtaccggc gcgccgttct  6660
atagtgtcac ctaaatcgta tgtgtatgat acataaggtt atgtattaat tgtagccgcg  6720
ttctaacgac aatatgtcca tatggtgcac tctcagtaca atctgctctg atgccgcata  6780
gttaagccag ccccgacacc cgccaacacc cgctgacgcg ccctgacggg cttgtctgct  6840
cccggcatcc gcttacagac aagctgtgac cgtctccggg agctgcatgt gtcagaggtt  6900
ttcaccgtca tcaccgaaac gcgcgagacg aaagggcctc gtgatacgcc tattttttata  6960
ggttaatgtc atgaccaaaa tcccttaacg tgagttttcg ttccactgag cgtcagaccc  7020
cgtagaaaag atcaaaggat cttcttgaga tccttttttt ctgcgcgtaa tctgctgctt  7080
gcaaacaaaa aaaccaccgc taccagcggt ggtttgtttg ccggatcaag agctaccaac  7140
tcttttttccg aaggtaactg gcttcagcag agcgcagata ccaaatactg ttcttctagt  7200
gtagccgtag ttaggccacc acttcaagaa ctctgtacca gcgcctacat acctcgctct  7260
gctaatcctg ttaccagtgg ctgctgccaa tggcgataag tcgtgtctta ccgggttgga  7320
ctcaagacga tagttaccgg ataaggcgca gcggtcgggc tgaacggggg gttcgtgcac  7380
acagcccagc ttggagcgaa cgacctacac cgaactgaga tacctacagc gtgagctatg  7440
agaaagcgcc acgcttcccg aagggagaaa ggcggacagg tatccggtaa gcggcagggt  7500
cggaacagga gagcgcacga gggagcttcc aggggggaaac gcctggtatc tttatagtcc  7560
tgtcgggttt cgccacctct gacttgagcg tcgatttttg tgatgctcgt cagggggggcg  7620
gagcctatgg aaaaacgcca gcaacgcggc ctttttacgg ttcctggcct tttgctggcc  7680
ttttgctcac atgttctttc ctgcgttatc ccctgattct gtggataacc gtattaccgc  7740
ctttgagtga gctgataccg ctcgccgcag ccgaacgacc gagcgcagcg agtcagtgag  7800
cgaggaagcg gaagagcgcc caatacgcaa accgcctctc cccgcgcgtt ggccgattca  7860
ttaatgcagg ttgatcagat ctcgatcccg cgaaattaat acgactcact atagggagac  7920
cacaacggtt tccctctaga aataattttg tttaacttta agaaggagat atacccatgg  7980
aaaagcctga actcaccgcg acgtctgtcg agaagtttct gatcgaaaag ttcgacagcg  8040
tctccgacct gatgcagctc tcggagggcg aagaatctcg tgctttcagc ttcgatgtag  8100
gagggcgtgg atatgtcctg cgggtaaata gctgcgccga tggtttctac aaagatcgtt  8160
atgtttatcg gcactttgca tcggccgcgc tcccgattcc ggaagtgctt gacattgggg  8220
aattcagcga gagcctgacc tattgcatct cccgccgtgc acagggtgtc acgttgcaag  8280
acctgcctga aaccgaactg cccgctgttc tgcagccggt cgcggaggcc atggatgcga  8340
tcgctgcggc cgatcttagc cagacgagcg ggttcggccc attcggaccg caaggaatcg  8400
gtcaatacac tacatggcgt gatttcatat gcgcgattgc tgatccccat gtgtatcact  8460
ggcaaactgt gatggacgac accgtcagtg cgtccgtcgc gcaggctctc gatgagctga  8520
tgctttgggc cgaggactgc cccgaagtcc ggcacctcgt gcacgcggat ttcggctcca  8580
acaatgtcct gacggacaat ggccgcataa cagcggtcat tgactggagc gaggcgatgt  8640
tcggggattc ccaatacgag gtcgccaaca tcttcttctg gaggccgtgg ttggcttgta  8700
tggagcagca gacgcgctac ttcgagcgga gcatccgga gcttcagga tcgccgcggc  8760
tccgggcgta tatgctccgc attggtcttg accaactcta tcagagcttg gttgacggca  8820
atttcgatga tgcagcttgg gcgcagggtc gatgcgacgc aatcgtccga tcccggggca  8880
ggactgtcgg cgctacacaa atcgcccgca gaagcgcggc cgtctggacc gatggctgtg  8940
tagaagtact cgccgatagt ggaaaccgac gccccagcac tcgtccgagg caaaggaat  9000
agtgaggtac agcttggatc gatccggctg ctaacaaagc ccgaaaggaa gctgagttgg  9060
ctgctgccac cgctgagcaa taactagcat aaccccttgg ggcctctaaa cgggtcttga  9120
ggggttttttt gctgaaagga ggaactatat ccggatgctc gggcgcgccg gtac        9174
```

| SEQ ID NO: 507 | moltype = DNA length = 6113 |
| --- | --- |
| FEATURE | Location/Qualifiers |
| misc_feature | 1..6113 |
| | note = synthesized sequence- RTW1192A |
| source | 1..6113 |
| | mol_type = other DNA |
| | organism = synthetic construct |

SEQUENCE: 507

```
caagtagttc tagtcttaat acaaatgtca aatggcacaa gtgagatttt gaatttctga    60
tgttgtaaaa atctcaggac atgaatacta ttgggaagca attattcata cttcaccaat   120
ccaaactgac ccaaaattct caatcacat gaaagcaaaa atgcatataa cacgaagaat    180
aagaagaaga ggaactaacc tggggtttcg atgattaaag cgttgttgtt gatgatgaaa   240
acgatgatta tggagagaaa ttgttgttga atggtgaaat tgttatagaa agagaacgaa   300
gatagagaaa aagatatata gattttttcaa ggctcaaacc ctaaaatcac catgagagag  360
aacaaagatt gagaaaccta caaccactat gagagagaat gagcagaaca gaagcgtgag   420
atagagaacg agagttaagg tgcgagagga cacgaagaac aaaaggtgtg agagaaagaa   480
caaaggagcc tacggtgtga gatgaagaa tttgaaattc ttaccattta ggtggaattt     540
caattctaca attttattct attaaaatta ttttaaaaaa tgatgtcatt ttaaattctt   600
taaaatctca tatccaacaa ctgaattatg atagaggtat ttcaaattca cttaaaaaaa   660
ttatcttatt taaataccc atccaaacat agcgaaatgt tcatgagaag gatcaagtgg    720
tttggaaaca tagtactaat ggtgtttata cagttcatgg aatccttgat agataattta   780
aaggttgctg gaaattggat gaaggtgtgg agattaaata ttcttccaaa aataaagcgt   840
tttatttgga gagtgttgtg tggttgtctc ccctgtaggc aaaagcttcg atgtaaagga   900
gttcaatgtc caataaccta tgctttctat ccctcgatta ttgaaaatga atgacacatt   960
ttatttggtt gaaatcaaga aataagcatg tggcaagcaa cgggtatttg acaattcata  1020
gaacaaaagg tgaatgcagc aaaagaatta atgaactcct tttcgatcta cttggatcac  1080
tacatggaga tattatcaac aaatttgatg ttacttatg gagcagttgg aattcttgga   1140
atgacaagat atgaaatgaa catcaccaacc ctcctcttgt ttctgtttcg gtttctatgc  1200
agtatttgt tgaatggcaa agtgcaaggt aatatgctcc tcaacatcaa ttaacaaatg   1260
ttcatgacat ctcttaccag ctccaacttg gggacgtttg acaaacacca ccgtcaagtt   1320
tccttaaatg caacattaat gttgctcatt tcaaggagga gaatagtttt ggtgtcggca   1380
tgatactcca tcaaggaaga ttcgtcaaag ctcactcacg ttttcgacat gggtcgacat   1440
gggttacctg acccaaaggc tgaggcttag gcttgggttt gcttcaagta ttgatctggg   1500
cccagactat tggtttacat aatatcattt tgaaaacct aacatctaaa actcaaggtt    1560
gtttagaggt gcgccattcc aaaataagat tatcctattt gtgcatgaat gcgaccaact   1620
atctcctgtt tcagcattat aaagtataaa caacaaactt ctttaatcaa gggactaaaa   1680
gatattggac atacaagcta aaagtgatag aatttgaaga aacaaatatt gacaacaata   1740
ttcaagagga cactaaaaca taattctcaa attttttttg ttttatttaaa ataaagtggt   1800
tcattaggta gctccgggtg attgcggtta catcatgtac ggaaaaataa ttctaatcct   1860
tgatttaaat ttgaacttga ctatttattt attcttatt tcattttgta aatcatttta    1920
tgtatctcct ggcaagcaat tttatccacc ttgccaccac accttcgggt tccataatca   1980
aaccaccta acttcacacc atgctgtaac tcacaccgcc cagcatctcc aatgtgaaag   2040
aagctaaaat ttaataaaca atcatacgaa gcagtgacaa ataccagat ggtattaatg     2100
cttcgataaa attaattgga aagtataaaa tggtagaaaa taataaatta taattaattt   2160
aagtaagata aaaaataatt aaaaactaaa atgttaaaat tttaaaaaaa ttattttaaa   2220
taatatttaa aaaacattaaa aatcatttta aaaaatttat ttatagaaca attaaataaa  2280
tatttcagct aataaaaaac aaaagcttac ctagccttag aagacaactt gtccaacaat   2340
tagatgatac ccattgccct tacgttttct ttaacatcaa ttattgtttt tgtcaacaag   2400
ctatcttta gttttatttt attggtaaaa atatgtcgc cttcaagttg catcatttaa     2460
cacatctcgt cattagaaaa ataaaactct tccctaaacg attagtagaa aaaatcattc   2520
gataataaat aagaaagaaa aattagaaaa aaataacttc attttaaaaa aatcattaag   2580
gctatatttt ttaaatgact aattttatat agactgtaac taaaagtata caatttatta   2640
tgctatgtat cttaaagaat tacttataaa aatctacgga agaatatctt acaaagtgaa   2700
aaacaaatga gaaagaattt agtgggatga ttatgatttt attgtaaaaa tgaaaaaata   2760
attattaaag actttagtgg agtaagaag cttttccctatt agtctttttct tatccataaa  2820
aaaaaaaaaa aaaatctagc gtgacagctt ttccatagat tttaatatg taaaatactg    2880
gtagcagccg accgttcagg taatggacac tgtggtccta acttgcaacg ggtgcgggcc   2940
caattaata acgccgtggt aacgataaa gccaagcgtg aagcggtgaa ggtacatctc     3000
tgactccgtc aagattacga aaccgtcaac tacgaaggac tccccgaaat atcatctgtg   3060
tcataaacac caagtcacac catacatggg cacgcgtcac aatatgattg gagaacggtt   3120
ccaccgcata tgctataaaa tgcccccaca cccctcgacc ctaatcgcac ttcaattgca   3180
atcaaattag ttcattctct ttgcgcagtt ccctacctct cctttcaagg ttcgtagatt   3240
tcttccgttt tttttttctte ttctttattg tttgttctac atcagcatga tgttgatttg   3300
attgtgtttt ctatcgtttc atcgattata aatttttcata atcagaagat tcagcttttta  3360
ttaatgcaag aacgtcctta attgatgatt ttataaccgt aaattaggtc taattagagt   3420
tttttttcata aagattttca gatccgttta caacaagcct taattgttga ttctgtagtc   3480
gtagattaag gtttttttca tgaactactt cagatccgtt aaacaacagc cttatttgtt   3540
gatacttcag tcgttttttca agaaattgtt cagatccgtt gataaaagct ttattcgttg   3600
attctgtatg gtatttcaag agatattgct caggtccttt agcaactacc ttatttgttg    3660
attctgtggc catagattag gatttttttt cacgaaattg cttcttgaaa ttacgtgatg   3720
gatttttgatt ctgatttatc ttgtgattgt tgactctaca gatggcccaa gtgagcagag   3780
tgcacaatct tgctcaaagc actcaaattt tggccattc ttccaactcc aacaaactca    3840
atgcggtgaa ttcggtttca ttgaggccac gcctttgggg ggcctcaaaa tctcgcatcc   3900
cgatgcataa aaatggaagc tttatggaa attttaatgt ggggaaggga aattccggcg    3960
tgtttaaggt ttctgcatcg gtcgccgccg cagagaagcc gtcaacgtcg ccggagatcg   4020
tgttggaacc catcaaagac ttctcgggta ccatcacatt gccagggtcc aagtctctgt   4080
ccaatcgaat tttgcttctt gctgctctct ctgaggtgaa gttatttat ttatttatttt  4140
gtttgtttgt tgttgggtgt gggaatagga gtttgatgtg tagagtggat tttgaatatt   4200
```

-continued

```
tgattttttt ttgtattatt ctgtgaaaat gaagcatcat gtcccatgaa agaaatggac    4260
acgaaattaa gtggcttatg atgtgaaatg aggatagaaa tgtgtgtagg gttttttaat    4320
gggtagcaat aagcatattc aatatctgga ttgatttgga cgtttctgta taaaggagta    4380
tgctagcaat gtgttaatgt atggcttgct aaaatactcc taaaaatcaa gtgggagtag    4440
tatacatatc tacagcaaat gtattaggtg aggcatttga cttctctatt gtaaggaaca    4500
aataatatca gttaatgtga aaatcaatgt tgatattcc aatacattca tgatgtgtta     4560
tttatatgta cctaatattg actgttgttt ttctccgcaa tgaccaagat tatttatttt    4620
atcctctaaa gtgactaatt gagttgctta ctttagagaa gttggaccca ttaggtgaga    4680
gcgtgggggg aactaatctt gaatatacaa tctgagtctt gattatccaa gtatggttgt    4740
atgaacaatg ttagctctag aagtaaaacc ctccccaaa acacaaatta gaatgacatt      4800
tcaagttcca tgtatgtcac tttcattcta ttatttttac aacttttagt tacttaacag    4860
atgtcttgtt cagcataaat tataatttat tctgttttt tttagggaac aactgttgta     4920
gacaacttgt tgtatagtga ggatattcat tacatgcttg gtgcattaag gacccttgga    4980
ctgcgtgtgg aagatgacaa aacaaccaaa caagcaattg ttgaaggctg tgggggattg    5040
tttcccacta gtaaggaatc taaagatgaa atcaatttat tccttggaaa tgctggtatt    5100
gcaatgagat ctttgacagc agctgttgtt gctgcaggtg gaaatgcaag gtctgttttt    5160
tttttttttg ttcagcataa tctttgaatt gttcctcgta taactaatca caacagagta    5220
cgtgttcttc ttcctgttat aatctaaaaa tctcatccag attagtcatc ctttcttctt    5280
aaaaggaacc tttaattatc aatgtattta tttaatattt aaattagctt gtcaaagtct    5340
agcatataca tattttgatt atattctgag aaatgcacct gagggtgttc ctcatgatct    5400
acttcaacct ctgttattat tagattttct atcatgatta ctggtttgag tctctaagta    5460
gaccatcttg atgttcaaaa tatttcagct acgtacttga tttgggtgcc tcgaatgagag   5520
agaggccaat tggggatttg gttgctggtc ttaagcaact tggtgcagat gttgattgct    5580
ttcttggcac aaactgtcca cctgttcgtg taaatgggaa gggaggactt cctggcggaa    5640
aggtatggtt tggatttcat ttagaataag gtggagtaac tttcctggat caaaattcta    5700
atttaagaag cctccctgtt ttcctctctt tagaataaga ctaagggtag gtttaggagt    5760
tgggttttgg agagaaatgg aagggagagc aattttttc ttcttctaat aaatattctt     5820
taatttgata catttttttaa gtaaaagaat ataagatag attagcataa cttaatgttt    5880
taatcttttta tttatttta taaatattat atacctgtct atttaaaaat caaatatttg    5940
tcctccattc cctttccctt caaaacctca gttccaaata taccgtagtt gaattatatt    6000
ttggaaggcc tattggttgg agacttttcc ttttcagaga ttatccctca cctttattat    6060
agcctttcta ttttaaact tcatatagac gccattcttg gggcggccgc gat            6113
```

```
SEQ ID NO: 508          moltype = DNA  length = 32
FEATURE                 Location/Qualifiers
misc_feature            1..32
                        note = synthesized sequence- primer, soy1-F4
source                  1..32
                        mol_type = other DNA
                        organism = synthetic construct
SEQUENCE: 508
tcaataatac tactctctta gacaccaaac aa                                   32

SEQ ID NO: 509          moltype = DNA  length = 23
FEATURE                 Location/Qualifiers
misc_feature            1..23
                        note = synthesized sequence- primer, soy1-R4
source                  1..23
                        mol_type = other DNA
                        organism = synthetic construct
SEQUENCE: 509
caaggaaaat gaatgatggc ttt                                             23

SEQ ID NO: 510          moltype = DNA  length = 18
FEATURE                 Location/Qualifiers
misc_feature            1..18
                        note = synthesized sequence- probe, soy1-T3(FAM-MGB)
source                  1..18
                        mol_type = other DNA
                        organism = synthetic construct
SEQUENCE: 510
ccttcccaaa ctataatc                                                   18

SEQ ID NO: 511          moltype = DNA  length = 27
FEATURE                 Location/Qualifiers
misc_feature            1..27
                        note = synthesized sequence- WOL1005, Forward_primer
source                  1..27
                        mol_type = other DNA
                        organism = synthetic construct
SEQUENCE: 511
aaatgttatc agaggaacat gagctgc                                         27

SEQ ID NO: 512          moltype = DNA  length = 28
FEATURE                 Location/Qualifiers
misc_feature            1..28
                        note = synthesized sequence- WOL1006, Reverse_primer
source                  1..28
                        mol_type = other DNA
```

```
                            organism = synthetic construct
SEQUENCE: 512
attattttc cgtacatgat gtaaccgc                                          28

SEQ ID NO: 513          moltype = DNA  length = 438
FEATURE                 Location/Qualifiers
source                  1..438
                        mol_type = unassigned DNA
                        organism = Cauliflower mosaic virus
SEQUENCE: 513
cccatggagt caaagattca aatagaggac ctaacagaac tcgccgtaaa gactggcgaa        60
cagttcatac agagtctctt acgactcaat gacaagaaga aaatcttcgt caacatggtg      120
gagcacgaca cgcttgtcta ctccaaaaat atcaaagata cagtctcaga agaccaaagg      180
gcaattgaga cttttcaaca aagggtaata tccggaaacc tcctcggatt ccattgccca      240
gctatctgtc actttattgt gaagatagtg gaaaggaag gtggctccta caaatgccat      300
cattgcgata aaggaaaggc catcgttgaa gatgcctctg ccgacagtgg tcccaaagat      360
ggaccccac ccacgaggag catcgtggaa aagaagacg ttccaaccac gtcttcaaag       420
caagtggatt gatgtgat                                                    438

SEQ ID NO: 514          moltype = DNA  length = 19
FEATURE                 Location/Qualifiers
source                  1..19
                        mol_type = unassigned DNA
                        organism = Cauliflower mosaic virus
SEQUENCE: 514
gtctcagaag accaaaggg                                                    19

SEQ ID NO: 515          moltype = DNA  length = 25
FEATURE                 Location/Qualifiers
source                  1..25
                        mol_type = unassigned DNA
                        organism = Cauliflower mosaic virus
SEQUENCE: 515
tgccatcatt gcgataaagg aaagg                                             25

SEQ ID NO: 516          moltype = DNA  length = 20
FEATURE                 Location/Qualifiers
source                  1..20
                        mol_type = unassigned DNA
                        organism = Cauliflower mosaic virus
SEQUENCE: 516
gatgcctctg ccgacagtgg                                                   20

SEQ ID NO: 517          moltype = DNA  length = 3708
FEATURE                 Location/Qualifiers
source                  1..3708
                        mol_type = unassigned DNA
                        organism = Zea mays
SEQUENCE: 517
ctgcagccca tcaaggagat ctccggcacc gtcaagctgc cggggtccaa gtcgctttcc        60
aacaggatcc tcctgctcgc cgccctgtcc gaggtgagcg attttggtgc ttgctgcgct      120
gccctgtctc actgctacct aaatgttttg cctgtcgaat accatggatt ctcggtgtaa      180
tccatctcac gatcagatgc accgcatgtc gcatgcctag ctctctctaa tttgtcagt       240
agtttgtata cggattaaga ttgataaatc ggtaccgcaa aagctaggtg taaataaaca      300
ctacaaaatt ggatgttccc ctatcggcct gtactcgtct actcgttctt gtgatggcat      360
gttatttctt cttggtgttt ggtgaactcc cttatgaaat ttgggcgcaa agaaatcgcc      420
ctcaagggtt gatcttatgc catcgtcatg ataaacagtg aagcacggat gatccttta       480
gttgttttta acaaactttg tcagaaaact agcaatgtta acttcttaat gatgatttca      540
caacaaaaaa ggtaaccttg ctactaacat aacaaaagac ttgttgctta ttaattat        600
gtttttttaa tctttgatca ggggacaaca gtggttgata acctgttgaa cagtgaggat      660
gtccactaca tgctcggggc cttgaggact cttggtctct ctgtcgaagc ggacaaagct      720
gccaaaagc ctgtagttgt tggctgtggt ggaaagttcc cagttgagga tgctagagag       780
gaagtgcagc tcttcttggg gaatgctgga atcgcaatgc ggtcattgac agcagctgtt      840
actgctgctg gtgaaatgc aacgtatgtt tcctctctct ctctacaata cttgttggag       900
ttagtatgaa acccatgtgt atgtctagtg gcttatggtg tattggtttt tgaacttcag      960
ttacgtgctt gatggagtac caagaatgag ggagagaccc attggcgact tggttgtcgg     1020
attgaagcag cttggtgcag atgttgattg ttttccttgg cactgactgcc cacctgttcg     1080
tgtcaatgga atcggagggc tacctggtgg caaggttagt tactaagggc cacatgttac     1140
attcttctgt aaatggtaca actattgtcg agcttttgca tttgtaagga aaacattgat     1200
tgatctgaat ttgatgctac accacaaaat atctacaaat ggtcatccct aactagcaaa     1260
ccatgtctcc attaagctca atgaagtaat acttggcatg tgtttatcaa cttaatttcc     1320
atcttctggg gtattgcctg ttttctagtc taatagcatt tgttttttaga attagctctt     1380
acaactgtta tgttctacag gtcaagctgt ctggctccat cagcagtcag tacttgagtg     1440
cctttgcgat ggctgctcct ttggctcttg gggatgtgga gattgaaatc attgataaat     1500
taatctccat tccctacgtc gaaatgacat tgagattgat ggagcgtttt ggtgtgaaag     1560
cagagcattc tgatagctgg gacagattct acattaaggg aggtcaaaaa tacaagtaag     1620
ctctgtaatg tatttcacta ctttgatgcc aatgtttcag tttttcagttt tccaaacagt     1680
cgcatcaata tttgaataga tgcactgtag aaaaaaatca ttgcagggaa aaactagtac     1740
tgagtatttt gactgtaaat tatttaaccca gtcggaatat agtcagtcta ttggagtcaa     1800
```

```
gagcgtgaac cgaaatagcc agttaattat cccattatac agaggacaac catgtatact   1860
attgaaactt ggtttaagag aatctaggta gctggactcg tagctgcttg gcatggatac   1920
cttcttatct ttaggaaaag acactgatt tttttctgt ggccctctat gatgtgtgaa    1980
cctgcttctc tattgcttta gaaggatata tctatgtcgt tatgcaacat gcttcctta    2040
gtcatttgta ctgaaatcag tttcataagt tcgttagtgg ttccctaaac gaaaccttgt   2100
ttttctttgc aatcaacagg tccctaaaa atgcctatgt tgaaggtgat gcctcaagcg    2160
caagctattt cttggctggt gctgcaatta ctggagggac tgtgactgtg gaaggttgtg   2220
gcaccaccag tttgcaggta aagatttctt ggctggtgct acgataactg cttttgtctt   2280
tttggtttca gcattgttct cagagtcact aaataacatt atcatctgca aacgtcaaat   2340
agacatactt aggtgaatgg atattcatgt aaccgtttcc ttacaaattt gctgaaacct   2400
cagggtgatg tgaagtttgc tgaggtactg gagatgatgg gagcgaaggt tacatggacc   2460
gagactagcg taactgttac tggcccaccg cgggagccat ttgggaggaa acacctcaag   2520
gcgattgatg tcaacatgaa caagatgcct gatgtcgcca tgactcttgc tgtggttgcc   2580
ctctttgccg atggcccgac agccatcaga gacggtaaaa cattctcagc cctacaacca   2640
tgcctcttct acatcactac ttgacaagac taaaaactat tggctcgttg gcagtggctt   2700
cctggagagt aaaggagacc gagaggatgg ttgcgatccg gacggagcta accaaggtaa   2760
ggctacatac ttcacatgtc tcacgtcgtc tttccatagc tcgctgcctc ttagcggctt   2820
gcctgcggtc gctccatcct cggttgctgt ctgtgttttc cacagctggg acatctcgtt   2880
gaggaagggc cggactactg catcatcacg ccgccggaga agctgaacgt gacggcgatc   2940
gacacgtacg acgaccacag gatggccatg gccttctccc ttgccgcctg tgccgaggtc   3000
cccgtgacca tccgggaccc tgggtgcacc cggaagacct tccccgacta cttcgatgtg   3060
ctgagcactt tcgtcaagaa ttaataaagc gtgcgatact accacgcgc ttgattgaag    3120
tgataggctt gtgctgagga aatacatttc ttttgttctg tttttctct ttcacgggat    3180
taagttttga gtctgtaacg ttagttgttt gtagcaagtt tctatttcgg atcttaagtt   3240
tgtgcactgt aagccaaatt tcatttcaag agtggttcgt tggaataata agaataataa   3300
attacgtttc agtggctgtc aagcctgctg ctacgtttcg ggagatggca ttagacattc   3360
atcatcaaca acaataaaac ctttagcct caaacaataa tagtgaagtt atttttttagt    3420
cctaaacaag ttgcattagg atatagttaa aacacaaaag aagctaaagt tagggtttag   3480
acatgtggat attgttttcc atgtatagta tgttctttct ttgagtctca tttaactacc   3540
tctacacata ccaactttag ttttttttct acctcttca gttactatgg tgccttctta    3600
tcccactgag cattggtata tttagaggtt tttgttgaac atgcctaaat catctcaatc   3660
aacgatggac aatctttct tcgattgagc tgaggtacgt catctaga               3708

SEQ ID NO: 518        moltype = DNA   length = 3714
FEATURE               Location/Qualifiers
source                1..3714
                      mol_type = unassigned DNA
                      organism = Zea mays
SEQUENCE: 518
ctgcagccca tcaaggagat ctccggcacc gtcaagctgc cggggtccaa gtcgctttcc    60
aacaggatcc tcctgctcgc cgccctgtcc gaggtgagcg attttggtgc ttgctgcgct   120
gccctgtctc actgctacct aaatgttttg cctgtcgaat accatggatt ctcggtgtaa   180
tccatatctg cacgatcaga tatgcaccgc atgtcgctct ctctaatttg               240
tctagtagtt tgtatacgga ttaagattga taaatcggta ccgcaaaagc taggtgtaaa   300
taaacactac aaaattggat gttccctat cggcctgtac tcggctactc gttcttgtga    360
tggcatgtta tttcttcttg gtgtttggtg aactcccctta tgaaatttgg gcgcaaagaa   420
atcgccctca agggttgatc ttatgccatc atcatgataa acagtgaagc acggatgatc   480
ctttacgttg ttttttaacaa actttgtcag aaaactagca atgttaactt cttaatgatg   540
atttcacaac aaaaaggta accttgctac taacataaca aaagacttgt tgcttattaa    600
ttatatgttt tttttaatctt tgatcagggg acaacagtgg ttgataaccct gttgaacagt   660
gaggatgtcc actacatgct cggggccttg aggactcttg gtctctctgt cgaagcggac    720
aaagctgcca aaagagctgt agttgttggc tgtggtggaa agttcccagt tgaggatgct   780
aaagaggaag tgcagctctt cttggggaat gctggaatcg caatgcggtc attgacagca    840
gctgttactg ctgctggtgg aaatgcaacg tatgtttcct ctctctctct acaatacttg    900
ttggagttag tatgaaaccc atgtgtatgt ctagtggctt atggtgtatt ggttttttgaa   960
cttcagttac gtgcttgatg gagtaccaag aatgagggag agacccattg gcgacttggt   1020
tgtcggattg aagcagcttg gtgcagatgt tgattgtttc cttggcactg actgccacc    1080
tgttcgtgtc aatggaatcg gagggctacc tggtggcaag gttagttact aagggccaca   1140
tgttacattc ttctgtaaat ggtacaacta ttgtcgagct tttgcatttg taaggaaaac   1200
attgattgat ctgaatttga tgctacacca caaaatact acaaatggtc atccctaact    1260
agcaaaccat gtctccatta agctcaatga agtaatactt ggcatgtgtt tatcaactta   1320
atttccatct tctggggtat tgcctgtttt ctagtctaat agcatttgtt tttagaatta   1380
gctcttacaa ctgttatgtt ctacaggtca agctgtctgg ctccatcagc agtcagtact   1440
tgagtgcctt gctgatggct gctccttttgg tcttgggaa tgtggagatt gaaatcattg    1500
ataaattaat ctccattccc tacgtcgaaa tgacattgaa attgatgag cgttttggtg     1560
tgaaagcaga gcattctgat agctgggaca gattctacat aagggaggt caaaaataca    1620
agtaagctct gtaatgtatt tcactacttt gatgccaatg tttcagtttt cagttttcca   1680
aacagtcgca tcaatatttg aatagatgca ctgtagaaaa aaatcattgc agggaaaaac   1740
tagtactgag tatttgact gtaaattatt taaccagtcg gaatatagtc agtctattgg    1800
agtcaagagc gtgaaccgaa atagccagtt aattatccca ttatacagag gacaaccatg   1860
tatactattg aaacttggtt taagagaatc taggtagctg gactcgtagc tgcttggcat   1920
ggatacctcc ttatctttag gaaaagacac ttgattttt ttctgtggcc ctctatgatg    1980
tgtgaacctg cttctctatt gctttagaag gatatatcta tgtcgttatg caacatgctt   2040
cccttagtca tttgtactga aatcagtttc ataagttcgt tagtggttcc ctaaacgaaa   2100
ccttgttttc tttgcaatca acaggtcccc taaaaatgc ctatgttgaa ggtgatgcct    2160
caagcgcaag ctatttcttg gctggtgctg caattactgg agggactgtg actggaag     2220
gttgtggcac caccagtttg caggtaaaga tttcttggct ggtgctacga taactgcttt   2280
tgtcttttgg tttcagcat tgttctcaga gtcactaaat aacattatca tctgcaaacg    2340
tcaaatagac atacttaggt gaatggatat tcatgtaacc gtttccttac aaatttgctg   2400
```

```
aaacctcagg gtgatgtgaa gtttgctgag gtactggaga tgatgggagc gaaggttaca   2460
tggaccgaga ctagcgtaac tgttactggc ccaccgcggg agccatttgg gaggaaacac   2520
ctcaaggcga ttgatgtcaa catgaacaag atgcctgatg tcgccatgac tcttgctgtg   2580
gttgccctct ttgccgatgg cccgacagcc atcagagacg gtaaacatt  ctcagcccta   2640
caaccatgcc tcttctacat cactacttga caagactaaa aactattggc tcgttggcag   2700
tggcttcctg gagagtaaag gagaccgaga ggatggttgc gatccggacg gagctaacca   2760
aggtaaggct acatacttca catgtctcac gtcgtctttc catagctcgc tgcctcttag   2820
cggcttgcct gcggtcgctc catcctcggt tgctgtctgt gttttccaca gctgggagca   2880
tctgttgagg aagggccgga ctactgcatc atcacgccgc cggagaagct gaacgtgacg   2940
gcgatcgaca cgtacgacga ccacaggatg gccatggcct tctcccttgc cgcctgtgcc   3000
gaggtccccg tgaccatccg ggaccctggg tgcaccggga agaccttccc cgactacttc   3060
gatgtgctga gcactttcgt caagaattaa taaagcgtgc gatactacca cgcagcttga   3120
ttgaagtgat aggcttgtgc tgaggaaata catttctttt gttctgtttt ttctctttca   3180
cgggattaag ttttgagtct gtaacgttag ttgtttgtag caagtttcta tttcggatct   3240
taagtttgtg cactgtaagc caaatttcat ttcaagagtg gttcgttgga ataataagaa   3300
taataaatta cgtttcagtg gctgtcaagc ctgctgctac gttttaggag atggcattag   3360
acattcatca tcaacaacaa taaaacctt  tagcctcaaa caataatagt gaagttattt   3420
tttagtccta aacaagttgc attaggatat agttaaaaca caaagaagc  taaagttagg   3480
gtttagacat gtggatattg ttttccatgt atagtatgtt cttcttttga gtctcattta   3540
actacctcta cacataccaa ctttagtttt ttttctacct cttcatgtta ctatggtgcc   3600
ttcttatccc actgagcatt ggtatattta gaggttttg  ttgaacatgc ctaaatcatc   3660
tcaatcaacg atggacaatc tttcttcga ttgagctgag gtacgtcatc taga         3714

SEQ ID NO: 519        moltype = DNA   length = 3708
FEATURE               Location/Qualifiers
source                1..3708
                      mol_type = unassigned DNA
                      organism = Zea mays
SEQUENCE: 519
ctgcagccca tcaaggagat ctccggcacc gtcaagctgc cggggtccaa gtcgctttcc     60
aacaggatcc tcctgctcgc cgccctgtcc gaggtgagcg attttggtgc ttgctgcgct    120
gccctgtctc actgctacct aaatgttttg cctgtcgaat accatggatt ctcggtgtaa    180
tccatctcac gatcagatgc accgcatgtc gcatgcctag ctctctctaa tttgtctagt    240
agtttgtata cggattaaga ttgataaatc ggtaccgaca aagctaggtg taaataaaca    300
ctacaaaatt ggatgttccc ctatcggcct gtactcggct actcgttctt gtgatggcat    360
gttatttctt cttggtgttt ggtgaactcc cttatgaaat ttgggcgcaa agaaatcgcc    420
ctcaaggggt tgatcttatg ccatcgtcatg ataaacagtg aagcacggat gatcctttac    480
gttgttttta acaaactttg tcagaaaact agcaatgtta acttcttaat gatgatttat    540
caacaaaaaa ggtaaccttg ctactaacat aacaaaagac ttgttgctta ttaattatat    600
gtttttttaa tctttgatca ggggacaaca gtggttgata acctgttgaa cagtgaggat    660
gtccactaca tgctcgggc  cttgaggact cttggtctct ctgtcgaagc ggacaaagct    720
gccaaaagag ctgtagttgt tggctgtggt ggaaagttcc cagttgagga tgctagaaag    780
gaagtcgaca tcttcttggg gaatgctgga atcgcaatgc ggtcattgac agcagctgtt    840
actgctgctg gtggaaatgc aacgtatgtt tcctctctct ctctacaata cttgttggag    900
ttagtatgaa acccatgtgt atgtctagtg gcttatggtg tattggtttt tgaacttcag    960
gtacgtgctt gatggagtac caagaatgag ggagagaccc attggcgact tggttgtcgg   1020
attgaagcag cttggtgcag atgttgattg tttcttggc  actgactgcc cacctgttcg   1080
tgtcaatgga atcggagggc tacctggtgg caaggttagt tactaagggc cacatgttac   1140
attcttctgt aaatggtaca actattgtcg agctttgca  tttgtaagga aaacattgat   1200
tgatctgaat ttgatgctac accacaaaat atctacaaat ggtcatccct aactagcaaa   1260
ccatgtctcc attaagctca atgaagtaat acttggcatg tgtttatcaa cttaatttcc   1320
atcttctggg gtattgcctg ttttctagtc taatagcatt tgtttttaga attagctctt   1380
acaactgtta tgttctacag gtcaagctgt ctggctccat cagcagtcag tacttgagtg   1440
ccttgctgat ggctgctcct ttggctcttg gggatgtgga gattgaaatc attgataaat   1500
taatctccat tccctacgtc gaaatgacat tgagattgat ggagcgtttt ggtgtgaaag   1560
cagagcattc tgatagctgg gacagattct acattaaggg aggtcaaaaa tacaagtaag   1620
ctctgtaatg tatttcacta ctttgatgcc aatgtttcag ttttcagttt tccaaacagt   1680
cgcatcaata tttgaataga tgcactgtag aaaaaaatca ttgcagggaa aaactagtac   1740
tgatgtattt gactgtaaat tatttaacca gtcggaaat  agtcagtcta ttggagtcaa   1800
gagcgtgaac cgaaatagcc agttaattat cccattatac agaggacaac catgtatact   1860
attgaaactt ggtttaagag aatctaggta gctggactcg tagctgcttg gcatggatac   1920
cttcttatct ttaggaaaag acacttgatt ttttttctgt ggccctctat gatgtgtgaa   1980
cctgcttctc tattgcttta gaaggatata tctatgtcgt tatgcaacat gcttcccta    2040
gtcatttgta ctgaaatcag tttcataagt tcgttagtgg ttccctaaac gaaaccttgt   2100
ttttctttgc aatcaacagg tccctaaaa  atgcctatgt tgaaggtgat gcctcaagcg   2160
caagctattt cttggctggt gctgcaatta ctggagggac tgtgactgtg gaaggttgtg   2220
gcaccaccag tttgcaggta agatttcttg gctggtgct  acgataactg cttttgtctt   2280
tttggtttca gcattgttct cagagtcact aaataacatt atcatctgca aacgtcaaat   2340
agacatactt aggtgaatgg atattcatgt aaccgtttcc ttacaaattt gctgaaacct   2400
cagggtgatg tgaagtttgc tgaggtactg gagatgatgg gagcgaaggt tacatggacc   2460
gagactagcg taactgttac tggcccaccg cgggagccat tgggaggaa  acacctcaag   2520
gcgattgatg tcaacatgaa caagatgcct gatgtcgcca tgactcttgc tgtggttgcc   2580
ctctttgccg atgcccgac  agccatcaga acggtaaaa  cattctcagc cctacaacca   2640
tgcctcttct acatcactac ttgacaagac taaaactact acttgtcgttg gcagtggctt   2700
cctggagagt aaaggagacc gagaggatgg ttgcgatccg gacggagcta accaaggtaa   2760
ggctacatac ttcacatgtc tcacgtcgtc ttttccatagc tcgctgcctc ttagcggctt   2820
gcctgcggtc gctccatcct cggttgctgt ctgtgttttc cacagctggg agcatctgtt   2880
gaggaagggc cggactactg catcatcacg ccgccggaga agctgaacgt gacggcgatc   2940
gacacgtacg acgaccacag gatggccatg gccttctccc ttgccgcctg tgccgaggtc   3000
```

```
cccgtgacca tccgggaccc tgggtgcacc cggaagacct tccccgacta cttcgatgtg  3060
ctgagcactt tcgtcaagaa ttaataaagc gtgcgatact accacgcagc ttgattgaag  3120
tgataggctt gtgctgagga aatacatttc ttttgttctg tttttctct ttcacgggat    3180
taagttttga gtctgtaacg ttagttgttt gtagcaagtt tctatttcgg atcttaagtt  3240
tgtgcactgt aagccaaatt tcatttcaag agtggttcgt tggaataata agaataataa  3300
attacgtttc agtggctgtc aagcctgctg ctacgtttta ggagatggca ttagacattc  3360
atcatcaaca acaataaaac cttttagcct caaacaataa tagtgaagtt attttttagt   3420
cctaaacaag ttgcattagg atatagttaa aacacaaaag aagctaaagt tagggtttag   3480
acatgtggat attgttttcc atgtatagta tgttctttct ttgagtctca tttaactacc   3540
tctacacata ccaactttag tttttttct acctcttcat gttactatgg tgccttctta    3600
tcccactgag cattggtata tttagaggtt tttgttgaac atgcctaaat catctcaatc    3660
aacgatggac aatctttttct tcgattgagc tgaggtacgt catctaga                3708

SEQ ID NO: 520           moltype = AA   length = 464
FEATURE                  Location/Qualifiers
source                   1..464
                         mol_type = protein
                         organism = Zea mays
SEQUENCE: 520
MQLDLNVAEA PPPVEMEASD SGSSVLNASE AASAGGAPAP AEEGSSSTPA VLEFSILIRS    60
DSDAAGADED EDATPSPPPR HRHQHQQQLV TRELFPAGAG PPAPTPRHWA ELGFFRADLQ   120
QQQAPGPRIV PHPHAAPPPA KKSRRGPRSR SSQYRGVTFY RRTGRWESHI WDCGKQVYLG   180
GFDTAHAAAR AYDRAAIKFR GVDADINFNL SDYEDDMKQM GSLSKEEFVH VLRRQSTGFS   240
RGSSYRYGVT LHKCGRWEAR MGQFLGKKYI YLGLFDSEVE AARAYDKAAI KCNGREAVTN   300
FEPSTYHGEL PTEVADVDLN LSISQPSPQR DKNSCLGLQL HHGPFEGSEL KKTKIDDAPS   360
ELPGRPRQLS PLVAEHPPAW PAQPPHPFFV FTNHEMSASG DLHRRPAGAV PSWAWQVAAA   420
APPPAALPSS AAASSGFSNT ATTAATTAPS ASSLRYCPPP PPPS                    464

SEQ ID NO: 521           moltype = DNA   length = 1413
FEATURE                  Location/Qualifiers
source                   1..1413
                         mol_type = unassigned DNA
                         organism = Zea mays
SEQUENCE: 521
atgcagttgg atctgaacgt ggccgaggcg ccgccgccgg tggagatgga ggcgagcgac    60
tcggggtcgt cggtgctgaa cgcgtcggaa gcggcgtcgg cgggcggcgc gcccgcgccg   120
gcggaggagg gatctagctc aacgccggcc gtgctggagt tcagcatcct catccggagc   180
gatagcgacg cggccggcgc ggacgaggac gaggacgcca cgccatcgcc tcctcctcgc   240
caccgccacc agcaccagca gcagctcgtg acccgcgagc tgttcccggc cggcgccggt   300
ccgccgccc cgacgccgcg gcattgggcc gagctcggct tcttccgcgc cgacctgcag   360
cagcaacagg cgccgggccc caggatcgtg ccgcacccac acgccgcgcc gccgccggcc   420
aagaagagcc gccgcggccc gcgctcccgc agctcgcagt accgcggcgt caccttctac   480
cgccgcacag gccgctggga gtcccacatc tgggattgcg gcaagcaggt gtacctaggt   540
ggattcgaca ccgctcacgc cgctgcaagg cgtacgaccc gggcggcgat caagttccgc   600
ggcgtcgacg ccgacatcaa cttcaacctc agcgactacg aggacgacat gaagcagatg   660
gggagcctgt ccaaggagga gttcgtgcac gtcctgcgcc gtcagagcac cggcttctcg   720
agaggcagct ccaggtacag aggcgtcacc ctgcacaagt gcggccgctg ggaggcgcgc   780
atggggcagt tcctcggcaa gaagtacata taccttgggc tattcgacag cgaagtagag   840
gctgcaagag cctacgacaa ggccgccatc aaatgcaatg gcagagaggc cgtgacgaac   900
ttcgagccga gcacgtatca cggggagctg ccgactgaag ttgctgatgt cgatctgaac   960
ctgagcatat ctcagccgag cccccaaaga gacaagagca gctgcctagg tctgcagctc  1020
caccacggac cattcgaggg ctccgaactg aagaaaacca agatcgacga tgctccctct  1080
gagctaccgg gccgccctcg tcagctgtct cctctcgtgg ctgagcatcc gccggcctgg  1140
cctgcgcagc cgcctcaccc cttcttcgtc ttcacaaacc atgagatgag tgcatcagga  1200
gatctccaca ggaggcctgc aggggctgtt cccagctggg catggcaggt ggcagcagca  1260
gctcctcctc ctgccgccct ccgctcgtcc gctgcagcat catcaggatt ctccaacacc  1320
gccacgacag ctgccaccac cgccccatcg gcctcctccc tccggtactg cccgccgccg  1380
ccgccgccgt cgagccatca ccatcccgc tga                                1413

SEQ ID NO: 522           moltype = AA   length = 514
FEATURE                  Location/Qualifiers
source                   1..514
                         mol_type = protein
                         organism = Zea mays
SEQUENCE: 522
MTTSTTAKQL RRVRTLGRGA SGAVVWLASD EASGELVAVK SARAAGAAAQ LQREGRVLRG    60
LSSPHIVPCL GSRAAGGEY QLLLEFAPGG SLADEAARSG GGRLAERAIG AYAGDVARGL   120
AYLHGRSLVH GDVKARNVVI GGDGRARLTD FGCARPAGGS TRPVGGTPAF MAPEVARGQE   180
QGPAADVWAL GCMVVELATG RAPWSDVEGD DLLAALHRIG YTDDVPEVPA WLSPEAKDFL   240
AGCFERRAAA RPTAAQPAAH PFVVASASAA AAIRGPAKQE VVPSPKSTLH DAFWDSDAED   300
EADEMSTGAA AERIGALACA ASALPDWDTE EGWIDLQDDH SAGTADAPPA PVADYFISWA   360
EPSDAELEPF VAVAAAAGLP HVAGVALAGA TAVNLQGSYY YYPPMHLGVR GNEIPRPLLD   420
HHGDGLEKGQ GSHRVCNRET EKVTMKRISL KRRAAFLLDQ HHVRSLDKLE YRPRHDRMLR   480
RRQSIYRSNS VLGYDVSKGR QVRWRRAVCI AVAA                              514

SEQ ID NO: 523           moltype = DNA   length = 1545
FEATURE                  Location/Qualifiers
source                   1..1545
                         mol_type = unassigned DNA
```

```
                        organism = Zea mays
SEQUENCE: 523
atgacgacgt cgaccacggc gaagcagctc cggcgcgtgc gcacgctcgg ccgcggcgcg   60
tcgggcgccg tggtgtggct ggcctccgac gaggcctcgg gcgagctggt ggcggtcaag  120
tcggcgcgcg ccgccgggcg cgcggcgcag ctgcagcgcg agggccgcgt cctccggggc  180
ctctcgtcgc cgcacatcgt gccctgcctc ggctcccgcg ccgcggcggg cggcgagtac  240
cagctcctgc tggagttcgc gccgggcggg tcgctggccg acgaggccgc caggagcggg  300
gggggccgcc tcgcggagcg cgccatcggc gcctacgccg ggacgtggcg cgcgggctg   360
gcgtacctcc acggccggtc gctcgtgcac ggggacgtca aggcccggaa cgtggtcatc  420
ggcggcgacg ggcgcgccag gctgaccgac ttcgggtgcg cgaggccggc cggcgggtcg  480
acgcgccccg tcggggcac  cccggcgttc atggcgcccg aggtggcgcg cggccaggag  540
cagggccccg ccgccgacgt ctgggcgctc ggtgcatgg  tcgtcgagct ggccacgggc  600
cgcgcgccct ggagcgacgt ggagggcgac gacctcctcg ccgcgctcca ccggatcggg  660
tacacggacg acgtgccgga tggctgcca  ccgaggccaa ggacttcctg              720
gccggctgct tcgagcgccg cgccgccgcc cggcccacgg ccgcgcagcc gcggcgcac   780
ccgttcgtcg tcgcctccgc ctccgccgcc gccgccatcc gcggcccggc gaagcaggag  840
gtggtcccgt caccccaagag cacgctgcac gacgcgttct gggactcgga cgccgaggac  900
gaagcggacg agatgtcgac gggcgcggcg ccgagaagga tcggggcatt ggcgtgcgcc  960
gcctccgcgc tgcctgactg ggacaccgag gaaggctgga tcgacctcca ggacgaccac 1020
tcggccggaa ctgccgacgc accgccgcg  cccgtcgcgg actacttcat cagctggggc 1080
gagccgtcag acgcagagct ggaaccattc gtcgccgtcg ccgccgccgc aggtctcccg 1140
cacgttgcag gagttgcatt agcaggcgcc accgccgtca acctgccagg cagttattat 1200
tattacccgc ctatgcatct aggcgtccgc ggaaacgaga ttccacgccc gttgttggat 1260
catcatggcg acgggttaga aaaggggcag ggatccacc  gcgtttgtaa cagagaaaca 1320
gaaaaggtaa caatgaaacg aatttcgtta aaaagaagag ctgcttttcct tctcgaccag 1380
catcacgtgc gatcgctgga caaactggaa tatcgtccac gtcacgaccg aatgctgcgt 1440
cgacggcaat ctatatatcg gagcaatagc gtccttggtt acgacgttag caaaggtagg 1500
caggtccgtt ggcgccgtgc ggtttgcatt gccgttgctg cctga                 1545

SEQ ID NO: 524          moltype = DNA  length = 671
FEATURE                 Location/Qualifiers
source                  1..671
                        mol_type = unassigned DNA
                        organism = Zea mays
SEQUENCE: 524
cggatccact agtaacggcc gccagtgtgc tggaattcgc ccttgacggc ccgggctggt   60
atttcaaaac tatagtattt taaaattgca ttaacaaaca tgtcctaatt ggtactcctg  120
agatactata ccctcctgtt ttaaaatagt tggcattatc gaattatcat tttactttt   180
aatgttttct cttcttttaa tatattttat gaattttaat gtattttaaa atgttatgca  240
gttcgctctg gacttttctg ctgcgcctac acttgggtgt actgggccta aattcagcct  300
gaccgaccgc ctgcattgaa taatggatga gcaccggtaa aatccgcgta cccaactttc  360
gagaagaacc gagacgtggc gggccgggcc accgacgcac ggcaccagcg actgcacacg  420
tcccgccgac gtacgtgtac gtgctgttcc tcactgcgcc caatcca ctcatgcatg    480
cccacgtaca cccctgccgt ggcgcgccca gatcctaatc cttttcgcgt tctgcacttc  540
tgctgcctat aaatggcggc atcgaccgtc acctgcttca ccaccggcga gccacatcga  600
gaacacgatc gagcacacaa gcacgaagac tcgtttagga gaaaccacaa accaccaagc  660
cgtgcaagca c                                                       671

SEQ ID NO: 525          moltype = AA   length = 245
FEATURE                 Location/Qualifiers
source                  1..245
                        mol_type = protein
                        organism = Zea mays
SEQUENCE: 525
MGRGKVQLKR IENKINRQVT FSKRRSGLLK KAHEISVLCD AEVALIIFST KGKLYEYSTD   60
SCMDKILERY ERYSYAEKVL ISAEYETQGN WCHEYRKLKA KVETIQKCQK HLMGEDLETL  120
NLKELQQLEQ QLESSLKHIR TRKSQLMVES ISALQRKEKS LQEENKVLQK ELAEKQKDQR  180
QQVQRDQTQQ QTSSSSTSFM LREAAPTTNV SIFPVAAGGR VVEGAAAQPQ ARVGLPPWML  240
SHLSC                                                              245

SEQ ID NO: 526          moltype = DNA  length = 738
FEATURE                 Location/Qualifiers
source                  1..738
                        mol_type = unassigned DNA
                        organism = Zea mays
SEQUENCE: 526
atggggcgcg ggaaggtgca gctgaagcgg atcgagaaca agatcaaccg ccaggtgaca   60
ttctccaagc gccgctcggg gctactcaag aaggcgcacg agatctccgt gctctctgac  120
gccgaggtcg cgctcatcat cttctccacc aagggcaagc tctacgagta ctctaccgat  180
tcatgtatgg acaaaattct tgaacggtat gagcgctact cctatgcaga aaaggttctc  240
atttccgcag aatatgaaac tcaggggcaat tggtgccatg aatatagaaa actaaaggcg  300
aaggtcgaga caatacagaa atgtcaaaag cacctcatgg gagaggatct tgaaactttg  360
aatctcaaag agcttcagca actagagcag cagctggaga gttcactgaa acatatcaga  420
acaaggaaga gccagcttat ggtcgagtca atttcagcgt tccaacggaa gagaagtca   480
ctgcaggagg agaacaaggt tctgcagaag gagctcgcgg agaagcagaa agaccagcgg  540
cagcaagtgc aacgggacca aactcaacag cagaccagtt cgtcttccac gtccttcatg  600
ttaagggaag ctgccccaac aacaaatgtc agcatcttcc ctgtggcagc aggcgggagg  660
gtggtggaag ggcagcagc  gcagccgcag gctcgcgttg gactgccacc atggatgctt  720
agccatctga gctgctga                                                738
```

```
SEQ ID NO: 527          moltype = DNA   length = 80
FEATURE                 Location/Qualifiers
misc_feature            1..80
                        note = sequence of Figure 34B
source                  1..80
                        mol_type = unassigned DNA
                        organism = Zea mays
SEQUENCE: 527
gctaaagagg aagtgcagct cttcttgggg aatgctggaa ctgcaatgcg gccattgaca    60
gcagctgtta ctgctgctgg                                                80

SEQ ID NO: 528          moltype = DNA   length = 80
FEATURE                 Location/Qualifiers
misc_feature            1..80
                        note = sequence of Figure 34c
source                  1..80
                        mol_type = unassigned DNA
                        organism = Zea mays
SEQUENCE: 528
gctagagagg aagtgcagct cttcttgggg aatgctggaa tcgcaatgcg gtcattgaca    60
gcagctgtta ctgctgctgg                                                80

SEQ ID NO: 529          moltype = DNA   length = 37
FEATURE                 Location/Qualifiers
misc_feature            1..37
                        note = sequence of Figure 35b
source                  1..37
                        mol_type = unassigned DNA
                        organism = Zea mays
SEQUENCE: 529
catctcacga tcagatgcac cgcatgtcgc atgccta                              37

SEQ ID NO: 530          moltype = DNA   length = 42
FEATURE                 Location/Qualifiers
misc_feature            1..42
                        note = sequence of Figure 35c
source                  1..42
                        mol_type = unassigned DNA
                        organism = Zea mays
SEQUENCE: 530
catatctgca cgatcagata tgcaccgcat gtcgcatatc tg                        42

SEQ ID NO: 531          moltype = DNA   length = 31
FEATURE                 Location/Qualifiers
misc_feature            1..31
                        note = sequence of Figure 37
source                  1..31
                        mol_type = unassigned DNA
                        organism = Zea mays
SEQUENCE: 531
gtttttgaac ttcagttacg tgcttgatgg a                                    31

SEQ ID NO: 532          moltype = DNA   length = 31
FEATURE                 Location/Qualifiers
misc_feature            1..31
                        note = sequence of Figure 37
source                  1..31
                        mol_type = unassigned DNA
                        organism = Zea mays
SEQUENCE: 532
gtttttgaac ttcaggtacg tgcttgatgg a                                    31

SEQ ID NO: 533          moltype = DNA   length = 459
FEATURE                 Location/Qualifiers
misc_feature            1..459
                        note = synthesized sequence- Southern genomic probe
source                  1..459
                        mol_type = other DNA
                        organism = synthetic construct
SEQUENCE: 533
agctttatcc atccatccat cgcgctagct ggctgcaggc acgggttatc ttatcttgtc    60
gtccagagga cgcacacgg ccggccggtg aagtaaaagg gagtaatctt attttgccag    120
gacgagggc ggtacatgat attacacacg taccatgcat gcatatatgc atggacaagg    180
tacgtcgtcg tcgatcgacg tcgatgcata tgtgtgtatg tatgtacgtg cataatgcat    240
ggtaccagct gctggcttat atatatttgt caccgatcga tgcatgctgc tgctctacac    300
ggtttgacac tttaatttga ctcatcgatg accttgctag atagtagcgg ctcgtcaatt    360
aatgagccat caagttaaca agagggcacg ggcttgcgcg actgattcca ccttattaac    420
atacgccctg cgcccgcgcg tgctgtacgt acgagaatt                           459
```

```
SEQ ID NO: 534            moltype = DNA   length = 446
FEATURE                   Location/Qualifiers
misc_feature              1..446
                          note = synthesized sequence- Southern MoPAT probe
source                    1..446
                          mol_type = other DNA
                          organism = synthetic construct
SEQUENCE: 534
tcgaagtcgc gctgccagaa gccgacgtcg tgccagccgc cgtgcttgta gccggcggcg   60
cggagggtgc cgcgggcggt gtagccgagg gcctcgtgga ggcgcacgga cgggtcgttc  120
gggaggccga tcacggccac cacggacttg aagccctggg cctccatgct cttgaggagg  180
tgggtgtaga gggtggagcc gaggccgagg cgctggtggc ggtgggacac gtacacggtg  240
gactccacgg tccagtcgta ggcgttgcgg gccttccacg ccgatgccg                300
gccaccacgc cctccacctc ggccacgagc cacgggtagc ggtcctggag gcgctccagg  360
tcgtcgatcc actcctgcgg ggtctgcggc tcggtgcgga agttcacggt ggaggtctcg  420
atgtagtggt tcacgatgtc gcacac                                       446

SEQ ID NO: 535            moltype = DNA   length = 20
FEATURE                   Location/Qualifiers
misc_feature              1..20
                          note = synthesized sequence- RF-FPCas-1
source                    1..20
                          mol_type = other DNA
                          organism = synthetic construct
SEQUENCE: 535
gcaggtctca cgacggttgg                                               20

SEQ ID NO: 536            moltype = DNA   length = 23
FEATURE                   Location/Qualifiers
misc_feature              1..23
                          note = synthesized sequence- RF-FPCas-2
source                    1..23
                          mol_type = other DNA
                          organism = synthetic construct
SEQUENCE: 536
gtaaagtacg cgtacgtgtg agg                                           23

SEQ ID NO: 537            moltype = DNA   length = 23
FEATURE                   Location/Qualifiers
misc_feature              1..23
                          note = synthesized sequence- ALSCas-4
source                    1..23
                          mol_type = other DNA
                          organism = synthetic construct
SEQUENCE: 537
gctgctcgat tccgtcccca tgg                                           23

SEQ ID NO: 538            moltype = DNA   length = 804
FEATURE                   Location/Qualifiers
misc_feature              1..804
                          note = synthesized sequence- ALS modification repair
                            template 804
source                    1..804
                          mol_type = other DNA
                          organism = synthetic construct
SEQUENCE: 538
agcttacagc cgccgcaacc atggccaccg ccgccgccgc gtctaccgcg ctcactggcg   60
ccactaccgc tgcgcccaag gcgaggcgcc gggcgcaccg ccggccacc cgccgcgccc  120
tcgccgcgcc catcaggtgc tcagcggcgt caccgccat gccgatggct ccccggcca  180
ccccgctccg gccgtggggc cccaccgatc cccgcaaggg cgccgacatc ctcgtcgagt  240
ccctcgagcg ctgcggcgtc cgcgacgtct tcgcctaccc cggcggcgcg tccatggaga  300
tccaccaggc actcacccgc tccccgtca tcgccaacca cctcttccgc cacgagcaag  360
gggaggcctt tgcggcctcc ggctacgcgc gctcctcggg ccgcgtcgcg gtctgcatcg  420
ccacctccgg ccccggcgcc accaaccttg tctccgcgct cgccgacgcg ttgctcgact  480
ccgtccccat tgtcgccatc acgggacagg tgtcgcgacg catgattggc accgacgcct  540
tccaggagac gcccatcgtc gaggtcaccc gctccatcac caagcacaac tacctggtcc  600
tcgacgtcga cgacatcccc cgcgtcgtgc aggaggcttt cttcctcgcc tcctctggtc  660
gaccagggcc ggtgcttgtc gacatcccca aggacatcca gcagcagtg gcggtgcctg  720
tctgggacaa gcccatgagt ctgcctgggt acattgcgcg ccttccaag cccctgcga  780
ctgagttgct tgagcagaag ggcg                                         804

SEQ ID NO: 539            moltype = DNA   length = 127
FEATURE                   Location/Qualifiers
misc_feature              1..127
                          note = synthesized sequence- ALS modification repair
                            template 127
source                    1..127
                          mol_type = other DNA
```

```
                       organism = synthetic construct
SEQUENCE: 539
aaccttgtct ccgcgctcgc cgacgcgttg ctcgactccg tccccattgt cgccatcacg   60
ggacaggtgt cgcgacgcat gattggcacc gacgccttcc aggagacgcc catcgtcgag  120
gtcaccc                                                            127

SEQ ID NO: 540          moltype = DNA  length = 25
FEATURE                 Location/Qualifiers
misc_feature            1..25
                        note = synthesized sequence- ALS Forward_primer;
source                  1..25
                        mol_type = other DNA
                        organism = synthetic construct
SEQUENCE: 540
ctacgcacat ccccctttct cccac                                         25

SEQ ID NO: 541          moltype = DNA  length = 36
FEATURE                 Location/Qualifiers
misc_feature            1..36
                        note = synthesized sequence- ALS Reverse_primer
source                  1..36
                        mol_type = other DNA
                        organism = synthetic construct
SEQUENCE: 541
atgcatacct agcatgcgca gagacagtgg gtcgtc                             36

SEQ ID NO: 542          moltype = DNA  length = 22
FEATURE                 Location/Qualifiers
source                  1..22
                        mol_type = unassigned DNA
                        organism = Glycine max
SEQUENCE: 542
caccggccag gtcccccgcc gg                                            22

SEQ ID NO: 543          moltype = DNA  length = 22
FEATURE                 Location/Qualifiers
source                  1..22
                        mol_type = unassigned DNA
                        organism = Glycine max
SEQUENCE: 543
ggcgtcggtg ccgatcatcc gg                                            22

SEQ ID NO: 544          moltype = DNA  length = 9093
FEATURE                 Location/Qualifiers
misc_feature            1..9093
                        note = synthesized sequence- QC880
source                  1..9093
                        mol_type = other DNA
                        organism = synthetic construct
SEQUENCE: 544
ccgggtgtga tttagtataa agtgaagtaa tggtcaaaag aaaaagtgta aaacgaagta    60
cctagtaata agtaatattg aacaaaataa atggtaaagt gtcagatata taaaataggc  120
tttaataaaa ggaagaaaaa aacaaacaa aaaataggtt gcaatggggc agagcagagt   180
catcatgaag ctagaaaggc taccgataga taaactatag ttaattaaat acattaaaaa  240
atacttggat cttttctctta ccctgtttat attgagacgt gaaacttgag agagatacac  300
taatcttgcc ttgttgtttc attcccctaac ttacaggact cagcgcatgt catgtggtct  360
cgttccccat ttaagtccca caccgtctaa acttattaaa ttattaatgt ttataactag  420
atgcacaaca acaaagcttg caccggccag gtccccccgcg ttttagagct agaaatagca  480
agttaaaata aggctagtcc gttatcaact tgaaaaagtg gcaccgagtc ggtgctttt   540
tttgcggccg caattggatc gggtttactt attttgttgg tatctatact tttattagat  600
ttttaatcag gctcctgatt tctttttatt tcgattgaat tcctgaactt gtattattca  660
gtagatcgaa taaattataa aaagataaaa tcataaaata atatttttatc ctatcaatca  720
tattaaagca atgaatatgt aaaattaatc ttatctttat tttaaaaaat catataggtt  780
tagtattttt ttaaaaataa agataggatt agttttacta ttccactgctt attacttta  840
aaaaaatcat aaaggtttag tattttttta aaataaaatat aggaatagtt ttactattca  900
ctgctttaat agaaaaatag tttaaaattt aagatagttt taatcccagc atttgccacg  960
tttgaacgtg agccgaaacg atgtcgttac attatcttaa cctagctgaa acgatgtcgt 1020
cataatatcg ccaaatgcca actggactac gtcgaaccca caaatcccac aaagcgcgtg 1080
aaatcaaatc gctcaaacca caaaaaagaa caacgcgttt gttacacgct caatcccacg 1140
cgagtagagc acagtaacct tcaaataagc gaatggggca taatcagaaa tccgaaataa 1200
acctaggggc attatcggaa atgaaaagta gctcactcaa tataaaaatc taggaaccct 1260
agttttcgtt atcactctgt gctccctcgc tctatttctc agtctctgtg tttgcggctg 1320
aggattccga acgagtgacc ttcttcgttt ctcgcaaagg taacagcctc tgctcttgtc 1380
tcttcgattc gatctatgcc tgtctcttat ttacgatgat gtttcttcgg ttatgttttt 1440
ttatttatgc tttatgctgt tgatgttcgg ttgtttgttt cgctttgttt ttgtggttca 1500
gttttttagg attctttttgg ttttttgaatc gattaatcgg aagagatttt cgagttattt 1560
ggtgtgttgg aggtgaatct ttttttttgag gtcatagatc tgttgtattt tgttataaa 1620
catgcgactt gtatgatttt tttacgaggt tatgatgttc tggttgtttt attatgaatc 1680
tgttgagaca gaaccatgat ttttgttgat gttcgttac actattaaag gtttgttta 1740
```

```
acaggattaa aagtttttta agcatgttga aggagtcttg tagatatgta accgtcgata   1800
gttttttgt  gggtttgttc acatgttatc aagcttaatc ttttactatg tatgcgacca   1860
tatctggatc cagcaaaggc gatttttaa  ttccttgtga aacttttgta atatgaagtt   1920
gaaatttgt  tattggtaaa ctataaatgt gtgaagttgg agtatacctt taccttctta   1980
tttggctttg tgatagttta attatatgt  attttgagtt ctgacttgta tttctttgaa   2040
ttgattctag tttaagtaat ccatggacaa aaagtactca ataggctcg  acatagggac   2100
taactccgtt ggatgggccg tcatcaccga cgagtacaag gtgccctcca agaagttcaa   2160
ggtgttggga aacaccgaca ggcacagcat aaagaagaat tgatcggtg  ccctcctctt   2220
cgactccgga gagaccgctg aggctaccag gctcaagagg accgctagaa ggcgctacac   2280
cagaaggaag aacagaatct gctacctgca ggagatcttc tccaacgaga tggccaaggt   2340
ggacgactcc ttcttccacc gccttgagga atcattcctg gtggaggagg ataaaaagca   2400
cgagagacac ccaatcttcg ggaacatcgt cgacgaggtg gcctaccatg aaaagtaccc   2460
taccatctac cacctgagga agaagctggt cgactctacc gacaaggctg acttgcgctt   2520
gatttacctg gctctcgctc acatgataaa gttccgcgga cacttcctca ttgagggaga   2580
cctgaaccca gacaactccg acgtggacaa gctcttcatc cagctcgttc agacctacaa   2640
ccagcttttc gaggagaacc caatcaacgc cagtggagtt gacgccaagg ctatcctctc   2700
tgctcgtctg tcaaagtcca ggaggcttga gaacttgatt gcccagctgc ctggcgaaaa   2760
gaagaacgga ctgttcggaa acttgatcgc tctctcccta ggattgactc ccaacttcaa   2820
gtccaacttc gacctcgccg aggacgctaa gttgcagttg tctaaagaca cctacgacga   2880
tgacctcgac aacttgctgg cccagatagg cgaccaatac gccgatctct tcctcgccgc   2940
taagaacttg tccgacgcaa tcctgctgtc cgacatcctg agagtcaaca ctgagattac   3000
caaagctcct ctgtctgctt ccatgattaa gcgctacgac gagcaccacc aagatctgac   3060
cctgctcaag gccctggtga cagcagct  gcccgagaag tacaaggaga tctttttcga   3120
ccagtccaag aacggctacg ccggatacat tgacggaggc gcctcccagg aagagttcta   3180
caagttcatc aagcccatcc ttgagaagat ggacggtacc gaggagctgt tggtgaagtt   3240
gaacagagag gacctgttga ggaagcagag aaccttcgac aacggaagca tccctccacca  3300
aatccacctg ggagagctcc acgccatctt gaggaggcag gaggatttct atcccttcct   3360
gaaggacaac cgcgagaaga ttgagaagat cttgaccttc agaattcctt actacgtcgg   3420
gccactcgcc agaggaaact ctaggttcgc ctggatgacc cgcaaatctg aagagaccat   3480
tactccctgg aacttcgagg aagtcgtgga caagggcgct tccgctcagt ctttcatcga   3540
gaggatgacc aacttcgata aaaatctgcc caacgagaag gtgctgccca agcactccct   3600
gttgtacgag tatttcacag tgtcaacga  gctcaccaag gtgaagtacg tcacagaggg   3660
aatgaggaag cctgccttct tgtccggaga gcagaagaag gccatcgtcg acctgctctt   3720
caagaccaac aggaaggtga ctgtcaagca gctcaaggag gactacttca agaagatcga   3780
gtgcttcgac tccgtcgaga tctctggtgt cgaggacagg ttcaacgcct cccttgggac   3840
ttaccacgat ctgctcaaga ttattaaaga caaggacttc ctggacaacg aggagaacga   3900
ggacatcctt gaggacatcg tgctcaccct gaccttgttc aagacaggg  aaatgatcga   3960
agagaggctc aagacctacg cccacctctt cgacgacaag gtgatgaaac agctgaagag   4020
acgcagatat accggctggg aaggctctc  ccgcaaattg atcaacggga tcagggacaa   4080
gcagtcaggg aagactatac tcgacttcct gaagtccgac ggattcgcca acaggaactt   4140
catgcagctc attcacgacg actccttgac cttcaaggag gacatccaga aggctcaggt   4200
gtctggacag ggtgactcct tgcatgagca cattgctaac ttggccggct ctcccgctat   4260
taagaagggc attttgcaga ccgtgaaggt cgttgacgag ctcgtgaagg tgatgggacg   4320
ccacaagcca gagaacatcg ttattgagat ggctcgcgag aaccaaacta cccgagaagg   4380
gcagaagaat tcccgcgaga ggatgaagcg cattcgagag ggcataaaag agcttggctc   4440
tcagatcctc aaggagcacc ccgtcgagaa cactcagctg cagaacgaga agctgtacct   4500
gtactacctc caaaacggaa gggacatgta cgtggaccag gactggaca  tcaacaggtt   4560
gtccgactac gacgtcgacc acatcgtgcc tcagtcctt  ctgaaggatg actccatcga   4620
caataaagtg ctgacacgct ccgataaaaa tagaggcaag tccgacaacg tccccctccga  4680
ggaggtcgtg aagaagatga aaaactactg gagacagctc ttgaacgcca agctcatcac   4740
ccagcgtaag ttcgacaacc tgactaaggc tgagagagga ggattgtccg agctcgataa   4800
ggccggattc atcaagagac agctcgtcga accccgccaa attaccaagc acgtggccca   4860
aattctggat tcccgcatga acaccaagta cgatgaaaat gacaagctga tccgcgaggt   4920
caaggtgatc accttgaagt ccaagctggt ctccgacttc cgcaaggact tccagttcta   4980
ctggaggagg gagatcaaca actaccacca cgcacacgac gcctacctca acgctgtcgt   5040
tggaaccgcc ctcatcaaaa aatatcctaa gctggagtct gagttcgtct acggcgacta   5100
caaggtgtac gacgtgagga agatgatcgc taagtctgag caggagatcg gcaaggccac   5160
cgccaagtac ttccttctact ccaacatcat gaacttcttc aagaccgaga tcactctcgc   5220
caacggtgag atcaggaagc gcccactgat cgagaccaac ggtgagactg gagagatcgt   5280
gtgggacaaa gggagggatt tcgctactgt gaggaaggtg tctctccatgc ctcaggtgaa   5340
catcgtcaag aagaccgaag ttcagaccgg aggattctcc aaggagtcca tcctcccaa    5400
gagaaactcc gacaagctga tcgctagaaa gaaagactgg gacctaaga  agtacgagg    5460
cttcgattct cctaccgtgg cctactctgt gctggtcgtg gccaaggtgg agaagggcaa   5520
gtccaagaag ctgaaatccg tcaaggagct cctcgggatt accatcatgg aggaggttc    5580
cttcgagaag aacccatcg  acttcctgga ggccaaggga tataagagg  tgaagaagga   5640
cctcatcatc aagctgccca gtactcccct cttgagttg  gagaacggaa ggaagaggat   5700
gctggcttct gccggagagt tgcagaaggg aaatgagctc gcccttccct ccaagtacgt   5760
gaacttcctg tacctcgcct ctcactatga aaagttgaag ggctctcctg aggacaacga   5820
gcagaagcag ctcttcgtgg agcagcacaa gcactacctg gacgaaatta tcgagcagat   5880
ctctgagttc tccaagcgcg tgatattggc cgacgccaac ctcgacaagg tgctgtccgc   5940
ctacaacaag cacagggata agcccattcg cgagcaggct gaaaacatta tccacctgtt   6000
taccctcaca aacttgggag cccctgctgc cttcaagtac ttcgacacca ccattgacag   6060
gaagagatac acctccacca aggaggtgct cgacgcaaca ctcatccacc aatccatcac   6120
cggcctctat gaaacaagga ttgacttgtc ccagctggga ggcgactcta gagccgatcc   6180
caagaagaag agaaaggtgt aggttaacct agacttgtcc atcttctgga ttggccaact   6240
taattaatgt atgaaataaa aggatgcaca catagtgaca tgctaatcac tataatgtgg   6300
gcatcaaagt tgtgtgttat gtgtaattac tagttatctg aataaaagag aaagagatca   6360
tccatatttc ttatcctaaa tgaatgtcac gtgtctttat aattctttga tgaaccgat    6420
gcatttcatt aaccaaatcc atatacatat aaatattaat catatataat taatatcaat   6480
```

```
tgggttagca aaacaaatct agtctaggtg tgttttgcga attcgatatc aagcttatcg   6540
ataccgtcga gggggggccc ggtaccggcg cgccgttcta tagtgtcacc taaatcgtat   6600
gtgtatgata cataaggtta tgtattaatt gtagccgcgt tctaacgaca atatgtccat   6660
atggtgcact ctcagtacaa tctgctctga tgccgcatag ttaagccagc ccgacaccc    6720
gccaacaccc gctgacgcgc cctgacgggc ttgtctgctc ccggcatccg cttacagaca   6780
agctgtgacc gtctccggga gctgcatgtg tcagaggttt tcaccgtcat caccgaaacg   6840
cgcgagacga aagggcctcg tgatacgcct atttttatag gttaatgtca tgaccaaaat   6900
cccttaacgt gagttttcgt tccactgagc gtcagacccc gtagaaaaga tcaaaggatc   6960
ttcttgagat cctttttttc tgcgcgtaat ctgctgcttg caaacaaaaa aaccaccgct   7020
accagcggtg gtttgtttgc cggatcaaga gctaccaact cttttccga aggtaactgg    7080
cttcagcaga gcgcagatac caaatactgt ccttctagtg tagccgtagt taggccacca   7140
cttcaagaac tctgtagcac cgcctacata cctcgctctg ctaatcctgt taccagtggc   7200
tgctgccagt ggcgataagt cgtgtcttac cgggttggac tcaagacgat agttaccgga   7260
taaggcgcag cggtcgggct gaacggggg ttcgtgcaca cagcccagct tggagcgaac    7320
gacctacacc gaactgagat acctacagcg tgagcattga aaagcgcca cgcttcccga    7380
agggagaaag gcggacaggt atccggtaag cggcagggtc ggaacaggag agcgcacgag   7440
ggagcttcca ggggaaacg cctggtatct ttatagtcct gtcgggtttc gccacctctg    7500
acttgagcgt cgatttttgt gatgctcgtc agggggggcg agcctatgga aaaacgccag   7560
caacgcggcc ttttacggt tcctggcctt ttgctggcct tttgctcaca tgttctttcc    7620
tgcgttatcc cctgattctg tggataaccg tattaccgcc tttgagtgag ctgataccgc   7680
tcgccgcagc cgaacgaccg agcgcagcga gtcagtgagc gaggaagcgg aagagcgccc   7740
aatacgcaaa ccgcctctcc ccgcgcgttg gccgattcat taatgcaggt tgatcagatc   7800
tcgatcccgc gaaattaata cgactcacta tagggagacc acaacggttt ccctctagaa   7860
ataattttgt ttaactttaa gaaggagata tacccatgga aaagcctgaa ctcaccgcga   7920
cgtctgtcga gaagtttctg atcgaaaagt tcgacacgcg ctccgacctg atgcagctct   7980
cggagggcga agaatctcgt gctttctgca tcgatgtagg agggcgtgga tatgtcctgc   8040
gggtaaatag ctgcgccgat ggtttctaca aagatcgtta tgtttatcgg cactttgcat   8100
cggccgcgct cccgattccg gaagtgcttg acattgggga attcagcgag agcctgacct   8160
attgcatctc ccgccgtgca cagggtgtca cgttgcaaga cctgcctgaa accgaactgc   8220
ccgctgttct gcagccgtc gcggaggcta tggatgcgc cgctcgcgc gatcttagcc       8280
agacgagcgg gttcggccca ttcggaccgc aaggaatcgg tcaatacact acatggcgtg   8340
atttcatatg cgcgattgct gatccccatg tgtatcactg gcaaactgtg atggacgaca   8400
ccgtcagtgc gtccgtcgcg caggctccg atgagctgat gctttgggcc gaggactgcc    8460
ccgaagtccg gcacctcgtg cacgcggatt tcggctccaa caatgtcctg acggacaatg   8520
gccgcataac agcggtcatt gactggagcg aggcgatgtt cggggattcc caatacgagg   8580
tcgccaacat cttcttctgg aggccgtggt tggcttgtat ggagcagcag acgcgctact   8640
tcgagcggag gcatccggag cttgcaggat cgccgcggct ccgggcgtat atgctccgca   8700
ttggtcttga ccaactctat cagagcttgg ttgacggcaa tttcgatgat gcagcttggg   8760
cgcagggtcg atgcgacgca atcgtccgat ccggagccgg gactgtcgg cgtacacaaa     8820
tcgcccgcag aagcgcggcc gtctggaccg atggctgtgt agaagtactc gccgatagtg   8880
gaaaccgacg ccccagcact cgtccgaggg caaaggaata gtgaggtaca gcttggatcg   8940
atccggctgc taacaaagcc cgaaaggaag ctgagttggc tgctgccacc gctgagcaat   9000
aactagcata acccccttggg gcctctaaac gggtcttgag gggttttttg ctgaaaggag   9060
gaactatatc cggatgatcg ggcgcgccgg tac                                  9093

SEQ ID NO: 545          moltype = DNA  length = 9093
FEATURE                 Location/Qualifiers
misc_feature            1..9093
                        note = synthesized sequence- QC881
source                  1..9093
                        mol_type = other DNA
                        organism = synthetic construct
SEQUENCE: 545
ccgggtgtga tttagtataa agtgaagtaa tggtcaaaag aaaaagtgta aaacgaagta   60
cctagtaata agtaatattg aacaaaataa atggtaaagt gtcagatata taaaatagcc   120
tttaataaaa ggaagaaaaa aaacaaacaa aaaataggtt gcaatggggc agagcagagt   180
catcatgaag ctagaaaggc taccgataga taaactatag ttaattaaat acattaaaaa   240
atacttggat ctttctctta ccctgtttat attgagacct gaaacttgag agagatacac   300
taatcttgcc ttgttgtttc attccctaac ttacaggact cagcgcatgt catgtggtct   360
cgttccccat ttaagtccca caccgtctaa acttattaaa ttattaatgt ttataactag   420
atgcacaaca acaaagcttg ggcgtcggtc ccgatcatcg ttttagagct agaaatagca   480
agttaaaata aggctagtcc gttatcaact gaaaaagtg gcaccgagtc ggtgcttttt    540
tttgcggccg caattggatc gggtttactt attttgtggg tatctatact tttattagat   600
ttttaatcag gctcctgatt tctttttatt tcgattgact gttattatca                660
gtagatcgaa taaattataa aaagataaaa tcataaaata atattttatc ctatcaatca   720
tattaaagca atgaatatgt aaaattaatc ttatcttttt ttaaaaaat catataggtt    780
tagtatttt ttaaaataaa ataggatt agttttacta ttcactgctt attactttta     840
aaaaaatcat aaaggtttag tatttttta aaatatat aggaatagtt ttactattca     900
ctgctttaat agaaaaatag ttaaaatt aagatagttt taatcccagc atttgccacg    960
tttgaacgtg agccgaaacg atgtcgttac attatcttaa cctagctgaa acgatgtcgt  1020
cataatatcg ccaaatgcca actggactac gtcgaaccca caaatccac aaagcgcgtg   1080
aaatcaaatc gctcaaacca caaaaaagaa caacgcgttt gttacacgct caatcccacg  1140
cgagtagagc acagtaacct tcaaataagc gaatgggca taatcagaaa tccgaaataa   1200
acctaggggc attatcggaa atgaaaagta gctcactcaa tataaaaatc taggaaccct  1260
agttttcgtt atcactctgt gctccctcgc tctatttctc agtctctgtg tttgcggctg  1320
aggattccga acgagtgacc ttcttcgttt ctcgcaaagg taacagcctc tgctcttgtc  1380
tcttcgattc gatctatgcc tgtctcttat ttacgtgat gttcttcgg ttatgttttt    1440
ttattatgc tttatgctgt tgatgttcgg ttgtttgttt cgctttgttt ttgtggttca   1500
gttttttagg attcttttgg ttttttgaatc gattaatcgg aagagatttt cgagttattt  1560
```

```
ggtgtgttgg aggtgaatct ttttttgag gtcatagatc tgttgtattt gtgttataaa 1620
catgcgactt tgtatgattt tttacgaggt tatgatgttc tggttgtttt attatgaatc 1680
tgttgagaca gaaccatgat ttttgttgat gttcgtttac actattaaag gtttgtttta 1740
acaggattaa aagttttta agcatgttga aggagtcttg tagatatgta accgtcgata 1800
gtttttttgt gggtttgttc acatgttatc aagcttaatc ttttactatg tatgcgacca 1860
tatctggatc cagcaaaggc gatttttaa ttccttgtga aacttttgta atatgaagtt 1920
gaaattttgt tattggtaaa ctataaatgt gtgaagttgg agtataccttt taccttctta 1980
tttggctttg tgatagttta atttatatgt attttgagtt ctgacttgta tttctttgaa 2040
ttgattctag tttaagtaat ccatggacaa aaagtactca ataggctcg acataggac 2100
taactccgtt ggatgggccg tcatcaccga cgagtacaag gtgccctcca agaagttcaa 2160
ggtgttggga acaccgaca ggcacagcat aaagaagaat ttgatcggtg ccctcctctt 2220
cgactccgga gagaccgctg aggctaccag gctcaagagg accgctagaa ggcgctacac 2280
cagaaggaag aacagaatct gctacctgca ggagatcttc tccaacgaga tggccaaggt 2340
ggacgactcc ttcttccacc gccttgagga atcattcctg gtggaggagg ataaaaagca 2400
cgagagacac ccaatcttcg gaacatcgt cgacgaggtg gcctaccatg aaaagtaccc 2460
taccatctac cacctgagga agaagctggt cgactctacc gacaaggctg acttgcgctt 2520
gatttacctg gctctcgctc acatgataaa gttccgcgga cacttcctca ttgagggaga 2580
cctgaaccca gacaactccg acgtggacaa gctcttcatc cagctcgttc agacctacaa 2640
ccagcttttc gaggagaacc caatcaacgc cagtggagtt gacgccaagg ctatcctctc 2700
tgctcgtctg tcaaagtcca ggaggcttga gaacttgatt gccagctgc ctggcgaaaa 2760
gaagaacgga ctgttcggaa acttgatcgc tctctccctg ggattgactc ccaacttcaa 2820
gtccaacttc gacctgcgcg aggacgctaa gttgcagttg tctaaagaca cctacgacga 2880
tgacctcgac aacttgctgg cccagatagg cgaccaatac gccgatctct tcctcgccgt 2940
taagaacttg tccgacgcaa tcctgctgtc cgacatcctg agagtcaaca ctgagattac 3000
caaagctcct ctgtctgctt ccatgattaa gcgctacgac gagcaccacc aagatctgac 3060
cctgctcaag gccctggtga gacagcagct gcccgaaag tacaaggaga tcttttcga 3120
ccagtccaag aacggctacg ccggatacat tgacgaggc gcctcccagg aagagttcta 3180
caagttcatc aagcccatcc ttgagaagat ggacggtacc gaggagctgt tggtgaagtt 3240
gaacagagag gacctgttga ggaagcagag aaccttcgac aacggaagca tccctcacca 3300
aatccacctg ggagagctcc acgccatctt gaggaggcag gaggatttct atcccttcct 3360
gaaggacaac cgcgagaaga ttgagaagat cttgaccttc agaattcctt actacgtcgg 3420
gccactcgcc agaggaaact ctaggttcgc ctggatgacc cgcaaatctg aagagaccat 3480
tactccctgg aacttcgagg aagtcgtgga caagggcgct tccgctcagt ctttcatcga 3540
gaggatgacc aacttcgata aaaatctgcc caacgaaag gtgcgcccca agcactccct 3600
gttgtacgag tatttcacag tgtacaacga gctcaccaag gtgaagtacg tcacagaggg 3660
aatgaggaag cctgccttct tgtccggaga gcagaagaag gccatcgtcg acctgctctt 3720
caagaccaac aggaaggtga ctgtcaagca gctgaaggag gactacttca agaagatcga 3780
gtgcttcgac tccgtcgaga tctctggtgt cgaggacagg ttcaacgcct cccttgggac 3840
ttaccacgat ctgctcaaga ttattaaaga caaggacttc ctggacaacg aggagaacga 3900
ggacatcctt gaggacatcg tgctcacct gaccttgttc gaagacaggg aaatgatcga 3960
agagaggctc aagacctacg cccacctctt cgacgacaag gtgatgaaac agctgaagag 4020
acgcagatat accggctggg gaaggctctc ccgcaaattg atcaacggga tcaggacaa 4080
gcagtcaggg aagactatac tcgacttcct gaagtccgac ggattcgcca acaggaactt 4140
catgcagctc attcacgacg actccttgac cttcaaggag gacatccaga aggctcaggt 4200
gtctggacag ggtgactcct tgcatgagca cattgctaac ttggccggct ctcccgctat 4260
taagaaggc atttttgcaga ccgtgaaggt cgttgacaga ctcgtgaagg tgatgggacg 4320
ccacaagcca gagaacatcg ttattgagat ggctcgcgag aaccaaacta cccagaaagg 4380
gcagaagaat tcccgcgaga ggatgaagcg cattgaggag ggcataaaag agcttggctc 4440
tcagatcctc aaggagcacc ccgtcgaaa cactcagctg cagaacgaga agctggtacct 4500
gtactacctc caaaacggaa gggacatgta cgtggaccag gagctggaca tcaacaggtt 4560
gtccgactac gacgtcgacc acatcgtgcc tcagtccttc ctgaaggatg actccatcga 4620
caataagtg ctgacacgct ccgataaaaa tagaggcaag tccgacaacg tccctccga 4680
ggaggtcgtg aagaagatga aaaactactg gagacagctc ttgaacgcca agctcatcac 4740
ccagcgtaag ttcgacaacc tgactaaggc tgagagagga ggattgtccg agctcgataa 4800
ggccggattc atcaagagac agctcgtcga acccgccaa attaccaagc acgtggccca 4860
aattctggat tcccgcatga acaccaagta cgatgaaaat gacaagctga tccgcgaggt 4920
caaggtgatc accttgaagt ccaagctggt ctccgacttc cgcaaggact tccagttcta 4980
caaggtgagg agatcaaca actaccacca cgcacacgac gcctacctca acgctgtcgt 5040
tggaaccgcc ctcatcaaaa aatatccaa gctggagtct gagttcgtct acggcgacta 5100
caaggtgtac gacgtgagga agatgatcgc taagtctgag caggagatcg gcaaggccac 5160
cgccaagtac ttcttctact ccaacatcat gaacttcttc aagaccgaga tcactctcgc 5220
caacggtgag atcaggaagc gcccactgat cgagaccaac ggtgagactg gagagatcgt 5280
gtgggacaaa gggaggggatt tcgctactgt gaggaaggtg ctctccatgc ctcaggtgaa 5340
catcgtcaag aagaccgaag ttcagaccgg aggattctcc aaggagtcca tcctccccaa 5400
gagaaactcc gacaagctga tcgctagaaa gaaagactgg gaccctaaga agtacgagg 5460
cttcgattct cctaccgtgg cctactctgt gctggtcgtg gccaaggtgg agaagggcaa 5520
gtccaagaag ctgaaatccg tcaaggagct cctcgggatt accatcatgg agaggagttc 5580
cttcgagaag aacccctatcg acttcctgga ggccaaggga tataagagg tgaagaagga 5640
cctcatcatc aagctgccca gtactctcg gtgagaacgga gaagaggat 5700
gctggcttct gccggagagt tgcagaaggg aaatgagctc gcccttccct ccaagtacgt 5760
gaacttcctg tacctcgcct ctcactatga aaagttgaag gctctcctg aggacaacga 5820
gcagaagcag ctcttcgtgg agcagcacaa gcactacctg gacgaaatta cgagcagat 5880
ctctgagttc tccaagcgcg tgatattggc cgacgccaac ctcgacaagg tgctgtccgc 5940
ctacaacaag cacagggata gccccattcg cgagcaggca gaaacatta tccacctgtt 6000
taccctcaca aacttgggag cccctgctgc cttcaagtac ttcgacacca ccattgacag 6060
gaagagatac acctccacca aggaggtgct cgacgcaaca ctcatccacc aatccatcac 6120
cggcctctat gaaacaagga ttgacttgtc ccagctggga ggcgactcta gagccgatcc 6180
caagaagaag agaaggtgt aggttaacct agacttgtcc atcttctgga ttggccaact 6240
taattaatgt atgaaataaa aggatgcaca catagtgaca tgctaatcac tataatgtgg 6300
```

```
gcatcaaagt tgtgtgttat gtgtaattac tagttatctg aataaaagag aaagagatca 6360
tccatatttc ttatcctaaa tgaatgtcac gtgtctttat aattctttga tgaaccagat 6420
gcatttcatt aaccaaatcc atatacatat aaatattaat catatataat taatatcaat 6480
tgggttagca aaacaaatct agtctaggtg tgttttgcga attcgatatc aagcttatcg 6540
ataccgtcga gggggggccc ggtaccggcg cgccgttcta tagtgtcacc taaatcgtat 6600
gtgtatgata cataaggtta tgtattaatt gtagcgcgt tctaacgaca atatgtccat 6660
atggtgcact ctcagtacaa tctgctctga tgccgcatag ttaagccagc ccgacaccc 6720
gccaacaccc gctgacgcgc cctgacgggc ttgtctgctc ccggcatccg cttacagaca 6780
agctgtgacc gtctccggga gctgcatgtg tcagaggttt tcaccgtcat caccgaaacg 6840
cgcgagacga aagggcctcg tgatacgcct attttttatag gttaatgtca tgaccaaaat 6900
cccttaacgt gagttttcgt tccactgagc gtcagacccc gtagaaaaga tcaaaggatc 6960
ttcttgagat cctttttttc tgcgcgtaat ctgctgcttg caaacaaaaa aaccaccgct 7020
accagcggt gtttgtttgc cggatcaaga gctaccaact cttttccga aggtaactgg 7080
cttcagcaga gcgcagatac caaatactgt ccttctagtg tagccgtagt taggccacca 7140
cttcaagaac tctgtagcac cgcctacata cctcgctctg ctaatcctgt taccagtggc 7200
tgctgccagt ggcgataagt cgtgtcttac cgggttggac tcaagacgat agttaccgga 7260
taaggcgcag cggtcgggct gaacggggg ttcgtgcaca cagcccagct tggagcgaac 7320
gacctacacc gaactgagat acctacagcg tgagcattga gaaagcgcca cgcttcccga 7380
agggagaaag gcggacaggt atccggtaag cggcagggtc ggaacaggag agcgcacgag 7440
ggagcttcca gggggaaacg cctggtatct ttatagtcct gtcgggttc gccacctctg 7500
acttgagcgt cgatttttgt gatgctcgtc aggggggcgg agcctatgga aaacgccag 7560
caacgcggcc tttttacggt tcctggcctt ttgctgcaca tgttctttcc 7620
tgcgttatcc cctgattctg tggataaccg tattaccgcc tttgagtgag ctgataccgc 7680
tcgccgcagc cgaacgaccg agcgcagcga gtcagtgagc gaggaagcgg aagagcgccc 7740
aatacgcaaa ccgcctctcc ccgcgcgttg gccgattcat taatgcaggt tgatcagatc 7800
tcgatcccgc gaaattaata cgactcacta tagggagacc acaacggttt ccctctagaa 7860
ataattttgt ttaactttaa gaaggagata tacccatgga aaagcctgaa ctcaccgcga 7920
cgtctgtcga gaagtttctg atcgaaaagt tcgacagcgt ctccgacctg atgcagctct 7980
cggagggcga agaatctcgt gcttcagct tcgatgtagg agggcgtgga tatgtcctgc 8040
gggtaaatag ctgcgccgat ggtttctaca aagatcgtta tgtttatcgg cactttgcat 8100
cggccgcgct cccgattccg gaagtgcttg acattgggga attcagcgag agcctgacct 8160
attgcatctc ccgccgtgca cagggtgtca cgttgcaaga cctgcctgaa accgaactgc 8220
ccgctgttct gcagccggtc gcggaggcta tggatgcgat cgctgcggcc gatcttagcc 8280
agacgagcgg gttcggccca ttcggaccgc aaggaatcgg tcaatacact acatggcgtg 8340
atttcatatg cgcgattgct gatccccatg tgtatcactg gcaaactgtg atggacgaca 8400
ccgtcagtgc gtccgtcgcg caggctctcg atgagctgat gctttgggcc gaggactgcc 8460
ccgaagtccg gcacctcgtg cacgcggatt tcggctccaa caatgtcctg acggacaatg 8520
gccgcataac agcggtcatt gactggagcg aggcgatgt cggggattcc caatacgagg 8580
tcgccaacat cttcttctgg aggccgtggt tggcttgtat ggagcagcag acgcgctact 8640
tcgagcggag gcatccggag cttgcaggat cgccgcggct ccgggcgtat atgctccgca 8700
ttggtcttga ccaactctat cagagcttgg ttgacggcaa tttcgatgat gcagcttggg 8760
cgcagggtcg atgcgacgca atcgtccgat ccggagccgg gactgtcggg cgtacacaaa 8820
tcgcccgcag aagcgcggcc gtctggaccg atggctgtgt agaagtactc gccgatagtg 8880
gaaaccgacg ccccagcact cgtccgaggg caaaggaata gtgaggtaca gcttggatcg 8940
atccggctgc taacaaagcc cgaaaggaag ctgagttggc tgctgccacc gctgagcaat 9000
aactagcata acccttgg gcctctaaac gggtcttgag gggttttttg ctgaaaggag 9060
gaactatatc cggatgatcg ggcgcgccgg tac                                9093
```

```
SEQ ID NO: 546          moltype = DNA   length = 1113
FEATURE                 Location/Qualifiers
misc_feature            1..1113
                        note = synthesized sequence- RTW1026A
source                  1..1113
                        mol_type = other DNA
                        organism = synthetic construct
SEQUENCE: 546
agcttggtac cgagctcgga tccactagta tggcggccac cgcttccaga accacccgat   60
tctcttcttc ctcttcacac cccaccttcc ccaaacgcat tactagatcc accctccctc  120
tctctcatca aaccctcacc aaacccaacc agcgtctcca aatcaaatgt tccatctcca  180
aaccccccac ggcggcgccc ttcaccaagg aagcgccgac cacggagccc ttcgtgtcac  240
ggttcgcctc cggcgaacct cgcaagggcg cggacatcct tgtggaggcg ctggagaggc  300
agggcgtgac gacggtgttc gcgtaccccg cggtgcgtc gatggagatc caccaggcgc  360
tcacgcgctc cgccgccatc cgcaacgtgc tcccgcgcca cgagcagggc ggcgtcttcg  420
ccgccgaagg ctacgcgcgt tcctccggcc tcccccggcc ctgcattgcc acctccgtgc  480
ccggcgccac caacctcgtg agcggcctcg ccgacgcttt aatggacagc gtcccagtcg  540
tcgccatcac cggccaggtc agccgtcgca tgatcggtac cgacgccttc caagaaaccc  600
cgatcgtgga ggtgagcaga tccatcacga agcacaacta cctcatcctc gacgtcgacg  660
acatccccg cgtcgtcgcc gaggctttct tcgtcgccac ctccgccgcc cccggtccgg  720
tcctcatcga cattcccaaa gacgttcagc agcaactcgc cgtgcctaat tgggacgagc  780
ccgttaacct ccccgttac ctcgccaggc tgcccaggcc cccgccgag gcccaattgg  840
aacacattgt cagactcatc atggaggccc aaaagcccgt tctctacgtc ggcggtggca  900
gtttgaattc cagtgctgaa ttgaggcgct tgttgaact cactggtatt cccgttgcta  960
gcactttaat gggtcttgga acttttccta ttggtgatga atattccctt cagatgctgg 1020
gtatgcatgg tactgtttat gctaactatg ctgttgacaa tagtgatttg ttgcttgcct 1080
ttgggtaag gtttgatgac cgtgttactg gga                               1113
```

```
SEQ ID NO: 547          moltype = DNA   length = 17
FEATURE                 Location/Qualifiers
misc_feature            1..17
```

-continued

```
                        note = synthesized sequence- WOL900, Forward_primer
source                  1..17
                        mol_type = other DNA
                        organism = synthetic construct
SEQUENCE: 547
atcaccggcc aggtcag                                                        17

SEQ ID NO: 548          moltype = DNA   length = 25
FEATURE                 Location/Qualifiers
misc_feature            1..25
                        note = synthesized sequence- WOL578, Reverse_primer
source                  1..25
                        mol_type = other DNA
                        organism = synthetic construct
SEQUENCE: 548
acttaccctc cactcctttc tcctc                                               25

SEQ ID NO: 549          moltype = DNA   length = 29
FEATURE                 Location/Qualifiers
misc_feature            1..29
                        note = synthesized sequence- WOL573, Forward_primer
source                  1..29
                        mol_type = other DNA
                        organism = synthetic construct
SEQUENCE: 549
atggcggcca ccgcttccag aaccacccg                                           29

SEQ ID NO: 550          moltype = AA   length = 638
FEATURE                 Location/Qualifiers
source                  1..638
                        mol_type = protein
                        organism = Zea mays
SEQUENCE: 550
MATAAAASTA LTGATTAAPK ARRRAHLLAT RRALAAPIRC SAASPAMPMA PPATPLRPWG  60
PTEPRKGADI LVESLERCGV RDVFAYPGGA SMEIHQALTR SPVIANHLFR HEQGEAFAAS  120
GYARSSGRVG VCIATSGPGA TNLVSALADA LLDSVPMVAI TGQVPRRMIG TDAFQETPIV  180
EVTRSITKHN YLVLDVDDIP RVVQEAFFLA SSGRPGPVLV DIPKDIQQQM AVPVWDKPMS  240
LPGYIARLPK PPATELLEQV LRLVGESRRP VLYVGGGCAA SGEELRRFVE LTGIPVTTTL  300
MGLGNFPSDD PLSLRMLGMH GTVYANYAVD KADLLLALGV RFDDRVTGKI EAFASRAKIV  360
HVDIDPAEIG KNKQPHVSIC ADVKLALQGM NALLEGSTSK KSFDFGSWND ELDQQKREFP  420
LGYKTSNEEI QPQYAIQVLD ELTKGEAIIG TGVGQHQMWA AQYYTYKRPR QWLSSAGLGA  480
MGFGLPAAAG ASVANPGVTV VDIDGDGSFL MNVQELAMIR IENLPVKVFV LNNQHLGMVV  540
QWEDRFYKAN RAHTYLGNPE NESEIYPDFV TIAKGFNIPA VRVTKKNEVR AAIKKMLETP  600
GPYLLDIIVP HQEHVLPMIP SGGAFKDMIL DGDGRTVY                          638

SEQ ID NO: 551          moltype = DNA   length = 43
FEATURE                 Location/Qualifiers
misc_feature            1..43
                        note = sense genome sequence Figure 2A and 2B
source                  1..43
                        mol_type = unassigned DNA
                        organism = Zea mays
SEQUENCE: 551
gatatatata cctcacacgt acgcgtacgc gtatatatac gtg                           43

SEQ ID NO: 552          moltype = DNA   length = 43
FEATURE                 Location/Qualifiers
misc_feature            1..43
                        note = complementary genome sequence Figure 2A and 2B
source                  1..43
                        mol_type = unassigned DNA
                        organism = Zea mays
SEQUENCE: 552
cacgtatata tacgcgtacg cgtacgtgtg aggtatatat atc                           43

SEQ ID NO: 553          moltype = DNA   length = 104
FEATURE                 Location/Qualifiers
misc_feature            1..104
                        note = synthesized sequence- sequence of Figure 8B
source                  1..104
                        mol_type = other DNA
                        organism = synthetic construct
SEQUENCE: 553
gtcccttgta cttgtacgta gttttagagc tagaaatagc aagttaaaat aaggctagtc  60
cgttatcaac ttgaaaaagt ggcaccgagt cggtgctttt tttt                         104

SEQ ID NO: 554          moltype = DNA   length = 70
FEATURE                 Location/Qualifiers
source                  1..70
```

```
                        mol_type = unassigned DNA
                        organism = Glycine max
SEQUENCE: 554
atcaaaattc ggaactgaca cacgacatga tggaacgtga ctaaggtggg tttttgactt    60
tgcatgtcga                                                           70

SEQ ID NO: 555          moltype = DNA  length = 70
FEATURE                 Location/Qualifiers
source                  1..70
                        mol_type = unassigned DNA
                        organism = Glycine max
SEQUENCE: 555
tcgacatgca aagtcaaaaa cccaccttag tcacgttcca tcatgtcgtg tgtcagttcc    60
gaattttgat                                                           70

SEQ ID NO: 556          moltype = DNA  length = 70
FEATURE                 Location/Qualifiers
source                  1..70
                        mol_type = unassigned DNA
                        organism = Glycine max
SEQUENCE: 556
ggcagactcc aattcctctt ttctagaata ccctccgtac gtacaagtac aagggacttg    60
tgagttgtaa                                                           70

SEQ ID NO: 557          moltype = DNA  length = 70
FEATURE                 Location/Qualifiers
source                  1..70
                        mol_type = unassigned DNA
                        organism = Glycine max
SEQUENCE: 557
ttacaactca caagtccctt gtacttgtac gtacggaggg tattctagaa aagaggaatt    60
ggagtctgcc                                                           70

SEQ ID NO: 558          moltype = AA  length = 8
FEATURE                 Location/Qualifiers
REGION                  1..8
                        note = MISC_FEATURE - Maize EPSPS polyubiquitination site
REGION                  1..8
                        note = MISC_FEATURE - Maize EPSPS polyubiquitination site
source                  1..8
                        mol_type = protein
                        organism = Zea mays
SEQUENCE: 558
VEDAKEEV                                                              8

SEQ ID NO: 559          moltype = AA  length = 8
FEATURE                 Location/Qualifiers
REGION                  1..8
                        note = MISC_FEATURE - Petunia EPSPS polyubiquitination site
source                  1..8
                        mol_type = protein
                        organism = Petunia hybrida
SEQUENCE: 559
GKESKEEI                                                              8

SEQ ID NO: 560          moltype = AA  length = 8
FEATURE                 Location/Qualifiers
REGION                  1..8
                        note = MISC_FEATURE - Tomato EPSPS polyubiquitination site
source                  1..8
                        mol_type = protein
                        organism = Solanum lycopersicum
SEQUENCE: 560
GKKSEEEI                                                              8

SEQ ID NO: 561          moltype = AA  length = 8
FEATURE                 Location/Qualifiers
REGION                  1..8
                        note = MISC_FEATURE - Sorghum EPSPS polyubiquitination site
source                  1..8
                        mol_type = protein
                        organism = Sorghum bicolor
SEQUENCE: 561
EKDAKEEV                                                              8

SEQ ID NO: 562          moltype = AA  length = 8
FEATURE                 Location/Qualifiers
REGION                  1..8
                        note = MISC_FEATURE - Rice EPSPS polyubiquitination site
```

```
source                  1..8
                        mol_type = protein
                        organism = Oryza sativa
SEQUENCE: 562
VEDSKEEV                                                                          8

SEQ ID NO: 563          moltype = AA  length = 8
FEATURE                 Location/Qualifiers
REGION                  1..8
                        note = MISC_FEATURE - Amaranthus EPSPS polyubiquitination
                         site
source                  1..8
                        mol_type = protein
                        organism = Amaranthus floridanus
SEQUENCE: 563
GKDGKEEI                                                                          8

SEQ ID NO: 564          moltype = DNA  length = 80
FEATURE                 Location/Qualifiers
source                  1..80
                        mol_type = unassigned DNA
                        organism = Zea mays
SEQUENCE: 564
gctaaagagg aagtgcagct cttcttgggg aatgctggaa ctgcaatgcg gccattgaca              60
gcagctgtta ctgctgctgg                                                          80

SEQ ID NO: 565          moltype = DNA  length = 80
FEATURE                 Location/Qualifiers
source                  1..80
                        mol_type = unassigned DNA
                        organism = Zea mays
SEQUENCE: 565
gctagagagg aagtgcagct cttcttgggg aatgctggaa tcgcaatgcg gtcattgaca              60
gcagctgtta ctgctgctgg                                                          80

SEQ ID NO: 566          moltype = DNA  length = 37
FEATURE                 Location/Qualifiers
source                  1..37
                        mol_type = unassigned DNA
                        organism = Zea mays
SEQUENCE: 566
catctcacga tcagatgcac cgcatgtcgc atgccta                                       37

SEQ ID NO: 567          moltype = DNA  length = 42
FEATURE                 Location/Qualifiers
source                  1..42
                        mol_type = unassigned DNA
                        organism = Zea mays
SEQUENCE: 567
catatctgca cgatcagata tgcaccgcat gtcgcatatc tg                                 42
```

"Plant Genome Modification Using Guide Rna/Cas Endonuclease Systems and Methods of Use," Co-Pending Related U.S. Appl. No. 14/463,687, filed Aug. 20, 2014, Abandoned Feb. 3, 2022, 262 Pages.
Puchta H., et al., "Gene Replacement by Homologous Recombination in Plants," Plant Molecular Biology, 2002, vol. 48, pp. 173-182.

(56) References Cited

OTHER PUBLICATIONS

Puchta H., et al., "Synthetic Nucleases for Genome Engineering in Plants: Prospects for a Bright Future," The Plant Journal, 2014, vol. 78, pp. 727-741.
Que Q., et al., "Maize Transformation Technology Development For Commercial Event Generation," Frontiers in Plant Science, Aug. 5, 2014, vol. 5, Article No. 379, 19 Pages, DOI:10.3389/fpls.2014.00379, XP055217826.
Que Q., et al., "Trait Stacking in Transgenic Crops Challenges and Opportunities," GM Crops, Jul.-Oct. 2010, vol. 1, No. 4, pp. 220-229.
Que Q., "Repurposing Macromolecule Delivery Tools for Plant Genetic Modification in the Era of Precision Genome Engineering," Methods and Protocols, Methods in Molecular Biology, 2019, Chapter 1, vol. 1864, 16 Pages.
Quinn T.P., et al., "A Streamlined Method for the Production, Screening, and Application of SgRNAs for CRISPR/Cas Gene Editing," Molecular Therapy, May 2014, vol. 22, Supplement 1, pp. S127-S128,(#336).
Raikhel N., "Nuclear Targeting in Plants," Plant Physiology, 1992, vol. 100, pp. 1627-1632.
Ramakrishna S., et al., "Gene Disruption by Cell -Penetrating Peptide-Mediated Delivery of Cas9 Protein and Guide RNA," Genome Research, 2014, vol. 24, No. 6, pp. 1020-1027, 9 Pages, DOI: 10.1101/gr.171264.113, XP055128944.
Rath D., et al., "Type I-E CRISPR-Cas System as an Immune System in a Eukaryote," BioRxiv, 2018, 20 Pages, DOI: 10.1101/357301.
Reeks J., et al., "CRISPR Interference: A Structural Perspective," Biochemical Journal, 2013, vol. 453, pp. 155-166, 17 Pages.
Ren X., et al., "Optimized Gene Editing Technology for Drosophila Melanogaster Using Germ Line-Specific Cas9," Proceedings of the National Academy of Sciences, Nov. 19, 2013, vol. 110, No. 47, pp. 19012-19017, XP055967811.
Retallack D.M., et al., "A Single-Base-Pair Mutation Changes the Specificities of Both a Transcription Activation Protein and its Binding Site," Proceedings of the National Academy of Sciences of the United States of America, Oct. 1993, vol. 90, pp. 9562-9565.
Rueda et al., "Mapping the sugar dependency for rational generation of a DNA-RNA hybrid- guided Cas9 andonuclease". Nature Communications, 2017, 8:1610, XP055688584 (and Supplemental).
Rueda F.O., et al., "Mapping the Sugar Dependency for Rational Generation of a DNA-RNA Hybrid-Guided Cas9 Endonuclease," Nature Communications, 2017, vol. 8, No. 1610, pp. 1-11, Jan. 1, 2017, XP055688584.
Rusk N., "New Kid on the CRISPR Block," Nature Methods, 2015, vol. 12, No. 12, p. 1117.
Sanozky-Dawes R., et al., "Occurrence and Activity of a Type II CRISPR-Cas System in Lactobacillus Gasseri," Microbiology, vol. 161, No. 9, pp. 1752-1761, Sep. 1, 2015.
Schaeffer S.M., et al., "The Expanding Footprint of CRISPR/CAs9 in the Plant Sciences," Plant Cell Reports, Springer International, DE, Apr. 30, 2016, vol. 35, No. 7, pp. 1451-1468.
Schirle N.T., et al., "Structural Basis for MicroRNA Targeting," Science, Oct. 31, 2014, vol. 346, Issue. 6209, pp. 608-613.
Schlake T., et al., "Use of Mutated FLP Recognition Target (FRT) Sites for the Exchange of Expression Cassettes at Defined Chromosomal Loci," Biochemistry, 1994, vol. 33, No. 43, pp. 12746-12751.
Schulze S., et al., "The Development of Genome Editing Tools as Powerful Techniques with Versatile Applications in Biotechnology and Medicine: CRISPR/Cas9, ZnF and TALE Nucleases, RNA Interference, and Cre/loxP," ChemTexts, 2021, vol. 7, No. 3, 18 Pages.
Shah S.A., et al., "Protospacer Recognition Motifs," RNA Biology, May 1, 2013, vol. 10, No. 5, pp. 891-899, ISSN: 1547-6286.
Shi J., et al., "ARGOS8 Variants Generated by CRISPR-Cas9 Improve Maize Grain Yield Under Field Drought Stress Conditions," Plant Biotechnology Journal, Published online Aug. 17, 2016, 2017, vol. 15, No. 2, pp. 207-216, XP002776694.
Shi J., et al., "Maize and Arabidopsis ARGOS Proteins Interact with Ethylene Receptor Signaling Complex, Supporting a Regulatory Role for ARGOS in Ethylene Signal Transduction [Open]," Plant Physiology, Published online Jun. 7, 2016, Aug. 2016, vol. 171, No. 4, pp. 2783-2797.
Shi J., et al., "Overexpression of ARGOS Genes Modifies Plant Sensitivity to Ethylene, Leading to Improved Drought Tolerance in Both Arabidopsis and Maize [Open]," Plant Physiology, Sep. 2015, vol. 169, pp. 266-282.
Shmakov S., et al., "Diversity and Evolution of Class 2 CRISPR-Cas Systems," Nature Reviews Microbiology, 2017, vol. 15, No. 3, pp. 1-14, Published Online Jan. 23, 2017.
Shou H., et al., "Assessment of Transgenic Maize Events Produced by Particle Bombardment or Agrobacterium-Mediated Transformation," Molecular Breeding, 2004, vol. 13, pp. 201-208.
Shukla V.K., et al., "Precise Genome Modification in the Crop Species *Zea mays* Using Zinc- finger Nucleases," Nature, May 21, 2009, vol. 459, No. 7245, pp. 437-441, and Supplementary Information, Total 23 pages.
Sinkunas T., et al., "Cas3 is a Single-Stranded DNA Nuclease and ATP-Dependent Helicase in the CRISPR/Cas Immune System," The EMBO Journal, (European Molecular Biology Organization), Apr. 2011, vol. 30, No. 7, pp. 1335-1342, XP002765626.
Sinkunas T., et al., "In Vitro Reconstitution of Cascade-Mediated CRISPR Immunity in *Streptococcus thermophilus*," The EMBO Journal, 2013, vol. 32, No. 3, pp. 385-394.
Sodeinde O.A., et al., "Homologous Recombination in the Nuclear Genome of Chlamydomonas Reinhardtii," Proceedings of the National Academy of Sciences of the United States of America, Oct. 1993, vol. 90, pp. 9199-9203.
Song Q., et al., "Development and Evaluation of SoySNP50K, a High Density Genotyping Array for Soybean," PLoSONE, Jan. 25, 2013, vol. 8 No. 1, p. e54985, 12 pages.
Sontheimer E.J., et al.,"Cas9 gets a classmate," Nature Biotechnology, Dec. 2015, vol. 33, No. 12, pp. 1240-1241.
Stemmer M., et al., "CCTop: An Intuitive, Flexible and Reliable CRISPR/Cas9 Target Prediction Tool," PLOS One, Apr. 24, 2015, vol. 10, No. 4, e0124633, 11 Pages.
Strauss A., et al., "Zinc Fingers, TAL Effectors, or Cas9-Based DNA Binding Proteins: What's Best for Targeting Desired Genome Loci?," Molecular Plant, Sep. 2013, vol. 6, No. 5, pp. 1384-1387.
Stryer L., et al., "A Nucleic Acid Consists of Four Kinds of Bases Linked to a SugarPhosphate Backbone", Stryer's Biochemistry, Sixth Edition, 2002, pp. 108-109, XP055688354.
Subburaj S., et al., "Site-Directed Mutagenesis in Petunia x Hybrida Protoplast System Using Direct Delivery of Purified Recombinant Cas9 Ribonucleoproteins," Plant Cell Reports, 2016, vol. 35, pp. 1535-1544.
Sun Z., et al., "Expanding the Biotechnology Potential of Lactobacilli Through Comparative Genomics of 213 Strains and Associated Genera," Nature Communications, Nature Publishing Group, UK, Sep. 29, 2015, vol. 6, Article No. 8322, 13 Pages.
Svitashev S., et al., "Genome Editing in Maize Directed by CRISPR-Cas9 Ribonucleoprotein Complexes," Nature Communications, Nov. 16, 2016, vol. 07, Article No. 13274, 7 Pages, DOI: 10.1038/ncomms13274, PMID: 27848933, PMCID: PMC5116081.
Svitashev S., et al., "Targeted Mutagenesis, Precise Gene Editing, and Site-Specific Gene Insertion in Maize using Cas9 and Guide RNA," Plant Physiology, 2015, vol. 169, No. 2, pp. 931-945.
Tan S., et al., "Imidazolinone-Tolerant Crops: History, Current Status and Future," Pest Management Science, Wiley & Sons, Bognor Regis; GB, Jan. 1, 2005, vol. 61, No. 03, pp. 246-257, DOI:10.1002/ps.993, ISSN 1526-498X, XP009058795.
Tang X., et al.: "A CRISPR-Cpf1 System for Efficient Genome Editing and Transcriptional Repression in Plants," Nature Plants, 2017, vol. 3, Article No. 17018, 16 Pages.
Ui-Tei K., et al., "Functional Dissection of siRNA Sequence by Systematic DNA Substitution: Modified siRNA with a DNA Seed Arm is a Powerful Tool for Mammalian Gene Silencing with Significantly Reduced Off-Target Effect," Nucleic Acids Research, 2008, vol. 36, No. 7, pp. 2146-2151.

(56) References Cited

OTHER PUBLICATIONS

UNIPROT: RecName: "Full-CRISPR-Associated Endonuclease Cas9," Database Accession No. AOAOF4LLEO, 2015, 2 Pages, Retrieved from URL: EBI.
UNIPROT: RecName: "Full-CRISPR-Associated Endonuclease Cas9," Database Accession No. HOUDA8, 2012, Retrieved from URL: EBI.
Unniyampurath U., et al., "RNA Interference in the Age of CRISPR: Will CRISPR Interfere with RNAi," International Journal of Molecular Sciences, Feb. 26, 2016, vol. 17, No. 291, 15 Pages.
Wang M., et al., "Multiplex Gene Editing in Rice Using the CRISPR-Cpf1 System," Molecular Plant, 2017, vol. 10, No. 7, pp. 1-3.
Wang M-B., et al., "Hairpin RNAs Derived from RNA Polymerase II and Polymerase III Promoter-Directed Transgenes are Processed Differently in Plants," RNA, May 2008, vol. 14, No. 5, pp. 903-913, Doi: 10.1261/RNA.760908, ISSN 1355-8382, XP002639663.
Wei F., et al., "Physical and Genetic Structure of the Maize Genome Reflects Its Complex Evolutionary History," PLOS Genetics, Jul. 20, 2007, vol. 3, No. 7, pp. 1254-1263.
Wendt T., et al., "TAL Effector Nucleases Induce Mutations at a Pre-Selected Location in the Genome of Primary Barley Transformants," Plant Molecular Biology, 2013, vol. 83, pp. 279-285, Retrieved from URL: https://doi.org/10.1007/s11103-013-0078-4.
Westra E.R., et al., "CRISPR Immunity Relies on the Consecutive Binding and Degradation of Negatively Supercoiled Invader DNA by Cascade and Cas3," Molecular Cell, Jun. 8, 2012, vol. 46, No. 5, pp. 595-605, E-Published on Apr. 19, 2012.
Wierzbicki A.T., et al., "Noncoding Transcription by RNA Polymerase Pol IVb/Pol V Mediates Transcriptional Silencing of Overlapping and Adjacent Genes," Cell, Nov. 14, 2008, vol. 135, pp. 635-648.
Wolter F., et al., "Knocking Out Consumer Concerns and Regulators Rules: Efficient Use of CRISPR/Cas Ribonucleoproteir Complexes for Genome Editing in Cereals," Genome Biology, 2017, vol. 18, No. 43, 3 Pages.
Woo J.W., et al., "DNA-Free Genome Editing in Plants with Preassembled CRISPR-Cas9 Ribonucleoproteins," Nature Biotechnology, US, Oct. 19, 2015, vol. 33, No. 11, pp. 1162-1164, DOI:10.1038/nbt.3389, ISSN 1087-0156, XP055290196.
Wu J., et al., "Tn5 Transposase-Assisted Transformation of Indica Rice," The Plant Journal, Oct. 2011, vol. 68, pp. 186-200.
Xiang G., et al., "Temperature Effect on CRISPR-Cas9 Mediated Genome Editing," Journal of Genetics Genomics, 2017, vol. 44, pp. 199-205.
Xiaoqing Y., et al., "Constitutive Expression of Human Coagulating Factor IX in Hela Cells by Homologous Recombination of the Promoter," Science in China (Series C), Life Science, Feb. 2001, vol. 44, No. 1, pp. 18-24.
Xie K., et al., "Boosting CRISPR/Cas9 Multiplex Editing Capability with the Endogenous tRNA-Processing System," PNAS, Mar. 17, 2015, vol. 112, No. 11, pp. 3570-3575.
Xing H-L., e al., "A CRISPR/Cas9 Toolkit for Multiplex Genome Editing in Plants," BMC Plant Biology, 2014, vol. 14, No. 1, pp. 327-338, 12 Pages.
Xu K., et al., "Efficient Genome Engineering in Eukaryotes Using Cas9 from *Streptococcus Thermophilus*," Cellular and Molecular Life Sciences, 2015, vol. 72, pp. 383-399, 40 Pages.
Xu L., et al., "Empower Multiplex Cell and Tissue-Specific CRISPR-Mediated Gene Manipulation with Self-Cleaving Ribozymes and tRNA," Nucleic Acids Research, 2016, vol. 45, No. 5(e28), 9 Pages.
Xue C., et al., "CRISPR Interference and Priming Varies with Individual Spacer Sequences," Nucleic Acids Research, 2015, vol. 43, No. 22, pp. 10831-10847, Published Online Nov. 19, 2015.
Yan W.X., et al., "Functionally Diverse Type V CRISPR-Cas Systems," Science, Jan. 4, 2019, vol. 363, pp. 88-91, 5 Pages.
Yao X., et al., "Homology-Mediated End Joining-Based Targeted Integration Using CRISPR/Cas9," Cell Research, Jun. 2017, vol. 27, No. 6, pp. 801-814.
Yin H., et al., "Partial DNA-Guided Cas9 Enables Genome Editing with Reduced Off-Target Activity," Nature Chemical Biology, Mar. 2018, vol. 14, pp. 311-317, 10 Pages (And Life Sciences Reporting Summary).
Yin X., et al., "CRISPR-Cas9 and CRISPR-Cpf1 Mediated Targeting of a Stomatal Developmental Gene EPFL9 in Rice," Plant Cell Reports, 2017, vol. 36, pp. 745-757.
Yu Q., et al., "Resistance to AHAS Inhibitor Herbicides: Current Understanding," Pest Management Science, Sep. 1, 2014, vol. 70, No. 9, pp. 1340 1350, DOI:10.1002/ps.3710, ISSN 1526498X, XP055978019.
Zetsche B., et al., "Cpf1 is a Single RNA-Guided Endonuclease of a Class 2 CRISPR-Cas System," Cell, Oct. 22, 2015, vol. 163, No. 3, pp. 759-771, 14 Pages, Oct. 1, 2015.
Zhang F., et al., "High Frequency Targeted Mutagenesis in Arabidopsis Thaliana Using Zinc Finger Nucleases," Proceedings of the National Academy of Sciences of the United States of America, Jun. 29, 2010, vol. 107, No. 26, pp. 12028-12033, Retrieved from URL: https://doi.org/10.1073/pnas.0914991107.
Zhang H., et al., "The CRISPR/Cas9 System Produces Specific and Homozygous Targeted Gene Editing in Rice in One Generation," Plant Biotechnology Journal, 2014, vol. 12, No. 6, pp. 797-807.
Zhang J-P., et al., "Efficient Precise Knockin with a Double Cut HDR Donor After CRISPR/Cas9-Mediated Double-Stranded DNA Cleavage," Genome Biology, 2017, vol. 18, No. 35, pp. 1-18.
Zhao Y., et al., "An Alternative Strategy for Targeted Gene Replacement in Plants Using a Dual-sgRNA/Cas9 design," Nature Scientific Reports, 2016, vol. 6, p. 23890, 11 pages.
Zuris J.A., et al., "Cationic Lipid-Mediated Delivery of Proteins Enables Efficient Protein-based Genome Editing in Vitro and in Vivo," Nature Biotechnology, Published Online Oct. 30, 2014, Jan. 2015, vol. 33, No. 1, pp. 73-80.
Che, P., Wu, E., Simon, M.K. et al. Wuschel2 enables highly efficient CRISPR/Cas-targeted genome editing during rapid de novo shoot regeneration in sorghum. Commun Biol 5, 344 (2022).
Morrell P., et al., "Crop Genomics: Advances and Applications" Nature Reviews Genetics, 2011, vol. 13 (2), pp. 85-96.
Songstad D.D et al., "Production of Transgenic Maize Plants and Progeny by Bombardment of Hi-II Immature Embryos," In Vitro Cellular Developmental Biology-plant, 1996, vol. 32, pp. 179-183.

\* cited by examiner

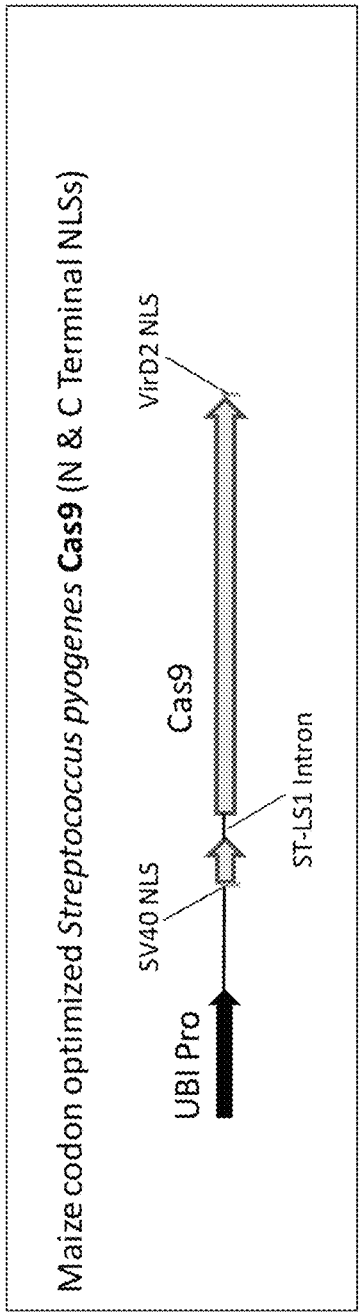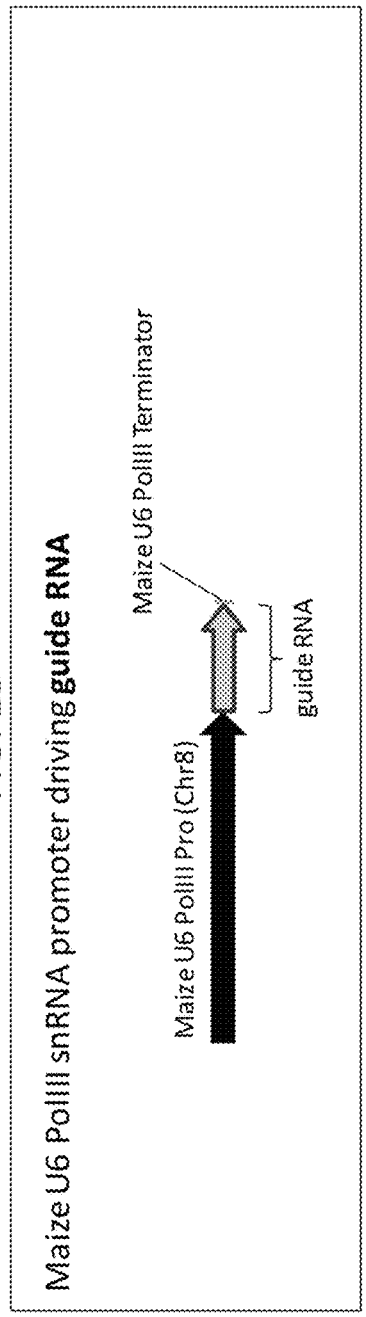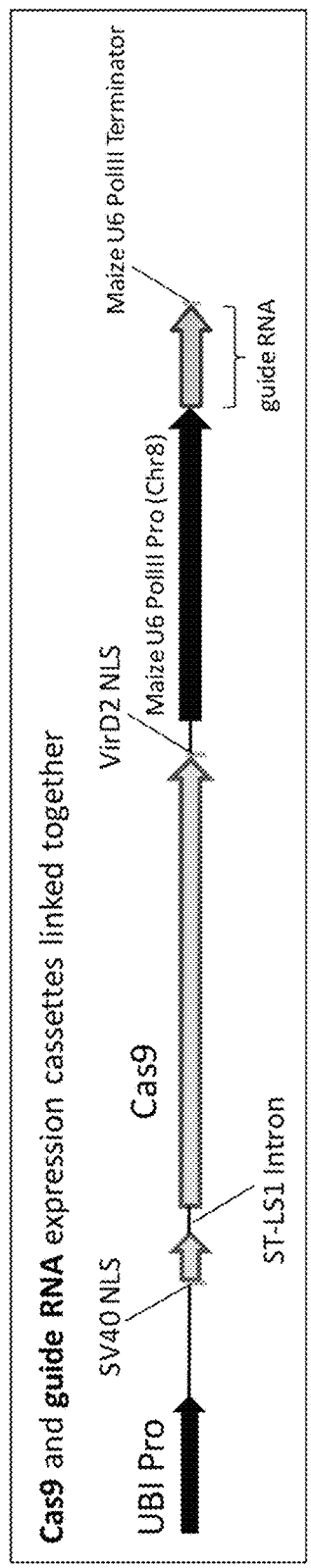
FIG. 1A
FIG. 1B
FIG. 1C

FIG. 3A

FIG. 3B

| | | | | |
|---|---|---|---|---|
| | | | Count | SEQ ID NO: |
| Reference | LIGCas-3 | CGCAAATGAGTAGCAGCGCACGTATATATACGCGTAGCGTGTAGTATATATATATCCTCGCGGGCACGTACGGTACAATTCCAG | | 76 |
| Mutation 1 | | AAGGCGCAAATGAGTAGCAGCGCACGCACGTATATATACGCGTACGTGTCCTCGCGTGTGTAGGTATATATATATCCTCGCGCCGGGCACGTACGGTACGTACAATTCCAG | 16861 | 77 |
| Mutation 2 | | AAGGCGCAAATGAGTAGCAGCGCACGCACGTATATATACGCGTACGGTACGTGTACG-GTGAGGTATATATATATCCTCGCCCGGGCACGTACGGTACGTACAATTCCAG | 3648 | 78 |
| Mutation 3 | | AAGGCGCAAATGAGTAGCAGCGCACGCACGTATATATACGCGTACGGTACGGTAC-TGTGAGGTATATATATATCCTCGCCCGGGCACGTACGGTACGTACAATTCCAG | 2263 | 79 |
| Mutation 4 | | AAGGCGCAAATGAGTAGCAGCGCACGCACGTATATATACGCGTATAGTATACGTAT-GTGTACG--TGAGGTATAGTATATATCCTCGCCGGGACACGTACGGTACGTACAATTCCAG | 2132 | 80 |
| Mutation 5 | | AAGGCGCAAATGAGTAGCAGCGCACGCACGTATATATACGCGTACG------TCCTCGCCCGGGCACGTACGGTACGTACAATTCCAG | 1191 | 81 |
| Mutation 6 | | AAGGCGCAAATGAGTAGCAGCGCACGCACGTATATATACG---------CGTAC-GGTACGGTACGTACAATTCCAG | 948 | 82 |
| Mutation 7 | | AAGGCGCAAATGAGTAGCAGCGCACGCACGTATATATACGCGTATATA----------GTGAGGTATATATATCCTCGGCGCACGTACGGTACGTACAATTCCAG | 327 | 83 |
| Mutation 8 | | AAGGCGCAAATGAGTAGCAGCGCACGCACGTATATATACGCGTATATAT----CGGGGCACGGTACGGTACGTACAATTCCAG | 263 | 84 |
| Mutation 9 | | AAGGCGCAAATGAGTAGCAGCGCACGCACGTATATATACGCGTATATAT-----------CCTCGCGCGGGCACGGCACGGTACGTACAATTCCAG | 227 | 85 |
| Mutation 10 | | AAGGCGCAAATGAGTAGCAGCGCACGCACGTATATATACGCGTACGGTATA--TGTGAGGTATATATATCCTCGCGGGCACGTACGGTACGTACAATTCCAG | 209 | 86 |

Expected Site of Cleavage → PAM

| | | | Count | SEQ ID NO: |
|---|---|---|---|---|
| Reference | LIG3-4 HOMING ENDONUCLEASE | CGCAAATGAGTAGCAGCGCACGTATATATACGCGTAGCGTGTAGTATATATATATCCTCGCGGGCACGTACGGTACAATTCCAG | | 76 |
| Mutation 1 | | CCTTCGCAAATGAGTAGCAGCGCACGCACGTATATATACGCGTACGGTG--AGGTATATATATATCCTTCGCGCCTCGCGGCACGTACGGTACGGTACAATTCCAG | 350 | 87 |
| Mutation 2 | | CCTTCGCAAATGAGTAGCAGCGCACGCACGTATATATACGCGTATATA-----TCCTCGCGCCGGGCACGGTACGGTACAATTCCAG | 241 | 88 |
| Mutation 3 | | CCTTCGCAAATGAGTAGCAGCGCACGCACGTACGGTACGGTACGGT-------ACGTACGGTACGGTACAATTCCAG | 150 | 89 |
| Mutation 4 | | CCTTCGCAAATGAGTAGCAGCGCACGCACGTATATATACG--------CGCCGGGCACGGTACGGTACAATTCCAG | 143 | 90 |
| Mutation 5 | | CCTTCGCAAATGAGTAGCAGCGCACGCACGTATATACGCGTATATATACGTA------CGTACGGTACGGTACAATTCCAG | 97 | 91 |
| Mutation 6 | | CCTTCGCAAATGAGTAGCAGCGCACGCGCACGCGTACGTACGGTATGT-----GAGGTATATATATCCTCGCGGGCGGCACGTACGGTACAATTCCAG | 52 | 92 |
| Mutation 7 | | CCTTCGCAAATGAGTAGCAGCGCACGGCACGCGGCGCACGTATACGCGGT------GTGAGGTATATATATCCTCGCGGCACGGTACGGTACAATTCCAG | 50 | 93 |
| Mutation 8 | | CCTTCGCAAATGAGTAGCAGCGCACGCACGCGTACGCGTACGGTA---------CCTCGCGCGGCACGGCGCACGGTACGGTACAATTCCAG | 46 | 94 |
| Mutation 9 | | CCTTCGCAAATGAGTAGCAGCGCACGCACGTATATATACGCGTACGGTGT--GGTATATATATACGCGGCACGGTACGGTACAATTCCAG | 42 | 95 |
| Mutation 10 | | CCTTCGCAAATGAGTAGCAGCGCACGCACGTATATATACGCGTACG------GTATATATATCGGCAGTATATATATCCTCGCGGGGCACGTACGGTACA | 32 | 96 |

Expected Site of Cleavage →

FIG. 6

| | | SEQ ID NO: |
|---|---|---|
| | 55CasRNA-1 | |
| Reference | CCGGTTTCGCGTGCTGCTGGCTTTACATTACATGGGCAGGTCTCACGACGGTTGGCTGGAGAGCCGGCTGGTAGGGGAGGACCTCAACGGC | 104 |
| Mutation 1 | CCGGTTTCGCGTGCTGCTGGCTCTGGCTTTACATTACATGGGCAGGTCTCACGA--GGTTGGGCTGGAGGCTGGAGGCTGGTAGGGGAGGACCTCAACGGC | 105 |
| Mutation 2 | CCGGTTTCGCGTGCTGCTGGCTCTGGCTTTACATTACATGGGCAGGTCTCAC-ACGGTTGGGCTGGAGAGCCGGCTGGTAGGGGAGGACCTCAACGGC | 106 |
| Mutation 3 | CGGGTTTCGCGTGCTGCTGGCTCTGGCTTTACATTACATGGGCAGGTCTCAGGACGGTTTGGGCTGGAGAGCCGGCTGGTAGGGGAGGACCTCAACGGC | 107 |
| Mutation 4 | CCGGTTTCGCGTGCTGCTGGCTCTGGCTTTACATTGCATGAGCAGGTCGT--GACGGTTGGGCTGGAGAGCCGGCTGGTAGGGGAGGACCTCAACGGC | 108 |
| Mutation 5 | GGGCAGGTTGT--CGACGGTTGGGCTGGAGAGCCGGCTGGTAGGGAGGAGGACCTCAACGGC | 109 |
| Mutation 6 | CCGGTTTCGCGTGCTC------------------------TTGGGCTGGAGAGCCGGCTGGTAGGGGAGGACCTCAACGGC | 110 |

Expected Site of Cleavage → PAM

DD43CR1 20 bp    Guide RNA 76 bp    Terminator

GTCCCTTGTACTTGTACGTAGTTTTAGAGCTAGAAATAGCAAGTTAAAATAAGGCTAGTCCGTTATCAACTTGAAAAAGTGGCACCGAGTCGGTGCTTTTTTT

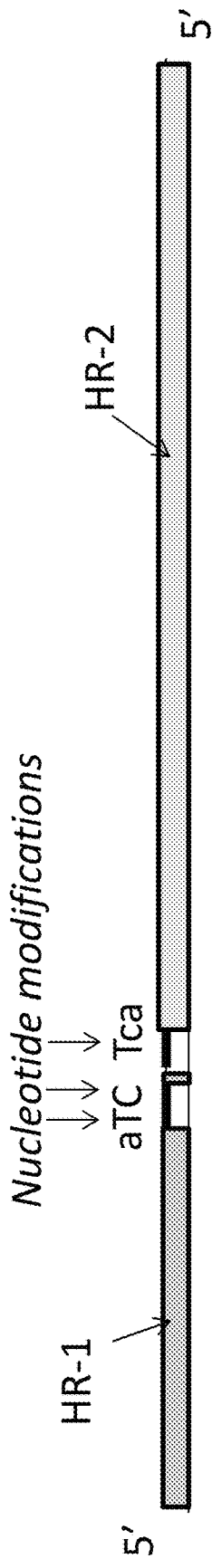
FIG. 12A: polynucleotide modification template (EPSPS template)
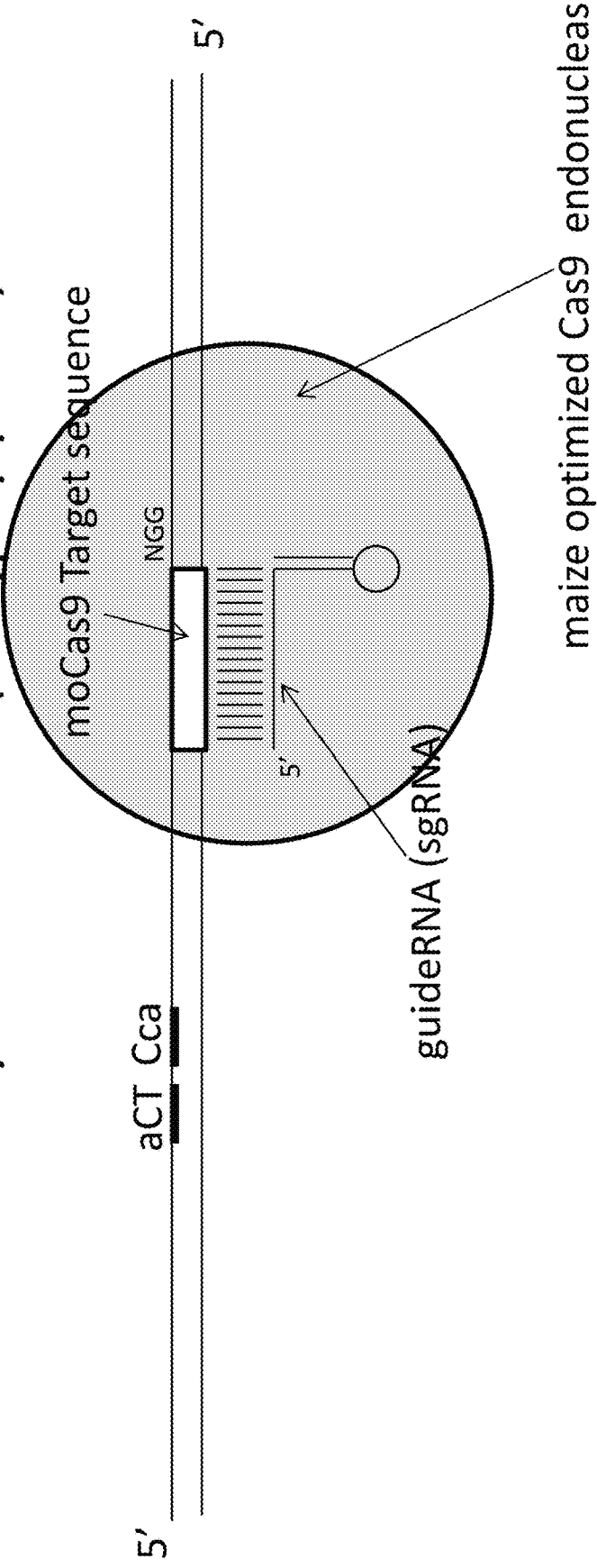
FIG. 12B: nucleotide sequence to be edited (wild type epsps locus)

FIG. 14

*Events with intact moCas target sequence (underlined)*
SEQ ID NO: 205  GGGGAATGCTGGAACTGGAATGCGGCCATTGACACAGCAGCTGTTACTGCTGCTGGTGGAAATGC

*Events with mutagenized moCas target sequences (underlined)*
SEQ ID NO: 206  GGGGAATGCTGGAACTGGAATGCGGCCATTG---GCAGCTGTTACTGCTGCTGGTGGAAATGC
SEQ ID NO: 207  GGGGAATGCTGGAACTGGAACTGCA--------CAGCAGCTGTTACTGCTGCTGGTGGAAATGC
SEQ ID NO: 208  GGGGAATGCTG-----------------------TTACTGCTGCTGGTGGAAATGC

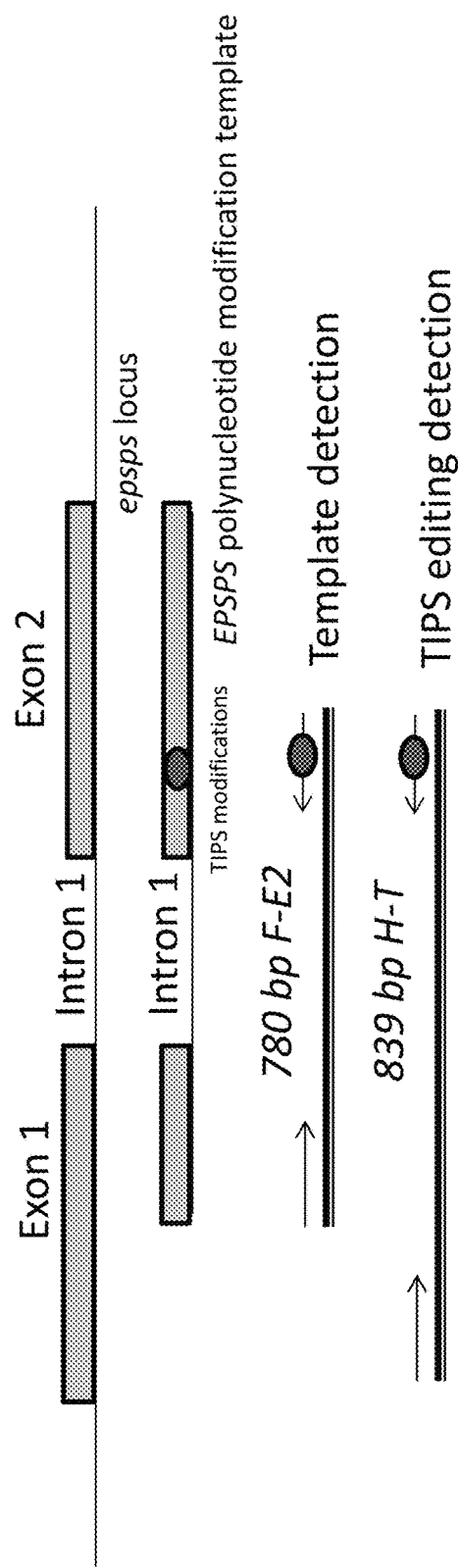
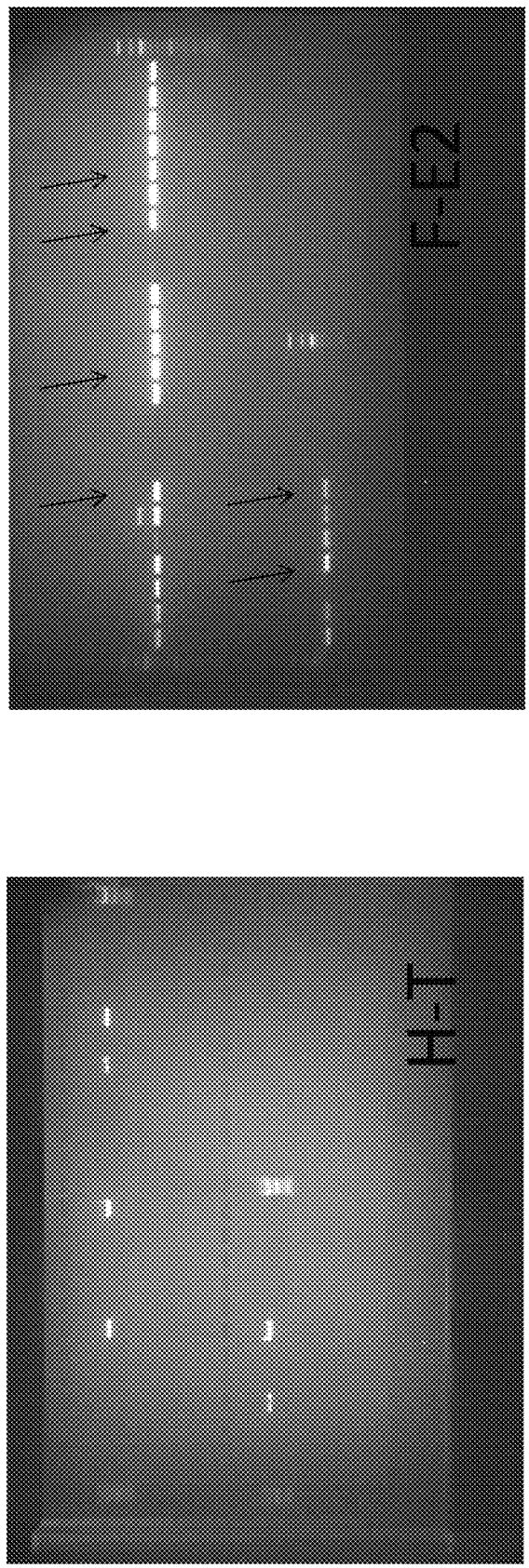
FIG. 16

TIPS edited *EPSPS* nucleotide sequence with the moCas target sequence (underlined) not changed.

*nucleotide modifications*
               ↓                        ↓

SEQ ID NO: 209    AATGCTGGAATCGCAATGCGGTCATTGACACAGCAGCTGTTACTGCTGGT

Wild-type *EPSPS* nucleotide sequence with the Cas target sequence not changed.

SEQ ID NO: 210    AATGCTGGAACTGCAATGCGGCCATTGACACAGCAGCTGTTACTGCTGGT

FIG. 19A
MHP14 locus

MHP14Cas-1
→
GTTAAATCTGACGTGAATCTGTTTGGAATTGAAAAACAAGTGCTTCCTTTCATACACCACTATGTCGCTTCAATGTTTGT  SEQ ID NO:237
CAATTTAGACTGCACTTAGACAAACCTTAACTTTTTTGTTCACGAAGGAAAGTATGTGGTGATACAGCGAAGTTACAAACA  SEQ ID NO:238
                                                              ←
                                                              MHP14Cas-3

FIG. 19B
TS8 locus

CCAGTACTGCACGTTACGTACGAACTAATATACTCCACCAGCTGATCACTGATGAGCCGAGC  SEQ ID NO: 239
GGTCAGTGCAATGCATGCTTGATTATATGAGGTCGACTAGTGACTACTCCGGCTCG       SEQ ID NO: 240
→                                  ←
TS8Cas-1                           TS8Cas-2

FIG. 19C
TS9 locus

CCGACTGCGTGCAACCTCGAGGCCGCAAACAGCC                               SEQ ID NO:241
GGCTGCACGCACGTTGGGAGCTCCGGCGTTTGTCGG                             SEQ ID NO:242
→                    ←
TS9Cas-3             TS9Cas-2

FIG. 19D
TS10 locus

GCTCGTGTTGGAGATACAGGGACAGCAAGTACTTGGCCCTTAACTAGGCGAAGGCGAGGCGGCCATGGA  SEQ ID NO:243
CGAGCACAACCTCTATGTCCCTGTTCGTTCATGAACCGGGAATTGATCGCTTCCGCTCCGCCGGTACCT  SEQ ID NO:244
→                                        ←
TS10Cas-3                                TS10Cas-1

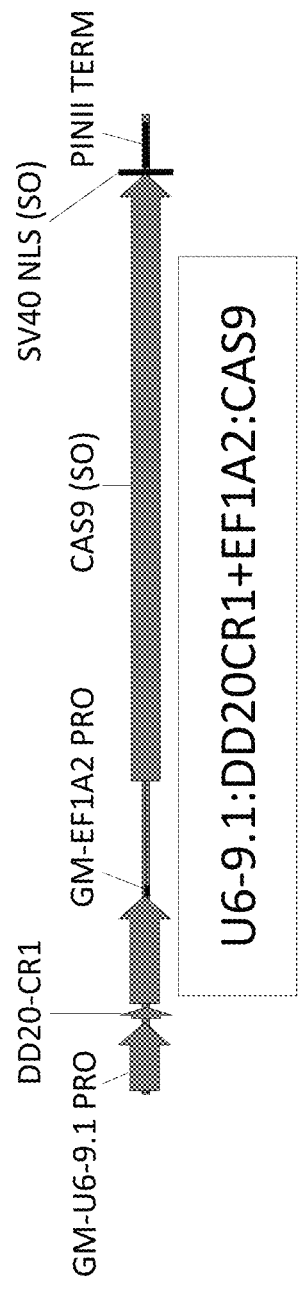
FIG. 23A Linked gRNA and Cas9 gene expression cassettes
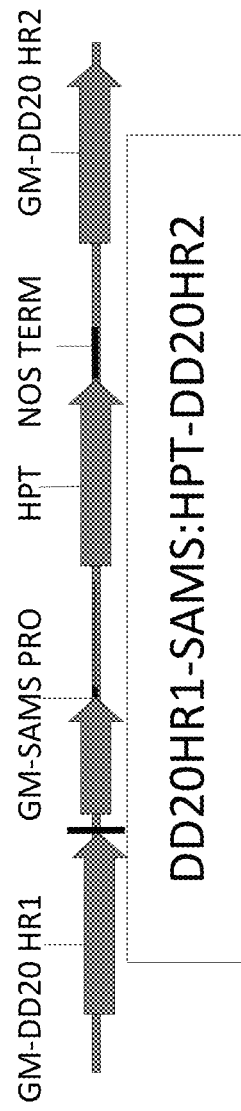
FIG. 23B Repair DNA cassette with homologous regions.

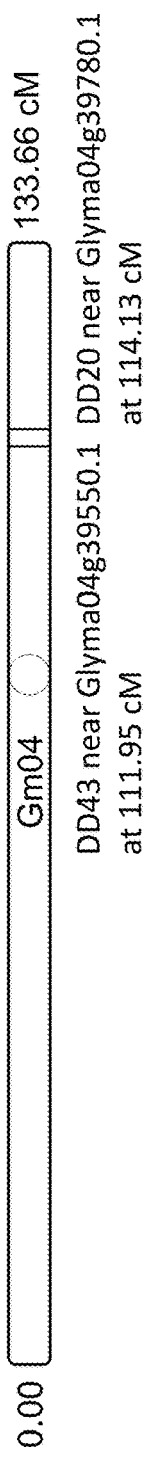
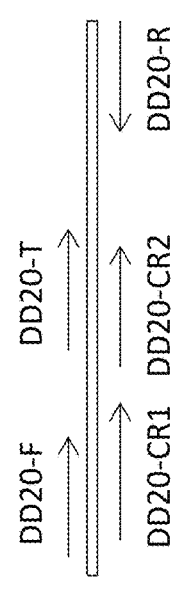
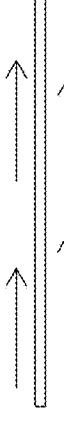
FIG. 24A Diagram of Glycine max chromosome 04 indicating relative positions of DD20 and DD43 target sites.
FIG. 24B DD20 qPCR amplicon, 45936307-45936370
FIG. 24C DD43 qPCR amplicon, 45731879-45731993

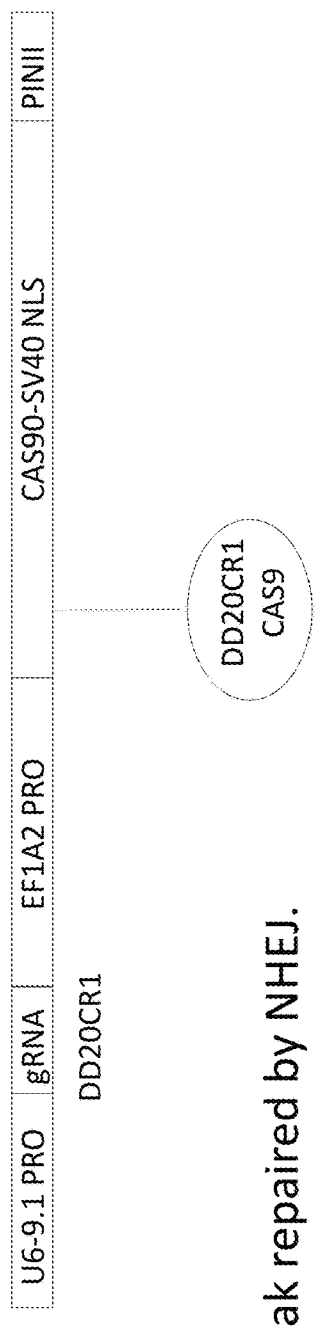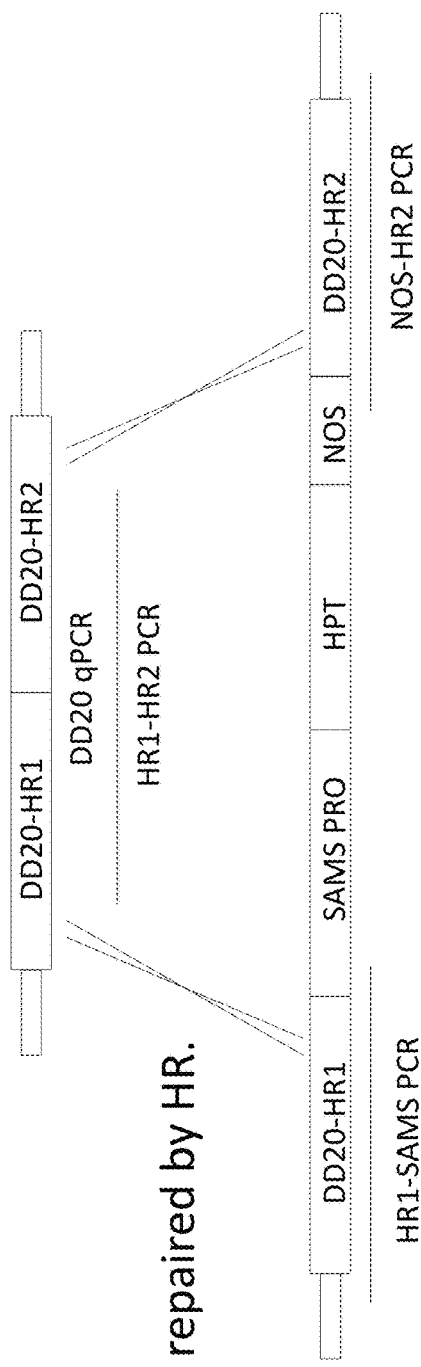
FIG. 25A Transiently expressed gRNA and Cas9 assembled in vivo capable to cleave genomic DNA at target DD20.
FIG. 25B DNA break repaired by NHEJ.
FIG. 25C DNA break repaired by HR.

FIG. 26A

DD20CR1 target site

```
SEQID NO:335  ACTTGTACTTATCAAAATTCGGAACTGACACGACATGA TGGAACGTGACTAAGGTGGG
SEQID NO:336  ACTTGTACTTATCAAAATTCGGAACTGACACGACACGAC-TGATGGAACGTGACTAAGGTGGG
SEQID NO:337  ACTTGTACTTATCAAAATTCGGAACTGACACGACACACGA-ATGATGGAACGTGACTAAGGTGGG
SEQID NO:338  ACTTGTACTTATCAAAATTCGGAACTGACACGACACACGA--TGATGGAACGTGACTAAGGTGGG
SEQID NO:339  ACTTGTACTTATCAAAATTCGGAACTGACACGACACACGAC--GATGGAACGTGACTAAGGTGGG
SEQID NO:340  ACTTGTACTTATCAAAATTCGGAACTGACACGACACACGAC--TGATGGAACGTGACTAAGGTGGG
SEQID NO:341  ACTTGTACTTATCAAAATTCGGAACTGACACGACACACGG---ATGATGGAACGTGACTAAGGTGGG
SEQID NO:342  ACTTGTACTTATCAAAATTCGGAACTGACACGACACACG----TGATGGAACGTGACTAAGGTGGG
SEQID NO:343  ACTTGTACTTATCAAAATTCGGAACTGACACGACACAC-----TGATGGAACGTGACTAAGGTGGG
SEQID NO:344  ACTTGTACTTATCAAAATTCGGAACTGACACGACACACG----GATGGAACGTGACTAAGGTGGG
SEQID NO:345  ACTTGTACTTATCAAAATTCGGAACTGACACGACACAC-----GATGGAACGTGACTAAGGTGGG
SEQID NO:346  ACTTGTACTTATCAAAATTCGGAACTGACACGACACA------TGATGGAACGTGACTAAGGTGGG
SEQID NO:347  ACTTGTACTTATCAAAATTCGGAACTGACACGACACA------ATGGAACGTGACTAAGGTGGG
SEQID NO:348  ACTTGTACTTATCAAAATTCGGAACTGACACGACAC-------TGATGGAACGTGACTAAGGTGGG
SEQID NO:349  ACTTGTACTTATCAAAATTCGGAACTGACACGACAC-------GATGGAACGTGACTAAGGTGGG
SEQID NO:350  ACTTGTACTTATCAAAATTCGGAACTGACACGACA--------TGATGGAACGTGACTAAGGTGGG
SEQID NO:351  ACTTGTACTTATCAAAATTCGGAACTGACACGACA---------TGGAACGTGACTAAGGTGGG
SEQID NO:352  ACTTGTACTTATCAAAATTCGGAACTGACACGACTG--------TGATGGAACGTGACTAAGGTGGG
SEQID NO:353  ACTTGTACTTATCAAAATTCGGAACTGACACGACAC--------GAACGTGACTAAGGTGGG
SEQID NO:354  ACTTGTACCTATCAAAATTCGGAACTGACACGACTGA-------GGAACGTGACTAAGGTGGG
SEQID NO:355  ACTTGTACTTATCAAAATTCGGAACTGACACGACTGA-------ATGGAACGTGACTAAGGTGGG
SEQID NO:356  ACTTGTACTTATCAAAATTCGGAACTGACACGACTGA-------TGGAACGTGACTAAGGTGGG
SEQID NO:357  ACTTGTACTTATCAAAATTCGGAACTGACACGACTGA--------GAACGTGACTAAGGTGGG
SEQID NO:358  ACTTGTACTTATCAAAATTCGGAACTGACACGACACGACAT^TC-----------GG
SEQID NO:359  ACTTGTACTTATCAAAATTCGGAACTGACACGACA---------------AAGGTGGG
SEQID NO:360  ACTTGTACTTATCAAAATTCGGAAC-------------------GTGACTAAGGTGGG
SEQID NO:361  ACT-------------------------------------ATGGAACGTGACTAAGGTGGG
Insertion starts at ^ with the insert size indicated.
SEQID NO:362  ACTTGTACTTATCAAAA^50----GAACTGACACGACACACG^155-GATGGAACGTGACTAAGGTGGG
SEQID NO:363  ACTTGTACTTATCAAA^----------------------------TGATGGAACGTGACTAAGGTGGG
```

FIG. 26B

DD20CR2 target site

| SEQ ID NO: 364 | GACACACGACATGATGATGGAACGTGACTA↑AGGTGGGTTTTTTGACTTTTGCATGTCGAAGTGAG |
| SEQ ID NO: 365 | GACACACGACATGATGATGGAACGTGAACTAAGGTGGGTTTTTTGACTTTTGCATGTCGAAGTGAG |
| SEQ ID NO: 366 | GACACACGACATGATGATGGAACGTA-CTAAGGTGGGTTTTTTGACTTTTGCATGTCGAAGTGAG |
| SEQ ID NO: 367 | GACACACGACATGATGATGGAACGT--CTAAGGTGGGTTTTTTGACTTTTGCATGTCGAAGTGAG |
| SEQ ID NO: 368 | GACACACGACATGATGATGGAACGTGA--AAGGTGGGTTTTTTGACTTTTGCATGTCGAAGTGAG |
| SEQ ID NO: 369 | GACACACGACATGATGATGGAACG----CTAAGGTGGGTTTTTTGACTTTTGCATGTCGAAGTGAG |
| SEQ ID NO: 370 | GACACACGACATGATGATGGAACGTG---AAGGTGGGTTTTTTGACTTTTGCATGTCGAAGTGAG |
| SEQ ID NO: 371 | GACACACGACATGATGATGGAACGTG----AGGTGGGTTTTTTGACTTTTGCATGTCGAAGTGAG |
| SEQ ID NO: 372 | GACACACGACATGATGATGGAACG-----TAAGGTGGGTTTTTTGACTTTTGCATGTCGAAGTGAG |
| SEQ ID NO: 373 | GACACACGACATGATGATGGAACGTG----CTAAGGTGGGTTTTTTGACTTTTGCATGTCGAAGTGAG |
| SEQ ID NO: 374 | GACACACGACATGATGATGGAACGTG-----AGGTGGGTTTTTTGACTTTTGCATGTCGAAGTGAG |
| SEQ ID NO: 375 | GACACACGACATGATGATGGAACGTGAA------CTAAGGTGGGTTTTTTGACTTTTGCATGTCGAAGTGAG |
| SEQ ID NO: 376 | GACACACGACATGATGATGGAA-----TAAGGTGGGTTTTTTGACTTTTGCATGTCGAAGTGAG |
| SEQ ID NO: 377 | GACACACGACATGATGATGG-------CTAAGGTGGGTTTTTTGACTTTTGCATGTCGAAGTGAG |
| SEQ ID NO: 378 | GACACACGACATGATGATGA--------TAAGGTGGGTTTTTTGACTTTTGCATGTCGAAGTGAG |
| SEQ ID NO: 379 | GACACACGACATGATGATGGA-------AGGTGGGTTTTTTGACTTTTGCATGTCGAAGTGAG |
| SEQ ID NO: 380 | GACACACGACATGATGATGG--------AGGTGGGTTTTTTGACTTTTGCATGTCGAAGTGAG |
| SEQ ID NO: 381 | GACACACGACATGATGATGG----------GTTTTTGACTTTTGCATGTCGAAGTGAG |
| SEQ ID NO: 382 | GACACACGAC------------AGGTGGGTTTTTTGACTTTTGCATGTCGAAGTGAG |
| SEQ ID NO: 383 | GACAC------------------GTGAG |
| SEQ ID NO: 384 | GACACACGACATGATGATGGAAC---------------------133bp deletion---------- |
| SEQ ID NO: 385 | GACACACGACATGATGATGG--------------------------------- |

FIG. 26C

DD43CR1 target site

```
SEQID NO:386  AGCCTTACAACTCACAAGTCCCTTGTACTTGTACGTA|CGGAGGGTATTCTAGAAAAGAGG
SEQID NO:387  AGCCTTACAACTCACAAGTCCCTTGTACTTGTACGTA-CGGAGGGTATTCTAGAAAAGAGG
SEQID NO:388  AGCCTTACAACTCACAAGTCCCTTGTACTTGTACGTA--CGGAGGGTATTCTAGAAAAGAGG
SEQID NO:389  AGCCTTACAACTCACAAGTCCCTTGTACTTGTA-GTACGGAGGGTATTCTAGAAAAGAGG
SEQID NO:390  AGCCTTACAACTCACAAGTCCCTTGTACTTGTGT--GTACGGAGGGTATTCTAGAAAAGAGG
SEQID NO:391  AGCCTTACAACTCACAAGTCCCTTGTACTTG---CGTACGGAGGGTATTCTAGAAAAGAGG
SEQID NO:392  AGCCTTACAACTCACAAGTCCCTTGTACTTG----GTACGGAGGGTATTCTAGAAAAGAGG
SEQID NO:393  AGCCTTACAACTCACAAGTCCCTTGTACTTGT----TACGGAGGGTATTCTAGAAAAGAGG
SEQID NO:394  AGCCTTACAACTCACAAGTCCCTTGTACTT-----GTACGGAGGGTATTCTAGAAAAGAGG
SEQID NO:395  AGCCTTACAACTCACAAGTCCCTTGTACTT------TACGGAGGGTATTCTAGAAAAGAGG
SEQID NO:396  AGCCTTACAACTCACAAGCCCCTTGTACT-------TACGGAGGGTATTCTAGAAAAGAGG
SEQID NO:397  AGCCTTACAACTCACAAGTCCCTTGTACT--------TACGGAGGGTATTCTAGAAAAGAGG
SEQID NO:398  AGCCTTACAACTCACAAGTCCCTTGTA---------GTACGGAGGGTATTCTAGAAAAGAGG
SEQID NO:399  AGCCTTACAACTCACAAGTCCCTTGT----------TACGGAGGGTATTCTAGAAAAGAGG
SEQID NO:400  AGCCTTACAACTCACAAGTCCCTTG-----------TACGGAGGGTATTCTAGAAAAGAGG
SEQID NO:401  AGCCTTACAACTCACAAGTCCCTT------------TACGGAGGGTATTCTAGAAAAGAGG
SEQID NO:402  AGCCTTACAACTCACAAGTCCCT-------------TACGGAGGGTATTCTAGAAAAGAGG
SEQID NO:403  AGCCTTACAACTCACAAGTCCCTTGTACTTGTA-------------AGAAAAGAGG
SEQID NO:404  AGCCTTACAACTCACAAGTCC------------TAAATTAA^AGGTTATTCTAGAAAAGAGG
```

Insertion starts at ^ with the insert size indicated.

```
SEQID NO:405  AGCCTTACAACTCACAAGTCCCTTGTACTTGTAC^167GTACGGAGGGTATTCTAGAAAAGAGG
SEQID NO:406  AGCCTTACAACTCACAAGTCCCTTGTACTTGTAC^38--GTACGGAGGGTATTCTAGAAAAGAGG
SEQID NO:407  AGCCTTACAACTCACAAGTCCCTTGTACTTGTA^130----GTACGGAGGGTATTCTAGAAAAGAGG
SEQID NO:408  AGCCTTACAACTCACAAGTCCCTTGTACTTGTAC^171GTACGGAGGGTATTCTAGAAAAGAGG
SEQID NO:409  AGCCTTACAACTCACAAGTCCCTTGTACTTGTAC^220GTACGGAGGGTATTCTAGAAAAGAGG
SEQID NO:410  AGCCTTACAACTCACAAGTCCCTTGTACTTGTAC^190GTACGGAGGGTATTCTAGAAAAGAGG
SEQID NO:411  AGCCTTACAACTCACAAGTCCCTTGTACTTGTA^110----GTACGGAGGGTATTCTAGAAAAGAGG
SEQID NO:412  AGCCTTACAACTCACAAGTCCCTTGTACTTGTAC^125GTACGGAGGGTATTCTAGAAAAGAGG
SEQID NO:413  AGCCTTACAACTCACAAGTCCCTTGTACTTGTAC^154GTACGGAGGGTATTCTAGAAAAGAGG
SEQID NO:414  AGCCTTACAACTCACAAGTCCCTTGTACTTGTA^177------GAGGGTATTCTAGAAAAGAGG
```

FIG. 27A

| LIGCas-1 | Count | SEQ ID NO: |
|---|---|---|
| CTGTAACGATTACGCACCTGCTGTAATTGTACGTACCTGCCCGGG[AG]ATATATATATACCTCACACGTACGGTACGCGTATATATAC | | 55 |
| TCCTCTGTAACGATTACGCACCTGCTGTAATTGTACGTACCTGGCCCGGTGCCCCGGGACGGAGGATATATATATACCTCACACGTACGCGTACGCGTATATATAC | 2116 | 415 |
| TCCTCTGTAACGATTACGCACCTGCTGTAATTGTACGTACCTGCTGGAATTGTACGTACGTGCCCCGGCCCGGGCGGGGATATATATATACCTCACACGTACGCGTAPATATATAC | 1156 | 416 |
| TCCTCTGTAACGATTACGCACCTGCGACCTGCTGGAATTGTACGTACGTGGCGCCGCGGCCCGGATATATATATACCTCACACGTACGCGTACGCGTATATATAC | 473 | 417 |
| TCCTCTGTAACGATTACGCACCTGCTGCTGCTGGAATTGTACGGTACCTGGGCCCGGGCCCGAAGGATATATATATACCTCACACGTACGGTACGAGTATATATAC | 161 | 418 |
| TCCCTCTGTAACGATTACGCACCTGCCACCTGCACGTACGGTACCTGCCCACCTGGGCCCGGATCGGAAGGATATATATATCCTCACACGTACGCGTATACGCGTATATATAC | 133 | 419 |
| TCCTCTGTAACGATTACGCACCTGCTGCTGGAATTGTACGTACCTGCTGGAATTGTACGTCGTACCTGCGGGAGGATATATATCCTCACACGTACGCGTATATATAC | 82 | 420 |
| TCCCTCTGTAACGATTACGCACCTGCTGCCACCTGCTGGAATTGTACGTACGT----------------TTCACACGTACGCGTATATATAC | 77 | 421 |
| TCCTCTGTAACGATTACGCACCTGCTGGAACCTGCTGGAATTGTACGGTACGT--------------AGGGTAGCGTACGGTATATATAC | 55 | 422 |
| TCCTCTGTAACGATTACGGACCTGCGACCTGCTGGAATTGTACGGTACGTGCCCGGGTTCGGAGGATATATATACCTCACACGTACGCGTATATGCGGTATATATAC | 39 | 423 |
| TCCTCTGTAACGATTACGCACCTGGGAATTGTACCCGTACGGTGCCCC--------------CGGAAGGATATATATACCTCACACGTACGCGTATATATAC | 39 | 424 |

Expected Site of Cleavage → PAM

FIG. 27B

| | | Count | SEQ ID NO: |
|---|---|---|---|
| LIGCas-2 | CTGTAACGATTACGCACCTGCTGGAATTGTACGTACGTGCCGGAGGATATATATACCTCACACGTACGGTACGGTATATATAC | | 55 |
| | GAAGCTGTAACGATTACGCACCTGCTGGAATTGTACGTACGTGACCCCGAGGATATATATACCTCACACGTACGGTACGGTATATATAC | 1048 | 425 |
| | GAAGCTGTAACGATTACGCACCTGCTGGAATTGTACGTACGTGTCCCGGAGGATATATATACCTCACACGTACGGTACGGTATATATAC | 743 | 426 |
| | GAAGCTGTAACGATTACGCACCTGCTGGAATTGTACGTACGT--CCCGGAGGATATATATACCTCACACGTACGGTACGGTATATATAC | 543 | 427 |
| | GAAGCTGTAACGATTACGCACCTGCTGGAATTGTACGTACGTGCCCGGCGGAGGATATATATACCTCACACGTACGGTACGGTATATATAC | 220 | 428 |
| | GAAGCTGTAACGATTACGCACCTGCTGGAATTGTACGTACGTGA-CCCCGGCGGAGGATATATATACCTCACACGTACGGTACGGTATATATAC | 193 | 429 |
| | GAAGCTGTAACGATTACGCACCTGCTGGAATTGTACC---------CGGCGGCGGAGGATATATATACCTCACACGTACGGTACGGTATATATAC | 159 | 430 |
| | GAAGCTGTAACGATTACGCACCTGCTGGAATTGTACGT-------CCCCGGCGGAGGATATATATACCTCACACGTACGGTACGGTATATATAC | 137 | 431 |
| | GAAGCTGTAACGATTACGCACCTGCTGGAATTGTACGTAC----CCCCGGCGGAGGATATATATACCTCACACGTACGGTACGGTATATATAC | 94 | 432 |
| | GAAGCTGTAACGATTACGCACCTGCTGGAATTGTACGTACG---CCCCGGCGGAGGATATATATACCTCACACGTACGGTACGGTATATATAC | 93 | 433 |
| | GAAGCTGTAACGATTACGCACCTGCTGGAATTGTACC---------CCCCGGCGGAGGATATATATACCTCACACGTACGGTACGGTATATATAC | 60 | 434 |

Expected Site of Cleavage → PAM

FIG. 27C

| LIGCas-3 | Sequence | Count | SEQ ID NO: |
|---|---|---|---|
| | CGCAAATGAGTAGCAGCGCACGTATATATATCCTCCGCGGGGCACGTACGTACGGTACAATTCCCAG | | 76 |
| | AAGCGCAAATGAGTAGCAGCGCACGTATATATATAGCGTATATATATCCTCCGCGGGGCACGTACGTACAATTCCCAG | 1208 | 435 |
| | AAGCGCAAATGAGTAGCAGCGCACGTATATATACGCGTATATATATCCTCCGCGGGGCACGTACGGTACAATTCCCAG | 453 | 436 |
| | AAGCGCAAATGAGTAGCAGCGCACGTATATATACGCGTATATATATCCTCCGCGGGGCACGTACGGTACAATTCCCAG | 339 | 437 |
| | AAGCGCAAATGAGTAGCAGCGCACGTACGTACGCGTATATATATCCTCCGCGGGGCACGTACGGTACAATTCCCAG | 145 | 438 |
| | AAGCGCAAATGAGTAGCAGCGCACGTACGTACGCGTA------TCCTCCGCGGGGCACGTACGGTACAATTCCCAG | 94 | 439 |
| | AAGCGCAAATGAGTAGCAGCGCACGTACGTACG--------GTGAGGTATATATATCCTCCGCGGGGCACGTACGGTACAATTCCCAG | 53 | 440 |
| | AAGCGCAAATGAGTAGCAGCGCACGCACGTATATATACGCGTACG----------TGAGGTATATATATCCTCCGCGGGGCACGTACGGTACAATTCCCAG | 42 | 441 |
| | AAGCGCAAATGAGTAGCAGCGCACGCACGTATATATACGCGTACG-----TATATATATCCTCCGCGGGGCACGTACGGTACAATTCCCAG | 37 | 442 |
| | AAGCGCAAATGAGTAGCAGCGCACGTATATATACGCGTACG-----CAGGTATATATATCCTCCGCGGGGCACGTACGGTACAATTCCCAG | 20 | 443 |
| | AAGCGCAAATGAGTAGCAGCGCACGCACGTATATATACGCGTACG--ATGAGGTATATATATCCTCCGCGGGGCACGTACGGTACAATTCCCAG | 19 | 444 |

Expected Site of Cleavage → PAM

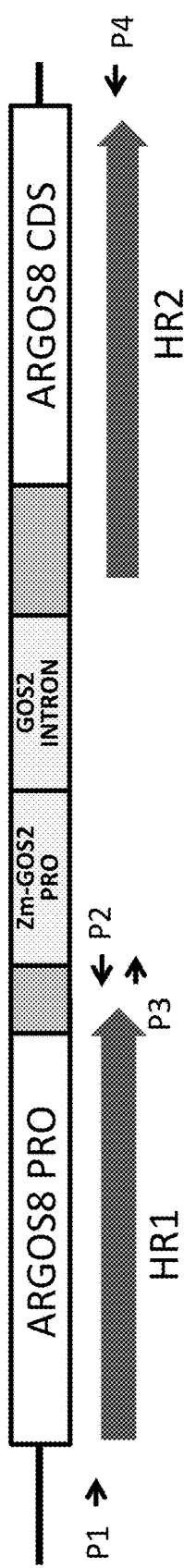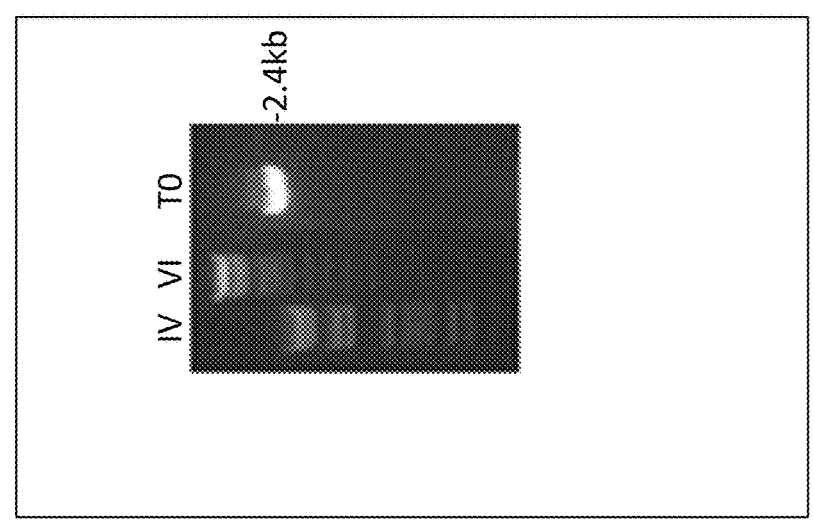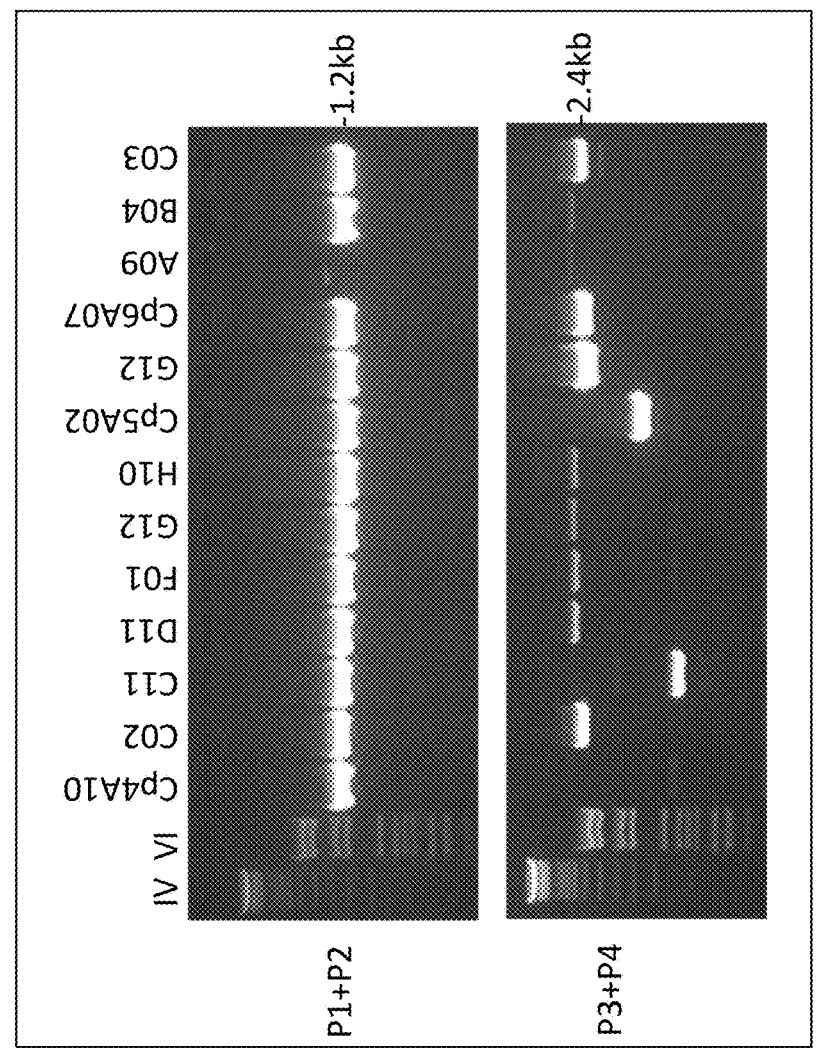
FIG. 29A
FIG. 29C
FIG. 29B

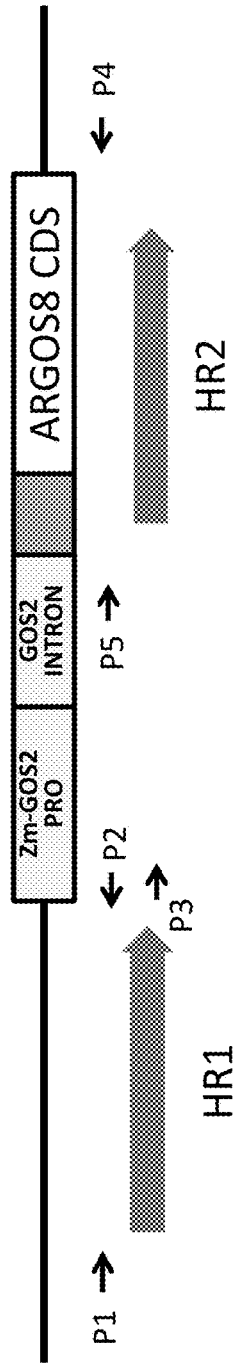
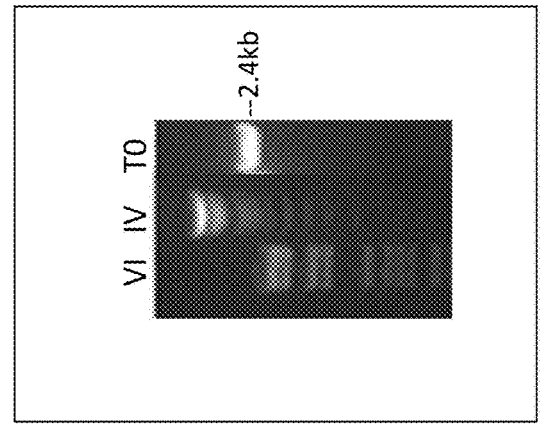
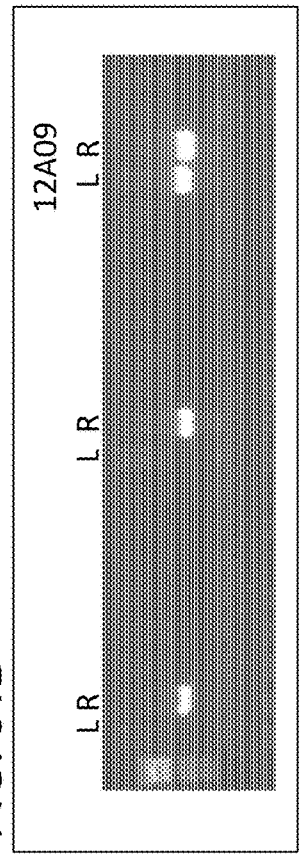
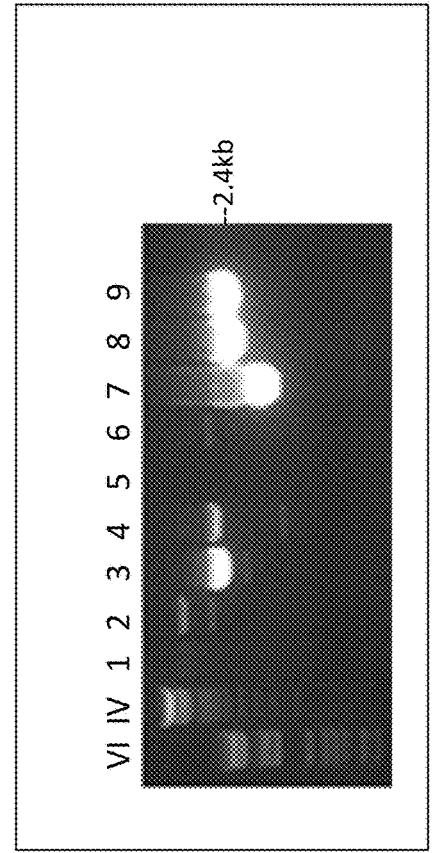
FIG. 31A
FIG. 31B
FIG. 31C
FIG. 31D

FIG. 34A

| | |
|---|---|
| VEDAKEEV | Maize |
| GKESKEEI | Petunia |
| GKKSEEEI | Tomato |
| EKDAKEEV | Sorghum |
| VEDSKEEV | Rice |
| GKDGKEEI | Amarathus |

FIG. 34B

K ... T ... P   moCas9 target sequence

GCTAAAGAGGAAGTGCAGCTCTTCTTGGGGAATGCTGGAACTGCAATGCGGCCATTGACACAGCAGCTGTTACTGCTGCTGG

FIG. 34C

R ... I ... S   moCas9 target sequence

GCTAGAGAGGAAGTGCAGCTCTTCTTGGGGAATGCTGGAATCGCAATGCGGTCATTGACAGCAGCAGCTGTTACTGCTGCTGG

FIG. 35A

CATATCTG

FIG. 35B

CATCTC...ACGATCAGAT..GCACCGCATGTCGCCTA

FIG. 35C

CATATCTTGCACGATCAGATATGCACCGCATGTCGCATATCTG

PLANT GENOME MODIFICATION USING GUIDE RNA/CAS ENDONUCLEASE SYSTEMS AND METHODS OF USE

CROSS-REFERENCE TO RELATED APPLICATIONS

This application is a continuation of U.S. patent application Ser. No. 14/913,614, filed Feb. 22, 2016, which is a 371 National Stage Entry of PCT Application No. PCT/US2014/051778, filed Aug. 20, 2014, which, in turn, claims the benefit of U.S. Provisional Application No. 61/868,706, filed Aug. 22, 2013, U.S. Provisional Application No. 61/882,532, filed Sep. 25, 2013, U.S. Provisional Application No. 61/937,045, filed Feb. 7, 2014, U.S. Provisional Application No. 61/953,090, filed Mar. 14, 2014, and U.S. Provisional Application No. 62/023,239, filed Jul. 11, 2014; all of which are hereby incorporated by reference herein in their entireties.

FIELD

The disclosure relates to the field of plant molecular biology, in particular, to methods for altering the genome of a plant cell.

REFERENCE TO SEQUENCE LISTING SUBMITTED ELECTRONICALLY

The official copy of the sequence listing is submitted electronically via Patent Center as an XML formatted sequence listing with a file named BB2284-US-PCN2_Sequence_Listing_ST26 created on Mar. 24, 2023 and having a size of 928 kilobytes, and is filed concurrently with the specification. The sequence listing comprised in this XML formatted document is part of the specification and is herein incorporated by reference in its entirety.

BACKGROUND

Recombinant DNA technology has made it possible to insert foreign DNA sequences into the genome of an organism, thus, altering the organism's phenotype. The most commonly used plant transformation methods are *Agrobacterium* infection and biolistic particle bombardment in which transgenes integrate into a plant genome in a random fashion and in an unpredictable copy number. Thus, efforts are undertaken to control transgene integration in plants.

One method for inserting or modifying a DNA sequence involves homologous DNA recombination by introducing a transgenic DNA sequence flanked by sequences homologous to the genomic target. U.S. Pat. No. 5,527,695 describes transforming eukaryotic cells with DNA sequences that are targeted to a predetermined sequence of the eukaryote's DNA. Specifically, the use of site-specific recombination is discussed. Transformed cells are identified through use of a selectable marker included as a part of the introduced DNA sequences.

It was shown that artificially induced site-specific genomic double-stranded breaks in plant cells were repaired by homologous recombination with exogenously supplied DNA using two different pathways. (Puchta et al., (1996) *Proc. Natl. Acad. Sci. USA* 93:5055-5060; U.S. Patent Application Publication No. 2005/0172365A1 published Aug. 4, 2005; U.S. Patent Application Publication No. 2006/0282914 published Dec. 14, 2006; WO 2005/028942 published Jun. 2, 2005).

Since the isolation, cloning, transfer and recombination of DNA segments, including coding sequences and non-coding sequences, is most conveniently carried out using restriction endonuclease enzymes. Much research has focused on studying and designing endonucleases such as WO 2004/067736 published Aug. 12, 2004; U.S. Pat. No. 5,792,632 issued to Dujon et al., Aug. 11, 1998; U.S. Pat. No. 6,610,545 B2 issued to Dujon et al., Aug. 26, 2003; Chevalier et al., (2002) *Mol Cell* 10:895-905; Chevalier et al., (2001) *Nucleic Acids Res* 29:3757-3774; Seligman et al., (2002) *Nucleic Acids Res* 30:3870-3879.

Although several approaches have been developed to target a specific site for modification in the genome of a plant, there still remains a need for more efficient and effective methods for producing a fertile plant, having an altered genome comprising specific modifications in a defined region of the genome of the plant.

BRIEF SUMMARY

Compositions and methods are provided employing a guide RNA/Cas endonuclease system in plants for genome modification of a target sequence in the genome of a plant or plant cell, for selecting plants, for gene editing, and for inserting a polynucleotide of interest into the genome of a plant. The methods and compositions employ a guide RNA/Cas endonuclease system to provide for an effective system for modifying or altering target sites and nucleotides of interest within the genome of a plant, plant cell or seed. Once a genomic target site is identified, a variety of methods can be employed to further modify the target sites such that they contain a variety of polynucleotides of interest. Breeding methods and methods for selecting plants utilizing a two component RNA guide and Cas endonuclease system are also disclosed. Also provided are nucleic acid constructs, plants, plant cells, explants, seeds and grain having the guide RNA/Cas endonuclease system. Compositions and methods are also provided employing a guide polynucleotide/Cas endonuclease system for genome modification of a target sequence in the genome of a cell or organism, for gene editing, and for inserting or deleting a polynucleotide of interest into or from the genome of a cell or organism. The methods and compositions employ a guide polynucleotide/Cas endonuclease system to provide for an effective system for modifying or altering target sites and editing nucleotide sequences of interest within the genome of a cell, wherein the guide polynucleotide is comprised of a RNA sequence, a DNA sequence, or a DNA-RNA combination sequence.

Thus in a first embodiment of the disclosure, the method comprises a method for selecting a plant comprising an altered target site in its plant genome, the method comprising: a) obtaining a first plant comprising at least one Cas endonuclease capable of introducing a double strand break at a target site in the plant genome; b) obtaining a second plant comprising a guide RNA that is capable of forming a complex with the Cas endonuclease of (a), c) crossing the first plant of (a) with the second plant of (b); d) evaluating the progeny of (c) for an alteration in the target site and e) selecting a progeny plant that possesses the desired alteration of said target site.

In another embodiment, the method comprises, a method for selecting a plant comprising an altered target site in its plant genome, the method comprising selecting at least one progeny plant that comprises an alteration at a target site in its plant genome, wherein said progeny plant was obtained by crossing a first plant comprising at least one Cas endonuclease with a second plant comprising a guide RNA, wherein said Cas endonuclease is capable of introducing a double strand break at said target site.

In another embodiment, the method comprises, a method for selecting a plant comprising an altered target site in its plant genome, the method comprising: a) obtaining a first plant comprising at least one Cas endonuclease capable of introducing a double strand break at a target site in the plant genome; b) obtaining a second plant comprising a guide RNA and a donor DNA, wherein said guide RNA is capable of forming a complex with the Cas endonuclease of (a), wherein said donor DNA comprises a polynucleotide of interest; c) crossing the first plant of (a) with the second plant of (b); d) evaluating the progeny of (c) for an alteration in the target site e) selecting a progeny plant that comprises the polynucleotide of interest inserted at said target site.

In another embodiment, the method comprises, a method for selecting a plant comprising an altered target site in its plant genome, the method comprising selecting at least one progeny plant that comprises an alteration at a target site in its plant genome, wherein said progeny plant was obtained by crossing a first plant expressing at least one Cas endonuclease to a second plant comprising a guide RNA and a donor DNA, wherein said Cas endonuclease is capable of introducing a double strand break at said target site, wherein said donor DNA comprises a polynucleotide of interest.

In another embodiment, the method comprises, method for modifying a target site in the genome of a plant cell, the method comprising introducing a guide RNA into a plant cell having a Cas endonuclease, wherein said guide RNA and Cas endonuclease are capable of forming a complex that enables the Cas endonuclease to introduce a double strand break at said target site.

In another embodiment, the method comprises, a method for modifying a target site in the genome of a plant cell, the method comprising introducing a guide RNA and a Cas endonuclease into said plant cell, wherein said guide RNA and Cas endonuclease are capable of forming a complex that enables the Cas endonuclease to introduce a double strand break at said target site.

In another embodiment, the method comprises, a method for modifying a target site in the genome of a plant cell, the method comprising introducing a guide RNA and a donor DNA into a plant cell having a Cas endonuclease, wherein said guide RNA and Cas endonuclease are capable of forming a complex that enables the Cas endonuclease to introduce a double strand break at said target site, wherein said donor DNA comprises a polynucleotide of interest.

In another embodiment, the method comprises a method for modifying a target site in the genome of a plant cell, the method comprising: a) introducing into a plant cell a guide RNA and a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site.

In another embodiment, the method comprises, method for modifying a target DNA sequence in the genome of a plant cell, the method comprising: A) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; and, B) identifying at least one plant cell that has a modification at said target, wherein the modification includes at least one deletion or substitution of one or more nucleotides in said target site.

In another embodiment, the method comprises, a method for introducing a polynucleotide of Interest into a target site in the genome of a plant cell, the method comprising: a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; (b) contacting the plant cell of (a) with a donor DNA comprising a polynucleotide of Interest; and, (c) identifying at least one plant cell from (b) comprising in its genome the polynucleotide of Interest integrated at said target site.

In some of these embodiments, the guide RNA can be introduced directly by particle bombardment or can be introduced via particle bombardment or *Agrobacterium* transformation of a recombinant DNA construct comprising the corresponding guide DNA operably linked to a plant U6 polymerase III promoter.

In some of these embodiments, the Cas endonuclease gene is a plant optimized Cas9 endonuclease.

In some of these embodiments, the Cas endonuclease gene is operably linked to a SV40 nuclear targeting signal upstream of the Cas codon region and a VirD2 nuclear localization signal downstream of the Cas codon region.

The plant in these embodiments is a monocot or a dicot. More specifically, the monocot is selected from the group consisting of maize, rice, sorghum, rye, barley, wheat, millet, oats, sugarcane, turfgrass, or switchgrass. The dicot is selected from the group consisting of soybean, canola, alfalfa, sunflower, cotton, tobacco, peanut, potato, tobacco, *Arabidopsis*, or safflower.

In some embodiments, the target site is located in the gene sequence of an acetolactate synthase (ALS) gene, an Enolpyruvylshikimate Phosphate Synthase Gene (ESPSP) gene, a male fertility (MS45, MS26 or MSCA1) gene.

In another embodiment the disclosure comprises a plant, plant part, or seed, comprising a recombinant DNA construct, said recombinant DNA construct comprising a promoter operably linked to a nucleotide sequence encoding a plant optimized Cas9 endonuclease, wherein said plant optimized Cas9 endonuclease is capable of binding to and creating a double strand break in a genomic target sequence said plant genome.

In another embodiment the plant comprises a recombinant DNA construct and a guide RNA, wherein said recombinant DNA construct comprises a promoter operably linked to a nucleotide sequence encoding a plant optimized Cas9 endonuclease, wherein said plant optimized Cas9 endonuclease and guide RNA are capable of forming a complex and creating a double strand break in a genomic target sequence said plant genome.

In another embodiment, the recombinant DNA construct comprises a promoter operably linked to a nucleotide sequence encoding a plant optimized Cas9 endonuclease, wherein said plant optimized Cas9 endonuclease is capable of binding to and creating a double strand break in a genomic target sequence said plant genome.

In another embodiment, the recombinant DNA construct comprises a promoter operably linked to a nucleotide sequence expressing a guide RNA, wherein said guide RNA is capable of forming a complex with a plant optimized Cas9 endonuclease, and wherein said complex is capable of binding to and creating a double strand break in a genomic target sequence said plant genome.

In another embodiment, the method comprises a method for selecting a male sterile or male fertile plant, the method comprising selecting at least one progeny plant that comprises an alteration at a genomic target site located in a male fertility gene locus, wherein said progeny plant is obtained by crossing a first plant expressing a Cas9 endonuclease to a second plant comprising a guide RNA, wherein said Cas endonuclease is capable of introducing a double strand break at said genomic target site.

In another embodiment, the method comprises a method for producing a male sterile or male fertile plant, the method comprising: a) obtaining a first plant comprising at least one Cas endonuclease capable of introducing a double strand break at a genomic target site located in a male fertility gene locus in the plant genome; b) obtaining a second plant comprising a guide RNA that is capable of forming a complex with the Cas endonuclease of (a), c) crossing the first plant of (a) with the second plant of (b); d) evaluating the progeny of (c) for an alteration in the target site; and e) selecting a progeny plant that is male sterile or male fertile. Male fertility genes can be selected from, but are not limited to MS26, MS45, MSCA1 genes Compositions and methods are also provided for editing a nucleotide sequence in the genome of a cell. In one embodiment, the disclosure describes a method for editing a nucleotide sequence in the genome of a plant cell, the method comprising providing a guide RNA, a polynucleotide modification template, and at least one maize optimized Cas9 endonuclease to a plant cell, wherein the maize optimized Cas9 endonuclease is capable of introducing a double-strand break at a target site in the plant genome, wherein said polynucleotide modification template includes at least one nucleotide modification of said nucleotide sequence. The nucleotide to be edited (the nucleotide sequence of interest) can be located within or outside a target site that is recognized and cleaved by a Cas endonuclease. Cells include, but are not limited to, human, animal, bacterial, fungal, insect, and plant cells as well as plants and seeds produced by the methods described herein.

Additional embodiments of the methods and compositions of the present disclosure are shown herein.

BRIEF DESCRIPTION OF THE DRAWINGS AND THE SEQUENCE LISTING

The disclosure can be more fully understood from the following detailed description and the accompanying drawings and Sequence Listing, which form a part of this application. The sequence descriptions and sequence listing attached hereto comply with the rules governing nucleotide and amino acid sequence disclosures in patent applications as set forth in 37 C.F.R. §§ 1.821-1.825. The sequence descriptions contain the three letter codes for amino acids as defined in 37 C.F.R. §§ 1.821-1.825, which are incorporated herein by reference.

FIGURES

FIG. 1A shows a maize optimized Cas9 gene (encoding a Cas9 endonuclease) containing a potato ST-LS1 intron, a SV40 amino terminal nuclear localization sequence (NLS), and a VirD2 carboxyl terminal NLS, operably linked to a plant ubiquitin promoter (SEQ ID NO: 5). The maize optimized Cas9 gene (just Cas9 coding sequence, no NLSs) corresponds to nucleotide positions 2037-2411 and 2601-6329 of SEQ ID NO: 5 with the potato intron residing at positions 2412-2600 of SEQ ID NO: 5.SV40 NLS is at positions 2010-2036 of SEQ ID NO: 5. VirD2 NLS is at positions 6330-6386 of SEQ ID NO: 5. FIG. 1B shows a long guide RNA operably linked to a maize U6 polymerase III promoter terminating with a maize U6 terminator (SEQ ID NO: 12). The long guide RNA containing the variable targeting domain corresponding to the maize LIGCas-3 target site (SEQ ID NO: 8) is transcribed from/corresponds to positions 1001-1094 of SEQ ID NO: 12. FIG. 1C shows the maize optimized Cas9 and long guide RNA expression cassettes combined on a single vector DNA (SEQ ID NO: 102).

Figure 2B:
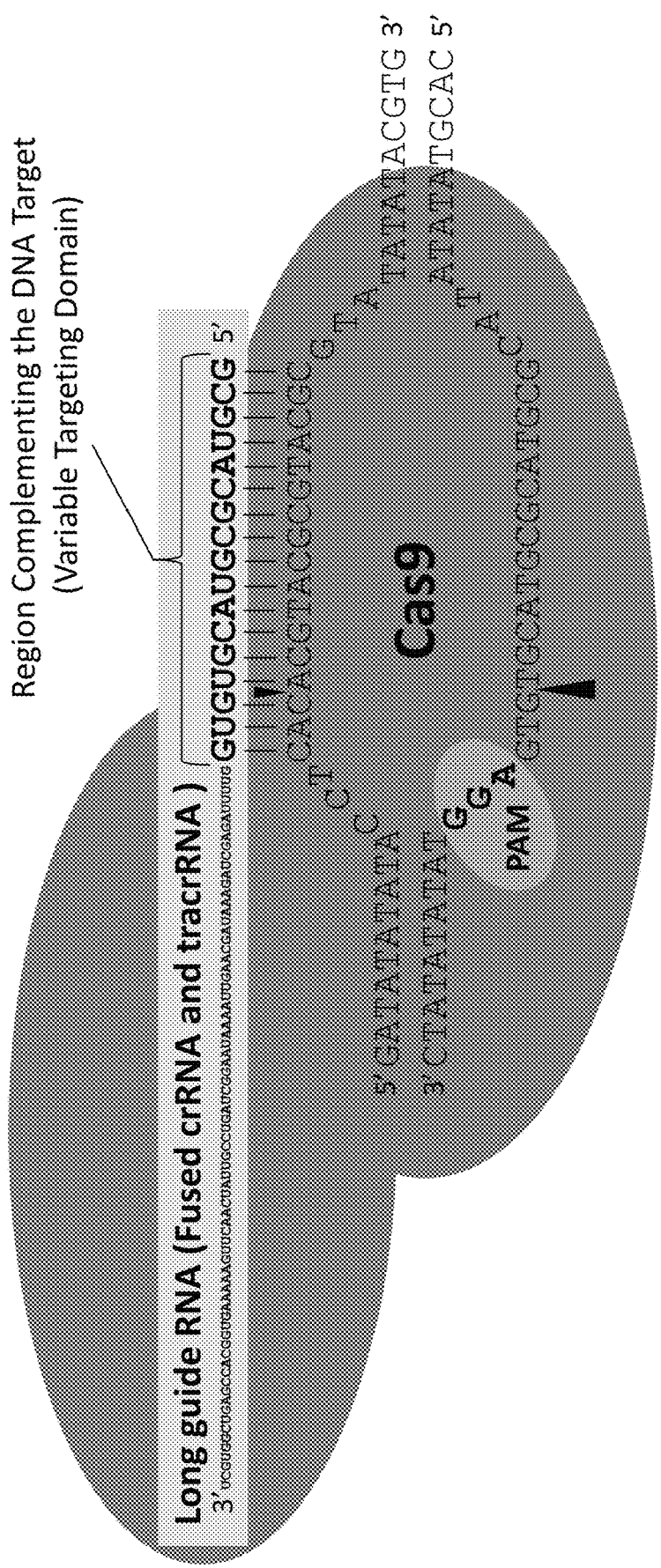

FIG. 2A illustrates the duplexed crRNA (SEQ ID NO:6)-tracrRNA (SEQ ID NO:7)/Cas9 endonuclease system and target DNA complex relative to the appropriately oriented PAM sequence at the maize LIGCas-3 (SEQ ID NO: 18, Table 1) target site with triangles pointing towards the expected site of cleavage on both sense and anti-sense DNA strands. FIG. 2B illustrates the guide RNA/Cas9 endonuclease complex interacting with the genomic target site relative to the appropriately oriented PAM sequence (GGA) at the maize genomic LIGCas-3 target site (SEQ ID NO:18, Table 1). The guide RNA (shown as boxed-in in light gray, SEQ ID NO:8) is a fusion between a crRNA and tracrRNA and comprises a variable targeting domain that is complementary to one DNA strand of the double strand DNA genomic target site. The Cas9 endonuclease is shown in dark gray. Triangles point towards the expected site of DNA cleavage on both sense and anti-sense DNA strands. The sense genome sequence shown in FIGS. 2A and 2B is listed in SEQ ID NO: 551, while the complementary genome sequence shown in FIGS. 2A and 2B is listed in SEQ ID NO: 552.

FIGS. 3A-3B shows an alignment and count of the top 10 most frequent NHEJ mutations induced by the maize optimized guide RNA/Cas endonuclease system described herein compared to a LIG3-4 homing endonuclease control at the maize genomic Liguleless 1 locus. The mutations were identified by deep sequencing. The reference sequence represents the unmodified locus with each target site underlined. The PAM sequence and expected site of cleavage are also indicated. Deletions or insertions as a result of imperfect NHEJ are shown by a "-" or an italicized underlined nucleotide, respectively. The reference and mutations 1-10 of the LIGCas-1 target site correspond to SEQ ID NOs: 55-65, respectively. The reference and mutations 1-10 of the LIGCas-2 correspond to SEQ ID NOs: 55, 65-75, respectively. The reference and mutations 1-10 of the LIGCas-3 correspond to SEQ ID NOs: 76-86, respectively. The reference and mutations 1-10 of the LIG3-4 homing endonuclease target site correspond to SEQ ID NOs: 76, 87-96, respectively.

Figure 4:
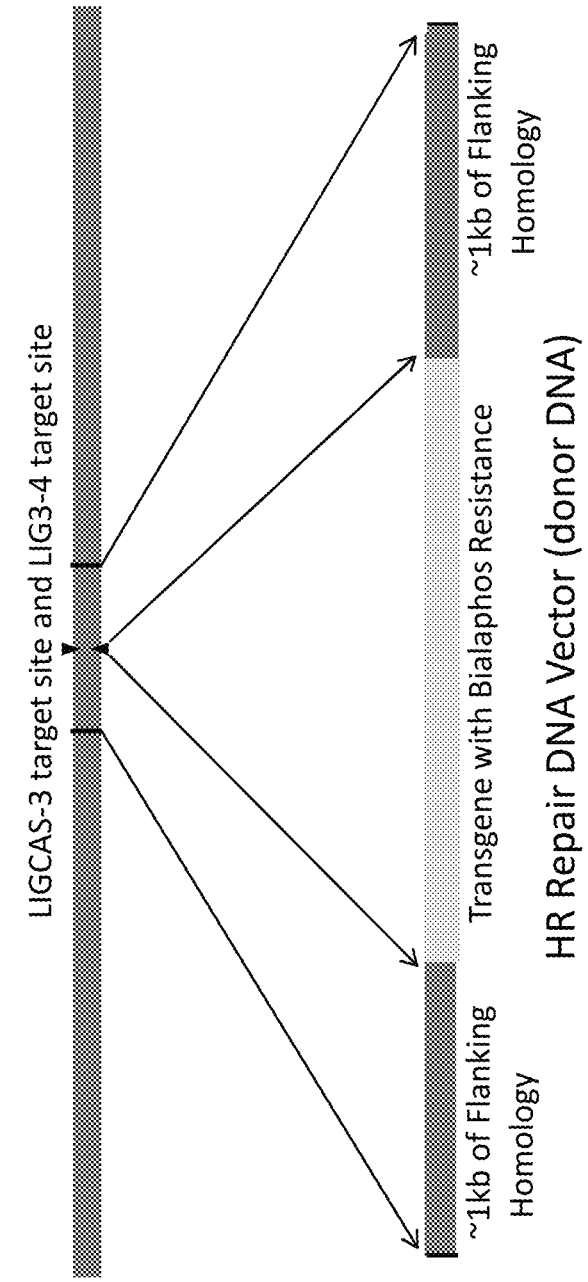

FIG. 4 illustrates how the homologous recombination (HR) repair DNA vector (SEQ ID NO: 97) was constructed. To promote site-specific transgene insertion by homologous recombination, the transgene (shown in light gray) was flanked on either side by approximately 1 kb of DNA with homology to the maize genomic regions immediately adjacent to the LIGCas3 and LIG3-4 homing endonuclease expected sites of cleavage.

Figure 5:
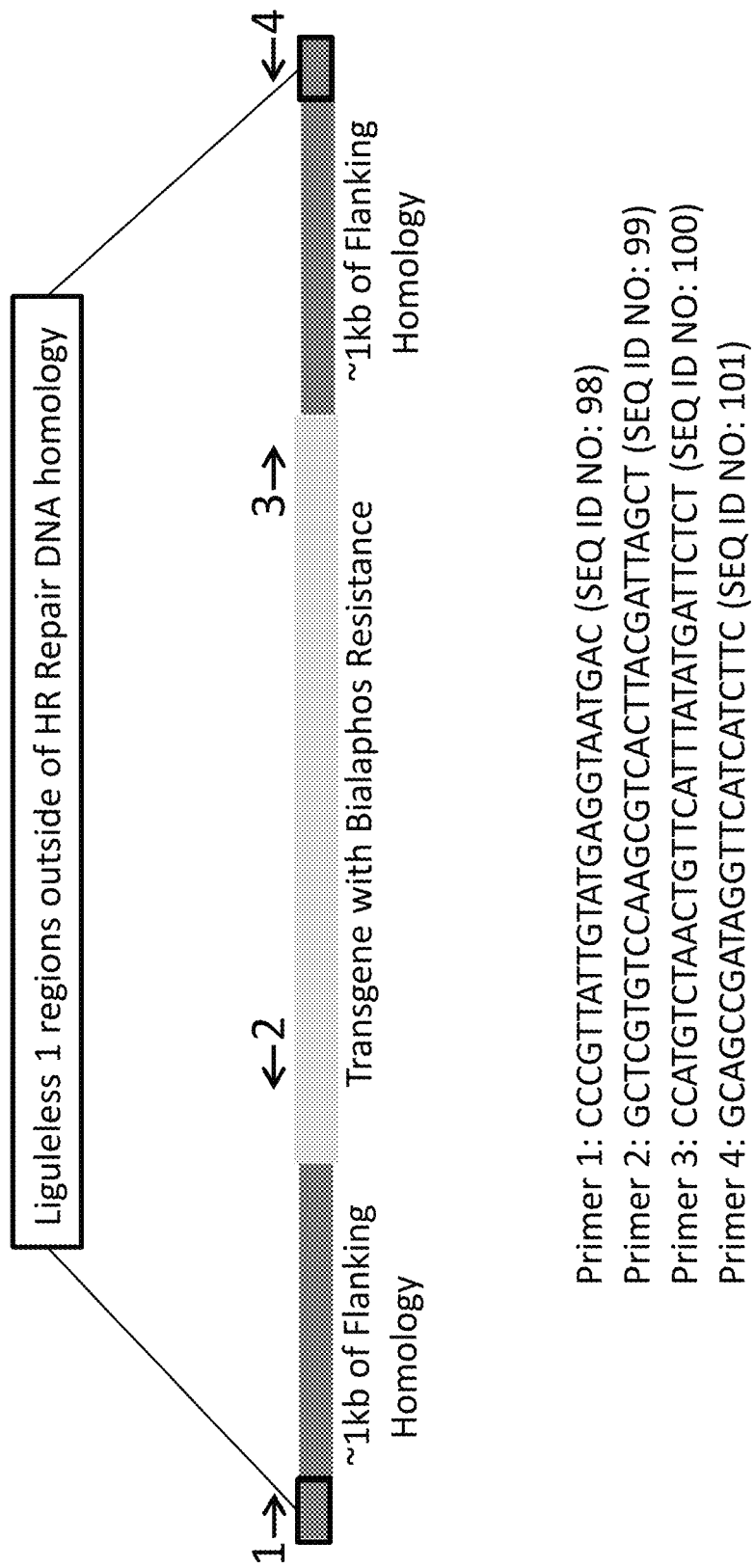

FIG. 5 illustrates how genomic DNA extracted from stable transformants was screened for site-specific transgene insertion by PCR. Genomic primers (corresponding to SEQ ID NOs: 98 and 101) within the Liguleless 1 locus were designed outside of the regions used in constructing the HR repair DNA vector (SEQ ID NO: 97) and were paired with primers inside the transgene (corresponding to SEQ ID NOs: 99 and 100) to facilitate PCR detection of unique genomic DNA junctions created by appropriately oriented site-specific transgene integration.

FIG. 6 shows an alignment of the NHEJ mutations induced by the maize optimized guide RNA/Cas endonuclease system, described herein, when the short guide RNA was delivered directly as RNA. The mutations were identified by deep sequencing. The reference illustrates the unmodified locus with the genomic target site underlined. The PAM sequence and expected site of cleavage are also indicated. Deletions or insertions as a result of imperfect NHEJ are shown by a "-" or an italicized underlined nucleotide, respectively. The reference and mutations 1-6 for 55CasRNA-1 correspond to SEQ ID NOs: 104-110, respectively.

Figure 7:
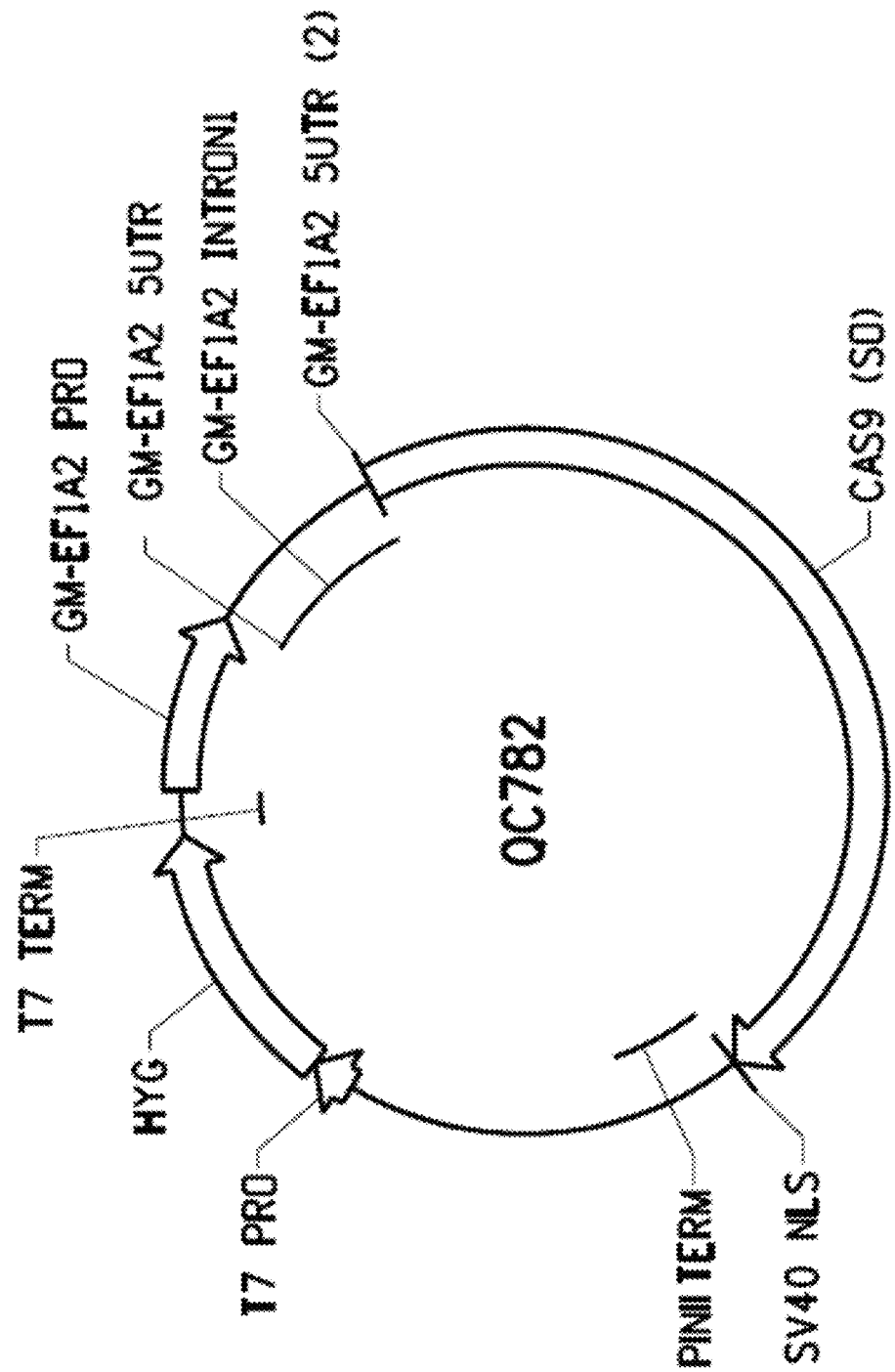

FIG. 7 shows the QC782 vector comprising the Cas9 expression cassette.

Figure 8A:
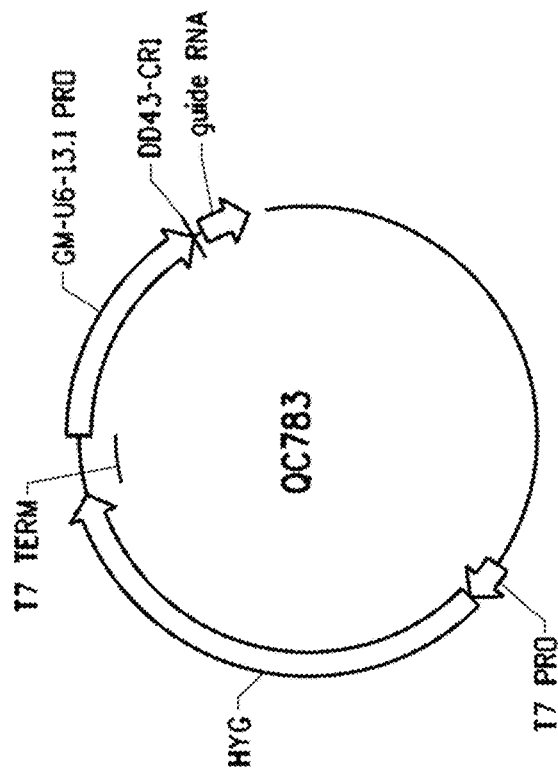
Figure 8B:

FIG. 8A shows the QC783 vector comprising the guide RNA expression cassette. FIG. 8B show the DNA sequence (coding sequence) of the DD43CR1 (20 bp) variable targeting domain of the guide RNA, as well as the terminator sequence linked to the guide RNA. The 20 bp variable targeting domain DD43CR1 is in bold. The sequence shown in FIG. 8B is listed in SEQ ID NO: 553

Figure 9:
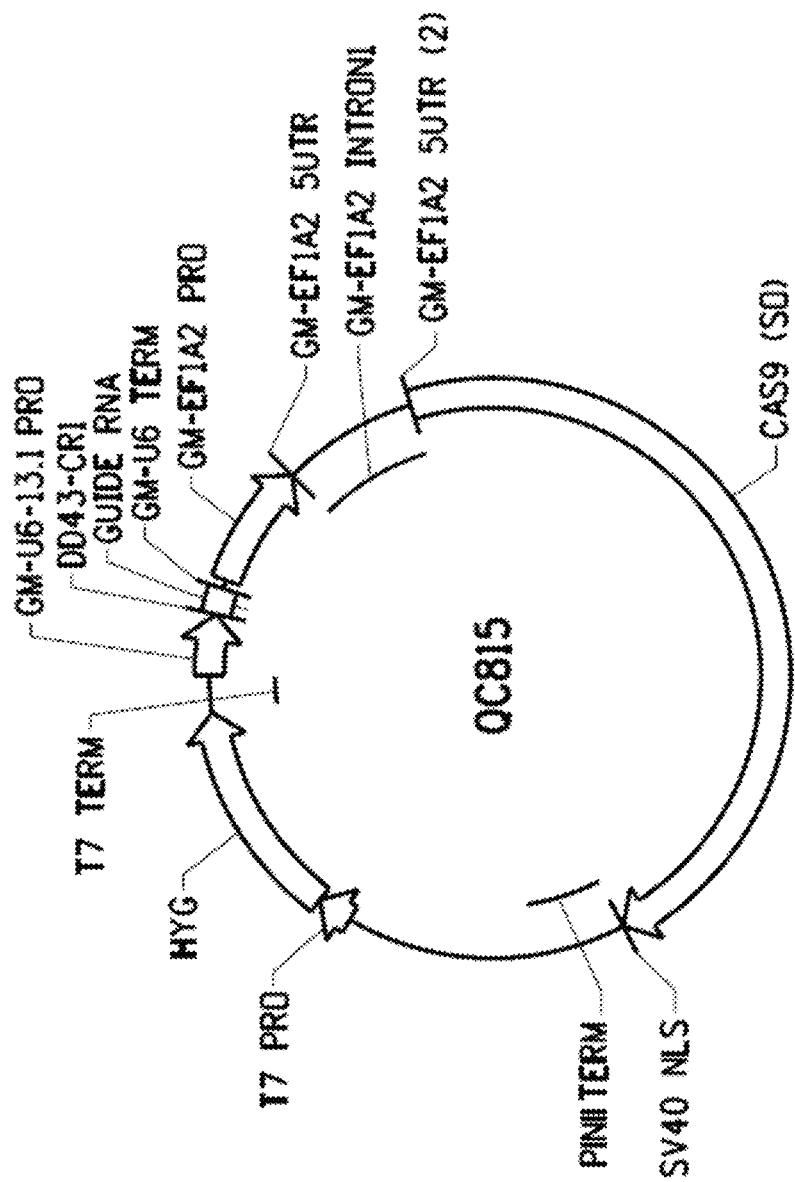

FIG. 9 shows the map of a linked soybean optimized Cas9 and guide RNA construct QC815.

Figure 10A:
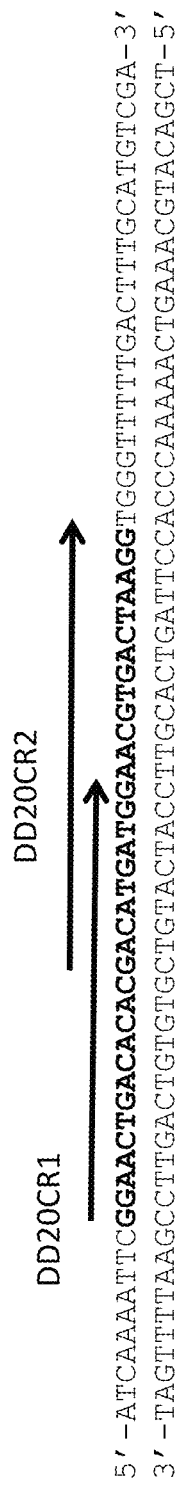
Figure 10B:
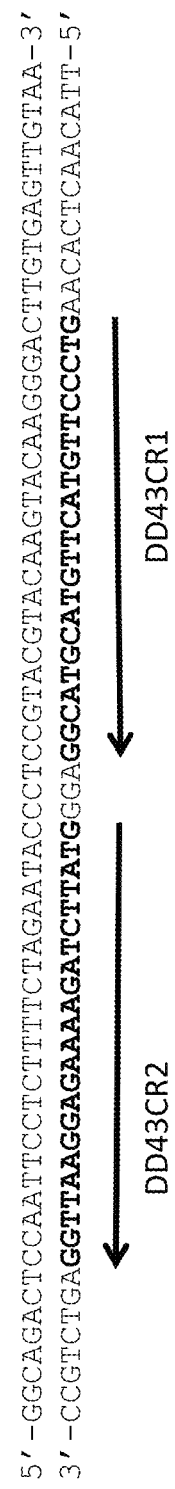

FIG. 10A shows the DD20 soybean locus on chromosome 4 and the DD20CR1 and DD20CR2 genomic target sites (indicated by bold arrows). The sense sequence shown in FIG. 10A is listed in SEQ ID NO: 554 and the complementary sequence shown in FIG. 10A is listed in SEQ ID NO: 555. FIG. 10B shows the DD43 soybean locus on chromosome 4 and the DD43CR1 and DD43CR2 genomic target sites (indicated by bold arrows). The sense sequence shown in FIG. 10B is listed in SEQ ID NO: 556 and the complementary sequence shown in FIG. 10B is listed in SEQ ID NO: 557.

Figures 11A, 11B:
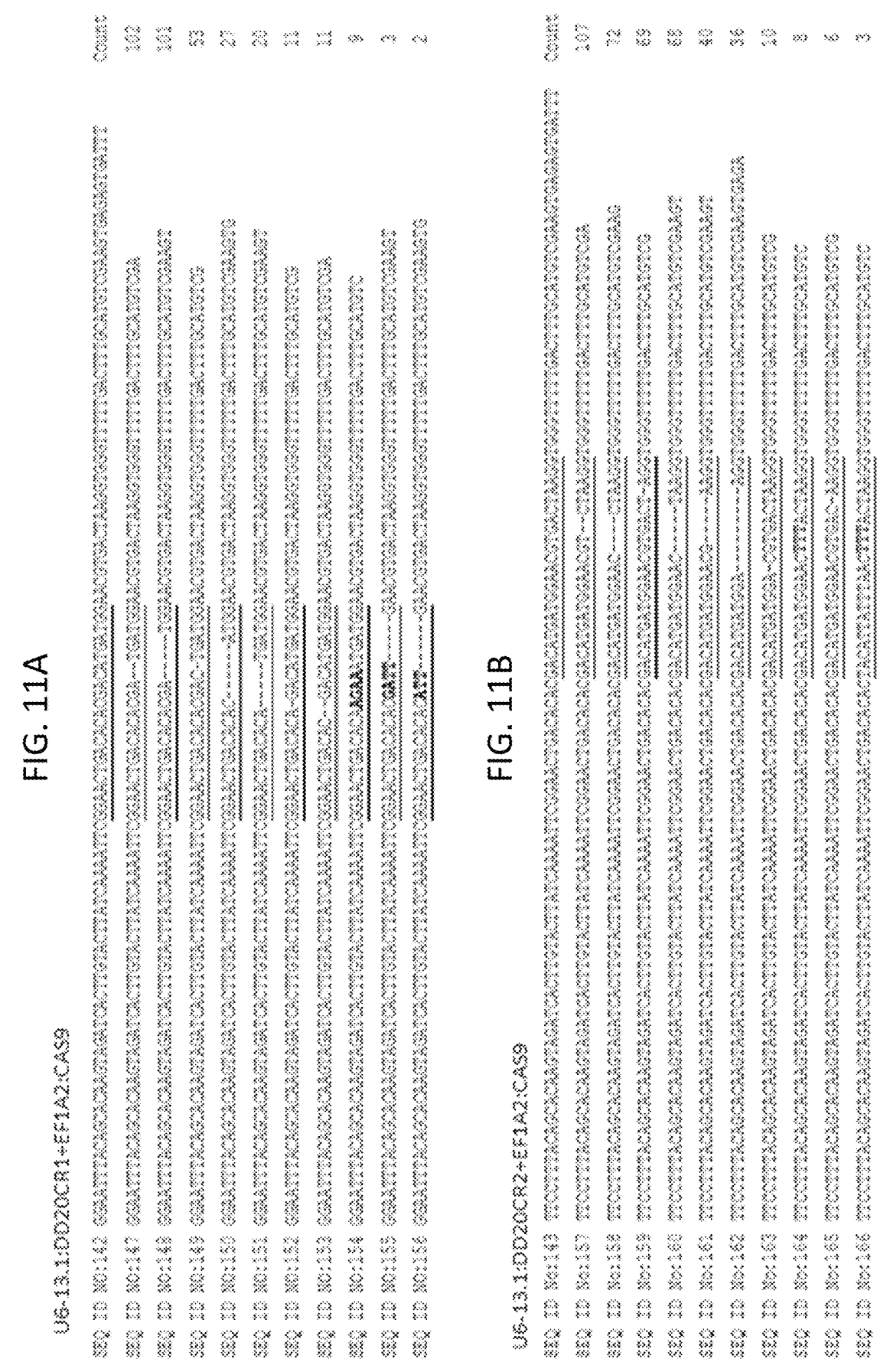
Figures 11C, 11D:
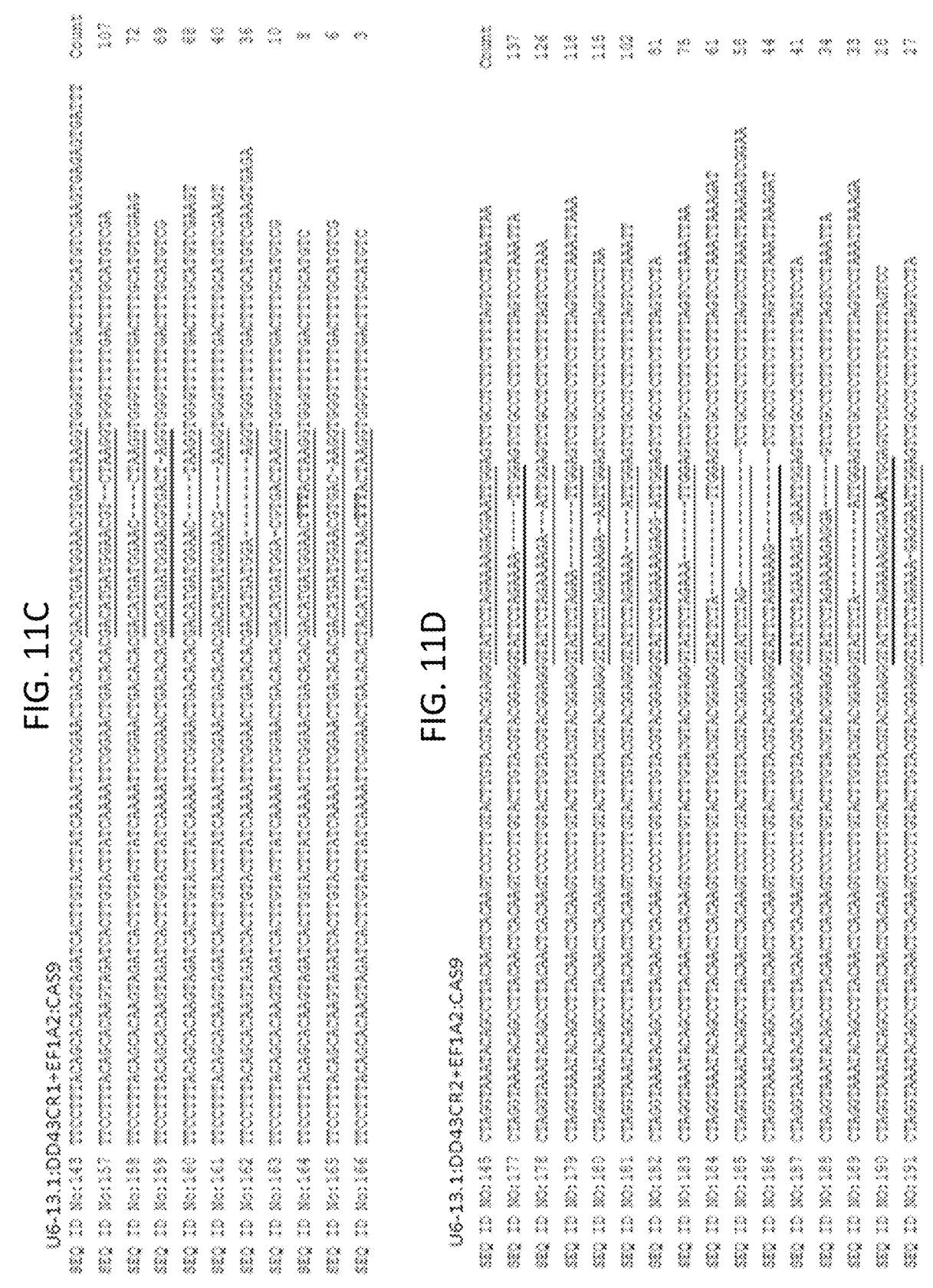

FIGS. 11A-11D. Alignments of expected target site sequences with mutant target sequences detected in four guide RNA induced NHEJ experiments. FIG. 11A shows the DD20CR1 PCR amplicon (reference sequence, SEQ ID NO:142, genomic target site is underlined) and the 10 mutations (SEQ ID NOs: 147-156) induced by the guideRNA/Cas endonuclease system at the DD20CR1 genomic target site. FIG. 11B shows the DD20CR2 PCR amplicon (reference sequence, SEQ ID NO:143) and the 10 mutations (SEQ ID NOs 157-166) induced by the guide RNA/Cas endonuclease system at the DD20CR2 genomic target site. FIG. 11C shows the DD43CR1 PCR amplicon (reference sequence, SEQ ID NO:144) and the 10 mutations (SEQ ID NOs:167-176) induced by the guide RNA/Cas endonuclease system at the DD43CR1 genomic target site. FIG. 11D shows the DD43CR2 PCR amplicon (reference sequence, SEQ ID NO: 145) and the 10 mutations (SEQ ID NOs: 177-191) induced by the guide RNA/Cas endonuclease system at the DD43CR2 genomic target site. The target sequences corresponding different guide RNAs are underlined. Each nucleotide deletions is indicated by "-". Inserted and replaced sequences are in bold. The total number of each mutant sequence is listed in the last column.

FIGS. 12A-12B shows a schematic representation of the guide RNA/Cas endonuclease system used for editing a nucleotide sequence of interest. To enable specific nucleotide editing, a polynucleotide modification template that includes at least one nucleotide modification (when compared to the nucleotide sequence to be edited) is introduced into a cell together with the guide RNA and Cas endonuclease expression cassettes. For example, as shown herein, the nucleotide sequence to be edited is an endogenous wild type enolpyruvylshikimate-3-phosphate synthase (EPSPS) gene in maize cells. The Cas endonuclease (shaded circle) is a maize optimized Cas9 endonuclease that cleaves a moCas9 target sequence within the epsps genomic locus using a guide RNA of SEQ ID NO:194. FIG. 12A shows a polynucleotide modification template that includes three nucleotide modifications (when compared to the wild type epsps locus depicted in FIG. 12B) flanked by two homology regions HR-1 and HR-2. FIG. 12B shows the guide RNA/ maize optimized Cas9 endonuclease complex interacting with the epsps locus. The original nucleotide codons of the EPSPS gene that needed to be edited are show as aCT and Cca (FIG. 12B). The nucleotide codons with modified nucleotides (shown in capitals) are shown as aTC and Tca (FIG. 12B).

Figure 13:
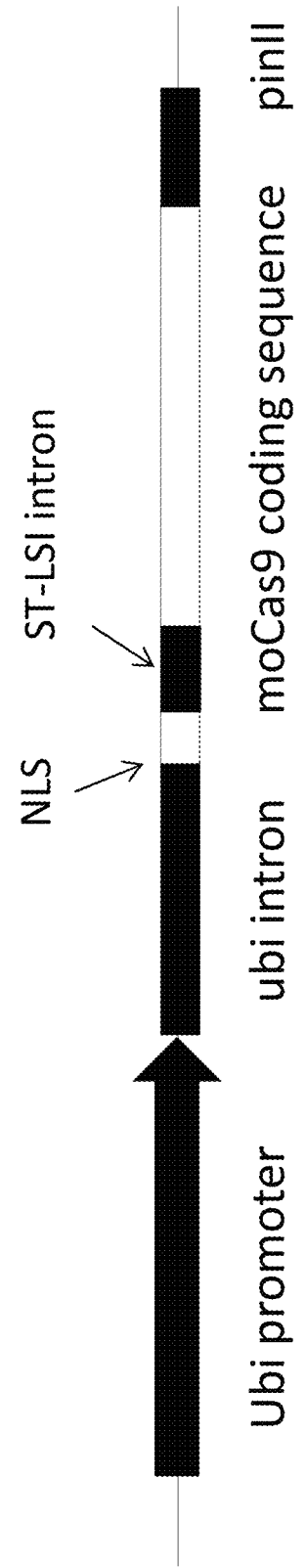

FIG. 13 shows a diagram of a maize optimized Cas9 endonuclease expression cassette. The bacterial cas9 coding sequence was codon optimized for expression in maize cells and supplemented with the ST-LS1 potato intron (moCas9 coding sequence, SEQ ID NO: 193). A DNA fragment encoding the SV40 nuclear localization signal (NLS) was fused to the 5'-end of the moCas9 coding sequence. A maize ubiquitin promoter (Ubi promoter) and its cognate intron (ubi intron) provided controlling elements for the expression of moCas9 in maize cells. The pinII transcription termination sequence (pinII) completed the maize moCAS9 gene design.

Figure 15:
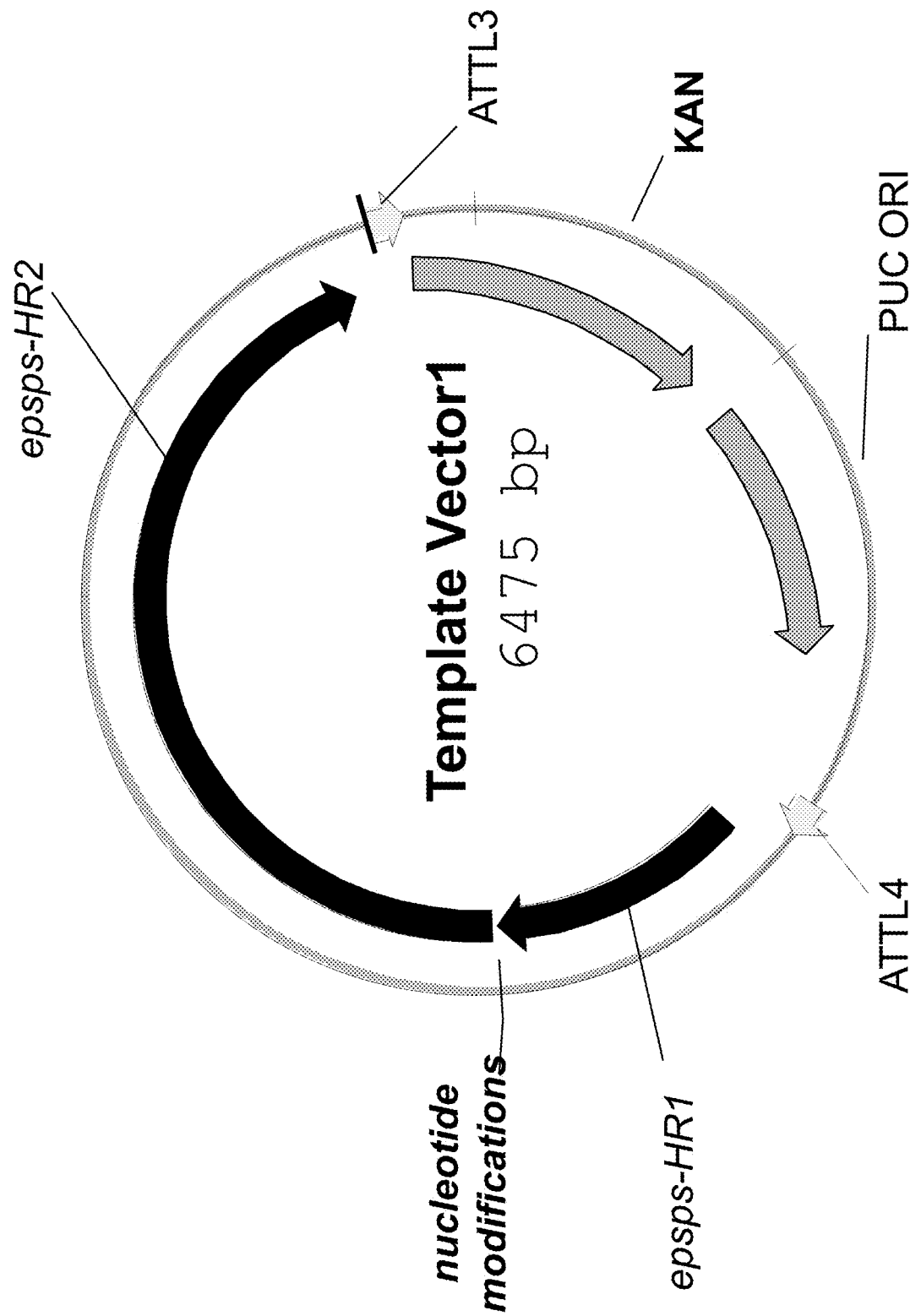

FIG. 14 shows some examples of the moCas9 target sequence (underlined), located on EPSPS DNA fragments, mutagenized by the introduction of double-strand breaks at the cleavage site of the moCas9 endonuclease (thick arrow) in maize cells. In SEQ ID NO: 206, three nucleotides were deleted (dashes) next to the moCas9 cleavage site. SEQ ID NOs: 207-208 indicate that the nucleotide deletion can expand beyond the moCAs9 cleavage site FIG. 15 depicts an EPSPS template vector used for delivery of the EPSPS polynucleotide modification template containing the three TIPS nucleotide modifications. The EPSP polynucleotide modification template includes a partial fragment of the EPSPS gene. The vector was 6,475 bp in length and consisted of two homology regions to the epsps locus (epsps-HR1 and epsps-HR2). Two Gateway cloning sites (ATTL4 and ATTL3), an antibiotic resistance gene (KAN), and the pUC origin of replication (PUC ORI) completed synthesis of the EPSPS template vector1.

FIG. 16 illustrates the PCR-based screening strategy for the identification of maize events with TIPS nucleotide modifications in maize cells. Two pairs of PCR primers were used to amplify the genomic fragments of the epsps locus (upper section). Both of them contained the TIPS specific primers (an arrow with a dot indicating the site of the three TIPS modifications). The shorter fragment (780 bp F-E2) was produced by amplification of the EPSPS polynucleotide modification template fragment (template detection). The amplified EPSPS polynucleotide modification template fragment was found in all but 4 analyzed events (panel F-E2). The longer fragment (839 bp H-T) was produced by amplification of the genomic EPSPS sequence providing that the epsps locus contained the three nucleotide modifications responsible for the TIPS modifications. Six events were identified as containing the three nucleotide modifications (panel H-T). The white arrows point to events that contain both the amplified EPSPS polynucleotide modification template and the nucleotide modifications responsible for the TIPS modification.

Figures 17A, 17B:
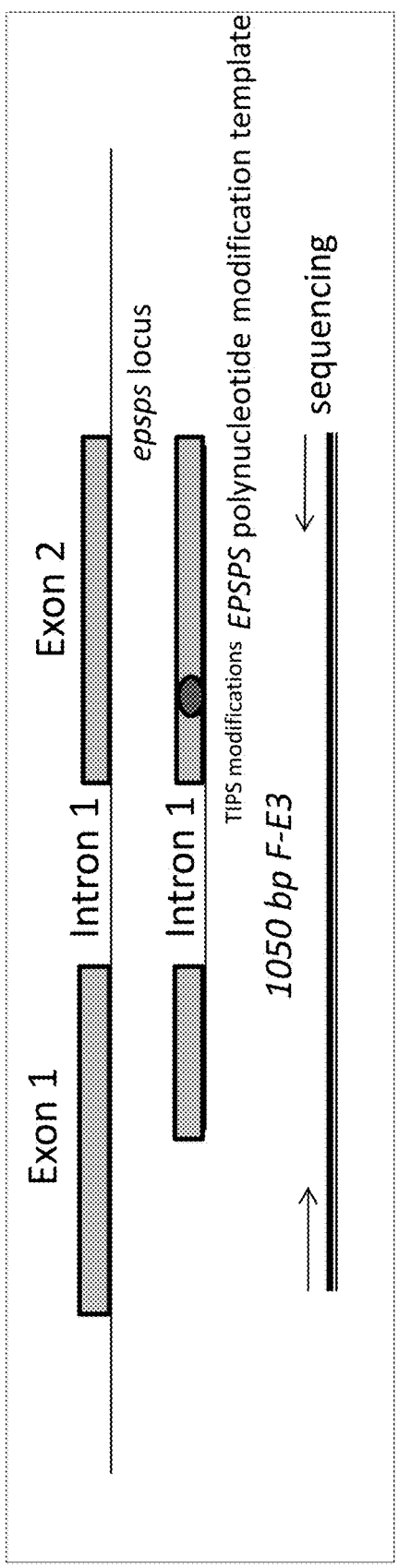

FIG. 17A shows a schematic diagram of the PCR protocol used to identify edited EPSPS DNA fragments in selected events. A partial genomic fragment, comprising parts of Exon1, Intron 1 and Exon2 of the epsps locus, was amplified regardless of the editing product (panel A, 1050 bp F-E3). The amplification products, representing only partial EPSPS gene sequences having one or more mutations, were cloned and sequenced. FIG. 17B shows 2 examples of sequenced amplification products. In some amplification products, the epsps nucleotides and the moCas9 target sequence (underlined) were unchanged indicating that one EPSPS allele was not edited (wild type allele; SEQ ID NO: 210). In other amplification products, three specific nucleotide substitutions (representing the TIPS modifications) were identified with no mutations at the moCas9 target sequence (underlined) (SEQ ID NO: 209).

Figure 18:
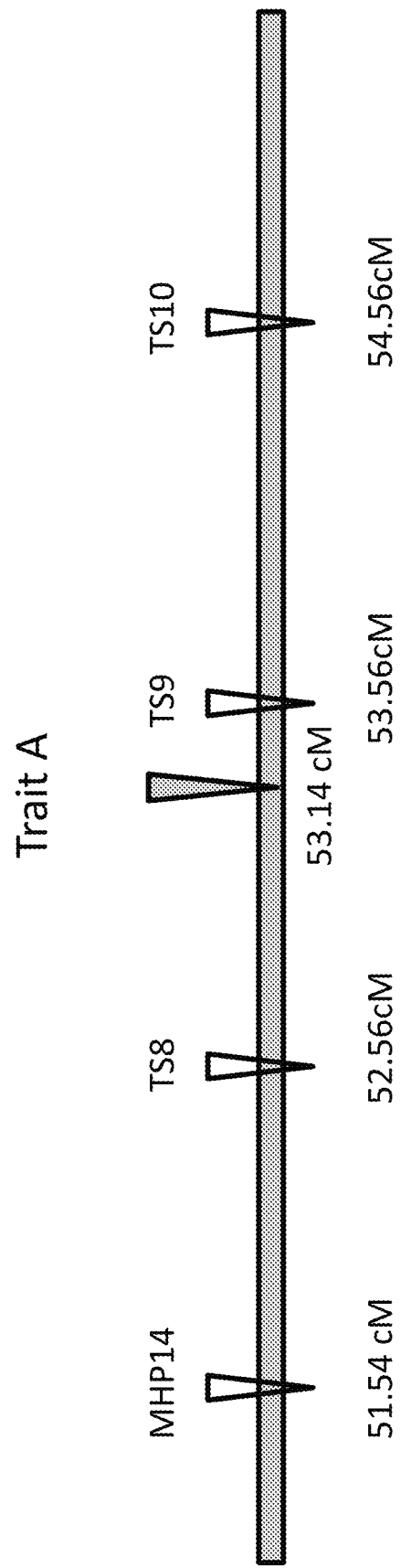

FIG. 18 shows the location of MHP14, TS8, TS9 and TS10 loci comprising target sites for the guide RNA/Cas endonuclease system near trait A (located at 53.14 cM) on chromosome 1 of maize.

FIG. 19A shows the location of the MHP14Cas1 maize genomic target sequence (SEQ ID NO: 229) and the MSP14Cas-3 maize genomic target sequence (SEQ ID NO: 230) on the MHP14 maize genomic DNA locus on chromosome1. The 5' to 3' sequence. FIG. 19B shows the location of the TS8Cas-1 (SEQ ID NO: 231) and TS8Cas-2 (SEQ ID NO: 232) maize genomic target sequences located on the TS8 locus. FIG. 19C shows the location of the TS9Cas-2 (SEQ ID NO: 233) and TS9Cas-3 (SEQ ID NO: 234) maize genomic target sequences located on the TS8 locus. FIG. 19D shows the location of the TS10Cas-1 (SEQ ID NO: 235), and TS10Cas-3 (SEQ ID NO: 236) maize genomic target sequences located on the TS10 locus. All these maize genomic target sites are recognized are recognized and cleaved by a guide RNA/Cas endonuclease system described herein. Each maize genomic target sequence (indicated by an arrow) is highlighted in bold and followed by the NGG PAM sequence shown boxed in.

Figure 20:
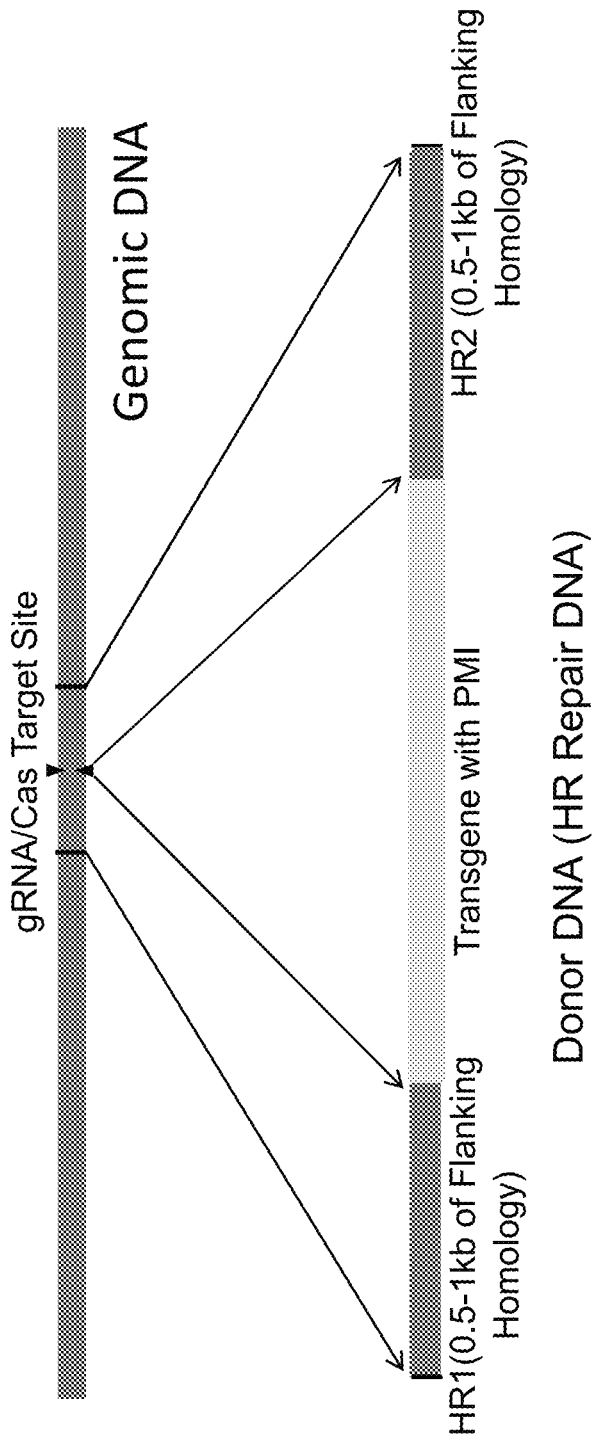

FIG. 20 shows a schematic of a donor DNA (also referred to as HR repair DNA) comprising a transgene cassette with a selectable marker (phosphomannose isomerase, depicted in grey), flanked by homologous recombination sequences (HR1 and HR2) of about 0.5 to 1 kb in length, used to introduce the transgene cassette into a genomic target site for the guide RNA/Cas endonuclease system. The arrows indicate the sections of the genomic DNA sequence on either side of the endonuclease cleavage site that corresponds to the homologous regions of the donor DNA. This schematic is representative for homologous recombination occurring at any one of the 8 target sites (4 loci) located on chromosome 1 from 51.54 cM to 54.56 cM in maize genome.

Figure 21:
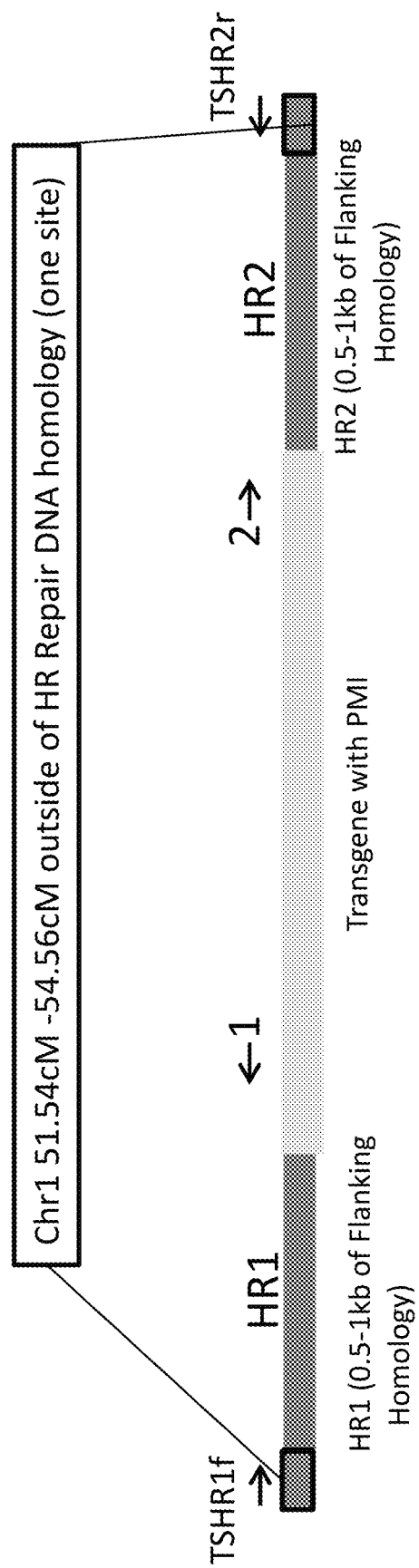

FIG. 21 shows the junction PCR screen for identification of insertion events. Primer 1 and 2 located on the transgene donor are common for all target sites. Primer TSHR1f is located on the genomic region outside of the homologous sequence HR1. Primer combination THR1f/primer1 amplify junction 1. Primer TSHR2r is located on the genomic region outside of the HR2 region. Primer combination primer2/TSHR2r amplify junction 2.

Figure 22:
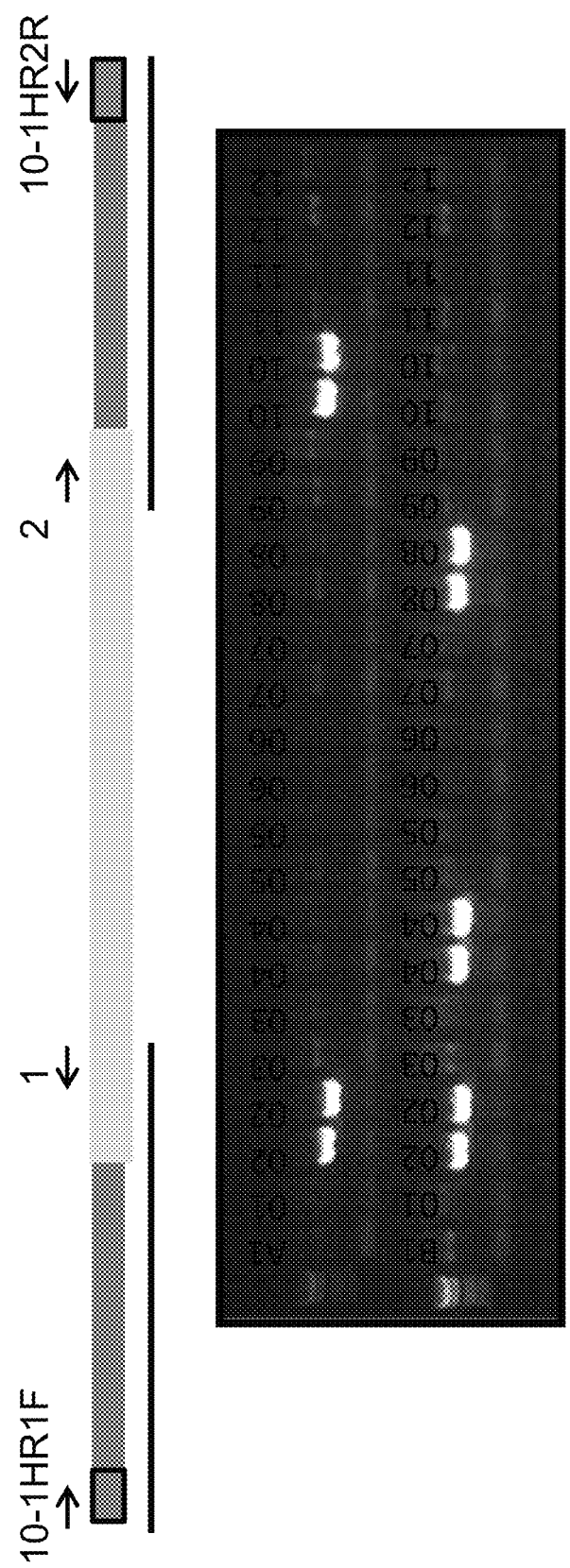

FIG. 22 shows a junction PCR screen for identification of insertion events at the TS10Cas10 locus. A gel picture indicates the presence of insertion events at the TS10Cas10-1 target site (lane 02 A1). PCR reaction of HR1 and HR2 junction loaded next to each other (lane 02-white label and lane 02-gray label), with white label representing HR1 junction PCR, gray label representing HR2 junction PCR.

FIGS. 23 A-B. DNA expression cassettes used in gRNA/Cas9 mediated genome modification experiments. FIG. 23A) The Cas9 endonuclease cassette (EF1A2:CAS9) comprising a soybean EF1A2 promoter (GM-EF1A2 PRO) driving the soybean codon optimized Cas9 endonucleases (CAS9(SO), a soybean optimized SV40 nuclear localization signal (SV40 NLS(SO)) and a PINII terminator (PINII TERM) was linked to a guide RNA expression cassette (U6-9.1:DD20CR1, comprising a soybean U6 promoter driving the DD20CR1 guide RNA) used in experiment U6-9.1DD20CR1 (Table 27). Other Guide RNA/Cas9 cassettes listed in Table 27 are identical except for the 20 bp variable targeting domains of the guide RNA targeting the genomic target sites DD20CR2, DD43CR1, or DD43CR2. FIG. 23B) The donor DNA cassette (DD20HR1-SAMS:HPT-DD20HR2) used in experiment U6-9.1DD20CR1 (Table 27). DD20HR1 and DD20HR2 homologous DNA regions between the donor DNA cassette and the genomic DNA sequences flanking the DD20 target site). Other Donor DNA cassettes listed in Table 27 are identical except for the DD43HR1 and DD43HR2 regions in two of them.

FIGS. 24 A-C. DD20 and DD43 soybean genomic target sites locations and qPCR amplicons. FIG. 24A) Diagram of *Glycine max* chromosome 04 indicating relative positions of DD20 and DD43 target sites. Genetic mapping positions of DD20 and DD43 sites are the positions of the most nearby genes Glyma04g39780.1 and Glyma04g39550.1. FIG. 24B) DD20 qPCR 64 bp amplicon 45936307-45936370 from chromosome 04 (SEQ ID NO: 304). Relative positions of the target sites DD20-CR1 and DD20-CR2, qPCR primers and probe DD20-F, DD20-R, and DD20-T are marked. FIG. 24C) DD43 qPCR 115 bp amplicon 45731879-45731993 from chromosome 04 (SEQ ID NO: 305). Relative positions of the target sites DD43-CR1 and DD43-CR2, qPCR primers and probe DD43-F2, DD43-F, DD43-R, and DD43-T are marked.

FIGS. 25 A-C. Schematic of guide RNA/Cas9 system mediated site-specific non-homologous end joining (NHEJ) and transgene insertion via homologous recombination (HR) at DD20CR1 site. FIG. 25A) Soybean plants are co-transformed with guide RNA/Cas9 and donor DNA cassettes as listed in Table 27. The DD20CR1 guide RNA/Cas9 complex transcribed from the linked guide RNA/Cas9 DNA cassettes will cleave specifically the DD20CR1 target site on chromosome 04 to make DNA double strand breaks. The breaks can be repaired spontaneously as NHEJs or repaired as a HR event by the donor DNA facilitated by the flanking homologous regions DD20-HR1 and DD20HR2. FIG. 25B) NHEJs are detected by DD20-specific qPCR and the mutated sequences are assessed by sequencing cloned HR1-HR2 PCR fragments. FIG. 25C) HR events are revealed by two border-specific PCR analyses HR1-SAMS and NOS-HR2, noting that the primers are only able to amplify DNA recombined between the DD20CR1 region of chromosome 04 and the donor DNA. Guide RNA/Cas9 mediated NHEJ and HR at DD20-CR2 site follow the same process except for using DD20-CR2 guide RNA. Guide RNA/Cas9 mediated site-specific NHEJ and HR at DD43CR1 and DD43CR2 sites follow the same process except for using guide RNA and homologous regions specific to the DD43 sites.

FIGS. 26 A-C. Sequences of gRNA/Cas9 system mediated NHEJs. Only 60 bp sequences surrounding the genomic target site shown in bold case are aligned to show the mutations. The PAM sequence is shown boxed in. Insertion sequences are indicated by symbol ^ marking the insertion position followed by the size of the insert. Actual insertion sequences are listed in the sequences listing. FIG. 26A) U6-9.1DD20CR1 sequences. Three colonies were sequenced for each of 54 events from experiment U6-9.1DD20CR1. A total of 150 sequences were returned, of which 26 were found to be short unique deletions while 2 of the events contained small insertions. FIG. 26B) U6-9.1DD20CR2 sequences. Three colonies were sequenced for each of 28 events from experiment U6-9.1DD20CR2. A total of 84 sequences were returned, of which 20 were found to be short unique deletions while 1 of the events contained a single bp insertion. FIG. 26C) U6-9.1DD43CR1 sequences. Three colonies were sequenced for each of 46 events from experiment U6-9.1DD43CR1. A total of 132 sequences were returned, of which 18 were found to be short unique deletions while 10 of the events contained small insertions. FIG. 26D) U6-9.1DD43CR2 sequences.

FIGS. 27 A-C shows the ten most prevalent types of NHEJ mutations recovered based on the crRNA/tracrRNA/Cas endonuclease system. FIG. 27A shows NHEJ mutations for LIGCas-1 target site, corresponding to SEQ ID NOs: 415-424), FIG. 27B shows NHEJ mutations for LIGCas-2 target site corresponding to SEQ ID NOs: 425-434) and FIG. 27V shows NHEJ mutations (for LIGCas-3 target site corresponding to SEQ ID NOs: 435-444).

Figure 28:
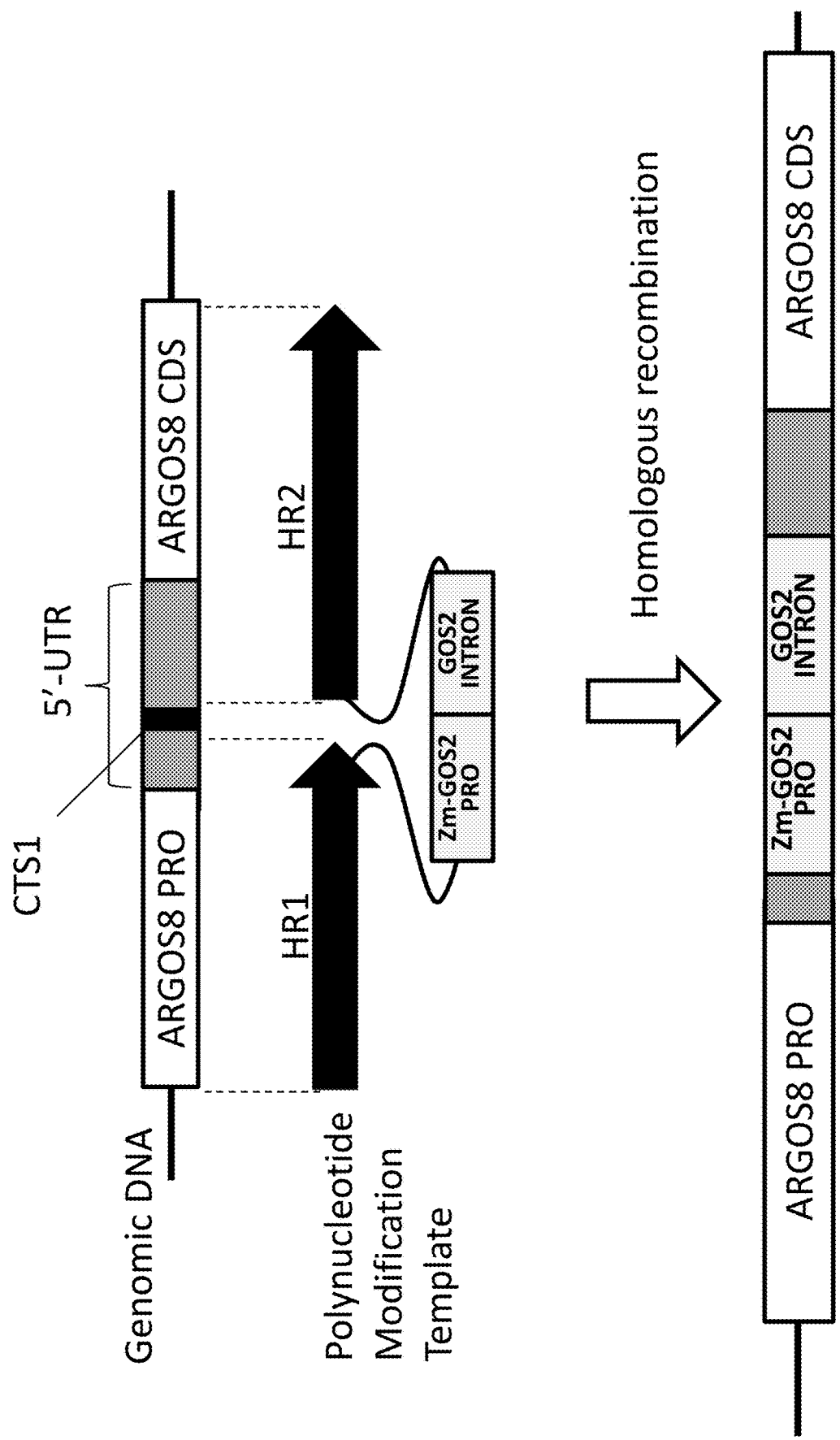

FIG. 28. Schematic representation of Zm-GOS2 PRO:GOS2 INTRON insertion in the 5'-UTR of maize ARGOS8 gene by targeting the guide RNA/Cas9 target sequence 1 (CTS1, SEQ ID NO: 1) with the gRNA1/Cas9 endonuclease system, described herein. HR1 and HR2 indicate homologous recombination regions.

FIGS. 29 A-C. Identification and analysis of Zm-GOS2 PRO:GOS2 INTRON insertion events in maize plants. FIG. 29A) Schematic representation of Zm-GOS2 PRO:GOS2 INTRON insertion in the 5'-UTR of Zm-ARGOS8. CTS1 was targeted with the gRNA1/Cas9 endonuclease system, described herein. HR1 and HR2 indicate homologous recombination regions. P1 to P4 indicate PCR primers. FIG. 29B) PCR screening of PMI-resistance calli to identify insertion events. PCR results are shown for 13 representative calli. The left and right junction PCRs were carried out with the primer pair P1+P2 and P3+P4, respectively. FIG. 29C) PCR analysis of a T0 plant. A PCR product with the expected size (2.4 kb, Lane T0) was amplified with the primer P3 and P4.

Figure 30:
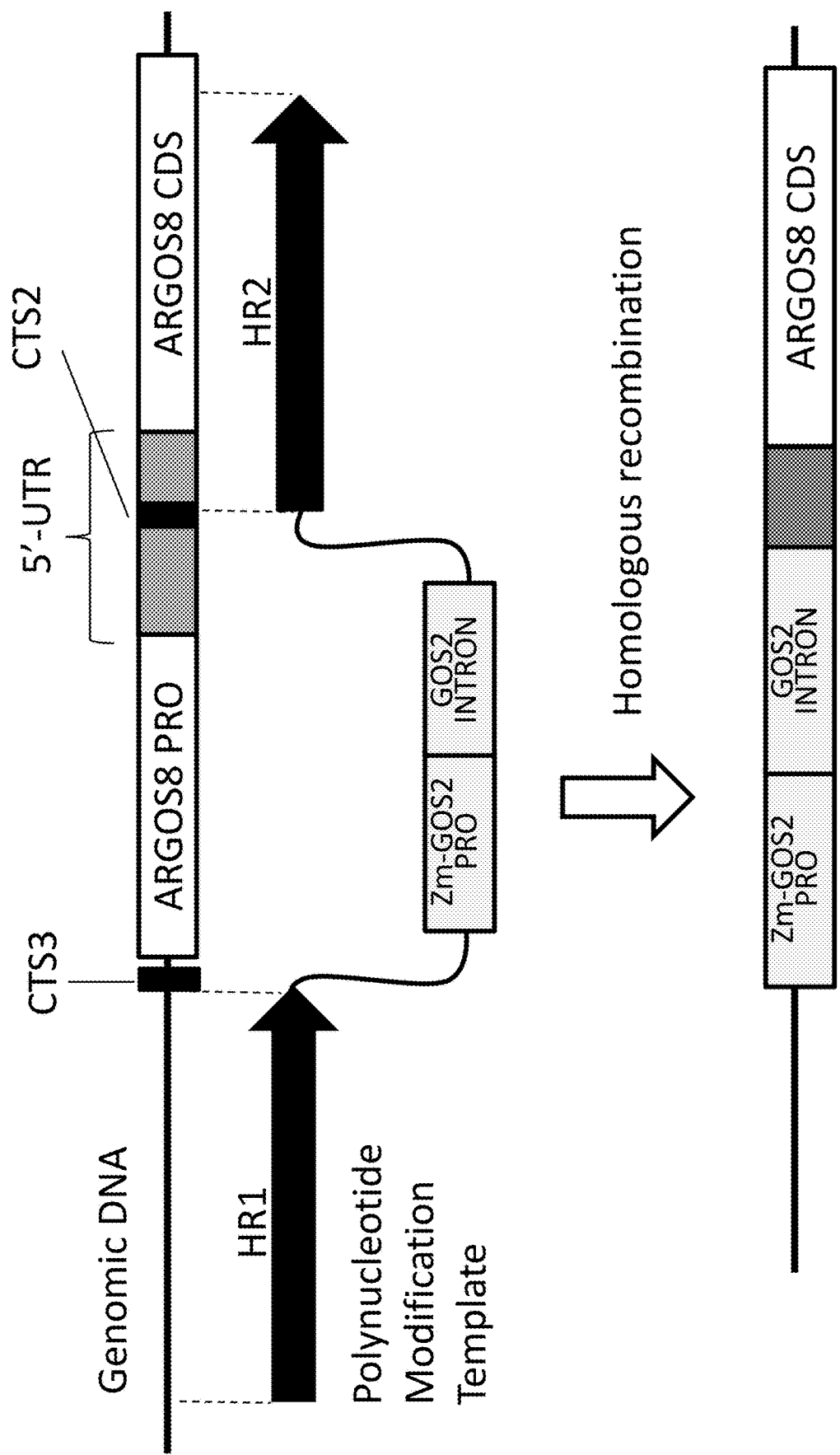

FIG. 30. Schematic representation of Zm-ARGOS8 promoter substitution with Zm-GOS2 PRO:GOS2 INTRON by targeting CTS3 (SEQ ID NO: 3) and CTS2 (SEQ ID NO:2). HR1 and HR2 indicate homologous recombination regions.

FIGS. 31 A-D. Substitution of the native promoter of the ARGOS8 gene with Zm-GOS2 PRO:GOS2 INTRON in maize plants. FIG. 31A) Schematic representation of the Zm-GOS2 PRO:GOS2 INTRON:ARGOS8 allele generated by promoter swap. Two guide RNA/Cas9 target sites, CTS3 (SEQ ID NO:3) and CTS2 (SEQ ID NO:2), were targeted with a gRNA3/gRNA2/Cas9 system. HR1 and HR2 indicate homologous recombination regions. P1 to P5 indicate PCR primers. FIG. 31B) PCR screening of PMI-resistance calli to identify swap events. PCR results are shown for 10 representative calli. One callus sample, 12A09, is positive for both left junction (L, primer P1+P2) and right junction (R, primer P5+P4) PCR, indicating that 12A09 is a swap event. FIG. 31C) PCR analysis of the callus events identified in primary screening. PCR products with the expected size (2.4 kb) were amplified using the primer P3 and P4 from event #3, 4, 6, 8 and 9, indicating presence of the Zm-GOS2 PRO:GOS2 INTRON:ARGOS8 allele. FIG. 31D) PCR analysis of a T0 plant. A PCR product with the expected size (2.4 kb, Lane T0) was amplified with the primer P3 and P4.

Figure 32A:
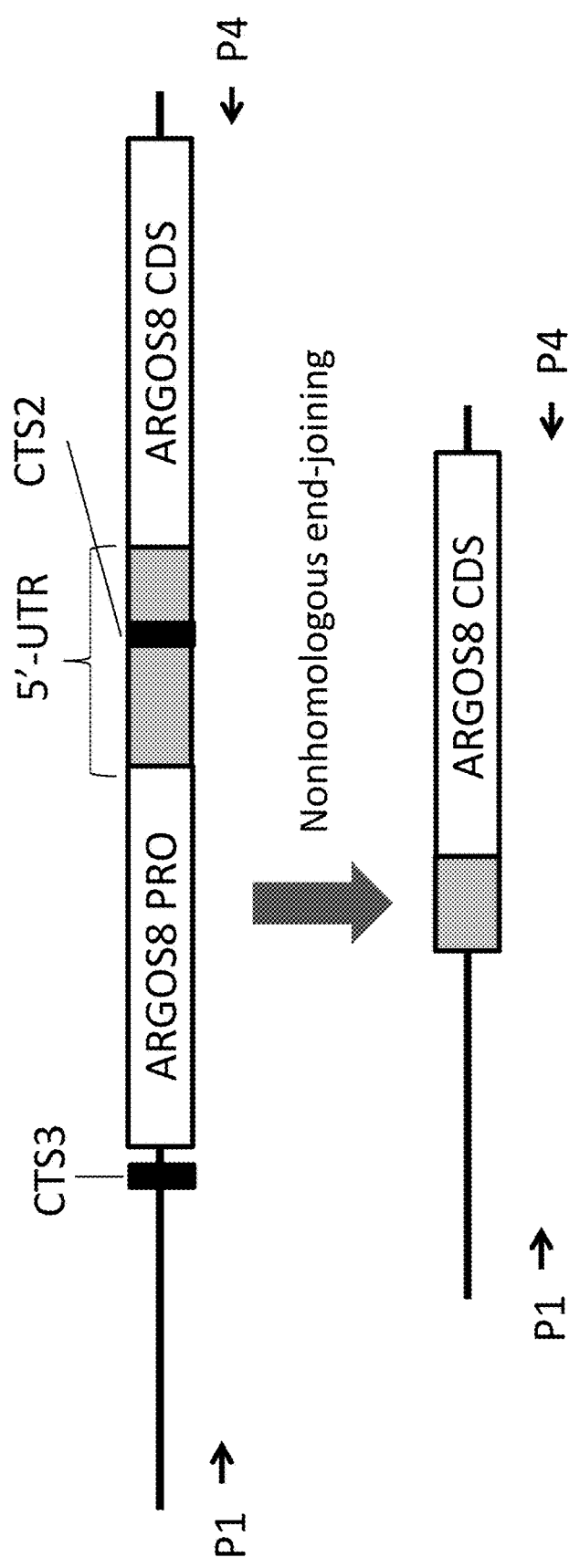
Figure 32B:
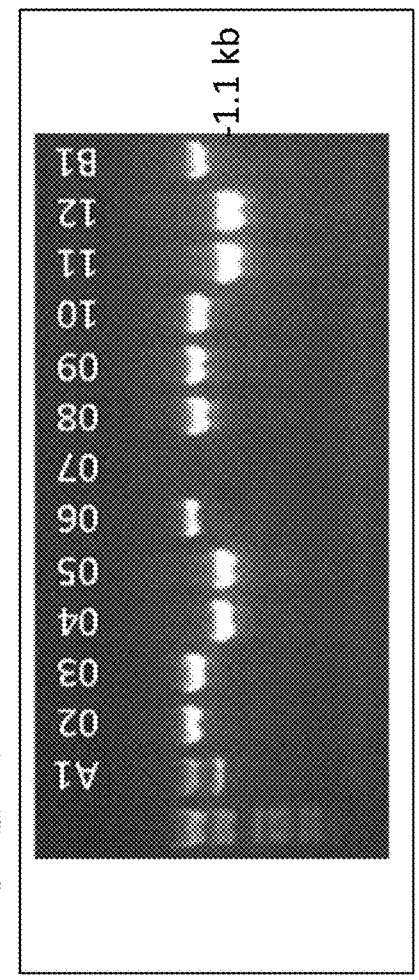

FIGS. 32 A-B. Deletion of the native promoter of the ARGOS8 gene in maize plants. FIG. 32A) Schematic representation of promoter deletion. Two guide RNA's and a Cas9 endonuclease system, referred to as a gRNA3/gRNA2/Cas9 system, were used to target the CTS3 and CTS2 sites in Zm-ARGOS8. P1 and P4 indicate PCR primers for deletion event screening. FIG. 32B) PCR screening of PMI-resistance calli to identify deletion events. PCR results are shown for 15 representative calli. A 1.1-kp PCR product indicates deletion of the CTS3/CTS2 fragment.

Figure 33:
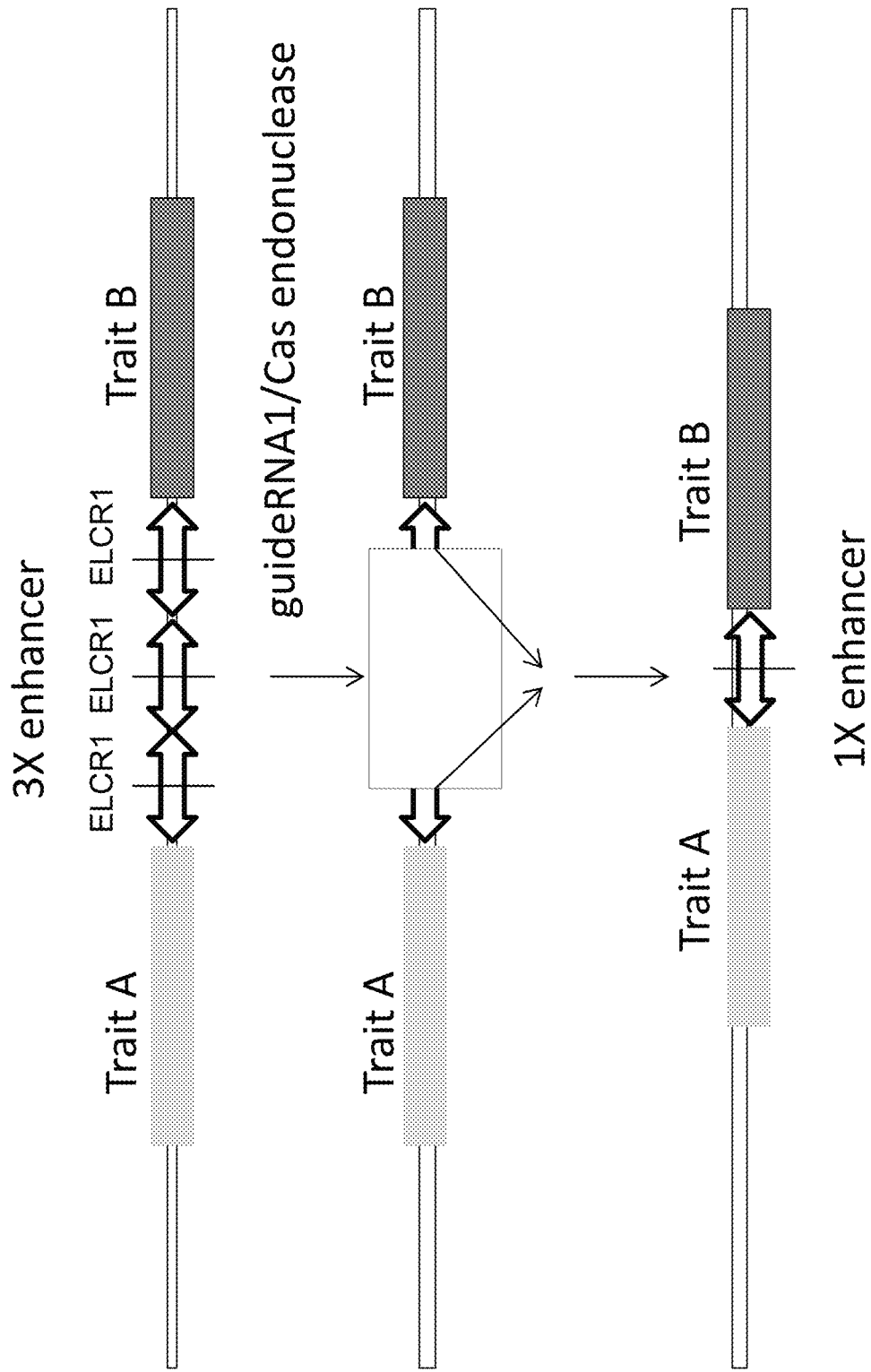

FIG. 33. Schematic representation of enhancer element deletions using the guide RNA/Cas9 target sequence. The enhancer element to be deleted can be, but is not limited to, a 35S enhancer element.

FIGS. 34 A-C. Modification of a maize EPSPS polyubiquitination site. FIG. 34A) The selected maize EPSPS polyubiquitination site is compared to the analogous sites of other plant species (SEQ ID NOs: 558-563). FIG. 34B) The nucleotides to be edited in the maize EPSPS coding sequence (underlined, encoded amino acid shown in bold). The sequence shown in FIG. 34B is listed in SEQ ID NO: 564 FIG. 34C) The edited EPSPS coding sequence identified in the selected T0 plant. The sequence shown in FIG. 34C is listed in SEQ ID NO: 565

FIGS. 35 A-C. The intron mediated enhanced element FIG. 35A). The 5' section of the first intron of the EPSPS gene (editing: substitutions underlined and deletions represented by dots) FIG. 35B) and its edited version conferring three IMEs elements (underlined). The edited nucleotides are shown in bold FIG. 35C). The sequence shown in FIG. 35B is listed in SEQ ID NO: 566. The sequence shown in FIG. 35 C is listed in SEQ ID NO: 567

Figure 36A:
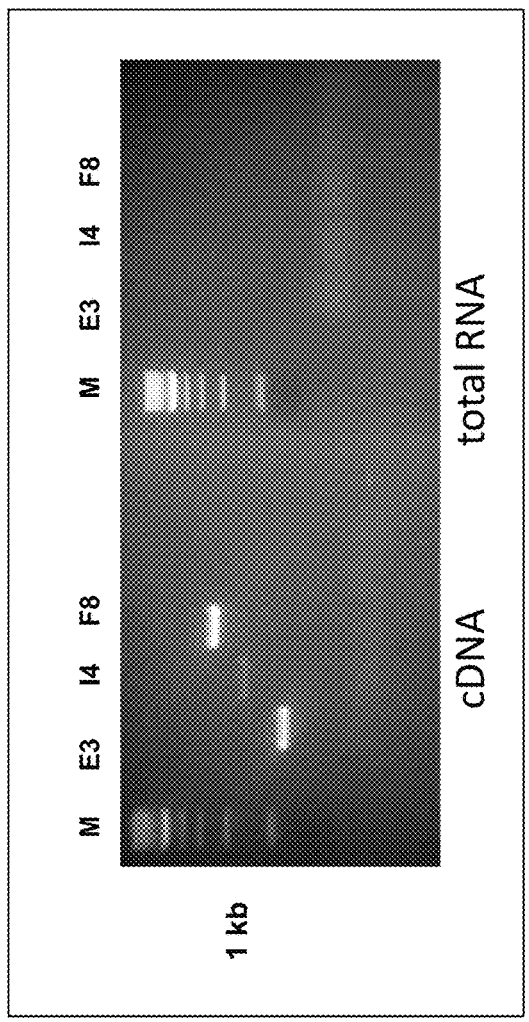

FIGS. 36 A-B. Alternatively spliced EPSPS mRNA in maize cells. FIG. 36A) left panel represents analysis of EPSPS cDNA. The lane 14 in FIG. 36A shows amplification of the EPSPS pre-mRNA containing the $3^{rd}$ intron unspliced (the 804 bp diagnostic fragment as shown in FIG. 36 B indicates an alternate splicing event). Lanes E3 and F8 show the EPSPS PCR amplified fragments with spliced introns. These diagnostic fragments are not amplified unless cDNA is synthesized (as is evident by the absence of bands in lanes E3, 14, and F8 comprising total RNA (shown in the total RNA panel on right of FIG. 36A). The grey boxes in FIG. 36 B represent the eight EPSPS exons (their sizes are indicated above each of them).

Figure 37:
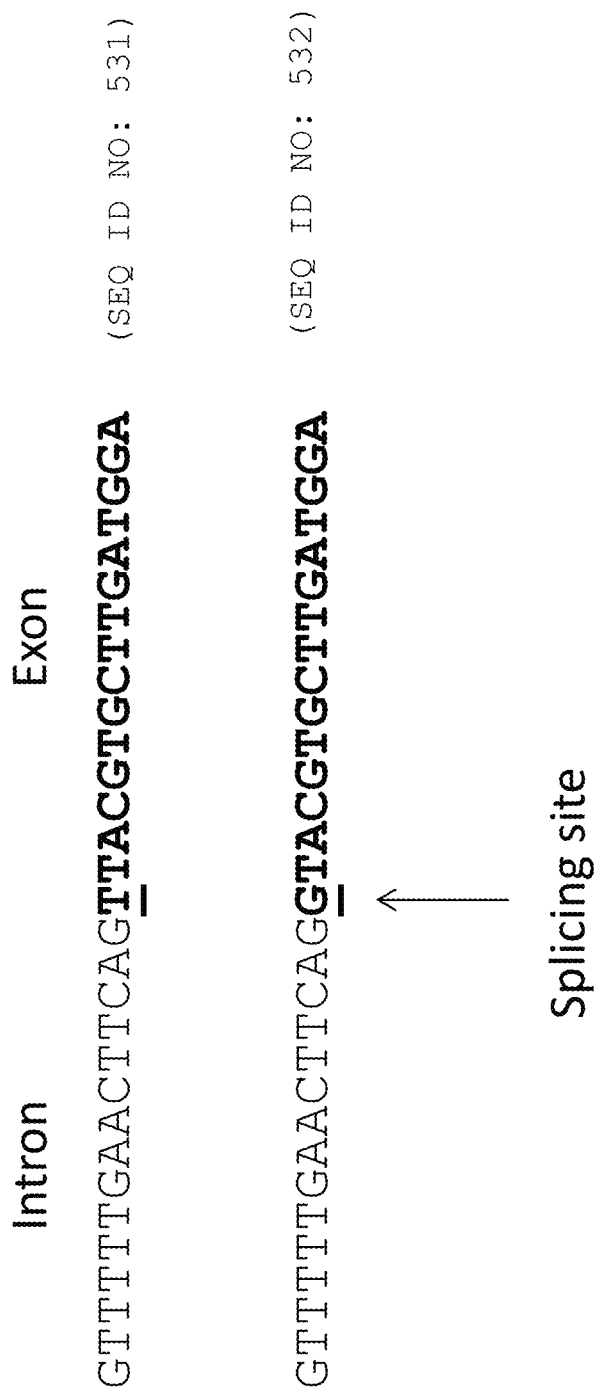

FIG. 37. Splicing site at the junction between the second EPSPS intron and the third exon (bolded). The nucleotide to be edited is underlined.

Figure 38:
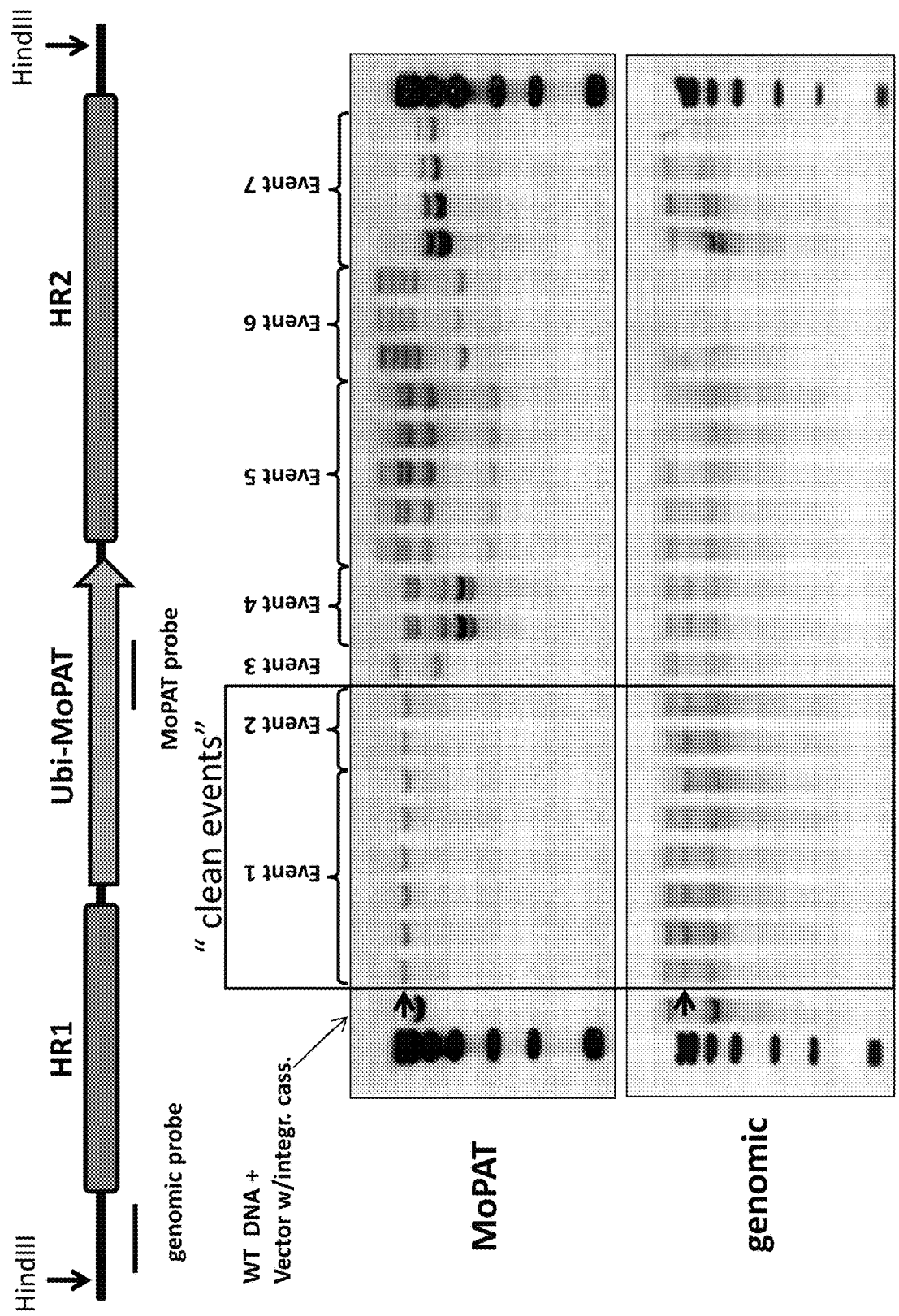

FIG. 38. Schematic representation of Southern hybridization analysis of T0 and T1 maize plants.

SEQUENCES

SEQ ID NO: 1 is the nucleotide sequence of the Cas9 gene from *Streptococcus pyogenes* M1 GAS (SF370).

SEQ ID NO: 2 is the nucleotide sequence of the potato ST-LS1 intron.

SEQ ID NO: 3 is the amino acid sequence of SV40 amino N-terminal.

SEQ ID NO: 4 is the amino acid sequence of *Agrobacterium tumefaciens* bipartite VirD2 T-DNA border endonuclease carboxyl terminal.

SEQ ID NO: 5 is the nucleotide sequence of an expression cassette expressing the maize optimized Cas9.

SEQ ID NO: 6 is the nucleotide sequence of crRNA containing the LIGCas-3 target sequence in the variable targeting domain.

SEQ ID NO: 7 is the nucleotide sequence of the tracrRNA.

SEQ ID NO: 8 is the nucleotide sequence of a long guide RNA containing the LIGCas-3 target sequence in the variable targeting domain.

SEQ ID NO: 9 is the nucleotide sequence of the Chromosome 8 maize U6 polymerase III promoter.

SEQ ID NO: 10 list two copies of the nucleotide sequence of the maize U6 polymerase III terminator.

SEQ ID NO: 11 is the nucleotide sequence of the maize optimized short guide RNA containing the LIGCas-3 variable targeting domain.

SEQ ID NO: 12 is the nucleotide sequence of the maize optimized long guide RNA expression cassette containing the LIGCas-3 variable targeting domain.

SEQ ID NO: 13 is the nucleotide sequence of the Maize genomic target site MS26Cas-1 plus PAM sequence.

SEQ ID NO: 14 is the nucleotide sequence of the Maize genomic target site MS26Cas-2 plus PAM sequence.

SEQ ID NO: 15 is the nucleotide sequence of the Maize genomic target site MS26Cas-3 plus PAM sequence.

SEQ ID NO: 16 is the nucleotide sequence of the Maize genomic target site LIGCas-2 plus PAM sequence.

SEQ ID NO: 17 is the nucleotide sequence of the Maize genomic target site LIGCas-3 plus PAM sequence.

SEQ ID NO: 18 is the nucleotide sequence of the Maize genomic target site LIGCas-4 plus PAM sequence.

SEQ ID NO: 19 is the nucleotide sequence of the Maize genomic target site MS45Cas-1 plus PAM sequence.

SEQ ID NO: 20 is the nucleotide sequence of the Maize genomic target site MS45Cas-2 plus PAM sequence.

SEQ ID NO: 21 is the nucleotide sequence of the Maize genomic target site MS45Cas-3 plus PAM sequence.

SEQ ID NO: 22 is the nucleotide sequence of the Maize genomic target site ALSCas-1 plus PAM sequence.

SEQ ID NO: 23 is the nucleotide sequence of the Maize genomic target site ALSCas-2 plus PAM sequence.

SEQ ID NO: 24 is the nucleotide sequence of the Maize genomic target site ALSCas-3 plus PAM sequence.

SEQ ID NO: 25 is the nucleotide sequence of the Maize genomic target site EPSPSCas-1 plus PAM sequence.

SEQ ID NO: 26 is the nucleotide sequence of the Maize genomic target site EPSPSCas-2 plus PAM sequence.

SEQ ID NO: 27 is the nucleotide sequence of the Maize genomic target site EPSPSCas-3 plus PAM sequence.

SEQ ID NOs: 28-52 are the nucleotide sequence of target site specific forward primers for primary PCR as shown in Table 2.

SEQ ID NO: 53 is the nucleotide sequence of the forward primer for secondary PCR.

SEQ ID NO: 54 is the nucleotide sequence of Reverse primer for secondary PCR SEQ ID NO: 55 is the nucleotide sequence of the unmodified reference sequence for LIGCas-1 and LIGCas-2 locus.

SEQ ID NOs: 56-65 are the nucleotide sequences of mutations 1-10 for LIGCas-1.

SEQ ID NOs: 66-75 are the nucleotide sequences of mutations 1-10 for LIGCas-2.

SEQ ID NO: 76 is the nucleotide sequence of the unmodified reference sequence for the LIGCas-3 and LIG3-4 homing endonuclease locus.

SEQ ID NOs: 77-86 are the nucleotide sequences of mutations 1-10 for LIGCas-3.

SEQ ID NOs: 88-96 are the nucleotide sequences of mutations 1-10 for LIG3-4 homing endonuclease locus.

SEQ ID NO: 97 is the nucleotide sequence of a donor vector referred to as an HR Repair DNA.

SEQ ID NO: 98 is the nucleotide sequence of forward PCR primer for site-specific transgene insertion at junction 1.

SEQ ID NO: 99 is the nucleotide sequence of reverse PCR primer for site-specific transgene insertion at junction 1.

SEQ ID NO: 100 is the nucleotide sequence of forward PCR primer for site-specific transgene insertion at junction 2.

SEQ ID NO: 101 is the nucleotide sequence of reverse PCR primer for site-specific transgene insertion at junction 2.

SEQ ID NO: 102 is the nucleotide sequence of the linked Cas9 endonuclease and LIGCas-3 long guide RNA expression cassettes SEQ ID NO: 103 is the nucleotide sequence of Maize genomic target site 55CasRNA-1 plus PAM sequence.

SEQ ID NO: 104 is the nucleotide sequence of the unmodified reference sequence for 55CasRNA-1 locus.

SEQ ID NOs: 105-110 are the nucleotide sequences of mutations 1-6 for 55CasRNA-1.

SEQ ID NO: 111 is the nucleotide sequence of LIG3-4 homing endonuclease target site SEQ ID NO: 112 is the nucleotide sequence of LIG3-4 homing endonuclease coding sequence.

SEQ ID NO: 113 is the nucleotide sequence of the MS26++ homing endonuclease target site.

SEQ ID NO: 114 is the nucleotide sequence of MS26++ homing endonuclease coding sequence SEQ ID NO: 115 is the nucleotide sequence of the soybean codon optimized Cas9 gene.

SEQ ID NO: 116 is the nucleotide sequence of the soybean constitutive promoter GM-EF1A2.

SEQ ID NO: 117 is the nucleotide sequence of linker SV40 NLS.

SEQ ID NO: 118 is the amino acid sequence of soybean optimized Cas9 with a SV40 NLS.

SEQ ID NO: 119 is the nucleotide sequence of vector QC782.

SEQ ID NO: 120 is the nucleotide sequence of soybean U6 polymerase III promoter described herein, GM-U6-13.1 PRO.

SEQ ID NO: 121 is the nucleotide sequence of the guide RNA in FIG. 8B.

SEQ ID NO: 122 is the nucleotide sequence of vector QC783.

SEQ ID NO: 123 is the nucleotide sequence of vector QC815.

SEQ ID NO: 124 is the nucleotide sequence of a Cas9 endonuclease (cas9-2) from *S. pyogenes*.

SEQ ID NO: 125 is the nucleotide sequence of the DD20CR1 soybean target site

SEQ ID NO: 126 is the nucleotide sequence of the DD20CR2 soybean target site

SEQ ID NO: 127 is the nucleotide sequence of the DD43CR1 soybean target site

SEQ ID NO: 128 is the nucleotide sequence of the DD43CR2 soybean target site

SEQ ID NO: 129 is the nucleotide sequence of the DD20 sequence in FIG. 10A.

SEQ ID NO: 130 is the nucleotide sequence of the DD20 sequence complementary in FIG. 10A.

SEQ ID NO: 131 is the nucleotide sequence of DD43 sequence.

SEQ ID NO: 132 is the nucleotide sequence of the DD43 complementary sequence.

SEQ ID NO: 133-141 are primer sequences.

SEQ ID NO: 142 is the nucleotide sequence of the DD20CR1 PCR amplicon.

SEQ ID NO: 143 is the nucleotide sequence of the DD20CR2 PCR amplicon.

SEQ ID NO: 144 is the nucleotide sequence of the DD43CR1 PCR amplicon.

SEQ ID NO: 145 is the nucleotide sequence of the DD43CR2 PCR amplicon.

SEQ ID NO: 146 is the nucleotide sequence of the DD43CR2 PCR amplicon.

SEQ ID NO: 147-156 are the nucleotide sequence of mutations 1 to 10 for the DD20CR1 target site SEQ ID NO: 157-166 are the nucleotide sequence of mutations 1 to 10 for the DD20CR2 target site SEQ ID NO: 167-176 are the nucleotide sequence of mutations 1 to 10 for the DD43CR1 target site SEQ ID NO: 177-191 are the nucleotide sequence of mutations 1 to 10 for the DD43CR2 target site.

SEQ ID NO: 192 is the amino acid sequence of a maize optimized version of the Cas9 protein.

SEQ ID NO: 193 is the nucleotide sequence of the maize optimized version of the Cas9 gene of SEQ ID NO: 192.

SEQ ID NO: 194 is the DNA version of guide RNA (EPSPS sgRNA).

SEQ ID NO: 195 is the EPSPS polynucleotide modification template.

SEQ ID NO: 196 is a nucleotide fragment comprising the TIPS nucleotide modifications.

SEQ ID NO: 197-204 are primer sequences shown in Table 15.

SEQ ID NO: 205-208 are nucleotide fragments shown in FIG. 14.

SEQ ID NO: 209 is an example of a TIPS edited EPSPS nucleotide sequence fragment shown in FIG. 17.

SEQ ID NO: 210 is an example of a Wild-type EPSPS nucleotide sequence fragment shown in FIG. 17.

SEQ ID NO: 211 is the nucleotide sequence of a maize enolpyruvylshikimate-3-phosphate synthase (epsps) locus SEQ ID NO: 212 is the nucleotide sequence of a Cas9 endonuclease (genbank CS571758.1) from *S. thermophiles*.

SEQ ID NO: 213 is the nucleotide sequence of a Cas9 endonuclease (genbank CS571770.1) from *S. thermophiles*.

SEQ ID NO: 214 is the nucleotide sequence of a Cas9 endonuclease (genbank CS571785.1) from *S. agalactiae*.

SEQ ID NO: 215 is the nucleotide sequence of a Cas9 endonuclease, (genbank CS571790.1) from *S. agalactiae*.

SEQ ID NO: 216 is the nucleotide sequence of a Cas9 endonuclease (genbank CS571790.1) from *S. mutant*.

SEQ ID NOs: 217-228 are primer and probe nucleotide sequences described in Example 17.

SEQ ID NOs: 229 is the nucleotide sequence of the MHP14Cas1 target site.

SEQ ID NOs: 230 is the nucleotide sequence of the MHP14Cas3 target site.

SEQ ID NOs: 231 is the nucleotide sequence of the TS8Cas1 target site.

SEQ ID NOs: 232 is the nucleotide sequence of the TS8Cas2 target site.

SEQ ID NOs: 233 is the nucleotide sequence of the TS9Cas2 target site.

SEQ ID NOs: 234 is the nucleotide sequence of the TS9Cas3 target site.

SEQ ID NOs: 235 is the nucleotide sequence of the TS10Cas1 target site.

SEQ ID NOs: 236 is the nucleotide sequence of the TS10Cas3 target site.

SEQ ID NOs: 237-244 are the nucleotide sequences shown in FIG. 19A-D.

SEQ ID NOs: 245-252 are the nucleotide sequences of the guide RNA expression cassettes described in Example 18.

SEQ ID NOs: 253-260 are the nucleotide sequences of donor DNA expression cassettes described in Example 18.

SEQ ID NOs: 261-270 are the nucleotide sequences of the primers described in Example 18.

SEQ ID NOs: 271-294 are the nucleotide sequences of the primers and probes described in Example 18.

SEQ ID NO: 295 is the nucleotide sequence of GM-U6-13.1 PRO, a soybean U6 polymerase III promoter described herein, SEQ ID NOs: 298, 300, 301 and 303 are the nucleotide sequences of the linked guideRNA/Cas9 expression cassettes.

SEQ ID NOs: 299 and 302 are the nucleotide sequences of the donor DNA expression cassettes.

SEQ ID NOs: 271-294 are the nucleotide sequences of the primers and probes described in Example 18.

SEQ ID NO: 304 is the nucleotide sequence of the DD20 qPCR amplicon.

SEQ ID NO: 305 is the nucleotide sequence of the DD43 qPCR amplicon.

SEQ ID NOs: 306-328 are the nucleotide sequences of the primers and probes described herein.

SEQ ID NOs: 329-334 are the nucleotide sequences of PCR amplicons described herein.

SEQ ID NO: 335 is the nucleotide sequence of a soybean genomic region comprising the DD20CR1 target site.

SEQ ID NO: 364 is the nucleotide sequence of a soybean genomic region comprising the DD20CR2 target site.

SEQ ID NO: 386 is the nucleotide sequence of a soybean genomic region comprising the DD43CR1 target site.

SEQ ID NOs: 336-363, 365-385 and 387-414 are the nucleotide sequences of shown in FIG. 26 A-C.

SEQ ID NOs: 415-444 are the nucleotide sequences of NHEJ mutations recovered based on the crRNA/tracrRNA/Cas endonuclease system shown in FIG. 27A-C.

SEQ ID NO: 445-447 are the nucleotide sequence of the LIGCas-1, LIGCas2 and LIGCas3 crRNA expression cassettes, respectively.

SEQ ID NO: 448 is the nucleotide sequence of the tracrRNA expression cassette.

SEQ ID NO: 449 is the nucleotide sequence of LIGCas-2 forward primer for primary PCR SEQ ID NO: 450 is the nucleotide sequence of LIGCas-3 forward primer for primary PCR.

SEQ ID NO: 451 is the nucleotide sequence of the maize genomic Cas9 endonuclease target site Zm-ARGOS8-CTS1.

SEQ ID NO: 452 is the nucleotide sequence of the maize genomic Cas9 endonuclease target site Zm-ARGOS8-CTS2.

SEQ ID NO: 453 is the nucleotide sequence of the maize genomic Cas9 endonuclease target site Zm-ARGOS8-CTS3

SEQ ID NOs: 454-458 are the nucleotide sequence of primers P1, P2, P3, P4, P5, respectively.

SEQ ID NO: 459 is the nucleotide sequence of a Primer Binding Site (PBS), a sequence to facilitate event screening.

SEQ ID NO: 460 is the nucleotide sequence of the Zm-GOS2 PRO-GOS2 INTRON, the maize GOS2 promoter and GOS2 intron1 including the promoter, 5'-UTR1, INTRON1 and 5'-UTR2.

SEQ ID NO: 461 is the nucleotide sequence of the maize Zm-ARGOS8 promoter.

SEQ ID NO: 462 is the nucleotide sequence of the maize Zm-ARGOS8 5'-UTR.

SEQ ID NO: 463 is the nucleotide sequence of the maize Zm-ARGOS8 codon sequence

SEQ ID NO: 464 is the nucleotide sequence of the maize Zm-GOS2 gene, including promoter, 5'-UTR, CDS, 3'-UTR and introns.

SEQ ID NO: 465 is the nucleotide sequence of the maize Zm-GOS2 PRO promoter.

SEQ ID NO: 466 is the nucleotide sequence of the maize GOS2 INTRON, maize GOS2 5'-UTR1 and intron1 and 5'-UTR2.

SEQ ID NOs: 467-468, 490-491, 503-504 are the nucleotide sequence of the soybean genomic Cas endonuclease target sequences soy EPSPS-CR1, soy EPSPS-CR2, soy EPSPS-CR4, soy EPSPS-CR5, soy EPSPS-CR6, soy EPSPS-CR7, respectively SEQ ID NO: 469 is the nucleotide sequence of the soybean U6 small nuclear RNA promoter GM-U6-13.1.

SEQ ID NOs: 470, 471 are the nucleotide sequences of the QC868, QC879 plasmids, respectively.

SEQ ID NOs: 472, 473, 492, 493, 494, 505, 506, 507 are the nucleotide sequences of the RTW1013A, RTW1012A, RTW1199, RTW1200, RTW1190A, RTW1201, RTW1202, RTW1192A respectively.

SEQ ID NOs: 474-488, 495-402, 508-512 are the nucleotide sequences of primers and probes.

SEQ ID NO: 489 is the nucleotide sequence of the soybean codon optimized Cas9.

SEQ ID NO: 513 is the nucleotide sequence of the 35S enhancer.

SEQ ID NO: 514 is the nucleotide sequence of the 35S-CRTS for gRNA1 at 163-181 (including pam at 3' end).

SEQ ID NO: 515 is the nucleotide sequence of the 35S-CRTS for gRNA2 at 295-319 (including pam at 3' end).

SEQ ID NO: 516 is the nucleotide sequence of the 35S-CRT for gRNA3 at 331-350 (including pam at 3' end).

SEQ ID NO: 517 is the nucleotide sequence of the EPSPS-K90R template.

SEQ ID NO: 518 is the nucleotide sequence of the EPSPS-IME template. S

SEQ ID NO: 519 is the nucleotide sequence of the EPSPS-Tspliced template.

SEQ ID NO: 520 is the amino acid sequence of ZM-RAP2.7 peptide

SEQ ID NO: 521 is the nucleotide sequence ZM-RAP2.7 coding DNA sequence

SEQ ID NOs: 522 is the amino acid sequence of ZM-NPK1B peptide

SEQ ID NO: 523 is the nucleotide sequence of the ZM-NPK1B coding DNA sequence

SEQ ID NOs: 524 is the nucleotide sequence of the RAB17 promoter

SEQ ID NOs: 525 is the amino acid sequence of the Maize FTM1.

SEQ ID NO: 526 is the nucleotide sequence of the Maize FTM1 coding DNA sequence.

SEQ ID NOs: 527-532 are the nucleotide sequences shown in FIGS. 34, 35 and 37.

SEQ ID NOs: 533-534 are the nucleotide sequences of the Southern genomic probe and Southern MoPAT probe of FIG. 38, respectively. SEQ ID NOs: 535-541 are the nucleotide sequences of the RF-FPCas-1, RF-FPCas-2, ALSCas-4, ALS modification repair template 804, ALS modification repair template 127, ALS Forward_primer and ALS Reverse_primer, respectively.

SEQ ID NOs: 542-549 are the nucleotide sequences of the soy ALS1-CR1, Cas9 target sequence, soy ALS2-CR2, Cas9 target sequence, QC880, QC881, RTW1026A, WOL900, Forward_primer, WOL578, Reverse_primer and WOL573, Forward_primer, respectively.

SEQ ID NO: 550 is the nucleotide sequence of a maize ALS protein.

DETAILED DESCRIPTION

The present disclosure includes compositions and methods for genome modification of a target sequence in the genome of a plant or plant cell, for selecting plants, for gene editing, and for inserting a polynucleotide of interest into the genome of a plant. The methods employ a guide RNA/Cas endonuclease system, wherein the Cas endonuclease is guided by the guide RNA to recognize and optionally introduce a double strand break at a specific target site into the genome of a cell. The guide RNA/Cas endonuclease system provides for an effective system for modifying target sites within the genome of a plant, plant cell or seed. Further provided are methods and compositions employing a guide polynucleotide/Cas endonuclease system to provide an effective system for modifying target sites within the genome of a cell and for editing a nucleotide sequence in the genome of a cell. Once a genomic target site is identified, a variety of methods can be employed to further modify the target sites such that they contain a variety of polynucleotides of interest. Breeding methods utilizing a two component guide RNA/Cas endonuclease system are also disclosed. Compositions and methods are also provided for editing a nucleotide sequence in the genome of a cell. The nucleotide sequence to be edited (the nucleotide sequence of interest) can be located within or outside a target site that is recognized by a Cas endonuclease.

CRISPR loci (Clustered Regularly Interspaced Short Palindromic Repeats) (also known as SPIDRs-SPacer Interspersed Direct Repeats) constitute a family of recently described DNA loci. CRISPR loci consist of short and highly conserved DNA repeats (typically 24 to 40 bp, repeated from 1 to 140 times—also referred to as CRISPR-repeats) which are partially palindromic. The repeated sequences (usually specific to a species) are interspaced by variable sequences of constant length (typically 20 to 58 by depending on the CRISPR locus (WO2007/025097 published Mar. 1, 2007).

CRISPR loci were first recognized in *E. coli* (Ishino et al. (1987) J. Bacterial. 169:5429-5433; Nakata et al. (1989) J. Bacterial. 171:3553-3556). Similar interspersed short sequence repeats have been identified in *Haloferax mediterranei, Streptococcus pyogenes, Anabaena*, and *Mycobacterium tuberculosis* (Groenen et al. (1993) Mol. Microbiol. 10:1057-1065; Hoe et al. (1999) Emerg. Infect. Dis. 5:254-263; Masepohl et al. (1996) Biochim. Biophys. Acta 1307: 26-30; Mojica et al. (1995) Mol. Microbiol. 17:85-93). The CRISPR loci differ from other SSRs by the structure of the repeats, which have been termed short regularly spaced repeats (SRSRs) (Janssen et al. (2002) OMICS J. Integ. Biol. 6:23-33; Mojica et al. (2000) Mol. Microbiol. 36:244-246). The repeats are short elements that occur in clusters, that are always regularly spaced by variable sequences of constant length (Mojica et al. (2000) Mol. Microbiol. 36:244-246).

Cas gene includes a gene that is generally coupled, associated or close to or in the vicinity of flanking CRISPR loci. The terms "Cas gene", "CRISPR-associated (Cas) gene" are used interchangeably herein. A comprehensive review of the Cas protein family is presented in Haft et al. (2005) Computational Biology, PLoS Comput Biol 1(6): e60. doi:10.1371/journal.pcbi.0010060.

As described therein, 41 CRISPR-associated (Cas) gene families are described, in addition to the four previously known gene families. It shows that CRISPR systems belong to different classes, with different repeat patterns, sets of genes, and species ranges. The number of Cas genes at a given CRISPR locus can vary between species.

Cas endonuclease relates to a Cas protein encoded by a Cas gene, wherein said Cas protein is capable of introducing a double strand break into a DNA target sequence. The Cas endonuclease is guided by the guide polynucleotide to recognize and optionally introduce a double strand break at a specific target site into the genome of a cell. As used herein, the term "guide polynucleotide/Cas endonuclease system" includes a complex of a Cas endonuclease and a guide polynucleotide that is capable of introducing a double strand break into a DNA target sequence. The Cas endonuclease unwinds the DNA duplex in close proximity of the genomic target site and cleaves both DNA strands upon recognition of a target sequence by a guide RNA, but only if the correct protospacer-adjacent motif (PAM) is approximately oriented at the 3' end of the target sequence (FIG. 2A, FIG. 2B).

In one embodiment, the Cas endonuclease gene is a Cas9 endonuclease, such as but not limited to, Cas9 genes listed in SEQ ID NOs: 462, 474, 489, 494, 499, 505, and 518 of WO2007/025097 published Mar. 1, 2007, and incorporated herein by reference. In another embodiment, the Cas endonuclease gene is plant, maize or soybean optimized Cas9 endonuclease (FIG. 1 A). In another embodiment, the Cas endonuclease gene is operably linked to a SV40 nuclear targeting signal upstream of the Cas codon region and a bipartite VirD2 nuclear localization signal (Tinland et al. (1992) Proc. Natl. Acad. Sci. USA 89:7442-6) downstream of the Cas codon region.

In one embodiment, the Cas endonuclease gene is a Cas9 endonuclease gene of SEQ ID NO:1, 124, 212, 213, 214, 215, 216, 193 or nucleotides 2037-6329 of SEQ ID NO:5, or any functional fragment or variant thereof.

The terms "functional fragment", "fragment that is functionally equivalent" and "functionally equivalent fragment" are used interchangeably herein. These terms refer to a portion or subsequence of the Cas endonuclease sequence of the present disclosure in which the ability to create a double-strand break is retained.

The terms "functional variant", "Variant that is functionally equivalent" and "functionally equivalent variant" are used interchangeably herein. These terms refer to a variant of the Cas endonuclease of the present disclosure in which the ability create a double-strand break is retained. Fragments and variants can be obtained via methods such as site-directed mutagenesis and synthetic construction.

In one embodiment, the Cas endonuclease gene is a plant codon optimized *Streptococcus pyogenes* Cas9 gene that can recognize any genomic sequence of the form N(12-30)NGG can in principle be targeted.

In one embodiment, the Cas endonuclease is introduced directly into a cell by any method known in the art, for example, but not limited to transient introduction methods, transfection and/or topical application.

Endonucleases are enzymes that cleave the phosphodiester bond within a polynucleotide chain, and include restriction endonucleases that cleave DNA at specific sites without damaging the bases. Restriction endonucleases include Type I, Type II, Type III, and Type IV endonucleases, which further include subtypes. In the Type I and Type III systems, both the methylase and restriction activities are contained in a single complex. Endonucleases also include meganucleases, also known as homing endonucleases (HEases), which like restriction endonucleases, bind and cut at a specific recognition site, however the recognition sites for meganucleases are typically longer, about 18 bp or more. (patent application WO-PCT PCT/US12/30061 filed on Mar. 22, 2012) Meganucleases have been classified into four families based on conserved sequence motifs, the families are the LAGLIDADG, GIY-YIG, H-N-H, and His-Cys box families. These motifs participate in the coordination of metal ions and hydrolysis of phosphodiester bonds. HEases are notable for their long recognition sites, and for tolerating some sequence polymorphisms in their DNA substrates. The naming convention for meganuclease is similar to the convention for other restriction endonuclease. Meganucleases are also characterized by prefix F-, I-, or PI- for enzymes encoded by free-standing ORFs, introns, and inteins, respectively. One step in the recombination process involves polynucleotide cleavage at or near the recognition site. This cleaving activity can be used to produce a double-strand break. For reviews of site-specific recombinases and their recognition sites, see, Sauer (1994) Curr Op Biotechnol 5:521-7; and Sadowski (1993) FASEB 7:760-7. In some examples the recombinase is from the Integrase or Resolvase families.

TAL effector nucleases are a new class of sequence-specific nucleases that can be used to make double-strand breaks at specific target sequences in the genome of a plant or other organism. (Miller et al. (2011) Nature Biotechnology 29:143-148). Zinc finger nucleases (ZFNs) are engineered double-strand break inducing agents comprised of a zinc finger DNA binding domain and a double-strand-break-inducing agent domain. Recognition site specificity is conferred by the zinc finger domain, which typically comprising two, three, or four zinc fingers, for example having a C2H2 structure, however other zinc finger structures are known and have been engineered. Zinc finger domains are amenable for designing polypeptides which specifically bind a selected polynucleotide recognition sequence. ZFNs include an engineered DNA-binding zinc finger domain linked to a non-specific endonuclease domain, for example nuclease domain from a Type IIs endonuclease such as FokI. Additional functionalities can be fused to the zinc-finger binding domain, including transcriptional activator domains, transcription repressor domains, and methylases. In some examples, dimerization of nuclease domain is required for cleavage activity. Each zinc finger recognizes three consecutive base pairs in the target DNA. For example, a 3 finger domain recognized a sequence of 9 contiguous nucleotides, with a dimerization requirement of the nuclease, two sets of zinc finger triplets are used to bind an 18 nucleotide recognition sequence.

Bacteria and archaea have evolved adaptive immune defenses termed clustered regularly interspaced short palindromic repeats (CRISPR)/CRISPR-associated (Cas) systems that use short RNA to direct degradation of foreign nucleic acids ((WO2007/025097 published Mar. 1, 2007). The type II CRISPR/Cas system from bacteria employs a crRNA and tracrRNA to guide the Cas endonuclease to its DNA target. The crRNA (CRISPR RNA) contains the region complementary to one strand of the double strand DNA target and base pairs with the tracrRNA (trans-activating CRISPR RNA) forming a RNA duplex that directs the Cas endonuclease to cleave the DNA target (FIG. 2 B).

As used herein, the term "guide RNA" relates to a synthetic fusion of two RNA molecules, a crRNA (CRISPR RNA) comprising a variable targeting domain, and a tracrRNA (FIG. 2 B). In one embodiment, the guide RNA comprises a variable targeting domain of 12 to 30 nucleotide sequences and a RNA fragment that can interact with a Cas endonuclease.

As used herein, the term "guide polynucleotide", relates to a polynucleotide sequence that can form a complex with a Cas endonuclease and enables the Cas endonuclease to recognize and optionally cleave a DNA target site. The guide polynucleotide can be a single molecule or a double molecule. The guide polynucleotide sequence can be a RNA sequence, a DNA sequence, or a combination thereof (a RNA-DNA combination sequence). Optionally, the guide polynucleotide can comprise at least one nucleotide, phosphodiester bond or linkage modification such as, but not limited, to Locked Nucleic Acid (LNA), 5-methyl dC, 2,6-Diaminopurine, 2'-Fluoro A, 2'-Fluoro U, 2'-O-Methyl RNA, phosphorothioate bond, linkage to a cholesterol molecule, linkage to a polyethylene glycol molecule, linkage to a spacer 18 (hexaethylene glycol chain) molecule, or 5' to 3' covalent linkage resulting in circularization. A guide polynucleotride that solely comprises ribonucleic acids is also referred to as a "guide RNA".

The guide polynucleotide can be a double molecule (also referred to as duplex guide polynucleotide) comprising a first nucleotide sequence domain (referred to as Variable Targeting domain or VT domain) that is complementary to a nucleotide sequence in a target DNA and a second nucleotide sequence domain (referred to as Cas endonuclease recognition domain or CER domain) that interacts with a Cas endonuclease polypeptide. The CER domain of the double molecule guide polynucleotide comprises two separate molecules that are hybridized along a region of complementarity. The two separate molecules can be RNA, DNA, and/or RNA-DNA-combination sequences. In some embodiments, the first molecule of the duplex guide polynucleotide comprising a VT domain linked to a CER domain is referred to as "crDNA" (when composed of a contiguous stretch of DNA nucleotides) or "crRNA" (when composed of a contiguous stretch of RNA nucleotides), or "crDNA-RNA" (when composed of a combination of DNA and RNA nucleotides). The crNucleotide can comprise a fragment of the cRNA naturally occurring in Bacteria and Archaea. In one embodiment, the size of the fragment of the cRNA naturally occurring in Bacteria and Archaea that is present in a crNucleotide disclosed herein can range from, but is not limited to, 2, 3, 4, 5, 6, 7, 8, 9, 10, 11, 12, 13, 14, 15, 16, 17, 18, 19, 20 or more nucleotides. In some embodiments the second molecule of the duplex guide polynucleotide comprising a CER domain is referred to as "tracrRNA" (when composed of a contiguous stretch of RNA nucleotides) or "tracrDNA" (when composed of a contiguous stretch of DNA nucleotides) or "tracrDNA-RNA" (when composed of a combination of DNA and RNA nucleotides In one embodiment, the RNA that guides the RNA/Cas9 endonuclease complex, is a duplexed RNA comprising a duplex crRNA-tracrRNA.

The guide polynucleotide can also be a single molecule comprising a first nucleotide sequence domain (referred to as Variable Targeting domain or VT domain) that is complementary to a nucleotide sequence in a target DNA and a second nucleotide domain (referred to as Cas endonuclease recognition domain or CER domain) that interacts with a Cas endonuclease polypeptide. By "domain" it is meant a contiguous stretch of nucleotides that can be RNA, DNA, and/or RNA-DNA-combination sequence. The VT domain and/or the CER domain of a single guide polynucleotide can comprise a RNA sequence, a DNA sequence, or a RNA-DNA-combination sequence. In some embodiments the single guide polynucleotide comprises a crNucleotide (comprising a VT domain linked to a CER domain) linked to a tracrNucleotide (comprising a CER domain), wherein the linkage is a nucleotide sequence comprising a RNA sequence, a DNA sequence, or a RNA-DNA combination sequence. The single guide polynucleotide being comprised of sequences from the crNucleotide and tracrNucleotide may be referred to as "single guide RNA" (when composed of a contiguous stretch of RNA nucleotides) or "single guide DNA" (when composed of a contiguous stretch of DNA nucleotides) or "single guide RNA-DNA" (when composed of a combination of RNA and DNA nucleotides). In one embodiment of the disclosure, the single guide RNA comprises a cRNA or cRNA fragment and a tracrRNA or tracrRNA fragment of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site. One aspect of using a single guide polynucleotide versus a duplex guide polynucleotide is that only one expression cassette needs to be made to express the single guide polynucleotide.

The term "variable targeting domain" or "VT domain" is used interchangeably herein and includes a nucleotide sequence that is complementary to one strand (nucleotide sequence) of a double strand DNA target site (FIGS. 2 A and 2 B). The % complementation between the first nucleotide sequence domain (VT domain) and the target sequence can be at least 50%, 51%, 52%, 53%, 54%, 55%, 56%, 57%, 58%, 59%, 60%, 61%, 62%, 63%, 63%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. The variable target domain can be at least 12, 13, 14, 15, 16, 17, 18, 19, 20, 21, 22, 23, 24, 25, 26, 27, 28, 29 or 30 nucleotides in length. In some embodiments, the variable targeting domain comprises a contiguous stretch of 12 to 30 nucleotides. The variable targeting domain can be composed of a DNA sequence, a RNA sequence, a modified DNA sequence, a modified RNA sequence, or any combination thereof.

The term "Cas endonuclease recognition domain" or "CER domain" of a guide polynucleotide is used interchangeably herein and includes a nucleotide sequence (such as a second nucleotide sequence domain of a guide polynucleotide), that interacts with a Cas endonuclease polypeptide. The CER domain can be composed of a DNA sequence, a RNA sequence, a modified DNA sequence, a modified RNA sequence (see for example modifications described herein), or any combination thereof.

The nucleotide sequence linking the crNucleotide and the tracrNucleotide of a single guide polynucleotide can comprise a RNA sequence, a DNA sequence, or a RNA-DNA combination sequence. In one embodiment, the nucleotide sequence linking the crNucleotide and the tracrNucleotide of a single guide polynucleotide can be at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 78, 79, 80, 81, 82, 83, 84, 85, 86, 87, 88, 89, 90, 91, 92, 93, 94, 95, 96, 97, 98, 99 or 100 nucleotides in length. In another embodiment, the nucleotide sequence linking the crNucleotide and the tracrNucleotide of a single guide polynucleotide can comprise a tetraloop sequence, such as, but not limiting to a GAAA tetraloop sequence.

Nucleotide sequence modification of the guide polynucleotide, VT domain and/or CER domain can be selected from, but not limited to, the group consisting of a 5' cap, a 3' polyadenylated tail, a riboswitch sequence, a stability control sequence, a sequence that forms a dsRNA duplex, a modification or sequence that targets the guide poly nucleotide to a subcellular location, a modification or sequence that provides for tracking, a modification or sequence that provides a binding site for proteins, a Locked Nucleic Acid (LNA), a 5-methyl dC nucleotide, a 2,6-Diaminopurine nucleotide, a 2'-Fluoro A nucleotide, a 2'-Fluoro U nucleotide; a 2'-O-Methyl RNA nucleotide, a phosphorothioate bond, linkage to a cholesterol molecule, linkage to a polyethylene glycol molecule, linkage to a spacer 18 molecule, a 5' to 3' covalent linkage, or any combination thereof. These modifications can result in at least one additional beneficial feature, wherein the additional beneficial feature is selected from the group of a modified or regulated stability, a subcellular targeting, tracking, a fluorescent label, a binding site for a protein or protein complex, modified binding affinity to complementary target sequence, modified resistance to cellular degradation, and increased cellular permeability.

In one embodiment, the guide RNA and Cas endonuclease are capable of forming a complex that enables the Cas endonuclease to introduce a double strand break at a DNA target site In one embodiment of the disclosure the variable target domain is 12, 13, 14, 15, 16, 17, 18, 19, 20, 21, 22, 23, 24, 25, 26, 27, 28, 29 or 30 nucleotides in length.

In one embodiment of the disclosure, the guide RNA comprises a cRNA (or cRNA fragment) and a tracrRNA (or tracrRNA fragment) of the type II CRISPR/Cas system that can form a complex with a type II Cas endonuclease, wherein said guide RNA/Cas endonuclease complex can direct the Cas endonuclease to a plant genomic target site, enabling the Cas endonuclease to introduce a double strand break into the genomic target site.

In one embodiment the guide RNA can be introduced into a plant or plant cell directly using any method known in the art such as, but not limited to, particle bombardment or topical applications.

In another embodiment the guide RNA can be introduced indirectly by introducing a recombinant DNA molecule comprising the corresponding guide DNA sequence operably linked to a plant specific promoter (as shown in FIG. 1 B) that is capable of transcribing the guide RNA in said plant cell. The term "corresponding guide DNA" includes a DNA molecule that is identical to the RNA molecule but has a "T" substituted for each "U" of the RNA molecule.

In some embodiments, the guide RNA is introduced via particle bombardment or *Agrobacterium* transformation of a recombinant DNA construct comprising the corresponding guide DNA operably linked to a plant U6 polymerase III promoter.

In one embodiment, the RNA that guides the RNA/Cas9 endonuclease complex, is a duplexed RNA comprising a duplex crRNA-tracrRNA (as shown in FIG. 2B). One advantage of using a guide RNA versus a duplexed crRNA-tracrRNA is that only one expression cassette needs to be made to express the fused guide RNA.

The terms "target site", "target sequence", "target DNA", "target locus", "genomic target site", "genomic target sequence", and "genomic target locus" are used interchangeably herein and refer to a polynucleotide sequence in the genome (including choroplastic and mitochondrial DNA) of a plant cell at which a double-strand break is induced in the plant cell genome by a Cas endonuclease. The target site can be an endogenous site in the plant genome, or alternatively, the target site can be heterologous to the plant and thereby not be naturally occurring in the genome, or the target site can be found in a heterologous genomic location compared to where it occurs in nature. As used herein, terms "endogenous target sequence" and "native target sequence" are used interchangeable herein to refer to a target sequence that is endogenous or native to the genome of a plant and is at the endogenous or native position of that target sequence in the genome of the plant.

In one embodiments, the target site can be similar to a DNA recognition site or target site that that is specifically recognized and/or bound by a double-strand break inducing agent such as a LIG3-4 endonuclease (US patent publication 2009-0133152 A1 (published May 21, 2009) or a MS26++ meganuclease (U.S. patent application Ser. No. 13/526,912 filed Jun. 19, 2012).

An "artificial target site" or "artificial target sequence" are used interchangeably herein and refer to a target sequence that has been introduced into the genome of a plant. Such an artificial target sequence can be identical in sequence to an endogenous or native target sequence in the genome of a plant but be located in a different position (i.e., a non-endogenous or non-native position) in the genome of a plant.

An "altered target site", "altered target sequence", "modified target site", "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Methods for modifying a plant genomic target site are disclosed herein. In one embodiment, a method for modifying a target site in the genome of a plant cell comprises introducing a guide RNA into a plant cell having a Cas endonuclease, wherein said guide RNA and Cas endonuclease are capable of forming a complex that enables the Cas endonuclease to introduce a double strand break at said target site.

Also provided is a method for modifying a target site in the genome of a plant cell, the method comprising introducing a guide RNA and a Cas endonuclease into said plant, wherein said guide RNA and Cas endonuclease are capable of forming a complex that enables the Cas endonuclease to introduce a double strand break at said target site.

Further provided is a method for modifying a target site in the genome of a plant cell, the method comprising introducing a guide RNA and a donor DNA into a plant cell having a Cas endonuclease, wherein said guide RNA and Cas endonuclease are capable of forming a complex that enables the Cas endonuclease to introduce a double strand break at said target site, wherein said donor DNA comprises a polynucleotide of interest.

Further provided is a method for modifying a target site in the genome of a plant cell, the method comprising: a) introducing into a plant cell a guide RNA comprising a variable targeting domain and a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site.

Further provided, a method for modifying a target DNA sequence in the genome of a plant cell, the method comprising: a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; and, b) identifying at least one plant cell that has a modification at said target, wherein the modification includes at least one deletion or substitution of one or more nucleotides in said target site.

The length of the target site can vary, and includes, for example, target sites that are at least 12, 13, 14, 15, 16, 17, 18, 19, 20, 21, 22, 23, 24, 25, 26, 27, 28, 29, 30 or more nucleotides in length. It is further possible that the target site can be palindromic, that is, the sequence on one strand reads the same in the opposite direction on the complementary strand. The nick/cleavage site can be within the target sequence or the nick/cleavage site could be outside of the target sequence. In another variation, the cleavage could occur at nucleotide positions immediately opposite each other to produce a blunt end cut or, in other Cases, the incisions could be staggered to produce single-stranded overhangs, also called "sticky ends", which can be either 5' overhangs, or 3' overhangs.

In some embodiment, the genomic target site capable of being cleaved by a Cas endonuclease comprises a 12 to 30 nucleotide fragment of a male fertility gene such as MS26 (see for example U.S. Pat. Nos. 7,098,388, 7,517,975, 7,612,251), MS45 (see for example U.S. Pat. Nos. 5,478, 369, 6,265,640) or MSCA1 (see for example U.S. Pat. No. 7,919,676), ALS or ESPS genes.

Active variants of genomic target sites can also be used. Such active variants can comprise at least 65%, 70%, 75%, 80%, 85%, 90%, 91%, 92%, 93%, 94%, 95%, 96%, 97%, 98%, 99% or more sequence identity to the given target site, wherein the active variants retain biological activity and hence are capable of being recognized and cleaved by an Cas endonuclease. Assays to measure the double-strand break of a target site by an endonuclease are known in the art and generally measure the overall activity and specificity of the agent on DNA substrates containing recognition sites.

Various methods and compositions can be employed to obtain a plant having a polynucleotide of interest inserted in a target site for a Cas endonuclease. Such methods can employ homologous recombination to provide integration of the polynucleotide of Interest at the target site. In one method provided, a polynucleotide of interest is provided to the plant cell in a donor DNA construct. As used herein, "donor DNA" is a DNA construct that comprises a polynucleotide of Interest to be inserted into the target site of a Cas endonuclease. The donor DNA construct further comprises a first and a second region of homology that flank the polynucleotide of Interest. The first and second regions of homology of the donor DNA share homology to a first and a second genomic region, respectively, present in or flanking the target site of the plant genome. By "homology" is meant DNA sequences that are similar. For example, a "region of homology to a genomic region" that is found on the donor DNA is a region of DNA that has a similar sequence to a given "genomic region" in the plant genome. A region of homology can be of any length that is sufficient to promote homologous recombination at the cleaved target site. For example, the region of homology can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800, 5-2900, 5-3000, 5-3100 or more bases in length such that the region of homology has sufficient homology to undergo homologous recombination with the corresponding genomic region. "Sufficient homology" indicates that two polynucleotide sequences have sufficient structural similarity to act as substrates for a homologous recombination reaction. The structural similarity includes overall length of each polynucleotide fragment, as well as the sequence similarity of the polynucleotides. Sequence similarity can be described by the percent sequence identity over the whole length of the sequences, and/or by conserved regions comprising localized similarities such as contiguous nucleotides having 100% sequence identity, and percent sequence identity over a portion of the length of the sequences.

The amount of homology or sequence identity shared by a target and a donor polynucleotide can vary and includes total lengths and/or regions having unit integral values in the ranges of about 1-20 bp, 20-50 bp, 50-100 bp, 75-150 bp, 100-250 bp, 150-300 bp, 200-400 bp, 250-500 bp, 300-600 bp, 350-750 bp, 400-800 bp, 450-900 bp, 500-1000 bp, 600-1250 bp, 700-1500 bp, 800-1750 bp, 900-2000 bp, 1-2.5 kb, 1.5-3 kb, 2-4 kb, 2.5-5 kb, 3-6 kb, 3.5-7 kb, 4-8 kb, 5-10 kb, or up to and including the total length of the target site. These ranges include every integer within the range, for example, the range of 1-20 bp includes 1, 2, 3, 4, 5, 6, 7, 8, 9, 10, 11, 12, 13, 14, 15, 16, 17, 18, 19 and 20 bp. The amount of homology can also described by percent sequence identity over the full aligned length of the two polynucleotides which includes percent sequence identity of about at least 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100%. Sufficient homology includes any combination of polynucleotide length, global percent sequence identity, and optionally conserved regions of contiguous nucleotides or local percent sequence identity, for example sufficient homology can be described as a region of 75-150 bp having at least 80% sequence identity to a region of the target locus. Sufficient homology can also be described by the predicted ability of two polynucleotides to specifically hybridize under high stringency conditions, see, for example, Sambrook et al., (1989) *Molecular Cloning: A Laboratory Manual*, (Cold Spring Harbor Laboratory Press, NY); *Current Protocols in Molecular Biology*, Ausubel et al., Eds (1994) Current Protocols, (Greene Publishing Associates, Inc. and John Wiley & Sons, Inc.); and, Tijssen (1993) *Laboratory Techniques in Biochemistry and Molecular Biology—Hybridization with Nucleic Acid Probes*, (Elsevier, New York).

As used herein, a "genomic region" is a segment of a chromosome in the genome of a plant cell that is present on either side of the target site or, alternatively, also comprises a portion of the target site. The genomic region can comprise at least 5-10, 5-15, 5-20, 5-25, 5-30, 5-35, 5-40, 5-45, 5-50, 5-55, 5-60, 5-65, 5-70, 5-75, 5-80, 5-85, 5-90, 5-95, 5-100, 5-200, 5-300, 5-400, 5-500, 5-600, 5-700, 5-800, 5-900, 5-1000, 5-1100, 5-1200, 5-1300, 5-1400, 5-1500, 5-1600, 5-1700, 5-1800, 5-1900, 5-2000, 5-2100, 5-2200, 5-2300, 5-2400, 5-2500, 5-2600, 5-2700, 5-2800. 5-2900, 5-3000, 5-3100 or more bases such that the genomic region has sufficient homology to undergo homologous recombination with the corresponding region of homology.

Polynucleotides of interest and/or traits can be stacked together in a complex trait locus as described in US-2013-0263324-A1, published 3 Oct. 2013 and in PCT/US13/22891, published Jan. 24, 2013, both applications are hereby incorporated by reference. The guide polynucleotide/Cas9 endonuclease system described herein provides for an efficient system to generate double strand breaks and allows for traits to be stacked in a complex trait locus.

In one embodiment, the guide polynucleotide/Cas endonuclease system is used for introducing one or more polynucleotides of interest or one or more traits of interest into one or more target sites by providing one or more guide polynucleotides, one Cas endonuclease, and optionally one or more donor DNAs to a plant cell. A fertile plant can be produced from that plant cell that comprises an alteration at said one or more target sites, wherein the alteration is selected from the group consisting of (i) replacement of at least one nucleotide, (ii) a deletion of at least one nucleotide, (iii) an insertion of at least one nucleotide, and (iv) any combination of (i)-(iii). Plants comprising these altered target sites can be crossed with plants comprising at least one gene or trait of interest in the same complex trait locus, thereby further stacking traits in said complex trait locus. (see also US-2013-0263324-A1, published 3 Oct. 2013 and in PCT/US13/22891, published Jan. 24, 2013).

In one embodiment, the method comprises a method for producing in a plant a complex trait locus comprising at least two altered target sequences in a genomic region of interest, said method comprising: (a) selecting a genomic region in a plant, wherein the genomic region comprises a first target sequence and a second target sequence; (b) contacting at least one plant cell with at least a first guide polynucleotide, a second polynucleotide, and optionally at least one donor DNA, and a Cas endonuclease, wherein the first and second guide polynucleotide and the Cas endonuclease can form a complex that enables the Cas endonuclease to introduce a double strand break in at least a first and a second target sequence; (c) identifying a cell from (b) comprising a first alteration at the first target sequence and a second alteration at the second target sequence; and (d) recovering a first fertile plant from the cell of (c) said fertile plant comprising the first alteration and the second alteration, wherein the first alteration and the second alteration are physically linked.

In one embodiment, the method comprises a method for producing in a plant a complex trait locus comprising at least two altered target sequences in a genomic region of interest, said method comprising: (a) selecting a genomic region in a plant, wherein the genomic region comprises a first target sequence and a second target sequence; (b) contacting at least one plant cell with a first guide polynucleotide, a Cas endonuclease, and optionally a first donor DNA, wherein the first guide polynucleotide and the Cas endonuclease can form a complex that enables the Cas endonuclease to introduce a double strand break a first target sequence; (c) identifying a cell from (b) comprising a first alteration at the first target sequence; (d) recovering a first fertile plant from the cell of (c), said first fertile plant comprising the first alteration; (e) contacting at least one plant cell with a second guide polynucleotide, a Cas endonuclease and optionally a second Donor DNA; (f) identifying a cell from (e) comprising a second alteration at the second target sequence; (g) recovering a second fertile plant from the cell of (f), said second fertile plant comprising the second alteration; and, (h) obtaining a fertile progeny plant from the second fertile plant of (g), said fertile progeny plant comprising the first alteration and the second alteration, wherein the first alteration and the second alteration are physically linked.

The structural similarity between a given genomic region and the corresponding region of homology found on the donor DNA can be any degree of sequence identity that allows for homologous recombination to occur. For example, the amount of homology or sequence identity shared by the "region of homology" of the donor DNA and the "genomic region" of the plant genome can be at least 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity, such that the sequences undergo homologous recombination The region of homology on the donor DNA can have homology to any sequence flanking the target site. While in some embodiments the regions of homology share significant sequence homology to the genomic sequence immediately flanking the target site, it is recognized that the regions of homology can be designed to have sufficient homology to regions that may be further 5' or 3' to the target site. In still other embodiments, the regions of homology can also have homology with a fragment of the target site along with downstream genomic regions. In one embodiment, the first region of homology further comprises a first fragment of the target site and the second region of homology comprises a second fragment of the target site, wherein the first and second fragments are dissimilar.

As used herein, "homologous recombination" includes the exchange of DNA fragments between two DNA molecules at the sites of homology. The frequency of homologous recombination is influenced by a number of factors. Different organisms vary with respect to the amount of homologous recombination and the relative proportion of homologous to non-homologous recombination. Generally, the length of the region of homology affects the frequency of homologous recombination events: the longer the region of homology, the greater the frequency. The length of the homology region needed to observe homologous recombination is also species-variable. In many cases, at least 5 kb of homology has been utilized, but homologous recombination has been observed with as little as 25-50 bp of homology. See, for example, Singer et al., (1982) Cell 31:25-33; Shen and Huang, (1986) Genetics 112:441-57; Watt et al., (1985) Proc. Natl. Acad. Sci. USA 82:4768-72, Sugawara and Haber, (1992) Mol Cell Biol 12:563-75, Rubnitz and Subramani, (1984) Mol Cell Biol 4:2253-8; Ayares et al., (1986) Proc. Natl. Acad. Sci. USA 83:5199-203; Liskay et al., (1987) Genetics 115:161-7.

Homology-directed repair (HDR) is a mechanism in cells to repair double-stranded and single stranded DNA breaks. Homology-directed repair includes homologous recombination (HR) and single-strand annealing (SSA) (Lieber. 2010 Annu. Rev. Biochem. 79:181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks (Davis and Maizels. PNAS (0027-8424), 111 (10), p. E924-E932.

Alteration of the genome of a plant cell, for example, through homologous recombination (HR), is a powerful tool for genetic engineering. Despite the low frequency of homologous recombination in higher plants, there are a few examples of successful homologous recombination of plant endogenous genes. The parameters for homologous recombination in plants have primarily been investigated by rescuing introduced truncated selectable marker genes. In these experiments, the homologous DNA fragments were typically between 0.3 kb to 2 kb. Observed frequencies for homologous recombination were on the order of $10^{-4}$ to $10^{-5}$. See, for example, Halfter et al., (1992) Mol Gen Genet 231:186-93; Offringa et al., (1990) EMBO J 9:3077-84; Offringa et al., (1993) Proc. Natl. Acad. Sci. USA 90:7346-50; Paszkowski et al., (1988) EMBO J 7:4021-6; Hourda and Paszkowski, (1994) Mol Gen Genet 243:106-11; and Risseeuw et al., (1995) Plant J 7:109-19.

Homologous recombination has been demonstrated in insects. In *Drosophila*, Dray and Gloor found that as little as 3 kb of total template:target homology sufficed to copy a large non-homologous segment of DNA into the target with reasonable efficiency (Dray and Gloor, (1997) Genetics 147:689-99). Using FLP-mediated DNA integration at a target FRT in *Drosophila*, Golic et al., showed integration was approximately 10-fold more efficient when the donor and target shared 4.1 kb of homology as compared to 1.1 kb of homology (Golic et al., (1997) Nucleic Acids Res 25:3665). Data from *Drosophila* indicates that 2-4 kb of homology is sufficient for efficient targeting, but there is some evidence that much less homology may suffice, on the order of about 30 bp to about 100 bp (Nassif and Engels, (1993) Proc. Natl. Acad. Sci. USA 90:1262-6; Keeler and Gloor, (1997) Mol Cell Biol 17:627-34).

Homologous recombination has also been accomplished in other organisms. For example, at least 150-200 bp of homology was required for homologous recombination in the parasitic protozoan *Leishmania* (Papadopoulou and Dumas, (1997) Nucleic Acids Res 25:4278-86). In the filamentous fungus *Aspergillus nidulans*, gene replacement has been accomplished with as little as 50 bp flanking homology (Chaveroche et al., (2000) Nucleic Acids Res 28:e97). Targeted gene replacement has also been demonstrated in the ciliate Tetrahymena *thermophila* (Gaertig et al., (1994) Nucleic Acids Res 22:5391-8). In mammals, homologous recombination has been most successful in the mouse using pluripotent embryonic stem cell lines (ES) that can be grown in culture, transformed, selected and introduced into a mouse embryo. Embryos bearing inserted transgenic ES cells develop as genetically offspring. By interbreeding siblings, homozygous mice carrying the selected genes can be obtained. An overview of the process is provided in Watson et al., (1992) Recombinant DNA, 2nd Ed., (Scientific American Books distributed by WH Freeman & Co.); Capecchi, (1989) Trends Genet 5:70-6; and Bronson, (1994) J Biol Chem 269:27155-8. Homologous recombination in mammals other than mouse has been limited by the lack of stem cells capable of being transplanted to oocytes or developing embryos. However, McCreath et al., Nature 405:1066-9 (2000) reported successful homologous recombination in sheep by transformation and selection in primary embryo fibroblast cells.

Error-prone DNA repair mechanisms can produce mutations at double-strand break sites. The Non-Homologous-End-Joining (NHEJ) pathways are the most common repair mechanism to bring the broken ends together (Bleuyard et al., (2006) DNA Repair 5:1-12). The structural integrity of chromosomes is typically preserved by the repair, but deletions, insertions, or other rearrangements are possible. The two ends of one double-strand break are the most prevalent substrates of NHEJ (Kirik et al., (2000) EMBO J 19:5562-6), however if two different double-strand breaks occur, the free ends from different breaks can be ligated and result in chromosomal deletions (Siebert and Puchta, (2002) Plant Cell 14:1121-31), or chromosomal translocations between different chromosomes (Pacher et al., (2007) Genetics 175: 21-9).

Episomal DNA molecules can also be ligated into the double-strand break, for example, integration of T-DNAs into chromosomal double-strand breaks (Chilton and Que, (2003) Plant Physiol 133:956-65; Salomon and Puchta, (1998) EMBO J 17:6086-95). Once the sequence around the double-strand breaks is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152: 1173-81).

Once a double-strand break is induced in the DNA, the cell's DNA repair mechanism is activated to repair the break. Error-prone DNA repair mechanisms can produce mutations at double-strand break sites. The most common repair mechanism to bring the broken ends together is the nonhomologous end-joining (NHEJ) pathway (Bleuyard et al., (2006) DNA Repair 5:1-12). The structural integrity of chromosomes is typically preserved by the repair, but deletions, insertions, or other rearrangements are possible (Siebert and Puchta, (2002) Plant Cell 14:1121-31; Pacher et al., (2007) Genetics 175:21-9).

Alternatively, the double-strand break can be repaired by homologous recombination between homologous DNA sequences. Once the sequence around the double-strand break is altered, for example, by exonuclease activities involved in the maturation of double-strand breaks, gene conversion pathways can restore the original structure if a homologous sequence is available, such as a homologous chromosome in non-dividing somatic cells, or a sister chromatid after DNA replication (Molinier et al., (2004) Plant Cell 16:342-52). Ectopic and/or epigenic DNA sequences may also serve as a DNA repair template for homologous recombination (Puchta, (1999) Genetics 152:1173-81).

DNA double-strand breaks appear to be an effective factor to stimulate homologous recombination pathways (Puchta et al., (1995) Plant Mol Biol 28:281-92; Tzfira and White, (2005) Trends Biotechnol 23:567-9; Puchta, (2005) J Exp Bot 56:1-14). Using DNA-breaking agents, a two- to nine-fold increase of homologous recombination was observed between artificially constructed homologous DNA repeats in plants (Puchta et al., (1995) Plant Mol Biol 28:281-92). In maize protoplasts, experiments with linear DNA molecules demonstrated enhanced homologous recombination between plasmids (Lyznik et al., (1991) Mol Gen Genet 230:209-18).

In one embodiment provided herein, the method comprises contacting a plant cell with the donor DNA and the endonuclease. Once a double-strand break is introduced in the target site by the endonuclease, the first and second regions of homology of the donor DNA can undergo homologous recombination with their corresponding genomic regions of homology resulting in exchange of DNA between the donor and the genome. As such, the provided methods result in the integration of the polynucleotide of interest of the donor DNA into the double-strand break in the target site in the plant genome, thereby altering the original target site and producing an altered genomic target site.

The donor DNA may be introduced by any means known in the art. For example, a plant having a target site is provided. The donor DNA may be provided by any transformation method known in the art including, for example, Agrobacterium-mediated transformation or biolistic particle bombardment. The donor DNA may be present transiently in the cell or it could be introduced via a viral replicon. In the presence of the Cas endonuclease and the target site, the donor DNA is inserted into the transformed plant's genome.

Another approach uses protein engineering of existing homing endonucleases to alter their target specificities. Homing endonucleases, such as I-SceI or I-CreI, bind to and cleave relatively long DNA recognition sequences (18 bp and 22 bp, respectively). These sequences are predicted to naturally occur infrequently in a genome, typically only 1 or 2 sites/genome. The cleavage specificity of a homing endonuclease can be changed by rational design of amino acid substitutions at the DNA binding domain and/or combinatorial assembly and selection of mutated monomers (see, for example, Arnould et al., (2006) J Mol Biol 355:443-58; Ashworth et al., (2006) Nature 441:656-9; Doyon et al., (2006) J Am Chem Soc 128:2477-84; Rosen et al., (2006) Nucleic Acids Res 34:4791-800; and Smith et al., (2006) Nucleic Acids Res 34:e149; Lyznik et al., (2009) U.S. Patent Application Publication No. 20090133152A1; Smith et al., (2007) U.S. Patent Application Publication No. 20070117128A1). Engineered meganucleases have been demonstrated that can cleave cognate mutant sites without broadening their specificity. An artificial recognition site specific to the wild type yeast I-SceI homing nuclease was introduced in maize genome and mutations of the recognition sequence were detected in 1% of analyzed F1 plants when a transgenic I-SceI was introduced by crossing and activated by gene excision (Yang et al., (2009) Plant Mol Biol 70:669-79). More practically, the maize liguleless locus was targeted using an engineered single-chain endonuclease designed based on the I-CreI meganuclease sequence. Mutations of the selected liguleless locus recognition sequence were detected in 3% of the TO transgenic plants when the designed homing nuclease was introduced by Agrobacterium-mediated transformation of immature embryos (Gao et al., (2010) Plant J 61:176-87).

Polynucleotides of interest are further described herein and are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for genetic engineering will change accordingly.

Genome Editing Using the Guide RNA Cas Endonuclease System

As described herein, the guide RNA/Cas endonuclease system can be used in combination with a co-delivered polynucleotide modification template to allow for editing of a genomic nucleotide sequence of interest. Also, as described herein, for each embodiment that uses a guide RNA/Cas endonuclease system, a similar guide polynucleotide/Cas endonuclease system can be deployed where the guide polynucleotide does not solely comprise ribonucleic acids but wherein the guide polynucleotide comprises a combination of RNA-DNA molecules or solely comprise DNA molecules.

While numerous double-strand break-making systems exist, their practical applications for gene editing may be restricted due to the relatively low frequency of induced double-strand breaks (DSBs). To date, many genome modification methods rely on the homologous recombination system. Homologous recombination (HR) can provide molecular means for finding genomic DNA sequences of interest and modifying them according to the experimental specifications. Homologous recombination takes place in plant somatic cells at low frequency. The process can be enhanced to a practical level for genome engineering by introducing double-strand breaks (DSBs) at selected endonuclease target sites. The challenge has been to efficiently make DSBs at genomic sites of interest since there is a bias in the directionality of information transfer between two interacting DNA molecules (the broken one acts as an acceptor of genetic information). Described herein is the use of a guide RNA/Cas system which provides flexible genome cleavage specificity and results in a high frequency of double-strand breaks at a DNA target site, thereby enabling efficient gene editing in a nucleotide sequence of interest, wherein the nucleotide sequence of interest to be edited can be located within or outside the target site recognized and cleaved by a Cas endonuclease.

A "modified nucleotide" or "edited nucleotide" refers to a nucleotide sequence of interest that comprises at least one alteration when compared to its non-modified nucleotide sequence. Such "alterations" include, for example: (i) replacement of at least one nucleotide, (ii) a deletion of at least one nucleotide, (iii) an insertion of at least one nucleotide, or (iv) any combination of (i)-(iii).

The term "polynucleotide modification template" includes a polynucleotide that comprises at least one nucleotide modification when compared to the nucleotide sequence to be edited. A nucleotide modification can be at least one nucleotide substitution, addition or deletion. Optionally, the polynucleotide modification template can further comprise homologous nucleotide sequences flanking the at least one nucleotide modification, wherein the flanking homologous nucleotide sequences provide sufficient homology to the desired nucleotide sequence to be edited.

In one embodiment, the disclosure describes a method for editing a nucleotide sequence in the genome of a cell, the method comprising providing a guide RNA, a polynucleotide modification template, and at least one Cas endonuclease to a cell, wherein the Cas endonuclease is capable of introducing a double-strand break at a target sequence in the genome of said cell, wherein said polynucleotide modification template includes at least one nucleotide modification of said nucleotide sequence. Cells include, but are not limited to, human, animal, bacterial, fungal, insect, and plant cells as well as plants and seeds produced by the methods described herein. The nucleotide to be edited can be located within or outside a target site recognized and cleaved by a Cas endonuclease. In one embodiment, the at least one nucleotide modification is not a modification at a target site recognized and cleaved by a Cas endonuclease. In another embodiment, there are at least 1, 2, 3, 4, 5, 6, 7, 8, 9, 10, 11, 12, 13, 14, 15, 16, 17, 18, 19, 20, 21, 22, 23, 24, 25, 26, 27, 30, 40, 50, 100, 200, 300, 400, 500, 600, 700, 900 or 1000 nucleotides between the at least one nucleotide to be edited and the genomic target site.

In another embodiment, the disclosure describes a method for editing a nucleotide sequence in the genome of a plant cell, the method comprising providing a guide RNA, a polynucleotide modification template, and at least one maize optimized Cas9 endonuclease to a plant cell, wherein the maize optimized Cas9 endonuclease is capable of providing a double-strand break at a moCas9 target sequence in the plant genome, wherein said polynucleotide modification template includes at least one nucleotide modification of said nucleotide sequence.

In another embodiment, the disclosure describes a method for editing a nucleotide sequence in the genome of a cell, the method comprising providing a guide RNA, a polynucleotide modification template and at least one Cas endonuclease to a cell, wherein said guide RNA and Cas endonuclease are capable of forming a complex that enables the Cas endonuclease to introduce a double strand break at a target site, wherein said polynucleotide modification template comprises at least one nucleotide modification of said nucleotide sequence.

In another embodiment of genome editing, editing of the endogenous enolpyruvylshikimate-3-phosphate synthase (EPSPS) gene is disclosed herein (Example 16). In this embodiment, the polynucleotide modification template (EPSPS polynucleotide modification template) includes a partial fragment of the EPSPS gene (and therefore does not encode a fully functional EPSPS polypeptide by itself). The EPSPS polynucleotide modification template contained three point mutations that were responsible for the creation of the T102I/P106S (TIPS) double mutant (Funke, T et al., J. Biol. Chem. 2009, 284:9854-9860), which provide glyphosate tolerance to transgenic plants expressing as EPSPS double mutant transgene.

As defined herein "Glyphosate" includes any herbicidally effective form of N-phosphonomethylglycine (including any salt thereof), other forms which result in the production of the glyphosate anion in plants and any other herbicides of the phosphonomethlyglycine family.

In one embodiment of the disclosure, an epsps mutant plant is produced by the method described herein, said method comprising: a) providing a guide RNA, a polynucleotide modification template and at least one Cas endonuclease to a plant cell, wherein the Cas endonuclease introduces a double strand break at a target site within an epsps (enolpyruvylshikimate-3-phosphate synthase) genomic sequence in the plant genome, wherein said polynucleotide modification template comprises at least one nucleotide modification of said epsps genomic sequence; b) obtaining a plant from the plant cell of (a); c) evaluating the plant of (b) for the presence of said at least one nucleotide modification and d) selecting a progeny plant that shows resistance to glyphosate.

Increased resistance to an herbicide is demonstrated when plants which display the increased resistance to an herbicide are subjected to the herbicide and a dose/response curve is shifted to the right when compared with that provided by an appropriate control plant. Such dose/response curves have "dose" plotted on the x-axis and "percentage injury", "herbicidal effect" etc. plotted on the y-axis. Plants which are substantially resistant to the herbicide exhibit few, if any, bleached, necrotic, lytic, chlorotic or other lesions and are not stunted, wilted or deformed when subjected to the herbicide at concentrations and rates which are typically employed by the agricultural community to kill weeds in the field. The terms resistance and tolerance may be used interchangeably.

FIG. 12 shows a schematic representation of components used in the genome editing procedure. A maize optimized Cas endonuclease, a guide RNA and a polynucleotide modification template were provided to a plant cell. For example, as shown in FIG. 12, the polynucleotide modification template included three nucleotide modifications (indicated by arrows) when compared to the EPSPS genomic sequence to be edited. These three nucleotide modifications are referred to as TIPS mutations as these nucleotide modifications result in the amino acid changes T-102 to I-102 and P-106 to S-106. The first point mutation results from the substitution of the C nucleotide in the codon sequence ACT with a T nucleotide, a second mutation results from the substitution of the T nucleotide on the same codon sequence ACT with a C nucleotide to form the isoleucine codon ATC, the third point mutation results from the substitution of the first C nucleotide in the codon sequence CCA with a T nucleotide in order to form a serine codon TCA (FIG. 12).

In one embodiment, the disclosure describes a method for producing an epsps (enolpyruvylshikimate-3-phosphate synthase) mutant plant, the method comprising: a) providing a guide RNA, a polynucleotide modification template and at least one Cas endonuclease to a plant cell, wherein the Cas endonuclease introduces a double strand break at a target site within an epsps genomic sequence in the plant genome, wherein said polynucleotide modification template comprises at least one nucleotide modification of said epsps genomic sequence; b) obtaining a plant from the plant cell of (a); c) evaluating the plant of (b) for the presence of said at least one nucleotide modification; and, d) screening a progeny plant of (c) that is void of said guide RNA and Cas endonuclease.

The nucleotide sequence to be edited can be a sequence that is endogenous, artificial, pre-existing, or transgenic to the cell that is being edited. For example, the nucleotide sequence in the genome of a cell can be a native gene, a mutated gene, a non-native gene, a foreign gene, or a transgene that is stably incorporated into the genome of a cell. Editing of such nucleotide may result in a further desired phenotype or genotype.

Regulatory Sequence Modifications Using the Guide Polynucleotide Cas Endonuclease System In one embodiment the nucleotide sequence to be modified can be a regulatory sequence such as a promoter wherein the editing of the promoter comprises replacing the promoter (also referred to as a "promoter swap" or "promoter replacement") or promoter fragment with a different promoter (also referred to as replacement promoter) or promoter fragment (also referred to as replacement promoter fragment), wherein the promoter replacement results in any one of the following or any one combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression in the same cell layer or other cell layer (such as but not limiting to extending the timing of gene expression in the tapetum of maize anthers (U.S. Pat. No. 5,837,850 issued Nov. 17, 1998), a mutation of DNA binding elements and/or a deletion or addition of DNA binding elements. The promoter (or promoter fragment) to be modified can be a promoter (or promoter fragment) that is endogenous, artificial, pre-existing, or transgenic to the cell that is being edited. The replacement promoter (or replacement promoter fragment) can be a promoter (or promoter fragment) that is endogenous, artificial, pre-existing, or transgenic to the cell that is being edited.

In one embodiment the nucleotide sequence can be a promoter wherein the editing of the promoter comprises replacing an ARGOS 8 promoter with a *Zea mays* GOS2 PRO:GOS2-intron promoter.

In one embodiment the nucleotide sequence can be a promoter wherein the editing of the promoter comprises replacing a native EPSPS1 promoter from with a plant ubiquitin promoter.

In one embodiment the nucleotide sequence can be a promoter wherein the editing of the promoter comprises replacing an endogenous maize NPK1 promoter with a stress inducible maize RAB17 promoter.

In one embodiment the nucleotide sequence can be a promoter wherein the promoter to be edited is selected from the group comprising *Zea mays*-PEPC1 promoter (Kausch et al, Plant Molecular Biology, 45: 1-15, 2001), *Zea mays* Ubiquitin promoter (UBI1ZM PRO, Christensen et al, plant Molecular Biology 18: 675-689, 1992), *Zea mays*-Rootmet2 promoter (U.S. Pat. No. 7,214,855), Rice actin promoter (OS-ACTIN PRO, U.S. Pat. No. 5,641,876; McElroy et al, The Plant Cell, Vol 2, 163-171, February 1990), Sorghum RCC3 promoter (US 2012/0210463 filed on 13 Feb. 2012), *Zea mays*-GOS2 promoter (U.S. Pat. No. 6,504,083), *Zea mays*-ACO2 promoter (U.S. application Ser. No. 14/210,711 filed 14 Mar. 2014) or *Zea mays*-oleosin promoter (U.S. Pat. No. 8,466,341 B2).

In another embodiment, the guide polynucleotide/Cas endonuclease system can be used in combination with a co-delivered polynucleotide modification template or donor DNA sequence to allow for the insertion of a promoter or promoter element into a genomic nucleotide sequence of interest, wherein the promoter insertion (or promoter element insertion) results in any one of the following or any one combination of the following: an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression a mutation of DNA binding elements and/or an addition of DNA binding elements. Promoter elements to be inserted can be, but are not limited to, promoter core elements (such as, but not limited to, a CAAT box, a CCAAT box, a Pribnow box, a and/or TATA box, translational regulation sequences and/or a repressor system for inducible expression (such as TET operator repressor/operator/inducer elements, or Sulphonylurea (Su) repressor/operator/inducer elements. The dehydration-responsive element (DRE) was first identified as a cis-acting promoter element in the promoter of the drought-responsive gene rd29A, which contains a 9 bp conserved core sequence, TACCGACAT (Yamaguch-Shinozai, K., and Shinozaki, K (1994) *Plant Cell* 6, 251 264). Insertion of DRE into an endogenous promoter may confer a drought inducible expression of the downstream gene. Another example are ABA-responsive elements (ABREs) which contain a (C/T) ACGTGGC consensus sequence found to be present in numerous ABA and/or stress-regulated genes (Busk P. K., Pages M. (1998) Plant Mol. Biol. 37:425-435). Insertion of 35S enhancer or MMV enhancer into an endogenous promoter region will increase gene expression (U.S. Pat. No. 5,196,525). The promoter (or promoter element) to be inserted can be a promoter (or promoter element) that is endogenous, artificial, pre-existing, or transgenic to the cell that is being edited.

In one embodiment, the guide polynucleotide/Cas endonuclease system can be used to insert an enhancer element, such as but not limited to a Cauliflower Mosaic Virus 35 S enhancer, in front of an endogenous FMT1 promoter to enhance expression of the FTM1.

In one embodiment, the guide polynucleotide/Cas endonuclease system can be used to insert a component of the TET operator repressor/operator/inducer system, or a component of the sulphonylurea (Su) repressor/operator/inducer system into plant genomes to generate or control inducible expression systems.

In another embodiment, the guide polynucleotide/Cas endonuclease system can be used to allow for the deletion of a promoter or promoter element, wherein the promoter deletion (or promoter element deletion) results in any one of the following or any one combination of the following: a permanently inactivated gene locus, an increased promoter activity (increased promoter strength), an increased promoter tissue specificity, a decreased promoter activity, a decreased promoter tissue specificity, a new promoter activity, an inducible promoter activity, an extended window of gene expression, a modification of the timing or developmental progress of gene expression, a mutation of DNA binding elements and/or an addition of DNA binding elements. Promoter elements to be deleted can be, but are not limited to, promoter core elements, promoter enhancer elements or 35 S enhancer elements (as described in Example 32) The promoter or promoter fragment to be deleted can be endogenous, artificial, pre-existing, or transgenic to the cell that is being edited.

In one embodiment, the guide polynucleotide/Cas endonuclease system can be used to delete the ARGOS 8 promoter present in a maize genome as described herein.

In one embodiment, the guide polynucleotide/Cas endonuclease system can be used to delete a 35S enhancer element present in a plant genome as described herein.

Terminator Modifications Using the Guide Polynucleotide Cas Endonuclease System

In one embodiment the nucleotide sequence to be modified can be a terminator wherein the editing of the terminator comprises replacing the terminator (also referred to as a "terminator swap" or "terminator replacement") or terminator fragment with a different terminator (also referred to as replacement terminator) or terminator fragment (also referred to as replacement terminator fragment), wherein the terminator replacement results in any one of the following or any one combination of the following: an increased terminator activity, an increased terminator tissue specificity, a decreased terminator activity, a decreased terminator tissue specificity, a mutation of DNA binding elements and/or a deletion or addition of DNA binding elements." The terminator (or terminator fragment) to be modified can be a terminator (or terminator fragment) that is endogenous, artificial, pre-existing, or transgenic to the cell that is being edited. The replacement terminator (or replacement terminator fragment) can be a terminator (or terminator fragment) that is endogenous, artificial, pre-existing, or transgenic to the cell that is being edited.

In one embodiment the nucleotide sequence to be modified can be a terminator wherein the terminator to be edited is selected from the group comprising terminators from maize Argos 8 or SRTF18 genes, or other terminators, such as potato PinII terminator, sorghum actin terminator (SB-ACTIN TERM, WO 2013/184537 A1 published December 2013), sorghum SB-GKAF TERM (WO2013019461), rice T28 terminator (OS-T28 TERM, WO 2013/012729 A2), AT-T9 TERM (WO 2013/012729 A2) or GZ-W64A TERM (U.S. Pat. No. 7,053,282).

In one embodiment, the guide polynucleotide/Cas endonuclease system can be used in combination with a co-delivered polynucleotide modification template or donor DNA sequence to allow for the insertion of a terminator or terminator element into a genomic nucleotide sequence of interest, wherein the terminator insertion (or terminator element insertion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements. The terminator (or terminator element) to be inserted can be a terminator (or terminator element) that is endogenous, artificial, pre-existing, or transgenic to the cell that is being edited.

In another embodiment, the guide polynucleotide/Cas endonuclease system can be used to allow for the deletion of a terminator or terminator element, wherein the terminator deletion (or terminator element deletion) results in any one of the following or any one combination of the following: an increased terminator activity (increased terminator strength), an increased terminator tissue specificity, a decreased terminator activity, a decreased terminator tissue specificity, a mutation of DNA binding elements and/or an addition of DNA binding elements. The terminator or terminator fragment to be deleted can be endogenous, artificial, pre-existing, or transgenic to the cell that is being edited.

Additional Regulatory Sequence Modifications Using the Guide Polynucleotide Cas Endonuclease System In one embodiment, the guide polynucleotide/Cas endonuclease system can be used to modify or replace a regulatory sequence in the genome of a cell. A regulatory sequence is a segment of a nucleic acid molecule which is capable of increasing or decreasing the expression of specific genes within an organism and/or is capable of altering tissue specific expression of genes within an organism. Examples of regulatory sequences include, but are not limited to, 3' UTR (untranslated region) region, 5' UTR region, transcription activators, transcriptional enhancers transcriptions repressors, translational repressors, splicing factors, miRNAs, siRNA, artificial miRNAs, promoter elements, CAMV 35 S enhancer, MMV enhancer elements (PCT/US14/23451 filed Mar. 11, 2013), SECIS elements, polyadenylation signals, and polyubiquitination sites. In some embodiments the editing (modification) or replacement of a regulatory element results in altered protein translation, RNA cleavage, RNA splicing, transcriptional termination or post translational modification. In one embodiment, regulatory elements can be identified within a promoter and these regulatory elements can be edited or modified do to optimize these regulatory elements for up or down regulation of the promoter.

In one embodiment, the genomic sequence of interest to be modified is a polyubiquitination site, wherein the modification of the polyubiquitination sites results in a modified rate of protein degradation. The ubiquitin tag condemns proteins to be degraded by proteasomes or autophagy. Proteasome inhibitors are known to cause a protein overproduction. Modifications made to a DNA sequence encoding a protein of interest can result in at least one amino acid modification of the protein of interest, wherein said modification allows for the polyubiquitination of the protein (a post translational modification) resulting in a modification of the protein degradation In one embodiment, the genomic sequence of interest to be modified is a polyubiquitination site on a maize EPSPS gene, wherein the polyubiquitination site modified resulting in an increased protein content due to a slower rate of EPSPS protein degradation.

In one embodiment, the genomic sequence of interest to be modified is a an intron site, wherein the modification consist of inserting an intron enhancing motif into the intron which results in modulation of the transcriptional activity of the gene comprising said intron.

In one embodiment, the genomic sequence of interest to be modified is a an intron site, wherein the modification consist of replacing a soybean EPSP1 intron with a soybean ubiquitin intron 1 as described herein (Example 25)

In one embodiment, the genomic sequence of interest to be modified is a an intron or UTR site, wherein the modification consist of inserting at least one microRNA into said intron or UTR site, wherein expression of the gene comprising the intron or UTR site also results in expression of said microRNA, which in turn can silence any gene targeted by the microRNA without disrupting the gene expression of the native/transgene comprising said intron.

In one embodiment, the guide polynucleotide/Cas endonuclease system can be used to allow for the deletion or mutation of a Zinc Finger transcription factor, wherein the deletion or mutation of the Zinc Finger transcription factor results in or allows for the creation of a dominant negative Zinc Finger transcription factor mutant (Li et al 2013 Rice zinc finger protein DST enhances grain production through controlling Gn1a/OsCKX2 expression PNAS 110:3167-3172). Insertion of a single base pair downstream zinc finger domain will result in a frame shift and produces a new protein which still can bind to DNA without transcription activity. The mutant protein will compete to bind to cytokinin oxidase gene promoters and block the expression of cytokinin oxidase gene. Reduction of cytokinin oxidase gene expression will increase cytokinin level and promote panicle growth in rice and ear growth in maize, and increase yield under normal and stress conditions.

Modifications of Splicing Sites and/or Introducing Alternate Splicing Sites Using the Guide Polynucleotide Cas Endonuclease System Protein synthesis utilizes mRNA molecules that emerge from pre-mRNA molecules subjected to the maturation process. The pre-mRNA molecules are capped, spliced and stabilized by addition of polyA tails. Eukaryotic cells developed a complex process of splicing that result in alternative variants of the original pre-mRNA molecules. Some of them may not produce functional templates for protein synthesis. In maize cells, the splicing process is affected by splicing sites at the exon-intron junction sites. An example of a canonical splice site is AGGT. Gene coding sequences can contains a number of alternate splicing sites that may affect the overall efficiency of the pre-mRNA maturation process and as such may limit the protein accumulation in cells. The guide polynucleotide/Cas endonuclease system can be used in combination with a co-delivered polynucleotide modification template to edit a gene of interest to introduce a canonical splice site at a described junction or any variant of a splicing site that changes the splicing pattern of pre-mRNA molecules.

In one embodiment, the nucleotide sequence of interest to be modified is a maize EPSPS gene, wherein the modification of the gene consists of modifying alternative splicing sites resulting in enhanced production of the functional gene transcripts and gene products (proteins).

In one embodiment, the nucleotide sequence of interest to be modified is a gene, wherein the modification of the gene consists of editing the intron borders of alternatively spliced genes to alter the accumulation of splice variants.

Modifications of Nucleotide Sequences Encoding a Protein of Interest Using the Guide Polynucleotide Cas Endonuclease System In one embodiment, the guide polynucleotide/Cas endonuclease system can be used to modify or replace a coding sequence in the genome of a cell, wherein the modification or replacement results in any one of the following, or any one combination of the following: an increased protein (enzyme) activity, an increased protein functionality, a decreased protein activity, a decreased protein functionality, a site specific mutation, a protein domain swap, a protein knock-out, a new protein functionality, a modified protein functionality.

In one embodiment the protein knockout is due to the introduction of a stop codon into the coding sequence of interest.

In one embodiment the protein knockout is due to the deletion of a start codon into the coding sequence of interest.

Amino Acid and/or Protein Fusions Using the Guide Polynucleotide Cas Endonuclease System In one embodiment, the guide polynucleotide/Cas endonuclease system can be used with or without a co-delivered polynucleotide sequence to fuse a first coding sequence encoding a first protein to a second coding sequence encoding a second protein in the genome of a cell, wherein the protein fusion results in any one of the following or any one combination of the following: an increased protein (enzyme) activity, an increased protein functionality, a decreased protein activity, a decreased protein functionality, a new protein functionality, a modified protein functionality, a new protein localization, a new timing of protein expression, a modified protein expression pattern, a chimeric protein, or a modified protein with dominant phenotype functionality.

In one embodiment, the guide polynucleotide/Cas endonuclease system can be used with or without a co-delivered polynucleotide sequence to fuse a first coding sequence encoding a chloroplast localization signal to a second coding sequence encoding a protein of interest, wherein the protein fusion results in targeting the protein of interest to the chloroplast.

In one embodiment, the guide polynucleotide/Cas endonuclease system can be used with or without a co-delivered polynucleotide sequence to fuse a first coding sequence encoding a chloroplast localization signal to a second coding sequence encoding a protein of interest, wherein the protein fusion results in targeting the protein of interest to the chloroplast.

In one embodiment, the guide polynucleotide/Cas endonuclease system can be used with or without a co-delivered polynucleotide sequence to fuse a first coding sequence encoding a chloroplast localization signal (e.g., a chloroplast transit peptide) to a second coding sequence, wherein the protein fusion results in a modified protein with dominant phenotype functionality Gene Silencing by Expressing an Inverted Repeat into a Gene of Interest Using the Guide Polynucleotide Cas Endonuclease System In one embodiment, the guide polynucleotide/Cas endonuclease system can be used in combination with a co-delivered polynucleotide sequence to insert an inverted gene fragment into a gene of interest in the genome of an organism, wherein the insertion of the inverted gene fragment can allow for an in-vivo creation of an inverted repeat (hairpin) and results in the silencing of said endogenous gene.

In one embodiment the insertion of the inverted gene fragment can result in the formation of an in-vivo created inverted repeat (hairpin) in a native (or modified) promoter of a gene and/or in a native 5' end of the native gene. The inverted gene fragment can further comprise an intron which can result in an enhanced silencing of the targeted gene.

Genome Deletion for Trait Locus Characterization

Trait mapping in plant breeding often results in the detection of chromosomal regions housing one or more genes controlling expression of a trait of interest. For a qualitative trait, the guide polynucleotide/Cas endonuclease system can be used to eliminate candidate genes in the identified chromosomal regions to determine if deletion of the gene affects expression of the trait. For quantitative traits, expression of a trait of interest is governed by multiple quantitative trait loci (QTL) of varying effect-size, complexity, and statistical significance across one or more chromosomes. In cases of negative effect or deleterious QTL regions affecting a complex trait, the guide polynucleotide/Cas endonuclease system can be used to eliminate whole regions delimited by marker-assisted fine mapping, and to target specific regions for their selective elimination or rearrangement. Similarly, presence/absence variation (PAV) or copy number variation (CNV) can be manipulated with selective genome deletion using the guide polynucleotide/Cas endonuclease system.

In one embodiment, the region of interest can be flanked by two independent guide polynucleotide/CAS endonuclease target sequences. Cutting would be done concurrently. The deletion event would be the repair of the two chromosomal ends without the region of interest. Alternative results would include inversions of the region of interest, mutations at the cut sites and duplication of the region of interest.

Methods for Identifying at Least One Plant Cell Comprising in its Genome a Polynucleotide of Interest Integrated at the Target Site.

Further provided are methods for identifying at least one plant cell, comprising in its genome, a polynucleotide of interest integrated at the target site. A variety of methods are available for identifying those plant cells with insertion into the genome at or near to the target site without using a screenable marker phenotype. Such methods can be viewed as directly analyzing a target sequence to detect any change in the target sequence, including but not limited to PCR methods, sequencing methods, nuclease digestion, Southern blots, and any combination thereof. See, for example, U.S. patent application Ser. No. 12/147,834, herein incorporated by reference to the extent necessary for the methods described herein. The method also comprises recovering a plant from the plant cell comprising a polynucleotide of Interest integrated into its genome. The plant may be sterile or fertile. It is recognized that any polynucleotide of interest can be provided, integrated into the plant genome at the target site, and expressed in a plant.

Polynucleotides/polypeptides of interest include, but are not limited to, herbicide-resistance coding sequences, insecticidal coding sequences, nematicidal coding sequences, antimicrobial coding sequences, antifungal coding sequences, antiviral coding sequences, abiotic and biotic stress tolerance coding sequences, or sequences modifying plant traits such as yield, grain quality, nutrient content, starch quality and quantity, nitrogen fixation and/or utilization, fatty acids, and oil content and/or composition. More specific polynucleotides of interest include, but are not limited to, genes that improve crop yield, polypeptides that improve desirability of crops, genes encoding proteins conferring resistance to abiotic stress, such as drought, nitrogen, temperature, salinity, toxic metals or trace elements, or those conferring resistance to toxins such as pesticides and herbicides, or to biotic stress, such as attacks by fungi, viruses, bacteria, insects, and nematodes, and development of diseases associated with these organisms. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, fertility or sterility, grain characteristics, and commercial products. Genes of interest include, generally, those involved in oil, starch, carbohydrate, or nutrient metabolism as well as those affecting kernel size, sucrose loading, and the like that can be stacked or used in combination with other traits, such as but not limited to herbicide resistance, described herein.

Agronomically important traits such as oil, starch, and protein content can be genetically altered in addition to using traditional breeding methods. Modifications include increasing content of oleic acid, saturated and unsaturated oils, increasing levels of lysine and sulfur, providing essential amino acids, and also modification of starch. Hordothionin protein modifications are described in U.S. Pat. Nos. 5,703,049, 5,885,801, 5,885,802, and 5,990,389, herein incorporated by reference. Another example is lysine and/or sulfur rich seed protein encoded by the soybean 2S albumin described in U.S. Pat. No. 5,850,016, and the chymotrypsin inhibitor from barley, described in Williamson et al. (1987) *Eur. J. Biochem.* 165:99-106, the disclosures of which are herein incorporated by reference.

Commercial traits can also be encoded on a polynucleotide of interest that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) *J. Bacteriol.* 170:5837-5847) facilitate expression of polyhydroxyalkanoates (PHAs).

Derivatives of the coding sequences can be made by site-directed mutagenesis to increase the level of preselected amino acids in the encoded polypeptide. For example, the gene encoding the barley high lysine polypeptide (BHL) is derived from barley chymotrypsin inhibitor, U.S. application Ser. No. 08/740,682, filed Nov. 1, 1996, and WO 98/20133, the disclosures of which are herein incorporated by reference. Other proteins include methionine-rich plant proteins such as from sunflower seed (Lilley et al. (1989) *Proceedings of the World Congress on Vegetable Protein Utilization in Human Foods and Animal Feedstuffs*, ed. Applewhite (American Oil Chemists Society, Champaign, Illinois), pp. 497-502; herein incorporated by reference); corn (Pedersen et al. (1986) *J. Biol. Chem.* 261:6279; Kirihara et al. (1988) *Gene* 71:359; both of which are herein incorporated by reference); and rice (Musumura et al. (1989) *Plant Mol. Biol.* 12:123, herein incorporated by reference). Other agronomically important genes encode latex, Floury 2, growth factors, seed storage factors, and transcription factors.

Polynucleotides that improve crop yield include dwarfing genes, such as Rht1 and Rht2 (Peng et al. (1999) *Nature* 400:256-261), and those that increase plant growth, such as ammonium-inducible glutamate dehydrogenase. Polynucleotides that improve desirability of crops include, for example, those that allow plants to have reduced saturated fat content, those that boost the nutritional value of plants, and those that increase grain protein. Polynucleotides that improve salt tolerance are those that increase or allow plant growth in an environment of higher salinity than the native environment of the plant into which the salt-tolerant gene(s) has been introduced.

Polynucleotides/polypeptides that influence amino acid biosynthesis include, for example, anthranilate synthase (AS; EC 4.1.3.27) which catalyzes the first reaction branching from the aromatic amino acid pathway to the biosynthesis of tryptophan in plants, fungi, and bacteria. In plants, the chemical processes for the biosynthesis of tryptophan are compartmentalized in the chloroplast. See, for example, US Pub. 20080050506, herein incorporated by reference. Additional sequences of interest include Chorismate Pyruvate Lyase (CPL) which refers to a gene encoding an enzyme which catalyzes the conversion of chorismate to pyruvate and pHBA. The most well characterized CPL gene has been isolated from *E. coli* and bears the GenBank accession number M96268. See, U.S. Pat. No. 7,361,811, herein incorporated by reference.

Polynucleotide sequences of interest may encode proteins involved in providing disease or pest resistance. By "disease resistance" or "pest resistance" is intended that the plants avoid the harmful symptoms that are the outcome of the plant-pathogen interactions. Pest resistance genes may encode resistance to pests that have great yield drag such as rootworm, cutworm, European Corn Borer, and the like. Disease resistance and insect resistance genes such as lysozymes or cecropins for antibacterial protection, or proteins such as defensins, glucanases or chitinases for antifungal protection, or *Bacillus thuringiensis* endotoxins, protease inhibitors, collagenases, lectins, or glycosidases for controlling nematodes or insects are all examples of useful gene products. Genes encoding disease resistance traits include detoxification genes, such as against fumonisin (U.S. Pat. No. 5,792,931); avirulence (avr) and disease resistance (R) genes (Jones et al. (1994) *Science* 266:789; Martin et al. (1993) *Science* 262:1432; and Mindrinos et al. (1994) *Cell* 78:1089); and the like. Insect resistance genes may encode resistance to pests that have great yield drag such as rootworm, cutworm, European Corn Borer, and the like. Such genes include, for example, *Bacillus thuringiensis* toxic protein genes (U.S. Pat. Nos. 5,366,892; 5,747,450; 5,736,514; 5,723,756; 5,593,881; and Geiser et al. (1986) *Gene* 48:109); and the like.

An "herbicide resistance protein" or a protein resulting from expression of an "herbicide resistance-encoding nucleic acid molecule" includes proteins that confer upon a cell the ability to tolerate a higher concentration of an herbicide than cells that do not express the protein, or to tolerate a certain concentration of an herbicide for a longer period of time than cells that do not express the protein. Herbicide resistance traits may be introduced into plants by genes coding for resistance to herbicides that act to inhibit the action of acetolactate synthase (ALS), in particular the sulfonylurea-type herbicides, genes coding for resistance to herbicides that act to inhibit the action of glutamine synthase, such as phosphinothricin or basta (e.g., the bar gene), glyphosate (e.g., the EPSP synthase gene and the GAT gene), HPPD inhibitors (e.g, the HPPD gene) or other such genes known in the art. See, for example, U.S. Pat. Nos. 7,626,077, 5,310,667, 5,866,775, 6,225,114, 6,248,876, 7,169,970, 6,867,293, and U.S. Provisional Application No. 61/401,456, each of which is herein incorporated by reference. The bar gene encodes resistance to the herbicide basta, the nptII gene encodes resistance to the antibiotics kanamycin and geneticin, and the ALS-gene mutants encode resistance to the herbicide chlorsulfuron.

Sterility genes can also be encoded in an expression cassette and provide an alternative to physical detasseling. Examples of genes used in such ways include male fertility genes such as MS26 (see for example U.S. Pat. Nos. 7,098,388, 7,517,975, 7,612,251), MS45 (see for example U.S. Pat. Nos. 5,478,369, 6,265,640) or MSCA1 (see for example U.S. Pat. No. 7,919,676). Maize plants (*Zea mays* L.) can be bred by both self-pollination and cross-pollination techniques. Maize has male flowers, located on the tassel, and female flowers, located on the ear, on the same plant. It can self-pollinate ("selfing") or cross pollinate. Natural pollination occurs in maize when wind blows pollen from the tassels to the silks that protrude from the tops of the incipient ears. Pollination may be readily controlled by techniques known to those of skill in the art. The development of maize hybrids requires the development of homozygous inbred lines, the crossing of these lines, and the evaluation of the crosses. Pedigree breeding and recurrent selections are two of the breeding methods used to develop inbred lines from populations. Breeding programs combine desirable traits from two or more inbred lines or various broad-based sources into breeding pools from which new inbred lines are developed by selfing and selection of desired phenotypes. A hybrid maize variety is the cross of two such inbred lines, each of which may have one or more desirable characteristics lacked by the other or which complement the other. The new inbreds are crossed with other inbred lines and the hybrids from these crosses are evaluated to determine which have commercial potential. The hybrid progeny of the first generation is designated F1. The F1 hybrid is more vigorous than its inbred parents. This hybrid vigor, or heterosis, can be manifested in many ways, including increased vegetative growth and increased yield.

Hybrid maize seed can be produced by a male sterility system incorporating manual detasseling. To produce hybrid seed, the male tassel is removed from the growing female inbred parent, which can be planted in various alternating row patterns with the male inbred parent. Consequently, providing that there is sufficient isolation from sources of foreign maize pollen, the ears of the female inbred will be fertilized only with pollen from the male inbred. The resulting seed is therefore hybrid (F1) and will form hybrid plants.

Field variation impacting plant development can result in plants tasseling after manual detasseling of the female parent is completed. Or, a female inbred plant tassel may not be completely removed during the detasseling process. In any event, the result is that the female plant will successfully shed pollen and some female plants will be self-pollinated. This will result in seed of the female inbred being harvested along with the hybrid seed which is normally produced. Female inbred seed does not exhibit heterosis and therefore is not as productive as F1 seed. In addition, the presence of female inbred seed can represent a germplasm security risk for the company producing the hybrid.

Alternatively, the female inbred can be mechanically detasseled by machine. Mechanical detasseling is approximately as reliable as hand detasseling, but is faster and less costly. However, most detasseling machines produce more damage to the plants than hand detasseling. Thus, no form of detasseling is presently entirely satisfactory, and a need continues to exist for alternatives which further reduce production costs and to eliminate self-pollination of the female parent in the production of hybrid seed.

Mutations that cause male sterility in plants have the potential to be useful in methods for hybrid seed production for crop plants such as maize and can lower production costs by eliminating the need for the labor-intensive removal of male flowers (also known as de-tasseling) from the maternal parent plants used as a hybrid parent. Mutations that cause male sterility in maize have been produced by a variety of methods such as X-rays or UV-irradiations, chemical treatments, or transposable element insertions (ms23, ms25, ms26, ms32) (Chaubal et al. (2000) Am J Bot 87:1193-1201). Conditional regulation of fertility genes through fertility/sterility "molecular switches" could enhance the options for designing new male-sterility systems for crop improvement (Unger et al. (2002) Transgenic Res 11:455-465).

Besides identification of novel genes impacting male fertility, there remains a need to provide a reliable system of producing genetic male sterility.

In U.S. Pat. No. 5,478,369, a method is described by which the Ms45 male fertility gene was tagged and cloned on maize chromosome 9. Previously, there had been described a male fertility gene on chromosome 9, ms2, which had never been cloned and sequenced. It is not allelic to the gene referred to in the '369 patent. See Albertsen, M. and Phillips, R. L., "Developmental Cytology of 13 Genetic Male Sterile Loci in Maize" Canadian Journal of Genetics & Cytology 23:195-208 (January 1981). The only fertility gene cloned before that had been the *Arabidopsis* gene described at Aarts, et al., supra.

Examples of genes that have been discovered subsequently that are important to male fertility are numerous and include the *Arabidopsis* ABORTED MICROSPORES (AMS) gene, Sorensen et al., The Plant Journal (2003) 33(2):413-423); the *Arabidopsis* MS1 gene (Wilson et al., The Plant Journal (2001) 39(2):170-181); the NEF1 gene (Ariizumi et al., The Plant Journal (2004) 39(2):170-181); *Arabidopsis* AtGPAT1 gene (Zheng et al., The Plant Cell (2003) 15:1872-1887); the *Arabidopsis* dde2-2 mutation was shown to be defective in the allene oxide synthase gene (Malek et al., Planta (2002)216:187-192); the *Arabidopsis* faceless pollen-1 gene (flp1) (Ariizumi et al, Plant Mol. Biol. (2003) 53:107-116); the *Arabidopsis* MALE MEIOCYTE DEATH1 gene (Yang et al., The Plant Cell (2003) 15: 1281-1295); the tapetum-specific zinc finger gene, TAZ1 (Kapoor et al., The Plant Cell (2002) 14:2353-2367); and the TAPETUM DETERMINANT1 gene (Lan et al, The Plant Cell (2003) 15:2792-2804).

Other known male fertility mutants or genes from *Zea mays* are listed in U.S. Pat. No. 7,919,676 incorporated herein by reference.

Other genes include kinases and those encoding compounds toxic to either male or female gametophytic development.

Furthermore, it is recognized that the polynucleotide of interest may also comprise antisense sequences complementary to at least a portion of the messenger RNA (mRNA) for a targeted gene sequence of interest. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, 80%, or 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used.

In addition, the polynucleotide of interest may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a nucleotide sequence that corresponds to the transcript of the endogenous gene. Typically, such a nucleotide sequence has substantial sequence identity to the sequence of the transcript of the endogenous gene, generally greater than about 65% sequence identity, about 85% sequence identity, or greater than about 95% sequence identity. See, U.S. Pat. Nos. 5,283,184 and 5,034,323; herein incorporated by reference.

The polynucleotide of interest can also be a phenotypic marker. A phenotypic marker is screenable or a selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) Curr Opin Biotech 3:506-11; Christopherson et al., (1992) Proc. Natl. Acad. Sci. USA 89:6314-8; Yao et al., (1992) Cell 71:63-72; Reznikoff, (1992) Mol Microbiol 6:2419-22; Hu et al., (1987) Cell 48:555-66; Brown et al., (1987) Cell 49:603-12; Figge et al., (1988) Cell 52:713-22; Deuschle et al., (1989) Proc. Natl. Acad. Sci. USA 86:5400-4; Fuerst et al., (1989) Proc. Natl. Acad. Sci. USA 86:2549-53; Deuschle et al., (1990) Science 248:480-3; Gossen, (1993) Ph.D. Thesis, University of Heidelberg; Reines et al., (1993) Proc. Natl. Acad. Sci. USA 90:1917-21; Labow et al., (1990) Mol Cell Biol 10:3343-56; Zambretti et al., (1992) Proc. Natl. Acad. Sci. USA 89:3952-6; Baim et al., (1991) Proc. Natl. Acad. Sci. USA 88:5072-6; Wyborski et al., (1991) Nucleic Acids Res 19:4647-53; Hillen and Wissman, (1989) Topics Mol Struc Biol 10:143-62; Degenkolb et al., (1991) Antimicrob Agents Chemother 35:1591-5; Kleinschnidt et al., (1988) Biochemistry 27:1094-104; Bonin, (1993) Ph.D. Thesis, University of Heidelberg; Gossen et al., (1992) Proc. Natl. Acad. Sci. USA 89:5547-51; Oliva et al., (1992) Antimicrob Agents Chemother 36:913-9; Hlavka et al., (1985) Handbook of Experimental Pharmacology, Vol. 78 (Springer-Verlag, Berlin); Gill et al., (1988) Nature 334:721-4. Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxyburyrate synthase), and acetoacetyl-CoA reductase (see Schubert et al. (1988) *J. Bacteriol.* 170:5837-5847) facilitate expression of polyhyroxyalkanoates (PHAs).

Exogenous products include plant enzymes and products as well as those from other sources including procaryotes and other eukaryotes. Such products include enzymes, cofactors, hormones, and the like. The level of proteins, particularly modified proteins having improved amino acid distribution to improve the nutrient value of the plant, can be increased. This is achieved by the expression of such proteins having enhanced amino acid content.

The transgenes, recombinant DNA molecules, DNA sequences of interest, and polynucleotides of interest can be comprise one or more DNA sequences for gene silencing. Methods for gene silencing involving the expression of DNA sequences in plant are known in the art include, but are not limited to, cosuppression, antisense suppression, double-stranded RNA (dsRNA) interference, hairpin RNA (hpRNA) interference, intron-containing hairpin RNA (ihpRNA) interference, transcriptional gene silencing, and micro RNA (miRNA) interference As used herein, "nucleic acid" means a polynucleotide and includes a single or a double-stranded polymer of deoxyribonucleotide or ribonucleotide bases. Nucleic acids may also include fragments and modified nucleotides. Thus, the terms "polynucleotide", "nucleic acid sequence", "nucleotide sequence" and "nucleic acid fragment" are used interchangeably to denote a polymer of RNA and/or DNA that is single- or double-stranded, optionally containing synthetic, non-natural, or altered nucleotide bases. Nucleotides (usually found in their 5'-monophosphate form) are referred to by their single letter designation as follows: "A" for adenosine or deoxyadenosine (for RNA or DNA, respectively), "C" for cytosine or deoxycytosine, "G" for guanosine or deoxyguanosine, "U" for uridine, "T" for deoxythymidine, "R" for purines (A or G), "Y" for pyrimidines (C or T), "K" for G or T, "H" for A or C or T, "I" for inosine, and "N" for any nucleotide.

"Open reading frame" is abbreviated ORF.

The terms "subfragment that is functionally equivalent" and "functionally equivalent subfragment" are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of genes to produce the desired phenotype in a transformed plant. genes can be designed for use in suppression by linking a nucleic acid fragment or subfragment thereof, whether or not it encodes an active enzyme, in the sense or antisense orientation relative to a plant promoter sequence.

The term "conserved domain" or "motif" means a set of amino acids conserved at specific positions along an aligned sequence of evolutionarily related proteins. While amino acids at other positions can vary between homologous proteins, amino acids that are highly conserved at specific positions indicate amino acids that are essential to the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family.

Polynucleotide and polypeptide sequences, variants thereof, and the structural relationships of these sequences can be described by the terms "homology", "homologous", "substantially identical", "substantially similar" and "corresponding substantially" which are used interchangeably herein. These refer to polypeptide or nucleic acid fragments wherein changes in one or more amino acids or nucleotide bases do not affect the function of the molecule, such as the ability to mediate gene expression or to produce a certain phenotype. These terms also refer to modification(s) of nucleic acid fragments that do not substantially alter the functional properties of the resulting nucleic acid fragment relative to the initial, unmodified fragment. These modifications include deletion, substitution, and/or insertion of one or more nucleotides in the nucleic acid fragment.

Substantially similar nucleic acid sequences encompassed may be defined by their ability to hybridize (under moderately stringent conditions, e.g., 0.5×SSC, 0.1% SDS, 60° C.) with the sequences exemplified herein, or to any portion of the nucleotide sequences disclosed herein and which are functionally equivalent to any of the nucleic acid sequences disclosed herein. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, or 90% sequence identity, up to and including 100% sequence identity (i.e., fully complementary) with each other.

The term "stringent conditions" or "stringent hybridization conditions" includes reference to conditions under which a probe will selectively hybridize to its target sequence in an in vitro hybridization assay. Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salt(s)) at pH 7.0 to 8.3, and at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

"Sequence identity" or "identity" in the context of nucleic acid or polypeptide sequences refers to the nucleic acid bases or amino acid residues in two sequences that are the same when aligned for maximum correspondence over a specified comparison window.

The term "percentage of sequence identity" refers to the value determined by comparing two optimally aligned sequences over a comparison window, wherein the portion of the polynucleotide or polypeptide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the results by 100 to yield the percentage of sequence identity. Useful examples of percent sequence identities include, but are not limited to, 50%, 55%, 60%, 65%, 70%, 75%, 80%, 85%, 90% or 95%, or any integer percentage from 50% to 100%. These identities can be determined using any of the programs described herein.

Sequence alignments and percent identity or similarity calculations may be determined using a variety of comparison methods designed to detect homologous sequences including, but not limited to, the MegAlign™ program of the LASERGENE bioinformatics computing suite (DNASTAR Inc., Madison, WI). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

The "Clustal V method of alignment" corresponds to the alignment method labeled Clustal V (described by Higgins and Sharp, (1989) *CABIOS* 5:151-153; Higgins et al., (1992) *Comput Appl Biosci* 8:189-191) and found in the MegAlign™ program of the LASERGENE bioinformatics computing suite (DNASTAR Inc., Madison, WI). For multiple alignments, the default values correspond to GAP PENALTY=10 and GAP LENGTH PENALTY=10. Default parameters for pairwise alignments and calculation of percent identity of protein sequences using the Clustal method are KTUPLE=1, GAP PENALTY=3, WINDOW=5 and DIAGONALS SAVED=5. For nucleic acids these parameters are KTUPLE=2, GAP PENALTY=5, WINDOW=4 and DIAGONALS SAVED=4. After alignment of the sequences using the Clustal V program, it is possible to obtain a "percent identity" by viewing the "sequence distances" table in the same program.

The "Clustal W method of alignment" corresponds to the alignment method labeled Clustal W (described by Higgins and Sharp, (1989) *CABIOS* 5:151-153; Higgins et al., (1992)

*Comput Appl Biosci* 8:189-191) and found in the MegAlign™ v6.1 program of the LASERGENE bioinformatics computing suite (DNASTAR Inc., Madison, WI). Default parameters for multiple alignment (GAP PENALTY=10, GAP LENGTH PENALTY=0.2, Delay Divergen Seqs (%)=30, DNA Transition Weight=0.5, Protein Weight Matrix=Gonnet Series, DNA Weight Matrix=IUB). After alignment of the sequences using the Clustal W program, it is possible to obtain a "percent identity" by viewing the "sequence distances" table in the same program.

Unless otherwise stated, sequence identity/similarity values provided herein refer to the value obtained using GAP Version 10 (GCG, Accelrys, San Diego, CA) using the following parameters: % identity and % similarity for a nucleotide sequence using a gap creation penalty weight of 50 and a gap length extension penalty weight of 3, and the nwsgapdna.cmp scoring matrix; % identity and % similarity for an amino acid sequence using a GAP creation penalty weight of 8 and a gap length extension penalty of 2, and the BLOSUM62 scoring matrix (Henikoff and Henikoff, (1989) *Proc. Natl. Acad. Sci. USA* 89:10915). GAP uses the algorithm of Needleman and Wunsch, (1970) *J Mol Biol* 48:443-53, to find an alignment of two complete sequences that maximizes the number of matches and minimizes the number of gaps. GAP considers all possible alignments and gap positions and creates the alignment with the largest number of matched bases and the fewest gaps, using a gap creation penalty and a gap extension penalty in units of matched bases.

"BLAST" is a searching algorithm provided by the National Center for Biotechnology Information (NCBI) used to find regions of similarity between biological sequences. The program compares nucleotide or protein sequences to sequence databases and calculates the statistical significance of matches to identify sequences having sufficient similarity to a query sequence such that the similarity would not be predicted to have occurred randomly. BLAST reports the identified sequences and their local alignment to the query sequence.

It is well understood by one skilled in the art that many levels of sequence identity are useful in identifying polypeptides from other species or modified naturally or synthetically wherein such polypeptides have the same or similar function or activity. Useful examples of percent identities include, but are not limited to, 50%, 55%, 60%, 65%, 70%, 75%, 80%, 85%, 90% or 95%, or any integer percentage from 50% to 100%. Indeed, any integer amino acid identity from 50% to 100% may be useful in describing the present disclosure, such as 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

"Gene" includes a nucleic acid fragment that expresses a functional molecule such as, but not limited to, a specific protein, including regulatory sequences preceding (5' non-coding sequences) and following (3' non-coding sequences) the coding sequence. "Native gene" refers to a gene as found in nature with its own regulatory sequences.

A "mutated gene" is a gene that has been altered through human intervention. Such a "mutated gene" has a sequence that differs from the sequence of the corresponding non-mutated gene by at least one nucleotide addition, deletion, or substitution. In certain embodiments of the disclosure, the mutated gene comprises an alteration that results from a guide polynucleotide/Cas endonuclease system as disclosed herein. A mutated plant is a plant comprising a mutated gene.

As used herein, a "targeted mutation" is a mutation in a native gene that was made by altering a target sequence within the native gene using a method involving a double-strand-break-inducing agent that is capable of inducing a double-strand break in the DNA of the target sequence as disclosed herein or known in the art.

In one embodiment, the targeted mutation is the result of a guideRNA/Cas endonuclease induced gene editing as described herein. The guide RNA/Cas endonuclease induced targeted mutation can occur in a nucleotide sequence that is located within or outside a genomic target site that is recognized and cleaved by a Cas endonuclease.

The term "genome" as it applies to a plant cells encompasses not only chromosomal DNA found within the nucleus, but organelle DNA found within subcellular components (e.g., mitochondria, or plastid) of the cell.

A "codon-modified gene" or "codon-preferred gene" or "codon-optimized gene" is a gene having its frequency of codon usage designed to mimic the frequency of preferred codon usage of the host cell.

An "allele" is one of several alternative forms of a gene occupying a given locus on a chromosome. When all the alleles present at a given locus on a chromosome are the same, that plant is homozygous at that locus. If the alleles present at a given locus on a chromosome differ, that plant is heterozygous at that locus.

"Coding sequence" refers to a polynucleotide sequence which codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to: promoters, translation leader sequences, 5' untranslated sequences, 3' untranslated sequences, introns, polyadenylation target sequences, RNA processing sites, effector binding sites, and stem-loop structures.

"A plant-optimized nucleotide sequence" is nucleotide sequence that has been optimized for increased expression in plants, particularly for increased expression in plants or in one or more plants of interest. For example, a plant-optimized nucleotide sequence can be synthesized by modifying a nucleotide sequence encoding a protein such as, for example, double-strand-break-inducing agent (e.g., an endonuclease) as disclosed herein, using one or more plant-preferred codons for improved expression. See, for example, Campbell and Gowri (1990) *Plant Physiol.* 92:1-11 for a discussion of host-preferred codon usage.

Methods are available in the art for synthesizing plant-preferred genes. See, for example, U.S. Pat. Nos. 5,380,831, and 5,436,391, and Murray et al. (1989) Nucleic Acids Res. 17:477-498, herein incorporated by reference. Additional sequence modifications are known to enhance gene expression in a plant host. These include, for example, elimination of: one or more sequences encoding spurious polyadenylation signals, one or more exon-intron splice site signals, one or more transposon-like repeats, and other such well-characterized sequences that may be deleterious to gene expression. The G-C content of the sequence may be adjusted to levels average for a given plant host, as calculated by reference to known genes expressed in the host plant cell. When possible, the sequence is modified to avoid one or more predicted hairpin secondary mRNA structures.

Thus, "a plant-optimized nucleotide sequence" of the present disclosure comprises one or more of such sequence modifications.

"Promoter" refers to a DNA sequence capable of controlling the expression of a coding sequence or functional RNA. The promoter sequence consists of proximal and more distal upstream elements, the latter elements often referred to as enhancers. An "enhancer" is a DNA sequence that can stimulate promoter activity, and may be an innate element of the promoter or a heterologous element inserted to enhance the level or tissue-specificity of a promoter. Promoters may be derived in their entirety from a native gene, or be composed of different elements derived from different promoters found in nature, and/or comprise synthetic DNA segments. It is understood by those skilled in the art that different promoters may direct the expression of a gene in different tissues or cell types, or at different stages of development, or in response to different environmental conditions. It is further recognized that since in most cases the exact boundaries of regulatory sequences have not been completely defined, DNA fragments of some variation may have identical promoter activity. Promoters that cause a gene to be expressed in most cell types at most times are commonly referred to as "constitutive promoters".

It has been shown that certain promoters are able to direct RNA synthesis at a higher rate than others. These are called "strong promoters". Certain other promoters have been shown to direct RNA synthesis at higher levels only in particular types of cells or tissues and are often referred to as "tissue specific promoters", or "tissue-preferred promoters" if the promoters direct RNA synthesis preferably in certain tissues but also in other tissues at reduced levels. Since patterns of expression of a chimeric gene (or genes) introduced into a plant are controlled using promoters, there is an ongoing interest in the isolation of novel promoters which are capable of controlling the expression of a chimeric gene or (genes) at certain levels in specific tissue types or at specific plant developmental stages.

Some embodiments of the disclosures relate to newly discovered U6 RNA polymerase III promoters, GM-U6-13.1 (SEQ ID NO: 120) as described in Example 12 and GM-U6-9.1 (SEQ ID NO: 295) described in Example 19.

Non-limiting examples of methods and compositions relating to the soybean promoters described herein are as follows:

A1. A recombinant DNA construct comprising a nucleotide sequence comprising
  any of the sequences set forth in SEQ ID NO:120 or SEQ ID NO:295, or a functional fragment thereof, operably linked to at least one heterologous sequence, wherein said nucleotide sequence is a promoter.

A2. The recombinant DNA construct of embodiment A1, wherein the nucleotide sequence has at least 95% identity, based on the Clustal V method of alignment with pairwise alignment default parameters (KTUPLE=2, GAP PENALTY=5, WINDOW=4 and DIAGONALS SAVED=4), when compared to the sequence set forth in SEQ ID NO:120 or SEQ ID NO: 295.

A3. A vector comprising the recombinant DNA construct of embodiment A1.

A4. A cell comprising the recombinant DNA construct of embodiment A1.

A5. The cell of embodiment A4, wherein the cell is a plant cell.

A6. A transgenic plant having stably incorporated into its genome the recombinant DNA construct of embodiment A1.

A7. The transgenic plant of embodiment A6, wherein said plant is a dicot plant.

A8. The transgenic plant of embodiment A7 wherein the plant is soybean.

A9. A transgenic seed produced by the transgenic plant of embodiment A7, wherein the transgenic seed comprises the recombinant DNA construct.

A10. The recombinant DNA construct of embodiment A1 wherein the at least one heterologous sequence codes for a gene selected from the group consisting of: a reporter gene, a selection marker, a disease resistance conferring gene, a herbicide resistance conferring gene, an insect resistance conferring gene; a gene involved in carbohydrate metabolism, a gene involved in fatty acid metabolism, a gene involved in amino acid metabolism, a gene involved in plant development, a gene involved in plant growth regulation, a gene involved in yield improvement, a gene involved in drought resistance, a gene involved in cold resistance, a gene involved in heat resistance and a gene involved in salt resistance in plants.

A11. The recombinant DNA construct of embodiment A1, wherein the at least one heterologous sequence encodes a protein selected from the group consisting of: a reporter protein, a selection marker, a protein conferring disease resistance, protein conferring herbicide resistance, protein conferring insect resistance; protein involved in carbohydrate metabolism, protein involved in fatty acid metabolism, protein involved in amino acid metabolism, protein involved in plant development, protein involved in plant growth regulation, protein involved in yield improvement, protein involved in drought resistance, protein involved in cold resistance, protein involved in heat resistance and protein involved in salt resistance in plants.

A12. A method of expressing a coding sequence or a functional RNA in a plant comprising:
  a) introducing the recombinant DNA construct of embodiment A1 into the plant, wherein the at least one heterologous sequence comprises a coding sequence or encodes a functional RNA;
  b) growing the plant of step a); and
  c) selecting a plant displaying expression of the coding sequence or the functional RNA of the recombinant DNA construct.

A13. A method of transgenically altering a marketable plant trait, comprising:
  a) introducing a recombinant DNA construct of embodiment A1 into the plant;
  b) growing a fertile, mature plant resulting from step a); and
  c) selecting a plant expressing the at least one heterologous sequence in at least one plant tissue based on the altered marketable trait.

A14. The method of embodiment A13 wherein the marketable trait is selected from the group consisting of: disease resistance, herbicide resistance, insect resistance carbohydrate metabolism, fatty acid metabolism, amino acid metabolism, plant development, plant growth regulation, yield improvement, drought resistance, cold resistance, heat resistance, and salt resistance.

A15. A method for altering expression of at least one heterologous sequence in a plant comprising:
  (a) transforming a plant cell with the recombinant DNA construct of embodiment A1;
  (b) growing fertile mature plants from transformed plant cell of step (a); and (c) selecting plants containing the transformed plant cell wherein the expression of the heterologous sequence is increased or decreased.

A16. The method of Embodiment A15 wherein the plant is a soybean plant.

A17. A plant stably transformed with a recombinant DNA construct comprising a soybean promoter and a heterologous nucleic acid fragment operably linked to said promoter, wherein said promoter is a capable of controlling expression of said heterologous nucleic acid fragment in a plant cell, and further wherein said promoter comprises any of the sequences set forth in SEQ ID NO: 120 or SEQ ID NO:295.

New promoters of various types useful in plant cells are constantly being discovered; numerous examples may be found in the compilation by Okamuro and Goldberg, (1989) In *The Biochemistry of Plants*, Vol. 115, Stumpf and Conn, eds (New York, NY: Academic Press), pp. 1-82.

"Translation leader sequence" refers to a polynucleotide sequence located between the promoter sequence of a gene and the coding sequence. The translation leader sequence is present in the mRNA upstream of the translation start sequence. The translation leader sequence may affect processing of the primary transcript to mRNA, mRNA stability or translation efficiency. Examples of translation leader sequences have been described (e.g., Turner and Foster, (1995) *Mol Biotechnol* 3:225-236).

"3' non-coding sequences", "transcription terminator" or "termination sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complimentary copy of the DNA sequence, it is referred to as the primary transcript or pre-mRNA. A RNA transcript is referred to as the mature RNA or mRNA when it is a RNA sequence derived from post-transcriptional processing of the primary transcript pre mRNAt. "Messenger RNA" or "mRNA" refers to the RNA that is without introns and that can be translated into protein by the cell. "cDNA" refers to a DNA that is complementary to, and synthesized from, a mRNA template using the enzyme reverse transcriptase. The cDNA can be single-stranded or converted into double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA, and that blocks the expression of a target gene (see, e.g., U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., the coding sequence is under the transcriptional control of the promoter). Coding sequences can be operably linked to regulatory sequences in a sense or antisense orientation. In another example, the complementary RNA regions can be operably linked, either directly or indirectly, 5' to the target mRNA, or 3' to the target mRNA, or within the target mRNA, or a first complementary region is 5' and its complement is 3' to the target mRNA.

Standard recombinant DNA and molecular cloning techniques used herein are well known in the art and are described more fully in Sambrook et al., *Molecular Cloning: A Laboratory Manual; Cold Spring Harbor Laboratory*: Cold Spring Harbor, NY (1989). Transformation methods are well known to those skilled in the art and are described infra.

"PCR" or "polymerase chain reaction" is a technique for the synthesis of specific DNA segments and consists of a series of repetitive denaturation, annealing, and extension cycles. Typically, a double-stranded DNA is heat denatured, and two primers complementary to the 3' boundaries of the target segment are annealed to the DNA at low temperature, and then extended at an intermediate temperature. One set of these three consecutive steps is referred to as a "cycle".

The term "recombinant" refers to an artificial combination of two otherwise separated segments of sequence, e.g., by chemical synthesis, or manipulation of isolated segments of nucleic acids by genetic engineering techniques.

The terms "plasmid", "vector" and "cassette" refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell. "Transformation cassette" refers to a specific vector containing a gene and having elements in addition to the gene that facilitates transformation of a particular host cell. "Expression cassette" refers to a specific vector containing a gene and having elements in addition to the gene that allow for expression of that gene in a host.

The terms "recombinant DNA molecule", "recombinant construct", "expression construct", "construct", "construct", and "recombinant DNA construct" are used interchangeably herein. A recombinant construct comprises an artificial combination of nucleic acid fragments, e.g., regulatory and coding sequences that are not all found together in nature. For example, a construct may comprise regulatory sequences and coding sequences that are derived from different sources, or regulatory sequences and coding sequences derived from the same source, but arranged in a manner different than that found in nature. Such a construct may be used by itself or may be used in conjunction with a vector. If a vector is used, then the choice of vector is dependent upon the method that will be used to transform host cells as is well known to those skilled in the art. For example, a plasmid vector can be used. The skilled artisan is well aware of the genetic elements that must be present on the vector in order to successfully transform, select and propagate host cells. The skilled artisan will also recognize that different independent transformation events may result in different levels and patterns of expression (Jones et al., (1985) *EMBO J* 4:2411-2418; De Almeida et al., (1989) *Mol Gen Genetics* 218:78-86), and thus that multiple events are typically screened in order to obtain lines displaying the desired expression level and pattern. Such screening may be accomplished standard molecular biological, biochemical, and other assays including Southern analysis of DNA, Northern analysis of mRNA expression, PCR, real time quantitative PCR (qPCR), reverse transcription PCR (RT-PCR), immunoblotting analysis of protein expression, enzyme or activity assays, and/or phenotypic analysis.

The term "expression", as used herein, refers to the production of a functional end-product (e.g., an mRNA, guide RNA, or a protein) in either precursor or mature form.

The term "introduced" means providing a nucleic acid (e.g., expression construct) or protein into a cell. Introduced includes reference to the incorporation of a nucleic acid into a eukaryotic or prokaryotic cell where the nucleic acid may be incorporated into the genome of the cell, and includes reference to the transient provision of a nucleic acid or protein to the cell. Introduced includes reference to stable or transient transformation methods, as well as sexually crossing. Thus, "introduced" in the context of inserting a nucleic acid fragment (e.g., a recombinant DNA construct/expression construct) into a cell, means "transfection" or "transformation" or "transduction" and includes reference to the incorporation of a nucleic acid fragment into a eukaryotic or prokaryotic cell where the nucleic acid fragment may be incorporated into the genome of the cell (e.g., chromosome, plasmid, plastid, or mitochondrial DNA), converted into an autonomous replicon, or transiently expressed (e.g., transfected mRNA).

"Mature" protein refers to a post-translationally processed polypeptide (i.e., one from which any pre- or propeptides present in the primary translation product have been removed). "Precursor" protein refers to the primary product of translation of mRNA (i.e., with pre- and propeptides still present). Pre- and propeptides may be but are not limited to intracellular localization signals.

"Stable transformation" refers to the transfer of a nucleic acid fragment into a genome of a host organism, including both nuclear and organellar genomes, resulting in genetically stable inheritance. In contrast, "transient transformation" refers to the transfer of a nucleic acid fragment into the nucleus, or other DNA-containing organelle, of a host organism resulting in gene expression without integration or stable inheritance. Host organisms containing the transformed nucleic acid fragments are referred to as "transgenic" organisms.

The commercial development of genetically improved germplasm has also advanced to the stage of introducing multiple traits into crop plants, often referred to as a gene stacking approach. In this approach, multiple genes conferring different characteristics of interest can be introduced into a plant. Gene stacking can be accomplished by many means including but not limited to co-transformation, retransformation, and crossing lines with different genes of interest.

The term "plant" refers to whole plants, plant organs, plant tissues, seeds, plant cells, seeds and progeny of the same. Plant cells include, without limitation, cells from seeds, suspension cultures, embryos, meristematic regions, callus tissue, leaves, roots, shoots, gametophytes, sporophytes, pollen and microspores. Plant parts include differentiated and undifferentiated tissues including, but not limited to roots, stems, shoots, leaves, pollens, seeds, tumor tissue and various forms of cells and culture (e.g., single cells, protoplasts, embryos, and callus tissue). The plant tissue may be in plant or in a plant organ, tissue or cell culture. The term "plant organ" refers to plant tissue or a group of tissues that constitute a morphologically and functionally distinct part of a plant. The term "genome" refers to the entire complement of genetic material (genes and non-coding sequences) that is present in each cell of an organism, or virus or organelle; and/or a complete set of chromosomes inherited as a (haploid) unit from one parent. "Progeny" comprises any subsequent generation of a plant.

A transgenic plant includes, for example, a plant which comprises within its genome a heterologous polynucleotide introduced by a transformation step. The heterologous polynucleotide can be stably integrated within the genome such that the polynucleotide is passed on to successive generations. The heterologous polynucleotide may be integrated into the genome alone or as part of a recombinant DNA construct. A transgenic plant can also comprise more than one heterologous polynucleotide within its genome. Each heterologous polynucleotide may confer a different trait to the transgenic plant. A heterologous polynucleotide can include a sequence that originates from a foreign species, or, if from the same species, can be substantially modified from its native form. Transgenic can include any cell, cell line, callus, tissue, plant part or plant, the genotype of which has been altered by the presence of heterologous nucleic acid including those transgenics initially so altered as well as those created by sexual crosses or asexual propagation from the initial transgenic. The alterations of the genome (chromosomal or extra-chromosomal) by conventional plant breeding methods, by the genome editing procedure described herein that does not result in an insertion of a foreign polynucleotide, or by naturally occurring events such as random cross-fertilization, non-recombinant viral infection, non-recombinant bacterial transformation, non-recombinant transposition, or spontaneous mutation are not intended to be regarded as transgenic.

In certain embodiments of the disclosure, a fertile plant is a plant that produces viable male and female gametes and is self-fertile. Such a self-fertile plant can produce a progeny plant without the contribution from any other plant of a gamete and the genetic material contained therein. Other embodiments of the disclosure can involve the use of a plant that is not self-fertile because the plant does not produce male gametes, or female gametes, or both, that are viable or otherwise capable of fertilization. As used herein, a "male sterile plant" is a plant that does not produce male gametes that are viable or otherwise capable of fertilization. As used herein, a "female sterile plant" is a plant that does not produce female gametes that are viable or otherwise capable of fertilization. It is recognized that male-sterile and female-sterile plants can be female-fertile and male-fertile, respectively. It is further recognized that a male fertile (but female sterile) plant can produce viable progeny when crossed with a female fertile plant and that a female fertile (but male sterile) plant can produce viable progeny when crossed with a male fertile plant.

A "centimorgan" (cM) or "map unit" is the distance between two linked genes, markers, target sites, loci, or any pair thereof, wherein 1% of the products of meiosis are recombinant. Thus, a centimorgan is equivalent to a distance equal to a 1% average recombination frequency between the two linked genes, markers, target sites, loci, or any pair thereof.

Breeding Methods and Methods for Selecting Plants Utilizing a Two Component RNA Guide and Cas Endonuclease System The present disclosure finds use in the breeding of plants comprising one or more transgenic traits. Most commonly, transgenic traits are randomly inserted throughout the plant genome as a consequence of transformation systems based on *Agrobacterium*, biolistics, or other commonly used procedures. More recently, gene targeting protocols have been developed that enable directed transgene insertion. One important technology, site-specific integration (SSI) enables the targeting of a transgene to the same chromosomal location as a previously inserted transgene. Custom-designed meganucleases and custom-designed zinc finger meganucleases allow researchers to design nucleases to target specific chromosomal locations, and these reagents allow the targeting of transgenes at the chromosomal site cleaved by these nucleases.

The currently used systems for precision genetic engineering of eukaryotic genomes, e.g. plant genomes, rely upon homing endonucleases, meganucleases, zinc finger nucleases, and transcription activator-like effector nucleases (TALENs), which require de novo protein engineering for every new target locus. The highly specific, RNA-directed DNA nuclease, guide RNA/Cas9 endonuclease system described herein, is more easily customizable and therefore more useful when modification of many different target sequences is the goal. This disclosure takes further advantage of the two component nature of the guide RNA/Cas system, with its constant protein component, the Cas endonuclease, and its variable and easily reprogrammable targeting component, the guide RNA or the crRNA.

The guide RNA/Cas system described herein is especially useful for genome engineering, especially plant genome engineering, in circumstances where nuclease off-target cutting can be toxic to the targeted cells. In one embodiment of the guide RNA/Cas system described herein, the constant component, in the form of an expression-optimized Cas9 gene, is stably integrated into the target genome, e.g. plant genome. Expression of the Cas9 gene is under control of a promoter, e.g. plant promoter, which can be a constitutive promoter, tissue-specific promoter or inducible promoter, e.g. temperature-inducible, stress-inducible, developmental stage inducible, or chemically inducible promoter. In the absence of the variable component, i.e. the guide RNA or crRNA, the Cas9 protein is not able to cut DNA and therefore its presence in the plant cell should have little or no consequence. Hence a key advantage of the guide RNA/Cas system described herein is the ability to create and maintain a cell line or transgenic organism capable of efficient expression of the Cas9 protein with little or no consequence to cell viability. In order to induce cutting at desired genomic sites to achieve targeted genetic modifications, guide RNAs or crRNAs can be introduced by a variety of methods into cells containing the stably-integrated and expressed cas9 gene. For example, guide RNAs or crRNAs can be chemically or enzymatically synthesized, and introduced into the Cas9 expressing cells via direct delivery methods such a particle bombardment or electroporation.

Alternatively, genes capable of efficiently expressing guide RNAs or crRNAs in the target cells can be synthesized chemically, enzymatically or in a biological system, and these genes can be introduced into the Cas9 expressing cells via direct delivery methods such a particle bombardment, electroporation or biological delivery methods such as *Agrobacterium* mediated DNA delivery.

One embodiment of the disclosure is a method for selecting a plant comprising an altered target site in its plant genome, the method comprising: a) obtaining a first plant comprising at least one Cas endonuclease capable of introducing a double strand break at a target site in the plant genome; b) obtaining a second plant comprising a guide RNA that is capable of forming a complex with the Cas endonuclease of (a), c) crossing the first plant of (a) with the second plant of (b); d) evaluating the progeny of (c) for an alteration in the target site and e) selecting a progeny plant that possesses the desired alteration of said target site.

Another embodiment of the disclosure is a method for selecting a plant comprising an altered target site in its plant genome, the method comprising: a) obtaining a first plant comprising at least one Cas endonuclease capable of introducing a double strand break at a target site in the plant genome; b) obtaining a second plant comprising a guide RNA and a donor DNA, wherein said guide RNA is capable of forming a complex with the Cas endonuclease of (a), wherein said donor DNA comprises a polynucleotide of interest; c) crossing the first plant of (a) with the second plant of (b); d) evaluating the progeny of (c) for an alteration in the target site and e) selecting a progeny plant that comprises the polynucleotide of interest inserted at said target site.

Another embodiment of the disclosure is a method for selecting a plant comprising an altered target site in its plant genome, the method comprising selecting at least one progeny plant that comprises an alteration at a target site in its plant genome, wherein said progeny plant was obtained by crossing a first plant expressing at least one Cas endonuclease to a second plant comprising a guide RNA and a donor DNA, wherein said Cas endonuclease is capable of introducing a double strand break at said target site, wherein said donor DNA comprises a polynucleotide of interest.

As disclosed herein, a guide RNA/Cas system mediating gene targeting can be used in methods for directing transgene insertion and/or for producing complex transgenic trait loci comprising multiple transgenes in a fashion similar as disclosed in WO2013/0198888 (published Aug. 1, 2013) where instead of using a double strand break inducing agent to introduce a gene of interest, a guide RNA/Cas system or a guide polynucleotide/Cas system as disclosed herein is used. In one embodiment, a complex transgenic trait locus is a genomic locus that has multiple transgenes genetically linked to each other. By inserting independent transgenes within 0.1, 0.2, 0.3, 04, 0.5, 1, 2, or even 5 centimorgans (cM) from each other, the transgenes can be bred as a single genetic locus (see, for example, U.S. patent application Ser. No. 13/427,138) or PCT application PCT/US2012/030061. After selecting a plant comprising a transgene, plants containing (at least) one transgenes can be crossed to form an F1 that contains both transgenes. In progeny from these F1 (F2 or BC1) 1/500 progeny would have the two different transgenes recombined onto the same chromosome. The complex locus can then be bred as single genetic locus with both transgene traits. This process can be repeated to stack as many traits as desired.

Chromosomal intervals that correlate with a phenotype or trait of interest can be identified. A variety of methods well known in the art are available for identifying chromosomal intervals. The boundaries of such chromosomal intervals are drawn to encompass markers that will be linked to the gene controlling the trait of interest. In other words, the chromosomal interval is drawn such that any marker that lies within that interval (including the terminal markers that define the boundaries of the interval) can be used as a marker for northern leaf blight resistance. In one embodiment, the chromosomal interval comprises at least one QTL, and furthermore, may indeed comprise more than one QTL. Close proximity of multiple QTLs in the same interval may obfuscate the correlation of a particular marker with a particular QTL, as one marker may demonstrate linkage to more than one QTL. Conversely, e.g., if two markers in close proximity show co-segregation with the desired phenotypic trait, it is sometimes unclear if each of those markers identifies the same QTL or two different QTL. The term "quantitative trait locus" or "QTL" refers to a region of DNA that is associated with the differential expression of a quantitative phenotypic trait in at least one genetic background, e.g., in at least one breeding population. The region of the QTL encompasses or is closely linked to the gene or genes that affect the trait in question. An "allele of a QTL" can comprise multiple genes or other genetic factors within a contiguous genomic region or linkage group, such as a haplotype. An allele of a QTL can denote a haplotype within a specified window wherein said window is a contiguous genomic region that can be defined, and tracked, with a set of one or more polymorphic markers. A haplotype can be defined by the unique fingerprint of alleles at each marker within the specified window.

A variety of methods are available to identify those cells having an altered genome at or near a target site without using a screenable marker phenotype. Such methods can be viewed as directly analyzing a target sequence to detect any change in the target sequence, including but not limited to PCR methods, sequencing methods, nuclease digestion, Southern blots, and any combination thereof.

Proteins may be altered in various ways including amino acid substitutions, deletions, truncations, and insertions. Methods for such manipulations are generally known. For example, amino acid sequence variants of the protein(s) can be prepared by mutations in the DNA. Methods for mutagenesis and nucleotide sequence alterations include, for example, Kunkel, (1985) *Proc. Natl. Acad. Sci. USA* 82:488-92; Kunkel et al., (1987) *Meth Enzymol* 154:367-82; U.S. Pat. No. 4,873,192; Walker and Gaastra, eds. (1983) *Techniques in Molecular Biology* (MacMillan Publishing Company, New York) and the references cited therein. Guidance regarding amino acid substitutions not likely to affect biological activity of the protein is found, for example, in the model of Dayhoff et al., (1978) *Atlas of Protein Sequence and Structure* (Natl Biomed Res Found, Washington, D.C.). Conservative substitutions, such as exchanging one amino acid with another having similar properties, may be preferable. Conservative deletions, insertions, and amino acid substitutions are not expected to produce radical changes in the characteristics of the protein, and the effect of any substitution, deletion, insertion, or combination thereof can be evaluated by routine screening assays. Assays for double-strand-break-inducing activity are known and generally measure the overall activity and specificity of the agent on DNA substrates containing target sites.

A variety of methods are known for the introduction of nucleotide sequences and polypeptides into an organism, including, for example, transformation, sexual crossing, and the introduction of the polypeptide, DNA, or mRNA into the cell.

Methods for contacting, providing, and/or introducing a composition into various organisms are known and include but are not limited to, stable transformation methods, transient transformation methods, virus-mediated methods, and sexual breeding. Stable transformation indicates that the introduced polynucleotide integrates into the genome of the organism and is capable of being inherited by progeny thereof. Transient transformation indicates that the introduced composition is only temporarily expressed or present in the organism.

Protocols for introducing polynucleotides and polypeptides into plants may vary depending on the type of plant or plant cell targeted for transformation, such as monocot or dicot. Suitable methods of introducing polynucleotides and polypeptides into plant cells and subsequent insertion into the plant genome include microinjection (Crossway et al., (1986) *Biotechniques* 4:320-34 and U.S. Pat. No. 6,300,543), meristem transformation (U.S. Pat. No. 5,736,369), electroporation (Riggs et al., (1986) *Proc. Natl. Acad. Sci. USA* 83:5602-6, *Agrobacterium*-mediated transformation (U.S. Pat. Nos. 5,563,055 and 5,981,840), direct gene transfer (Paszkowski et al., (1984) *EMBO J* 3:2717-22), and ballistic particle acceleration (U.S. Pat. Nos. 4,945,050; 5,879,918; 5,886,244; 5,932,782; Tomes et al., (1995) "Direct DNA Transfer into Intact Plant Cells via Microprojectile Bombardment" in *Plant Cell, Tissue, and Organ Culture: Fundamental Methods*, ed. Gamborg & Phillips (Springer-Verlag, Berlin); McCabe et al., (1988) *Biotechnology* 6:923-6; Weissinger et al., (1988) *Ann Rev Genet* 22:421-77; Sanford et al., (1987) *Particulate Science and Technology* 5:27-37 (onion); Christou et al., (1988) *Plant Physiol* 87:671-4 (soybean); Finer and McMullen, (1991) *In Vitro Cell Dev Biol* 27P:175-82 (soybean); Singh et al., (1998) *Theor Appl Genet* 96:319-24 (soybean); Datta et al., (1990) *Biotechnology* 8:736-40 (rice); Klein et al., (1988) *Proc. Natl. Acad. Sci. USA* 85:4305-9 (maize); Klein et al., (1988) *Biotechnology* 6:559-63 (maize); U.S. Pat. Nos. 5,240,855; 5,322,783 and 5,324,646; Klein et al., (1988) *Plant Physiol* 91:440-4 (maize); Fromm et al., (1990) *Biotechnology* 8:833-9 (maize); Hooykaas-Van Slogteren et al., (1984) *Nature* 311:763-4; U.S. Pat. No. 5,736,369 (cereals); Bytebier et al., (1987) *Proc. Natl. Acad. Sci. USA* 84:5345-9 (Liliaceae); De Wet et al., (1985) in The Experimental Manipulation of Ovule Tissues, ed. Chapman et al., (Longman, New York), pp. 197-209 (pollen); Kaeppler et al., (1990) *Plant Cell Rep* 9:415-8) and Kaeppler et al., (1992) *Theor Appl Genet* 84:560-6 (whisker-mediated transformation); D'Halluin et al., (1992) *Plant Cell* 4:1495-505 (electroporation); Li et al., (1993) *Plant Cell Rep* 12:250-5; Christou and Ford (1995) *Annals Botany* 75:407-13 (rice) and Osjoda et al., (1996) *Nat Biotechnol* 14:745-50 (maize via *Agrobacterium tumefaciens*).

Alternatively, polynucleotides may be introduced into plants by contacting plants with a virus or viral nucleic acids. Generally, such methods involve incorporating a polynucleotide within a viral DNA or RNA molecule. In some examples a polypeptide of interest may be initially synthesized as part of a viral polyprotein, which is later processed by proteolysis in vivo or in vitro to produce the desired recombinant protein. Methods for introducing polynucleotides into plants and expressing a protein encoded therein, involving viral DNA or RNA molecules, are known, see, for example, U.S. Pat. Nos. 5,889,191, 5,889,190, 5,866,785, 5,589,367 and 5,316,931. Transient transformation methods include, but are not limited to, the introduction of polypeptides, such as a double-strand break inducing agent, directly into the organism, the introduction of polynucleotides such as DNA and/or RNA polynucleotides, and the introduction of the RNA transcript, such as an mRNA encoding a double-strand break inducing agent, into the organism. Such methods include, for example, microinjection or particle bombardment. See, for example Crossway et al., (1986) *Mol Gen Genet* 202:179-85; Nomura et al., (1986) *Plant Sci* 44:53-8; Hepler et al., (1994) *Proc. Natl. Acad. Sci. USA* 91:2176-80; and, Hush et al., (1994) *J Cell Sci* 107:775-84.

The term "dicot" refers to the subclass of angiosperm plants also knows as "dicotyledoneae" and includes reference to whole plants, plant organs (e.g., leaves, stems, roots, etc.), seeds, plant cells, and progeny of the same. Plant cell, as used herein includes, without limitation, seeds, suspension cultures, embryos, meristematic regions, callus tissue, leaves, roots, shoots, gametophytes, sporophytes, pollen, and microspores.

The term "crossed" or "cross" or "crossing" in the context of this disclosure means the fusion of gametes via pollination to produce progeny (i.e., cells, seeds, or plants). The term encompasses both sexual crosses (the pollination of one plant by another) and selfing (self-pollination, i.e., when the pollen and ovule (or microspores and megaspores) are from the same plant or genetically identical plants).

The term "introgression" refers to the transmission of a desired allele of a genetic locus from one genetic background to another. For example, introgression of a desired allele at a specified locus can be transmitted to at least one progeny plant via a sexual cross between two parent plants, where at least one of the parent plants has the desired allele within its genome. Alternatively, for example, transmission of an allele can occur by recombination between two donor genomes, e.g., in a fused protoplast, where at least one of the donor protoplasts has the desired allele in its genome. The desired allele can be, e.g., a transgene, a modified (mutated or edited) native allele, or a selected allele of a marker or QTL.

Standard DNA isolation, purification, molecular cloning, vector construction, and verification/characterization methods are well established, see, for example Sambrook et al., (1989) *Molecular Cloning: A Laboratory Manual*, (Cold Spring Harbor Laboratory Press, NY). Vectors and constructs include circular plasmids, and linear polynucleotides, comprising a polynucleotide of interest and optionally other components including linkers, adapters, regulatory regions, introns, restriction sites, enhancers, insulators, selectable markers, nucleotide sequences of interest, promoters, and/or other sites that aid in vector construction or analysis. In some examples a recognition site and/or target site can be contained within an intron, coding sequence, 5' UTRs, 3' UTRs, and/or regulatory regions.

The present disclosure further provides expression constructs for expressing in a plant, plant cell, or plant part a guide RNA/Cas system that is capable of binding to and creating a double strand break in a target site. In one embodiment, the expression constructs of the disclosure comprise a promoter operably linked to a nucleotide sequence encoding a Cas gene and a promoter operably linked to a guide RNA of the present disclosure. The promoter is capable of driving expression of an operably linked nucleotide sequence in a plant cell.

A promoter is a region of DNA involved in recognition and binding of RNA polymerase and other proteins to initiate transcription. A plant promoter is a promoter capable of initiating transcription in a plant cell, for a review of plant promoters, see, Potenza et al., (2004) *In Vitro Cell Dev Biol* 40:1-22. Constitutive promoters include, for example, the core promoter of the Rsyn7 promoter and other constitutive promoters disclosed in WO99/43838 and U.S. Pat. No. 6,072,050; the core CaMV 35S promoter (Odell et al., (1985) *Nature* 313:810-2); rice actin (McElroy et al., (1990) *Plant Cell* 2:163-71); ubiquitin (Christensen et al., (1989) *Plant Mol Biol* 12:619-32; Christensen et al., (1992) *Plant Mol Biol* 18:675-89); pEMU (Last et al., (1991) *Theor Appl Genet* 81:581-8); MAS (Velten et al., (1984) *EMBO J* 3:2723-30); ALS promoter (U.S. Pat. No. 5,659,026), and the like. Other constitutive promoters are described in, for example, U.S. Pat. Nos. 5,608,149; 5,608,144; 5,604,121; 5,569,597; 5,466,785; 5,399,680; 5,268,463; 5,608,142 and 6,177,611. In some examples an inducible promoter may be used. Pathogen-inducible promoters induced following infection by a pathogen include, but are not limited to those regulating expression of PR proteins, SAR proteins, beta-1, 3-glucanase, chitinase, etc.

Chemical-regulated promoters can be used to modulate the expression of a gene in a plant through the application of an exogenous chemical regulator. The promoter may be a chemical-inducible promoter, where application of the chemical induces gene expression, or a chemical-repressible promoter, where application of the chemical represses gene expression. Chemical-inducible promoters include, but are not limited to, the maize In2-2 promoter, activated by benzene sulfonamide herbicide safeners (De Veylder et al., (1997) *Plant Cell Physiol* 38:568-77), the maize GST promoter (GST-II-27, WO93/01294), activated by hydrophobic electrophilic compounds used as pre-emergent herbicides, and the tobacco PR-1a promoter (Ono et al., (2004) *Biosci Biotechnol Biochem* 68:803-7) activated by salicylic acid. Other chemical-regulated promoters include steroid-responsive promoters (see, for example, the glucocorticoid-inducible promoter (Schena et al., (1991) *Proc. Natl. Acad. Sci. USA* 88:10421-5; McNellis et al., (1998) *Plant J* 14:247-257); tetracycline-inducible and tetracycline-repressible promoters (Gatz et al., (1991)*Mol Gen Genet* 227:229-37; U.S. Pat. Nos. 5,814,618 and 5,789,156).

Tissue-preferred promoters can be utilized to target enhanced expression within a particular plant tissue. Tissue-preferred promoters include, for example, Kawamata et al., (1997) *Plant Cell Physiol* 38:792-803; Hansen et al., (1997) *Mol Gen Genet* 254:337-43; Russell et al., (1997) *Transgenic Res* 6:157-68; Rinehart et al., (1996) *Plant Physiol* 112:1331-41; Van Camp et al., (1996) *Plant Physiol* 112: 525-35; Canevascini et al., (1996) *Plant Physiol* 112:513-524; Lam, (1994) *Results Probl Cell Differ* 20:181-96; and Guevara-Garcia et al., (1993) Plant J4:495-505. Leaf-preferred promoters include, for example, Yamamoto et al., (1997) *Plant J* 12:255-65; Kwon et al., (1994) *Plant Physiol* 105:357-67; Yamamoto et al., (1994) *Plant Cell Physiol* 35:773-8; Gotor et al., (1993) Plant J3:509-18; Orozco et al., (1993) *Plant Mol Biol* 23:1129-38; Matsuoka et al., (1993) *Proc. Natl. Acad. Sci. USA* 90:9586-90; Simpson et al., (1958) *EMBO J* 4:2723-9; Timko et al., (1988) *Nature* 318:57-8. Root-preferred promoters include, for example, Hire et al., (1992) *Plant Mol Biol* 20:207-18 (soybean root-specific glutamine synthase gene); Miao et al., (1991) *Plant Cell* 3:11-22 (cytosolic glutamine synthase (GS)); Keller and Baumgartner, (1991) *Plant Cell* 3:1051-61 (root-specific control element in the GRP 1.8 gene of French bean); Sanger et al., (1990) *Plant Mol Biol* 14:433-43 (root-specific promoter of *A. tumefaciens* mannopine synthase (MAS)); Bogusz et al., (1990) *Plant Cell* 2:633-41 (root-specific promoters isolated from *Parasponia andersonii* and *Trema tomentosa*); Leach and Aoyagi, (1991) *Plant Sci* 79:69-76 (*A. rhizogenes* rolC and rolD root-inducing genes); Teeri et al., (1989) *EMBO J* 8:343-50 (*Agrobacterium* wound-induced TR1' and TR2' genes); VfENOD-GRP3 gene promoter (Kuster et al., (1995) *Plant Mol Biol* 29:759-72); and rolB promoter (Capana et al., (1994) *Plant Mol Biol* 25:681-91; phaseolin gene (Murai et al., (1983) *Science* 23:476-82; Sengopta-Gopalen et al., (1988) *Proc. Natl. Acad. Sci. USA* 82:3320-4). See also, U.S. Pat. Nos. 5,837,876; 5,750,386; 5,633,363; 5,459,252; 5,401,836; 5,110,732 and 5,023,179.

Seed-preferred promoters include both seed-specific promoters active during seed development, as well as seed-germinating promoters active during seed germination. See, Thompson et al., (1989) *BioEssays* 10:108. Seed-preferred promoters include, but are not limited to, Cim1 (cytokinin-induced message); cZ19B1 (maize 19 kDa zein); and milps (myo-inositol-1-phosphate synthase); (WO00/11177; and U.S. Pat. No. 6,225,529). For dicots, seed-preferred promoters include, but are not limited to, bean β-phaseolin, napin, β-conglycinin, soybean lectin, cruciferin, and the like. For monocots, seed-preferred promoters include, but are not limited to, maize 15 kDa zein, 22 kDa zein, 27 kDa gamma zein, waxy, shrunken 1, shrunken 2, globulin 1, oleosin, and nuc1. See also, WO00/12733, where seed-preferred promoters from END1 and END2 genes are disclosed.

A phenotypic marker is a screenable or selectable marker that includes visual markers and selectable markers whether it is a positive or negative selectable marker. Any phenotypic marker can be used. Specifically, a selectable or screenable marker comprises a DNA segment that allows one to identify, or select for or against a molecule or a cell that contains it, often under particular conditions. These markers can encode an activity, such as, but not limited to, production of RNA, peptide, or protein, or can provide a binding site for RNA, peptides, proteins, inorganic and organic compounds or compositions and the like.

Examples of selectable markers include, but are not limited to, DNA segments that comprise restriction enzyme sites; DNA segments that encode products which provide resistance against otherwise toxic compounds including antibiotics, such as, spectinomycin, ampicillin, kanamycin, tetracycline, Basta, neomycin phosphotransferase II (NEO) and hygromycin phosphotransferase (HPT)); DNA segments that encode products which are otherwise lacking in the recipient cell (e.g., tRNA genes, auxotrophic markers); DNA segments that encode products which can be readily identified (e.g., phenotypic markers such as β-galactosidase, GUS; fluorescent proteins such as green fluorescent protein (GFP), cyan (CFP), yellow (YFP), red (RFP), and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; and, the inclusion of a DNA sequences required for a specific modification (e.g., methylation) that allows its identification.

Additional selectable markers include genes that confer resistance to herbicidal compounds, such as glufosinate ammonium, bromoxynil, imidazolinones, and 2,4-dichlorophenoxyacetate (2,4-D). See for example, Yarranton, (1992) *Curr Opin Biotech* 3:506-11; Christopherson et al., (1992) *Proc. Natl. Acad. Sci. USA* 89:6314-8; Yao et al., (1992) *Cell* 71:63-72; Reznikoff, (1992) *Mol Microbiol* 6:2419-22; Hu et al., (1987) *Cell* 48:555-66; Brown et al., (1987) *Cell* 49:603-12; Figge et al., (1988) *Cell* 52:713-22; Deuschle et al., (1989) *Proc. Natl. Acad. Sci. USA* 86:5400-4; Fuerst et al., (1989) *Proc. Natl. Acad. Sci. USA* 86:2549-53; Deuschle et al., (1990) *Science* 248:480-3; Gossen, (1993) 5 Ph.D. Thesis, University of Heidelberg; Reines et al., (1993) *Proc. Natl. Acad. Sci. USA* 90:1917-21; Labow et al., (1990) *Mol Cell Biol* 10:3343-56; Zambretti et al., (1992) *Proc. Natl. Acad. Sci. USA* 89:3952-6; Baim et al., (1991) *Proc. Natl. Acad. Sci. USA* 88:5072-6; Wyborski et al., (1991) *Nucleic Acids Res* 19:4647-53; Hillen and Wissman, (1989) *Topics Mol Struc Biol* 10:143-62; Degenkolb et al., (1991) *Antimicrob Agents Chemother* 35:1591-5; Kleinschnidt et al., (1988) *Biochemistry* 27:1094-104; Bonin, (1993) Ph.D. Thesis, University of Heidelberg; Gossen et al., (1992) *Proc. Natl. Acad. Sci. USA* 89:5547-51; Oliva et al., (1992) *Antimicrob Agents Chemother* 36:913-9; Hlavka et al., (1985) *Handbook of Experimental Pharmacology*, Vol. 78 (Springer-Verlag, Berlin); Gill et al., (1988) *Nature* 334:721-4.

The cells having the introduced sequence may be grown or regenerated into plants using conventional conditions, see for example, McCormick et al., (1986) *Plant Cell Rep* 5:81-4. These plants may then be grown, and either pollinated with the same transformed strain or with a different transformed or untransformed strain, and the resulting progeny having the desired characteristic and/or comprising the introduced polynucleotide or polypeptide identified. Two or more generations may be grown to ensure that the polynucleotide is stably maintained and inherited, and seeds harvested.

Any plant can be used, including monocot and dicot plants. Examples of monocot plants that can be used include, but are not limited to, corn (*Zea mays*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), wheat (*Triticum aestivum*), sugarcane (*Saccharum* spp.), oats (*Avena*), barley (*Hordeum*), switchgrass (*Panicum virgatum*), pineapple (*Ananas comosus*), banana (*Musa* spp.), palm, ornamentals, turfgrasses, and other grasses. Examples of dicot plants that can be used include, but are not limited to, soybean (*Glycine max*), canola (*Brassica napus* and *B. campestris*), alfalfa (*Medicago sativa*), tobacco (*Nicotiana tabacum*), Arabidopsis (*Arabidopsis thaliana*), sunflower (*Helianthus annuus*), cotton (*Gossypium arboreum*), and peanut (*Arachis hypogaea*), tomato (*Solanum lycopersicum*), potato (*Solanum tuberosum*) etc.

The transgenes, recombinant DNA molecules, DNA sequences of interest, and polynucleotides of interest can comprise one or more genes of interest. Such genes of interest can encode, for example, a protein that provides agronomic advantage to the plant.

Marker Assisted Selection and Breeding of Plants

A primary motivation for development of molecular markers in crop species is the potential for increased efficiency in plant breeding through marker assisted selection (MAS). Genetic marker alleles, or alternatively, quantitative trait loci (QTL alleles, are used to identify plants that contain a desired genotype at one or more loci, and that are expected to transfer the desired genotype, along with a desired phenotype to their progeny. Genetic marker alleles (or QTL alleles) can be used to identify plants that contain a desired genotype at one locus, or at several unlinked or linked loci (e.g., a haplotype), and that would be expected to transfer the desired genotype, along with a desired phenotype to their progeny. It will be appreciated that for the purposes of MAS, the term marker can encompass both marker and QTL loci.

After a desired phenotype and a polymorphic chromosomal locus, e.g., a marker locus or QTL, are determined to segregate together, it is possible to use those polymorphic loci to select for alleles corresponding to the desired phenotype—a process called marker-assisted selection (MAS). In brief, a nucleic acid corresponding to the marker nucleic acid is detected in a biological sample from a plant to be selected. This detection can take the form of hybridization of a probe nucleic acid to a marker, e.g., using allele-specific hybridization, southern blot analysis, northern blot analysis, in situ hybridization, hybridization of primers followed by PCR amplification of a region of the marker or the like. A variety of procedures for detecting markers are well known in the art. After the presence (or absence) of a particular marker in the biological sample is verified, the plant is selected, i.e., used to make progeny plants by selective breeding.

Plant breeders need to combine traits of interest with genes for high yield and other desirable traits to develop improved plant varieties. Screening for large numbers of samples can be expensive, time consuming, and unreliable. Use of markers, and/or genetically-linked nucleic acids is an effective method for selecting plant having the desired traits in breeding programs. For example, one advantage of marker-assisted selection over field evaluations is that MAS can be done at any time of year regardless of the growing season. Moreover, environmental effects are irrelevant to marker-assisted selection.

When a population is segregating for multiple loci affecting one or multiple traits, the efficiency of MAS compared to phenotypic screening becomes even greater because all the loci can be processed in the lab together from a single sample of DNA.

The DNA repair mechanisms of cells are the basis to introduce extraneous DNA or induce mutations on endogenous genes. DNA homologous recombination is a specialized way of DNA repair that the cells repair DNA damages using a homologous sequence. In plants, DNA homologous recombination happens at frequencies too low to be routinely used in gene targeting or gene editing until it has been found that the process can be stimulated by DNA double-strand breaks (Bibikova et al., (2001) Mol. Cell Biol. 21:289-297; Puchta and Baltimore, (2003) Science 300:763; Wright et al., (2005) Plant J. 44:693-705).

The meaning of abbreviations is as follows: "sec" means second(s), "min" means minute(s), "h" means hour(s), "d" means day(s), "µL" means microliter(s), "mL" means milliliter(s), "L" means liter(s), "µM" means micromolar, "mM" means millimolar, "M" means molar, "mmol" means millimole(s), "pmole" mean micromole(s), "g" means gram(s), "µg" means microgram(s), "ng" means nanogram(s), "U" means unit(s), "bp" means base pair(s) and "kb" means kilobase(s).

Also, as described herein, for each example or embodiment that cites a guide RNA, a similar guide polynucleotide can be designed wherein the guide polynucleotide does not solely comprise ribonucleic acids but wherein the guide polynucleotide comprises a combination of RNA-DNA molecules or solely comprises DNA molecules. Non-limiting examples of compositions and methods disclosed herein are as follows:

1. A method for selecting a plant comprising an altered target site in its plant genome, the method comprising:
   a) obtaining a first plant comprising at least one Cas endonuclease capable of introducing a double strand break at a target site in the plant genome;
   b) obtaining a second plant comprising a guide RNA that is capable of forming a complex with the Cas endonuclease of (a);
   c) crossing the first plant of (a) with the second plant of (b);
   d) evaluating the progeny of (c) for an alteration in the target site; and,
   e) selecting a progeny plant that possesses the desired alteration of said target site.

2. A method for selecting a plant comprising an altered target site in its plant genome, the method comprising selecting at least one progeny plant that comprises an alteration at a target site in its plant genome, wherein said progeny plant was obtained by crossing a first plant comprising at least one a Cas endonuclease with a second plant comprising a guide RNA, wherein said Cas endonuclease is capable of introducing a double strand break at said target site.

3. A method for selecting a plant comprising an altered target site in its plant genome, the method comprising:
   a) obtaining a first plant comprising at least one Cas endonuclease capable of introducing a double strand break at a target site in the plant genome;
   b) obtaining a second plant comprising a guide RNA and a donor DNA, wherein said guide RNA is capable of forming a complex with the Cas endonuclease of (a), wherein said donor DNA comprises a polynucleotide of interest;
   c) crossing the first plant of (a) with the second plant of (b);
   d) evaluating the progeny of (c) for an alteration in the target site; and,
   e) selecting a progeny plant that comprises the polynucleotide of interest inserted at said target site.

4. A method for selecting a plant comprising an altered target site in its plant genome, the method comprising selecting at least one progeny plant that comprises an alteration at a target site in its plant genome, wherein said progeny plant was obtained by crossing a first plant expressing at least one Cas endonuclease to a second plant comprising a guide RNA and a donor DNA, wherein said Cas endonuclease is capable of introducing a double strand break at said target site, wherein said donor DNA comprises a polynucleotide of interest.

5. A method for modifying a target site in the genome of a plant cell, the method comprising introducing a guide RNA into a plant cell having a Cas endonuclease, wherein said guide RNA and Cas endonuclease are capable of forming a complex that enables the Cas endonuclease to introduce a double strand break at said target site.

6. A method for modifying a target site in the genome of a plant cell, the method comprising introducing a guide RNA and a Cas endonuclease into said plant cell, wherein said guide RNA and Cas endonuclease are capable of forming a complex that enables the Cas endonuclease to introduce a double strand break at said target site.

7. A method for modifying a target site in the genome of a plant cell, the method comprising introducing a guide RNA and a donor DNA into a plant cell having a Cas endonuclease, wherein said guide RNA and Cas endonuclease are capable of forming a complex that enables the Cas endonuclease to introduce a double strand break at said target site, wherein said donor DNA comprises a polynucleotide of interest.

8. A method for modifying a target site in the genome of a plant cell, the method comprising:
   a) introducing into a plant cell a guide RNA and a Cas endonuclease, wherein said guide RNA and Cas endonuclease are capable of forming a complex that enables the Cas endonuclease to introduce a double strand break at said target site; and,
   b) identifying at least one plant cell that has a modification at said target, wherein the modification includes at least one deletion or substitution of one or more nucleotides in said target site.

9. A method for modifying a target DNA sequence in the genome of a plant cell, the method comprising:
   a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site; and,
   b) identifying at least one plant cell that has a modification at said target, wherein the modification includes at least one deletion or substitution of one or more nucleotides in said target site.

10. A method for introducing a polynucleotide of Interest into a target site in the genome of a plant cell, the method comprising:
    a) introducing into a plant cell a first recombinant DNA construct capable of expressing a guide RNA and a second recombinant DNA construct capable of expressing a Cas endonuclease, wherein said guide RNA and Cas endonuclease are capable of forming a complex that enables the Cas endonuclease to introduce a double strand break at said target site;
    b) contacting the plant cell of (a) with a donor DNA comprising a polynucleotide of Interest; and,
    c) identifying at least one plant cell from (b) comprising in its genome the polynucleotide of Interest integrated at said target site.

10-B A method for introducing a polynucleotide of Interest into a target site in the genome of a plant cell, the method comprising:
    a) introducing into a plant cell a guide RNA and a Cas endonuclease, wherein said guide RNA and Cas endonuclease are capable of forming a complex that enables the Cas endonuclease to introduce a double strand break at said target site;
    b) contacting the plant cell of (a) with a donor DNA comprising a polynucleotide of Interest; and,
    c) identifying at least one plant cell from (b) comprising in its genome the polynucleotide of Interest integrated at said target site.

11. The method of any one of embodiments 5-8, wherein the guide RNA is introduced directly by particle bombardment.

12. The method of any one of embodiments 5-9, wherein the guide RNA is introduced via particle bombardment or *Agrobacterium* transformation of a recombinant DNA construct comprising the corresponding guide DNA operably linked to a plant U6 polymerase III promoter.

13. The method of any one of embodiments 1-10, wherein the Cas endonuclease gene is a plant optimized Cas9 endonuclease.

14. The method of any one of embodiments 1-10, wherein the Cas endonuclease gene is operably linked to a SV40 nuclear targeting signal upstream of the Cas codon region and a VirD2 nuclear localization signal downstream of the Cas codon region.

15. The method of any one of embodiments 1-14, wherein the plant is a monocot or a dicot.

16. The method of embodiment 15, wherein the monocot is selected from the group consisting of maize, rice, sorghum, rye, barley, wheat, millet, oats, sugarcane, turfgrass, or switchgrass.

17. The method of embodiment 16, wherein the dicot is selected from the group consisting of soybean, canola, alfalfa, sunflower, cotton, tobacco, peanut, potato, tobacco, *Arabidopsis*, or safflower.

18. The method of any one of embodiments 1-17 wherein the target site is located in the gene sequence of an acetolactate synthase (ALS) gene, an Enolpyruvylshikimate Phosphate Synthase Gene (ESPSP) gene, a male fertility (MS45, MS26 or MSCA1).

19. A plant or seed produced by any one of embodiments 1-17.

20. A plant comprising a recombinant DNA construct, said recombinant DNA construct comprising a promoter operably linked to a nucleotide sequence encoding a plant optimized Cas9 endonuclease, wherein said plant optimized Cas9 endonuclease is capable of binding to and creating a double strand break in a genomic target sequence said plant genome.

21. A plant comprising a recombinant DNA construct and a guide RNA, wherein said recombinant DNA construct comprises a promoter operably linked to a nucleotide sequence encoding a plant optimized Cas9 endonuclease, wherein said plant optimized Cas9 endonuclease and guide RNA are capable of forming a complex and creating a double strand break in a genomic target sequence said plant genome.

22. A recombinant DNA construct comprising a promoter operably linked to a nucleotide sequence encoding a plant optimized Cas9 endonuclease, wherein said plant optimized Cas9 endonuclease is capable of binding to and creating a double strand break in a genomic target sequence said plant genome.

23. A recombinant DNA construct comprising a promoter operably linked to a nucleotide sequence expressing a guide RNA, wherein said guide RNA is capable of forming a complex with a plant optimized Cas9 endonuclease, and wherein said complex is capable of binding to and creating a double strand break in a genomic target sequence said plant genome.

24. A method for selecting a male sterile plant, the method comprising selecting at least one progeny plant that comprises an alteration at a genomic target site located in a male fertility gene locus, wherein said progeny plant is obtained by crossing a first plant expressing a Cas9 endonuclease to a second plant comprising a guide RNA, wherein said Cas endonuclease is capable of introducing a double strand break at said genomic target site.

25. A method for producing a male sterile plant, the method comprising:
    a) obtaining a first plant comprising at least one Cas endonuclease capable of introducing a double strand break at a genomic target site located in a male fertility gene locus in the plant genome;
    b) obtaining a second plant comprising a guide RNA that is capable of forming a complex with the Cas endonuclease of (a);
    c) crossing the first plant of (a) with the second plant of (b);
    d) evaluating the progeny of (c) for an alteration in the target site; and,
    e) selecting a progeny plant that is male sterile.

26. The method of any of embodiments 23-24 wherein the male fertility gene is selected from the list comprising MS26, MS45, M.

27. The method of any one of embodiments 24-26, wherein the plant is a monocot or a dicot.

28. The method of embodiment 27, wherein the monocot is selected from the group consisting of maize, rice, sorghum, rye, barley, wheat, millet, oats, sugarcane, turfgrass, or switchgrass.

29. A method for editing a nucleotide sequence in the genome of a cell, the method comprising introducing a guide RNA, a polynucleotide modification template and at least one Cas endonuclease into a cell, wherein the Cas endonuclease introduces a double-strand break at a target site in the genome of said cell, wherein said polynucleotide modification template comprises at least one nucleotide modification of said nucleotide sequence.

30. The method of embodiment 29, wherein the cell is a plant cell.

31. The method of embodiment 29 wherein the nucleotide sequence is a promoter, a regulatory sequence or a gene of interest of interest.

32. The method of embodiment 31 wherein the gene of interest is an EPSPS gene.

33. The method of embodiment 30 wherein the plant cell is a monocot or dicot plant cell.

34. A method for producing an epsps mutant plant, the method comprising:
   a) providing a guide RNA, a polynucleotide modification template and at least one Cas endonuclease to a plant cell, wherein the Cas endonuclease introduces a double strand break at a target site within an epsps genomic sequence in the plant genome, wherein said_polynucleotide modification template comprises at least one nucleotide modification of said epsps genomic sequence.
   b) obtaining a plant from the plant cell of (a);
   c) evaluating the plant of (b) for the presence of said at least one nucleotide modification; and,
   c) selecting a progeny plant that shows tolerance to glyphosate.

35. A method for producing an epsps mutant plant, the method comprising:
   a) providing a guide RNA, a polynucleotide modification template and at least one Cas endonuclease into a plant cell, wherein the Cas endonuclease introduces a double strand break at a target site within an epsps genomic sequence in the plant genome, wherein said polynucleotide modification template comprises at least one nucleotide modification of said epsps genomic sequence.
   b) obtaining a plant from the plant cell of (a);
   c) evaluating the plant of (b) for the presence of said at least one nucleotide modification; and,
   d) screening a progeny plant of (c) that is void of said guide RNA and Cas endonuclease.

36. The method of embodiment 35, further comprising selecting a plant that shows resistance to glyphosate.

37. A plant, plant cell or seed produced by any one of embodiments 29-36 38. The method of any one of embodiments 29-36 wherein the Cas endonuclease is a Cas9 endonuclease.

39. The method of embodiment 38 wherein the Cas9 endonuclease is expressed by SEQ ID NO:5.

40. The method of embodiment 38 wherein the Cas9 endonuclease is encoded by any one of SEQ ID NOs: 1, 124, 212, 213, 214, 215, 216, 193 or nucleotides 2037-6329 of SEQ ID NO:5, or any functional fragment or variant thereof.

41. The plant or plant cell of embodiment 37, wherein said plant cell shows resistance to glyphosate.

42. A plant cell comprising a modified nucleotide sequence, wherein the modified nucleotide sequence was produced by providing a guide RNA, a polynucleotide modification template and at least one Cas endonuclease to a plant cell, wherein the Cas endonuclease is capable of introducing a double-strand break at a target site in the plant genome wherein said polynucleotide modification template comprises at least one nucleotide modification of said nucleotide sequence.

43. The method of embodiments 29, 34 and 35 wherein the at least one nucleotide modification is not a modification at said target site.

44. A method for producing a male sterile plant, the method comprising:
   a) introducing into a plant cell a guide RNA and a Cas endonuclease, wherein said guide RNA and Cas endonuclease are capable of forming a complex that enables the Cas endonuclease to introduce a double strand break at a target site located in or near a male fertility gene;
   b) identifying at least one plant cell that has a modification in said male fertility gene, wherein the modification includes at least one deletion or substitution of one or more nucleotides in said male sterility gene; and,
   c) obtaining a plant from the plant cell of b).

45. The method of embodiment 43, further comprising selecting a progeny plant from the plant of c) wherein said progeny plant is male sterile.

46. The method of embodiment 43, wherein the male fertility gene is selected from the group comprising MS26, MS45 and MSCA1.

47. A plant comprising at least one altered target site, wherein the at least one altered target site originated from a corresponding target site that was recognized and cleaved by a guide RNA/Cas endonuclease system, and wherein the at least one altered target site is in a genomic region of interest that extends from the target sequence set forth in SEQ ID NO: 229 to the target site set forth in SEQ ID NO: 235.

48. The plant of embodiment 47, wherein the at least one altered target site has an alteration selected from the group consisting of (i) replacement of at least one nucleotide, (ii) a deletion of at least one nucleotide, (iii) an insertion of at least one nucleotide, and (iv) any combination of (i)-(iii).

49. The plant of embodiment 47, wherein the at least one altered target site comprises a recombinant DNA molecule.

50. The plant of embodiment 47, wherein the plant comprises at least two altered target sites, wherein each of the altered target site originated from corresponding target site that was recognized and cleaved by a guide RNA/Cas endonuclease system, wherein the corresponding target site is selected from the group consisting of SEQ ID NOs: 229, 230, 231, 232, 233, 234, 235 and 236.

51. A recombinant DNA construct comprising a nucleotide sequence set forth in SEQ ID NO: 120 or SEQ ID NO:295, or a functional fragment thereof, operably linked to at least one heterologous sequence, wherein said nucleotide sequence is a promoter.

52. A plant stably transformed with a recombinant DNA construct comprising a soybean promoter and a heterologous nucleic acid fragment operably linked to said soybean promoter, wherein said promoter is a capable of controlling expression of said heterologous nucleic acid fragment in a plant cell, and further wherein said promoter comprises any of the sequences set forth in SEQ ID NO: 120 or SEQ ID NO: 295.

53. A method for editing a nucleotide sequence in the genome of a cell, the method comprising introducing a guide polynucleotide, a Cas endonuclease, and optionally a polynucleotide modification template, into a cell, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said nucleotide sequence.

54. The method of embodiment 53, wherein the nucleotide sequence in the genome of a cell is selected from the group consisting of a promoter sequence, a terminator sequence, a regulatory element sequence, a splice site, a coding sequence, a polyubiquitination site, an intron site and an intron enhancing motif.

55. A method for editing a promoter sequence in the genome of a cell, the method comprising introducing a guide polynucleotide, a polynucleotide modification template and at least one Cas endonuclease into a cell, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said nucleotide sequence.

56. A method for replacing a first promoter sequence in a cell, the method comprising introducing a guide RNA, a polynucleotide modification template, and a Cas endonuclease into said cell, wherein said guide RNA and Cas endonuclease are capable of forming a complex that enables the Cas endonuclease to introduce a double strand break at a target site in the genome of said cell, wherein said polynucleotide modification template comprises a second promoter or second promoter fragment that is different from said first promoter sequence.

57. The method of embodiment 56, wherein the replacement of the first promoter sequence results in any one of the following, or any one combination of the following: an increased promoter activity, an increased promoter tissue specificity, a decreased promoter activity, a decreased promoter tissue specificity, a new promoter activity, an inducible promoter activity, an extended window of gene expression, or a modification of the timing or developmental progress of gene expression in the same cell layer or other cell layer 58. The method of embodiment 56, wherein the first promoter sequence is selected from the group consisting of Zea mays ARGOS 8 promoter, a soybean EPSPS1 promoter, a maize EPSPS promoter, maize NPK1 promoter, wherein the second promoter sequence is selected from the group consisting of a Zea mays GOS2 PRO:GOS2-intron promoter, a soybean ubiquitin promoter, a stress inducible maize RAB17 promoter, a Zea mays-PEPC1 promoter, a Zea mays Ubiquitin promoter, a Zea mays-Rootmet2 promoter, a rice actin promoter, a sorghum RCC3 promoter, a Zea mays-GOS2 promoter, a Zea mays-ACO2 promoter and a Zea mays oleosin promoter.

59. A method for deleting a promoter sequence in the genome of a cell, the method comprising introducing a guide polynucleotide, a Cas endonuclease into a cell, wherein said guide RNA and Cas endonuclease are capable of forming a complex that enables the Cas endonuclease to introduce a double strand break in at least one target site located inside or outside said promoter sequence.

60. A method for inserting a promoter or a promoter element in the genome of a cell, the method comprising introducing a guide polynucleotide, a polynucleotide modification template comprising the promoter or the promoter element, and a Cas endonuclease into a cell, wherein said guide RNA and Cas endonuclease are capable of forming a complex that enables the Cas endonuclease to introduce a double strand break at a target site in the genome of said cell.

61. The method of embodiment 60, wherein the insertion of the promoter or promoter element results in any one of the following, or any one combination of the following: an increased promoter activity, an increased promoter tissue specificity, a decreased promoter activity, a decreased promoter tissue specificity, a new promoter activity, an inducible promoter activity, an extended window of gene expression, a modification of the timing or developmental progress of gene expression, a mutation of DNA binding elements, or an addition of DNA binding elements.

62. A method for editing a Zinc Finger transcription factor, the method comprising introducing a guide polynucleotide, a Cas endonuclease, and optionally a polynucleotide modification template, into a cell, wherein the Cas endonuclease introduces a double-strand break at a target site in the genome of said cell, wherein said polynucleotide modification template comprises at least one nucleotide modification or deletion of said Zinc Finger transcription factor, wherein the deletion or modification of said Zinc Finger transcription factor results in the creation of a dominant negative Zinc Finger transcription factor mutant.

63. A method for creating a fusion protein, the method comprising introducing a guide polynucleotide, a Cas endonuclease, and a polynucleotide modification template, into a cell, wherein the Cas endonuclease introduces a double-strand break at a target site located inside or outside a first coding sequence in the genome of said cell, wherein said polynucleotide modification template comprises a second coding sequence encoding a protein of interest, wherein the protein fusion results in any one of the following, or any one combination of the following: a targeting of the fusion protein to the chloroplast of said cell, an increased protein activity, an increased protein functionality, a decreased protein activity, a decreased protein functionality, a new protein functionality, a modified protein functionality, a new protein localization, a new timing of protein expression, a modified protein expression pattern, a chimeric protein, or a modified protein with dominant phenotype functionality.

64. A method for producing in a plant a complex trait locus comprising at least two altered target sequences in a genomic region of interest, said method comprising:
(a) selecting a genomic region in a plant, wherein the genomic region comprises a first target sequence and a second target sequence;
(b) contacting at least one plant cell with at least a first guide polynucleotide, a second polynucleotide, and optionally at least one Donor DNA, and a Cas endonuclease, wherein the first and second guide polynucleotide and the Cas endonuclease can form a complex that enables the Cas endonuclease to introduce a double strand break in at least a first and a second target sequence;
- (c) identifying a cell from (b) comprising a first alteration at the first target sequence and a second alteration at the second target sequence; and,
- (d) recovering a first fertile plant from the cell of (c) said fertile plant comprising the first alteration and the second alteration, wherein the first alteration and the second alteration are physically linked.

65. A method for producing in a plant a complex trait locus comprising at least two altered target sequences in a genomic region of interest, said method comprising:
- (a) selecting a genomic region in a plant, wherein the genomic region comprises a first target sequence and a second target sequence;
- (b) contacting at least one plant cell with a first guide polynucleotide, a Cas endonuclease, and optionally a first Donor DNA, wherein the first guide polynucleotide and the Cas endonuclease can form a complex that enables the Cas endonuclease to introduce a double strand break a first target sequence;
- (c) identifying a cell from (b) comprising a first alteration at the first target sequence;
- (d) recovering a first fertile plant from the cell of (c), said first fertile plant comprising the first alteration;
- (e) contacting at least one plant cell with a second guide polynucleotide, a Cas endonuclease, and optionally a second Donor DNA;
- (f) identifying a cell from (e) comprising a second alteration at the second target sequence;
- (g) recovering a second fertile plant from the cell of (f), said second fertile plant comprising the second alteration; and,
- (h) obtaining a fertile progeny plant from the second fertile plant of (g), said fertile progeny plant comprising the first alteration and the second alteration, wherein the first alteration and the second alteration are physically linked.

66. A method for editing a nucleotide sequence in the genome of a cell, the method comprising introducing at least one guide RNA, at least one polynucleotide modification template and at least one Cas endonuclease into a cell, wherein the Cas endonuclease introduces a double-strand break at a target site in the genome of said cell, wherein said polynucleotide modification template comprises at least one nucleotide modification of said nucleotide sequence.

67. The method of embodiment 66 wherein the editing of said nucleotide sequence renders said nucleotide sequence capable of conferring herbicide resistance to said cell.

68. The method of embodiment 67, wherein the cell is a plant cell.

69. The method of embodiment 66 wherein the nucleotide sequence is a promoter, a regulatory sequence or a gene of interest of interest.

70. The method of embodiment 69 wherein the gene of interest is an enolpyruvylshikimate-3-phosphate synthase (EPSPS) gene or an ALS gene.

71. The method of embodiment 66 wherein the plant cell is a monocot or dicot plant cell.

72. A method for producing an acetolactate synthase (ALS) mutant plant, the method comprising:
- a) providing a guide RNA, a polynucleotide modification template, and a Cas endonuclease to a plant cell comprising an ALS nucleotide sequence, wherein said guide RNA and Cas endonuclease are capable of forming a complex that enables the Cas endonuclease to introduce a double strand break at a target site in the genome of said plant cell, wherein said polynucleotide modification template comprises at least one nucleotide modification of said ALS nucleotide sequence;
- b) obtaining a plant from the plant cell of (a);
- c) evaluating the plant of (b) for the presence of said at least one nucleotide modification; and,
- d) selecting a progeny plant that shows resistance to sulphonylurea.

73. A method for producing an acetolactate synthase (ALS) mutant plant, the method comprising:
- a) providing a guide RNA and a polynucleotide modification template to a plant cell comprising a Cas endonuclease and an ALS nucleotide sequence, wherein said Cas endonuclease introduces a double strand break at a target site in the genome of said plant cell, wherein said polynucleotide modification template comprises at least one nucleotide modification of said ALS nucleotide sequence;
- b) obtaining a plant from the plant cell of (a);
- c) evaluating the plant of (b) for the presence of said at least one nucleotide modification; and,
- d) selecting a progeny plant that shows resistance to sulphonylurea.

74. The method of any of embodiments 72-73, wherein said polynucleotide modification template comprises a non-functional or partial fragment of the ALS nucleotide sequence.

75. The method of any of embodiments 72-73, wherein the target site is located within the ALS nucleotide sequence.

76. The method of any of embodiments 72-73, further comprising selecting a progeny plant that is void of said guide RNA and Cas endonuclease.

77. A method for producing an acetolactate synthase (ALS) mutant plant, the method comprising:
- a) obtaining a plant or a seed thereof, wherein the plant or the seed comprises a modification in an endogenous ALS gene, the modification generated by a Cas endonuclease, a guide RNA and a polynucleotide modification template, wherein the plant or the seed is resistant to sulphonylurea; and,
- b) producing a progeny plant that is void of said guide RNA and Cas endonuclease.

78. The method of embodiment 77, further comprising selecting a plant that shows resistance to sulphonylurea.

79. The method of any one of embodiments 72-78, wherein the plant is a monocot or a dicot.

80. The method of embodiment 79, wherein the monocot is selected from the group consisting of maize, rice, sorghum, rye, barley, wheat, millet, oats, sugarcane, turfgrass, or switchgrass.

81. The method of embodiment 79, wherein the dicot is selected from the group consisting of soybean, canola, alfalfa, sunflower, cotton, tobacco, peanut, potato, tobacco, *Arabidopsis*, or safflower.

82. A method of generating a sulphonylurea resistant plant, the method comprising providing a plant cell wherein its endogenous chromosomal ALS gene by has been modified through a guide RNA/Cas endonuclease system to produce a sulphonylurea resistant ALS protein and growing a plant from said maize plant cell, wherein said plant is resistant to sulphonylurea.

83. The method of embodiment 82, wherein the plant is a monocot or a dicot.

84. A plant produced by the method of embodiment 82.

85. A seed produced by the plant of embodiment 84.

86. A guide RNA wherein the variable targeting domain targets a fragment of a plant EPSPS or ALS nucleotide sequence.

87. A method for producing an acetolactate synthase (ALS) mutant plant cell, the method comprising:
  a) providing to a cell comprising an ALS nucleotide sequence, a guide RNA, a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises at least one nucleotide modification of said ALS nucleotide sequence; and,
  b) obtaining at least one plant cell of (a) that has at least one nucleotide modification at said ALS nucleotide sequence, wherein the modification includes at least one deletion, insertion or substitution of one or more nucleotides in said ALS nucleotide sequence.

88. A method for producing an acetolactate synthase (ALS) mutant plant cell, the method comprising:
  a) providing a guide RNA and a polynucleotide modification template to a plant cell comprising a Cas endonuclease and a ALS nucleotide sequence, wherein said Cas endonuclease introduces a double strand break at a target site in the genome of said plant cell, wherein said polynucleotide modification template comprises at least one nucleotide modification of said ALS nucleotide sequence; and,
  b) identifying at least one plant cell of (a) that has at least one nucleotide modification at said ALS nucleotide sequence, wherein the modification includes at least one deletion, insertion or substitution of one or more nucleotides in said ALS nucleotide sequence.

89. A method for producing an acetolactate synthase (ALS) mutant cell, the method comprising:
  a) providing to a cell comprising an ALS nucleotide sequence, a first recombinant DNA construct capable of expressing a guide RNA, a second recombinant DNA construct capable of expressing a Cas endonuclease, and a polynucleotide modification template, wherein said guide RNA and Cas endonuclease are capable of forming a complex that enables the Cas endonuclease to introduce a double strand break at a target site in the genome of said cell, wherein said polynucleotide modification template comprises a non-functional fragment of the ALS gene and at least one nucleotide modification of said ALS nucleotide sequence; and,
  b) identifying at least one cell of (a) that has at least one nucleotide modification at said ALS nucleotide sequence, wherein the modification includes at least one deletion, insertion or substitution of one or more nucleotides in said ALS nucleotide sequence.

EXAMPLES

In the following Examples, unless otherwise stated, parts and percentages are by weight and degrees are Celsius. It should be understood that these Examples, while indicating embodiments of the disclosure, are given by way of illustration only. From the above discussion and these Examples, one skilled in the art can make various changes and modifications of the disclosure to adapt it to various usages and conditions. Such modifications are also intended to fall within the scope of the appended claims.

Example 1

Maize Optimized Expression Cassettes for Guide RNA/Cas Endonuclease Based Genome Modification in Maize Plants For genome engineering applications, the type II CRISPR/Cas system minimally requires the Cas9 protein and a duplexed crRNA/tracrRNA molecule or a synthetically fused crRNA and tracrRNA (guide RNA) molecule for DNA target site recognition and cleavage (Gasiunas et al. (2012) *Proc. Natl. Acad. Sci. USA* 109:E2579-86, Jinek et al. (2012) *Science* 337:816-21, Mali et al. (2013) *Science* 339:823-26, and Cong et al. (2013) *Science* 339:819-23). Described herein is a guideRNA/Cas endonuclease system that is based on the type II CRISPR/Cas system and consists of a Cas endonuclease and a guide RNA (or duplexed crRNA and tracrRNA) that together can form a complex that recognizes a genomic target site in a plant and introduces a double-strand-break into said target site.

To test the guide RNA/Cas endonuclease system in maize, the Cas9 gene from *Streptococcus pyogenes* M1 GAS (SF370) (SEQ ID NO: 1) was maize codon optimized per standard techniques known in the art and the potato ST-LS1 intron (SEQ ID NO: 2) was introduced in order to eliminate its expression in *E. coli* and *Agrobacterium* (FIG. 1 A). To facilitate nuclear localization of the Cas9 protein in maize cells, Simian virus 40 (SV40) monopartite amino terminal nuclear localization signal (MAPKKKRKV, SEQ ID NO: 3) and *Agrobacterium tumefaciens* bipartite VirD2 T-DNA border endonuclease carboxyl terminal nuclear localization signal (KRPRDRIDGELGGRKRAR, SEQ ID NO: 4) were incorporated at the amino and carboxyl-termini of the Cas9 open reading frame (FIG. 1 A), respectively. The maize optimized Cas9 gene was operably linked to a maize constitutive or regulated promoter by standard molecular biological techniques. An example of the maize optimized Cas9 expression cassette (SEQ ID NO: 5) is illustrated in FIG. 1 A. FIG. 1A shows a maize optimized Cas9 gene containing the ST-LS1 intron, SV40 amino terminal nuclear localization signal (NLS) and VirD2 carboxyl terminal NLS driven by a plant Ubiquitin promoter.

The second component necessary to form a functional guide RNA/Cas endonuclease system for genome engineering applications is a duplex of the crRNA and tracrRNA molecules or a synthetic fusing of the crRNA and tracrRNA molecules, a guide RNA. To confer efficient guide RNA expression (or expression of the duplexed crRNA and tracrRNA) in maize, the maize U6 polymerase III promoter (SEQ ID NO: 9) and maize U6 polymerase III terminator (first 8 bases of SEQ ID NO: 10) residing on chromosome 8 were isolated and operably fused to the termini of a guide RNA (FIG. 1 B) using standard molecular biology techniques. Two different guide RNA configurations were developed for testing in maize, a short guide RNA (SEQ ID NO: 11) based on Jinek et al. (2012) *Science* 337:816-21 and a long guide RNA (SEQ ID NO: 8) based on Mali et al. (2013) *Science* 339:823-26. An example expression cassette (SEQ ID NO: 12) is shown in FIG. 1 B which illustrates a maize U6 polymerase III promoter driving expression of a long guide RNA terminated with a U6 polymerase III terminator.

As shown in FIGS. 2 A and 2B, the guide RNA or crRNA molecule contains a region complementary to one strand of the double strand DNA target (referred to as the variable targeting domain) that is approximately 12-30 nucleotides in length and upstream of a PAM sequence (5'NGG3' on antisense strand of FIG. 2A-2B, corresponding to 5'CCN3' on sense strand of FIG. 2A-2B) for target site recognition and cleavage (Gasiunas et al. (2012) *Proc. Natl. Acad. Sci. USA* 109:E2579-86, Jinek et al. (2012) *Science* 337:816-21, Mali et al. (2013) *Science* 339:823-26, and Cong et al. (2013) *Science* 339:819-23). To facilitate the rapid introduction of maize genomic DNA target sequences into the crRNA or guide RNA expression constructs, two Type IIS BbsI restriction endonuclease target sites were introduced in an inverted tandem orientation with cleavage orientated in an outward direction as described in Cong et al. (2013) *Science* 339:819-23. Upon cleavage, the Type IIS restriction endonuclease excises its target sites from the crRNA or guide RNA expression plasmid, generating overhangs allowing for the in-frame directional cloning of duplexed oligos containing the desired maize genomic DNA target site into the variable targeting domain. In this example, only target sequences starting with a G nucleotide were used to promote favorable polymerase III expression of the guide RNA or crRNA.

Expression of both the Cas endonuclease gene and the guide RNA then allows for the formation of the guide RNA/Cas complex depicted in FIG. 2 B (SEQ ID NO: 8). Alternatively, expression of the Cas endonucleases gene, crRNA, and tracrRNA allow for the formation of the crRNA/tracrRNA/Cas complex as depicted in FIG. 2 A, (SEQ ID NOs: 6-7).

Example 2

The Guide RNA/Cas Endonuclease System Cleaves Chromosomal DNA in Maize and Introduces Mutations by Imperfect Non-Homologous End-Joining To test whether the maize optimized guide RNA/Cas endonuclease described in example 1 could recognize, cleave, and mutate maize chromosomal DNA through imprecise non-homologous end-joining (NHEJ) repair pathways, three different genomic target sequences in 5 maize loci were targeted for cleavage (see Table 1) and examined by deep sequencing for the presence of NHEJ mutations.

TABLE 1

Maize genomic target sites targeted by a guideRNA/Cas endonuclease system.

| Locus | Location | Guide RNA Used | Target Site Designation | Maize Genomic Target Site Sequence | PAM Sequence | SEQ ID NO: |
|---|---|---|---|---|---|---|
| MS26 | Chr. 1: 51.81 cM | Long | MS26Cas-1 | GTACTCCATCCGCCCCATCGAGTA | GGG | 13 |
|  |  | Long | MS26Cas-2 | GCACGTACGTCACCATCCCGC | CGG | 14 |
|  |  | Long | MS26Cas-3 | GACGTACGTGCCCTACTCGAT | GGG | 15 |
| LIG | Chr. 2: 28.45 cM | Long | LIGCas-1 | GTACCGTACGTGCCCCGGCGG | AGG | 16 |
|  |  | Long | LIGCas-2 | GGAATTGTACCGTACGTGCCC | CGG | 17 |
|  |  | Long | LIGCas-3 | GCGTACGCGTACGTGTG | AGG | 18 |
| MS45 | Chr. 9: 119.15 cM | Long | MS45Cas-1 | GCTGGCCGAGGTCGACTAC | CGG | 19 |
|  |  | Long | MS45Cas-2 | GGCCGAGGTCGACTACCGGC | CGG | 20 |
|  |  | Long | MS45Cas-3 | GGCGCGAGCTCGTGCTTCAC | CGG | 21 |
| ALS | Chr. 4: 107.73 cM and Chr. 5: 115.49 cM | Long | ALSCas-1 | GGTGCCAATCATGCGTCG | CGG | 22 |
|  |  | Long | ALSCas-2 | GGTCGCCATCACGGGAC | AGG | 23 |
|  |  | Long | ALSCas-3 | GTCGCGGCACCTGTCCCGTGA | TGG | 24 |
| EPSPS | Chr. 9: 69.43 cM | Long | EPSPSCas-1 | GGAATGCTGGAACTGCAATG | CGG | 25 |
|  |  | Long | EPSPSCas-2 | GCAGCTCTTCTTGGGGAATGC | TGG | 26 |
|  |  | Long | EPSPSCas-3 | GCAGTAACAGCTGCTGTCAA | TGG | 27 |

MS26 = Male Sterility Gene 26,
LIG = Liguleless 1 Gene Promoter,
MS45 = Male Sterility Gene 45,
ALS = Acetolactate Synthase Gene,
EPSPS = Enolpyruvylshikimate Phosphate Synthase Gene The maize optimized Cas9 endonuclease and long guide RNA expression cassettes containing the specific maize variable targeting domains were co-delivered to 60-90 Hi-II immature maize embryos by particle-mediated delivery (see Example 10) in the presence of BBM and WUS2 genes (see Example 11). Hi-II maize embryos transformed with either the LIG3-4 or MS26++ homing endonucleases (see Example 9) targeting the same maize genomic loci as the LIGCas or MS26Cas target sites served as a positive control and embryos transformed with only the Cas9 or guide RNA expression cassette served as negative controls. After 7 days, the 20-30 most uniformly transformed embryos from each treatment were pooled and total genomic DNA was extracted. The region surrounding the intended target site was PCR amplified with Phusion® High Fidelity PCR Master Mix (New England Biolabs, M0531L) adding on the sequences necessary for amplicon-specific barcodes and Illumnia sequencing using "tailed" primers through two rounds of PCR. The primers used in the primary PCR reaction are shown in Table 2 and the primers used in the secondary PCR reaction were AATGATACGGCGAC-CACCGAGATCTACACTCTTTCCCTACACG (forward, SEQ ID NO: 53) and CAAGCAGAAGACGGCATA (reverse, SEQ TD NO: 54).

TABLE 2

PCR primer sequences

| Target SIte | Primer Orientation | Primary PCR Primer Sequence | SEQ ID NO: |
|---|---|---|---|
| MS26Cas-1 | Forward | CTACACTCTTTCCCTACACGACGCTCTTCC GATCTAGGACCGGAAGCTCGCCGCGT | 28 |
| MS26Cas-1 | Reverse | CAAGCAGAAGACGGCATACGAGCTCTTCC GATCTTCCTGGAGGACGACGTGCTG | 29 |
| MS26Cas-2 | Forward | CTACACTCTTTCCCTACACGACGCTCTTCC GATCTAAGGTCCTGGAGGACGACGTGCTG | 30 |
| MS26Cas-2 | Reverse | CAAGCAGAAGACGGCATACGAGCTCTTCC GATCTCCGGAAGCTCGCCGCGT | 31 |
| MS26Cas-3 | Forward | CTACACTCTTTCCCTACACGACGCTCTTCC GATCTTCCTCCGGAAGCTCGCCGCGT | 32 |
| MS26Cas-3 | Reverse | CAAGCAGAAGACGGCATACGAGCTCTTCC GATCTTCCTGGAGGACGACGTGCTG | 29 |
| MS26 Meganuclease | Forward | CTACACTCTTTCCCTACACGACGCTCTTCC GATCTTTCCTCCTGGAGGACGACGTGCTG | 33 |
| MS26 Meganuclease | Reverse | CAAGCAGAAGACGGCATACGAGCTCTTCC GATCTCCGGAAGCTCGCCGCGT | 31 |
| LIGCas-1 | Forward | CTACACTCTTTCCCTACACGACGCTCTTCC GATCTAGGACTGTAACGATTTACGCACCTG CTG | 34 |
| LIGCas-1 | Reverse | CAAGCAGAAGACGGCATACGAGCTCTTCC GATCTGCAAATGAGTAGCAGCGCACGTAT | 35 |
| LIGCas-2 | Forward | CTACACTCTTTCCCTACACGACGCTCTTCC GATCTTCCTCTGTAACGATTTACGCACCTG CTG | 36 |
| LIGCas-2 | Reverse | CAAGCAGAAGACGGCATACGAGCTCTTCC GATCTGCAAATGAGTAGCAGCGCACGTAT | 35 |
| LIGCas-3 | Forward | CTACACTCTTTCCCTACACGACGCTCTTCC GATCTAAGGCGCAAATGAGTAGCAGCGCA C | 37 |
| LIGCas-3 | Reverse | CAAGCAGAAGACGGCATACGAGCTCTTCC GATCTCACCTGCTGGGAATTGTACCGTA | 38 |
| LIG3-4 Meganuclease | Forward | CTACACTCTTTCCCTACACGACGCTCTTCC GATCTCCTTCGCAAATGAGTAGCAGCGCAC | 39 |
| LIG3-4 Meganuclease | Reverse | CAAGCAGAAGACGGCATACGAGCTCTTCC GATCTCACCTGCTGGGAATTGTACCGTA | 38 |
| MS45Cas-1 | Forward | CTACACTCTTTCCCTACACGACGCTCTTCC GATCTAGGAGGACCCGTTCGGCCTCAGT | 40 |
| MS45Cas-1 | Reverse | CAAGCAGAAGACGGCATACGAGCTCTTCC GATCTGCCGGCTGGCATTGTCTCTG | 41 |
| MS45Cas-2 | Forward | CTACACTCTTTCCCTACACGACGCTCTTCC GATCTTCCTGGACCCGTTCGGCCTCAGT | 42 |
| MS45Cas-2 | Reverse | CAAGCAGAAGACGGCATACGAGCTCTTCC GATCTGCCGGCTGGCATTGTCTCTG | 41 |

TABLE 2-continued

PCR primer sequences

| Target SIte | Primer Orientation | Primary PCR Primer Sequence | SEQ ID NO: |
|---|---|---|---|
| MS45Cas-3 | Forward | CTACACTCTTTCCCTACACGACGCTCTTCC GATCTGAAGGGACCCGTTCGGCCTCAGT | 43 |
| MS45Cas-3 | Reverse | CAAGCAGAAGACGGCATACGAGCTCTTCC GATCTGCCGGCTGGCATTGTCTCTG | 41 |
| ALSCas-1 | Forward | CTACACTCTTTCCCTACACGACGCTCTTCC GATCTAAGGCGACGATGGGCGTCTCCTG | 44 |
| ALSCas-1 | Reverse | CAAGCAGAAGACGGCATACGAGCTCTTCC GATCTGCGTCTGCATCGCCACCTC | 45 |
| ALSCas-2 | Forward | CTACACTCTTTCCCTACACGACGCTCTTCC GATCTTTCCCGACGATGGGCGTCTCCTG | 46 |
| ALSCas-2 | Reverse | CAAGCAGAAGACGGCATACGAGCTCTTCC GATCTGCGTCTGCATCGCCACCTC | 45 |
| ALSCas-3 | Forward | CTACACTCTTTCCCTACACGACGCTCTTCC GATCTGGAACGACGATGGGCGTCTCCTG | 47 |
| ALSCas-3 | Reverse | CAAGCAGAAGACGGCATACGAGCTCTTCC GATCTGCGTCTGCATCGCCACCTC | 45 |
| EPSPSCas-1 | Forward | CTACACTCTTTCCCTACACGACGCTCTTCC GATCTGGAAGAGGAAACATACGTTGCATT TCCA | 48 |
| EPSPSCas-1 | Reverse | CAAGCAGAAGACGGCATACGAGCTCTTCC GATCTGGTGGAAAGTTCCCAGTTGAGGA | 49 |
| EPSPSCas-2 | Forward | CTACACTCTTTCCCTACACGACGCTCTTCC GATCTAAGCGGTGGAAAGTTCCCAGTTGA GGA | 50 |
| EPSPSCas-2 | Reverse | CAAGCAGAAGACGGCATACGAGCTCTTCC GATCTGAGGAAACATACGTTGCATTTCCA | 51 |
| EPSPSCas-3 | Forward | CTACACTCTTTCCCTACACGACGCTCTTCC GATCTCCTTGAGGAAACATACGTTGCATTT CCA | 52 |
| EPSPSCas-3 | Reverse | CAAGCAGAAGACGGCATACGAGCTCTTCC GATCTGGTGGAAAGTTCCCAGTTGAGGA | 49 |

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on Illumina's MiSeq Personal Sequencer with a 30-40% (v/v) spike of PhiX control v3 (Illumina, FC-110-3001) to off-set sequence bias. Only those reads with a ≥1 nucleotide indel arising within the 10 nucleotide window centered over the expected site of cleavage and not found in a similar level in the negative control were classified as NHEJ mutations. NHEJ mutant reads with the same mutation were counted and collapsed into a single read and the top 10 most prevalent mutations were visually confirmed as arising within the expected site of cleavage. The total numbers of visually confirmed NHEJ mutations were then used to calculate the % mutant reads based on the total number of reads of an appropriate length containing a perfect match to the barcode and forward primer.

The frequency of NHEJ mutations recovered by deep sequencing for the guide RNA/Cas endonuclease system targeting the three LIGCas targets (SEQ ID NOS: 16, 17, 18) compared to the LIG3-4 homing endonuclease targeting the same locus is shown in Table 3. The ten most prevalent types of NHEJ mutations recovered based on the guide RNA/Cas endonuclease system compared to the LIG3-4 homing endonuclease are shown in FIG. 3 A (corresponding to SEQ ID NOs: 55-75) and FIG. 3 B (corresponding to SEQ ID NOs: 76-96). Approximately, 12-23 fold higher frequencies of NHEJ mutations were observed when using a guide RNA/Cas system to introduce a double strand break at a maize genomic target site (Cas target sites), relative to the LIG3-4 homing endonuclease control. As shown in Table 4, a similar difference between the guide RNA/Cas system and meganuclease double-strand break technologies was observed at the MS26 locus with approximately 14-25 fold higher frequencies of NHEJ mutations when a guide RNA/Cas endonuclease system was used. High frequencies of NHEJ mutations were also recovered at the MS45, ALS and EPSPS Cas targets (see Table 5) when using a guide RNA/Cas endonuclease system. This data indicates that the guide RNA/Cas9 endonuclease system described herein can be effectively used to introduce an alteration at genomic sites of interest such as those related to male fertility, wherein an alteration results in the creation of a male sterile gene locus and male sterile plants. Altering the EPSPS target can result in the production of plants that are tolerant and/or resistant against glyphosate based herbicides. Altering the acetolactate synthase (ALS) gene target site can result in the production of plants that are tolerant and/or resistant to imidazolinone and sulphonylurea herbicides.

TABLE 3

Percent (%) mutant reads at maize Liguleless 1 target locus produced by a guide RNA/Cas system versus a homing endonuclease system.

| System | Total Number of Reads | Number of Mutant Reads | % Mutant Reads |
|---|---|---|---|
| Cas9 Only Control | 640,063 | 1 | 0.00% |
| guide RNA Only Control | 646,774 | 1 | 0.00% |
| LIG3-4 Homing Endonuclease | 616,536 | 1,211 | 0.20% |
| LIGCas-1 guide/Cas9 | 716,854 | 33,050 | 4.61% |
| LIGCas-2 guide/Cas9 | 711,047 | 16,675 | 2.35% |
| LIGCas-3 guide/Cas9 | 713,183 | 27,959 | 3.92% |

TABLE 4

Percent (%) mutant reads at maize Male Sterility 26 target locus produced by a guide RNA/Cas system versus a homing endonuclease.

| System | Total Number of Reads | Number of Mutant Reads | % Mutant Reads |
|---|---|---|---|
| Cas9 Only Control | 403,123 | 15 | 0.00% |
| MS26++ Homing Endonuclease | 512,784 | 642 | 0.13% |
| MS26Cas-1 guide/Cas9 | 575,671 | 10,073 | 1.75% |
| MS26Cas-2 guide/Cas9 | 543,856 | 16,930 | 3.11% |
| MS26Cas-3 guide/Cas9 | 538,141 | 13,879 | 2.58% |

TABLE 5

Percent (%) mutant reads at maize Male Sterility 45, Acetolactate Synthase and Enolpyruvylshikimate Phosphate Synthase target loci produced by the guide RNA/Cas system.

| System | Total Number of Reads | Number of Mutant Reads | % Mutant Reads |
|---|---|---|---|
| Cas9 Only Control (MS45) | 899,500 | 27 | 0.00% |
| MS45Cas-1 guide/Cas9 | 812,644 | 3,795 | 0.47% |
| MS45Cas-2 guide/Cas9 | 785,183 | 14,704 | 1.87% |
| MS45Cas-3 guide/Cas9 | 728,023 | 9,203 | 1.26% |
| Cas9 Only Control (ALS) | 534,764 | 19 | 0.00% |
| ALSCas-1 guide/Cas9 | 434,452 | 9,669 | 2.23% |
| ALSCas-2 guide /Cas9 | 472,351 | 6,352 | 1.345% |
| ALSCas-3 guide/Cas9 | 497,786 | 8,535 | 1.715% |
| Cas9 Only Control EPSPS) | 1,347,086 | 6 | 0.00% |
| EPSPSCas-1 guide/Cas9 | 1,420,274 | 13,051 | 0.92% |
| EPSPSCas-2 guide/Cas9 | 1,225,082 | 26,340 | 2.15% |
| EPSPSCas-3 guide/Cas9 | 1,406,905 | 53,603 | 3.81% |

Taken together, our data indicate that the maize optimized guide RNA/Cas endonuclease system described herein using a long guide RNA expression cassette efficiently cleaves maize chromosomal DNA and generates imperfect NHEJ mutations at frequencies greater than the engineered LIG3-4 and MS26++ homing endonucleases.

Example 3

Long Guide RNA of the Maize Optimized Guide RNA/Cas Endonuclease System Cleaves Maize Chromosomal DNA More Efficiently than the Short Guide RNA To determine the most effective guide RNA (comprising a fusion of the crRNA and tracrRNA) for use in maize, the recovery of NHEJ mutations using a short guide RNA (SEQ ID NO: 11) based on Jinek et al. (2012) Science 337:816-21 and a long guide RNA (SEQ ID NO: 8) based on Mali et al. (2013) Science 339:823-26 was examined.

The variable targeting domains of the guide RNA targeting the maize genomic target sites at the LIG locus (LIGCas-1, LIGCas-2 and LIGCas-3, SEQ ID NOs: 16, 17 and 18, Table1) were introduced into both the maize optimized long and short guide RNA expression cassettes as described in Example 1 and co-transformed along with the maize optimized Cas9 endonuclease expression cassette into immature maize embryos and deep sequenced for NHEJ mutations as described in Example 2. Embryos transformed with only the Cas9 endonuclease expression cassette served as a negative control.

As shown in Table 6 below, the frequency of NHEJ mutations recovered with the long guide RNA far exceeded those obtained with the short guide RNA. This data indicates that the long guide RNA paired with the maize optimized Cas9 endonuclease gene described herein more efficiently cleaves maize chromosomal DNA.

TABLE 6

Percent (%) mutant reads at the maize Liguleless 1 target locus produced by a guide RNA/Cas system with a long versus a short guide RNA.

| System | guide RNA Used | Total Number of Reads | Number of Mutant Reads | % Mutant Reads |
|---|---|---|---|---|
| Cas9 Only | N/A | 640,063 | 1 | 0.00% |
| LIGCas-1 guide/Cas9 | Short | 676,870 | 43 | 0.01% |
| LIGCas-2 guide/Cas9 | Short | 747,945 | 91 | 0.01% |
| LIGCas-3 guide/Cas9 | Short | 655,157 | 10 | 0.00% |

TABLE 6-continued

Percent (%) mutant reads at the maize Liguleless 1 target locus produced by a guide RNA/Cas system with a long versus a short guide RNA.

| System | guide RNA Used | Total Number of Reads | Number of Mutant Reads | % Mutant Reads |
|---|---|---|---|---|
| LIGCas-1 guide/Cas9 | Long | 716,854 | 33,050 | 4.61% |
| LIGCas-2 guide/cas9 | Long | 711,047 | 16,675 | 2.35% |
| LIGCas-3 guide/Cas9 | Long | 713,183 | 27,959 | 3.92% |

Example 4

The Guide RNA/Cas Endonuclease System May be Multiplexed to Simultaneously Target Multiple Chromosomal Loci in Maize for Mutagenesis by Imperfect Non-Homologous End-Joining To test if multiple chromosomal loci may be simultaneously mutagenized with the guide RNA/maize optimized Cas endonuclease system described herein, the long guide RNA expression cassettes targeting the MS26Cas-2 target site (SEQ ID NO: 14), the LIGCas-3 target site (SEQ ID NO: 18) and the MS45Cas-2 target site (SEQ ID NO: 20), were co-transformed into maize embryos either in duplex or in triplex along with the Cas9 endonuclease expression cassette and examined by deep sequencing for the presence of imprecise NHEJ mutations as described in Example 2.

Hi-II maize embryos co-transformed with the Cas9 expression cassette and the corresponding guide RNA expression cassette singly served as a positive control and embryos transformed with only the Cas9 expression cassette served as a negative control.

As shown in Table 7 below, mutations resulting from imprecise NHEJ were recovered at all relevant loci when multiple guide RNA expression cassettes were simultaneously introduced either in duplex or triplex with frequencies of mutant reads near those of the positive control. Thus, demonstrating that the maize optimized guide RNA/Cas endonuclease system described herein may be used to simultaneously introduce imprecise NHEJ mutations at multiple loci in maize.

TABLE 7

Percent (%) mutant reads at maize target loci produced by a multiplexed guide RNA/Cas system.

| Target Site Examined for NHEJ Mutations | guide RNAs Co-transformed Individually, in Duplex, or in Triplex with Cas9 | Total Number of Reads | Number of Mutant Reads | % Mutant Reads |
|---|---|---|---|---|
| LIGCas-3, MS26Cas-2, MS45Cas-2 | None (Cas9 Only control) | 527,691 | 9 | 0.00% |
| LIGCas-3 | LIGCas-3 | 645,107 | 12,631 | 1.96% |
|  | LIGCas-3 MS26Cas-2 | 579,992 | 10,348 | 1.78% |
|  | LIGCas-3 MS26Cas-2 MS45Cas-2 | 648,901 | 12,094 | 1.86% |

TABLE 7-continued

Percent (%) mutant reads at maize target loci produced by a multiplexed guide RNA/Cas system.

| Target Site Examined for NHEJ Mutations | guide RNAs Co-transformed Individually, in Duplex, or in Triplex with Cas9 | Total Number of Reads | Number of Mutant Reads | % Mutant Reads |
|---|---|---|---|---|
| MS26Cas-2 | MS26 Cas 2 | 699,154 | 17,247 | 2.47% |
|  | LIGCas-3 MS26Cas-2 | 717,158 | 10,256 | 1.43% |
|  | MS26Cas-2 MS45Cas-2 | 613,431 | 9,931 | 1.62% |
|  | LIGCas-3 MS26Cas-2 MS45Cas-2 | 471,890 | 7,311 | 1.55% |
| MS45Cas-2 | MS45Cas-2 | 503,423 | 10,034 | 1.99% |
|  | MS26Cas-2 MS45Cas-2 | 480,178 | 8,008 | 1.67% |
|  | LIGCas-3 MS26Cas-2 MS45Cas-2 | 416,711 | 7,190 | 1.73% |

Example 5

Guide RNA/Cas Endonuclease Mediated DNA Cleavage in Maize Chromosomal Loci can Stimulate Homologous Recombination Repair-Mediated Transgene Insertion To test the utility of the maize optimized guide RNA/Cas system described herein to cleave maize chromosomal loci and stimulate homologous recombination (THR) repair pathways to site-specifically insert a transgene, a HR repair DNA vector (also referred to as a donor DNA) (SEQ ID NO: 97) was constructed as illustrated in FIG. 4 using standard molecular biology techniques and co-transformed with a long guide RNA expression cassette, comprising a variable targeting domain corresponding to the LIGCas-3 genomic target site, and a Cas9 endonuclease expression cassette into immature maize embryos as described in Example 2.

Maize embryos co-transformed with the HR repair DNA vector and LIG3-4 homing endonuclease (see Example 9) targeting the same genomic target site as LIGCas-3 served as a positive control. Since successful delivery of the HR repair DNA vector confers bialaphos herbicide resistance, callus events containing putative HR-mediated transgenic insertions were selected by placing the callus on herbicide containing media. After selection, stable callus events were sampled, total genomic DNA extracted, and using the primer pairs shown in FIG. 5 (corresponding to SEQ ID NOs: 98-101), PCR amplification was carried out at both possible transgene genomic DNA junctions to identify putative HR-mediated transgenic insertions. The resulting amplifications were sequenced for confirmation.

Sequence confirmed PCR amplifications indicating site-specific transgene insertion for the guide RNA/Cas system were detected for 37 out of 384 stable transformants with 15 containing amplifications across both transgene genomic DNA junctions indicating near perfect site-specific transgene insertion. The LIG3-4 homing endonuclease positive control yielded PCR amplifications indicating site-specific transgene insertion for 3 out of 192 stable transformants with 1 containing amplifications across both transgene genomic DNA junctions. The data clearly demonstrates that maize chromosomal loci cleaved with the maize optimized guide RNA/Cas system described herein can be used to stimulate HR repair pathways to site-specifically insert transgenes at frequencies greater than the LIG3-4 homing endonuclease.

Example 6

Guide RNA/Cas Endonuclease System Transformed Together on a Single Vector Results in Greater Recovery of Imperfect Non-Homologous End-Joining Mutations To evaluate different delivery methods for the maize optimized guide RNA/Cas endonuclease system described herein, the recovery of NHEJ mutations when the guide RNA/Cas expression cassettes were either co-transformed as separate DNA vectors as in Examples 2, 3, 4 and 5 or transformed as a single vector DNA (comprising both guide RNA and Cas endonuclease expression cassettes, as shown in FIG. 1C) was examined.

The long guide RNA expression cassette for LIGCas-3 and the Cas9 expression cassette were consolidated onto a single vector DNA (FIG. 1 C, SEQ ID NO: 102) by standard molecular biology techniques and transformed into immature Hi-II maize embryos as described in Examples 10 and 11 by particle-mediated delivery. Hi-II embryos co-transformed with the Cas9 and LIGCas-3 long guide RNA expression cassettes served as a positive control while embryos transformed with only the Cas9 expression cassette served as a negative control. Deep sequencing for NHEJ mutations was performed as described in Example 2.

As shown in Table 8 below, the frequency of NHEJ mutations recovered when the Cas endonuclease and long guide RNA expression cassettes were delivered together as a single vector DNA was approximately 2-fold greater than that observed from the equivalent co-transformation experiment. This indicates that delivery of the guide RNA/Cas system expression cassettes together on a single vector DNA results in a greater recovery of imperfect non-homologous end-joining mutations.

TABLE 8

Percent (%) mutant reads at the maize Liguleless 1 target locus produced by a guide RNA/Cas system with Cas9 and guide RNA expression cassettes combined into one DNA vector versus two separate DNA vectors.

| System | Total Number of Reads | Number of Mutant Reads | % Mutant Reads |
|---|---|---|---|
| Cas9 Only Control | 1,519,162 | 97 | 0.01% |
| LIGCas-3 guide/Cas9 (Two vector DNAs) | 1,515,0607 | 36,346 | 2.40% |
| LIGCas-3 guide/Cas9 (Single vector DNA) | 1,860,031 | 105,854 | 5.69% |

Example 7

Delivery Methods for Plant Genome Editing Using the Guide RNA/Cas Endonuclease System This example describes methods to deliver or maintain and express the Cas9 endonuclease and guide RNA (or individual crRNA and tracrRNAs) into, or within plants, respectively, to enable directed DNA modification or gene insertion via homologous recombination. More specifically this example describes a variety of methods which include, but are not limited to, delivery of the Cas9 endonuclease as a DNA, RNA (5'-capped and polyadenylated) or protein molecule. In addition, the guide RNA may be delivered as a DNA or RNA molecule.

Shown in Example 2, a high mutation frequency was observed when Cas9 endonuclease and guide RNA were delivered as DNA vectors by biolistic transformation of immature corn embryos. Other embodiments of this disclosure can be to deliver the Cas9 endonuclease as a DNA, RNA or protein and the guide RNA as a DNA or RNA molecule or as a duplex crRNA/tracrRNA molecule as RNA or DNA or a combination. Various combinations of Cas9 endonuclease, guide RNA and crRNA/tracrRNA delivery methods can be, but are not limited to, the methods shown in Table 9.

TABLE 9

Various combinations of delivery of the cas9 endonuclease, guide RNA or CRNA + tracrRNA.

| combination | Components delivered. (Delivery method is shown between brackets) |
|---|---|
| 1 | Cas9 (DNA vector), guide RNA (DNA vector) |
| 2 | Cas9 (DNA vector), guide RNA (RNA) |
| 3 | Cas9 (RNA), guide RNA (DNA) |
| 4 | Cas9 (RNA), guide RNA (RNA) |
| 5 | Cas9 (Protein), guide RNA (DNA) |
| 6 | Cas9 (Protein), guide RNA (RNA) |
| 7 | Cas9 (DNA vector), crRNA (DNA), tracrRNA (DNA) |
| 8 | Cas9 (DNA vector), crRNA (RNA), tracrRNA (DNA) |
| 9 | Cas9 (DNA vector), crRNA (RNA), tracrRNA (RNA) |
| 10 | Cas9 (DNA vector) crRNA (DNA), tracrRNA (RNA) |
| 11 | Cas9 (RNA), crRNA (DNA), tracrRNA (DNA) |
| 12 | Cas9 (RNA), crRNA (RNA), tracrRNA (DNA) |
| 13 | Cas9 (RNA), crRNA (RNA), tracrRNA (RNA) |
| 14 | Cas9 (RNA), crRNA (DNA), tracrRNA (RNA) |
| 15 | Cas9 (Protein), crRNA (DNA), tracrRNA (DNA) |
| 16 | Cas9 (Protein), crRNA (RNA), tracrRNA (DNA) |
| 17 | Cas9 (Protein), crRNA (RNA), tracrRNA 18(RNA) |
| 18 | Cas9 (Protein), crRNA (DNA), tracrRNA (RNA) |

Delivery of the Cas9 (as DNA vector) and guide RNA (as DNA vector) example (Table 9, combination1) can also be accomplished by co-delivering these DNA cassettes on a single or multiple *Agrobacterium* vectors and transforming plant tissues by *Agrobacterium* mediated transformation. In addition, a vector containing a constitutive, tissue-specific or conditionally regulated Cas9 gene can be first delivered to plant cells to allow for stable integration into the plant genome to establish a plant line that contains only the Cas9 gene in the plant genome. In this example, single or multiple guide RNAs, or single or multiple crRNA and a tracrRNA can be delivered as either DNA or RNA, or combination, to the plant line containing the genome-integrated version of the Cas9 gene for the purpose of generating mutations or promoting homologous recombination when HR repair DNA vectors for targeted integration are co-delivered with the guide RNAs. As extension of this example, plant line containing the genome-integrated version of the Cas9 gene and a tracrRNA as a DNA molecule can also be established. In this example single or multiple crRNA molecules can be delivered as RNA or DNA to promote the generation of mutations or to promote homologous recombination when HR repair DNA vectors for targeted integration are co-delivered with crRNA molecule(s) enabling the targeted mutagenesis or homologous recombination at single or multiple sites in the plant genome.

Example 8

Components of the Guide RNA/Cas Endonuclease System Delivered Directly as RNA in Plants This example illustrates the use of the methods as described in Table 9 configuration of Example 7 [Cas9 (DNA vector), guide RNA (RNA)] for modification or mutagenesis of chromosomal loci in plants. The maize optimized Cas9 endonuclease expression cassette described in Example 1 was co-delivered by particle gun as described in Example 2 along with single stranded RNA molecules (synthesized by Integrated DNA Technologies, Inc.) constituting a short guide RNA targeting the maize locus and sequence shown in Table 10. Embryos transformed with only the Cas9 expression cassette or short guide RNA molecules served as negative controls. Seven days post-bombardment, the immature embryos were harvested and analyzed by deep sequencing for NHEJ mutations as described in Example 2. Mutations not present in the negative controls were found at the site (FIG. 6, corresponding to SEQ ID NOs: 104-110). These mutations were similar to those found in Examples 2, 3, 4 and 6. This data indicates that component(s) of the maize optimized guide RNA/Cas endonuclease system described herein may be delivered directly as RNA.

TABLE 10

Maize genomic target site and location for short guide RNA delivered as RNA.

| Locus | Location | Guide RNA Used | Designation | Maize Target Site | PAM Sequence | SEQ ID NO |
|---|---|---|---|---|---|---|
| 55 | Chr. 1: 51.78 cM | Short | 55CasRNA-1 | TGGGCAGGTCTCACGACGGT | TGG | 103 |

Example 9

Creation of Rare Cutting Engineered Meganucleases
Lig3-4 Meganuclease and Lig3-4 Intended Recognition Sequence An endogenous maize genomic target site comprising the LIG3-4 intended recognition sequence (SEQ ID NO: 111) was selected for design of a rare-cutting double-strand break inducing agent (SEQ ID NO: 112) as described in US patent publication 2009-0133152 A1 (published May 21, 2009). The LIG3-4 intended recognition sequence is a 22 bp polynucleotide having the following sequence: ATATACCT-CACACGTACGCGTA (SEQ ID NO: 111).
MS 26++ Meganuclease An endogenous maize genomic target site designated "TS-MS26" (SEQ ID NO: 113) was selected for design of a custom double-strand break inducing agent MS26++ as described in U.S. patent application Ser. No. 13/526,912 filed Jun. 19, 2012). The TS-MS26 target site is a 22 bp polynucleotide positioned 62 bps from the 5' end of the fifth exon of the maize MS26 gene and having the following sequence: gatggtgac<u>gtac</u>^gtgccctac (SEQ ID NO: 113). The double strand break site and overhang region is underlined, the enzyme cuts after C13, as indicated by the ^. Plant optimized nucleotide sequences for an engineered endonuclease (SEQ ID NO: 114) encoding an engineered MS26++ endonuclease were designed to bind and make double-strand breaks at the selected TS-MS26 target site.

Example 10

Transformation of Maize Immature Embryos

Transformation can be accomplished by various methods known to be effective in plants, including particle-mediated delivery, *Agrobacterium*-mediated transformation, PEG-mediated delivery, and electroporation.
A. Particle-Mediated Delivery Transformation of maize immature embryos using particle delivery is performed as follows. Media recipes follow below.

The ears are husked and surface sterilized in 30% Clorox bleach plus 0.5% Micro detergent for 20 minutes, and rinsed two times with sterile water. The immature embryos are isolated and placed embryo axis side down (scutellum side up), 25 embryos per plate, on 560Y medium for 4 hours and then aligned within the 2.5-cm target zone in preparation for bombardment. Alternatively, isolated embryos are placed on 560 L (Initiation medium) and placed in the dark at temperatures ranging from 26° C. to 37° C. for 8 to 24 hours prior to placing on 560Y for 4 hours at 26° C. prior to bombardment as described above.

Plasmids containing the double strand brake inducing agent and donor DNA are constructed using standard molecular biology techniques and co-bombarded with plasmids containing the developmental genes ODP2 (AP2 domain transcription factor ODP2 (Ovule development protein 2); US20090328252 A1) and Wushel (US2011/0167516).

The plasmids and DNA of interest are precipitated onto 0.6 μm (average diameter) gold pellets using a water-soluble cationic lipid transfection reagent as follows. DNA solution is prepared on ice using 1 μg of plasmid DNA and optionally other constructs for co-bombardment such as 50 ng (0.5 μl) of each plasmid containing the developmental genes ODP2 (AP2 domain transcription factor ODP2 (Ovule development protein 2); US20090328252 A1) and Wushel. To the pre-mixed DNA, 20 μl of prepared gold particles (15 mg/ml) and 5 μl of a water-soluble cationic lipid transfection reagent is added in water and mixed carefully. Gold particles are pelleted in a microfuge at 10,000 rpm for 1 min and supernatant is removed. The resulting pellet is carefully rinsed with 100 ml of 100% EtOH without resuspending the pellet and the EtOH rinse is carefully removed. 105 μl of 100% EtOH is added and the particles are resuspended by brief sonication. Then, 10 μl is spotted onto the center of each macrocarrier and allowed to dry about 2 minutes before bombardment.

Alternatively, the plasmids and DNA of interest are precipitated onto 1.1 μm (average diameter) tungsten pellets using a calcium chloride ($CaCl_2$)) precipitation procedure by mixing 100 μl prepared tungsten particles in water, 10 μl (1 μg) DNA in Tris EDTA buffer (1 μg total DNA), 100 μl 2.5 M CaCl2, and 10 μl 0.1 M spermidine. Each reagent is added sequentially to the tungsten particle suspension, with mixing. The final mixture is sonicated briefly and allowed to incubate under constant vortexing for 10 minutes. After the precipitation period, the tubes are centrifuged briefly, liquid is removed, and the particles are washed with 500 ml 100% ethanol, followed by a 30 second centrifugation. Again, the liquid is removed, and 105 µl of 100% ethanol is added to the final tungsten particle pellet. For particle gun bombardment, the tungsten/DNA particles are briefly sonicated. 10 µl of the tungsten/DNA particles is spotted onto the center of each macrocarrier, after which the spotted particles are allowed to dry about 2 minutes before bombardment.

The sample plates are bombarded at level #4 with a Biorad Helium Gun. All samples receive a single shot at 450 PSI, with a total of ten aliquots taken from each tube of prepared particles/DNA.

Following bombardment, the embryos are incubated on 560P (maintenance medium) for 12 to 48 hours at temperatures ranging from 26 C to 37 C, and then placed at 26 C. After 5 to 7 days the embryos are transferred to 560R selection medium containing 3 mg/liter Bialaphos, and subcultured every 2 weeks at 26 C. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to a lighted culture room. Approximately 7-10 days later, developing plantlets are transferred to 272V hormone-free medium in tubes for 7-10 days until plantlets are well established. Plants are then transferred to inserts in flats (equivalent to a 2.5" pot) containing potting soil and grown for 1 week in a growth chamber, subsequently grown an additional 1-2 weeks in the greenhouse, then transferred to Classic 600 pots (1.6 gallon) and grown to maturity. Plants are monitored and scored for transformation efficiency, and/or modification of regenerative capabilities.

Initiation medium (560L) comprises 4.0 g/l N6 basal salts (SIGMA C-1416), 1.0 ml/l Eriksson's Vitamin Mix (1000× SIGMA-1511), 0.5 mg/l thiamine HCl, 20.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Maintenance medium (560P) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, 2.0 mg/l 2,4-D, and 0.69 g/l L-proline (brought to volume with D-I H2O following adjustment to pH 5.8 with KOH); 3.0 g/l Gelrite (added after bringing to volume with D-I H2O); and 0.85 mg/l silver nitrate (added after sterilizing the medium and cooling to room temperature).

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I H2O following adjustment to pH 5.8 with KOH); 2.0 g/l Gelrite (added after bringing to volume with D-I H2O); and 8.5 mg/l silver nitrate (added after sterilizing the medium and cooling to room temperature).

Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I H2O following adjustment to pH 5.8 with KOH); 3.0 g/l Gelrite (added after bringing to volume with D-I H2O); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I H2O) (Murashige and Skoog (1962) Physiol. Plant. 15:473), 100 mg/l myo-inositol, 0.5 mg/l zeatin, 60 g/l sucrose, and 1.0 ml/l of 0.1 mM abscisic acid (brought to volume with polished D-I H2O after adjusting to pH 5.6); 3.0 g/l Gelrite (added after bringing to volume with D-I H2O); and 1.0 mg/l indoleacetic acid and 3.0 mg/l bialaphos (added after sterilizing the medium and cooling to 60° C.).

Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I H2O), 0.1 g/l myo-inositol, and 40.0 g/l sucrose (brought to volume with polished D-I H2O after adjusting pH to 5.6); and 6 g/l bacto-agar (added after bringing to volume with polished D-I H2O), sterilized and cooled to 60° C.

b. *Agrobacterium*-Mediated Transformation

*Agrobacterium*-mediated transformation was performed essentially as described in Djukanovic et al. (2006) *Plant Biotech J* 4:345-57. Briefly, 10-12 day old immature embryos (0.8-2.5 mm in size) were dissected from sterilized kernels and placed into liquid medium (4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 68.5 g/L sucrose, 36.0 g/L glucose, pH 5.2). After embryo collection, the medium was replaced with 1 ml *Agrobacterium* at a concentration of 0.35-0.45 OD550. Maize embryos were incubated with *Agrobacterium* for 5 min at room temperature, then the mixture was poured onto a media plate containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.690 g/L L-proline, 30.0 g/L sucrose, 0.85 mg/L silver nitrate, 0.1 nM acetosyringone, and 3.0 g/L Gelrite, pH 5.8. Embryos were incubated axis down, in the dark for 3 days at 20° C., then incubated 4 days in the dark at 28° C., then transferred onto new media plates containing 4.0 g/L N6 Basal Salts (Sigma C-1416), 1.0 ml/L Eriksson's Vitamin Mix (Sigma E-1511), 1.0 mg/L thiamine HCl, 1.5 mg/L 2, 4-D, 0.69 g/L L-proline, 30.0 g/L sucrose, 0.5 g/L MES buffer, 0.85 mg/L silver nitrate, 3.0 mg/L Bialaphos, 100 mg/L carbenicillin, and 6.0 g/L agar, pH 5.8. Embryos were subcultured every three weeks until transgenic events were identified. Somatic embryogenesis was induced by transferring a small amount of tissue onto regeneration medium (4.3 g/L MS salts (Gibco 11117), 5.0 ml/L MS Vitamins Stock Solution, 100 mg/L myo-inositol, 0.1 M ABA, 1 mg/L IAA, 0.5 mg/L zeatin, 60.0 g/L sucrose, 1.5 mg/L Bialaphos, 100 mg/L carbenicillin, 3.0 g/L Gelrite, pH 5.6) and incubation in the dark for two weeks at 28° C. All material with visible shoots and roots were transferred onto media containing 4.3 g/L MS salts (Gibco 11117), 5.0 ml/L MS Vitamins Stock Solution, 100 mg/L myo-inositol, 40.0 g/L sucrose, 1.5 g/L Gelrite, pH 5.6, and incubated under artificial light at 28° C. One week later, plantlets were moved into glass tubes containing the same medium and grown until they were sampled and/or transplanted into soil.

Example 11

Transient Expression of BBM Enhances Transformation

Parameters of the transformation protocol can be modified to ensure that the BBM activity is transient. One such method involves precipitating the BBM-containing plasmid in a manner that allows for transcription and expression, but precludes subsequent release of the DNA, for example, by using the chemical PEI.

In one example, the BBM plasmid is precipitated onto gold particles with PEI, while the transgenic expression cassette (UBI::moPAT~GFPm::PinII; moPAT is the maize optimized PAT gene) to be integrated is precipitated onto gold particles using the standard calcium chloride method.

Briefly, gold particles were coated with PEI as follows. First, the gold particles were washed. Thirty-five mg of gold particles, 1.0 in average diameter (A.S.I. #162-0010), were weighed out in a microcentrifuge tube, and 1.2 ml absolute EtOH was added and vortexed for one minute. The tube was incubated for 15 minutes at room temperature and then centrifuged at high speed using a microfuge for 15 minutes at 4° C. The supernatant was discarded and a fresh 1.2 ml aliquot of ethanol (EtOH) was added, vortexed for one minute, centrifuged for one minute, and the supernatant again discarded (this is repeated twice). A fresh 1.2 ml aliquot of EtOH was added, and this suspension (gold particles in EtOH) was stored at −20° C. for weeks. To coat particles with polyethylimine (PEI; Sigma #P3143), 250 µl of the washed gold particle/EtOH mix was centrifuged and the EtOH discarded. The particles were washed once in 100 µl ddH2O to remove residual ethanol, 250 µl of 0.25 mM PEI was added, followed by a pulse-sonication to suspend the particles and then the tube was plunged into a dry ice/EtOH bath to flash-freeze the suspension, which was then lyophilized overnight. At this point, dry, coated particles could be stored at −80° C. for at least 3 weeks. Before use, the particles were rinsed 3 times with 250 µl aliquots of 2.5 mM HEPES buffer, pH 7.1, with 1× pulse-sonication, and then a quick vortex before each centrifugation. The particles were then suspended in a final volume of 250 µl HEPES buffer. A 25 µl aliquot of the particles was added to fresh tubes before attaching DNA. To attach uncoated DNA, the particles were pulse-sonicated, then 1 g of DNA (in 5 µl water) was added, followed by mixing by pipetting up and down a few times with a Pipetteman and incubated for 10 minutes. The particles were spun briefly (i.e. 10 seconds), the supernatant removed, and 60 µl EtOH added. The particles with PEI-precipitated DNA-1 were washed twice in 60 µl of EtOH. The particles were centrifuged, the supernatant discarded, and the particles were resuspended in 45 µl water. To attach the second DNA (DNA-2), precipitation using a water-soluble cationic lipid transfection reagent was used. The 45 µl of particles/DNA-1 suspension was briefly sonicated, and then 5 µl of 100 ng/l of DNA-2 and 2.5 µl of the water-soluble cationic lipid transfection reagent were added. The solution was placed on a rotary shaker for 10 minutes, centrifuged at 10,000 g for 1 minute. The supernatant was removed, and the particles resuspended in 60 µl of EtOH. The solution was spotted onto macrocarriers and the gold particles onto which DNA-1 and DNA-2 had been sequentially attached were delivered into scutellar cells of 10 DAP Hi-II immature embryos using a standard protocol for the PDS-1000. For this experiment, the DNA-1 plasmid contained a UBI::RFP::pinII expression cassette, and DNA-2 contained a UBI:CFP::pinII expression cassette. Two days after bombardment, transient expression of both the CFP and RFP fluorescent markers was observed as numerous red & blue cells on the surface of the immature embryo. The embryos were then placed on non-selective culture medium and allowed to grow for 3 weeks before scoring for stable colonies. After this 3-week period, 10 multicellular, stably-expressing blue colonies were observed, in comparison to only one red colony. This demonstrated that PEI-precipitation could be used to effectively introduce DNA for transient expression while dramatically reducing integration of the PEI-introduced DNA and thus reducing the recovery of RFP-expressing transgenic events. In this manner, PEI-precipitation can be used to deliver transient expression of BBM and/or WUS2.

For example, the particles are first coated with UBI:: BBM::pinII using PEI, then coated with UBI::moPAT-YFP using a water-soluble cationic lipid transfection reagent, and then bombarded into scutellar cells on the surface of immature embryos. PEI-mediated precipitation results in a high frequency of transiently expressing cells on the surface of the immature embryo and extremely low frequencies of recovery of stable transformants Thus, it is expected that the PEI-precipitated BBM cassette expresses transiently and stimulates a burst of embryogenic growth on the bombarded surface of the tissue (i.e. the scutellar surface), but this plasmid will not integrate. The PAT-GFP plasmid released from the Ca++/gold particles is expected to integrate and express the selectable marker at a frequency that results in substantially improved recovery of transgenic events. As a control treatment, PEI-precipitated particles containing a UBI::GUS::pinII (instead of BBM) are mixed with the PAT-GFP/Ca++ particles. Immature embryos from both treatments are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

As an alternative method, the BBM plasmid is precipitated onto gold particles with PEI, and then introduced into scutellar cells on the surface of immature embryos, and subsequent transient expression of the BBM gene elicits a rapid proliferation of embryogenic growth. During this period of induced growth, the explants are treated with *Agrobacterium* using standard methods for maize (see Example 1), with T-DNA delivery into the cell introducing a transgenic expression cassette such as UBI:: moPAT~GFPm::pinII. After co-cultivation, explants are allowed to recover on normal culture medium, and then are moved onto culture medium containing 3 mg/l bialaphos. After 6-8 weeks, it is expected that GFP+, bialaphos-resistant calli will be observed in the PEI/BBM treatment at a much higher frequency relative to the control treatment (PEI/GUS).

It may be desirable to "kick start" callus growth by transiently expressing the BBM and/or WUS2 polynucleotide products. This can be done by delivering BBM and WUS2 5'-capped polyadenylated RNA, expression cassettes containing BBM and WUS2 DNA, or BBM and/or WUS2 proteins. All of these molecules can be delivered using a biolistics particle gun. For example 5'-capped polyadenylated BBM and/or WUS2 RNA can easily be made in vitro using Ambion's mMessage mMachine kit. RNA is co-delivered along with DNA containing a polynucleotide of interest and a marker used for selection/screening such as Ubi::moPAT~GFPm::PinII. It is expected that the cells receiving the RNA will immediately begin dividing more rapidly and a large portion of these will have integrated the agronomic gene. These events can further be validated as being transgenic clonal colonies because they will also express the PAT-GFP fusion protein (and thus will display green fluorescence under appropriate illumination). Plants regenerated from these embryos can then be screened for the presence of the polynucleotide of interest.

Example 12

DNA Constructs to Test the Guide RNA/Cas Endonuclease System for Soybean Genome Modifications To test if a guide RNA/Cas endonuclease system, similar to that described in Example 1 for maize, is functional in a dicot such as soybean, a Cas9 (SO) gene (SEQ ID NO:115) soybean codon optimized from *Streptococcus pyogenes* M1 GAS (SF370) was expressed with a strong soybean constitutive promoter GM-EF1A2 (US patent application 20090133159 (SEQ ID NO: 116). A simian vacuolating virus 40 (SV40) large T-antigen nuclear localization signal (SEQ ID NO:117), representing the amino acid molecules of PKKKRKV (with a linker SRAD (SRADPKKKRKV), was added to the carboxyl terminus of the codon optimized Cas9 to facilitate transporting the codon optimized Cas9 protein (SEQ ID NO:118) to the nucleus. The codon optimized Cas9 gene was synthesized as two pieces by GenScript USA Inc. (Piscataway, NJ) and cloned in frame downstream of the GM-EF1A2 promoter to make DNA construct QC782 shown in FIG. 7 (SEQ ID NO:119).

Plant U6 RNA polymerase III promoters have been cloned and characterized from such as *Arabidopsis* and *Medicago truncatula* (Waibel and Filipowicz, NAR 18:3451-3458 (1990); Li et al., J. Integrat. Plant Biol. 49:222-229 (2007); Kim and Nam, Plant Mol. Biol. Rep. 31:581-593 (2013); Wang et al., RNA 14:903-913 (2008)). Soybean U6 small nuclear RNA (snRNA) genes were identified herein by searching public soybean variety Williams82 genomic sequence using *Arabidopsis* U6 gene coding sequence. Approximately 0.5 kb genomic DNA sequence upstream of the first G nucleotide of a U6 gene was selected to be used as a RNA polymerase III promoter for example, GM-U6-13.1 promoter (SEQ ID NO:120), to express guide RNA to direct Cas9 nuclease to designated genomic site. The guide RNA coding sequence was 76 bp long (FIG. 8B) and comprised a 20 bp variable targeting domain from a chosen soybean genomic target site on the 5' end and a tract of 4 or more T residues as a transcription terminator on the 3' end. (SEQ ID NO:121, FIG. 8 B). The first nucleotide of the 20 bp variable targeting domain was a G residue to be used by RNA polymerase III for transcription. The U6 gene promoter and the complete guide RNA was synthesized and then cloned into an appropriate vector to make, for example, DNA construct QC783 shown in FIG. 8 A (SEQ ID NO:122). Other soybean U6 homologous genes promoters were similarly cloned and used for small RNA expression.

Since the Cas9 endonuclease and the guide RNA need to form a protein/RNA complex to mediate site-specific DNA double strand cleavage, the Cas9 endonuclease and guide RNA must be expressed in same cells. To improve their co-expression and presence, the Cas9 endonuclease and guide RNA expression cassettes were linked into a single DNA construct, for example, QC815 in FIG. 9 A (SEQ ID NO:123), which was then used to transform soybean cells to test the soybean optimized guide RNA/Cas system for genome modification. Similar DNA constructs were made to target different genomic sites using guide RNAs containing different target sequences.

Example 13

Selection of Soybean Genomic Sites to be Cleaved by the Guide RNA/Cas Endonuclease System A region of the soybean chromosome 4 (Gm04) was selected to test if the soybean optimized guide RNA/Cas endonuclease system could recognize, cleave, and mutate soybean chromosomal DNA through imprecise non-homologous end-joining (NHEJ) repair. Two genomic target sites were selected one close to a predicted gene Glyma04g39780.1 at 114.13 cM herein named DD20 locus (FIG. 10A) and another close to Glyma04g39550.1 at 111.95 cM herein named DD43 locus (FIG. 10B). Each of the 20 bp variable targeting domain of the guide RNA started with a G residue required by RNA polymerase III and was followed in the soybean genome by a 3 bp PAM motif (Table 11). The chromosome positions of the soybean genomic targets sites in close proximity to the PAM sequences were determined by blast searching the public soybean variety Williams82 genomic sequence. The soybean genomic target sites DD20CR1 (SEQ ID NO: 125), DD20CR2 (SEQ ID NO: 126), and DD43CR1 (SEQ ID NO: 127) were identified as all unique in soybean genome while a second identical 23 bp genomic target site DD43CR2 (SEQ ID NO: 128) was found at Gm06:12072339-12072361 so there are two potential cleavage sites targeted by DD43CR2 guide RNA. Both DD43CR1 and DD43CR2 are complementary strand sequences indicated by "c" after the positions.

TABLE 11

Soybean genomic target sites for a guide RNA/Cas endonuclease system.

| Chromosome | Positions | Designation | Genomic Target Sites | PAM |
|---|---|---|---|---|
| Gm04, 114.13 cM | 45936311-45936333 | DD20CR1 | GGAACTGACACACGACATGA | TGG |
| | 45936324-45936346 | DD20CR2 | GACATGATGGAACGTGACTA | AGG |
| Gm04, 111.95 cM | 45731921-45731943c | DD43CR1 | GTCCCTTGTACTTGTACGTA | CGG |
| | 45731895-45731917c | DD43CR2 | GTATTCTAGAAAAGAGGAAT | TGG |

Guide RNA expression cassette comprising a variable targeting domain targeting one of DD20CR1, DD20CR2, DD43CR2 genomic target sites were similarly constructed and linked to the soybean Cas9 expression cassette to make DNA constructs QC817, QC818, and QC816 that are similar to QC815 in FIG. 9 A (SEQ ID NO:123) except for the 20 bp variable targeting domain of the guide RNA Since up to six continuous mismatches in the 5' regions of the genomic target site (protospacer) with the 20 bp variable targeting domain can be tolerated, i.e., a continuous stretch of 14 base pairs between the variable targeting domain and the crRNA sequence proximate to the PAM is necessarily enough for efficient targets cleavage any 23 bp genomic DNA sequence following the pattern N(20)NGG can be selected as a target site for the guide RNA/Cas endonuclease system. The last NGG is the PAM sequence that should not be included in the 20 bp variable targeting domain of the guide RNA. If the first N is not endogenously a G residue it must be replaced with a G residue in guide RNA target sequence to accommodate RNA polymerase III, which should not sacrifice recognition specificity of the target site by the guide RNA.

Example 14

Delivery of the Guide RNA/Cas Endonuclease System DNA to Soybean by Transient Transformation The soybean optimized Cas9 endonuclease and guide RNA expression cassettes were delivered to young soybean somatic embryos in the form of embryogenic suspension cultures by particle gun bombardment. Soybean embryogenic suspension cultures were induced as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in the light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, CA). To 50 µl of a 60 mg/ml 1.0 mm gold particle suspension were added (in order): 30 µl of 30 ng/µl QC815 DNA fragment U6-13.1:DD43CR1+EF1A2:CAS9 as an example, 20 µl of 0.1 M spermidine, and 25 µl of 5 M CaCl$_2$). The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 100 mg of a two-week-old suspension cultures were placed in an empty 60×15 mm Petri dish and the residual liquid removed from the tissue with a pipette. Membrane rupture pressure was set at 1100 psi and the chamber was evacuated to a vacuum of 28 inches mercury. The tissue was placed approximately 3.5 inches away from the retaining screen and bombarded once. The tissue clumps were rearranged and bombarded another time. Minimum amount of liquid MS media without 2,4-D supplement was added to the tissue to prevent the cultures from drying or overgrowing. The 60×15 mm Petri dish was sealed in a 100×25 mm Petri dish containing agar solid MS media to as another measure to keep the tissues from drying up. The tissues were harvested seven days after and genomic DNA was extracted for PCR analysis.

Example 15

Analysis of Guide RNA/Cas Endonuclease System Mediated Site-Specific NHEJ by Deep Sequencing To evaluate DNA double strand cleavage at a soybean genomic target site mediated by the guide RNA/Cas endonuclease system, a region of approximately 100 bp genomic DNA surrounding the target site was amplified by PCR and the PCR product was then sequenced to check mutations at the target site as results of NHEJs. The region was first amplified by 20 cycles of PCR with Phusion High Fidelity mastermix (New England Biolabs) from 100 ng genomic DNA using gene-specific primers that also contain adaptors and amplicon-specific barcode sequences needed for a second round PCR and subsequence sequence analysis. For examples, the first PCR for the four experiments listed in Table 2 were done using primers DD20-S3 (SEQ ID NO:133)/DD20-A (SEQ ID NO:134), DD20-S4 (SEQ ID NO:135)/DD20-A, DD43-S3 (SEQ ID NO:136)/DD43-A (SEQ ID NO:137) and DD43-S4 (SEQ ID NO:138)/DD43-A. One micro liter of the first round PCR products was further amplified by another 20 cycles of PCR using universal primers (SEQ ID NOs:140, 141) with Phusion High Fidelity mastermix. The resulting PCR products were separated on 1.5% agarose gel and the specific DNA bands were purified with Qiagen gel purification spin columns. DNA concentrations were measured with a DNA Bioanalyzer (Agilent) and equal molar amounts of DNA for up to 12 different samples each with specific barcode were mixed as one sample for Illumina deep sequencing analysis. Single read 100 nucleotide-length deep sequencing was performed at a DuPont core facility on a Illumnia's MiSeq Personal Sequencer with a 40% (v/v) spike of PhiX control v3 (Illumina, FC-110-3001) to off-set sequence bias.

Since the genomic target site is located in the middle of the ~100 bp long PCR amplicon (SEQ ID NOs: 142, 143, 144, 145), the 100 nucleotide-length deep sequencing is sufficient to cover the targets site region. A window of 10 nucleotides centered over the expected cleavage site, i.e., 3 bp upstream of the PAM, was selected for sequence analysis. Only those reads with one or more nucleotide indel arising within the 10 nucleotide window and not found in a similar level in negative controls were classified as NHEJ mutations. NHEJ mutant reads of different lengths but with the same mutation were counted into a single read and up to 10 most prevalent mutations were visually confirmed to be specific mutations before they were then used to calculate the % mutant reads based on the total analyzed reads containing specific barcode and forward primer.

The frequencies of NHEJ mutations revealed by deep sequencing for four target sites DD20CR1, DD20CR2, DD43CR1, DD43CR2 with one RNA polymerase III promoter GM-U6-13.1 are shown in Table 2. The visually confirmed most prevalent NHEJ mutations are shown in FIG. 11A-11D. The mutant sequences in FIG. 11A-11E are listed as SEQ ID NOs:147-201. The top row is the original reference sequence with the target site sequence underlined. Deletions in the mutated sequences are indicated by "---" while additions and replacements are indicated by bold letters. Total count of each mutation of different reads is given in the last column. Cas9 nuclease construct only, guide RNA construct only, and no DNA bombardment negative controls were similarly performed and analyzed but data not shown since no-specific mutations were detected. Other targets sites and guide RNAs were also tested with similar positive results and data not shown.

TABLE 12

Target site-specific mutations introduced by guide
RNA/Cas endonuclease mediated NHEJ.

| Experiment | DNA | Mutant reads | Total reads | % Mutants |
|---|---|---|---|---|
| U6-13.1:DD20CR1 + EF1A2:CAS9 | QC817 | 339 | 710,339 | 0.048% |
| U6-13.1:DD20CR2 + EF1A2:CAS9 | QC818 | 419 | 693,483 | 0.060% |
| U6-13.1:DD43CR1 + EF1A2:CAS9 | QC815 | 489 | 682,207 | 0.072% |
| U6-13.1:DD43CR2 + EF1A2:CAS9 | QC816 | 917** | 539,681 | 0.170% |

**At least the top 15 reads are specific mutations but only the top 10 are counted in the table to be consistent with other experiments. If all top 15 mutations are counted, the total Mutant reads is 1080 and the % Mutants is 0.200%.

In conclusion, our data indicate that the soybean optimized guide RNA/Cas endonuclease system is able to effectively cleave soybean endogenous genomic DNA and create imperfect NHEJ mutations at the specified genomic target sites.

Example 16

The Guide RNA/Cas Endonuclease System Delivers Double-Strand Breaks (DBSs) to the Maize Epsps Locus Resulting in Desired Point Mutations Two maize optimized Cas9 endonucleases were developed and evaluated for their ability to introduce a double-strand break at a genomic target sequence. A first Cas9 endonuclease was as described in FIG. 1A (Example 2 and expression cassette SEQ ID NO:5). A second maize optimized Cas9 endonuclease (moCas9 endonuclease; SEQ ID NO:192) was supplemented with the SV40 nuclear localization signal by adding the signal coding sequence to the 5' end of the moCas9 coding sequence (FIG. 13). The plant moCas9 expression cassette was subsequently modified by the insertion of the ST-LS1 intron into the moCas9 coding sequence in order to enhance its expression in maize cells and to eliminate its expression in E. coli and Agrobacterium. The maize ubiquitin promoter and the potato proteinase inhibitor II gene terminator sequences complemented the moCas9 endonuclease gene designs. The structural elements of the moCas9 expression cassette are shown in FIG. 13 and its amino acid and nucleotide sequences are listed as SEQ ID Nos: 192 and 193.

A single guide RNA (sgRNA) expression cassette was essentially as described in Example 1 and shown in FIG. 1B. It consists of the U6 polymerase III maize promoter (SEQ ID NO: 9) and its cognate U6 polymerase III termination sequences (TTTTTTTT). The guide RNA (SEQ ID NO: 194) comprised a 20 nucleotide variable targeting domain (nucleotide1-20 of SEQ ID NO: 194) followed by a RNA sequence capable of interacting with the double strand break inducing endonuclease.

A maize optimized Cas9 endonuclease target sequence (moCas9 target sequence) within the EPSPS codon sequence was complementary to the 20 nucleotide variable sequence of the guide sgRNA determined the site of the Cas9 endonuclease cleavage within the EPSPS coding sequence.

The moCAS9 target sequence (nucleotides 25-44 of SEQ ID NO:209) was synthesized and cloned into the guide RNA-Cas9 expression vector designed for delivery of the components of the guide RNA-Cas9 system to the BMS (Black Mexican Sweet) cells through Agrobacterium-mediated transformation. Agrobacterium T-DNA delivered also the yeast FLP site-specific recombinase and the WDV (wheat dwarf virus) replication-associated protein (replicase). Since the moCas9 target sequences were flanked by the FLP recombination targets (FRT), they were excised by FLP in maize cells forming episomal (chromosome-like) structures. Such circular DNA fragments were replicated by the WDV replicase (the origin of replication was embedded into the WDV promoter) allowing their recovery in E. coli cells. If the maize optimized Cas9 endonuclease made a double-strand break at the moCas9 target sequence, its repair might produce mutations. The procedure is described in detail in: Lyznik, L. A., Djukanovic, V., Yang, M. and Jones, S. (2012) Double-strand break-induced targeted mutagenesis in plants. In: Transgenic plants: Methods and Protocols (Dunwell, J. M. and Wetten, A. C. eds). New York Heidelberg Dordrecht London: Springer, pp. 399-416.

The guideRNA/Cas endonuclease systems using either one of the maize optimized Cas9 endonucleases described herein, generated double-strand breaks in the moCas9 target sequence (Table 13). Table 13 shows the percent of the moCas9 target sequences mutagenized in the maize BMS cells using the moCas9 endonuclease of SEQ ID NO: 192 or the maize optimized cas9 endonuclease described in FIG. 1A and expressed by the expression cassette of SEQ ID NO:5. Both guideRNA/Cas endonuclease systems generated double-strand breaks (as judged by the number of targeted mutagenesis events) ranging from 67 to 84% of the moCas9 target sequences available on episomal DNA molecules in maize BMS cells. A sample of mutagenized EPSPS target sequences is shown in FIG. 14. This observation indicates that the maize optimized Cas9 endonuclease described herein is functional in maize cells and efficiently generates double-strand breaks at the moCas9 target sequence.

TABLE 13

Percent of the moCas9 target sequences mutagenized in the maize BMS cells by maize optimized Cas9 endonucleases.

| Cas9 endonuclease version | # of moCas9 target sequences analyzed | # of intact moCas9 target sequences recovered | # of mutagenized moCas9 target sequences found | Percent mutagenesis (%) |
|---|---|---|---|---|
| SEQ ID NO:193 (FIG.13) | 81 | 13 | 68 | 84% |
| SEQ ID NO: 5 (FIG. 1A) | 93 | 31 | 62 | 67% |

In order to accomplish targeted genome editing of the maize chromosomal EPSPS gene, a polynucleotide modification template which provided genetic information for editing the EPSPS coding sequence was created (SEQ ID NO:195) and co-delivered with the guide RNA/Cas9 system components.

As shown in FIG. 12, the polynucleotide modification template comprised three nucleotide modifications (indicated by arrows) when compared to the EPSPS genomic sequence to be edited. These three nucleotide modifications are referred to as TIPS mutations as these nucleotide modifications result in the amino acid changes T-102 to I-102 and P-106 to S-106. The first point mutation results from the substitution of the C nucleotide in the codon sequence ACT with a T nucleotide, a second mutation results from the substitution of the T nucleotide on the same codon sequence ACT with a C nucleotide to form the isoleucine codon (ATC), the third point mutation results from the substitution of the first C nucleotide in the codon sequence CCA with a T nucleotide in order to form a serine codon, TCA. (FIG. 12). Both codon sequences were located within 9 nucleotides of each other as shown in SEQ ID NO: 196: atcgcaatgcggtca. The three nucleotide modifications are shown in bold. The nucleotides between the two codon sequences were homologous to the non-edited EPSPS gene on the epsps locus. The polynucleotide modification template further comprised DNA fragments of maize EPSPS genomic sequence that were used as homologous sequence for the EPSPS gene editing. The short arm of homologous sequence (HR1-FIG. 12) was 810 base pairs long and the long arm of homologous sequence (HR2-FIG. 12) was 2,883 base pairs long (SEQ ID NO: 195).

In this example, the EPSPS polynucleotide modification template was co-delivered using particle gun bombardment as a plasmid (see template vector 1, FIG. 15) together with the guide sgRNA expression cassette and a maize optimized Cas9 endonuclease expression vector which contained the maize optimized Cas9 endonuclease expression cassette described in FIG. 1A (Example 1, SEQ ID NO:5) and also contained a moPAT selectable marker gene. Ten to eleven day-old immature embryos were placed, embryo-axis down, onto plates containing the N6 medium (Table 14) and incubated at 28° C. for 4-6 hours before bombardment. The plates were placed on the third shelf from the bottom in the PDS-1000 apparatus and bombarded at 200 psi. Post-bombardment, embryos were incubated in the dark overnight at 28° C. and then transferred to plates containing the N6-2 media for 6-8 days at 28° C. The embryos were then transferred to plates containing the N6-3 media for three weeks, followed by transferring the responding callus to plates containing the N6-4 media for an additional three-week selection. After six total weeks of selection at 28° C., a small amount of selected tissue was transferred onto the MS regeneration medium and incubated for three weeks in the dark at 28° C.

TABLE 14

Composition of Culture Media.

| Culture medium | Composition |
|---|---|
| N6 | 4.0 g/L N$_6$ Basal Salts (Sigma C-1416; Sigma-Aldrich Co., St. Louis, MO, USA), 1.0 ml/L Ericksson's Vitamin Mix (Sigma E-1511), 0.5 mg/L thiamine HCl, 190 g/L sucrose, 1.0 mg/L 2,4-dichlorophenoxyacetic acid (2,4-D), 2.88 g/L L-proline, 8.5 mg/L silver nitrate, 25 mg/L cefotaxime, and 6.36 g/L at Sigma agar pH 5.8 |
| N6-2 | 4.0 g/L N$_6$ Basal Salts (Sigma C-1416), 1.0 ml/L Ericksson's Vitamin Mix (Sigma E-1511), 0.5 mg/L thiamine HCl, 20 g/L sucrose, 1.0 mg/L 2,4-D, 2.88 g/L L-proline, 8.5 mg/L silver nitrate, 25 mg/L cefotaxime, and 8.5 g/L Sigma agar at pH 5.8 |
| N6-3 | 4.0 g/L N$_6$ Basal Salts (Sigma C-1416), 1.0 ml/L Ericksson's Vitamin Mix (Sigma E-1511), 0.5 mg/L thiamine HCl, 30 g/L sucrose, 1.5 mg/L 2,4-D, 0.69 g/L L-proline, 0.5 g/L 2-(N-morpholino)ethanesulphonic acid (MES) buffer, 0.85 mg/L silver nitrate, 5 mg/L glufosinate NH$_4$, and 8.0 g/L Sigma agar at pH 5.8 |
| N6-4 | 4.0 g/L N$_6$ Basal Salts (Sigma C-1416), 1.0 ml/L Ericksson's Vitamin Mix (Sigma E-1511), 0.5 mg/L thiamine HCl, 30 g/L sucrose, 1.5 mg/L 2,4-D, 0.69 g/L L-proline, 0.5 g/L MES buffer, 0.85 mg/L silver nitrate, 3 mg/L bialaphos, and 8.0 g/L Sigma agar at pH 5.8 |
| MS | 4.3 g/L Murashige and Skoog (MS) salts (Gibco 11117; Gibco, Grand Island, NY), 5.0 ml/L MS Vitamins Stock Solution (Sigma M3900), 100 mg/L myo-inositol, 0.1 µmol abscisic acid (ABA), 1 mg/L indoleacetic acid (IAA), 0.5 mg/L zeatin, 60.0 g/L sucrose, 3.0 mg/L Bialaphos, and 8.0 g/L Sigma agar at pH 5.6 |

DNA was extracted by placing callus cell samples, two stainless-steel beads, and 450 ul of extraction buffer (250 mM NaCl, 200 mM Tris-HCl pH 7.4, 25 mM EDTA, 4.2 M Guanidine HCl) into each tube of a Mega titer rack. The rack was shaken in the Genogrinder at 1650 r.p.m. for 60 seconds and centrifuged at 3000×g for 20 min at 4° C. Three hundred µl of supernatant was transferred to the wells of the Unifilter 96-well DNA Binding GF/F Microplate (770-2810, Whatman, GE Healthcare). The plate was placed on the top of a Multi-well plate vacuum manifold (5017, Pall Life Sciences). A vacuum pressure was applied until the wells were completely dried. The vacuum filtration procedure was repeated one time with 100 ul extraction buffer and two times with 250 ul washing buffer (50 mM Tris-HCl pH 7.4, 200 mM NaCl, 70% ethanol). The residual ethanol was removed by placing the GF/F filter plate on an empty waste collection plate and centrifuged for 10 min at 3000×g. The DNA was eluted in 100 ul Elution Buffer (10 mM Tris-HCl, pH 8.3) and centrifuged at 3000×g for 1 min. For each sample, four PCR reactions were run. They included approximately 40 ng genomic DNA, 10 ul REDExtract-N-Amp PCR ReadyMix (R4775, Sigma-Aldrich Co.), and 5 picomoles of each primer in a total volume of 20 ul. Primer combinations for each PCR reaction are listed in the Table 15.

TABLE 15

Primer combinations for PCR reactions.

| PCR reaction | Primer sequence | SEQ ID NO: | PCR product |
|---|---|---|---|
| F-E2 | CCGAGGAGATCGTGCTGCA CAATGGCCGCATTGCAGTTC | 197 198 | Template randomly integrated or gene editing event |
| F-T | CCGAGGAGATCGTGCTGCA TGACCGCATTGCGATTCCAG | 199 200 | Wild-type EPSPS allele |
| H-T | TCCAAGTCGCTTTCCAACAGGATC TGACCGCATTGCGATTCCAG | 201 202 | TIPS editing event |
| F-E3 | CCGAGGAGATCGTGCTGCA ACCAAGCTGCTTCAATCCGACAAC | 203 204 | A fragment of the epsps locus for cloning and sequencing |

The same PCR reactions were done on five samples of genomic DNA obtained from untransformed maize inbred plantlets. After an initial denaturation at 95° C. for 5 minutes, each PCR amplification was carried out over 35 cycles using DNA Engine Tetrad2 Thermal Cycler (BioRad Laboratories, Hercules, CA) at 94° C. for 30 sec denaturation, 68° C. for 30 sec annealing, and 72° C. for 1 min extension. PCR products F-E2, F-T and H-T were separated in 1% agarose gel at 100 Volts for 45 minutes, with 100 bp DNA Ladder (N0467S, NewEngland Biolabs). For sequencing, the F-F3 PCR amplified fragments from selected calli were cloned into pCR 2.1-TOPO vectors using the TOPO TA Cloning Kit (Invitrogen Corp, Carlsbad, CA). DNA sequencing was done with BigDye Terminator chemistry on ABI 3700 capillary sequencing machines (Applied Biosystems, Foster City, CA). Each sample contained about 0.5 ug Topo plasmid DNA and 6.4 pmole primer E3-EPex3 Rev (ACCAAGCTGCTTCAATCCGACAAC, SEQ ID NO: 204). Sequences were analyzed using the Sequencer program.

A sample of thirty one callus events selected on media containing bialophos (the moPAT selectable marker gene was part of the guide RNA-moCas9 expression vector) were screened for the presence of the TIPS point mutations. Twenty four events contained the TIPS point mutations integrated into genomic DNA (FIG. 16, the F-E2 treatment). Among them, six events showed the PCR amplification product of the chromosomal EPSPS gene with TIPS mutations (FIG. 16, the H-T treatment). The pair of PCR primers (one that can hybridize to the genomic epsps sequence not present in the EPSPS polynucleotide modification template and the other one binding to the edited EPSPS sequence present in the EPSPS polynucleotide modification template) distinguished the EPSPS-TIPS editing products from the wild-type epsps alleles or random insertions of the TIPS mutations. If one EPSPS allele was edited to contain the TIPS substitutions, it should be detected as a DNA fragment originating from the genomic epsps locus, regardless whether the TIPS substitutions were selected for during the PCR amplification process. The TIPS primer was replaced with the wild-type EPSPS primer (Table 15, the F-E3 pair of primers) and the PCR amplification products were cloned into the TOPO cloning vectors and sequenced. The sequencing data represented a random sample of the genomic epsps locus sequences in one of the selected events (FIG. 17, callus A12 3360.92). FIG. 17 shows that the method disclosed herein resulted in the successful nucleotide editing of three nucleotides (FIG. 17 bold) responsible for the TIPS mutations without altering any of the other epsps nucleotides, while the moCas9 target sequence (the site of guide RNA binding underlined in FIG. 17) was not mutagenized.

Also, the other EPSPS allele was not edited indicating that only one EPSPS allele was edited in this particular event (FIG. 17, lower section).

This data further shows that the present disclosure of the use of the guide RNA/Cas system for the gene editing demonstrates the ability to recover gene editing events at a high efficiency of 1 out of fewer than 10 selected events.

Example 17

The Guide RNA/Cas Endonuclease System Delivers Double-Strand Breaks to the Maize Epsps Locus Resulting in Maize Plants Containing an EPSPS-TIPS Edited Gene.

The EPSPS gene edited events were produced and selected as described in the Example 16. In short, the EPSPS polynucleotide modification template was co-delivered using particle gun bombardment as a plasmid (see template vector 1, FIG. 15) together with the guide RNA expression cassette and a maize optimized Cas9 endonuclease expression vector which contained the maize optimized Cas9 endonuclease expression cassette described in FIG. 1A (Example 1, SEQ ID NO:5) and also contained a moPAT selectable marker gene.

After six weeks of selection at 28° C., a small amount of selected tissue was transferred onto the MS regeneration medium and incubated for three weeks in the dark at 28° C. After the three week incubation visible shoots were transferred to plates containing the MS-1 medium and incubated at 26° C. in the light for 1-2 weeks until they were ready to be sent to a greenhouse and transferred into soil flats. The Ms-1 medium contained: 4.3 g/L MS salts (Gibco 11117), 5.0 ml/L MS Vitamins Stock Solution (Sigma M3900), 100 mg/L myo-inositol, 40.0 g/L sucrose, and 6.0 g/L Bacto-Agar at pH 5.6.

Using the procedures described above, 390 T0 maize plants were produced originating from 3282 embryos, resulting in an overall transformation efficiency of 12%, further indicating that the guide RNA/Cas system used herein results in low or no toxicity (Table 16).

TABLE 16

Transformation efficiency of the EPSPS editing.

| Treatment | # Embryos | # Calli selected | Selection efficiency | T0 plants to GH | Overall Efficiency |
| --- | --- | --- | --- | --- | --- |
| Particle bombardment | 3282 | 489 | 15% | 390 | 12% |

DNA was extracted from each T0 plantlet 7-10 days after transfer to the greenhouse and PCR procedures were conducted as described in the Example 16 to screen the T0 plants for mutations at the epsps locus.

Seventy two percent of analyzed T0 plants (270/375, Table 17) contained mutagenized EPSPS alleles as determined by the end-point PCR procedure described in the Example 16. Most of the mutations (230/375 or 89%) were produced as a result of error-prone non-homologous end joining (NHEJ) while forty T0 plants (40/375 or 11%) contained the TIPS edited EPSPS alleles indicating the involvement of a templated double-strand break repair mechanism (Table 17).

TABLE 17

Mutations at the epsps locus.

| Transformation | T0 Plants Analyzed | Mutations at the epsps locus | Mutation rate | TIPS editing | Gene Editing Rate (TIPS) |
| --- | --- | --- | --- | --- | --- |
| Particle bombardment | 375 | 270 | 72% | 40 | 11% |

A pair of primers (Table 15, the F-E3 pair of primers) was used to amplify a native, endogenous fragment of the epsps locus containing the moCas6 target sequence and the EPSPS editing site from the genomic DNA of selected T0 plants. The PCR amplification products were cloned into the TOPO cloning vectors and sequenced as described in Example 16. The sequencing data represent a random sample of the genomic epsps locus sequences from a particular T0 plant (Table 18) and indicate the genotype of the selected T0 plants. The list of the EPSPS-TIPS allele-containing T0 plants transferred to the pots is presented in Table 18 (a selected set of T0 plants from the original 40 TIPS-containing events).

TABLE 18

The epsps locus genotypes observed in T0 plants. TIPS refers to a clone comprising the TIPS edited EPSPS sequence. NHEJ refers to the presence of a NHEJ mutation and WT refers to the presence of a wild-type EPSPS sequence amplified from the native epsps locus.

| Event (T0 plant) | Observed Sequences found at the epsps locus |
|---|---|
| E1 | 16 TIPS, 13 NHEJ |
| E2 | 28 TIPS, 0 NHEJ |
| E3 | 2 TIPS, 20 WT |

TIPS. In one event, E2, the T0 plant contained only TIPS-edited sequence at the epsps locus indicating that the guide RNA/Cas endonuclease system disclosed herein resulted in the successful nucleotide editing of three nucleotides (FIG. 17 bold) responsible for the two EPSPS-TIPS alleles at the epsps locus in maize plants.

A qPCR analysis was performed on the selected T0 plants to estimate the copy number of the wild-type EPSPS genes and the moCas9 endonuclease sequences. Multiplex qPCR amplifications of the maize EPSPS gene and the ADH housekeeping gene were carried out on the DNA samples from T0 plants. The primers and probes used in the PCR reaction are shown in Table 19.

TABLE 19

Primers used in qPCR analysis of T0 plants.

| Primer/probe | Primary PCR Primer Sequence | SEQ ID NO: |
|---|---|---|
| primer qADH F | 5'-CAAGTCGCGGTTTTCAATCA-3 | SEQ ID NO: 217 |
| Primer qADH R | 5'-TGAAGGTGGAAGTCCCAACAA-3' | SEQ ID NO: 218 |
| probe ADH-VIC | VIC-TGGGAAGCCTATCTACCAC | SEQ ID NO: 219 |
| Probe wtEPSPS | 6FAM-CGGCCATTGACAGCA-MGB-NFQ | SEQ ID NO: 220 |
| Forward primer qEPSPS F | 5'-TCTTGGGGAATGCTGGAACT-3' | , SEQ ID NO: 221 |
| reverse primer qEPSPSR | 5'-CACCAGCAGCAGTAACAGCTG-3' | SEQ ID NO: 222 |
| FAM-wtEPSPS R probe | 6FAM-TGCTGTCAATGGCCGCA | SEQ ID NO: 223 |
| forward primer qEPSPS F | 5'-TCTTGGGGAATGCTGGAACT-3' | SEQ ID NO: 224 |
| reverse primer q wtEPSPS RA | 5'-CCACCAGCAGCAGTAACAGC-3 | SEQ ID NO: 225) |

TABLE 18-continued

The epsps locus genotypes observed in T0 plants. TIPS refers to a clone comprising the TIPS edited EPSPS sequence. NHEJ refers to the presence of a NHEJ mutation and WT refers to the presence of a wild-type EPSPS sequence amplified from the native epsps locus.

| Event (T0 plant) | Observed Sequences found at the epsps locus |
|---|---|
| E4 | 1 TIPS, 28 NHEJ |
| E5 | 2 TIPS, 2 NHEJ, 9 WT |
| E6 | 10 TIPS, 17 NHEJ |
| E7 | 12 TIPS, 17 NHEJ |
| E8 | 11 TIPS, 15 NHEJ |
| E9 | 17 TIPS, 10 NHEJ |

As presented in Table 18, the selected plants of E1 and E3 to E9 contained the EPSPS-TIPS edited version of the EPSPS gene either accompanied by a wild-type EPSPS allele (WT) or a NHEJ mutagenized EPSPS allele (NHEJ). The numbers before TIPS, WT, NHEJ in Table18 indicate the frequency at which a particular version of the EPSPS allele was identified. If all clones contained the TIPS-edited EPSPS sequence, the analyzed plant was likely to be homozygous for the EPSPS-TIPS allele (see for example E2). If only about 50% of clones contained a TIPS-edited EPSPS sequence, the analyzed plant was likely to be hemizygous for the EPSPS-TIPS allele (see for example E1). Other plants, such as E3 or E4, were likely to be chimeric for All analyses were conducted using the LightCycler 480 Real-Time PCR System (Roche Diagnostics). A threshold value for the wtEPSPS genotype was set at 1.76. Every sample showing less than 1.76 copies of EPSPS, with the end-point florescence measurements up to two times lower than the wild-type control, was categorized as the One Allele EPSPS genotype (hemizygous for the wild-type EPSPS allele).

A qPCR method was used to estimate the TIPS sequence copy number. The primers and probes used in the qPCR reaction are shown in Table 20.

TABLE 20

Primers used in qPCR analysis to estimate the TIPS sequence copy number.

| Primer/probe | Primary PCR Primer Sequence | SEQ ID NO: |
|---|---|---|
| forward primer q epTIPS F | 5'-GGAAGTGCAGCTCTTCTTGGG-3' | SEQ ID NO: 226 |
| reverse primer q epTIPS R | 5'-AGCTGCTGTCAATGACCGC-3' | SEQ ID NO: 227 |
| TIPS probe | 6FAM-AATGCTGGAATCGCA | SEQ ID NO: 228) |

A comparative Ct method with Delta Ct values normalized to the average Delta Ct from the bi-allelic TIPS genotypes provided a copy number estimation for the TIPS sequence detected in the analyzed plant samples.

TABLE 21 qPCR genotyping and copy number of selected T0 plants.

| Event name | TIPS EPSPS allele | Wild-type EPSPS allele # | TIPS copy # | moCas9 coding sequence |
|---|---|---|---|---|
| E1 | positive | Null | 5 | positive |
| E2 | positive | Null | 2 | positive |
| E7 | positive | Null | 6 | positive |
| E8 | positive | Null | 1 | positive |
| E9 | positive | Null | 3 | positive |

The qPCR genotyping indicated that no wild-type EPSPS alleles were detected in the selected T0 plants of Events E1, E2, E7, E8 and E9 (Table 21). Both, the TIPS template sequences and the moCas9 coding sequence were found in the selected T0 plants, presumably, as a result of random insertions associated with the transformation process (Table 21: for the TIPS template sequences E1, E7, and E9 T0 plants). Both genetic elements (the randomly inserted TIPS templates and the moCas9 expression cassette) can be segregated out by standard breeding procedures in the T1 progeny generation, if not linked to the edited EPSPS-TIPS gene.

T0 plants grew well in the greenhouse and were fertile. A sample of T0 plants was sprayed with a 1× dose of glyphosate (Roundup Powermax) at V3 growth stage using the spray booth setting of 20 gallons per acre. The 1× dose of glyphosate was prepared as follow: 2.55 ml Powermax in 300 ml water (active ingredient: glyphosate, N-(phosphonomethyl) glycine, in the form of its potassium salt at 48.7%). Seven days after glyphosate application, no leaf tissue damage was observed in some of the T0 plants. These plantlets were hemizygous for the EPSPS-TIPS alleles, while other plantlets were severely damaged. One plant showing no damage to the leaf tissue 14 days after herbicide application contained 21 EPSPS-TIPS alleles among 44 genomic clones of the epsps locus (cloned and sequenced as described in the Example 16).

These data indicate that a guide RNA/Cas system can be used to create a TIPS-edited EPSPS allele in maize. Maize plants homozygous at the epsps-tips locus (two EPSPS alleles edited) with no additional insertion of the TIPS template (plant E2) were obtained. Furthermore, some EPSPS-TIPS edited maize plants did show some level of tolerance against a 1× dose of glyphosate.

Example 18

Guide RNA/Cas Endonuclease Mediated DNA Cleavage in Maize Chromosomal Loci Enables Transgene Insertion in an Elite Maize Line To test whether a maize optimized guide RNA/Cas system can cleave an maize chromosomal locus and enable homologous recombination (HR) mediated pathways to site-specifically insert a transgene in an elite maize line, 4 loci were selected on the maize chromosome 1 located between 51.54 cM to 54.56 cM (FIG. 18). Two target sites for a Cas endonuclease were identified at each of the four loci and are referred to as MHP14Cas-1, MHP14Cas-3, TS8Cas-1, TS8Cas2, TS9Cas-2, TS9Cas-3, TS10Cas-1 and TS10Cas-3 (FIG. 19, Table 22, SEQ ID NOs:229-236).

TABLE 22

Maize genomic target sites targeted by a guide RNA/Cas endonuclease.

| Locus | Location | Target Site | Maize Genomic Target Site Sequence | PAM | SEQ ID NO: |
|---|---|---|---|---|---|
| MHP14 | Chr. 1: 51.54cM | MHP14Cas-1 | gttaaatctgacgtgaatctgtt | TGG | 229 |
|  |  | MHP14Cas-3 | acaaacattgaagcgacatag | TGG | 230 |
| TS8 | Chr. 1: 52.56cM | TS8Cas-1 | gtacgtaacgtgcagtac | TGG | 231 |
|  |  | TS8Cas-2 | gctcatcagtgatcagctgg | TGG | 232 |
| TS9 | Chr. 1: 53.56cM | TS9Cas-2 | ggctgtttgcggcctcg | AGG | 233 |
|  |  | TS9Cas-3 | gcctcgaggttgcacgcacgt | CGG | 234 |
| TS10 | Chr.1: 54.56cM | TS10Cas-1 | gcctcgccttcgctagttaa | GGG | 235 |
|  |  | TS10Cas-3 | gctcgtgttggagataca | GGG | 236 |

The maize optimized Cas endonuclease cassette (SEQ ID NO: 5 was as prepared as describe in Example 1. Long guide RNA expression cassettes comprising a variable targeting domain targeting one of the 8 genomic target sites, driven by a maize U6 polymerase III promoter, and terminated by a maize U6 polymerase III terminator were designed as described in Example 1 and 3 and listed in Table 23. A donor DNA (HR repair DNA) containing a selectable marker (a phosphonannose-isomerase (PMI) expression cassette) flanked by two homologous regions was constructed using standard molecular biology techniques (FIG. 20).

TABLE 23

List of guide RNA (gRNA) and Donor DNA expression cassettes

| Locus | Target Site | gRNA (SEQ ID NO:) | Donor DNA (SEQ ID NO:) |
|---|---|---|---|
| MHP 14 | MHP14Cas-1 | 245 | 253 |
|  | MHP 14Cas-3 | 246 | 254 |
| TS8 | TS8Cas-1 | 247 | 255 |
|  | TS8Cas-2 | 248 | 256 |
| TS9 | TS9Cas-2 | 249 | 257 |
|  | TS9Cas-3 | 250 | 258 |
| TS10 | TS10Cas-1 | 251 | 259 |
|  | TS10Cas-3 | 252 | 260 |

A vector containing the maize optimized Cas9 endonuclease of SEQ TD NO: 5, a vector containing one of eight long guide RNA expression cassettes of SEQ TD NOs: 245-252, and a vector containing one of eight donor DNAs of SEQ ID NOs: 253-260 were co-delivered to maize elite line immature embryos by particle-mediated delivery as described in Example 10. About 1000 embryos were bombarded for each target site. Since the donor DNA contained a selectable marker, PMI, successful delivery of the donor DNA allowed for callus growth on mannose media. Putative HR-mediated transgenic insertions were selected by placing the callus on mannose containing media. After selection, stable shoots on maturation plates were sampled, total genomic DNA extracted, and using the primer pairs shown in Table 24 (corresponding to SEQ ID NOs: 261-270), PCR amplification was carried out at both possible transgene genomic DNA junctions to identify putative HR-mediated transgenic insertions.

TABLE 24

Primer sequences used for integration event screening at each target site.

| Locus | Target Site | Junction | Primer | SEQ ID NO: |
|---|---|---|---|---|
| UBIR | donor | 1 | CCATGTCTAACTGTTCATTTATATGATTCTCT | 261 |
| PSBF | donor | 2 | GCTCGTGTCCAAGCGTCACTTACGATTAGCT | 262 |
| MHP14 | MHP14Cas-1 | 14-1HR1f | CTCACATGAGGCTCTTCTTTGCTTGCT | 263 |
|  | MHP14Cas-3 | 14-1HR2r | AGGATCCTATTCCCCAATTTGTAGAT | 264 |
| CHR1-8 | TS8Cas-1 | 8HR1f | CAGTCCGTGGATTGAAGCCAT | 265 |
|  | TS8Cas-2 | 8HR2r | CTCTGTCTCCGAGACGTGCTTA | 266 |
| CHR1-9 | TS9Cas-2 | 9HR1f | GGAGCAAATGTTTTAGGTATGAAATG | 267 |
|  | TS9Cas-3 | 9HR2r | CGGATTCTAAAGATCATACGTAAATGAA | 268 |
| CHR1-10 | TS10Cas-1 | 10HR1f | TGGCTTGTCTATGCGCATCTC | 269 |
|  | TS10Cas-3 | 10HR2r | CCAGACCCAAACAGCAGGTT | 270 |

The same genomic primers were used for each of the two target sites at one locus. The resulting amplifications were sequenced to determine if these sites were mutated or contained a transgene insertion.

The "Event Recovery frequency" was calculated using the number of events recovered divided by the total number of embryos bombarded, and may indicate if an endonuclease has some toxic effect or not (Table 26). Hence, if 1000 embryos were bombarded and 240 were recovered, the Event Recovery frequency is 24%. Table 26 indicates that for all target sites analyzed the Event Recovery frequency ranged between 17 and 28%, indicating that the guide RNA/Cas system used herein results in low or no toxicity. Cas endonuclease activity was measured in-planta by determining the "Target Site Mutation frequency" (Table 26) which is defined as: (number of events with target site modification/total number recovered events)*100%. Hence, if 240 events were recovered and 180 events showed a mutation, the Target Site Mutation frequency is 75%. The target site mutation frequency was measured using target site allele copy number as described in Example 9 of U.S. application Ser. No. 13/886,317, filed on May 3, 2013. The primers and probes for obtaining the target site copy number using qPCR at each site were as listed in Table 25 (SEQ ID NO: 271-294).

TABLE 25

Primer and probe sequences used to assess DNA cleavage at 8 maize genomic target sites

| Target Site Designation | Probe primers | Primer sequence | SEQ ID NO: |
|---|---|---|---|
| MHP14Cas-1 | probe | CAGATTCACGTCAGATTT | 271 |
|  | forward | CATAGTGGTGTATGAAAGGAAGCACTT | 272 |
|  | reverse | CATTTTGGATTGTAATATGTGTACCTCATA | 273 |
| MHP14Cas-3 | probe | CACCACTATGTCGCTTC | 274 |
|  | forward | CGGATGCACGAAAATTGTAGGA | 275 |
|  | reverse | CTGACGTGAATCTGTTTGGAATTG | 276 |

TABLE 25-continued

Primer and probe sequences used to assess DNA cleavage at 8 maize genomic target sites

| Target Site Designation | Probe primers | Primer sequence | SEQ ID NO: |
|---|---|---|---|
| TS8Cas-1 | probe | TACGTAACGTGCAGTACT | 277 |
|  | forward | ACGGACGGACCATACGTTATG | 278 |
|  | reverse | TCAGCTGGTGGAGTATATTAGTTCGT | 279 |
| TS8Cas-2 | probe | CCAGCTGATCACTGATGA | 280 |
|  | forward | ACGGACGGACCATACGTTATG | 281 |
|  | reverse | CGCACATGTTATAAATTACAATGCAT | 282 |
| TS9Cas-2 | probe | CTGTTTGCGGCCTC | 283 |
|  | forward | CTGCGGAGCTGCTGGCGAT | 284 |
|  | reverse | CTTGCTGGCTTCGTCTGTCA | 285 |
| TS9Cas-3 | probe | CCGACGTGCGTGCAA | 286 |
|  | forward | CTGCGGAGCTGCTGGCGAT | 287 |
|  | reverse | CTTGCTGGCTTCGTCTGTCA | 288 |
| TS10Cas-1 | probe | TCGCCTTCGCTAGTTAA | 289 |
|  | forward | AAGACCTGGCCGGTTTTCCA | 290 |
|  | reverse | TAGCGGCCATTGCCATCA | 291 |
| TS10Cas-3 | probe | CTGTATCTCCAACACGAGC | 292 |
|  | forward | AAGACCTGGCCGGTTTTCCA | 293 |
|  | reverse | TAGCGGCCATTGCCATCA | 294 |

As shown in Table 26, all 8 guide RNA/Cas9 systems were very efficient in cleaving their target DNA and inducing mutations (by non-homologous end joining (NTIEJ) as is evidenced by a mutation frequency ranging from 33-90%.

All events were also screened for the presence of an inserted transgene. The insertion event screening for each target site is illustrated in FIG. 21. The primers used for insertion PCR analysis at each site are listed in Table 24. FIG. 22 shows one example of an insertion event screening PCR result. The frequency of transgene insertion was determined by calculating the "Insertion frequency" which is defined as: (number of events with target site insertion/total number recovered events)*100%. Hence, if 240 events were recovered and 21 events showed a transgene insertion, the Insertion frequency was 900.

TABLE 26

Activity of the guide RNA/Cas 9 system at 8 target sites as determined by target site mutation frequency and transgene insertion frequency at the desired target site in maize plant tissue

| Target Site | Event Recovery (%) | Target Site Mutation (%) | Insertion frequency % |
|---|---|---|---|
| TS10Cas-1 | 24% | 75% | 9%(7*) |
| TS10Cas-3 | 22% | 83% | 16%(20*) |
| TS8Cas-1 | 17% | 90% | 14%(9*) |
| TS8Cas-2 | 27% | 84% | 8%(10*) |
| MHP14Cas-1 | 17% | 33% | 2%(2*) |
| MHP14Cas-3 | 28% | 68% | 4%(1*) |
| TS9Cas-2 | 23% | 62% | 8%** |
| TS9Cas-3 | 28% | 84% | 8%** |

*Number of events with HR1 and HR2 both junctions positive
**only HR2 junction available Sequence-confirmed-PCR amplifications indicated a site-specific transgene insertion for each of the 8 target sites as shown in Table 26 (column Insertion frequency). A transgene cassette was inserted at all 8 target sites with high efficiency (2-16%). The number of events containing amplifications across both transgene genomic DNA junctions, indicating near perfect site-specific transgene insertion, are show in brackets in Table 26.

Taken together, these data demonstrates that maize chromosomal loci cleaved with the maize optimized guide RNA/Cas system described herein can be used to insert transgenes at high frequencies in maize elite inbred line.

Example 19

Delivery of the Guide RNA/Cas9 Endonuclease System DNA to Soybean by Stable Transformation A soybean U6 small nuclear RNA promoter (GM-U6-9.1; SEQ ID NO: 295) was identified in a similar manner as the soybean promoter GM-U6-13.1 (SEQ ID NO:120) described in Example 12. The GM-U6-9.1 promoter was used to express guide RNA to direct Cas9 nuclease to designated genomic target site.

A soybean codon optimized Cas9 endonuclease expression cassette (such as for example EF1A2:CAS9, SEQ ID NO: 296) and a guide RNA expression cassette (such as for example U6-9.1:DD20CR1; SEQ ID NO: 297) were linked (such as U6-9.1: DD20CR1+EF1A2:CAS9; SEQ ID NO: 298, FIG. 23A) and integrated into a DNA plasmid that was co-delivered with another plasmid comprising a donor DNA (repair DNA) cassette (such as DD20HR1-SAMS:HPT-DD20HR2; SEQ ID NO: 299) to young soybean somatic embryos in the form of embryogenic suspension cultures by particle gun bombardment (FIGS. 23A and 23B). Other guide RNA/Cas9 DNA constructs targeting various soybean genomic sites and donor DNA constructs for site-specific transgene integration through homologous recombination were similarly configured and are listed in Table 27. The four gRNA/Cas9 constructs differed only in the 20 bp guide RNA targeting domain (variable targeting domain) targeting the soybean genomic target sites DD20CR1 (SEQ ID NO: 125), DD20CR2 (SEQ ID NO: 126), DD43CR1 (SEQ ID NO: 127), or DD43CR2 (SEQ ID NO: 128). The two donor DNA constructs differed only in the homologous regions such as DD20HR1 and DD20HR (FIG. 23B), or DD43HR1 and DD43HR2. These guide RNA/Cas9 DNA constructs and donor DNAs were co-delivered to an elite (93B86) or a non-elite (Jack) soybean genome by the stable transformation procedure described below.

TABLE 27

Guide RNA/Cas9 Mediated Soybean Stable Transformation.

| Experiment | Guide RNA/Cas9 | Donor DNA | SEQ ID NOs: |
|---|---|---|---|
| U6-9.1DD20CR1 | U6-9.1:DD20CR1 + EF1A2:CAS9 | DD20HR1-SAMS: HPT-DD20HR2 | 298, 299 |
| U6-9.1DD20CR2 | U6-9.1:DD20CR2 + EF1A2:CAS9 | DD20HR1-SAMS: HPT-DD20HR2 | 300, 299 |
| U6-9.1DD43CR1 | U6-9.1:DD43CR1 + EF1A2:CAS9 | DD43HR1-SAMS: HPT-DD43HR2 | 301, 302 |
| U6-9.1DD43CR2 | U6-9.1:DD43CR2 + EF1A2:CAS9 | DD43HR1-SAMS: HPT-DD43HR2 | 303, 302 |

Soybean somatic embryogenic suspension cultures were induced from a DuPont Pioneer proprietary elite cultivar 93B86 as follows. Cotyledons (~3 mm in length) were dissected from surface sterilized, immature seeds and were cultured for 6-10 weeks in the light at 26° C. on a Murashige and Skoog (MS) media containing 0.7% agar and supplemented with 10 mg/ml 2,4-D (2,4-Dichlorophenoxyacetic acid). Globular stage somatic embryos, which produced secondary embryos, were then excised and placed into flasks containing liquid MS medium supplemented with 2,4-D (10 mg/ml) and cultured in light on a rotary shaker. After repeated selection for clusters of somatic embryos that multiplied as early, globular staged embryos, the soybean embryogenic suspension cultures were maintained in 35 ml liquid media on a rotary shaker, 150 rpm, at 26° C. with fluorescent lights on a 16:8 hour day/night schedule. Cultures were subcultured every two weeks by inoculating approximately 35 mg of tissue into 35 ml of the same fresh liquid MS medium.

Soybean embryogenic suspension cultures were then transformed by the method of particle gun bombardment using a DuPont Biolistic™ PDS1000/HE instrument (Bio-Rad Laboratories, Hercules, CA). To 50 µl of a 60 mg/ml 1.0 mm gold particle suspension were added in order: 30 µl of equal amount (30 ng/µl) plasmid DNA comprising, for example, U6-9.1:DD20CR1+EF1A2:CAS9 (SEQ ID NO:298) and plasmid DNA comprising, for example, (DD20HR1-SAMS:HPT-DD20HR2, SEQ ID NO: 299) (Experiment U6-9.1DD20CR1 listed in Table 27) 20 µl of 0.1 M spermidine, and 25 µl of 5 M CaCl$_2$). The particle preparation was then agitated for 3 minutes, spun in a centrifuge for 10 seconds and the supernatant removed. The DNA-coated particles were then washed once in 400 µl 100% ethanol and resuspended in 45 µl of 100% ethanol. The DNA/particle suspension was sonicated three times for one second each. Then 5 µl of the DNA-coated gold particles was loaded on each macro carrier disk.

Approximately 300-400 mg of a two-week-old suspension culture was placed in an empty 60×15 mm Petri dish and the residual liquid removed from the tissue with a pipette. For each transformation experiment, approximately 5 to 10 plates of tissue were bombarded. Membrane rupture pressure was set at 1100 psi and the chamber was evacuated to a vacuum of 28 inches mercury. The tissue was placed approximately 3.5 inches away from the retaining screen and bombarded once. Following bombardment, the tissue was divided in half and placed back into liquid media and cultured as described above.

Five to seven days post bombardment, the liquid media was exchanged with fresh media containing 30 mg/ml hygromycin as selection agent. This selective media was refreshed weekly. Seven to eight weeks post bombardment, green, transformed tissue was observed growing from untransformed, necrotic embryogenic clusters. Isolated green tissue was removed and inoculated into individual flasks to generate new, clonally propagated, transformed embryogenic suspension cultures. Each clonally propagated culture was treated as an independent transformation event and subcultured in the same liquid MS media supplemented with 2,4-D (10 mg/ml) and 30 ng/ml hygromycin selection agent to increase mass. The embryogenic suspension cultures were then transferred to agar solid MS media plates without 2,4-D supplement to allow somatic embryos to develop. A sample of each event was collected at this stage for quantitative PCR analysis.

Cotyledon stage somatic embryos were dried-down (by transferring them into an empty small Petri dish that was seated on top of a 10 cm Petri dish containing some agar gel to allow slow dry down) to mimic the last stages of soybean seed development. Dried-down embryos were placed on germination solid media and transgenic soybean plantlets were regenerated. The transgenic plants were then transferred to soil and maintained in growth chambers for seed production. Transgenic events were sampled at somatic embryo stage or T0 leaf stage for molecular analysis.

Similar transformation experiments (U6-9.1DD20CR2, U6-9.1DD43CR1, U6-9.1DD43CR2) with the components listed in Table 27 and using the elite cultivar 93B86 were performed as described above.

Two transformation experiments, U6-9.1DD20CR1 and U6-9.1DD43CR1 listed in Table 27, were also performed in a non-elite soybean cultivar "Jack" to test the gRNA/Cas9 system performance in different soybean genotypes.

Example 20

Detection of Site-Specific NHEJ Mediated by the Guide RNA/Cas9 System in Stably Transformed Soybean Genomic DNA was extracted from somatic embryo samples and analyzed by quantitative PCR using a 7500 real time PCR system (Applied Biosystems, Foster City, CA) with target site-specific primers and FAM-labeled fluorescence probe to check copy number changes of the target site DD20 or DD43 (FIG. 24 A-C). The qPCR analysis was done in duplex reactions with a heat shock protein (HSP) gene as the endogenous controls and a wild type 93B86 genomic DNA sample that contains one copy of the target site with 2 alleles, as the single copy calibrator. The HSP endogenous control qPCR employed primer probe set HSP-F/HSP-T/HSP-R. The DD20-CR1 (SEQ ID NO:306) and DD20-CR2 (SEQ ID NO:307) specific qPCR employed primer probe set DD20-F (SEQ ID NO:308)/DD20-T (SEQ ID NO:309)/DD20-R(SEQ ID NO:310). The DD43-CR1 (SEQ ID NO:311) specific qPCR employed primer probe set DD43-F (SEQ ID NO:313)/DD43-T (SEQ ID NO:315)/DD43-R (SEQ ID NO:316) while the DD43-CR2 (SEQ ID NO:312) specific qPCR employed primer probe set DD43-F2 (SEQ ID NO:314)/DD43-T/DD43-R. The guide RNA/Cas9 DNA (SEQ ID NOs: 298, 300, 301, and 303) specific qPCR employed primer probe set Cas9-F (SEQ ID NO:317/Cas9-T (SEQ ID NO:318)/Cas-9-R(SEQ ID NO:319). The donor DNA (SEQ ID NOS: 299, and 302) specific qPCR employed primer probe set Sams-76F (SEQ ID NO:320)/FRT1I63-T (SEQ ID NO:321)/FRT1I-41F (SEQ ID NO:322). The endogenous control probe HSP-T was labeled with VIC and the gene-specific probes DD20-T, DD43-T, Cas9-T, and FRT1I63-T were labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

Since the wild type 93B86 genomic DNA with two alleles of the target site was used as the single copy calibrator, events without any change of the target site would be detected as one copy herein termed Wt-Homo (qPCR value>=0.7), events with one allele changed, which is no longer detectable by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1). The wide range of the qPCR values suggested that most of the events contained mixed mutant and wild type sequences of the target site. High percentage of NHEJ-Hemi (ranging from 10.1 to 33.5%, Table 28) and NHEJ-Null (ranging from 32.3 to 46.4%, Table 21) were detected in all four experiments with combined NHEJ average frequencies of more than 60% (Table 28).

TABLE 28

Target Site Mutations and Site Specific Gene Integration Induced by the Guide RNA/Cas9 system in elite soybean germplasm. Numbers indicate no. of events (numbers in parentheses are %). NA = not analyzed.

| Project | Total event | Wt-Homo (%) | NHEJ-Hemi (%) | NHEJ-Null (%) | Insertion Frequency(%) |
|---|---|---|---|---|---|
| U6-9.1DD20CR1 | 239 | 85 (35.6%) | 77 (32.2%) | 77 (32.2%) | 11 (4.6%) |
| U6-9.1DD20CR2 | 79 | 43 (54.4%) | 8 (10.1%) | 28 (35.4%) | NA |
| U6-9.1DD43CR1 | 263 | 53 (20.2%) | 88 (33.5%) | 122 (46.4%) | 10 (3.8%) |

TABLE 29

Target Site Mutations and Site Specific Gene Integration Induced by the
Guide RNA/Cas9 system in non-elite soybean germplasm. Numbers indicate
no. of events (numbers in parentheses are % of the total analyzed events).

| Project | Total event | Wt-Homo (%) | NHEJ-Hemi (%) | NHEJ-Null (%) | Insertion frequency (%) |
|---|---|---|---|---|---|
| U6-9.1DD20CR1-Jack | 149 | 99 (66.4%) | 34 (22.8%) | 16 (10.7%) | 0 (0%) |
| U6-9.1DD43CR1-Jack | 141 | 84 (59.6%) | 27 (19.1%) | 30 (21.3%) | 1 (0.7%) |

Both NHEJ-Hemi and NHEJ-Null were detected in the two experiments U6-9.1DD20CR1-Jack and U6-9.1DD43CR1-Jack repeated in "Jack" genotype though at lower frequencies (Table 29). The differences between NHEJ frequencies were likely caused by variations between transformation experiments.

The target region of NHEJ-Null events were amplified by regular PCR from the same genomic DNA samples using DD20-LB (SEQ ID NO: 323) and DD20-RB (SEQ ID NO: 326) primers specific respectively to DD20-HR1 and DD20-HR2 for DD20 target site specific HR1-HR2 PCR amplicon (FIG. 25 A-C; SEQ ID NO: 329), or DD43-LB (SEQ ID NO: 327) and DD43-RB (SEQ ID NO: 328) primers specific respectively to DD43-HR1 and DD43-HR2 for DD43 target site specific HR1-HR2 PCR amplicon (SEQ ID NO: 332). The PCR bands were cloned into pCR2.1 vector using a TOPO-TA cloning kit (Invitrogen) and multiple clones were sequenced to check for target site sequence changes as the results of NHEJ. Various small deletions at the Cas9 cleavage site, 3 bp upstream of the PAM, were revealed at all four tested target sites (FIG. 26 A-C). Small insertions were also detected in some sequences. Different mutated sequences were identified from some of the same events indicating the chimeric nature of these events. Some of the same mutated sequences were also identified from different events suggesting that the same mutations could have happened independently or some of the events could be clonal events. These sequence analysis confirmed the occurrence of NHEJ mediated by the guide RNA/Cas9 system at the specific Cas9 target sites.

Example 21

Identification of Site-Specific Gene Integration Via Homologous Recombination Mediated by the Guide RNA/Cas9 System in Stably Transformed Soybean Site-specific gene integration via guide RNA/Cas9 system mediated DNA homologous recombination was determined by border-specific PCR analysis. The 5' end borders of DD20CR1 and DD20CR2 events were amplified as a 1204 bp DD20 HR1-SAMS PCR amplicon (SEQ ID NO: 330) by PCR with primers DD20-LB (SEQ ID NO: 323) and Sams-A1 (SEQ ID NO: 324) while the 3' borders of the same events were amplified as a 1459 bp DD20 NOS-HR2 PCR amplicon (SEQ ID NO: 331) with primers QC498A-S1 and DD20-RB (FIG. 25 A-C). Any events with both the 5' border and 3' border-specific bands amplified are considered as site-specific integration events through homologous recombination containing the transgene from the donor DNA fragment DD20HR1-SAMS:HPT-DD20HR2 or its circular form (FIG. 23). The 5' end borders of DD43CR1 and DD43CR2 events were amplified as a 1202 bp DD43 HR1-SAMS PCR amplicon (SEQ ID NO: 333) by PCR with primers DD43-LB and Sams-A1 while the 3' borders of the same events were amplified as a 1454 bp DD43 NOS-HR2 PCR amplicon (SEQ ID NO: 334) with primers QC498A-S1 (SEQ ID NO: 325) and DD43-RB (SEQ ID NO: 328). Any events with both the 5' border and 3' border-specific bands amplified are considered as site-specific integration events through homologous recombination containing the transgene from repair DNA fragment DD43HR1-SAMS:HPT-DD43HR2 or its circular form. Some of the border-specific PCR fragments were sequenced and were all confirmed to be recombined sequences as expected from homologous recombination. On average, gene integration through the guide RNA/Cas9 mediated homologous recombination occurred at approximately 4% of the total transgenic events (Insertion frequency, Table 28 and Table 29). One homologous recombination event was identified from experiment U6-9.1DD43CR1-Jack repeated in "Jack" genotype (Table 29).

Example 22

The crRNA/tracrRNA/Cas Endonuclease System Cleaves Chromosomal DNA in Maize and Introduces Mutations by Imperfect Non-Homologous End-Joining To test whether the maize optimized crRNA/tracrRNA/Cas endonuclease system described in Example 1 could recognize, cleave, and mutate maize chromosomal DNA through imprecise non-homologous end-joining (NHEJ) repair pathways, three different genomic target sequences were targeted for cleavage (see Table 30) and examined by deep sequencing for the presence of NHEJ mutations.

TABLE 30

Maize genomic target sequences targeted by a
crRNA/tracrRNA/Cas endonuclease system.

| Locus | Location | Cas RNA System Used | Target Site Designation | Maize Genomic Target Site Sequence | PAM Sequence | SEQ ID NO: |
|---|---|---|---|---|---|---|
| LIG | Chr. 2: 28.45cM | crRNA/ tracrRNA | LIGCas-1 | GTACCGTACGTGCCCCGGCGG | AGG | 16 |

TABLE 30-continued

Maize genomic target sequences targeted by a crRNA/tracrRNA/Cas endonuclease system.

| Locus | Location | Cas RNA System Used | Target Site Designation | Maize Genomic Target Site Sequence | PAM Sequence | SEQ ID NO: |
|---|---|---|---|---|---|---|
| | | crRNA/ tracrRNA | LIGCas-2 | GGAATTGTACCGTACGTGCCC | CGG | 17 |
| | | crRNA/ tracrRNA | LIGCas-3 | GCGTACGCGTACGTGTG | AGG | 18 |

LIG = Liguleless 1 Gene Promoter

The maize optimized Cas9 endonuclease expression cassette, crRNA expression cassettes containing the specific maize variable targeting domains (SEQ ID NOs: 445-447) complementary to the antisense strand of the maize genomic target sequences listed in Table 30 and tracrRNA expression cassette (SEQ ID NO: 448) were co-delivered to 60-90 Hi-II immature maize embryos by particle-mediated delivery (see Example 5) in the presence of BBM and WUS2 genes (see Example 6). Hi-II maize embryos transformed with the Cas9 and long guide RNA expression cassettes targeting the LIGCas-3 genomic target site (SEQ ID NO: 18) for cleavage served as a positive control and embryos transformed with only the Cas9 expression cassette served as a negative control. After 7 days, the 20-30 most uniformly transformed embryos from each treatment were pooled and total genomic DNA was extracted. The region surrounding the intended target site was PCR amplified with Phusion® High Fidelity PCR Master Mix (New England Biolabs, M0531L) adding on the sequences necessary for amplicon-specific barcodes and Illumnia sequencing using "tailed" primers through two rounds of PCR. The primers used in the primary PCR reaction are shown in Table 31 and the primers used in the secondary PCR reaction were AATGATACGGCGACCACCGAGATCTACACTCTTTCCCTACACG (forward, SEQ ID NO: 53) and CAAGCAGAAGACGGCATA (reverse, SEQ ID NO: 54).

TABLE 31

PCR primer sequences

| Target Site | Cas RNA System Used | Primer Orientation | Primary PCR Primer Sequence | SEQ ID NO: |
|---|---|---|---|---|
| LIGCas-1 | crRNA/ tracrRNA | Forward | CTACACTCTTTCCCTACACGACGCTCTTCC GATCTTCCTCTGTAACGATTTACGCACCTG CTG | 36 |
| LIGCas-1 | crRNA/ tracrRNA | Reverse | CAAGCAGAAGACGGCATACGAGCTCTTCC GATCTGCAAATGAGTAGCAGCGCACGTAT | 35 |
| LIGCas-2 | crRNA/ tracrRNA | Forward | CTACACTCTTTCCCTACACGACGCTCTTCC GATCTGAAGCTGTAACGATTTACGCACCTG CTG | 449 |
| LIGCas-2 | crRNA/ tracrRNA | Reverse | CAAGCAGAAGACGGCATACGAGCTCTTCC GATCTGCAAATGAGTAGCAGCGCACGTAT | 35 |
| LIGCas-3 | crRNA/ tracrRNA | Forward | CTACACTCTTTCCCTACACGACGCTCTTCC GATCTAAGGCGCAAATGAGTAGCAGCGCAC | 37 |
| LIGCas-3 | crRNA/ tracrRNA | Reverse | CAAGCAGAAGACGGCATACGAGCTCTTCC GATCTCACCTGCTGGGAATTGTACCGTA | 38 |
| LIGCas-3 | Long guide RNA | Forward | CTACACTCTTTCCCTACACGACGCTCTTCC GATCTTTCCCGCAAATGAGTAGCAGCGCAC | 450 |
| LIGCas-3 | Long guide RNA | Reverse | CAAGCAGAAGACGGCATACGAGCTCTTCC GATCTCACCTGCTGGGAATTGTACCGTA | 38 |

The resulting PCR amplifications were purified with a Qiagen PCR purification spin column, concentration measured with a Hoechst dye-based fluorometric assay, combined in an equimolar ratio, and single read 100 nucleotide-length deep sequencing was performed on Illumina's MiSeq Personal Sequencer with a 30-40% (v/v) spike of PhiX control v3 (Illumina, FC-1 10-3001) to off-set sequence bias. Only those reads with a >1 nucleotide indel arising within the 10 nucleotide window centered over the expected site of cleavage and not found in a similar level in the negative control were classified as NHEJ mutations. NHEJ mutant reads with the same mutation were counted and collapsed into a single read and the top 10 most prevalent mutations were visually confirmed as arising within the expected site of cleavage. The total numbers of visually confirmed NHEJ mutations were then used to calculate the 00 mutant reads based on the total number of reads of an appropriate length containing a perfect match to the barcode and forward primer.

The frequency of NHEJ mutations recovered by deep sequencing for the crRNA/tracrRNA/Cas endonuclease system targeting the three LIGCas targets (SEQ ID NOS: 16, 17, 18) compared to the long guide RNA/Cas endonuclease system targeting the same locus is shown in Table 32.

TABLE 32

Percent (%) mutant reads at maize Liguleless 1 target locus produced by crRNA/tracrRNA/Cas endonuclease system compared to the long guide RNA/Cas endonuclease system

| System | Total Number of Reads | Number of Mutant Reads | % Mutant Reads |
|---|---|---|---|
| Cas9 Only Control | 1,744,427 | 0 | 0.00% |
| LIGCas-3 long guide RNA | 1,596,955 | 35,300 | 2.21% |
| LIGCas-1 crRNA/tracrRNA | 1,803,163 | 4,331 | 0.24% |
| LIGCas-2 crRNA/tracrRNA | 1,648,743 | 3,290 | 0.20% |
| LIGCas-3 crRNA/tracrRNA | 1,681,130 | 2,409 | 0.14% |

The ten most prevalent types of NHEJ mutations recovered based on the crRNA/tracrRNA/Cas endonuclease system are shown in FIG. 27A (for LIGCas-1 target site, corresponding to SEQ ID NOs:415-424), FIG. 27B (for LIGCas-2 target site corresponding to SEQ ID NOs: 425-434) and FIG. 27C (for LIGCas-3 target site corresponding to SEQ ID NOs:435-444). Approximately, 9-16 fold lower frequencies of NHEJ mutations were observed when using a crRNA/tracrRNA/Cas endonuclease system to introduce a double strand break at a maize genomic target site, relative to the long guide RNA/Cas endonuclease system control.

Taken together, our data indicate that the maize optimized crRNA/tracrRNA/Cas endonuclease system described herein cleaves maize chromosomal DNA and generates imperfect NHEJ mutations.

Example 23

Modifying the ARGOS8 Gene to Improve Drought Tolerance and Nitrogen Use Efficiency in Maize Plants ARGOS is a negative regulator for ethylene responses in plants (WO 2013/066805 A1, published 10 May 2013). ARGOS proteins target the ethylene signal transduction pathway. When over-expressed in maize plants, ARGOS reduces plant sensitivity to ethylene and promotes organ growth, leading to increased drought tolerance (DRT) and improved nitrogen use efficiency (NUE) ((WO 2013/066805 A1, published 10 May 2013). To achieve optimal ethylene sensitivity, promoters have been tested for driving Zm-ARGOS8 over-expression in transgenic maize plants. Field trials showed that a maize promoter, Zm-GOS2 PRO:GOS2 INTRON (SEQ ID NO:460, U.S. Pat. No. 6,504,083 patent issued on Jan. 7, 2003; Zm-GOS2 is a maize homologous gene of rice GOS2. Rice GOS2 stands for Gene from *Oryza Sativa* 2), provided a favorable expression level and tissue coverage for Zm-ARGOS8 and the transgenic plants have a higher grain yield than non-transgenic controls under drought stress and low nitrogen conditions (WO 2013/066805 A1, published 10 May 2013). However, these transgenic plants contain two ARGOS8 genes, the endogenous gene and the transgene. ARGOS8 protein levels, therefore, are determined by these two genes. Because the endogenous ARGOS8 gene varies in sequence and the expression level among different inbred lines, the ARGOS8 protein level will be different when the transgene is integrated into different inbreds. Here we present a mutagenization (gene editing) method to modify the promoter region of the endogenous ARGOS8 gene to attain desired expression patterns and eliminate the need for a transgene.

The promoter Zm-GOS2 PRO:GOS2 INTRON (SEQ ID NO:460; U.S. Pat. No. 6,504,083 patent issued on Jan. 7, 2003) was inserted into the 5'-UTR of Zm-ARGOS8 (SEQ ID NO:462) by using a guideRNA/Cas9 system. The Zm-GOS2 PRO:GOS2 INTRON fragment also included a primer binding site (SEQ ID NO:459) at its 5' end to facilitate event screening with PCR. We also substituted the native promoter of Zm-ARGOS8 (SEQ ID NO:461) with Zm-GOS2 PRO::GOS2 INTRON (SEQ ID NO:460). Resulted maize lines carry a new ARGOS8 allele whose expression levels and tissue specificity will differ from the native form. We expect that these lines will recapitulate the phenotype of increased drought tolerance and improved NUE as observed in the Zm-GOS2 PRO:Zm-ARGOS8 transgenic plants (WO 2013/066805 A1, published 10 May 2013). These maize lines are different from those conventional transgenic events: (1) there is only one ARGOS8 gene in the genome; (2) this modified version of Zm-ARGOS8 resides at its native locus; (3) the ARGOS8 protein level and the tissue specificity of gene expression are entirely controlled by the edited allele. The DNA reagents used during the mutagenization, such as guideRNA, Cas9 endonuclease, transformation selection marker and other DNA fragments are not required for function of the newly generated ARGOS8 allele and can be eliminated from the genome by segregation through standard breeding methods. Because the promoter Zm-GOS2 PRO:GOS2 INTRON was copied from maize GOS2 gene (SEQ ID NO:464) and inserted into the ARGOS8 locus through homologous recombination, this ARGOS8 allele is indistinguishable from natural mutant alleles.

A. Insertion of *Zea mays*-GOS2 PRO:GOS2 INTRON into Maize-ARGOS 8 Promoter

To insert Zm-GOS2 PRO:GOS2 INTRON into the 5'-UTR of maize ARGOS8 gene, a guideRNA construct, gRNA1, was made using maize U6 promoter and terminator as described herein. The 5'-end of the guide RNA contained a 19-bp variable targeting domain targeting the genomic target sequence 1 (CTS1; SEQ ID NO; 451) in the 5'-UTR of Zm-ARGOS8 (FIG. 28). A polynucleotide modification template containing the Zm-GOS2 PRO:GOS2 INTRON that was flanked by two genomic DNA fragments (HR1 and HR2, 370 and 430-bp in length, respectively) derived from the upstream and downstream region of the CTS1 (FIG. 28). The gRNA1 construct, the polynucleotide modification template, a Cas9 cassette and transformation selection marker phosphomannose isomerase (PMI) were introduced into maize immature embryo cells by using a particle bombardment method. PMI-resistant calli were screened with PCR for Zm-GOS2 PRO:GOS2 INTRON insertion (FIGS. 29A and 29B). Multiple callus events were identified and plants were regenerated. The insertion events were confirmed by amplifying the Zm-ARGOS8 region in TO plants with PCR (FIG. 29C) and sequencing the PCR products.

B. Replacement of Zm-ARGOS 8 Promoter with Zm-GOS2 PRO:GOS2 INTRON Promoter (Promoter Swap).

To substitute (replace) the native promoter of Zm-ARGOS8 with Zm-GOS2 PRO:GOS2 INTRON, a guide RNA construct, gRNA3, was made for targeting the genomic target site CTS3 (SEQ ID NO:453), located 710-bp upstream of the Zm-ARGOS8 start codon (FIG. 30). Another guide RNA, gRNA2, was designed to target the genomic target site CTS2 (SEQ ID NO:452) located in the 5'-UTR of Zm-ARGOSO8 (FIG. 30). The polynucleotide modification template contained a 400-bp genomic DNA fragment derived from the upstream region of CTS3, Zm-GOS2 PRO:GOS2 INTRON and a 360-bp genomic DNA fragment derived from the downstream region of CTS2 (FIG. 30). The gRNA3 and gRNA2, the Cas9 cassette, the polynucleotide modification template and the PMI selection marker were used to transform immature embryo cells. Multiple promoter swap (promoter replacement) events were identified by PCR screening of the PMI-resistance calli (FIGS. 31A, 31B & 31C) and plants were regenerated. The swap events were confirmed by PCR analysis of the Zm-ARGOS8 region in TO plants (FIG. 31D).

C. Deletion of Zm-ARGOS 8 Promoter

To delete the promoter of Zm-ARGOS8, we screened the PMI-resistance calli obtained from the above gRNA3/gRNA2 experiment to look for events that produce a 1.1-kb PCR product (FIG. 32A). Multiple deletion events were identified (FIG. 32B) and plants were regenerated. The deletion events were confirmed by amplifying the Zm-ARGOS8 region in TO plants with PCR and sequencing of the PCR products.

Example 24

Gene Editing of the Soybean EPSPS1 Gene Using the Guide RNA/Cas Endonuclease System A. GuideRNA Cas9 Endonuclease Target Site Design on the Soybean EPSPS Genes.

Two guideRNA/Cas9 endonuclease target sites (soy EPSPS-CR1 and soy EPSPS-CR2) were identified in the Exon2 of the soybean EPSPS1 gene Glyma01g33660 (Table 33).

TABLE 33

Guide RNA/Cas9 endonuclease target sites on soybean EPSPS1 gene

| Name of gRNA-Cas9 endonuclease target site | Cas endonuclease target sequence (SEQ ID NO:) | Physical location |
|---|---|---|
| soy EPSPS-CR1 | 467 | Gm01: 45865337 . . . 45865315 |
| soy EPSPS-CR2 | 468 | Gm01: 45865311 . . . 45865333 |

B. Guide-RNA Expression Cassettes, Cas9 Endonuclease Expression Cassettes and Polynucleotide Modification Templates for Introduction of Specific Amino Acid Changes in the Soybean EPSPS1 Gene The soybean U6 small nuclear RNA promoter, GM-U6-13.1 (SEQ ID. NO: 469), was used to express guide RNAs to direct Cas9 nuclease to designated genomic target sites (Table 34). A soybean codon optimized Cas9 endonuclease (SEQ ID NO: 489) expression cassette and a guide RNA expression cassette were linked in a first plasmid that was co-delivered with a polynucleotide modification template. The polynucleotide modification template contained specific nucleotide changes that encoded for amino acid changes in the EPSPS1 polypeptide (Glyma01g33660), such as the T183I and P187S (TIPS) in the Exon2. Other amino acid changes in the EPSPS1 polypeptide can also be obtained using the guide RNA/Cas endonuclease system described herein. Specific amino acid modifications can be achieved by homologous recombination between the genomic DNA and the polynucleotide modification template facilitated by the guideRNA/Cas endonuclease system.

TABLE 34

Guide RNA/Cas9 expression cassettes and polynucleotide modification templates used in soybean stable transformation for the specific amino acid modifications of the EPSPS1 gene.

| Experiment | Guide RNA/Cas9 (plasmid name) | SEQ ID NO: | polynucleotide modification template | SEQ ID NO: |
|---|---|---|---|---|
| soy EPSPS-CR1 | U6-13.1:EPSPS ECR1 + F1A2: CAS9 (QC878) | 470 | RTW1013A | 472 |
| soy EPSPS-CR2 | U6-13.1:EPSPS CR2 + EF1A2: CAS9 (QC879) | 471 | RTW1012A | 473 |

C. Detection of Site-Specific Non-Homologous-End-Joining (NHEJ) Mediated by the Guide RA/Cas9 System in Stably Transformed Soybean Genomic DNA was extracted from somatic embryo samples and analyzed by quantitative PCR using a 7500 real time PCR system (Applied Biosystems, Foster City, CA) with target site-specific primers and FAM-labeled fluorescence probe to check copy number changes of the double strand break target sites. The qPCR analysis was done in duplex reactions with a syringolide induced protein (STP) as the endogenous controls and a wild type 93B86 genomic DNA sample that contains one copy of the target site with 2 alleles, as the single copy calibrator. The presence or absence of the guide RNA-Cas9 expression cassette in the transgenic events was also analyzed with the qPCR primer/probes for guideRNA/Cas9 (SEQ IDs: 477-479) and for PinII (SEQ ID: 480-482). he qPCR primers/probes are listed in Table 35.

TABLE 35

Primers/Probes used in qPCR analyses of transgenic soybean events.

| Target Site | Primer/ Probe Name | Sequences | SEQ ID NOs: |
|---|---|---|---|
| EPSPS-CR1 & EPSPS-CR2 | Soy1-F1 | CCACTAGTAAGGAATCTAAAGATGAA ATCA | 474 |
| | Soy1-R2 | CCTGCAGCAACCACAGCTGCTGTC | 475 |
| | Soy1-T1 (FAM-MGB) | CTGCAATGCGTCCTT | 476 |
| gRNA/CAS9 | Cas9-F | CCTTCTTCCACCGCCTTGA | 477 |
| | Cas9-R | TGGGTGTCTCTCGTGCTTTTT | 478 |
| | Cas9-T (FAM-MGB) | AATCATTCCTGGTGGAGGA | 479 |
| pINII | pINII-99F | TGATGCCCACATTATAGTGATTAGC | 480 |
| | pINII-13R | CATCTTCTGGATTGGCCAACTT | 481 |
| | pINII-69T (FAM-MGB) | ACTATGTGTGCATCCTT | 482 |
| SIP | SIP-130F | TTCAAGTTGGGCTTTTTCAGAAG | 483 |
| | SIP-198R | TCTCCTTGGTGCTCTCATCACA | 484 |
| | SIP-170T (VIC-MGB) | CTGCAGCAGAACCAA | 485 |

The endogenous control probe SIP-T was labeled with VIC and the gene-specific probes for all the target sites were labeled with FAM for the simultaneous detection of both fluorescent probes (Applied Biosystems). PCR reaction data were captured and analyzed using the sequence detection software provided with the 7500 real time PCR system and the gene copy numbers were calculated using the relative quantification methodology (Applied Biosystems).

Since the wild type 93B86 genomic DNA with two alleles of the double strand break target site was used as the single copy calibrator, events without any change of the target site would be detected as one copy herein termed Wt-Homo (qPCR value>=0.7), events with one allele changed, which is no longer detectible by the target site-specific qPCR, would be detected as half copy herein termed NHEJ-Hemi (qPCR value between 0.1 and 0.7), while events with both alleles changed would be detected as null herein termed NHEJ-Null (qPCR value=<0.1). As shown in Table 36, both guideRNA/Cas endonuclease systems targeting the soy EPSPS-CR1 and EPSPS-CR2 sites can introduce efficient Double Strand Break (DSB) efficiency at their designed target sites. Both NHEJ-Hemi and NHEJ-Null were detected in the 93B86 genotype. NHEJ (Non-Homologous-End-Joining) mutations mediated by the guide RNA/Cas9 system at the specific Cas9 target sites were confirmed by PCR/topo cloning/sequencing.

TABLE 36

Target Site Double Strand Break Rate Mutations Induced by the Guide RNA/Cas9 system on soybean EPSPS1 gene. Numbers indicate no. of events (numbers in parentheses are %).

| Project | Total event | Wt-Homo (%) | NHEJ-Hemi (%) | NHEJ-Null (%) |
|---|---|---|---|---|
| U6-13.1 EPSPS-CR1 | 168 | 63 (38%) | 66 (39%) | 39 (23%) |
| U6-13.1 EPSPS-CR2 | 111 | 50 (45%) | 21 (19%) | 40 (36%) |

D. Detection of the TIPS Mutation in the Soybean EPSPS Gene

In order to edit specific amino acids at the native EPSPS gene (such as those resulting in a TIPS modification), a polynucleotide modification template, such as RTW1013A or RTW1012A (Table 34), was co-delivered with the guideRNA/Cas9 expression cassettes into soybean cells.

The modification of the native EPSPS1 gene via guide RNA/Cas9 system mediated DNA homologous recombination was determined by specific PCR analysis. A specific PCR assay with primer pair WOL569 (SEQ ID NO: 486) and WOL876 (SEQ ID NO: 487) was used to detect perfect TIPS modification at the native EPSPS1 gene. A second primer pair WOL569 (SEQ ID NO: 486) and WOL570 (SEQ ID NO: 488) was used to amplify both TIPS modified EPSPS1 allele and WT (wild type)/NHEJ mutated allele. Topo cloning/sequencing was used to verify the sequences.

Example 25

Intron Replacement of Soybean Genes Using the guideRNA/Cas Endonuclease System

A. GuideRNA Cas9 Endonuclease Target Site Design.

Four guideRNA/Cas9 endonuclease target sites were identified in the soybean EPSPS1 gene Glyma01g33660 (Table 37). Two of the target sites (soy EPSPS-CR1 and soy EPSPS-CR2) were identified to target the Exon2 of the soybean EPSPS gene as described in Example 24. Another two target sites (soy EPSPS-CR4 and soy EPSPS-CR5) were designed near the 5' end of the intron1 of the soybean EPSPS gene.

TABLE 37

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR1 | 467 | Gm01: 45865337 . . . 45865315 |
| soy EPSPS-CR2 | 468 | Gm01: 45865311 . . . 45865333 |
| soy EPSPS-CR4 | 490 | Gm01: 45866302 . . . 45866280 |
| soy EPSPS-CR5 | 491 | Gm01: 45866295 . . . 45866274 |

B. Guide RNA Cas9 Endonuclease Expression Cassettes and Polynucleotide Modification Templates Used in Soybean Stable Transformation for the Replacement of the Intron1 of the Soybean EPSPS1 Gene with the Soybean Ubiquitin (UBQ) Intron1

The soybean U6 small nuclear RNA promoter GM-U6-13.1 (SEQ ID. NO: 469) was used to express two guide RNAs (soy-EPSPS-CR1 and soy-EPSPS-CR4, or soy-EPSPS-CR1 and soy-EPSPS-CR5) to direct Cas9 endonuclease to designated genomic target sites (Table 38). One of the target sites (soy-EPSPS-CR1) was located in the exon2, as described in Example 24, and a second target site (soy-EPSPS-CR4 or soy-EPSPS-CR5) was located near the 5' end of intron1 of the native EPSPS1 gene. A soybean codon optimized Cas9 endonuclease expression cassette and a guide RNA expression cassette were linked in the expression plasmids QC878/RTW1199 (SEQ ID NO:470/492) or QC878/RTW1200 (SEQ ID NO:470/493) that was co-delivered with a polynucleotide modification template. The polynucleotide modification template, RTW1190A (SEQ ID NO:494), contained 532 bp intron1 of the soybean UBQ gene and the TIPS modified Exon2. Soybean EPSPS1 intron 1 replacement with the soybean UBQ intron1 can be achieved with the guide RNA/Cas system by homologous recombination between the genomic DNA and the polynucleotide modification template, resulting in enhancement of the native or modified soy EPSPS1 gene expression.

TABLE 38

Guide RNA/Cas9 endonuclease expression cassettes and polynucleotide modification templates used in soybean stable transformation for the replacement of the Intron1 of the soybean EPSPS1 gene with the soybean ubiquitin (UBQ) intron1

| Experiment | Guide RNA/Cas9 | SEQ ID NO: | polynucleotide modification template | SEQ ID NO: |
|---|---|---|---|---|
| soy EPSPS-CR1 and soy EPSPS-CR4 | U6-13.1:EPSPS CR1 + CR4 + EF1A2:CAS9 (QC878/RTW1199) | 470/492 | RTW1190A | 494 |
| soy EPSPS-CR1 and soy EPSPS-CR5 | U6-13.1:EPSPS CR1 + CR5 + EF1A2:CAS9 (QC878/RTW1200) | 470/493 | RTW1190A | 494 |

C. Detection of Site-Specific NHEJ Mediated by the Guide RNA Cas9 System in Stably Transformed Soybean Site-specific NHEJ was detected as described in Example 24 C, using the qPCR primers/probes listed in Table 39.

TABLE 39

Primers/Probes used in qPCR analyses of transgenic soybean events.

| Target Site | Primer/Probe Name | Sequences | SEQ ID NOs: |
|---|---|---|---|
| EPSPS-CR1 & EPSPS-CR2 | Soy1-F1 | CCACTAGTAAGGAATCTAAAGATGAAATCA | 474 |
| | Soy1-R2 | CCTGCAGCAACCACAGCTGCTGTC | 475 |
| | Soy1-T1 (FAM-MGB) | CTGCAATGCGTCCTT | 476 |
| EPSPS-CR4 | Soy1-F3 | GTTTGTTTGTTGTTGGGTGTGGG | 495 |
| | Soy1-R3 | GACATGATGCTTCATTTTCACAGAA | 496 |
| | Soy-T2 (FAM-MGB) | TGTGTAGAGTGGATTTTG | 497 |
| EPSPS-CR5 | Soy1-F2 | TGTTGTTGGGTGTGGGAATAGG | 498 |
| | Soy1-R3 | GACATGATGCTTCATTTTCACAGAA | 496 |
| | Soy1-T2 (FAM-MGB) | TGTGTAGAGTGGATTTTG | 497 |
| gRNA/CAS9 | Cas9-F | CCTTCTTCCACCGCCTTGA | 477 |
| | Cas9-R | TGGGTGTCTCTCGTGCTTTTT | 478 |
| | Cas9-T (FAM-MGB) | AATCATTCCTGGTGGAGGA | 479 |
| pINII | pINII-99F | TGATGCCCACATTATAGTGATTAGC | 480 |
| | pINII-13R | CATCTTCTGGATTGGCCAACTT | 481 |
| | pINII-69T (FAM-MGB) | ACTATGTGTGCATCCTT | 482 |
| SIP | SIP-130F | TTCAAGTTGGGCTTTTTCAGAAG | 483 |
| | SIP-198R | TCTCCTTGGTGCTCTCATCACA | 484 |
| | SIP-170T (VIC-MGB) | CTGCAGCAGAACCAA | 485 |

D. Detection of the Replacement of the Soybean EPSPS1 Intron1 with the Soybean UBQ Intron1 Using the Guide RNA Cas9 Endonuclease System.

In order to replace the soybean EPSPS1 intron1 with the soybean UBQ intron1 at the native EPSPS1 gene, two guideRNA expression vectors were used as shown in Table 38. The QC878 vector (SEQ ID NO: 470) was targeting the exon2 and the RTW1199 (SEQ ID NO:492) or RTW1200 (SEQ ID NO:493) was targeting the 5' end of the intron1. The double cleavage of soybean EPSPS gene with the two guide RNA/Cas systems resulted in the removal of the native EPSPS1 intron1/partial Exon2 fragment. At the same time, a polynucleotide modification template RTW1190A (SEQ ID NO:494) was co-delivered into soybean cells and homologous recombination between the polynucleotide modification template and the genomic DNA resulted in the replacement of EPSPS1 intron1 with the soybean UBQ intron1 and the desired amino acid modifications in exon2 as evidenced by PCR analysis. PCR assays with primer WOL1001/WOL1002 pair (SEQ ID NO: 499 and 500) and WOL1003/WOL1004 pair (SEQ ID NO: 501 and 502) were used to detect the intron replacement events.

Example 26

Promoter Replacement (Promoter Swap) of Soybean Genes Using the guideRNA/Cas Endonuclease System
A. GuideRNA Cas9 Endonuclease Target Site Design.

Four guideRNA/Cas9 endonuclease target sites were identified in the soybean EPSPS1 gene Glyma01g33660 (Table 40). Two of the target sites (soy EPSPS-CR1 and soy EPSPS-CR2) were identified to target the Exon2 of the soybean EPSPS gene as described in Example 24. The soy EPSPS-CR6 and soy EPSPS-CR7 were identified near the 5' end of the −798 bp of the native EPSPS promoter.

TABLE 40

Guide RNA/Cas9 endonuclease target sites on soybean EPSPS1 gene.

| Name of gRNA-Cas9 endonuclease target site | Cas endonuclease target sequence (SEQ ID NO:) | Physical location |
|---|---|---|
| soy EPSPS-CR1 | 467 | Gm01: 45865337 . . . 45865315 |
| soy EPSPS-CR2 | 468 | Gm01: 45865311 . . . 45865333 |
| soy EPSPS-CR6 | 503 | Gm01: 45867471 . . . 45867493 |
| soy EPSPS-CR7 | 504 | Gm01: 45867459 . . . 45867481 |

B. Guide RNA Cas9 Endonuclease Expression Cassettes and Polynucleotide Modification Templates Used in Soybean Stable Transformation for the Replacement of the −798 bp Soybean EPSPS1 Promoter with the Soybean UBQ Promoter.

The soybean U6 small nuclear RNA promoter GM-U6-13.1 (SEQ ID. NO: 469) was used to express two guide RNAs (soyEPSPS-CR1 and soyEPSPS-CR6, or soyEPSPS-CR1 and soyEPSPS-CR7) to direct Cas9 nuclease to designated genomic target sites (Table 41). One of the target sites (soy-EPSPS-CR1) was located in the exon2 as described in Example 24 and a second target site (soy-EPSPS-CR6 or soy-EPSPS-CR7) was located near 5' end of the −798 bp of the native EPSPS1 promoter. A soybean codon optimized Cas9 endonuclease expression cassette and a guide RNA expression cassette were linked in the expression plasmids QC878/RTW1201 (SEQ ID NO:470/505) or QC878/RTW1202 (SEQ ID NO:470/506) that was co-delivered with a polynucleotide modification template, RTW1192A (SEQ ID NO:507). The polynucleotide modification template contained 1369 bp of the soybean UBQ gene promoter, 47 bp 5UTR and 532 bp UBQ intron1. Specific soybean EPSPS1 promoter replacement with the soybean UBQ promoter can be achieved with the guide RNA/Cas system by homologous recombination between the genomic DNA and the polynucleotide modification template, resulting enhancement of the native or modified soy EPSPS1 gene expression

TABLE 41

Guide RNA/Cas9 endonuclease expression cassettes and polynucleotide modification templates used in soybean stable transformation for the replacement of the -798bp soybean EPSPS1 promoter with the soybean UBQ promoter

| Experiment | Guide RNA/Cas9 | SEQ ID NO: | polynucleotide modification template | SEQ ID NO: |
|---|---|---|---|---|
| soy EPSPS-CR1 and soy EPSPS-CR6 | U6-13.1:EPSPS CR1 + CR6 + EF1A2:CAS9 (QC878/RTW1201) | 470, 505 | RTW1192A | 507 |
| soy EPSPS-CR1 and soy EPSPS-CR7 | U6-13.1:EPSPS CR1 + CR7 + EF1A2:CAS9 (QC878/RTW1202) | 470, 506 | RTW1192A | 507 |

C. Detection of Site-Specific NHEJ Mediated by the Guide RNA Cas9 System in Stably Transformed Soybean Site-specific NHEJ was detected as described in Example 24 C, using the qPCR primers/probes listed in Table 42.

TABLE 42

Primers/Probes used in qPCR analyses of transgenic soybean events

| Target Site | Primer/ Probe Name | Sequences | SEQ ID NOs: |
|---|---|---|---|
| EPSPS-CR1 & EPSPS-CR12 | Soy1-F1 | CCACTAGTAAGGAATCTAAAGATGAAATCA | 474 |
| | Soy1-R2 | CCTGCAGCAACCACAGCTGCTGTC | 475 |
| | Soy1-T1 (FAM-MGB) | CTGCAATGCGTCCTT | 476 |
| EPSPS-CR6 & EPSPS-CR7 | Soy1-F4 | TCAATAATACTACTCTCTTAGACACCAAACAA | 508 |
| | Soy1-R4 | CAAGGAAAATGAATGATGGCTTT | 509 |
| | Soy1-T3 (FAM-MGB) | CCTTCCCAAACTATAATC | 510 |
| gRNA/CAS9 | Cas9-F | CCTTCTTCCACCGCCTTGA | 477 |
| | Cas9-R | TGGGTGTCTCTCGTGCTTTTT | 478 |
| | Cas9-T (FAM-MGB) | AATCATTCCTGGTGGAGGA | 479 |
| pINII | pINII-99F | TGATGCCCCATTATAGTGATTAGC | 480 |
| | pINII-13R | CATCTTCTGGATTGGCCAACTT | 481 |
| | pINII-69T (FAM-MGB) | ACTATGTGTGCATCCTT | 482 |
| SIP | SIP-130F | TTCAAGTTGGGCTTTTTCAGAAG | 483 |
| | SIP-198R | TCTCCTTGGTGCTCTCATCACA | 484 |
| | SIP-170T (VIC-MGB) | CTGCAGCAGAACCAA | 485 |

D. Detection of the Promoter Replacement of the Soybean EPSPS1 Promoter with the Soybean UBQ Promoter Using the Guide RNA Cas9 Endonuclease System.

In order to replace the soybean EPSPS1 promoter with the soybean UBQ promoter at the native EPSPS1 gene, two guideRNA expression vectors were used in each soybean transformation experiment as shown in Table 41. The QC878 (SEQ ID NO: 470) was targeting the exon2 and the RTW1201 (SEQ ID NO: 505) or RTW1202 (SEQ ID NO: 506) was targeting the 5' end of the soybean -798 bp promoter. The double cleavage of the soybean EPSPS1 gene with the two guide RNA/Cas systems resulted in removal of the native EPSPS1 promoter/5'UTR-Exon1/Intron1/partial Exon2 fragment at the native EPSPS gene. At the same time, a polynucleotide modification template RTW1192A (SEQ ID NO: 507) was co-delivered into soybean cells. This RTW1192A DNA contained 1369 bp soybean UBQ promoter, its 47 bp 5-UTR and 532 bp UBQ intron1 in front of the EPSPS1 exon1-Intron1-modified Exon2. Homologous recombination between the polynucleotide modification template and the genomic DNA resulted in the replacement of EPSPS1 promoter/5'UTR with the soybean UBQ promoter/5'UTR/Intron1 and the desired amino acid modifications evidenced by PCR analysis. PCR assays with primer WOL1005/WOL1006 pair (SEQ ID NO: 511 and 512) and WOL1003/WOL1004 pair (SEQ ID NO: 501 and 502) were used to detect the promoter replacement events.

Example 27

Enhancer Element Deletions Using the guideRNA/Cas Endonuclease System

The guide RNA/Cas endonuclease system described herein can be used to allow for the deletion of a promoter element from either a transgenic (pre-existing, artificial) or endogenous gene. Promoter elements, such enhancer elements, or often introduced in promoters driving gene expression cassettes in multiple copies (3X=3 copies of enhancer element, FIG. 33) for trait gene testing or to produce transgenic plants expressing specific trait. Enhancer elements can be, but are not limited to, a 35S enhancer element (Benfey et al, EMBO J, August 1989; 8(8): 2195-2202, SEQ ID NO:513). In some plants (events), the enhancer elements can cause an unwanted phenotype, a yield drag, or a change in expression pattern of the trait of interest that is not desired. For example, as shown in FIG. 33, a plant comprising multiple enhancer elements (3 copies, 3X) in its genomic DNA located between two trait cassettes (Trait A en Trait B) was characterized to show an unwanted phenotype. It is desired to remove the extra copies of the enhancer element while keeping the trait gene cassettes intact at their integrated genomic location. The guide RNA/Cas endonuclease system described herein can be used to removing the unwanted enhancing element from the plant genome. A guide RNA can be designed to contain a variable targeting region targeting a target site sequence of 12-30 bps adjacent to a NGG (PAM) in the enhancer. If a Cas endonuclease target site sequence is present in all copies of the enhancer elements (such as the three Cas endonuclease target sites 35S-CRTS1 (SEQ ID NO:514), 35S-CRTS2 (SEQ ID NO:515), 35S-CRTS3 (SEQ ID NO:516)), only one guide RNA is needed to guide the Cas endonuclease to the target sites and induce a double strand break in all the enhancer elements at once. The Cas endonuclease can make cleavage to remove one or multiple enhancers. The guideRNA/Cas endonuclease system can introduced by either *agrobacterium* or particle gun bombardment. Alternatively, two different guide RNAs (targeting two different genomic target sites) can be used to remove all 3× enhancer elements from the genome of an organism, in a manner similar to the removal of a (transgenic or endogenous) promoter described herein.

Example 28

Regulatory Sequence Modifications Using the Guide RNA/Cas Endonuclease System

A. Modification of Polyubiquitination Sites

There are defined ubiquitination sites on proteins to be degraded and they were found within the maize EPSPS protein by using dedicated computer programs (for example, the CKSAAP_UbSite (Ziding Zhang's Laboratory of Protein Bioinformatics College of Biological Sciences, China Agricultural University, 100193 Beijing, China). One of the selected polyubiquitination site within the maize EPSPS coding sequence is shown in FIG. 34A and its amino acid signature sequence is compared to the equivalent EPSPS sites from the other plants (FIG. 34A). The lysine amino acid (K) at position 90 (highly conserved in other plant species) was selected as a potential site of the EPSPS protein polyubiquitination. The polynucleotide modification template (referred to as EPSPS polynucleotide maize K90R template) used to edit the epsps locus is listed as SEQ ID NO: 517. This template allowed for editing the epsps locus to contain the lysine (K) to arginine (R) substitution at position 90 (K90R) and two additional TIPS substitutions at positions 102 and 106 (FIGS. 34B and 34C). Maize genomic DNA was edited using the guideRNA/Cas endonuclease system described herein and TO plants were produced as described herein. The TO plants that contained the nucleotide modifications, as specified by the information provided on the K90R template (FIG. 34C), were selected by the genotyping methods described herein. F1 EPSPS-K90R plants can be selected for elevated protein content due to a slower rate of the EPSPS protein degradation.

B. Editing Intron Elements to Introduce Intron Mediated Enhancer Elements (IMEs)

Transcriptional activity of the native EPSPS gene can be modulated by transcriptional enhancers positioned in the vicinity of other transcription controlling elements. Introns are known to contain enhancer elements affecting the overall rate of transcription from native promoters including the EPSPS promoter. For example, the first intron of the maize ubiquitin 5'UTR confers a high level of expression in monocot plants as specified in the WO 2011/156535 A1 patent application. An intron enhancing motif CATATCTG (FIG. 35 A), also referred to as a intron-mediated enhancer element, IME) was identified by proprietary analysis (WO2011/156535 A1, published on Dec. 15, 2011) and appropriate nucleotide sites at the 5' end of the EPSPS first intron were selected for editing in order to introduce the intron-mediated enhancer elements (IMEs) (FIG. 35B-35C). The polynucleotide modification template (referred to as EPSPS polynucleotide maize IME template) is listed as SEQ ID No: 518. The polynucleotide modification template allows for editing of the epsps locus to contain three IMEs (two on one strand of the DNA, one on the reverse strand) in the first EPSPS intron and the TIPS substitutions at positions 102 and 106. The genomic DNA of maize plants was edited using the guideRNA/Cas endonuclease system described herein. Maize plants containing the IME edited EPSPS coding sequence can be selected by genotyping the TO plants and can be further evaluated for elevated EPSPS-TIPS protein content due to the enhanced transcription rate of the native EPSPS gene.

Example 29

Figure 36B:
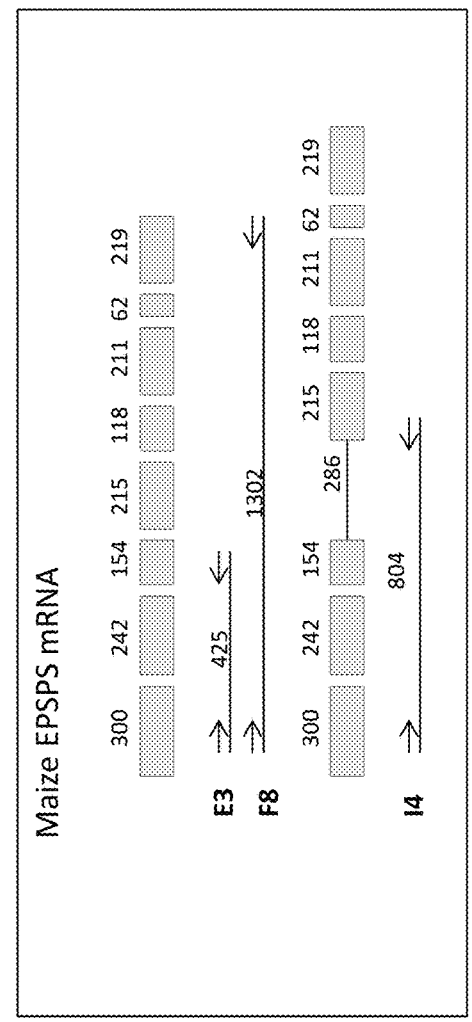

Modifications of Splicing Sites and/or Introducing Alternate Splicing Sites Using the Guide RNA/Cas Endonuclease System In maize cells, the splicing process is affected by splicing sites at the exon-intron junction sites as illustrated in the EPSPS mRNA production (FIG. 36A-36B). FIG. 36A shows analysis of EPSPS amplified pre-mRNA (cDNA panel on left). Lane 14 in FIG. 36A shows amplification of the EPSPS pre-mRNA containing the $3^{rd}$ intron unspliced, resulting in a 804 bp diagnostic fragment indicative for an alternate splicing event. Lanes E3 and F8 show the EPSPS PCR amplified fragments resulting from regular spliced introns. Diagnostic fragments such as the 804 bp fragment of lane 14 are not amplified unless cDNA is synthesized (as is evident by the absence of bands in lanes E3, 14, and F8 comprising total RNA (shown in the total RNA panel on right of FIG. 36A). The canonical splice site in the maize EPSPS gene and genes from other species is AGGT, while other (alterative) variants of the splice sites may lead to the aberrant processing of pre-mRNA molecules. The EPSPS coding sequence contains a number of alternate splicing sites that may affect the overall efficiency of the pre-mRNA maturation process and as such may limit the EPSPS protein accumulation in maize cells.

In order to limit the occurrence of alternate splicing events during EPSPS gene expression, a guideRNA/Cas endonuclease system as described herein can be used to edit splicing sites. The splicing site at the junction of the second native EPSPS intron and the third exon is AGTT and can be edited in order to introduce the canonical AGGT splice site at this junction (FIG. 37). The T>G substitution does not affect the native EPSPS open reading frame and it does not change the EPSPS amino acid sequence. The polynucleotide modification template (referred to as EPSPS polynucleotide maize Tspliced template) is listed as SEQ ID NO: 519. This polynucleotide modification template allows for editing of the epsps locus to contain the canonical AGGT splice site at the $2^{nd}$ intron-$3^{rd}$ exon junction site and the TIPS substitutions at positions 102 and 106. Maize plants are edited using the procedures described herein. F1 EPSPS-Tspliced maize plants can be evaluated for increased protein content due to the enhanced production of functional EPSPS mRNA messages.

Example 30

Shortening Maturity Via Manipulation of Early Flowering Phenotype with ZmRap2.7 Down-Regulation Using the Guide RNA/Cas Endonuclease System Overall plant maturity can be shortened by modulating the flowering time phenotype of plants through modulation of a maize ZmRap2.7 gene. Shortening of plant maturity can be obtained by an early flowering phenotype.

RAP2.7 is an acronym for Related to APETALA 2.7. RAPL means RAP2.7 LIKE and RAP2.7 functions as an AP2-family transcription factor that suppresses floral transition (SEQ ID NOs:520 and 521). Transgenic phenotype upon silencing or knock-down of Rap2.7 resulted in early flowering, reduced plant height, but surprisingly developed normal ear and tassel as compared the wild-type plants (PCT/US14/26279 application, filed Mar. 13, 2014). The guide RNA/Cas endonuclease system described herein can be used to target and induce a double strand break at a Cas endonuclease target site located within the RAP2.7 gene. Plants comprising NHEJ within the RAP2.7 gene can be selected and evaluated for the presence of a shortened maturity phenotype.

Example 31

Modulating Expression of a Maize NPK1B Gene for Engineering Frost Tolerance in Maize Using a Guide RNA/Cas Endonuclease System

*Nicotiana* Protein Kinase1 (NPK1) is a mitogen activated protein kinase kinase kinase that is involved in cytokinesis regulation and oxidative stress signal transduction. The ZM-NPK1B (SEQ ID NO: 522 and SEQ ID NO: 523) which has about 70% amino acid similarity to rice NPKL3 has been tested for frost tolerance in maize seedlings and reproductive stages (PCT/US14/26279 application, filed Mar. 13, 2014). Transgenic seedlings and plants comprising a ZM-NPK1B driven by an inducible promoter Rab17, had significantly higher frost tolerance than control seedlings and control plants. The gene seemed inducted after cold acclimation and during −3° C. treatment period in most of the events but at low levels. (PCT/US14/26279 application, filed Mar. 13, 2014).

A guide RNA/Cas endonuclease system described herein can be used to replace the endogenous promoter of NPK1 gene, with a stress-inducible promoter such as the maize RAB17 promoter stages (SEQ ID NO: 524; PCT/US14/26279 application, filed Mar. 13, 2014), thus modulate NPK1B expression in a stress-responsive manner and provide frost tolerance to the modulated maize plants.

Example 32

Shortening Maturity Via Manipulation of Early Flowering Phenotype with FTM1 Expression Using a Guide RNA/Cas Endonuclease Systems Overall plant maturity can be shortened by modulating the flowering time phenotype of plants through expressing a transgene. Such a phenotype modification can also be achieved with additional transgenes or through a breeding approach.

FTM1 stands for Floral Transition MADS 1 transcription factor (SEQ ID NOs: 525 and 526). It is a MADS Box transcriptional factor and induces floral transition. Upon expression of FTM1 under a constitutive promoter, transgenic plants exhibited early flowering and shortened maturity, but surprisingly ear and tassel developed normally as compared to the wild-type plants (PCT/US14/26279 application, filed Mar. 13, 2014).

FTM1-expressing maize plants demonstrated that by manipulating a floral transition gene, time to flowering can be reduced significantly, leading to a shortened maturity for the plant. As maturity can be generally described as time from seeding to harvest, a shorter maturity is desired for ensuring that a crop can finish in the northern continental dry climatic environment (PCT/US14/26279 application, filed Mar. 13, 2014).

A guide RNA/Cas endonuclease system described herein can be used to introduce enhancer elements such as the CaMV35S enhancers (Benfey et al, EMBO J, August 1989; 8(8): 2195-2202, SEQ ID NO:512), specifically targeted in front of the endogenous promoter of FTM1, in order to enhance the expression of FTM1 while preserving most of the tissue and temporal specificities of native expression, providing shortened maturity to the modulated plants.

Example 33

Inserting Inducible Responsive Elements in Plant Genomes

Inducible expression systems controlled by an external stimulus are desirable for functional analysis of cellular proteins as well as trait development as changes in the expression level of the gene of interest can lead to an accompanying phenotype modification. Ideally such a system would not only mediate an "on/off" status for gene expression but would also permit limited expression of a gene at a defined level.
The guide RNA/Cas endonuclease system described herein can be used to introduce components of repressor/operator/inducer systems to regulate gene expression of an organism. Repressor/operator/inducer systems and their components are well known I the art (US 2003/0186281 published Oct. 2, 2003; U.S. Pat. No. 6,271,348). For example, nut not limited to, components of the tetracycline (Tc) resistance system of E. coli have been found to function in eukaryotic cells and have been used to regulate gene expression (U.S. Pat. No. 6,271,348) Nucleotide sequences of tet operators of different classes are known in the art see for example: classA, calssB, classC, classD, classE TET operator sequences lists as SEQ ID NOs:11-15 of U.S. Pat. No. 6,271,348.

Components of a sulfonylurea-responsive repressor system (as described in U.S. Pat. No. 8,257,956, issued on Sep. 4, 2012) can also be introduced into plant genomes to generate a epressor/operator/inducer systems into said plant where polypeptides can specifically bind to an operator, wherein the specific binding is regulated by a sulfonylurea compound.

Example 34

Genome Deletion for Trait Locus Characterization

Trait mapping in plant breeding often results in the detection of chromosomal regions housing one or more genes controlling expression of a trait of interest. For quantitative traits, expression of a trait of interest is governed by multiple quantitative trait loci (QTL) of varying effect-size, complexity, and statistical significance across one or more chromosomes. A QTL or haplotype that is associated with suppression of kernel-row number in the maize ear can be found to be endemic in elite breeding germplasm. The negative effect of this QTL for kernel row number can be fine-mapped to an acceptable resolution to desire selective elimination of this negative QTL segment within specific recipient germplasm. Two flanking cut sites for the guide polynucleotide/Cas endonuclease system are designed via haplotype, marker, and/or DNA sequence context at the targeted QTL region, and the two guide polynucleotide/Cas endonuclease systems are deployed simultaneously or sequentially to produce the desired end product of two independent double strand breaks (cuts) that liberate the intervening region from the chromosome. Individuals harboring the desired deletion event would result by the NHEJ repair of the two chromosomal ends and eliminating the intervening DNA region. Assays to identify these individuals is based on the presence of flanking DNA marker regions, but absence of intervening DNA markers. A proprietary haplotype for kernel-row-number is created that is not extant in the previously defined elite breeding germplasm pool.
An alternative approach would be to delete a region containing a fluorescent gene. Recovery of plants with, and without, fluorescence would give an approximate indication of the efficiency of the deletion process.

Example 35

Engineering Drought Tolerance and Nitrogen Use Efficiency into Maize Via Gene Silencing by Expressing an Inverted Repeat into an ACS6 Gene Using the Guide RNA/Cas Endonuclease System ACC (1-aminocyclopropane-1-carboxylic acid) synthase (ACS) genes encode enzymes that catalyze the rate limiting step in ethylene biosynthesis. A construct containing one of the maize ACS genes, ZM-ACS6, in an inverted repeat configuration, has been extensively tested for improved abiotic stress tolerance in maize (PCT/US2010/051358, filed Oct. 4, 2010; PCT/US2010/031008, filed Apr. 14, 2010). Multiple transgenic maize events containing a ZM-ACS6 RNAi sequence driven by a ubiquitin constitutive promoter had reduced ethylene emission, and a concomitant increase in grain yield relative to controls under both drought and low nitrogen field conditions (Plant Biotechnology Journal: 12 Mar. 2014, DOI: 10.1111/pbi.12172).

In one embodiment, the guide RNA/Cas endonuclease system can be used in combination with a co-delivered polynucleotide sequence to insert an inverted ZM-ACS6 gene fragment into the genome of maize, wherein the insertion of the inverted gene fragment allows for the in-vivo creation of an inverted repeat (hairpin) and results in the silencing of the endogenous ethylene biosynthesis gene.

In an embodiment the insertion of the inverted gene fragment can result in the formation of an in-vivo created inverted repeat (hairpin) in a native (or modified) promoter of an ACS6 gene and/or in a native 5' end of the native ACS6 gene. The inverted gene fragment can further comprise an intron which can result in an enhanced silencing of the targeted ethylene biosynthetic gene.

Example 36

T0 Plants from the Multiplexed Guide RNA/Cas Experiment Carried High Frequency of Bi-Allelic Mutations and Demonstrated Proper Inheritance of Mutagenized Alleles in the T1 Population.

This example demonstrates the high efficiency of the guide RNA/Cas endonuclease system in generating maize plants with multiple mutagenized loci and their inheritance in the consecutive generation(s).

Mutated events generated in the multiplexed experiment described in Example 4 were used to regenerate TO plants with mutations at 3 different target sites: MS26Cas-2 target site (SEQ ID NO: 14), LIGCas-3 target site (SEQ ID NO: 18) and MS45Cas-2 target site (SEQ ID NO: 20).

For further analysis, total genomic DNA was extracted from leaf tissue of individual TO plants. Fragments spanning all 3 target sites were PCR amplified using primer pairs for the corresponding target sites, cloned into the pCR2.1-TOPO cloning vector (Invitrogen), and sequenced. Table 43 shows examples of mutations detected in four TO plants resulting from imprecise NHEJ at all relevant loci when multiple guide RNA expression cassettes were simultaneously introduced either in duplex (see TS=Lig34/MS26) or triplex (see TS=Lig34/MS26/MS45), respectively.

TABLE 43

Examples of mutations at maize target loci produced by a multiplexed guide RNA/Cas system

| Target sites (TS) | T0 plant | qPCR data | Sequencing data | | |
|---|---|---|---|---|---|
| | | | Lig3/4 TS | Ms26 TS | Ms45 TS |
| Lig34/ MS26 | 1 | NULL/ NULL* | 1 bp ins/ 2 bp del + 1 bp ins | 1 bp ins/ 19 bp del | |
| | 2 | NULL/ NULL | 1 bp ins/ 1 bp del | 1 bp ins/ 1 bp ins | |
| Lig34/ MS26/ | 1 | NULL/ NULL/ NULL | 1 bp ins/ large del | 1 bp ins/ 1 bp del | 15 bp del/ large del |

TABLE 43-continued

Examples of mutations at maize target loci produced by a multiplexed guide RNA/Cas system

| Target sites (TS) | T0 plant | qPCR data | Sequencing data | | |
|---|---|---|---|---|---|
| | | | Lig3/4 TS | Ms26 TS | Ms45 TS |
| MS45 | 2 | INDEL**/ NULL/ NULL | 1 bp ins/ WT | 1 bp (T) ins/ 1 bp (C) ins | 1 bp ins/ large del |

*NULL indicates that both alleles are mutated **INDEL indicates mutation in one of the two alleles. del = deletion, ins = insertion, bp = base pair All T0 plants were crossed with wild type maize plants to produce T1 seeds. T1 progeny plants (32 plants) of the second TO plant from the triplex experiment (see Table 43, Lig34/MS26/MS45) were analyzed by sequencing to evaluate segregation frequencies of the mutated alleles. Our results demonstrated proper inheritance and expected (1:1) segregation of the mutated alleles as well as between mutated and wild type alleles at all three target sites.

The data clearly demonstrate that the guide RNA/maize optimized Cas endonuclease system described herein, can be used to simultaneously mutagenize multiple chromosomal loci and produce progeny plants containing the stably inherited multiple gene knock-outs.

Example 37

Guide RNA/Cas Endonuclease Mediated DNA Cleavage in Maize Chromosomal Loci can Stimulate Homologous Recombination Repair-Mediated Transgene Insertion and Resulting T1 Progeny Plants Demonstrated Proper Inheritance of the Modified Alleles.

Maize events generated in the experiment described in Example 5 were used to regenerate T0 plants. T0 plants were regenerated from 7 independent callus events with correct amplifications across both transgene genomic DNA junctions and analyzed. Leaf tissue was sampled, total genomic DNA extracted, and PCR amplification at both transgene genomic DNA junctions was carried out using the primer pairs (corresponding to SEQ ID NOs: 98-101). The resulting amplification products were sequenced for confirmation. Plants with confirmed junctions at both ends were further analyzed by Southern hybridization (FIG. 38) using two probes, genomic (outside HR1 region, SEQ ID: 533) and transgenic (within MoPAT gene, SEQ ID: 534). PCR, sequencing and Southern hybridization data demonstrated that plants regenerated from two of the 7 events (events 1 and 2) demonstrated perfect, clean, single copy transgene integration at the expected target site via homologous recombination. Plants regenerated from the remaining 5 events contained either additional, randomly integrated copies of the transgene (events 4, 5, and 6) or rearranged copies of the transgene integrated into the target site (events 3 and 7).

T0 plants from events 1 and 2 were crossed with wild type maize plants to produce T1 seeds. Ninety-six T1 plants from events 1 and 2 were analyzed by Southern hybridization (using the same probes as above) to evaluate segregation frequencies of the transgene locus. Southern results demonstrated proper inheritance and expected (1:1) segregation of the transgene and wild type loci.

The data clearly demonstrate that maize chromosomal loci cleaved with the maize optimized guide RNA/Cas system described herein can be used to stimulate HR repair pathways to site-specifically insert transgenes and produce progeny plants that have the inserted transgene stably inherited.

Example 38

Production of Maize Transgenic Lines with Pre-Integrated Cas9 for Transient Delivery of Guide RNA This example describes the rationale, production, and testing of maize transgenic lines with an integrated Cas9 gene under constitutive and temperature inducible promoters.

As demonstrated in Example 2, a high mutation frequency was observed when Cas9 endonuclease and guide RNA were delivered as DNA vectors by biolistic transformation to immature corn embryo cells. When Cas9 endonuclease was delivered as a DNA vector and guide RNA as RNA molecules, a reduced mutation frequency was observed (Table 44).

TABLE 44

Mutant reads at LigCas-3 target site produced by transiently delivered guide RNA

| Target Site Examined for Mutations | Transient Delivery | Expression Cassette | Mutant Reads | Total Reads |
|---|---|---|---|---|
| LIGCas-3 | — | Cas9 | 24.2 | 1,599,492 |
| LIGCas-3 | — | Cas9/guide RNA | 44170 | 1,674,825 |
| LIGCas-3 | 35 ng guide RNA | Cas9 | 418 | 1,622,180 |
| LIGCas-3 | 70 ng guide RNA | Cas9 | 667 | 1,791,388 |
| LIGCas-3 | 140 ng guide RNA | Cas9 | 239 | 1,632,137 |

Increased efficiency (increased mutant reads) may occur when the Cas9 protein and guide RNA are present in the cell at the same time. To facilitate the presence of both Cas9 endonuclease and guide RNA in the same cell, a vector containing a constitutive and conditionally regulated Cas9 gene can be first delivered to plant cells to allow for stable integration into the plant genome to establish a plant line that contains only the Cas9 gene in the plant genome. Then, single or multiple guide RNAs can be delivered as either DNA or RNA, or combination, to the embryo cells of the plant line containing the genome-integrated version of the Cas9 gene.

Transgenic maize (genotype Hi-II) lines with an integrated Cas9 gene driven by either a constitutive (Ubi) or an inducible (CAS) promoter were generated via *Agrobacterium*-mediated transformation. Besides the Cas9 gene, the Agro vector also contained a visible marker (END2:Cyan) and a Red Fluorescent Protein sequence interrupted with a 318 bp long linker (H2B:RF-FP) (as described in U.S. patent Ser. No. 13/526,912, filed Jun. 19, 2012). The linker sequence was flanked with 370 bp long direct repeats to promote recombination and restoration of a functional RFP gene sequence upon double strand break within the linker.

Lines with single copies of the transgene were identified and used for further experiments. Two guide RNA constructs targeting 2 different sites (Table 45 in the linker sequence, were delivered into immature embryo cells via particle bombardment. Meganuclease variant LIG3-4 B65 with very high cutting activity previously used in similar experiments was used as the positive control.

TABLE 45

Target sites in the RF-FP linker for guideRNA/Cas endonuclease system.

| Locus | Guide RNA Used | Target Site Designation | Target Site Sequence | PAM Sequence | SEQ ID NO: |
|---|---|---|---|---|---|
| RF-FP linker | Long | RF-FPCas-1 | GCAGGTCTCACGAC GGT | TGG | 535 |
| | Long | RF-FPCas-2 | GTAAAGTACGCGTA CGTGTG | AGG | 536 |

After transformation, embryos with Cas9 gene under Ubiquitin promoter were incubated at 28° C. while embryos with Cas9 gene under temperature inducible CAS promoter were first incubated at 37° C. for 15-20 hours and then transferred to 28° C. Embryos were examined 3-5 days after bombardment under luminescent microscope. Expression and activity of the pre-integrated Cas9 protein was visually evaluated based on the number of embryo cells with RFP protein expression. In most lines, the guide RNA/Cas endonuclease system demonstrated similar or higher frequency of RFP repair than LIG3-4 B65 meganuclease indicating high level of Cas9 protein expression and activity in the generated transgenic lines.

This example describes the production of transgenic lines with a pre-integrated Cas9 gene that can be used in further experiments to evaluate efficiency of mutagenesis at a target site upon transient delivery of guide RNA in the form of RNA molecules.

Example 39

The Guide RNA/Cas Endonuclease System Delivers Double-Strand Breaks to the Maize ALS Locus and Facilitates Editing of the ALS Gene This example demonstrates that the guide RNA/Cas endonuclease system can be efficiently used to introduce specific changes into the nucleotide sequence of the maize ALS gene resulting in resistance to sulfonylurea class herbicides, specifically, chlorsulfuron.

Endogenous ALS protein is the target site of ALS inhibitor sulfonylurea class herbicides. Expression of the herbicide tolerant version of ALS protein in crops confers tolerance to this class of herbicides. The ALS protein contains N-terminal transit peptides, and the mature protein is formed following transport into the chloroplast and subsequent cleavage of the transit peptide. The mature protein starts at residue 541, resulting in a mature protein of 598 amino acids with a predicted molecular weight of 65 kDa (SEQ ID NO: 550).

TABLE 46

Deduced Amino Acid Sequence of the Full-Length ZM-ALS Protein (SEQ ID no: 550)

```
  1 MATAAAASTA LTGATTAAPK ARRRAHLLAT RRALAAPIRC SAASPAMPMA

51 PPATPLRPWG PTEPRKGADI LVESLERCGV RDVFAYPGGA SMEIHQALTR

101 SPVIANHLFR HEQGEAFAAS GYARSSGRVG VCIATSGPGA TNLVSALADA
```

TABLE 46-continued

Deduced Amino Acid Sequence of the Full-Length
ZM-ALS Protein (SEQ ID no: 550)

```
151 LLDSVPMVAI TGQVPRRMIG TDAFQETPIV EVTRSITKHN YLVLDVDDIP

201 RVVQEAFFLA SSGRPGPVLV DIPKDIQQQM AVPVWDKPMS LPGYIARLPK

251 PPATELLEQV LRLVGESRRP VLYVGGGCAA SGEELRRFVE LTGIPVTTTL

301 MGLGNFPSDD PLSLRMLGMH GTVYANYAVD KADLLLALGV RFDDRVTGKI

351 EAFASRAKIV HVDIDPAEIG KNKQPHVSIC ADVKLALQGM NALLEGSTSK

401 KSFDFGSWND ELDQQKREFP LGYKTSNEEI QPQYAIQVLD ELTKGEAIIG

451 TGVGQHQMWA AQYYTYKRPR QWLSSAGLGA MGFGLPAAAG ASVANPGVTV

501 VDIDGDGSFL MNVQELAMIR IENLPVKVFV LNNQHLGMVV QWEDRFYKAN

551 RAHTYLGNPE NESEIYPDFV TIAKGFNIPA VRVTKKNEVR AAIKKMLETP

601 GPYLLDIIVP HQEHVLPMIP SGGAFKDMIL DGDGRTVY
```

Modification of a single amino acid residue (P165A or P165S, shown in bold) from the endogenous maize acetoacetate synthase protein provides resistance to herbicides in maize.

There are two ALS genes in maize, ALS1 and ALS2, located on chromosomes 5 and 4, respectively. As described in Example 2, guide RNA expressing constructs for 3 different target sites within the ALS genes were tested. Based on polymorphism between ALS1 and ALS2 nucleotide sequences, ALS1-specific and ALSCas-4 target site were identified and tested. ALSCas-1 guide RNA expressing construct targeting both ALS1 and ALS2 genes was used as control (Table 47)

TABLE 47

Maize ALS genomic target sites tested.

| Locus | Location | Guide RNA | Target Site Designation | Maize Genomic Target Site Sequence | PAM Sequence | SEQ ID NO: |
|---|---|---|---|---|---|---|
| ALS | Chr. 4: 107.73cM and Chr. 5: 115.49cM | Long | ALSCas-1 | GGTGCCAATCATGC GTCG | CGG | 22 |
| | | Long | ALSCas-4 | GCTGCTCGATTCC GTCCCCA | TGG* | 537 |

*Target site in the ALS1 gene; bolded nucleotides are different in the ALS2 gene.

The experiment was conducted and mutation frequency determined as described in Example 2 and results are shown in Table 48.

TABLE 48

Frequencies of NHEJ mutations at the two ALS target sites recovered by deep sequencing.

| TS | Total Reads | Mutant reads (ALS1) | Mutant reads (ALS2) |
|---|---|---|---|
| ALSCas-1 | 204,230 | 5072 (2.5%) | 2704 (1.3%) |
| ALSCas-4 | 120,766 | 3294 (2.7%) | 40 (0.03%) |

The results demonstrated that ALSCas-4 guide RNA/Cas9 system mutates the ALS1 gene with approximately 90 times higher efficiency than the ALS2 gene. Therefore, the ALS-Cas-4 target site and the corresponding guide RNA were selected for the ALS gene editing experiment.

To produce edited events, the ALS polynucleotide modification repair template was co-delivered using particle bombardment as a plasmid with an 804 bp long homologous region (SEQ ID NO: 538) or as a single-stranded 127 bp DNA fragment (SEQ ID NO: 539), the maize optimized Cas9 endonuclease expression vector described in Example 1, the guide RNA expression cassette (targeting ALSCas-4 site), a moPAT-DsRed fusion as selectable and visible markers, and developmental genes (ODP-2 and WUS). Approximately 1000 Hi-II immature embryos were bombarded with each of the two repair templates described above. Forty days after bombardment, 600 young callus events (300 for each repair template) were collected and transferred to the media with bialaphos selection. The embryos with remaining events were transferred to the media with 100 ppm of chlorsulfuron for selection. A month later, events that continued growing under chlorsulfuron selection were collected and used for analysis.

A small amount of callus tissue from each selected event was used for total DNA extraction. A pair of genomic primers outside the repair/donor DNA fragment (SEQ ID NO:540 and SEQ ID NO:541) was used to amplify an endogenous fragment of the ALS1 locus containing the ALSCas4 target sequence. The PCR amplification products were gel purified, cloned into the pCR2.1 TOPO cloning vector (Invitrogen) and sequenced. A total of 6 events demonstrated the presence of the specifically edited ALS1 allele as well as either a wild type or a mutagenized second allele.

These data indicate that a guide RNA/Cas system can be successfully used to create edited ALS allele in maize. The data further demonstrates that the guide RNA/maize optimized Cas endonuclease system described herein, can be used to produce progeny plants containing gene edits that are stably inherited.

Example 40

Gene Editing of the Soybean ALS1 Gene and Use as a Transformation Selectable Marker for Soybean Transformation with the Guide RNA/Cas Endonuclease System
A. guideRNA Cas9 Endonuclease Target Site Design on the Soybean ALS1 Gene.

There are four ALS genes in soybean (Glyma04g37270, Glyma06g17790, Glyma13g31470 and Glyma15g07860). Two guideRNA/Cas9 endonuclease target sites (soy ALS1-CR1 and soy ALS1-CR2) were designed near the Proline 178 of the soybean ALS1 gene Glyma04g37270 (Table 49).

TABLE 49

Guide RNA/Cas9 endonuclease target sites on soybean ALS1 gene

| Name of gRNA-Cas9 endonuclease target site | Cas endonuclease target sequence (SEQ ID NO:) | Physical location |
|---|---|---|
| soy ALS1-CR1 | 542 | Gm04: 43645633 . . . 43645612 |
| soy ALS1-CR2 | 543 | Gm04: 43645594 . . . 43645615 |

B. Guide-RNA Expression Cassettes, Cas9 Endonuclease Expression Cassettes, Polynucleotide Modification Templates for Introduction of Specific Amino Acid Changes and Use the P178S Modified ALS1 Allele as a Soybean Transformation Selectable Marker The soybean U6 small nuclear RNA promoter, GM-U6-13.1 (SEQ ID. NO: 469), was used to express guide RNAs to direct Cas9 nuclease to designated genomic target sites (Table 50). A soybean codon optimized Cas9 endonuclease (SEQ ID NO:489) expression cassette and a guide RNA expression cassette were linked in a first plasmid that was co-delivered with a polynucleotide modification template. The polynucleotide modification template contained specific nucleotide changes that encoded for amino acid changes in the soy ALS1 polypeptide (Glyma04g37270), such as the P178S. Other amino acid changes in the ALS1 polypeptide can also be obtained using the guide RNA/Cas endonuclease system described herein. Specific amino acid modifications can be achieved by homologous recombination between the genomic DNA and the polynucleotide modification template facilitated by the guideRNA/Cas endonuclease system.

TABLE 50

Guide RNA/Cas9 expression cassettes and polynucleotide modification templates used in soybean stable transformation for the specific amino acid modifications of the soy ALS1 gene.

| Experiment | Guide RNA/Cas9 (plasmid name) | SEQ ID NO: | polynucleotide modification template | SEQ ID NO: |
|---|---|---|---|---|
| soy ALS1-CR1 | U6-13.1:ALS1-CR1 + EF1A2:CAS9 (QC880) | 544 | RTW1026A | 546 |
| soy ALS-CR2 | U6-13.1:ALS1-CR2 + EF1A2:CAS9 (QC881) | 545 | RTW1026A | 546 |

C. Detection of the P178S Mutation in the Soybean ALS1 Gene in the Event Selected by Chlorsulfuron In order to edit specific amino acids at the native ALS1 gene (such as the P178S modification), a polynucleotide modification template such as RTW1026A (Table 50), was co-delivered with the guideRNA/Cas9 expression cassettes into soybean cells. Chlorsulfuron (100 ppb) was used to select the P178S ALS1 gene editing events in soybean transformation process.

The modification of the native ALS1 gene via guide RNA/Cas9 system mediated DNA homologous recombination was determined by specific PCR analysis. A specific PCR assay with primer pair WOL900 (SEQ ID NO: 547) and WOL578 (SEQ ID NO: 548) was used to detect perfect P178S modification at the native ALS1 gene. A second primer pair WOL573 (SEQ ID NO: 549) and WOL578 (SEQ ID NO: 548) was used to amplify both a P178S modified Soy ALS1 allele and a NHEJ mutated allele. A chlorsulfuron tolerant event (MSE3772-18) was generated from the soy ALS1-CR2 experiment. The event contained a perfect P178S modified allele and a $2^{nd}$ allele with a 5 bp deletion at the soyALS1-CR2 cleavage site. Topo cloning/sequencing was used to verify the sequences. Our results demonstrated one P178S modified ALS1 allele is sufficient to provide chlorsulfuron selection in soybean transformation process.

The invention claimed is:

1. A method for modifying a target site in the genome of a plant cell, the method comprising:

transforming at least one plant cell with a guide polynucleotide, a polynucleotide sequence encoding a Cas endonuclease, and an expression cassette encoding at least one developmental gene polypeptide, wherein the at least one developmental gene polypeptide comprises a Babyboom (BBM), an Ovule Development Protein 2 (ODP2), and/or a Wuschel (WUS) polypeptide, wherein the guide polynucleotide and the Cas endonuclease form a guide polynucleotide-Cas endonuclease complex that introduces a double-strand break at the target site in the plant cell, and wherein the at least one developmental gene polypeptide increases the frequency of modification of the target site by the guide polynucleotide-Cas endonuclease complex in the plant cell relative to a control plant cell comprising a guide polynucleotide-Cas endonuclease complex and not comprising an expression cassette encoding a developmental gene polypeptide; and regenerating a plantlet or a plant from the plant cell, the plantlet or plant comprising a modified target site, wherein the plantlet or the plant does not contain the Cas endonuclease or the expression cassette encoding the at least one developmental gene polypeptide.

2. The method of claim 1, wherein the at least one plant cell is an embryogenic plant cell.

3. The method of claim 2, wherein the embryogenic plant cell is transformed by particle bombardment.

4. The method of claim 2, wherein the at least one plant cell comprises a plurality of embryogenic plant cells and the double-strand break at the target site is induced in the plurality of embryogenic plant cells at a frequency of at least 10.1%.

5. The method of claim 1, wherein the at least one plant cell is an embryo.

6. The method of claim 5, wherein the embryo is transformed by particle bombardment or bacterial-mediated transformation.

7. The method of claim 5, wherein the at least one plant cell comprises a plurality of embryos and the double-strand break at the target site is induced in the plurality of embryos at a frequency of at least 33%.

8. The method of claim 2, wherein the modified target site comprises at least one nucleotide insertion, deletion, or substitution.

9. The method of claim 2, wherein the modified target site is a promoter sequence, a terminator sequence, a regulatory element sequence, a splice site, a coding sequence, a polyubiquitination site, an intron site, an intron-enhancing motif, or a gene of interest.

10. The method of claim 2, wherein the plant cell is monocot or dicot.

11. The method of claim 10, wherein the monocot is maize, rice, sorghum, rye, barley, wheat, millet, oats, sugarcane, turfgrass, or switchgrass.

12. The method of claim 10, wherein the dicot is soybean, canola, alfalfa, sunflower, cotton, tobacco, peanut, potato, *Arabidopsis*, or safflower.

13. The method of claim 2, further comprising transforming the at least one plant cell with a polynucleotide modification template comprising at least one nucleotide modification relative to a polynucleotide sequence of the target site.

14. The method of claim 2, wherein the polynucleotide sequence encoding the Cas endonuclease comprises a Cas coding region that is operably linked to a first nuclear localization signal upstream of the Cas coding region and a second nuclear localization signal downstream of the Cas coding region, wherein the first nuclear localization signal and the second nuclear localization signal are derived from different sources.

15. The method of claim 14, wherein the first nuclear localization signal is a monopartite nuclear localization signal.

16. The method of claim 14, wherein the second nuclear localization signal is a bipartite nuclear localization signal.

17. The method of claim 1, wherein the plant cell is a non-protoplast plant cell.

18. The method of claim 1, wherein the plant cell is transformed with the one or more expression cassettes by particle bombardment or bacterial-mediated transformation.

* * * * *